US008318718B2

(12) United States Patent
Allen et al.

(10) Patent No.: US 8,318,718 B2
(45) Date of Patent: Nov. 27, 2012

(54) PYRIDINE AND PYRIMIDINE DERIVATIVES AS PHOSPHODIESTERASE 10 INHIBITORS

(75) Inventors: Jennifer R. Allen, Newbury Park, CA (US); Biswas Kaustav, Agoura Hills, CA (US); Frank Chavez, Camarillo, CA (US); Ning Chen, Thousand Oaks, CA (US); Frenel Fils De Morin, Thousand Oaks, CA (US); James R. Falsey, Moorpark, CA (US); Michael J. Frohn, Thousand Oaks, CA (US); Paul E. Harrington, Camarillo, CA (US); Daniel B. Horne, Simi Valley, CA (US); Essa Hu Harrington, Camarillo, CA (US); Matthew R. Kaller, Ventura, CA (US); Roxanne Kunz, Santa Monica, CA (US); Holger Monenschein, Jupiter, FL (US); Thomas T. Nguyen, Newbury Park, CA (US); Alexander J. Pickrell, Westlake Village, CA (US); Andreas Reichelt, Moorpark, CA (US); Shannon Rumfelt, Camarillo, CA (US); Robert M. Rzasa, Ventura, CA (US); Kelvin Sham, Thousand Oaks, CA (US); Guomin Yao, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 376 days.

(21) Appl. No.: 12/619,573

(22) Filed: Nov. 16, 2009

(65) Prior Publication Data

US 2010/0125062 A1      May 20, 2010

Related U.S. Application Data

(60) Provisional application No. 61/114,595, filed on Nov. 14, 2008, provisional application No. 61/166,215, filed on Apr. 2, 2009.

(51) Int. Cl.

| | |
|---|---|
| A61K 31/4439 | (2006.01) |
| A61K 31/437 | (2006.01) |
| A61K 31/52 | (2006.01) |
| A61K 31/5377 | (2006.01) |
| A61K 31/55 | (2006.01) |
| A61K 31/397 | (2006.01) |
| C07D 401/12 | (2006.01) |
| C07D 471/04 | (2006.01) |
| C07D 473/00 | (2006.01) |
| C07D 413/14 | (2006.01) |
| C07D 401/14 | (2006.01) |
| A61P 25/00 | (2006.01) |

(52) U.S. Cl. ............... 514/210.21; 514/303; 514/338; 514/263.22; 514/235.8; 514/212.08; 546/273.4; 546/118; 544/277; 544/131

(58) Field of Classification Search ............ 514/210.21, 514/303, 338, 263.22, 235.8, 212.08; 546/273.4, 546/118; 544/277, 131
See application file for complete search history.

(56) References Cited

U.S. PATENT DOCUMENTS

| | | | |
|---|---|---|---|
| 4,198,417 A | 4/1980 | Ong et al. | |
| 7,470,702 B2 | 12/2008 | Staehle et al. | |
| 7,868,177 B2 * | 1/2011 | Cee et al. | 546/268.1 |
| 2006/0281762 A1 | 12/2006 | Staehle et al. | |
| 2007/0021456 A1 | 1/2007 | Mitjans et al. | |
| 2007/0155779 A1 | 7/2007 | Verhoest et al. | |
| 2008/0194605 A1 | 8/2008 | Heinrich et al. | |
| 2009/0082404 A1 | 3/2009 | Staehle et al. | |

FOREIGN PATENT DOCUMENTS

| | | |
|---|---|---|
| DE | 103 44 223 A1 | 4/2005 |
| WO | WO 2004/087155 A1 | 10/2004 |
| WO | WO 2005/019216 A1 | 3/2005 |
| WO | WO 2005/037829 A1 | 4/2005 |
| WO | WO 2005/042520 A1 | 5/2005 |
| WO | WO 2005/070920 A1 | 8/2005 |
| WO | WO 2007/016228 A1 | 2/2007 |
| WO | WO 2007/100646 A1 | 9/2007 |
| WO | WO 2008/057280 A1 | 5/2008 |
| WO | WO 2009/081259 A1 | 7/2009 |
| WO | WO 2010/008739 A2 | 1/2010 |

OTHER PUBLICATIONS

Kehler, J. et al., "The potential therapeutic use of phosphodiesterase 10 inhibitors," Expert Opinion on Therapeutic Patents, Informa Healthcare, GB. Feb. 1, 2007, pp. 147-158, vol. 17, No. 2.

Dounay et al., "Design, synthesis, and pharmacological evaluation of phenoxy pyridyl derivatives as dual norepinephrine reuptake inhibitors and 5-HT1A partial agonists," Bioorganic & Medicinal Chemistry Letters, 2010, 20 (3):1114-1117.

Villani et al., "Benzopyranopyridine Derivatives. 1. Aminoalkyl Derivatives of the Azaxanthenes as Bronchodilating Agents," Journal of Medicinal Chemistry, 1975, 18(1):1-8.

* cited by examiner

*Primary Examiner* — Niloofar Rahmani

(74) *Attorney, Agent, or Firm* — Elsa D. Lemoine

(57) ABSTRACT

Pyridine and pyrimidine compounds, and compositions containing them, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

94 Claims, No Drawings

PYRIDINE AND PYRIMIDINE DERIVATIVES AS PHOSPHODIESTERASE 10 INHIBITORS

CROSS-REFERENCE TO RELATED APPLICATIONS

This application claims the benefit of U.S. Provisional Application No. 61/114,595, filed Nov. 14, 2008, and U.S. Provisional Application No. 61/166,215, filed Apr. 2, 2009, which is hereby incorporated by reference.

FIELD OF THE INVENTION

Provided herein are certain pyridine and pyrimidine compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

BACKGROUND OF THE INVENTION

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kb, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

SUMMARY OF THE INVENTION

The present invention comprises a new class of compounds useful in the treatment of diseases, such as PDE10-mediated diseases and other maladies, such as schizophrenia, bipolar disorder, or obsessive-compulsive disorder. Accordingly, the invention also comprises pharmaceutical compositions comprising the compounds, methods for the treatment of PDE10-mediated diseases and other maladies, such as schizophrenia, bipolar disorder, or obsessive-compulsive disorder, using the compounds and compositions of the invention, and intermediates and processes useful for the preparation of the compounds of the invention.

The compounds of the invention are represented by the following general structure:

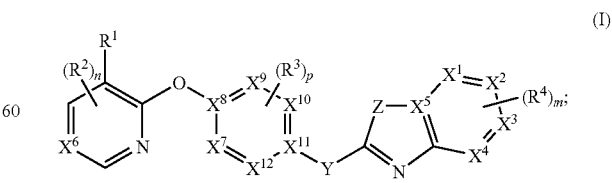

(I)

or a pharmaceutically acceptable salt thereof, wherein m, n, p, $R^1$, $R^2$, $R^3$, $R^4$, $X^1$, $X^2$, $X^3$, $X^4$, $X^5$, $X^6$, $X^7$, $X^8$, $X^9$, $X^{10}$, $X^{11}$, $X^{12}$, Y and Z are defined below.

Other compounds of the invention are represented by the following general structure:

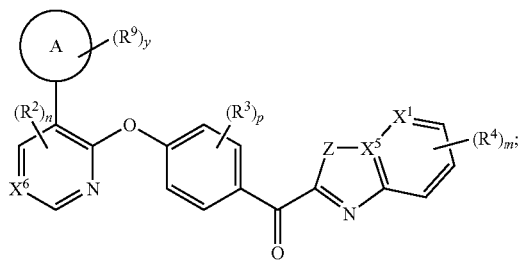

(II)

or a pharmaceutically acceptable salt thereof, wherein m, n, p, y, $R^2$, $R^3$, $R^4$, $R^9$, $X^1$, $X^5$, $X^6$, and Z are defined below.

Other compounds of the invention are represented by the following general structure:

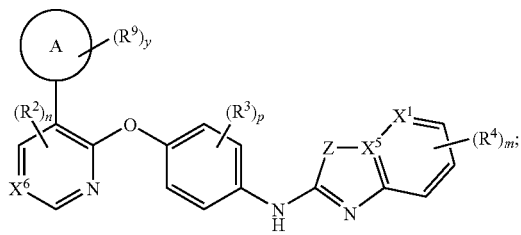

(III)

or a pharmaceutically acceptable salt thereof, wherein m, n, p, y, $R^2$, $R^3$, $R^4$, $R^9$, $X^1$, $X^5$, $X^6$, and Z are defined below.

Other compounds of the invention are represented by the following general structure:

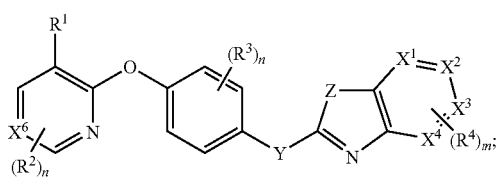

(IV)

or a pharmaceutically acceptable salt thereof, wherein m, n, $R^1$, $R^2$, $R^3$, $R^4$, $X^1$, $X^2$, $X^3$, $X^4$, $X^6$, Y and Z are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula (I):

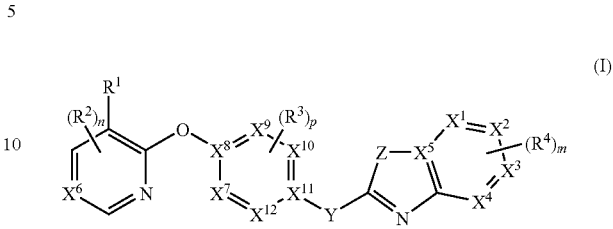

(I)

or any pharmaceutically-acceptable salt thereof, wherein:
Each of $X^1$, $X^2$, $X^3$, and $X^4$ is independently N or CH, and $X^5$ is independently N, CH, or C; wherein no more than two of $X^1$, $X^2$, $X^3$ and $X^4$ are N;

$X^6$ is N or CH;

Each of $X^7$, $X^9$, $X^{10}$, and $X^{12}$ is independently N or CH; each of $X^8$ and $X^{11}$ is C; wherein no more than three of $X^7$, $X^9$, $X^{10}$, and $X^{12}$ are N;

Y is NH, $NR^5$, CH(OH), C(=O), —$CR^aR^b$, or $CF_2$; or alternatively Y and $R^3$ form a 5- to 6-membered ring fused to the ring containing both said Y and $R^3$;

Z is NH, $NR^6$, S, SO, $SO_2$, O, CH, or —$CH_2$—; wherein Z is only CH when $X^5$ is N;

m is 0, 1, 2, 3 or 4;
n is 0, 1 or 2;
p is 0, 1 or 2;
$R^1$ is selected from the group consisting of
(a) H, F, Cl, Br, I, $C_{1-8}$alk, $C_{1-4}$haloalk, —$OR^a$, —$NR^aR^a$, —$N(R^a)C(=O)R^b$, —$C(=O)NR^aR^a$, —$C(=O)R^d$, —$C(=O)$—O—$R^a$, —$OR^c$, —$NR^aR^c$, —$N(R^c)C(=O)R^b$, —$N(R^a)C(=O)R^c$, —$C(=O)NR^aR^b$, or —$C(=O)NR^aR^c$;

(b) a saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O and S, and wherein each said ring is substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR$^a$R$^a$, —$OC_{2-6}$ alkOR$^a$, —$SR^a$, —$S(=O)R^b$, —$S(=O)_2R^b$, —$S(=O)_2NR^aR^a$, —$NR^aR^a$, —$NR^aR^c$, —$N(R^a)C(=O)R^b$, —$N(R^a)C(=O)OR^b$, —$N(R^a)C(=O)$ $NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR$^a$R$^a$, —$NR^aC_{2-6}$alkOR$^a$, —$C_{1-6}$alkNR$^a$R$^a$, —$C_{1-6}$alkOR$^a$, —$C_{1-6}$alkN(R$^a$)C(=O)R$^b$, —$C_{1-6}$alkOC(=O)R$^b$, —$C_{1-6}$alkC(=O)NR$^a$R$^a$, —$C_{1-6}$alkC(=O)OR$^a$, $R^7$, $R^8$ and oxo;

with a proviso that said unsaturated 6-membered monocyclic ring is not of formula:

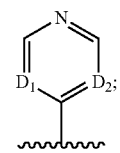

wherein each $D_1$ and $D_2$ are independently N or CH; and said partially unsaturated 5-membered monocyclic ring is not of formula:

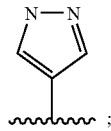

(c) group -L-$R^7$, wherein L is $CH_2$, NH, $N(C_{1-4}alk)$, —C(=O)$NR^aR^a(C_{1-4}alk)$, O, S, S=O, or $S(=O)_2$; or (d) $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —$N(R^a)$C(=O)$R^b$, —$N(R^a)$C(=O)$OR^b$, —$N(R^a)$C(=O)$NR^aR^a$, —$N(R^a)$C(=$NR^a$)$NR^aR^a$, —$N(R^a)$S(=O)$_2R^b$, —$N(R^a)$S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, $R^8$ and oxo;

$R^2$ is, independently in each instance, F, Cl, Br, CN, OH, $OC_{1-4}$alk, $C_{1-4}$alk or $C_{1-4}$haloalk;

$R^3$ is, independently in each instance, F, Cl, Br, CN, OH, $OC_{1-4}$alk, $C_{1-4}$alk, $C_{1-4}$haloalk, or —$NR^aC_{1-4}$alk;

$R^4$ is independently in each instance, F, Cl, $CH_3$, CN, $CF_3$, $CHF_2$, $CH_2F$, $OR^a$, or $NR^aR^a$;

$R^5$ is $C_{1-8}$alk, $C_{1-4}$haloalk, —C(=O)$R^b$, or $R^c$; s $R^6$ is $C_{1-8}$alk, $C_{1-4}$haloalk, or —C(=O)$R^b$, or $R^c$;

$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —$N(R^a)$C(=O)$R^b$, —$N(R^a)$C(=O)$OR^b$, —$N(R^a)$C(=O)$NR^aR^a$, —$N(R^a)$C(=$NR^a$)$NR^aR^a$, —$N(R^a)$S(=O)$_2R^b$, —$N(R^a)$S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alk$N(R^a)$C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo;

$R^8$ is a $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —$N(R^a)$C(=O)$R^b$, —$N(R^a)$C(=O)$OR^b$, —$N(R^a)$C(=O)$NR^aR^a$, —$N(R^a)$C(=$NR^a$)$NR^aR^a$, —$N(R^a)$S(=O)$_2R^b$, —$N(R^a)$S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alk$N(R^a)$C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —$N(C_{1-4}alk)C_{1-4}$alk;

$R^c$ is a $C_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, wherein said $C_{0-4}$alk and said ring moiety may be substituted by 0, 1, 2 or 3 groups selected from F, Cl, Br, $C_{1-6}$alk, $C_{1-4}$haloalk, $R^7$, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —$N(R^a)$C(=O)$R^b$, —$N(R^a)$C(=O)$OR^b$, —$N(R^a)$C(=O)$NR^aR^a$, —$N(R^a)$C(=$NR^a$)$NR^aR^a$, —$N(R^a)$S(=O)$_2R^b$, —$N(R^a)$S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alk$N(R^a)$C(=O)$R^b$, —$C_{1-6}$alkOC(=O)$R^b$, —$C_{1-6}$alkC(=O)$NR^aR^a$, —$C_{1-6}$alkC(=O)$OR^a$, $R^7$, $R^8$, and oxo; and $R^d$ is a nitrogen-linked saturated, partially-saturated, or unsaturated 5-, 6- or 7-membered ring heterocycle containing the linking nitrogen and 0, 1 or 2 additional nitrogen atoms and containing 0 or 1 sulfur or oxygen atom, the heterocycle being substituted by 0, 1, 2 or 3 substituents selected from oxo, halo, $C_{1-4}$alk, $C_{1-3}$haloalk, —$OC_{1-4}$alk, —$NH_2$, —$NHC_{1-4}$alk, and —$N(C_{1-4}alk)C_{1-4}$alk.

In another embodiment, the group:

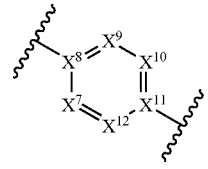

is selected from the group consisting of;

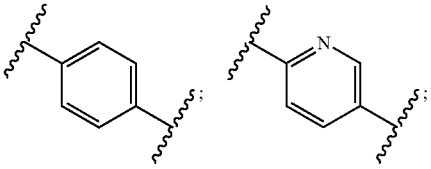

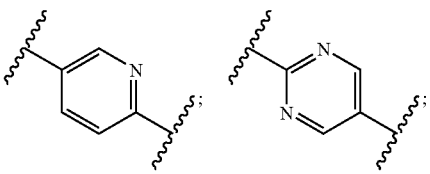

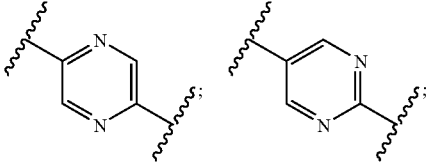

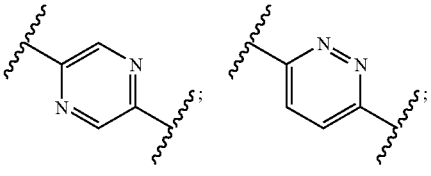

-continued

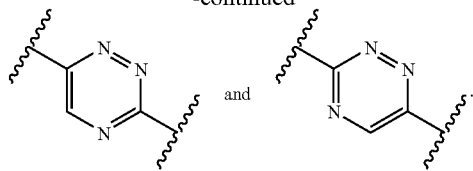 and 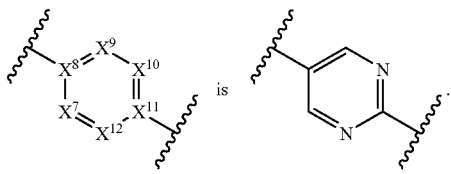.

In another embodiment, the group

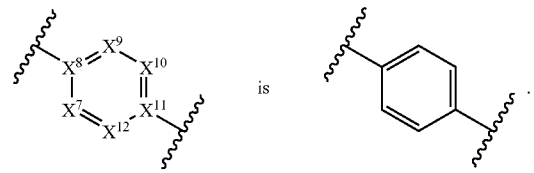 is 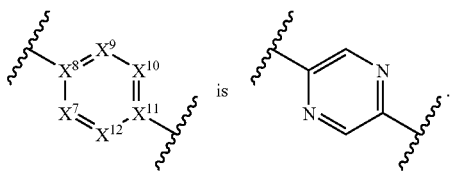.

In another embodiment, the group

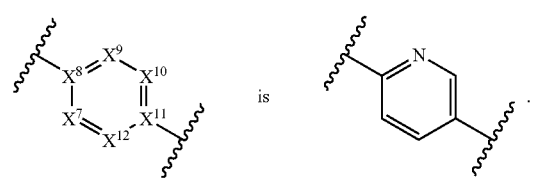 is 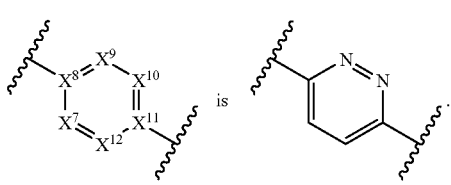.

In another embodiment, the group

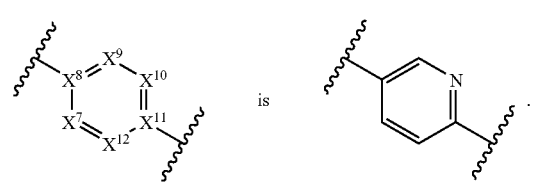 is 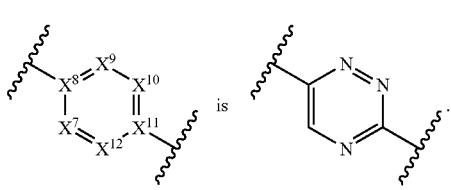.

In another embodiment, the group

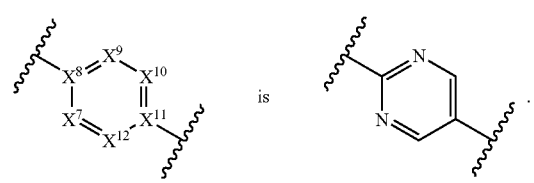 is 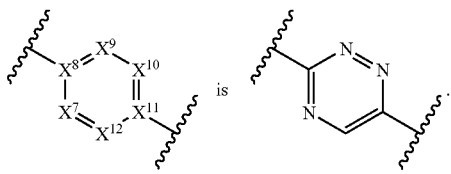.

In another embodiment, the group

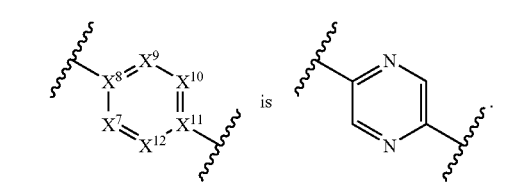 is 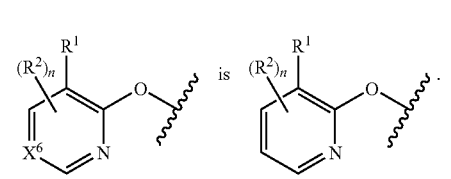.

In another embodiment, the group

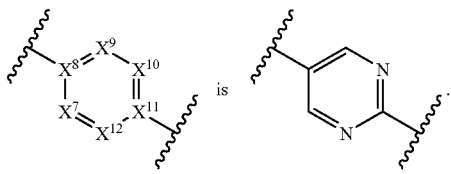 is 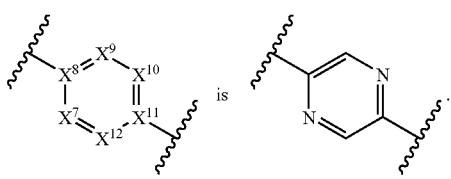.

In another embodiment, the group

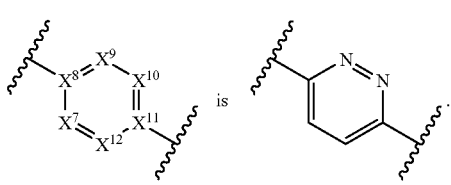 is 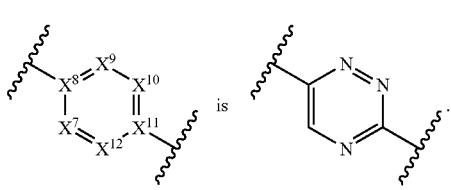.

In another embodiment, the group

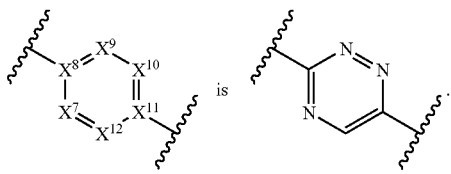 is 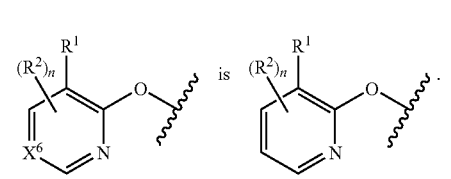.

In another embodiment, the group

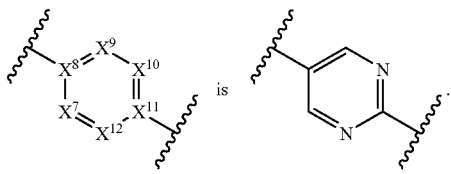 is 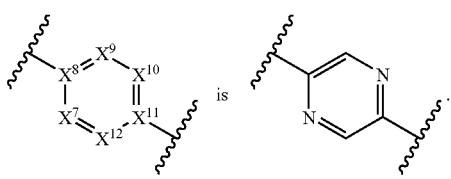.

In another embodiment, the group

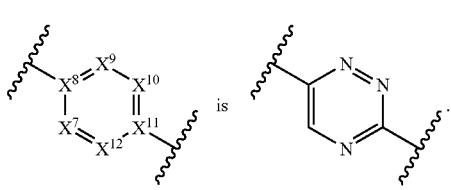 is 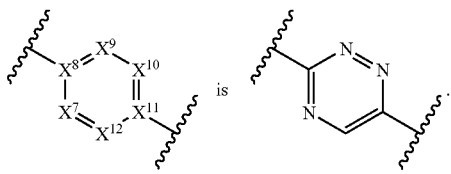.

In another embodiment, the group

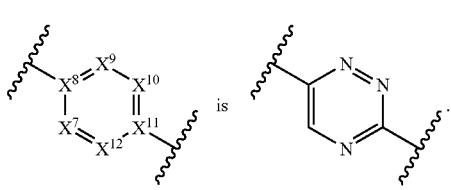 is 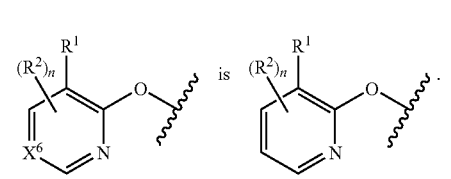.

In another embodiment, the group

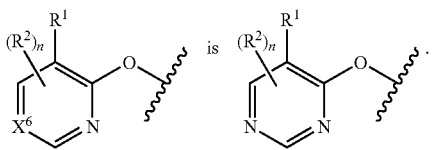

Another aspect of the current invention relates to compounds having the general structure of formula (Ia):

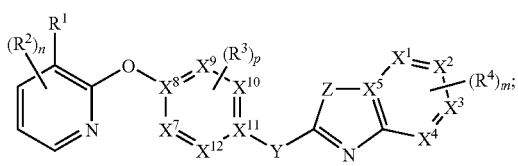

(Ia)

or a pharmaceutically acceptable salt thereof, wherein m, n, p, $R^1$, $R^2$, $R^3$, $R^4$, $X^1$, $X^2$, $X^3$, $X^4$, $X^5$, $X^7$, $X^8$, $X^9$, $X^{10}$, $X^{11}$, $X^{12}$, Y and Z are as defined in compounds of formula (I), and any other embodiments below.

Another aspect of the current invention relates to compounds having the general structure of formula (Ib):

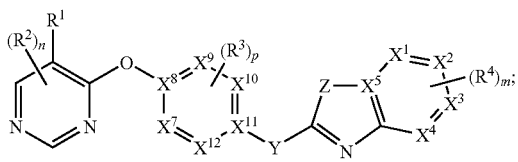

(Ib)

or a pharmaceutically acceptable salt thereof, wherein m, n, p, $R^1$, $R^2$, $R^3$, $R^4$, $X^1$, $X^2$, $X^3$, $X^4$, $X^5$, $X^7$, $X^8$, $X^9$, $X^{10}$, $X^{11}$, $X^{12}$, Y and Z are as defined in compounds of formula (I), and any other embodiments below.

Another aspect of the current invention relates to compounds having the general structure of formula (Ic):

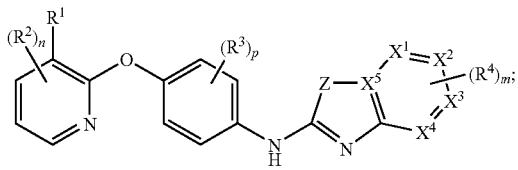

(Ic)

or a pharmaceutically acceptable salt thereof, wherein m, n, p, $R^1$, $R^2$, $R^3$, $R^4$, $X^1$, $X^2$, $X^3$, $X^4$, $X^5$, and Z are as defined in compounds of formula (I), and any other embodiments below.

Another aspect of the current invention relates to compounds having the general structure of formula (Id):

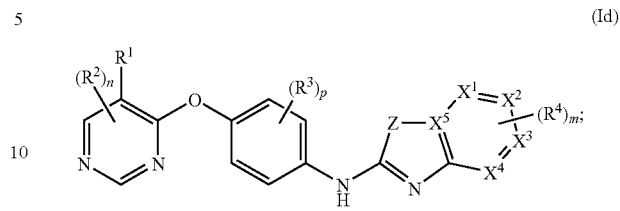

(Id)

or a pharmaceutically acceptable salt thereof, wherein m, n, p, $R^1$, $R^2$, $R^3$, $R^4$, $X^1$, $X^2$, $X^3$, $X^4$, $X^5$, and Z are as defined in compounds of formula (I), and any other embodiments below.

Another aspect of the current invention relates to compounds having the general structure of formula (Ie):

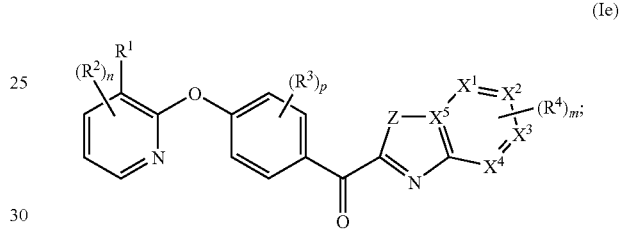

(Ie)

or a pharmaceutically acceptable salt thereof, wherein m, n, p, $R^1$, $R^2$, $R^3$, $R^4$, $X^1$, $X^2$, $X^3$, $X^4$, $X^5$, and Z are as defined in compounds of formula (I), and any other embodiments below.

Another aspect of the current invention relates to compounds having the general structure of formula (If):

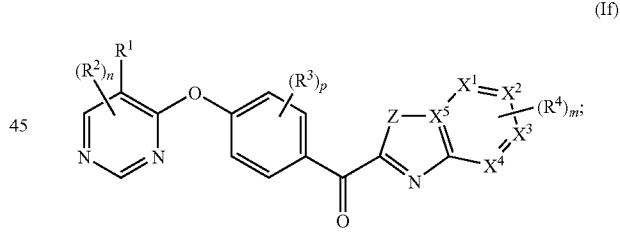

(If)

or a pharmaceutically acceptable salt thereof, wherein m, n, p, $R^1$, $R^2$, $R^3$, $R^4$, $X^1$, $X^2$, $X^3$, $X^4$, $X^5$, and Z are as defined in compounds of formula (I), and any other embodiments below.

In another embodiment, Y is NH, N—$CH_3$, $CF_2$, or —C(=O).

In another embodiment, Y is NH.
In another embodiment, Y is —C(=O).
In another embodiment, Y is —N—$CH_2$—$C_6C_5$—F.
In another embodiment, Y is —$CH_2$—.
In another embodiment, Y and $R^3$ form a 5- to 6-membered ring fused to the ring containing both said Y and $R^3$; wherein Y is NH, and $R^3$ is $C_{1-4}$alk or —$NR^aC_{1-4}$alk.

In another embodiment, $X^1$ is N or CH, and each of $X^2$, $X^3$, and $X^4$ is CH, and $X^5$ is C.

In another embodiment, $X^5$ is N.
In another embodiment, $X^5$ is C.

In another embodiment, Z is NH, N—C$_{1-4}$alk, N-haloC$_{1-4}$alk, S, or CH, or —CH$_2$; wherein Z is only CH when X$^5$ is N.

In another embodiment, Z is N or —C=.

In another embodiment, m is 0 or 1.

In another embodiment, n is 0 or 1.

In another embodiment, p is 0 or 1.

In another embodiment, p is 0.

In another embodiment, R$^1$ is selected from the group consisting of H, F, Cl, Br, I, —OR$^a$, C$_{1-8}$alk, C$_{1-4}$haloalk, —C(=O)—O—R$^a$, —C(=O)NR$^a$R$^a$, —OR$^c$ and —C(=O)NR$^a$R$^c$.

In another embodiment, R$^1$ is selected from the group consisting of H, F, Cl, Br, —OR$^a$, —C(=O)NR$^a$R$^a$, —OR$^c$ and —C(=O)NR$^a$R$^c$.

In another embodiment, R$^1$ is selected from the group consisting of a saturated 4-, 5-, 6-, or 7-membered monocyclic ring, wherein each said ring contains 0, 1, 2, or 3 N atoms and 0, 1, or 2 O atoms, and wherein each said ring is substituted by 0, 1 or 2 groups selected from F, Cl, Br, C$_{1-6}$alk, C$_{1-4}$haloalk, —OR$^a$, —CN, —C(=O)R$^b$, —C(=O)OR$^a$, and oxo.

In another embodiment, R$^1$ is selected from the group consisting of a partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1 or 2 groups selected from F, Cl, Br, C$_{1-6}$alk, C$_{1-4}$haloalk, —OR$^a$, —CN, —C(=O)R$^b$, —C(=O)OR$^a$, and oxo; with a proviso that said unsaturated 6-membered monocyclic ring and said unsaturated 5-membered monocyclic ring is not of formula:

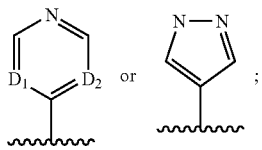

wherein each D$_1$ and D$_2$ are independently N or C.

In another embodiment, R$^1$ is selected from the group consisting of a saturated, partially-saturated or unsaturated 9- or 10-membered bicyclic ring, wherein each said ring contains 0, 1, 2, 3 or 4 N atoms and 0, 1, or 2 O atoms, and wherein each said ring is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —NR$^a$R$^a$, —NR$^a$R$^c$, R$^7$, R$^8$ and oxo.

In another embodiment, R$^1$ is selected from the group consisting of cyclohexyl, cyclopentyl, cyclopentenyl, cyclohexenyl, cycloheptyl, azetidinyl, phenyl, 2-pyridyl, 3-pyridyl, morpholinyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, all of which are substituted by 0, 1, 2 or 3 groups selected from all of which are substituted by 0, 1 or 2 groups selected from F, Cl, Br, C$_{1-6}$alk, C$_{1-4}$haloalk, —OR$^a$, CN, —C(=O)R$^b$, —C(=O)OR$^a$, —SR$^a$, R$^7$, and oxo.

In another embodiment, R$^1$ is -L-R$^7$ wherein L is —CH$_2$—.

In another embodiment, R$^1$ is C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo.

In another embodiment, R$^1$ is selected from the group consisting of: Cl, Br, I, COOH,

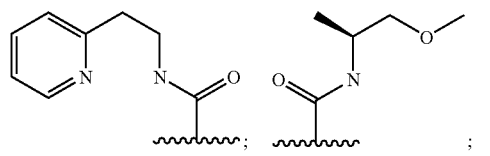

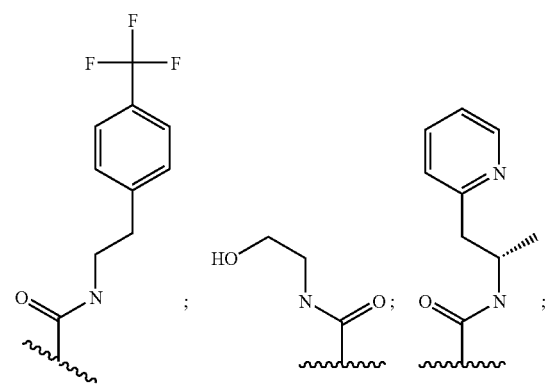

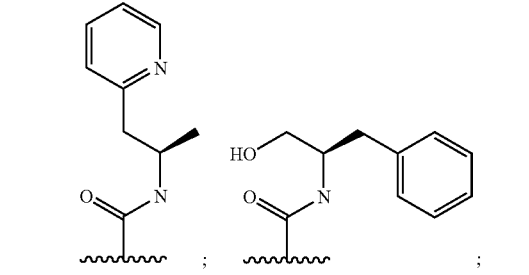

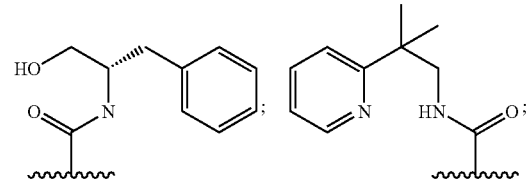

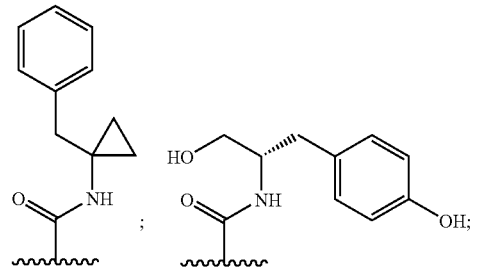

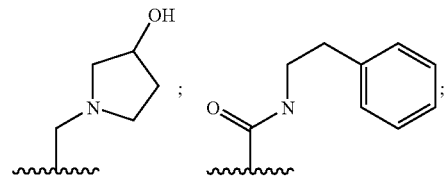

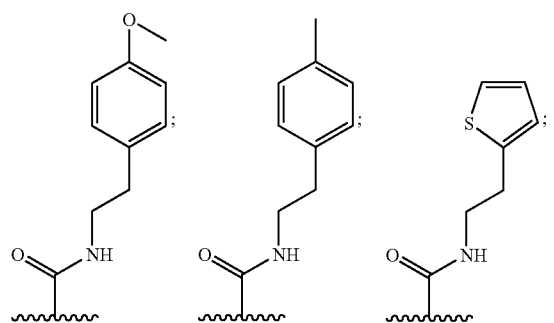
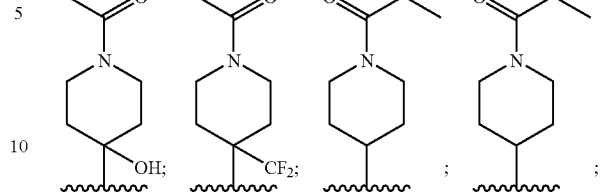
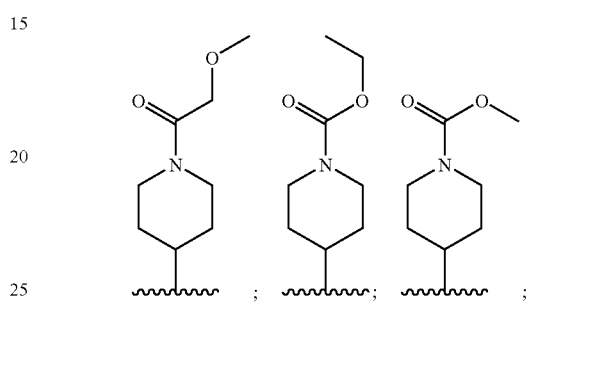
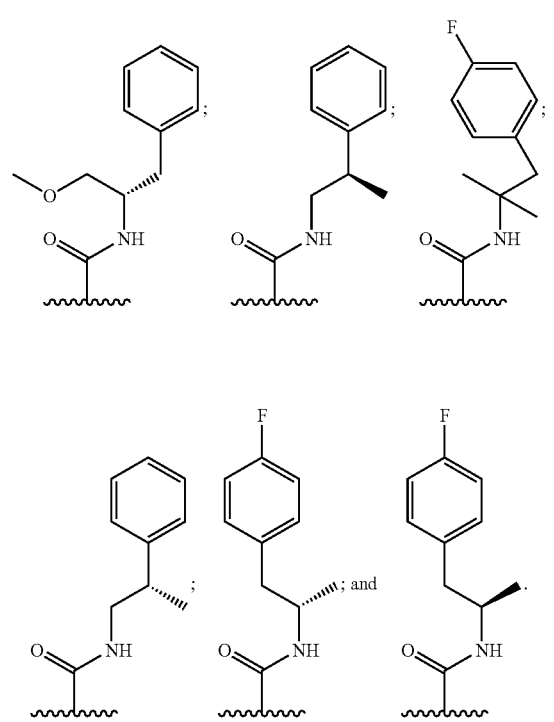
In another embodiment, R¹ is selected from the group consisting of:
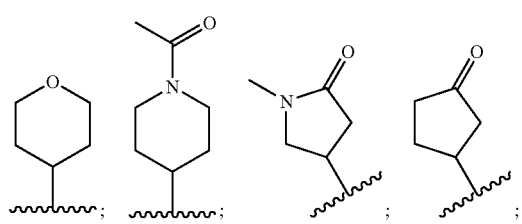
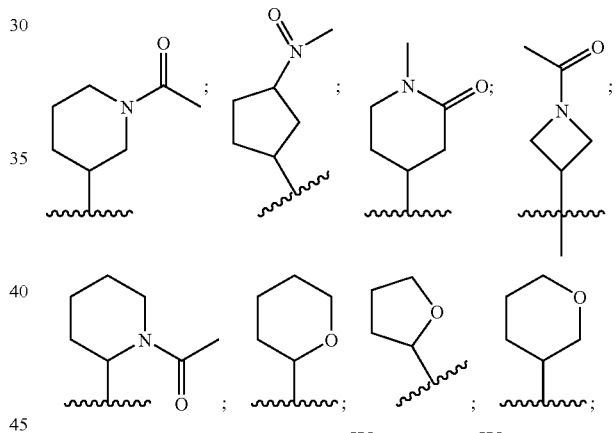
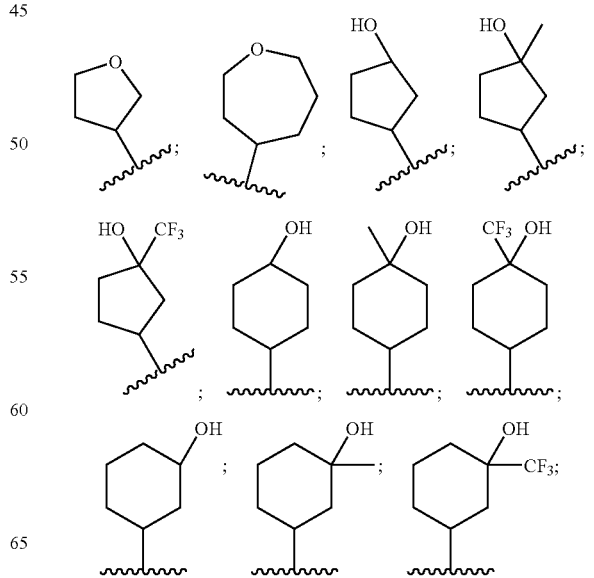

-continued

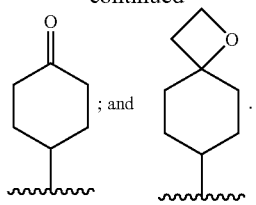
; and

In another embodiment, $R^2$ is, independently in each instance, F, Cl, Br, CN, OH, $OC_{1-4}$alk, $C_{1-4}$alk or $C_{1-4}$haloalk.

In another embodiment, $R^3$ is, independently in each instance, F, Cl, Br, CN, OH, $OC_{1-4}$alk, $C_{1-4}$alk or $C_{1-4}$haloalk.

In another embodiment, $R^4$ is F or CN.

In another embodiment, $R^5$ is methyl or —$CH_2$—$C_6H_5$—F.

In another embodiment, $R^6$ is methyl, —$CH_2$—$CH_2$—F, or $R^c$.

In another embodiment, $R^7$ is a saturated 3-, 4-, 5- or 6-membered monocyclic ring containing 0 or 1 N atom and 0 or 1 O atom, which is substituted by 0, 1, 2 or 3 groups selected from F, Cl, Br, $C_{1-6}$alk, $C_{1-4}$haloalk, —$OR^a$, —$OC_{1-4}$ haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alk$N(R^a)C(=O)R^b$, —$C_{1-6}$alk$OC(=O)R^b$, —$C_{1-6}$alk$C(=O)NR^aR^a$, —$C_{1-6}$alk$C(=O)OR^a$, $R^8$ and oxo.

In another embodiment, $R^7$ is a saturated 3-, 4-, 5-, or 6-membered monocyclic ring containing 0 or 1 N atom and 0 or 1 O atom, which is substituted by 0, 1, 2 or 3 —$OR^a$.

In another embodiment, $R^8$ is $C_{1-6}$alk substituted by 0 or 1 —$OR^a$.

In another embodiment, $R^a$ is H or $C_{1-6}$alk substituted by 0 or 1 —OH, —$OC_{1-4}$alk, —$OC(=O)C_{1-4}$alk, or —$N(C_{1-4}$alk)$C_{1-4}$alk.

In another embodiment, $R^c$ is a $C_{0-4}$alk-linked saturated, partially-saturated or unsaturated 3-, 5-, or 6-membered monocyclic ring containing 0 or 1 N atom and 0 or 1 atom selected from O and S, which is substituted by 0 or 1 groups selected from F, $C_{1-6}$alk, $C_{1-4}$haloalk, —$OR^a$, $R^7$, or $R^8$.

In another embodiment, $R^c$ is a $C_{0-4}$alk-linked saturated, partially-saturated or unsaturated 9- or 10-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

In another embodiment, the group of formula:

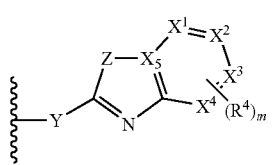

is selected from the group consisting of

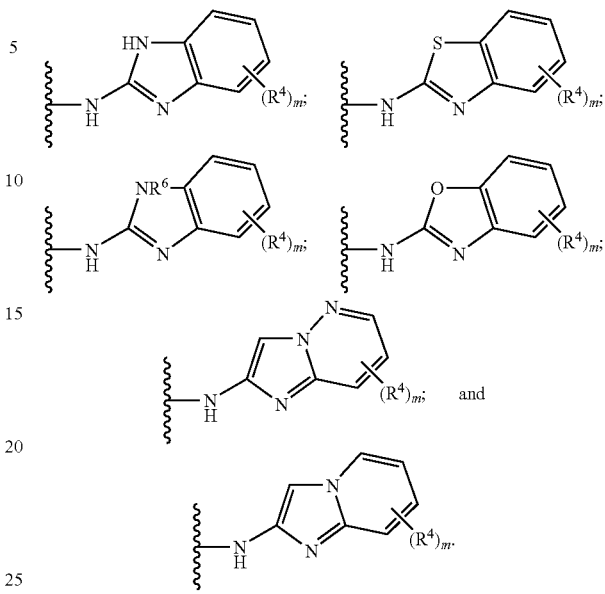

In another embodiment, the group of formula:

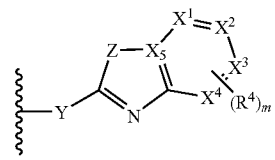

is selected from the group consisting of

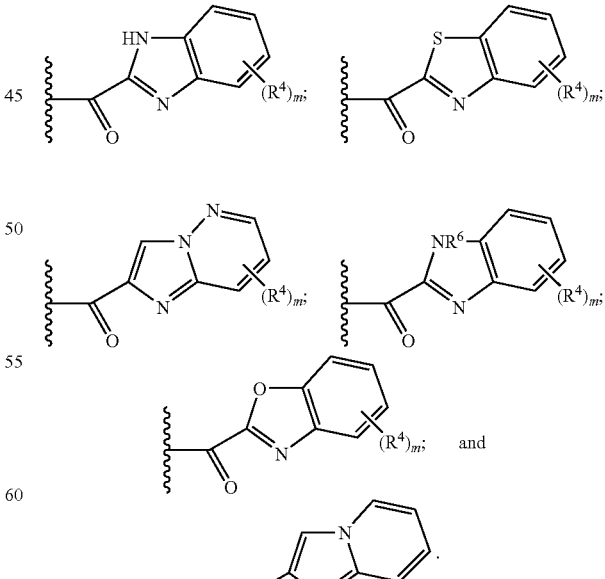

In another embodiment, the group of formula:

[chemical structure: Z—X5(=X1—X2)(—X3=X4(R4)m)—Y—... with N]

is selected from the group consisting of

[structure: benzimidazole-NH linked via NH, (R4)m]

[structure: benzimidazole linked via C(=O), (R4)m]

[structure: benzothiazole-NH linked via NH, (R4)m]; and

[structure: benzothiazole linked via C(=O), (R4)m].

Another aspect of the invention relates to a method of treating conditions that may be treated with PDE10 inhibitors comprising the step of administering a compound of formula (I).

Another aspect of the invention relates to a method wherein said condition that may be treated with PDE10 inhibitors is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method wherein said condition that may be treated with PDE10 inhibitors is selected from the group consisting of schizophrenia, bipolar disorder, and obsessive-compulsive disorder.

Another aspect of the invention relates to a pharmaceutical composition comprising a compound of formula (I) and a pharmaceutically-acceptable diluent or carrier.

Another aspect of the current invention relates to compounds having the general structure of formula (II):

[structure of formula (II)]

(II)

or any pharmaceutically-acceptable salt thereof, wherein:

Z is NH, $NR^6$, S, or O;
m is 0, 1, 2, 3 or 4;
n is 0, 1 or 2;
p is 0, 1 or 2;
y is 0, 1, 2, 3 or 4;
$X^1$ is N or CH;
$X^5$ is C;
$X^6$ is N or CH;
Ring A is a carbon-linked-saturated- or carbon-linked-partially-unsaturated-4-, 5-, 6-, 7-, 8-, 9-, 10-, 11-, or 12-membered carbocyclic ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;
$R^2$ is, independently in each instance, F, Cl, Br, CN, OH, $OC_{1-4}$alk, $C_{1-4}$alk or $C_{1-4}$haloalk;
$R^3$ is, independently in each instance, F, Cl, Br, CN, OH, $OC_{1-4}$alk, $C_{1-4}$alk or $C_{1-4}$haloalk;
$R^4$ is independently in each instance, F, Cl, $CH_3$, CN, $CF_3$, $CHF_2$, $CH_2F$, $OR^a$, or $NR^aR^a$;
$R^5$ is $C_{1-8}$alk, $C_{1-4}$haloalk, —C(=O)$R^b$, or $R^c$;
$R^6$ is $C_{1-8}$alk, $C_{1-4}$haloalk, —C(=O)$R^b$, or $R^c$;
$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2, 3, or 4 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo;
$R^8$ is a $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo;
$R^9$ is independently selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —$NR^aR^c$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^7$, $R^8$ and oxo;
$R^a$ is independently, at each instance, H or $R^b$;
$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OH, —O$C_{1-4}$alk, —NH$_2$, —NHC$_{1-4}$alk, —OC(=O)$C_{1-4}$alk, or —N($C_{1-4}$alk)$C_{1-4}$alk; and $R^c$ is a $C_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, wherein said $C_{0-4}$alk and said ring moiety may be substituted by 0, 1, 2 or 3 groups selected from F, Cl, Br, $C_{1-6}$alk, $C_{1-4}$haloalk, $R^7$, —OR$^a$, —O$C_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, $R^7$, $R^8$, and oxo.

In another embodiment, Z is NH, N—$C_{1-4}$alk, or S.
In another embodiment, Z is NH.
In another embodiment, Z is S.
In another embodiment, $X^6$ is N.
In another embodiment, $X^6$ is CH.

Another aspect of the current invention relates to compounds having the general structure of formula (IIa):

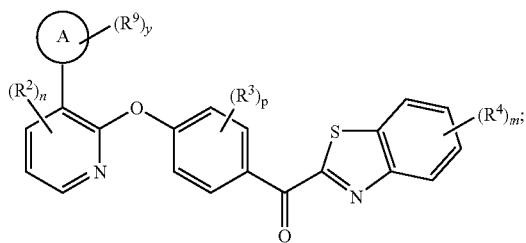

(IIa)

or a pharmaceutically acceptable salt thereof, wherein m, n, p, y, $R^2$, $R^3$, $R^4$, and $R^9$ are as defined in compounds of formula (II), and any other embodiments below.

In one embodiment of compounds of formula (IIa), ring A is bonded to the 3-pyridinyl ring via a carbon atom having an sp3 hybridization.

In one embodiment of compounds of formula (IIa), ring A is bonded to the 3-pyridinyl ring via a carbon atom having an sp2 hybridization.

In one embodiment of compounds of formula (IIa), ring A is bonded to the 3-pyridinyl ring via a carbon atom having an sp hybridization.

In one embodiment of compounds of formula (IIa), ring A is bonded to the 3-pyridinyl ring via a nitrogen atom having an sp3 hybridization.

In one embodiment of compounds of formula (IIa), ring A is bonded to the 3-pyridinyl ring via a nitrogen atom having an sp2 hybridization.

In another embodiment of compounds of formula (IIa), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 4-membered ring unsaturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IIb):

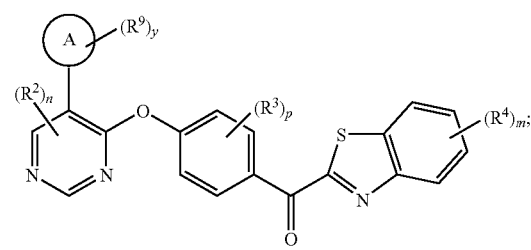

(IIb)

or a pharmaceutically acceptable salt thereof, wherein m, n, p, y, $R^2$, $R^3$, $R^4$, and $R^9$ are as defined in compounds of formula (II), and any other embodiments below.

In one embodiment of compounds of formula (IIb), ring A is bonded to the pyrimidinyl ring via a carbon atom having an sp3 hybridization.

In one embodiment of compounds of formula (IIb), ring A is bonded to the pyrimidinyl ring via a carbon atom having an sp2 hybridization.

In one embodiment of compounds of formula (IIb), ring A is bonded to the pyrimidinyl ring via a carbon atom having an sp hybridization.

In one embodiment of compounds of formula (IIb), ring A is bonded to the pyrimidinyl ring via a nitrogen atom having an sp3 hybridization.

In another embodiment of compounds of formula (IIb), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IIc):

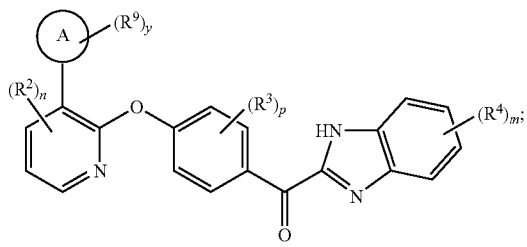

(IIc)

or a pharmaceutically acceptable salt thereof, wherein m, n, p, y, R$^2$, R$^3$, R$^4$, and R$^9$ are as defined in compounds of formula (II), and any other embodiments below.

In one embodiment of compounds of formula (IIc), ring A is bonded to the 3-pyridinyl ring via a carbon atom having an sp3 hybridization.

In one embodiment of compounds of formula (IIc), ring A is bonded to the 3-pyridinyl ring via a carbon atom having an sp2 hybridization.

In one embodiment of compounds of formula (IIc), ring A is bonded to the 3-pyridinyl ring via a carbon atom having an sp hybridization.

In one embodiment of compounds of formula (IIc), ring A is bonded to the 3-pyridinyl ring via a nitrogen atom having an sp3 hybridization.

In another embodiment of compounds of formula (IIc), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIc), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIc), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIc), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIc), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIc), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IId):

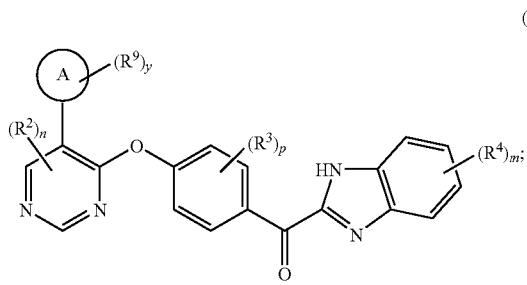

(IId)

or a pharmaceutically acceptable salt thereof, wherein m, n, p, y, R$^2$, R$^3$, R$^4$, and R$^9$ are as defined in compounds of formula (II), and any other embodiments below.

In one embodiment of compounds of formula (IId), ring A is bonded to the pyrimidinyl ring via a carbon atom having an sp3 hybridization.

In one embodiment of compounds of formula (IId), ring A is bonded to the pyrimidinyl ring via a carbon atom having an sp2 hybridization.

In one embodiment of compounds of formula (IId), ring A is bonded to the pyrimidinyl ring via a carbon atom having an sp hybridization.

In one embodiment of compounds of formula (IId), ring A is bonded to the pyrimidinyl ring via a nitrogen atom having an sp3 hybridization.

In another embodiment of compounds of formula (IId), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IId), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IId), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IId), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IId), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IId), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment, the group of formula:

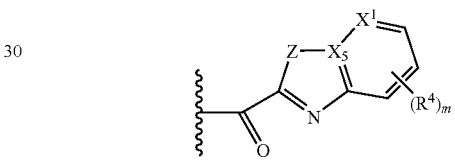

is selected from the group consisting of

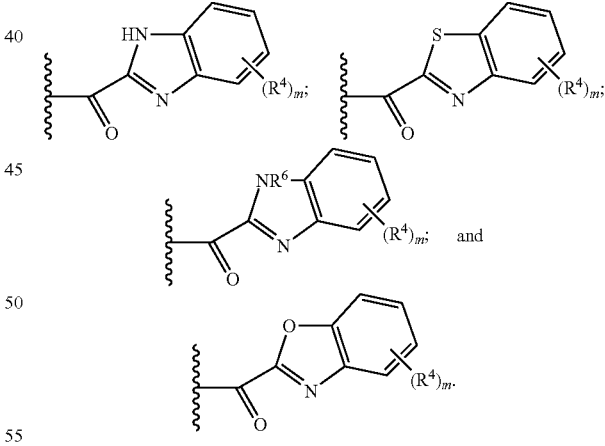

In another embodiment, ring A is a carbon-linked-saturated or carbon-linked-partially-saturated 4-, 5-, 6-, 7-, 8-, 9-, 10-, 11-, or 12-membered carbocycle ring containing 0, 1 or 2 N atoms and containing 0 or 1 S or O atom.

In another embodiment, ring A is a carbon-linked-saturated 4-, 5-, 6-, 7-membered carbocycle ring containing 0, 1 or 2 N atoms and containing 0 or 1 S or O atom.

In another embodiment, ring A is a carbon-linked-partially-saturated 4-, 5-, 6-, 7-, 8-, 9-, 10-membered carbocycle ring containing 0, 1 or 2 N atoms and containing 0 or 1 S or O atom.

In another embodiment, ring A is a nitrogen-linked-saturated 4-, 5-, 6-, 7-membered carbocycle ring containing 0, 1 or 2 N atoms and containing 0 or 1 S or O atom.

In another embodiment, ring A is a nitrogen-linked-partially-saturated 4-, 5-, 6-, 7-, 8-, 9-, 10-membered carbocycle ring containing 0, 1 or 2 N atoms and containing 0 or 1 S or O atom.

In another embodiment, ring A is a nitrogen-linked-unsaturated 4-, 5-, 6-, 8-, 10-, or 12-membered carbocycle ring containing 0, 1 or 2 N atoms and containing 0 or 1 S or O atom.

In another embodiment, ring A is selected from the group consisting of cyclohexyl, cyclopentyl, cyclopentenyl, cyclohexenyl, and cycloheptyl.

In another embodiment, ring A is selected from the group consisting of azetidinyl, morpholinyl, piperazinyl, piperidinyl, dihydropyranyl, tetrahydropyranyl, tetrahydrofuranyl, tetrahydropyridinyl, and tetrahydrothiopyranyl.

In another embodiment, ring A is selected from the group consisting of oxaspiro[3.5]nonyl, azepanyl, oxepanyl, and quinolinyl.

In another embodiment, ring A is selected from the group consisting of cyclohexyl, cyclopentyl, cyclopentenyl, cyclohexenyl, cycloheptyl, azetidinyl, morpholinyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, all of which are substituted by 0, 1, 2 or 3 groups selected from all of which are substituted by 0, 1 or 2 groups selected from F, Cl, Br, $C_{1-6}$alk, $C_{1-4}$haloalk, —OR$^a$, CN, —C(=O)R$^b$, —C(=O)OR$^a$, —SR$^a$, R$^7$, and oxo.

In another embodiment, ring A is selected from the group consisting of:

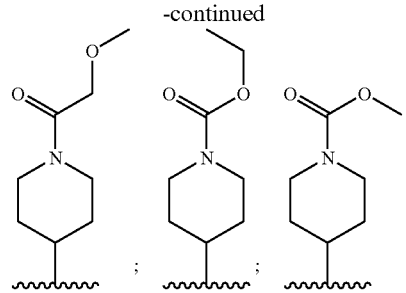

-continued

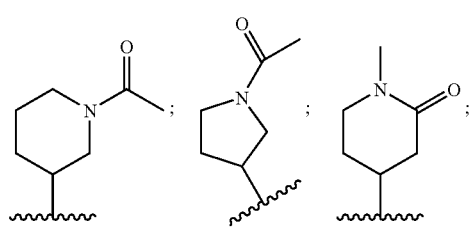

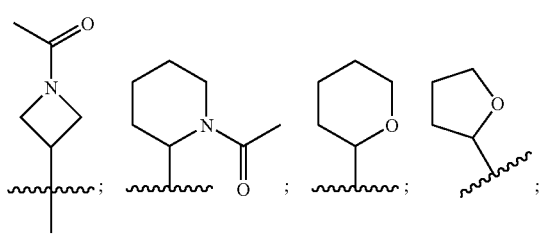

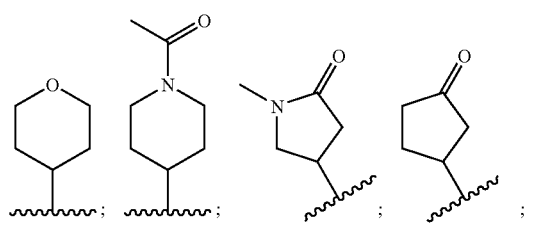

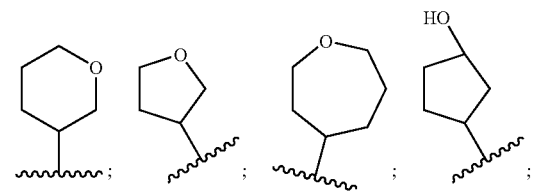

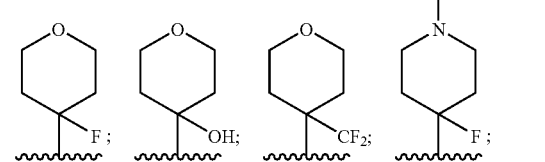

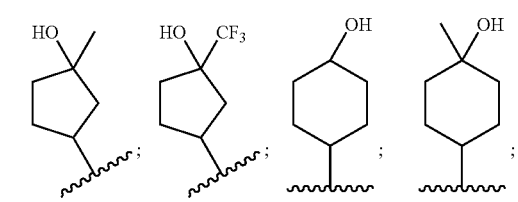

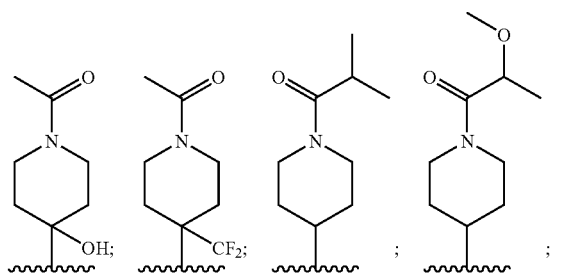

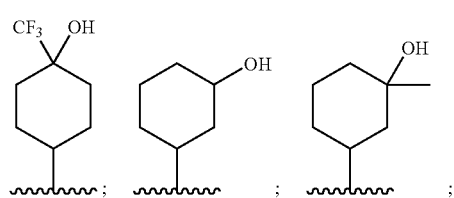

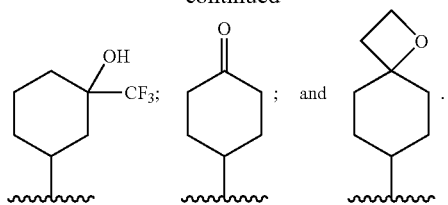

In another embodiment, m is 0 or 1.

In another embodiment, n is 0 or 1.

In another embodiment, p is 0 or 1.

In another embodiment, y is 0, 1, 2, or 3.

In another embodiment, $R^9$ is selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, —$NR^aR^c$, $R^7$, $R^8$ and oxo.

In another embodiment, $R^2$ is, independently in each instance, F, Cl, Br, CN, OH, $OC_{1-4}$alk, $C_{1-4}$alk or $C_{1-4}$haloalk.

In another embodiment, $R^3$ is, independently in each instance, F, Cl, Br, CN, OH, $OC_{1-4}$alk, $C_{1-4}$alk or $C_{1-4}$haloalk.

In another embodiment, $R^4$ is F or CN.

In another embodiment, $R^6$ is methyl, —$CH_2$—$CH_2$—F, or $R^c$.

In another embodiment, $R^7$ is a saturated 3-, 4-, 5-, or 6-membered monocyclic ring containing 0 or 1 N atom and 0 or 1 O atom, which is substituted by 0, 1, 2 or 3 groups selected from F, Cl, Br, $C_{1-6}$alk, $C_{1-4}$haloalk, —$OR^a$, —$OC_{1-4}$ haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo.

In another embodiment, $R^8$ is $C_{1-6}$alk substituted by 0 or 1 —$OR^a$.

In another embodiment, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment, $R^c$ is a $C_{0-4}$alk-linked saturated, partially-saturated or unsaturated 3-, 4-, 5-, or 6-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

In another embodiment, $R^c$ is a $C_{0-4}$alk-linked saturated, partially-saturated 9- or 10-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

Another aspect of the invention relates to a method of treating conditions that may be treated with PDE10 inhibitors comprising the step of administering a compound of formula (II).

Another aspect of the invention relates to a method of treating conditions that may be treated with PDE10 inhibitors comprising the step of administering a compound of formula (II); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering a compound of formula (II); wherein said condition is selected from the group consisting of schizophrenia, bipolar disorder, and obsessive-compulsive disorder.

Another aspect of the invention relates to a pharmaceutical composition comprising a compound of formula (II) and a pharmaceutically-acceptable diluent or carrier.

Another aspect of the current invention relates to compounds having the general structure of formula (III):

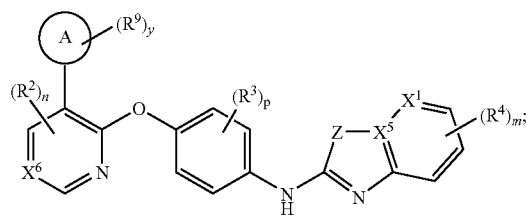

(III)

or any pharmaceutically-acceptable salt thereof, wherein:

Z is NH, $NR^6$, S, or O;

m is 0, 1, 2, 3 or 4;

n is 0, 1 or 2;

p is 0, 1 or 2;

y is 0, 1, 2, 3 or 4;

$X^1$ is N or CH;

$X^5$ is C;

$X^6$ is N or CH;

Ring A is a carbon-linked-saturated or carbon-linked-partially-unsaturated 4-, 5-, 6-, 7-, 8-, 9-, 10-, 11-, or 12-membered carbocyclic ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;

$R^2$ is, independently in each instance, F, Cl, Br, CN, OH, $OC_{1-4}$alk, $C_{1-4}$alk or $C_{1-4}$haloalk;

$R^3$ is, independently in each instance, F, Cl, Br, CN, OH, $OC_{1-4}$alk, $C_{1-4}$alk or $C_{1-4}$haloalk;

$R^4$ is independently in each instance, F, Cl, $CH_3$, CN, $CF_3$, $CHF_2$, $CH_2F$, $OR^a$, or $NR^aR^a$;

$R^5$ is $C_{1-8}$alk, $C_{1-4}$haloalk, —C(=O)$R^b$, or $R^c$;

$R^6$ is $C_{1-8}$alk, $C_{1-4}$haloalk, —C(=O)$R^b$, or $R^c$;

$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2, 3, or 4 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$ alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo;

R$^8$ is a C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo;

R$^9$ is independently selected from the group consisting of H, F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —NR$^a$C, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^7$, R$^8$ and oxo;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, a —OH, —OC$_{1-4}$alk, —NH$_2$, —NHC$_{1-4}$alk, —OC(=O)C$_{1-4}$alk, or —N(C$_{1-4}$alk)C$_{1-4}$alk; and R$^c$ is a C$_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, wherein said C$_{0-4}$alk and said ring moiety may be substituted by 0, 1, 2 or 3 groups selected from F, Cl, Br, C$_{1-6}$alk, C$_{1-4}$haloalk, R$^7$, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^7$, R$^8$, and oxo.

In another embodiment, Z is NH, N—C$_{1-4}$alk, or S.
In another embodiment, Z is NH.
In another embodiment, Z is S.
In another embodiment, X$^6$ is N.
In another embodiment, X$^6$ is CH.

Another aspect of the current invention relates to compounds having the general structure of formula (IIIa):

(IIIa)

or a pharmaceutically acceptable salt thereof, wherein m, n, p, y, R$^2$, R$^3$, R$^4$, and R$^9$ are as defined in compounds of formula (III), and any other embodiments below.

In one embodiment of compounds of formula (IIIa), ring A is bonded to the 3-pyridinyl ring via a carbon atom having an sp3 hybridization.

In one embodiment of compounds of formula (IIIa), ring A is bonded to the 3-pyridinyl ring via a carbon atom having an sp2 hybridization.

In one embodiment of compounds of formula (IIIa), ring A is bonded to the 3-pyridinyl ring via a carbon atom having an sp hybridization.

In one embodiment of compounds of formula (Ma), ring A is bonded to the 3-pyridinyl ring via a nitrogen atom having an sp3 hybridization.

In one embodiment of compounds of formula (IIIa), ring A is bonded to the 3-pyridinyl ring via a nitrogen atom having an sp2 hybridization.

In another embodiment of compounds of formula (IIIa), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIa), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIa), ring A is a 4-membered ring unsaturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIa), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIa), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIa), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IIIb):

(IIIb)

or a pharmaceutically acceptable salt thereof, wherein m, n, p, y, R$^2$, R$^3$, R$^4$, and R$^9$ are as defined in compounds of formula (III), and any other embodiments below.

In one embodiment of compounds of formula (IIIb), ring A is bonded to the pyrimidinyl ring via a carbon atom having an sp3 hybridization.

In one embodiment of compounds of formula (IIIb), ring A is bonded to the pyrimidinyl ring via a carbon atom having an sp2 hybridization.

In one embodiment of compounds of formula (IIIb), ring A is bonded to the pyrimidinyl ring via a carbon atom having an sp hybridization.

In one embodiment of compounds of formula (IIIb), ring A is bonded to the pyrimidinyl ring via a nitrogen atom having an sp3 hybridization.

In another embodiment of compounds of formula (IIIb), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIb), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIb), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIb), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIb), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIb), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IIIc):

(IIIc)

or a pharmaceutically acceptable salt thereof, wherein m, n, p, y, R$^2$, R$^3$, R$^4$, and R$^9$ are as defined in compounds of formula (III), and any other embodiments below.

In one embodiment of compounds of formula (IIIc), ring A is bonded to the 3-pyridinyl ring via a carbon atom having an sp3 hybridization.

In one embodiment of compounds of formula (IIIc), ring A is bonded to the 3-pyridinyl ring via a carbon atom having an sp2 hybridization.

In one embodiment of compounds of formula (IIIc), ring A is bonded to the 3-pyridinyl ring via a carbon atom having an sp hybridization.

In one embodiment of compounds of formula (IIIc), ring A is bonded to the 3-pyridinyl ring via a nitrogen atom having an sp3 hybridization.

In another embodiment of compounds of formula (IIIc), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIc), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIc), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIc), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIc), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIIc), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IIId):

(IIId)

or a pharmaceutically acceptable salt thereof, wherein m, n, p, y, R$^2$, R$^3$, R$^4$, and R$^9$ are as defined in compounds of formula (III), and any other embodiments below.

In one embodiment of compounds of formula (IIId), ring A is bonded to the pyrimidinyl ring via a carbon atom having an sp3 hybridization.

In one embodiment of compounds of formula (IIId), ring A is bonded to the pyrimidinyl ring via a carbon atom having an sp2 hybridization.

In one embodiment of compounds of formula (IIId), ring A is bonded to the pyrimidinyl ring via a carbon atom having an sp hybridization.

In one embodiment of compounds of formula (IIId), ring A is bonded to the pyrimidinyl ring via a nitrogen atom having an sp3 hybridization.

In another embodiment of compounds of formula (IIId), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIId), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIId), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIId), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIId), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIId), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment, the group of formula:

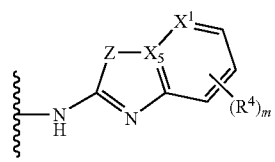

is selected from the group consisting of

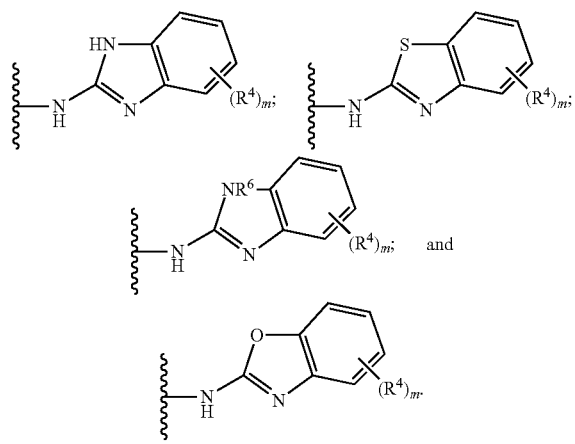

In another embodiment, ring A is a carbon-linked-saturated or carbon-linked-partially-saturated 4-, 5-, 6-, 7-, 8-, 9-, 10-, 11-, or 12-membered carbocycle ring containing 0, 1 or 2 N atoms and containing 0 or 1 S or O atom.

In another embodiment, ring A is a carbon-linked-saturated 4-, 5-, 6-, 7-membered carbocycle ring containing 0, 1 or 2 N atoms and containing 0 or 1 S or O atom.

In another embodiment, ring A is a carbon-linked-partially-saturated 4-, 5-, 6-, 7-, 8-, 9-, 10-membered carbocycle ring containing 0, 1 or 2 N atoms and containing 0 or 1 S or O atom.

In another embodiment, ring A is a nitrogen-linked-saturated 4-, 5-, 6-, 7-membered carbocycle ring containing 0, 1 or 2 N atoms and containing 0 or 1 S or O atom.

In another embodiment, ring A is a nitrogen-linked-partially-saturated 4-, 5-, 6-, 7-, 8-, 9-, 10-membered carbocycle ring containing 0, 1 or 2 N atoms and containing 0 or 1 S or O atom.

In another embodiment, ring A is a nitrogen-linked-unsaturated 4-, 5-, 6-, 8-, 10-, or 12-membered carbocycle ring containing 0, 1 or 2 N atoms and containing 0 or 1 S or O atom.

In another embodiment, ring A is selected from the group consisting of cyclohexyl, cyclopentyl, cyclopentenyl, cyclohexenyl, and cycloheptyl.

In another embodiment, ring A is selected from the group consisting of azetidinyl, morpholinyl, piperazinyl, piperidinyl, dihydropyranyl, tetrahydropyranyl, tetrahydrofuranyl, tetrahydropyridinyl, and tetrahydrothiopyranyl.

In another embodiment, ring A is selected from the group consisting of oxaspiro[3.5]nonyl, azepanyl, oxepanyl, and quinolinyl.

In another embodiment, ring A is selected from the group consisting of cyclohexyl, cyclopentyl, cyclopentenyl, cyclohexenyl, cycloheptyl, azetidinyl, morpholinyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, all of which are substituted by 0, 1, 2 or 3 groups selected from all of which are substituted by 0, 1 or 2 groups selected from F, Cl, Br, $C_{1-6}$alk, $C_{1-4}$haloalk, —OR$^a$, CN, —C(=O)R$^b$, —C(=O)OR$^a$, —SR$^a$, R$^7$, and oxo.

In another embodiment, ring A is selected from the group consisting of:

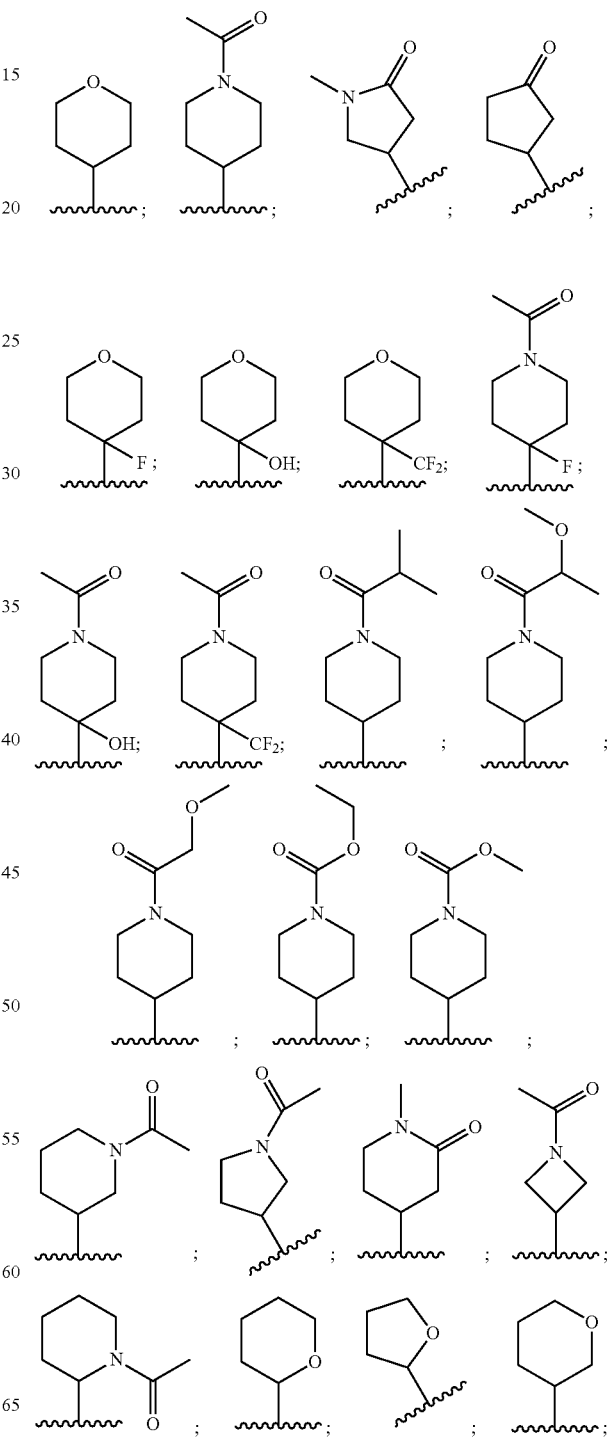

-continued

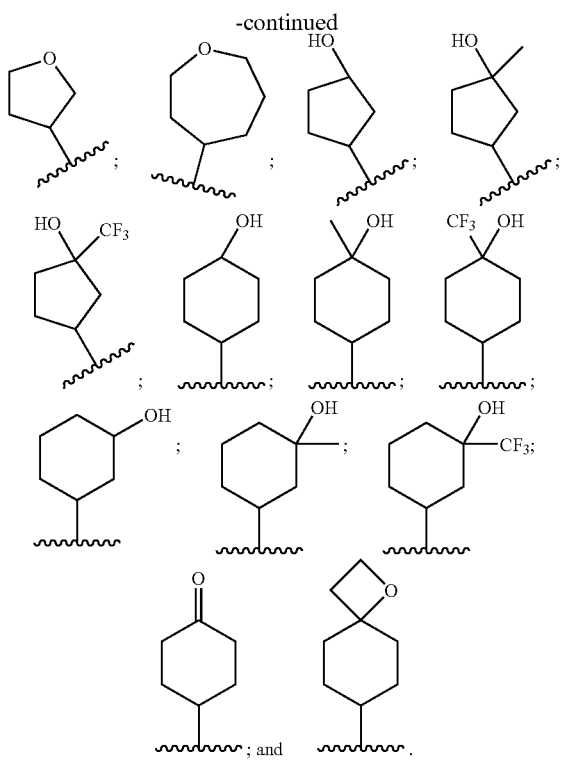

In another embodiment, m is 0 or 1.
In another embodiment, n is 0 or 1.
In another embodiment, p is 0 or 1.
In another embodiment, y is 0, 1, 2, or 3.
In another embodiment, $R^9$ is selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, —$NR^aR^c$, $R^7$, $R^8$ and oxo.
In another embodiment, $R^2$ is, independently in each instance, F, Cl, Br, CN, OH, $OC_{1-4}$alk, $C_{1-4}$alk or $C_{1-4}$haloalk.
In another embodiment, $R^3$ is, independently in each instance, F, Cl, Br, CN, OH, $OC_{1-4}$alk, $C_{1-4}$alk or $C_{1-4}$haloalk.
In another embodiment, $R^4$ is F or CN.
In another embodiment, $R^6$ is methyl, —$CH_2$—$CH_2$—F, or $R^c$.
In another embodiment, $R^7$ is a saturated 3-, 4-, 5-, or 6-membered monocyclic ring containing 0 or 1 N atom and 0 or 1 O atom, which is substituted by 0, 1, 2 or 3 groups selected from F, Cl, Br, $C_{1-6}$alk, $C_{1-4}$haloalk, —$OR^a$, —$OC_{1-4}$ haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo.
In another embodiment, $R^8$ is $C_{1-6}$alk substituted by 0 or 1 —$OR^a$.
In another embodiment, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.
In another embodiment, $R^c$ is a $C_{0-4}$alk-linked saturated, partially-saturated or unsaturated 3-, 4-, 5-, or 6-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

In another embodiment, $R^c$ is a $C_{0-4}$alk-linked saturated, partially-saturated or unsaturated 9- or 10-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

Another aspect of the invention relates to a method of treating conditions that may be treated with PDE10 inhibitors comprising the step of administering a compound of formula (III).

Another aspect of the invention relates to a method of treating conditions that may be treated with PDE10 inhibitors comprising the step of administering a compound of formula (III); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering a compound of formula (III); wherein said condition is selected from the group consisting of schizophrenia, bipolar disorder, and obsessive-compulsive disorder.

Another aspect of the invention relates to a pharmaceutical composition comprising a compound of formula (III) and a pharmaceutically-acceptable diluent or carrier.

Another aspect of the current invention relates to compounds having the general structure of formula (IV):

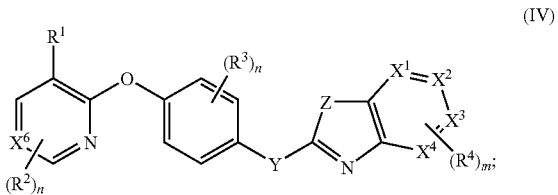

or any pharmaceutically-acceptable salt thereof, wherein:
$X^1$ is N or CH;
$X^2$ is N or CH;
$X^3$ is N or CH;
$X^4$ is N or CH; wherein no more than two of $X^1$, $X^2$, $X^3$ and $X^4$ are N;
$X^6$ is N or CH;
Y is NH, $NR^5$, CH(OH) or C(=O);
Z is NH, $NR^6$, S or O;
m is 0, 1, 2, 3 or 4;
n is independently in each instance 0, 1 or 2;
$R^1$ is selected from H, F, Cl, Br, $C_{1-8}$alk, $C_{1-4}$haloalk, —$OR^a$, —$NR^aR^a$, —N($R^a$)C(=O)$R^b$ and —C(=O)$NR^aR^a$, —C(=O)$R^d$, —$OR^c$, —$NR^aR^c$, —N($R^c$)C(=O)$R^b$, —N($R^a$)C(=O)$R^c$, —C(=O)$NR^aR^c$ and a saturated or partially saturated 3-, 4-, 5-, 6-, or 7-membered monocyclic ring or a saturated, partially-saturated or unsaturated 8-, 9-, 10-, 11-, or 12-membered bicyclic ring all of which contain 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo; or R$^1$ is -L-R$^7$, wherein L is CH$_2$, NH, N(C$_{1-4}$alk), O, S, S=O or S(=O)$_2$; or R$^1$ is C$_{3-4}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkN-R$^a$R$^a$, —C$_{1-6}$alkOR$^a$, R$^8$ and oxo; or R$^1$ is phenyl, 3-pyridyl or 4-pyridyl, all of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo;

R$^2$ is, independently in each instance, F, Cl, Br, CN, OH, OC$_{1-4}$alk, C$_{1-4}$alk or C$_{1-4}$haloalk;

R$^3$ is, independently in each instance, F, Cl, Br, CN, OH, OC$_{1-4}$alk, C$_{1-4}$alk or C$_{1-4}$haloalk;

R$^4$ is independently in each instance, F, Me or CN;

R$^5$ is C$_{1-8}$alk, C$_{1-4}$haloalk, or —C(=O)R$^b$;

R$^6$ is C$_{1-8}$alk, C$_{1-4}$haloalk, or —C(=O)R$^b$;

R$^7$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo;

R$^8$ is a C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk, and —N(C$_{1-4}$alk)C$_{1-4}$alk;

R$^c$ is a C$_{0-1}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo; and R$^d$ is a nitrogen-linked saturated, partially-saturated or unsaturated 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, C$_{1-4}$alk, C$_{1-3}$haloalk, —OC$_{1-4}$alk, —NH$_2$, —NHC$_{1-4}$alk, and —N(C$_{1-4}$alk)C$_{1-4}$alk.

In another embodiment, in conjunction with any above or below embodiment, Z is NH.

In another embodiment, in conjunction with any above or below embodiment, Z is NR$^6$.

In another embodiment, in conjunction with any above or below embodiment, Z is S.

In another embodiment, in conjunction with any above or below embodiment, Z is O.

In another embodiment, in conjunction with any above or below embodiment, Y is NH.

In another embodiment, in conjunction with any above or below embodiment, Y is NR$^5$.

In another embodiment, in conjunction with any above or below embodiment, Y is CH(OH).

In another embodiment, in conjunction with any above or below embodiment, Y is C(=O).

In another embodiment, in conjunction with any above or below embodiment, X$^1$ is N.

In another embodiment, in conjunction with any above or below embodiment, X$^2$ is N.

In another embodiment, in conjunction with any above or below embodiment, X$^3$ is N.

In another embodiment, in conjunction with any above or below embodiment, X$^4$ is N.

In another embodiment, in conjunction with any above or below embodiment, X$^1$, X$^2$, X$^3$ and X$^4$ are all CH.

In another embodiment, in conjunction with any above or below embodiment, X$^6$ is N.

In another embodiment, in conjunction with any above or below embodiment, X$^6$ is CH.

In another embodiment, in conjunction with any above or below embodiment, R$^1$ is a saturated or partially saturated 3-, 4-, 5-, 6-, or 7-membered monocyclic ring or a saturated, partially-saturated or unsaturated 8-, 9-, 10-, 11-, or 12-membered bicyclic ring all of which contain 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo; or R$^1$ is -L-R$^7$, wherein L is CH$_2$, NH, N(C$_{1-4}$alk), O, S, S=O or S(=O)$_2$.

In another embodiment, in conjunction with any above or below embodiment, R$^1$ is a saturated or partially saturated 3-, 4-, 5-, 6-, or 7-membered monocyclic ring which contains 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo; or R$^1$ is -L-R$^7$, wherein L is CH$_2$, NH, N(C$_{1-4}$alk), O, S, S=O or S(=O)$_2$.

In another embodiment, in conjunction with any above or below embodiment, R$^1$ is a saturated 3-, 4-, 5-, 6-, or 7-membered monocyclic ring which contains 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo; or R$^1$ is -L-R$^7$, wherein L is CH$_2$, NH, N(C$_{1-4}$alk), O, S, S=O or S(=O)$_2$.

In another embodiment, in conjunction with any above or below embodiment, R$^1$ is a saturated 5-, 6-, or 7-membered monocyclic ring which contains 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo; or R$^1$ is -L-R$^7$, wherein L is CH$_2$, NH, N(C$_{1-4}$alk), O, S, S=O or S(=O)$_2$.

In another embodiment, in conjunction with any above or below embodiment, R$^1$ is a saturated 5-, 6-, or 7-membered monocyclic ring which contains 0, 1, 2 or 3 N atoms and 0 or 1 atoms selected from O and S.

In another embodiment, in conjunction with any above or below embodiment, R$^1$ is a saturated, partially-saturated or unsaturated 8-, 9-, 10-, 11-, or 12-membered bicyclic ring which contains 0, 1, 2 or 3 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo; or R$^1$ is -L-R$^7$, wherein L is CH$_2$, NH, N(C$_{1-4}$alk), O, S, S=O or S(=O)$_2$.

In another embodiment, in conjunction with any above or below embodiment, R$^1$ is C$_{3-4}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo.

In another embodiment, in conjunction with any above or below embodiment, R$^1$ is selected from piperidine, piperazine, pyrrolidine and morpholine, all of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo.

In another embodiment, in conjunction with any above or below embodiment, R$^1$ is selected from cyclohexyl, cyclopentyl, tetrahydrofuran and tetrahydropyran, all of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo.

In another embodiment, in conjunction with any above or below embodiment, R$^1$ is phenyl substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo.

In another embodiment, in conjunction with any above or below embodiment, R$^1$ is 3-pyridyl or 4-pyridyl, both of which are substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, $R^8$ and oxo.

In another embodiment, in conjunction with any above or below embodiment, $R^1$ is selected from tetrahydropyran, tetrahydrofuran, piperidine, piperazine, pyrrolidine and morpholine, all of which are substituted by 0, 1, 2 or 3 groups selected from F, Cl, Br, $C_{1-6}$alk, $C_{1-4}$haloalk, —$OR^a$, —$OC_{1-4}$ haloalk, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$ alk$OR^a$, —$C_{1-6}$alk$NR^aR^a$, —$C_{1-6}$alk$OR^a$, $R^8$ and oxo.

In another embodiment, in conjunction with any above or below embodiment, $R^1$ is a saturated 5- or 6-membered carbocyclic ring substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^b$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, $R^8$ and oxo.

In another embodiment, in conjunction with any above or below embodiment, $R^1$ is selected from

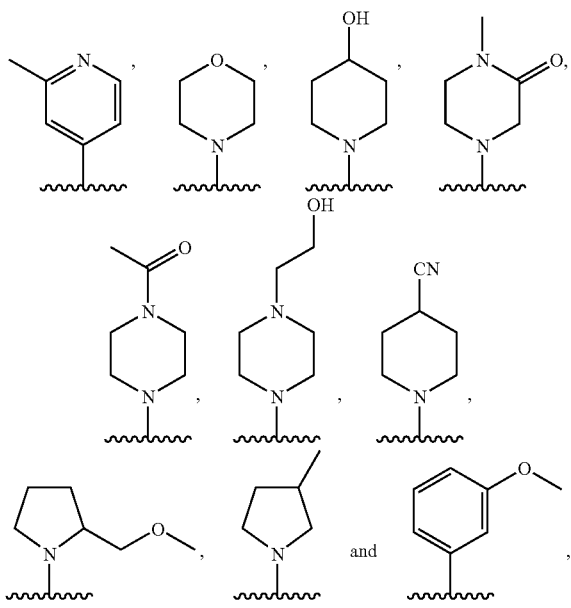

In another embodiment, in conjunction with any above or below embodiment, $R^1$ is selected from

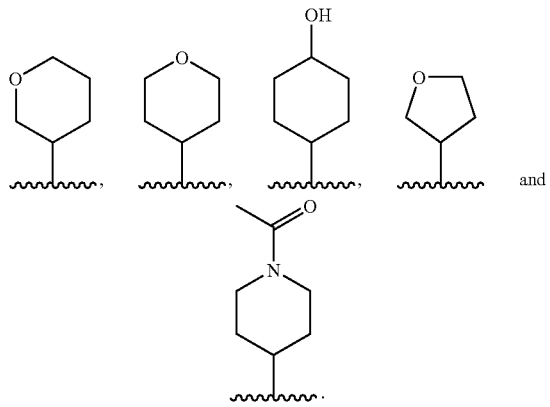

In another embodiment, in conjunction with any above or below embodiment, m is 0.

In another embodiment, in conjunction with any above or below embodiment, m is 1, and $R^4$ is F.

In another embodiment, in conjunction with any above or below embodiment, m is 2; and $R^4$ is F.

In another embodiment, in conjunction with any above or below embodiment, n is 0.

Another aspect of the invention relates to a method of treating schizophrenia, bipolar disorder, or obsessive-compulsive disorder using an effective amount of a compound of formula (IV).

Another aspect of the invention relates to a method of treating a disorder treatable by inhibition of PDE10 in a patient which method comprises administering to the patient a pharmaceutical composition comprising an effective amount of a compound of formula (IV).

Another aspect of the invention relates to a pharmaceutical composition comprising a compound of formula (IV) and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of schizophrenia, bipolar disorder, or obsessive-compulsive disorder.

Another aspect of the invention relates to compounds selected from the group consisting of:
(1H-Benzo[d]imidazol-2-yl)(4-(3-(trifluoromethyl)pyridin-2-yloxy)phenyl)methanone;
(4-(3-Ethynylpyridin-2-yloxy)phenyl)(1-methyl-1H-benzo[d]imidazol-2-yl)methanone;
4-(2-(4-(1H-benzo[d]imidazole-2-carbonyl)phenoxy)pyridin-3-yl)benzonitrile;
(4-(3,3'-Bipyridin-2-yloxy)phenyl)(1H-imidazo[4,5-b]pyridin-2-yl)methanone;
(4-(3-(9H-purin-6-yl)pyridin-2-yloxy)phenyl)(1H-benzo[d]imidazol-2-yl)methanone;
2-(4-(3-(2-methylpyridin-4-yl)pyridin-2-yloxy)benzyl)-1H-benzo[d]imidazole;
(1H-benzo[d]imidazol-2-yl)(4-(3-(piperidin-1-yl)pyridin-2-yloxy)phenyl)methanone;
(4-(3-chloropyridin-2-yloxy)phenyl)(6-fluoro-1H-benzo[d]imidazol-2-yl)methanone;
(4-(3-bromopyridin-2-yloxy)phenyl)(1H-imidazo[4,5-b]pyridin-2-yl)methanone;
(5-fluoro-1H-benzo[d]imidazol-2-yl)(4-(3-(trifluoromethyl)pyridin-2-yloxy)-phenyl)methanone;

(1H-imidazo[4,5-b]pyridin-2-yl)(4-(3-(trifluoromethyl)pyridin-2-yloxy)phenyl)methanone;
(5,6-difluoro-1H-benzo[d]imidazol-2-yl)(4-(3-(trifluoromethyl)pyridin-2-yloxy)phenyl)methanone;
(1H-benzo[d]imidazol-2-yl)(4-(3-bromopyridin-2-yloxy)phenyl)methanone;
(4-(3-bromopyridin-2-yloxy)phenyl)(1-methyl-1H-benzo[d]imidazol-2-yl)methanone;
(1H-benzo[d]imidazol-2-yl)(4-(3-(3-hydroxy-3-methylbut-1-ynyl)pyridin-2-yloxy)phenyl)methanone;
4-(2-(4-(1H-benzo[d]imidazole-2-carbonyl)phenoxy)pyridin-3-yl)benzoic acid;
3-(2-(4-(1H-benzo[d]imidazole-2-carbonyl)phenoxy)pyridin-3-yl)benzonitrile;
(1H-benzo[d]imidazol-2-yl)(4-(3-cyclopentenylpyridin-2-yloxy)phenyl)methanone;
(1H-benzo[d]imidazol-2-yl)(4-(3-(2-methylpyridin-4-yl)pyridin-2-yloxy)phenyl)methanone;
(1H-benzo[d]imidazol-2-yl)(4-(3-(2-(trifluoromethyl)pyridin-4-yl)pyridin-2-yloxy)phenyl)methanone;
tert-butyl 4-(2-(4-(1H-benzo[d]imidazole-2-carbonyl)phenoxy)pyridin-3-yl)-5,6-dihydropyridine-1(2H)-carboxylate;
3-(2-(4-(1H-benzo[d]imidazole-2-carbonyl)phenoxy)pyridin-3-yl)benzoic acid;
(1H-benzo[d]imidazol-2-yl)(4-(3-(4-(methylsulfonyl)phenyl)pyridin-2-yloxy)phenyl)methanone;
(1H-benzo[d]imidazol-2-yl)(4-(3-(3-(methylsulfonyl)phenyl)pyridin-2-yloxy)phenyl)methanone;
(1H-benzo[d]imidazol-2-yl)(4-(3-(4-methoxyphenyl)pyridin-2-yloxy)phenyl)methanone;
(1H-benzo[d]imidazol-2-yl)(4-(3-(3-methoxyphenyl)pyridin-2-yloxy)phenyl)methanone;
(4-(3-bromopyridin-2-yloxy)phenyl)(1-(tetrahydro-2H-pyran-2-yl)-1H-benzo[d]imidazol-2-yl)methanone;
(1H-benzo[d]imidazol-2-yl)(4-(3-(pyrimidin-5-yl)pyridin-2-yloxy)phenyl)methanone;
(4-(3,3'-bipyridin-2-yloxy)phenyl)(1H-benzo[d]imidazol-2-yl)methanone;
(1H-benzo[d]imidazol-2-yl)(4-(6'-methyl-3,3'-bipyridin-2-yloxy)phenyl)methanone;
(1H-benzo[d]imidazol-2-yl)(4-(3-(quinolin-5-yl)pyridin-2-yloxy)phenyl)methanone;
(1H-benzo[d]imidazol-2-yl)(4-(3-(quinolin-4-yl)pyridin-2-yloxy)phenyl)methanone;
2-(4-(1H-benzo[d]imidazole-2-carbonyl)phenoxy)-3,4'-bipyridine-2'-carbonitrile;
(1H-benzo[d]imidazol-2-yl)(4-(2'-methoxy-3,3'-bipyridin-2-yloxy)phenyl)methanone;
(1H-benzo[d]imidazol-2-yl)(4-(5'-methoxy-3,3'-bipyridin-2-yloxy)phenyl)methanone;
(1H-benzo[d]imidazol-2-yl)(4-(6'-methoxy-3,3'-bipyridin-2-yloxy)phenyl)methanone;
(1H-benzo[d]imidazol-2-yl)(4-(6-methoxy-2,3'-bipyridin-2'-yloxy)phenyl)methanone;
(1H-benzo[d]imidazol-2-yl)(4-(3-methoxy-2,3'-bipyridin-2'-yloxy)phenyl)methanone;
(1H-benzo[d]imidazol-2-yl)(4-(5-methoxy-2,3'-bipyridin-2'-yloxy)phenyl)methanone;
(1H-benzo[d]imidazol-2-yl)(4-(3-(2-methoxyquinolin-3-yl)pyridin-2-yloxy)phenyl)methanone;
(1H-benzo[d]imidazol-2-yl)(4-(3-(2-methoxyphenyl)pyridin-2-yloxy)phenyl)methanone;
(4-(3'-methoxy-3,4'-bipyridin-2-yloxy)phenyl)(1-methyl-1H-benzo[d]imidazol-2-yl)methanone;
(1H-benzo[d]imidazol-2-yl)(4-(3-(pyrrolidin-1-yl)pyridin-2-yloxy)phenyl)methanone;
(1H-benzo[d]imidazol-2-yl)(4-(3-morpholinopyridin-2-yloxy)phenyl)methanone;
(4-(2',6'-dimethoxy-3,3'-bipyridin-2-yloxy)phenyl)(1-methyl-1H-benzo[d]imidazol-2-yl)methanone;
(1H-benzo[d]imidazol-2-yl)(4-(4'-methoxy-3,3'-bipyridin-2-yloxy)phenyl)methanone;
(1H-benzo[d]imidazol-2-yl)(4-(5'-(methylthio)-3,3'-bipyridin-2-yloxy)phenyl)methanone;
(1H-benzo[d]imidazol-2-yl)(4-(2'-chloro-3,4'-bipyridin-2-yloxy)phenyl)methanone;
(1H-benzo[d]imidazol-2-yl)(4-(2'-fluoro-3,4'-bipyridin-2-yloxy)phenyl)methanone;
(4-(2'-chloro-3,4'-bipyridin-2-yloxy)phenyl)(1-methyl-1H-benzo[d]imidazol-2-yl)methanone;
(4-(2'-fluoro-3,4'-bipyridin-2-yloxy)phenyl)(1-methyl-1H-benzo[d]imidazol-2-yl)methanone;
(1-methyl-1H-benzo[d]imidazol-2-yl)(4-(2'-methyl-3,4'-bipyridin-2-yloxy)phenyl)methanone;
(1H-benzo[d]imidazol-2-yl)(4-(2'-fluoro-3,3'-bipyridin-2-yloxy)phenyl)methanone;
(1H-benzo[d]imidazol-2-yl)(4-(2'-hydroxy-3,4'-bipyridin-2-yloxy)phenyl)methanone;
2-(4-(2'-(trifluoromethyl)-3,4'-bipyridin-2-yloxy)benzyl)-1H-benzo[d]imidazole;
(1H-benzo[d]imidazol-2-yl)(4-(4-methoxy-2,3'-bipyridin-2'-yloxy)phenyl)methanone;
(4-(4-methoxy-2,3'-bipyridin-2'-yloxy)phenyl)(1-methyl-1H-benzo[d]imidazol-2-yl)methanone;
4-(2-(4-(1-methyl-1H-benzo[d]imidazole-2-carbonyl)phenoxy)pyridin-3-yl)pyridin-2(1H)-one;
(6-fluoro-1-methyl-1H-benzo[d]imidazol-2-yl)(4-(3-(tetrahydro-2H-pyran-4-yl)pyridin-2-yloxy)phenyl)methanone and (5-fluoro-1-methyl-1H-benzo[d]imidazol-2-yl)(4-(3-(tetrahydro-2H-pyran-4-yl)pyridin-2-yloxy)phenyl)methanone;
(4-(5-chloro-2'-methyl-3,4'-bipyridin-2-yloxy)phenyl)(1-methyl-1H-benzo[d]imidazol-2-yl)methanone;
(1H-benzo[d]imidazol-2-yl)(4-(2',5-dimethyl-3,4'-bipyridin-2-yloxy)phenyl)methanone;
(4-(2',5-dimethyl-3,4'-bipyridin-2-yloxy)phenyl)(1-methyl-1H-benzo[d]imidazol-2-yl)methanone;
(1H-benzo[d]imidazol-2-yl)(4-(5-chloro-2'-methyl-3,4'-bipyridin-2-yloxy)phenyl)methanone;
N-(4-(3-Cyclopropylpyridin-2-yloxy)phenyl)benzo[d]thiazol-2-amine;
2-(4-(Benzo[d]thiazol-2-ylamino)phenoxy)nicotinic acid;
2-(4-(benzo[d]thiazol-2-ylamino)phenoxy)-N-(cyclopropylmethyl)nicotinamide;
N-(4-(3-Morpholinopyridin-2-yloxy)phenyl)benzo[d]thiazol-2-amine;
N-(4-(3-(4-methoxypiperidin-1-yl)pyridin-2-yloxy)phenyl)benzo[d]thiazol-2-amine;
N-(4-(3-methylpyridin-2-yloxy)phenyl)benzo[d]thiazol-2-amine;
N-(4-(3-methylpyridin-2-yloxy)phenyl)benzo[d]oxazol-2-amine;
N-(4-(3-(2-methylpyridin-4-yl)pyridin-2-yloxy)phenyl)-1H-benzo[d]imidazol-2-amine;
N-(4-(3-methylpyridin-2-yloxy)phenyl)-1H-benzo[d]imidazol-2-amine;
N-(4-(3-morpholinopyridin-2-yloxy)phenyl)-1H-imidazo[4,5-b]pyridin-2-amine;
2-(4-(1-methyl-1H-benzo[d]imidazol-2-ylamino)phenoxy)nicotinonitrile;
1-methyl-N-(4-(3-(morpholinomethyl)pyridin-2-yloxy)phenyl)-1H-benzo[d]imidazol-2-amine;

benzo[d]thiazol-2-yl(4-(3-bromopyridin-2-yloxy)phenyl)methanone; Benzo[d]thiazol-2-yl(4-(3-(3,6-dihydro-2H-pyran-4-yl)pyridin-2-yloxy)phenyl)methanol;
N-(4-(3-(1,2,3,6-Tetrahydropyridin-4-yl)pyridin-2-yloxy)phenyl)benzo[d]thiazol-2-amine;
1-(4-(2-(4-(Benzo[d]thiazol-2-ylamino)phenoxy)pyridin-3-yl)piperazin-1-yl)ethanone;
N-(4-(3,3'-Bipyridin-2-yloxy)phenyl)-N-methylbenzo[d]thiazol-2-amine;
N-(4-(3,3'-Bipyridin-2-yloxy)phenyl)-1-methyl-1H-benzo[d]imidazol-2-amine;
N-(4-(3-(Tetrahydro-2H-pyran-4-yl)pyridin-2-yloxy)phenyl)-1H-benzo[d]imidazol-2-amine;
N-(4-(3-bromopyridin-2-yloxy)phenyl)-1H-benzo[d]imidazol-2-amine;
6,7-difluoro-N-(4-(3-methylpyridin-2-yloxy)phenyl)-1H-benzo[d]imidazol-2-amine;
N-(4-(3-(trifluoromethyl)pyridin-2-yloxy)phenyl)-1H-benzo[d]imidazol-2-amine;
6,7-difluoro-N-(4-(3-(trifluoromethyl)pyridin-2-yloxy)phenyl)-1H-benzo[d]imidazol-2-amine;
1-methyl-N-(4-(3-methylpyridin-2-yloxy)phenyl)-1H-benzo[d]imidazol-2-amine;
1-methyl-N-(4-(3-(trifluoromethyl)pyridin-2-yloxy)phenyl)-1H-benzo[d]imidazol-2-amine;
4-methyl-N-(4-(3-(trifluoromethyl)pyridin-2-yloxy)phenyl)-1H-benzo[d]imidazol-2-amine;
N-(4-(pyridin-2-yloxy)phenyl)-1H-benzo[d]imidazol-2-amine;
N-(4-(3-fluoropyridin-2-yloxy)phenyl)-1-methyl-1H-benzo[d]imidazol-2-amine;
5-fluoro-N-(4-(3-(trifluoromethyl)pyridin-2-yloxy)phenyl)-1H-benzo[d]imidazol-2-amine;
2-(4-(3-(trifluoromethyl)pyridin-2-yloxy)phenylamino)-1H-benzo[d]imidazole-5-carbonitrile;
6-chloro-5-fluoro-N-(4-(3-(trifluoromethyl)pyridin-2-yloxy)phenyl)-1H-benzo[d]imidazol-2-amine;
N-(4-(3-cyclopropylpyridin-2-yloxy)phenyl)-1-methyl-1H-benzo[d]imidazol-2-amine;
N-(4-(3-chloropyridin-2-yloxy)phenyl)-1-methyl-1H-benzo[d]imidazol-2-amine;
4-fluoro-N-(4-(3-(trifluoromethyl)pyridin-2-yloxy)phenyl)-1H-benzo[d]imidazol-2-amine;
5,7-difluoro-N-(4-(3-(trifluoromethyl)pyridin-2-yloxy)phenyl)-1H-benzo[d]imidazol-2-amine;
5,6-difluoro-N-(4-(3-(trifluoromethyl)pyridin-2-yloxy)phenyl)-1H-benzo[d]imidazol-2-amine;
N-(2-fluoro-4-(3-(trifluoromethyl)pyridin-2-yloxy)phenyl)-1H-benzo[d]imidazol-2-amine;
1-isopropyl-5-(trifluoromethyl)-N-(4-(3-(trifluoromethyl)pyridin-2-yloxy)phenyl)-1H-benzo[d]imidazol-2-amine;
N-(4-(3-(trifluoromethyl)pyridin-2-yloxy)phenyl)-1H-imidazo[4,5-b]pyridin-2-amine;
N-(4-(3-(trifluoromethyl)pyridin-2-yloxy)phenyl)-1H-imidazo[4,5-c]pyridin-2-amine;
N-(4-(3-(trifluoromethyl)pyridin-2-yloxy)phenyl)-7H-purin-8-amine;
1-methyl-5-(trifluoromethyl)-N-(4-(3-(trifluoromethyl)pyridin-2-yloxy)phenyl)-1H-benzo[d]imidazol-2-amine;
5-fluoro-1-methyl-N-(4-(3-(trifluoromethyl)pyridin-2-yloxy)phenyl)-1H-benzo[d]imidazol-2-amine;
5-chloro-1-ethyl-N-(4-(3-(trifluoromethyl)pyridin-2-yloxy)phenyl)-1H-benzo[d]imidazol-2-amine;
4-fluoro-N-(4-(3-(2-methylpyridin-4-yl)pyridin-2-yloxy)phenyl)-1H-benzo[d]imidazol-2-amine;
4,6-difluoro-N-(4-(3-(2-methylpyridin-4-yl)pyridin-2-yloxy)phenyl)-1H-benzo[d]imidazol-2-amine;
N-(4-(3-fluoropyridin-2-yloxy)phenyl)-1H-benzo[d]imidazol-2-amine;
N-(3-fluoro-4-(3-(trifluoromethyl)pyridin-2-yloxy)phenyl)-1H-benzo[d]imidazol-2-amine;
N-(6-(3-(trifluoromethyl)pyridin-2-yloxy)pyridin-3-yl)-1H-benzo[d]imidazol-2-amine;
N-(4-(3-cyclopropylpyridin-2-yloxy)phenyl)-1H-imidazo[4,5-b]pyridin-2-amine;
N-(4-(3-cyclopropylpyridin-2-yloxy)phenyl)-1H-imidazo[4,5-c]pyridin-2-amine;
N-(4-(3-morpholinopyridin-2-yloxy)phenyl)-1H-imidazo[4,5-c]pyridin-2-amine;
N-(4-(3-cyclopropylpyridin-2-yloxy)phenyl)benzo[d]oxazol-2-amine;
N-(2-fluoro-4-(3-(trifluoromethyl)pyridin-2-yloxy)phenyl)benzo[d]thiazol-2-amine;
N-(5-(3-(trifluoromethyl)pyridin-2-yloxy)pyridin-2-yl)-1H-benzo[d]imidazol-2-amine;
2-(4-(benzo[d]thiazol-2-ylamino)phenoxy)-N-(furan-2-ylmethyl)nicotinamide;
N-(4-(3-bromopyridin-2-yloxy)phenyl)benzo[d]thiazol-2-amine;
1-((2-(4-(benzo[d]thiazol-2-ylamino)phenoxy)pyridin-3-yl)methyl)pyrrolidin-3-ol;
4-(2-(4-(benzo[d]thiazole-2-carbonyl)phenoxy)pyridin-3-yl)benzonitrile;
(4-(3,3'-bipyridin-2-yloxy)phenyl)(benzo[d]thiazol-2-yl)methanone; benzo[d]thiazol-2-yl(4-(3-morpholinopyridin-2-yloxy)phenyl)methanone;
4-(2-(4-(benzo[d]thiazol-2-ylamino)phenoxy)pyridin-3-yl)benzonitrile;
3-(2-(4-(benzo[d]thiazol-2-ylamino)phenoxy)pyridin-3-yl)benzonitrile;
N-(4-(3-cyclopentenylpyridin-2-yloxy)phenyl)benzo[d]thiazol-2-amine;
N-(4-(3,3'-bipyridin-2-yloxy)phenyl)benzo[d]thiazol-2-amine;
N-(4-(3-(2-methoxypyrimidin-5-yl)pyridin-2-yloxy)phenyl)benzo[d]thiazol-2-amine;
N-(4-(3-(pyrimidin-5-yl)pyridin-2-yloxy)phenyl)benzo[d]thiazol-2-amine;
methyl 4-(2-(4-(benzo[d]thiazol-2-ylamino)phenoxy)pyridin-3-yl)benzoate;
N-(4-(3-(3-methoxyphenyl)pyridin-2-yloxy)phenyl)benzo[d]thiazol-2-amine;
N-(4-(6'-methoxy-3,3'-bipyridin-2-yloxy)phenyl)benzo[d]thiazol-2-amine;
N-(4-(6'-chloro-3,3'-bipyridin-2-yloxy)phenyl)benzo[d]thiazol-2-amine;
N-(4-(2'-methyl-3,4'-bipyridin-2-yloxy)phenyl)benzo[d]thiazol-2-amine;
N-(4-(2'-fluoro-3,4'-bipyridin-2-yloxy)phenyl)benzo[d]thiazol-2-amine;
N-(4-(3-(quinolin-5-yl)pyridin-2-yloxy)phenyl)benzo[d]thiazol-2-amine;
N-(4-(3-(2,3-dihydrobenzo[b][1,4]dioxin-6-yl)pyridin-2-yloxy)phenyl)benzo[d]thiazol-2-amine;
N-(4-(3-(2,3-dihydrobenzofuran-5-yl)pyridin-2-yloxy)phenyl)benzo[d]thiazol-2-amine;
N-(4-(3-(benzo[d][1,3]dioxol-5-yl)pyridin-2-yloxy)phenyl)benzo[d]thiazol-2-amine;
N-(4-(3-cyclohexenylpyridin-2-yloxy)phenyl)benzo[d]thiazol-2-amine;
N-(4-(3-(quinolin-4-yl)pyridin-2-yloxy)phenyl)benzo[d]thiazol-2-amine;
N-(4-(3-(3,6-dihydro-2H-pyran-4-yl)pyridin-2-yloxy)phenyl)benzo[d]thiazol-2-amine;

N-(4-(6'-methyl-3,3'-bipyridin-2-yloxy)phenyl)benzo[d]
   thiazol-2-amine;
N-(4-(2'-methoxy-3,4'-bipyridin-2-yloxy)phenyl)benzo[d]
   thiazol-2-amine;
N-(4-(3,3'-bipyridin-2-yloxy)phenyl)-1H-benzo[d]imidazol-2-amine;
1-methyl-N-(4-(6'-methyl-3,3'-bipyridin-2-yloxy)phenyl)-1H-benzo[d]imidazol-2-amine;
N-(4-(6'-methyl-3,3'-bipyridin-2-yloxy)phenyl)-1H-benzo[d]imidazol-2-amine;
N-(4-(3-cyclopentenylpyridin-2-yloxy)phenyl)benzo[d]
   thiazol-2-amine;
N-(4-(5'-(methylthio)-3,3'-bipyridin-2-yloxy)phenyl)benzo[d]thiazol-2-amine;
N-(4-(4'-methoxy-3,3'-bipyridin-2-yloxy)phenyl)benzo[d]
   thiazol-2-amine;
(1H-benzo[d]imidazol-2-yl)(4-(3-(tetrahydro-2H-pyran-4-yl)pyridin-2-yloxy)phenyl)methanone;
(1H-Imidazo[4,5-b]pyridin-2-yl)(4-(3-(tetrahydro-2H-pyran-4-yl)pyridin-2-yloxy)phenyl)methanol;
2-difluoro(4-(3-(tetrahydro-2H-pyran-4-yl)pyridin-2-yloxy)phenyl)methyl)-1H-benzo[d]imidazole;
(4-(3-(3,6-dihydro-2H-pyran-4-yl)pyridin-2-yloxy)phenyl)(1-methyl-1H-benzo[d]imidazol-2-yl)methanone;
(1-methyl-1H-benzo[d]imidazol-2-yl)(4-(3-(tetrahydro-2H-pyran-4-yl)pyridin-2-yloxy)phenyl)methanone;
1-(4-Methoxybenzyl)-N-(4-(3-(tetrahydro-2H-pyran-4-yl)pyridin-2-yloxy)phenyl)-1H-benzo[d]imidazol-2-amine;
7-Methoxy-N-(4-(3-(tetrahydro-2H-pyran-4-yl)pyridin-2-yloxy)phenyl)-1H-benzo[d]imidazol-2-amine;
N-(4-(3-(Tetrahydro-2H-pyran-4-yl)pyridin-2-yloxy)phenyl)benzo[d]thiazol-2-amine;
N-(4-(3-(tetrahydro-2H-pyran-4-yl)pyridin-2-yloxy)phenyl)benzo[d]oxazol-2-amine;
N-(4-(3-(4-fluorotetrahydro-2H-pyran-4-yl)pyridin-2-yloxy)phenyl)benzo[d]thiazol-2-amine;
4-(2-(4-(benzo[d]thiazol-2-ylamino)phenoxy)pyridin-3-yl)tetrahydro-2H-pyran-4-ol;
(1H-benzo[d]imidazol-2-yl)(4-(3-(4-(difluoromethyl)tetrahydro-2H-pyran-4-yl)pyridin-2-yloxy)phenyl)methanone;
(1H-benzo[d]imidazol-2-yl)(4-(3-(tetrahydro-2H-pyran-3-yl)pyridin-2-yloxy)phenyl)methanone;
N-(4-(3-(Tetrahydro-2H-pyran-3-yl)pyridin-2-yloxy)phenyl)benzo[d]thiazol-2-amine;
(±)-N-(4-(3-(tetrahydro-2H-pyran-2-yl)pyridin-2-yloxy)phenyl)benzo[d]thiazol-2-amine;
(1H-benzo[d]imidazol-2-yl)(4-((3R,4R)-4-hydroxycyclohexyl)pyridin-2-yloxy)phenyl)methanone;
(1H-benzo[d]imidazol-2-yl)(4-(3-((1S,4S)-4-hydroxycyclohexyl)pyridin-2-yloxy)phenyl)methanone;
4-(2-(4-(benzo[d]thiazol-2-ylamino)phenoxy)pyridin-3-yl)cyclohex-3-enol;
4-(2-(4-(benzo[d]thiazol-2-ylamino)phenoxy)pyridin-3-yl)cyclohexanol;
(1H-benzo[d]imidazol-2-yl)(4-(3-((1r,4r)-4-hydroxy-4-methylcyclohexyl)pyridin-2-yloxy)phenyl)methanone;
(1R,4R)-4-(2-(4-(benzo[d]thiazol-2-ylamino)phenoxy)pyridin-3-yl)-1-methylcyclohexanol;
(1H-Benzo[d]imidazol-2-yl)(4-(3-((1S,4S)-4-hydroxy-4-(trifluoromethyl)cyclohexyl)pyridin-2-yloxy)phenyl)methanone;
(1H-Benzo[d]imidazol-2-yl)(4-(3-((1R,4R)-4-hydroxy-4-(trifluoromethyl)cyclohexyl)pyridin-2-yloxy)phenyl)methanone;
(1H-benzo[d]imidazol-2-yl)(4-(3-((1S,4S)-4-ethyl-4-hydroxycyclohexyl)pyridin-2-yloxy)phenyl)methanone;
(1H-benzo[d]imidazol-2-yl)(4-(3-((1R,4R)-4-ethyl-4-hydroxycyclohexyl)pyridin-2-yloxy)phenyl)methanone;
(4-(3-((4S,7S)-1-Oxaspiro[3.5]nonan-7-yl)pyridin-2-yloxy)phenyl)(1H-benzo[d]imidazol-2-yl)methanone;
4-(2-(4-(1H-Benzo[d]imidazole-2-carbonyl)phenoxy)pyridin-3-yl)cyclohexanone;
4-(2-(4-(Benzo[d]thiazol-2-ylamino)phenoxy)pyridin-3-yl)cyclohexanone;
4-(2-(4-(1H-benzo[d]imidazole-2-carbonyl)phenoxy)pyridin-3-yl)cycloheptanone;
(1H-Benzo[d]imidazol-2-yl)(4-(3-(oxepan-4-yl)pyridin-2-yloxy)phenyl)methanone;
N-(4-(3-(oxepan-4-yl)pyridin-2-yloxy)phenyl)benzo[d]thiazol-2-amine;
5-(2-(4-(1H-benzo[d]imidazole-2-carbonyl)phenoxy)pyridin-3-yl)azepan-2-one;
5-(2-(4-(1H-benzo[d]imidazole-2-carbonyl)phenoxy)pyridin-3-yl)-1-methylazepan-2-one;
(rac)-cis-3-(2-(4-(benzo[d]thiazol-2-ylamino)phenoxy)pyridin-3-yl)cyclohexanol;
(rac)-trans-3-(2-(4-(benzo[d]thiazol-2-ylamino)phenoxy)pyridin-3-yl)cyclohexanol;
(rac)-E-3-(2-(4-(benzo[d]thiazol-2-ylamino)phenoxy)pyridin-3-yl)-1-methylcyclohexanol;
4-(2-(4-(Benzo[d]thiazol-2-ylamino)phenoxy)pyridin-3-yl)-1-methylpiperidin-2-one;
4-(2-(4-(1H-Benzo[d]imidazole-2-carbonyl)phenoxy)pyridin-3-yl)-1-methylpiperidin-2-one;
(R)-4-(2-(4-(1H-benzo[d]imidazole-2-carbonyl)phenoxy)pyridin-3-yl)-1-methylpyrrolidin-2-one;
(S)-4-(2-(4-(1H-benzo[d]imidazole-2-carbonyl)phenoxy)pyridin-3-yl)-1-methylpyrrolidin-2-one;
4-(2-(4-(benzo[d]thiazol-2-ylamino)phenoxy)pyridin-3-yl)-1-methylpyrrolidin-2-one
1-(4-(2-(4-(1H-benzo[d]imidazole-2-carbonyl)phenoxy)pyridin-3-yl)piperidin-1-yl)ethanone;
1-(4-(2-(4-(benzo[d]thiazol-2-ylamino)phenoxy)pyridin-3-yl)-5,6-dihydropyridin-1(2H)-yl)ethanone;
1-(4-(2-(4-(benzo[d]thiazol-2-ylamino)phenoxy)pyridin-3-yl)piperidin-1-yl)ethanone;
tert-butyl 4-(2-(4-(1H-benzo[d]imidazole-2-carbonyl)phenoxy)pyridin-3-yl)piperidine-1-carboxylate;
(1H-benzo[d]imidazol-2-yl)(4-(3-(piperidin-4-yl)pyridin-2-yloxy)phenyl)methanone;
1-(5-(2-(4-(1H-benzo[d]imidazole-2-carbonyl)phenoxy)pyridin-3-yl)-3,4-dihydropyridin-1(2H)-yl)ethanone;
(S)-1-(3-(2-(4-(1H-benzo[d]imidazole-2-carbonyl)phenoxy)pyridin-3-yl)piperidin-1-yl)ethanone;
(R)-1-(3-(2-(4-(1H-benzo[d]imidazole-2-carbonyl)phenoxy)pyridin-3-yl)piperidin-1-yl)ethanone;
(S)-1-(3-(2-(4-(benzo[d]thiazol-2-ylamino)phenoxy)pyridin-3-yl)piperidin-1-yl)ethanone;
(R)-1-(3-(2-(4-(benzo[d]thiazol-2-ylamino)phenoxy)pyridin-3-yl)piperidin-1-yl)ethanone;
(R)-1-(2-(2-(4-(1H-benzo[d]imidazole-2-carbonyl)phenoxy)pyridin-3-yl)piperidin-1-yl)ethanone;
(S)-1-(2-(2-(4-(1H-benzo[d]imidazole-2-carbonyl)phenoxy)pyridin-3-yl)piperidin-1-yl)ethanone;
1-(3-(2-(4-(1H-benzo[d]imidazole-2-carbonyl)phenoxy)pyridin-3-yl)pyrrolidin-1-yl)ethanone;
1-(3-(3-(4-(1H-benzo[d]imidazole-2-carbonyl)phenoxy)pyrazin-2-yl)piperidin-1-yl)ethanone;
N-(4-(3-(tetrahydrofuran-2-yl)pyridin-2-yloxy)phenyl)benzo[d]thiazol-2-amine;

(R)-(1H-benzo[d]imidazol-2-yl)(4-(3-(tetrahydrofuran-2-yl)pyridin-2-yloxy)phenyl)methanone (S)-(1H-benzo[d]imidazol-2-yl)(4-(3-(tetrahydrofuran-2-yl)pyridin-2-yloxy)phenyl)methanone;
N-(4-(3-(tetrahydrofuran-3-yl)pyridin-2-yloxy)phenyl)benzo[d]thiazol-2-amine;
(1-(2-fluoroethyl)-1H-benzo[d]imidazol-2-yl)(4-(3-(tetrahydrofuran-3-yl)pyridin-2-yloxy)phenyl)methanone;
3-(2-(4-(1H-benzo[d]imidazole-2-carbonyl)phenoxy)pyridin-3-yl)cyclopent-2-enone;
(1H-benzo[d]imidazol-2-yl)(4-(3-(3-hydroxycyclopentyl)pyridin-2-yloxy)phenyl)methanone;
3-(2-(4-(benzo[d]thiazol-2-ylamino)phenoxy)pyridin-3-yl)cyclopent-2-enone;
3-(2-(4-(benzo[d]thiazol-2-ylamino)phenoxy)pyridin-3-yl)cyclopentanol;
3-(2-(4-(1H-benzo[d]imidazole-2-carbonyl)phenoxy)pyridin-3-yl)cyclopentanone;
3-(2-(4-(benzo[d]thiazol-2-ylamino)phenoxy)pyridin-3-yl)cyclopentanone;
(1H-benzo[d]imidazol-2-yl)(4-(3-((1S,3S)-3-hydroxy-3-(trifluoromethyl)cyclopentyl)pyridin-2-yloxy)phenyl)methanone;
(1H-benzo[d]imidazol-2-yl)(4-(3-((1S,3R)-3-hydroxy-3-methylcyclopentyl)pyridin-2-yloxy)phenyl)methanone;
3-(2-(4-(benzo[d]thiazol-2-ylamino)phenoxy)pyridin-3-yl)-1-methylcyclopentanol;
1H-benzimidazol-2-yl(4-((3-(1,1-dioxidotetrahydro-2H-thiopyran-4-yl)-2-pyridinyl)oxy)phenyl)methanone;
N-(4-(5-(tetrahydro-2H-pyran-4-yl)pyrimidin-4-yloxy)phenyl)benzo[d]thiazol-2-amine;
(1H-benzo[d]imidazol-2-yl)(4-(5-(1,2,3,6-tetrahydropyridin-4-yl)pyrimidin-4-yloxy)phenyl)methanone;
1-(4-(4-(4-(benzo[d]thiazol-2-ylamino)phenoxy)pyrimidin-5-yl)-5,6-dihydropyridin-1(2H)-yl)ethanone;
(1H-Benzo[d]imidazol-2-yl)(4-(2'-fluoro-6-methoxy-3,4'-bipyridin-2-yloxy)phenyl)methanone;
(1H-benzo[d]imidazol-2-yl)(4-(3-(4-fluorotetrahydro-2H-pyran-4-yl)pyridin-2-yloxy)phenyl)methanone;
(4-(3-(4-fluorotetrahydro-2H-pyran-4-yl)pyridin-2-yloxy)phenyl)(1-methyl-1H-benzo[d]imidazol-2-yl)methanone;
1-(4-(2-(4-(1-methyl-1H-benzo[d]imidazole-2-carbonyl)phenoxy)pyridin-3-yl)piperidin-1-yl)ethanone;
(±)-(1H-benzo[d]imidazol-2-yl)(4-(3-(tetrahydro-2H-pyran-2-yl)pyridin-2-yloxy)phenyl)methanone;
(1H-benzo[d]imidazol-2-yl)(4-(3-((1s,4s)-4-hydroxy-4-methylcyclohexyl)pyridin-2-yloxy)phenyl)methanone;
(1 s,4s)-4-(2-(4-(benzo[d]thiazol-2-ylamino)phenoxy)pyridin-3-yl)-1-methylcyclohexanol;
(rac)-cis-(1H-benzo[d]imidazol-2-yl)(4-(3-(3-hydroxycyclohexyl)pyridin-2-yloxy)phenyl)methanone;
(rac)-trans-(1H-benzo[d]imidazol-2-yl)(4-(3-(3-hydroxycyclohexyl)pyridin-2-yloxy)phenyl)methanone;
(rac)-E-(1H-benzo[d]imidazol-2-yl)(4-(3-(3-hydroxy-3-methylcyclohexyl)pyridin-2-yloxy)phenyl)methanone;
(1H-benzo[d]imidazol-2-yl)(4-(3-(tetrahydrofuran-3-yl)pyridin-2-yloxy)phenyl)methanone;
2-(4-(1H-benzo[d]imidazole-2-carbonyl)phenoxy)-N-(2-(pyridin-2-yl)ethyl)nicotinamide;
2-(4-(1H-benzo[d]imidazole-2-carbonyl)phenoxy)-N-phenethylnicotinamide;
(S)-2-(4-(1H-benzo[d]imidazole-2-carbonyl)phenoxy)-N-(2-phenylpropyl)nicotinamide;
(R)-2-(4-(1H-benzo[d]imidazole-2-carbonyl)phenoxy)-N-(1-hydroxy-3-phenylpropan-2-yl)nicotinamide;
(S)-2-(4-(1H-benzo[d]imidazole-2-carbonyl)phenoxy)-N-(1-hydroxy-3-phenylpropan-2-yl)nicotinamide;
(S)-2-(4-(1H-benzo[d]imidazole-2-carbonyl)phenoxy)-N-(1-methoxy-3-phenylpropan-2-yl)nicotinamide;
2-(4-(1H-benzo[d]imidazole-2-carbonyl)phenoxy)-N-(2-(thiophen-2-yl)ethyl)nicotinamide;
(S)-2-(4-(1H-benzo[d]imidazole-2-carbonyl)phenoxy)-N-(1-methoxypropan-2-yl)nicotinamide;
2-(4-(1H-benzo[d]imidazole-2-carbonyl)phenoxy)-N-(2-(pyridin-2-yl)ethyl)nicotinamide;
2-(4-(1H-benzo[d]imidazole-2-carbonyl)phenoxy)-N-(2-hydroxyethyl)nicotinamide;
(rac)-2-(4-(1H-benzo[d]imidazole-2-carbonyl)phenoxy)-N-(1-(pyridin-2-yl)propan-2-yl)nicotinamide;
2-(4-(1H-benzo[d]imidazole-2-carbonyl)phenoxy)-N-(2-methyl-2-(pyridin-2-yl)propyl)nicotinamide;
2-(4-(1H-benzo[d]imidazole-2-carbonyl)phenoxy)-N-(1-benzylcyclopropyl)nicotinamide;
(S)-2-(4-(1H-benzo[d]imidazole-2-carbonyl)phenoxy)-N-(1-hydroxy-3-(4-methoxyphenyl)propan-2-yl)nicotinamide;
(S)-2-(4-(1H-benzo[d]imidazole-2-carbonyl)phenoxy)-N-(1-hydroxy-3-(4-hydroxyphenyl)propan-2-yl)nicotinamide;
2-(4-(1H-benzo[d]imidazole-2-carbonyl)phenoxy)-N-(2,3-dihydro-1H-inden-2-yl)nicotinamide;
(R)-2-(4-(1H-benzo[d]imidazole-2-carbonyl)phenoxy)-N-(2-phenylpropyl)nicotinamide;
2-(4-(1H-benzo[d]imidazole-2-carbonyl)phenoxy)-N-(1-(4-fluorophenyl)-2-methylpropan-2-yl)nicotinamide;
(rac)-2-(4-(1H-benzo[d]imidazole-2-carbonyl)phenoxy)-N-(1-(4-fluorophenyl)propan-2-yl)nicotinamide;
(R)-(1H-benzo[d]imidazol-2-yl)(4-(3-(tetrahydrofuran-3-yl)pyridin-2-yloxy)phenyl)methanone;
(S)-(1H-benzo[d]imidazol-2-yl)(4-(3-(tetrahydrofuran-3-yl)pyridin-2-yloxy)phenyl)methanone;
(R)—N-(4-(3-(tetrahydrofuran-3-yl)pyridin-2-yloxy)phenyl)benzo[d]thiazol-2-amine;
(S)—N-(4-(3-(tetrahydrofuran-3-yl)pyridin-2-yloxy)phenyl)benzo[d]thiazol-2-amine;
(S)-(1H-benzo[d]imidazol-2-yl)(4-(3-(tetrahydrofuran-2-yl)pyridin-2-yloxy)phenyl)methanone;
(R)-(1H-benzo[d]imidazol-2-yl)(4-(3-(tetrahydrofuran-2-yl)pyridin-2-yloxy)phenyl)methanone;
(1H-benzo[d]imidazol-2-yl)(4-(3-((1R,3R)-3-(hydroxymethyl)cyclopentyl)pyridin-2-yloxy)phenyl)methanone;
(1H-benzo[d]imidazol-2-yl)(4-(3-((1R,3S)-3-(hydroxymethyl)cyclopentyl)pyridin-2-yloxy)phenyl)methanone;
(1H-benzo[d]imidazol-2-yl)(4-(3-((1S,3S)-3-(hydroxymethyl)cyclopentyl)pyridin-2-yloxy)phenyl)methanone;
(1H-benzo[d]imidazol-2-yl)(4-(3-((1S,3R)-3-(hydroxymethyl)cyclopentyl)pyridin-2-yloxy)phenyl)methanone;
(1H-benzo[d]imidazol-2-yl)(4-(3-((1S,3R)-3-hydroxycyclohexyl)pyridin-2-yloxy)phenyl)methanone;
(1H-benzo[d]imidazol-2-yl)(4-(3-((1R,3S)-3-hydroxycyclohexyl)pyridin-2-yloxy)phenyl)methanone;
(1H-benzo[d]imidazol-2-yl)(4-(3-((1S,3S)-3-hydroxycyclohexyl)pyridin-2-yloxy)phenyl)methanone;
(1H-benzo[d]imidazol-2-yl)(4-(3-((1R,3R)-3-hydroxycyclohexyl)pyridin-2-yloxy)phenyl)methanone;
(1r,4r)-4-(2-(4-(benzo[d]thiazol-2-ylamino)phenoxy)pyridin-3-yl)cyclohexanol;
(1r,4s)-4-(2-(4-(benzo[d]thiazol-2-ylamino)phenoxy)pyridin-3-yl)cyclohexanol;
(1R,3S)-3-(2-(4-(benzo[d]thiazol-2-ylamino)phenoxy)pyridin-3-yl)cyclohexanol;
(1S,3R)-3-(2-(4-(benzo[d]thiazol-2-ylamino)phenoxy)pyridin-3-yl)cyclohexanol;

(1S,3S)-3-(2-(4-(benzo[d]thiazol-2-ylamino)phenoxy)pyridin-3-yl)cyclohexanol;
(1R,3R)-3-(2-(4-(benzo[d]thiazol-2-ylamino)phenoxy)pyridin-3-yl)cyclohexanol;
(R)-1-(3-(2-(4-(1H-benzo[d]imidazole-2-carbonyl)phenoxy)pyridin-3-yl)piperidin-1-yl)ethanone;
(S)-1-(3-(2-(4-(1H-benzo[d]imidazole-2-carbonyl)phenoxy)pyridin-3-yl)piperidin-1-yl)ethanone;
((1H-benzo[d]imidazol-2-yl)(4-(3-((1S,3R)-3-hydroxycyclopentyl)pyridin-2-yloxy)phenyl)methanone;
(1H-benzo[d]imidazol-2-yl)(4-(3-((1R,3S)-3-hydroxycyclopentyl)pyridin-2-yloxy)phenyl)methanone;
((1H-benzo[d]imidazol-2-yl)(4-(3-((1S,3S)-3-hydroxycyclopentyl)pyridin-2-yloxy)phenyl)methanone;
((1H-benzo[d]imidazol-2-yl)(4-(3-((1R,3R)-3-hydroxycyclopentyl)pyridin-2-yloxy)phenyl)methanone;
(1R,3S)-3-(2-(4-(benzo[d]thiazol-2-ylamino)phenoxy)pyridin-3-yl)cyclopentanol;
(1R,3R)-3-(2-(4-(benzo[d]thiazol-2-ylamino)phenoxy)pyridin-3-yl)cyclopentanol;
(1S,3R)-3-(2-(4-(benzo[d]thiazol-2-ylamino)phenoxy)pyridin-3-yl)cyclopentanol;
(1S,3S)-3-(2-(4-(benzo[d]thiazol-2-ylamino)phenoxy)pyridin-3-yl)cyclopentanol;
(S)-3-(2-(4-(1H-benzo[d]imidazole-2-carbonyl)phenoxy)pyridin-3-yl)cyclopentanone;
(R)-3-(2-(4-(1H-benzo[d]imidazole-2-carbonyl)phenoxy)pyridin-3-yl)cyclopentanone;
(1H-benzo[d]imidazol-2-yl)(4-(3-((1R,3S)-3-hydroxy-3-methylcyclopentyl)pyridin-2-yloxy)phenyl)methanone;
(1H-benzo[d]imidazol-2-yl)(4-(3-((1S,3S)-3-hydroxy-3-methylcyclopentyl)pyridin-2-yloxy)phenyl)methanone;
(1H-benzo[d]imidazol-2-yl)(4-(3-((1R,3R)-3-hydroxy-3-methylcyclopentyl)pyridin-2-yloxy)phenyl)methanone;
(1H-benzo[d]imidazol-2-yl)(4-(3-((1S,3R)-3-hydroxy-3-methylcyclopentyl)pyridin-2-yloxy)phenyl)methanone;
(1S,3R)-3-(2-(4-(benzo[d]thiazol-2-ylamino)phenoxy)pyridin-3-yl)-1-methylcyclopentanol;
(1R,3R)-3-(2-(4-(benzo[d]thiazol-2-ylamino)phenoxy)pyridin-3-yl)-1-methylcyclopentanol;
(1R,3S)-3-(2-(4-(benzo[d]thiazol-2-ylamino)phenoxy)pyridin-3-yl)-1-methylcyclopentanol;
(1S,3S)-3-(2-(4-(benzo[d]thiazol-2-ylamino)phenoxy)pyridin-3-yl)-1-methylcyclopentanol;
(1H-benzo[d]imidazol-2-yl)(4-(3-((1R,3R)-3-hydroxy-3-(trifluoromethyl)cyclopentyl)pyridin-2-yloxy)phenyl)methanone;
(1H-benzo[d]imidazol-2-yl)(4-(3-((1S,3S)-3-hydroxy-3-(trifluoromethyl)cyclopentyl)pyridin-2-yloxy)phenyl)methanone;
(S)-2-(4-(1H-benzo[d]imidazole-2-carbonyl)phenoxy)-N-(1-(4-fluorophenyl)propan-2-yl)nicotinamide;
(R)-2-(4-(1H-benzo[d]imidazole-2-carbonyl)phenoxy)-N-(1-(4-fluorophenyl)propan-2-yl)nicotinamide;
(S)-2-(4-(1H-benzo[d]imidazole-2-carbonyl)phenoxy)-N-(1-(pyridin-2-yl)propan-2-yl)nicotinamide;
(R)-2-(4-(1H-benzo[d]imidazole-2-carbonyl)phenoxy)-N-(1-(pyridin-2-yl)propan-2-yl)nicotinamide;
(1S,3S)-3-(2-(4-(benzo[d]thiazol-2-ylamino)phenoxy)pyridin-3-yl)-1-methylcyclohexanol;
(1R,3R)-3-(2-(4-(benzo[d]thiazol-2-ylamino)phenoxy)pyridin-3-yl)-1-methylcyclohexanol;
(1H-benzo[d]imidazol-2-yl)(4-(3-((1S,3S)-3-hydroxy-3-methylcyclohexyl)pyridin-2-yloxy)phenyl)methanone;
(1H-benzo[d]imidazol-2-yl)(4-(3-((1R,3R)-3-hydroxy-3-methylcyclohexyl)pyridin-2-yloxy)phenyl)methanone; or any pharmaceutically-acceptable salt thereof.

Another aspect of the invention relates to compounds selected from the group consisting of compounds of group (V) below:
(4-(3,4'-bipyridin-2-yloxy)phenyl)(1H-benzo[d]imidazol-2-yl)methanone
(1H-benzo[d]imidazol-2-yl)(4-(3-(2-methoxypyridin-4-yl)pyridin-2-yloxy)phenyl)methanone;
(1H-benzo[d]imidazol-2-yl)(4-(3-(1-methyl-1H-pyrazol-4-yl)pyridin-2-yloxy)phenyl)methanone;
(1H-benzo[d]imidazol-2-yl)(4-(3-(1-cyclopropyl-1H-pyrazol-4-yl)pyridin-2-yloxy)phenyl)methanone;
(1H-benzo[d]imidazol-2-yl)(4-(3-(pyrimidin-4-yl)pyridin-2-yloxy)phenyl)methanone;
(1H-benzo[d]imidazol-2-yl)(4-(3'-methoxy-3,4'-bipyridin-2-yloxy)phenyl)methanone;
(5-fluoro-1H-benzo[d]imidazol-2-yl)(4-(2'-fluoro-3,4'-bipyridin-2-yloxy)phenyl)methanone;
(1H-benzo[d]imidazol-2-yl)(4-(3'-methoxy-3,4'-bipyridin-2-yloxy)phenyl)methanone;
N-(4-(3,4'-Bipyridin-2-yloxy)phenyl)benzo[d]thiazol-2-amine;
N-(4-(3-(pyridin-4-yl)pyridin-2-yloxy)phenyl)-1H-benzo[d]imidazol-2-amine;
N-(4-(3-(pyrimidin-4-yl)pyridin-2-yloxy)phenyl)-1H-benzo[d]imidazol-2-amine;
4,6-difluoro-N-(4-(3-(pyrimidin-4-yl)pyridin-2-yloxy)phenyl)-1H-benzo[d]imidazol-2-amine;
4-fluoro-N-(4-(3-(pyrimidin-4-yl)pyridin-2-yloxy)phenyl)-1H-benzo[d]imidazol-2-amine;
4-fluoro-N-(4-(3-(pyridin-4-yl)pyridin-2-yloxy)phenyl)-1H-benzo[d]imidazol-2-amine;
4,6-difluoro-N-(4-(3-(pyridin-4-yl)pyridin-2-yloxy)phenyl)-1H-benzo[d]imidazol-2-amine;
N-(4-(3-(pyridin-4-yl)pyridin-2-yloxy)phenyl)benzo[d]thiazol-2-amine;
N-(4-(3'-methoxy-3,4'-bipyridin-2-yloxy)phenyl)benzo[d]thiazol-2-amine;
N-(4-(3-(pyrimidin-4-yl)pyridin-2-yloxy)phenyl)benzo[d]thiazol-2-amine;
N-(4-(2'-(trifluoromethyl)-3,4'-bipyridin-2-yloxy)phenyl)benzo[d]thiazol-2-amine;
(1H-Benzo[d]imidazol-2-yl)(4-(5-(2-fluoropyridin-4-yl)-2-methoxypyrimidin-4-yloxy)phenyl)methanone; or any pharmaceutically acceptable salt thereof.

Another aspect of the invention relates to a method of treating conditions that may be treated with PDE10 inhibitors comprising the step of administering a compound of group (V).

Another aspect of the invention relates to a method wherein said condition that may be treated with PDE10 inhibitors is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method wherein said condition that may be treated with PDE10 inhibitors is selected from the group consisting of schizophrenia, bipolar disorder, and obsessive-compulsive disorder.

Another aspect of the invention relates to a pharmaceutical composition comprising a compound of group (V) and a pharmaceutically-acceptable diluent or carrier.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

"Cα-βalk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

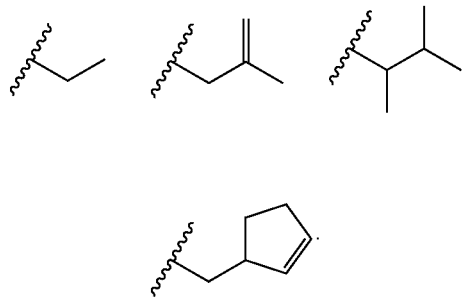

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V\text{-}W}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

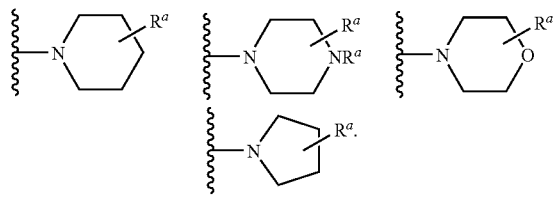

The group N(Cα-βalk)Cα-βalk, wherein α and β are as defined above, include substituents where the two Cα-βalk groups together form a ring, optionally including a N, O or S atom, and include groups such as:

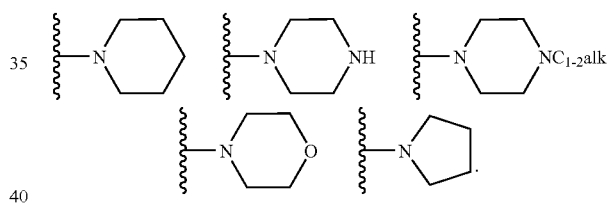

"Carbocycle" means a ring comprising by itself or in combination with other terms, represents, unless otherwise stated, cyclic version of "Cα-βalk". Thus, the term "carbocycle" is meant to be included in the terms "Cα-βalk". Examples of carbocycle include cyclopentyl, cyclohexyl, 1-cyclohexenyl, 3-cyclohexenyl, cycloheptyl, cyclobutylene, cyclohexylene and the like.

"Heterocycle" means a ring comprising at least one carbon atom and at least one other atom selected from N, O and S. Examples of heterocycles that may be found in the claims include, but are not limited to, the following:

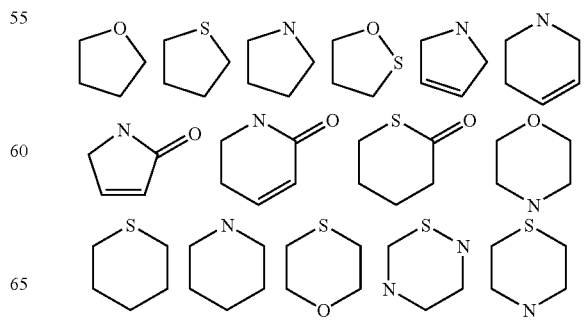

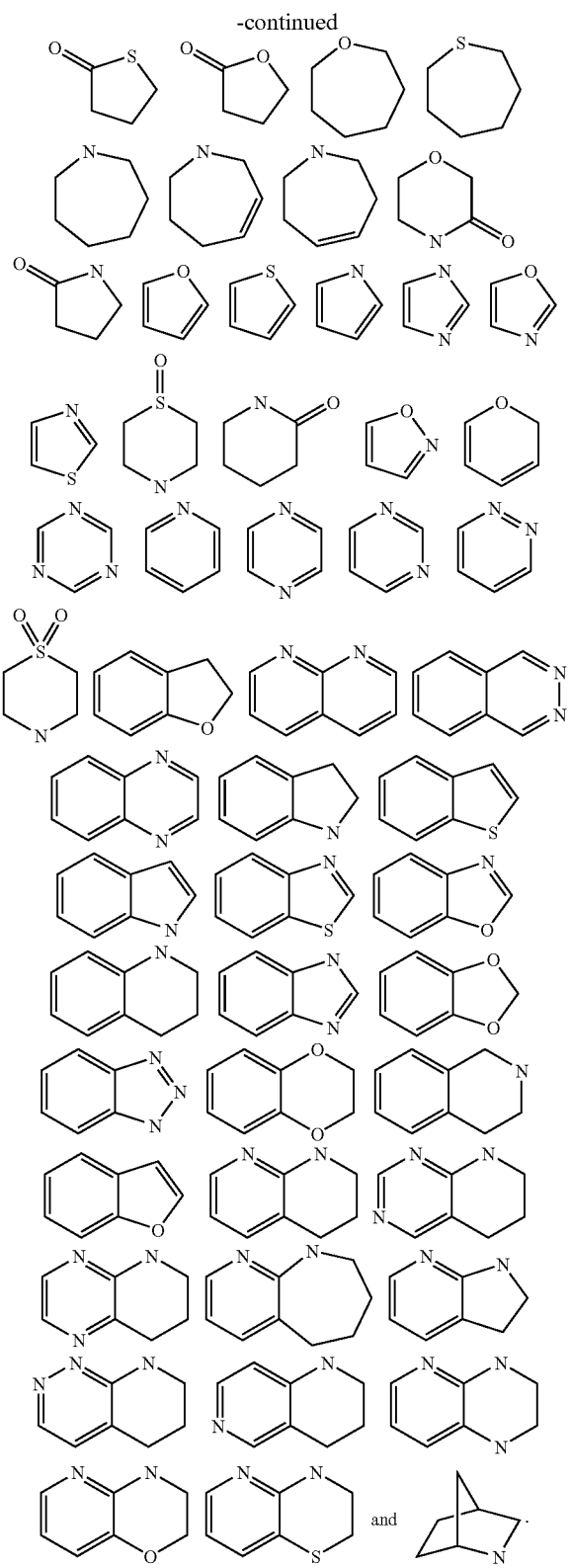

malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethyl- "Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, silyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

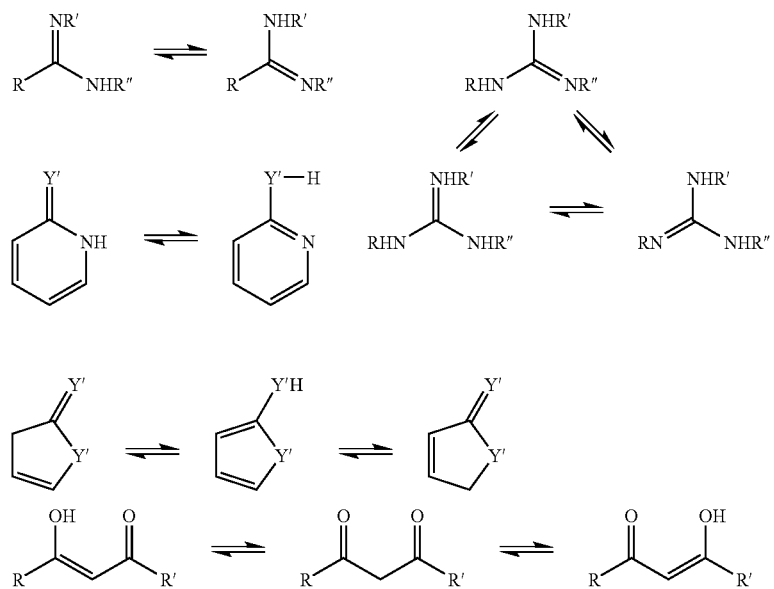

Utility and Methods of Use

Provided herein are methods for treating a disorder or disease by inhibiting PDE10 enzyme. The methods, in general, comprises the step of administering a therapeutically effective amount of a compound of Formula (I), or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., *Br. J. Psychiatry Suppl,* 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., *Am J Psychiatry.* 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE 10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485, which is hereby incorporated by reference in its entirety. The compounds of the present invention can also be used to treat diseases disclosed in US Patent application publication No. 2006/019975, the disclosure of which is incorporated herein by reference in its entirety.

Testing

The PDE10 inhibitory activities of the compounds of the present invention can be tested, for example, using the in vitro and in vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of the present invention may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compound of Formula (I) based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

In the following schemes, the compounds of the invention, along with their definitions, such as m, n, p, $R^1$, $R^2$, $R^3$, $R^4$, $R^9$, $X^1$, $X^2$, $X^3$, $X^4$, $X^5$, $X^6$, $X^7$, $X^8$, $X^9$, $X^{10}$, $X^{11}$, $X^{12}$, Y and Z, are as described above.

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at RT.

The following abbreviations are used:

| | |
|---|---|
| DCM | dichloromethane |
| DMSO- | dimethyl sulfoxide |
| DMF- | N,N-dimethylformamide |
| THF- | tetrahydrofuran |
| $Et_2O$- | diethyl ether |
| EtOAc- | ethyl acetate |
| MeOH- | methyl alcohol |
| EtOH- | ethyl alcohol |
| IPA- | isopropyl alcohol |
| MeCN- | acetonitrile |
| MeI- | iodomethane |
| NMP- | 1-methyl-2-pyrrolidinone |
| DCM- | dichloromethane |
| TFA- | trifluoroacetic acid |
| MTBE- | methyl tert-butyl ether |
| DIPEA- | diisopropylethyl amine |
| HBTU- | 2-(1H-Benzotriazole-1-yl)-1,1,3,3-tetramethylaminium hexafluorophosphate |
| HATU- | O-(7-Azobenzotriazol-1-yl)-1,1,3,3-tetramethyluronium hexafluorophosphate |
| Sat.- | saturated |
| h- | hour |
| min- | min |
| mL- | milliliters |
| g- | grams |
| mg- | milligrams |
| RT- | RT |

All compounds were divided in five classes based on their 1050 values against PDE10. The range of the $IC_{50}$ in each class is as follows:

"+" designates an $IC_{50}$ value in the range beginning from 1.0 uM and ending at 5.0 uM;

"++" designates an $IC_{50}$ value in the range beginning from 250 nM and ending at 1.0 uM;

"+++" designates an $IC_{50}$ value in the range beginning from 100 nM and ending at 250 nM;

"++++" designates an $IC_{50}$ value in the range beginning from 25 nM and ending at 100 nM; and "+++++" designates an $IC_{50}$ value of less than 25 nM.

SCHEME 1

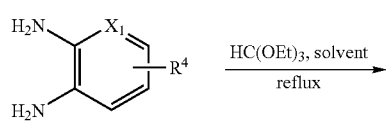

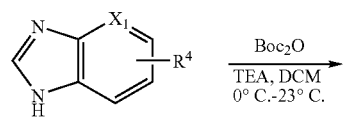

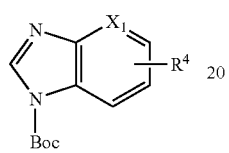

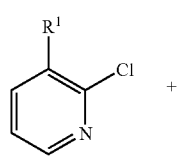

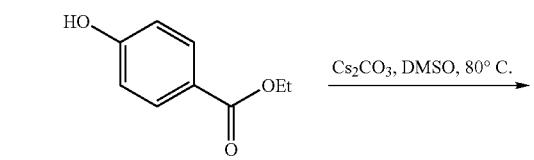

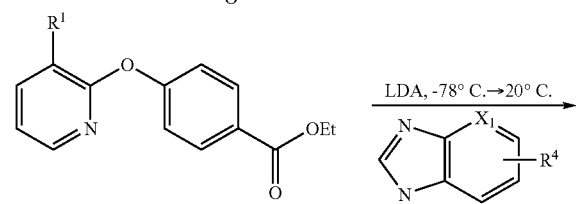

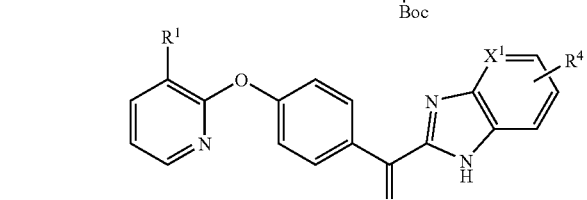

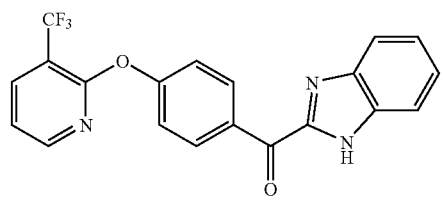

Example 1

(1H-BENZO[D]IMIDAZOL-2-YL)(4-(3-(TRIF-LUOROMETHYL)PYRIDIN-2-YLOXY)PHENYL) METHANONE

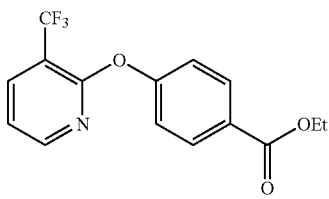

STEP 1. ETHYL 4-(3-(TRIFLUOROMETHYL)PYRIDIN-2-YLOXY)BENZOATE

2-Fluoro-3-(trifluoromethyl)pyridine (848 mg, 5137 µmol), cesium carbonate (2008 mg, 6164 µmol) and ethyl 4-hydroxybenzoate (854 mg, 5137 µmol) were combined in DMSO (12 mL) and heated to 80° C. overnight. After complete disappearance of starting material, the mixture was cooled to RT and diluted with water and extracted with ethyl acetate. The combined organics were washed with brine, dried over $Na_2SO_4$, filtered and concentrated to give the desired product which was used without further purification.

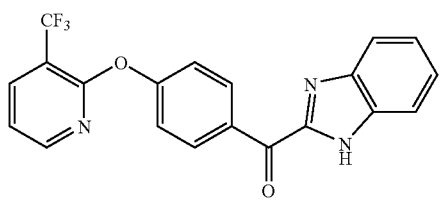

STEP 2. (1H-BENZO[D]IMIDAZOL-2-YL)(4-(3-(TRIFLUOROMETHYL)PYRIDIN-2-YLOXY) PHENYL)METHANONE

A solution of benzene-1,2-diamine (175 mg, 1618 µmol), triethyl orthoformate (665 µL, 4353 µmol), and benzenesulfonic acid (10 mg, 65 µmol) in toluene (1.6 mL) was heated to reflux for 4 h and then slowly distilled to remove half of the solvent. The mixture was then cooled to RT and neutralized with diisopropyl amine, followed by addition of a solution of ethyl 4-(3-(trifluoromethyl)pyridin-2-yloxy)benzoate (554 mg, 1780 µmol) in 1.7 mL of THF. The mixture was cooled to −78° C. and 1.2 equiv of LDA (0.971 mL, 2.0M) was added. After aging at −78° C. for 1.5 h, the mixture was warmed to RT and stirred for 1.5 h and then 2N HCl was added and the mixture was agitated for 15 min. Following that, the mixture was adjusted to pH 9 with 1N NaOH. Ethyl acetate was added and the layers were separated, the aqueous was extracted with ethyl acetate (3×), and the combined organics were washed with brine, dried over $Na_2SO_4$, filtered and concentrated. Following purification, (1H-benzo[d]imidazol-2-yl)(4-(3-(trifluoromethyl)pyridin-2-yloxy)phenyl)methanone was obtained. MS (ESI, pos. ion) m/z: 384 (M+1). IC50 (uM) +++++.

SCHEME 2

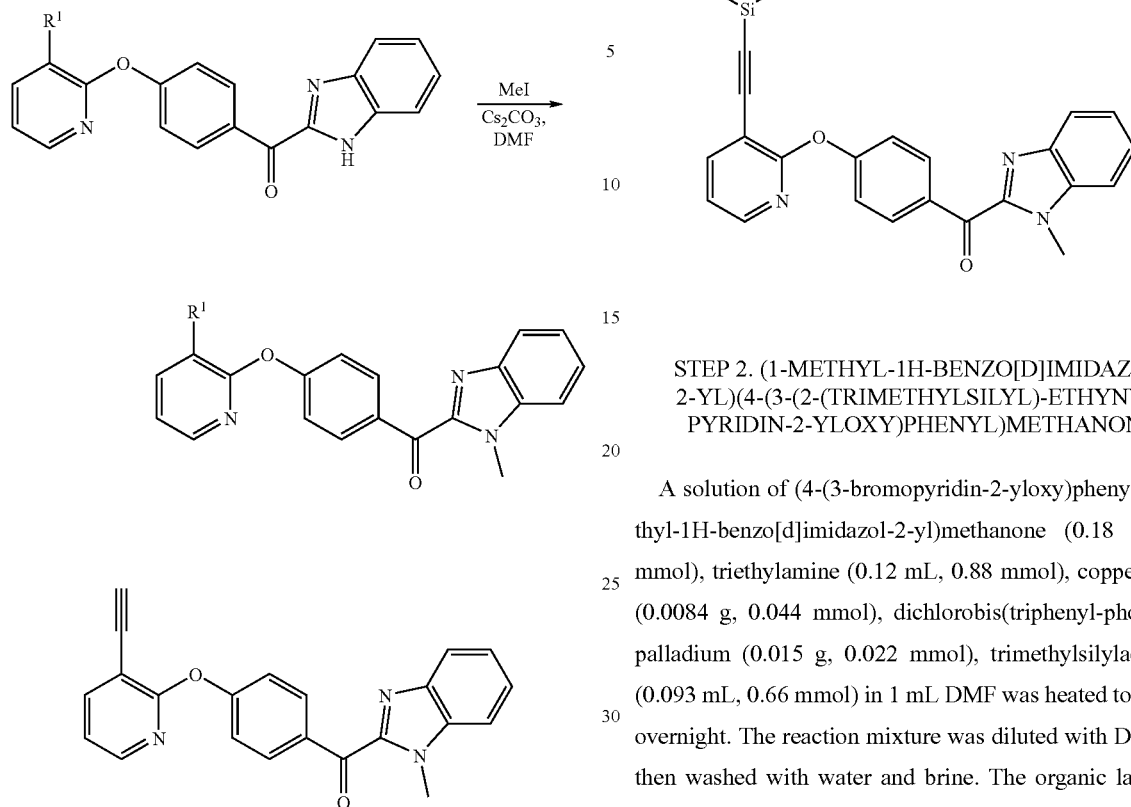

Example 2

(4-(3-ETHYNYLPYRIDIN-2-YLOXY)PHENYL)
(1-METHYL-1H-BENZO[D]IMIDAZOL-2-YL)
METHANONE

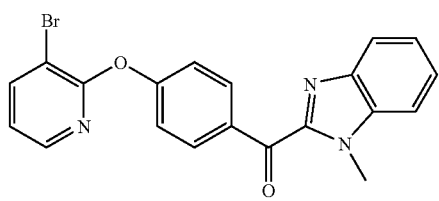

STEP 1. (4-(3-BROMOPYRIDIN-2-YLOXY)PHENYL)(1-METHYL-1H-BENZO[D]IMIDAZOL-2-YL)METHANONE

To a solution of (1H-benzo[d]imidazol-2-yl)(4-(3-bromopyridin-2-yloxy)-phenyl)methanone (0.5 g, 1 mmol) in DMF (3 mL) was added cesium carbonate (0.5 g, 2 mmol) and iodomethane (0.2 g, 1 mmol). Reaction was stirred at RT overnight. Reaction mixture was diluted with DCM and washed with water and brine. Purification by prep HPLC produced the desired product.

STEP 2. (1-METHYL-1H-BENZO[D]IMIDAZOL-2-YL)(4-(3-(2-(TRIMETHYLSILYL)-ETHYNYL)PYRIDIN-2-YLOXY)PHENYL)METHANONE

A solution of (4-(3-bromopyridin-2-yloxy)phenyl)(1-methyl-1H-benzo[d]imidazol-2-yl)methanone (0.18 g, 0.44 mmol), triethylamine (0.12 mL, 0.88 mmol), copper iodide (0.0084 g, 0.044 mmol), dichlorobis(triphenyl-phosphine)palladium (0.015 g, 0.022 mmol), trimethylsilylacetylene (0.093 mL, 0.66 mmol) in 1 mL DMF was heated to 110° C. overnight. The reaction mixture was diluted with DCM and then washed with water and brine. The organic layer was purified by silica gel chromatography (0-10% MeOH/DCM) to afford (1-methyl-1H-benzo[d]imidazol-2-yl)(4-(3-(2-(trimethylsilyl)ethynyl)pyridin-2-yloxy)phenyl)-methanone.

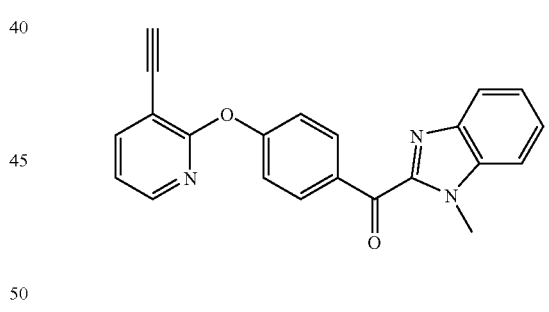

STEP 3. (4-(3-ETHYNYLPYRIDIN-2-YLOXY)PHENYL)(1-METHYL-1H-BENZO[D]IMIDAZOL-2-YL)METHANONE (1-M ethyl-1H-benzo[d]imidazol-2-yl)(4-(3-(2-(trimethylsilyl)ethynyl)pyridin-2-yloxy)phenyl)methanone (0.19 g, 0.44 mmol) and potassium carbonate (0.12 g, 0.88 mmol) was suspended in 1 mL MeOH. The mixture was stirred for 2 h at RT. Purification by prep-plate TLC (10% MeOH/DCM) afforded (4-(3-ethynylpyridin-2-yloxy)phenyl)(1-methyl-1H-benzo[d]imidazol-2-yl)methanone. MS (ESI, pos. ion) m/z: 354.0 (M+1). IC50 (uM) +++.

SCHEME 3

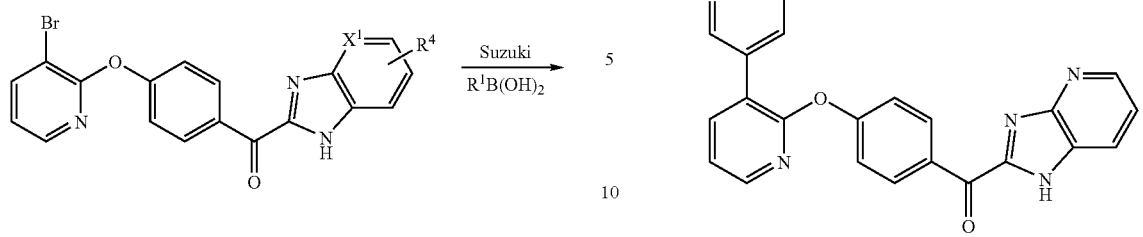

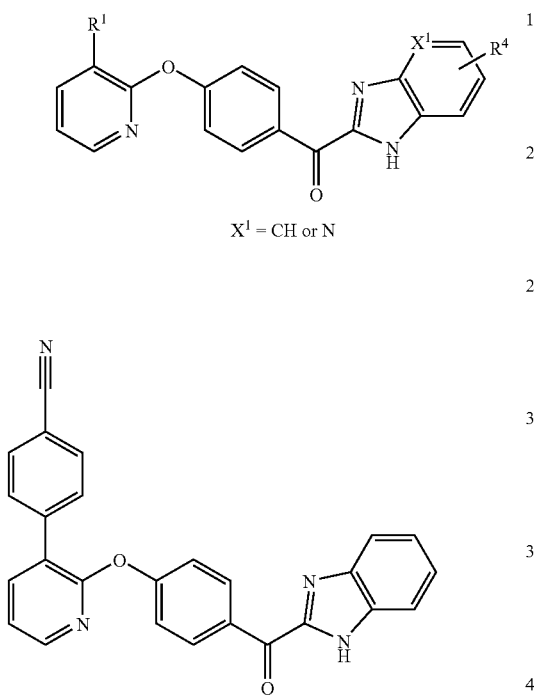

Example 3

4-(2-(4-(1H-BENZO[D]IMIDAZOLE-2-CARBO-NYL)PHENOXY)PYRIDIN-3-YL)BENZONI-TRILE

A glass microwave reaction vessel was charged with (1H-benzo[d]imidazol-2-yl)(4-(3-bromopyridin-2-yloxy)phenyl)methanone (0.1427 g, 0.36 mmol), 4-cyanophenylboronic acid (0.0760 g, 0.43 mmol), trans-dichlorobis(triphenylphosphine)palladium(ii) (0.0314 g, 0.029 mmol), and sodium carbonate monohydrate (0.13 mL, 1.8 mmol) in 1,2-dimethoxymethane (3 mL) and water (1 mL). The reaction mixture was stirred and heated in a Biotage™ Initiator™ microwave reactor at 135° C. for 10 min. The solvent was evaporated. The crude product was adsorbed onto a plug of silica gel and chromatographed through a Biotage™ pre-packed silica gel column (25M), eluting with a gradient of 10% to 80% ethyl acetate in hexane, to provide 4-(2-(4-(1H-benzo[d]imidazole-2-carbonyl)phenoxy)pyridin-3-yl)benzonitrile. MS (ESI, pos. ion) m/z: 417.5 (M+1). IC50 (uM) +++++.

Example 4

(4-(3,3'-BIPYRIDIN-2-YLOXY)PHENYL)(1H-IMIDAZO[4,5-B]PYRIDIN-2-YL)METHANONE

To a round bottomed flask was added (4-(3-bromopyridin-2-yloxy)phenyl)(1H-imidazo[4,5-b]pyridin-2-yl)methanone (0.250 g, 0.633 mmol), pyridin-3-ylboronic acid (0.233 g, 1.898 mmol), PdCl$_2$(dppf) (0.035 g, 0.063 mmol), and sodium carbonate (0.335 g, 3.16 mmol) in DMSO (1.581 mL) and Water (0.527 mL) at 80° C. to stir overnight. The reaction was worked up via seperatory funnel. The crude product was purified by reverse-phase preparative HPLC using a Phenomenex Synergi column, 4 micron, MAX-RP, 80 Å, 150×30 mM, 0.1% TFA in ACN/H$_2$O, gradient 25% to 100% over 15 min to provide (4-(3,3'-bipyridin-2-yloxy)phenyl)(1H-imidazo[4,5-b]pyridin-2-yl)methanone. MS (ESI, pos. ion) m/z: 394.0 (M+1). IC50 (uM) +++++.

SCHEME 4

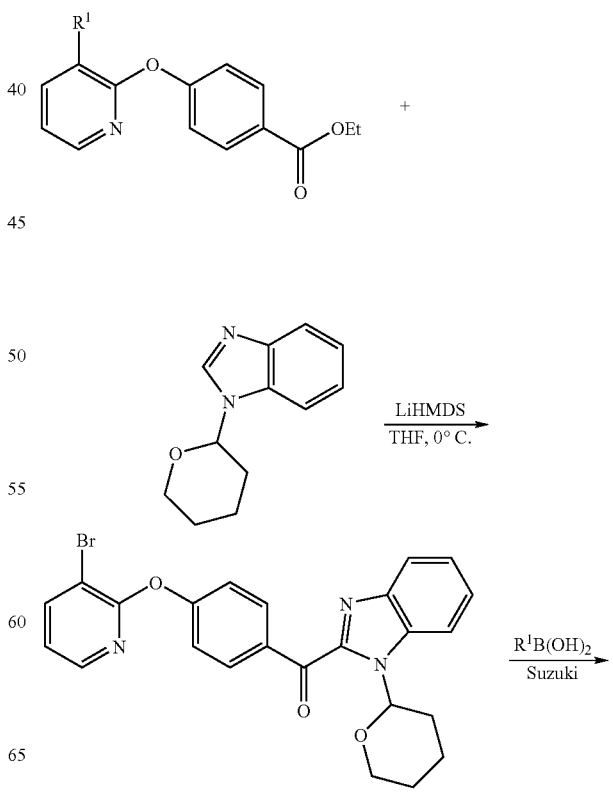

-continued

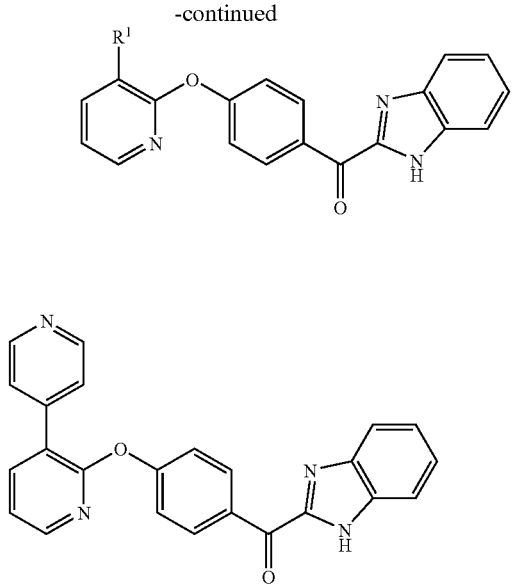

Example 5

(4-(3,4'-BIPYRIDIN-2-YLOXY)PHENYL)(1H-BENZO[D]IMIDAZOL-2-YL)METHANONE

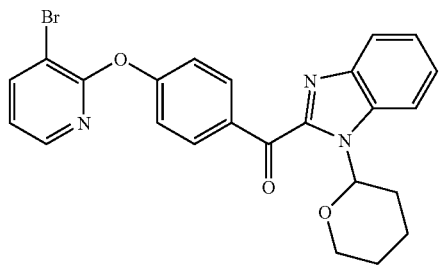

STEP 1: (4-(3-BROMOPYRIDIN-2-YLOXY)PHENYL)(1-(TETRAHYDRO-2H-PYRAN-2-YL)-1H-BENZO[D]IMIDAZOL-2-YL)METHANONE

A solution of 1-(tetrahydro-2H-pyran-2-yl)-1H-benzo[d]imidazole (39.5 g, 195 mmol) in anhydrous THF (300 ml) was cooled to 0° C. and treated with lithium bis(trimethylsilyl)amide (212 ml, 212 mmol) added dropwise over a 30 mins period. The reaction was allowed to stir for 1 hour and then methyl 4-(2-bromophenoxy)benzoate (50.00 g, 163 mmol), dissolved in 100 ml of anhydrous THF was added slowly to the reaction. The reaction was stirred for 1 hour at 0° C. and allowed to warm up to RT. After 1 hour, the reaction was cooled down to 0° C. and quenched with water (50 ml) dropwise. The reaction was diluted with 400 ml of Ethyl acetate and 400 ml of water. The layers were separated. The aqueous layer was extracted 2× (100 ml) with ethyl acetate. All the organic layers were combined, washed (2×) with an aqueous saturated solution of sodium bicarbonate, then with water and then brine. The organic layer was then dried with sodium sulfate and reduced to a smaller volume. The solid that precipitated out was filtered off, washed well with ether and dried to give product as solid. The mother liquor was concentrated and purified by column chromatography on silica gel using a gradient of 10 to 60% EtOAc in hexanes to give another batch of product.

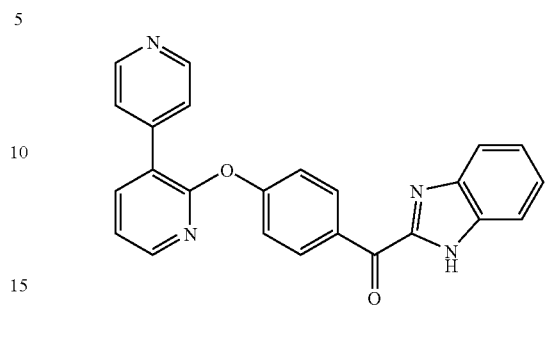

STEP 2: (4-(3,4'-BIPYRIDIN-2-YLOXY)PHENYL)(1H-BENZO[D]IMIDAZOL-2-YL)METHANONE

A clear microwave vial was charged with (4-(3-bromopyridin-2-yloxy)phenyl)(1-(tetrahydro-2H-pyran-2-yl)-1H-benzo[d]imidazol-2-yl)methanone (0.300 g, 0.627 mmol), pyridin-4-ylboronic acid (0.093 g, 0.753 mmol), bis(di-tert-butyl(4-dimethylaminophenyl)phosphine)dichloropalladium (II) (0.022 g, 0.031 mmol), potassium acetate (0.123 g, 1.254 mmol), Dioxane (4.5 mL) and Water (0.500 mL). The vial was capped and heated in a Personal Chemistry Smith-Synthesizer to 120° C. for 12 minutes. The reaction was diluted with EtOAc (10 ml) and water (10 ml). The organic portion was collected and washed (2×) with an aqueous saturated solution of sodium bicarbonate, then with water and then brine. The organic layer was then dried with sodium sulfate and purified by column chromatography on silica gel using a gradient of 20 to 60% EtOAc in hexanes.

The product obtained form part 1 was taken up in DCM (5 ml) and treated with TFA (2 ml) and a few drops of water. The mixture was allowed to stir 0/N at RT. The volatiles were removed under vacuum. The residue was taken up in 2M ammonia in MeOH (10 ml) and again reduced under vacuum. The residue was dissolved in ethyl acetate and washed (2×) with an aqueous saturated solution of sodium bicarbonate, then with water and then brine. The organic layer was then dried with sodium sulfate and reduced. The residue obtained was triturated with ether, collected by suction filtration and dried to give product. MS (ESI, pos. ion) m/z: 392.9 (M+1).

IC50 (uM) +++++.

SCHEME 5

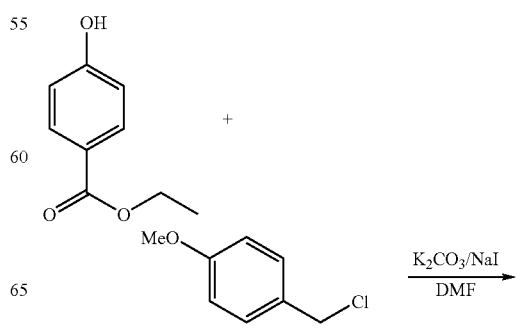

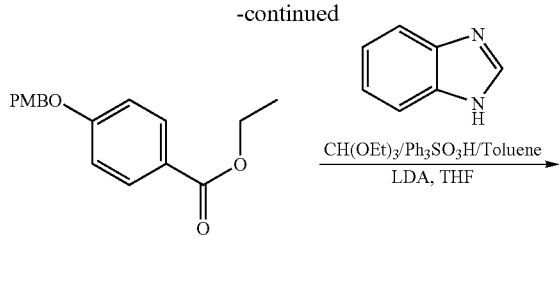

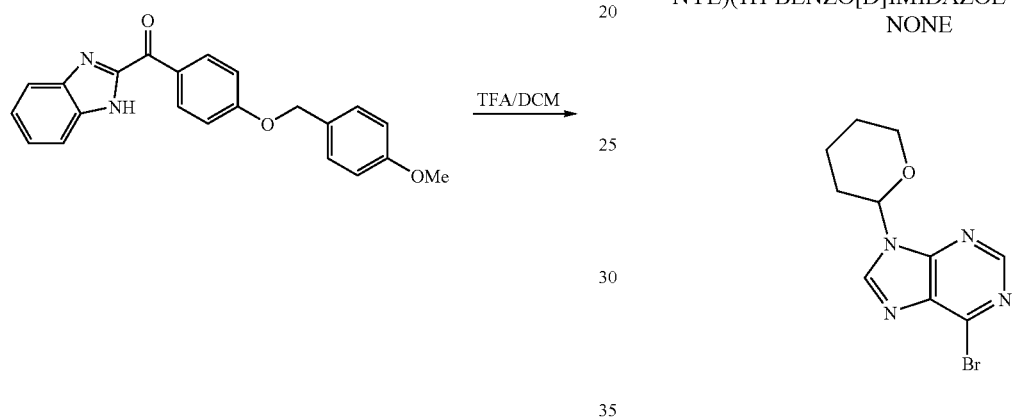

Example 6

(4-(3-(9H-PURIN-6-YL)PYRIDIN-2-YLOXY)PHENYL)(1H-BENZO[D]IMIDAZOL-2-YL)METHANONE

STEP 1: 6-BROMO-9-(TETRAHYDRO-2H-PYRAN-2-YL)-9H-PURINE

A mixture of 6-bromopurine (2.0 g, 10 mmol), 3,4-dihydro-2h-pyran (1.0 ml, 11 mmol), and p-toluenesulfonic acid monohydrate (0.050 g, 0.26 mmol) in EtOAc (30 mL) was stirred at reflux under a reflux condenser for 48 h. The reaction mixture (suspension) was allowed to cool to room temperature and the solid was removed by suction filtration and washed with EtOAc (50 mL). The combined wash was concentrated in vacuo to afford 2.1 g as oil. The oil was chromatographed through a Redi-Sep® pre-packed silica gel column, eluting with a gradient of 30% to 60% EtOAc in hexane, to provide product.

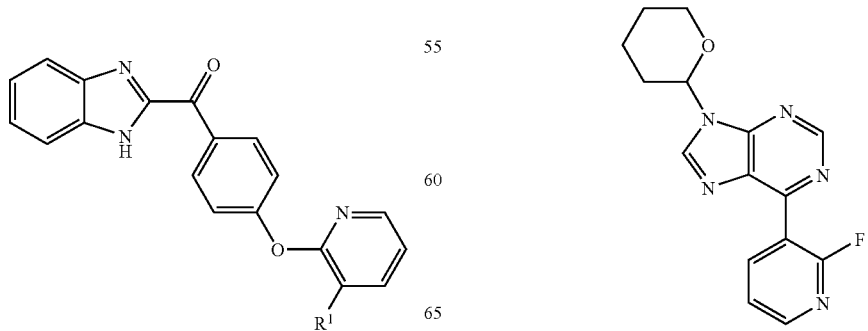

STEP 2: 6-(2-FLUOROPYRIDIN-3-YL)-9-(TETRAHYDRO-2H-PYRAN-2-YL)-9H-PURINE

To a round bottom flask, under a reflux condenser, was added 6-bromo-9-(tetrahydro-2H-pyran-2-yl)-9H-purine (1.0 g, 3.5 mmol), 2-fluoropyridin-3-ylboronic acid (0.75 g, 5.3 mmol), potassium acetate (1.0 g, 11 mmol), 1-butanol (50 mL) and DI water (10 mL). The mixture was purged with Ar (vacuum/purge three times) to remove oxygen, then $PdCl_2$(P-tert-$Bu_2$Ph)$_2$ (0.026 g, 0.042 mmol) was added. The reaction mixture was stirred in a 100° C. oil bath for 45 min (complete by TLC, 80% EtOAc/hex).

The reaction mixture was allowed to cool to room temperature and diluted with $Et_2O$ (500 mL). The mixture was washed with water (3×100 L), then saturated NaCl solution (100 mL). The solution was dried over $Na_2SO_4$, filtered and concentrated in vacuo. The butanol was removed in vacuo by azeotrope with toluene (2×200 mL) to afford 1 g as a yellow oily residue; 83947-12-1. The crude product was chromatographed through a Redi-Sep® pre-packed silica gel column (40 g), eluting with a gradient of 80% to 100% EtOAc in hexane, to provide product.

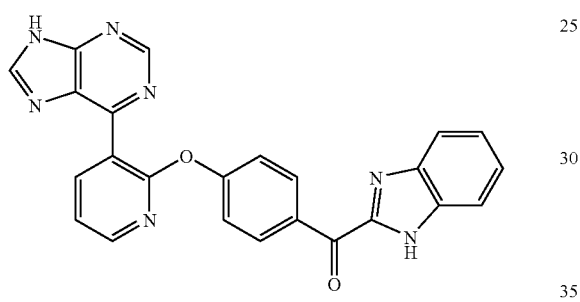

STEP 3: (4-(3-(9H-PURIN-6-YL)PYRIDIN-2-YLOXY)PHENYL)(1H-BENZO[D]IMIDAZOL-2-YL)METHANONE

A screw cap heavy wall flask was charged with (1H-benzo[d]imidazol-2-yl)(4-hydroxyphenyl)methanone (0.350 g, 1.469 mmol), 6-(2-fluoropyridin-3-yl)-9-(tetrahydro-2H-pyran-2-yl)-9H-purine (0.440 g, 1.469 mmol), cesium carbonate (0.957 g, 2.94 mmol) and DMF (6 mL). The vial was capped and heated to 100° C. After 12 hours, the reaction was allowed to cool to RT and diluted with 20 ml of water. The mixture was extracted (3×) with 10 ml of ethyl acetate. The organic layers were combined and washed (2×) with an aqueous saturated solution of sodium bicarbonate, then with water and then brine. The organic layer was then dried with sodium sulfate and purified by column chromatography on silica gel using a gradient of 20 to 60% EtOAc in hexanes. The pure fractions were combined and reduced under vacuum to give an oily residue. The residue was dissolved in DCM (10 mL) and treated with 1 mL of TFA and a few drops of water. The mixture was allowed to stir at room temperature overnight. 10 ml of 2N ammonia in MeOH was added to the reaction with was reduced in vacuo. The residue was partitioned in water and EtOAc. The organic layer was washed (2×) with an aqueous saturated solution of sodium bicarbonate, then with water and then brine. The organic layer was then dried with sodium sulfate and reduced. The residue obtained was triturated in 1:1 ethyl acetate:ether and then dried in a vacuum oven to give product as solid. MS (ESI, pos. ion) m/z: 434.0 (M+1). IC50 (uM) +++++.

SCHEME 6

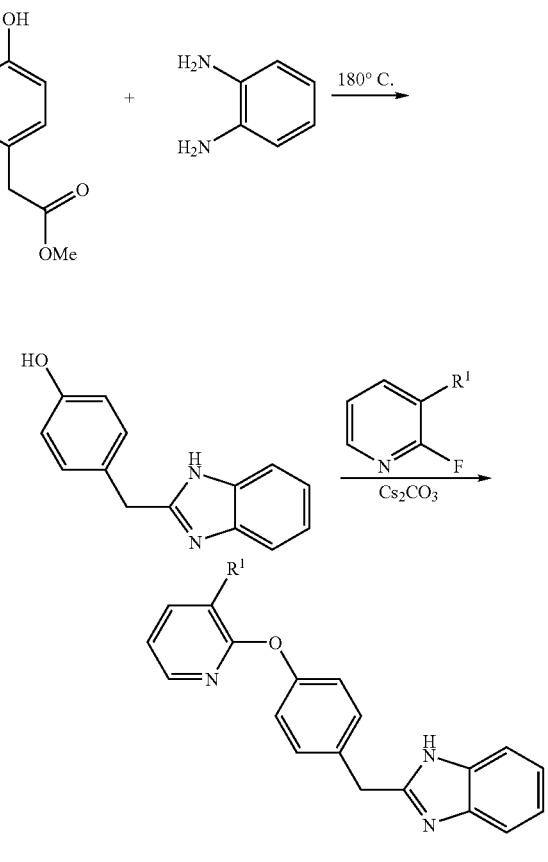

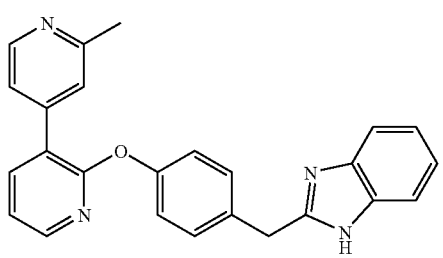

Example 7

2-(4-(3-(2-METHYLPYRIDIN-4-YL)PYRIDIN-2-YLOXY)BENZYL)-1H-BENZO[D]IMIDAZOLE

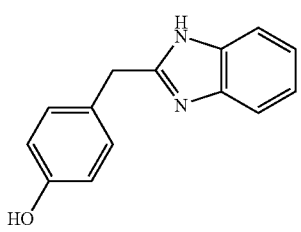

STEP 1. 4-((1H-BENZO[D]IMIDAZOL-2-YL)METHYL) PHENOL

A mixture of methyl 2-(4-hydroxyphenyl)acetate (40.0 g, 241 mmol) and benzene-1,2-diamine (26.0 g, 241 mmol) in a sealed vessel was heated to 150° C. for 18 h. After cooling to room temperature, the mixture was diluted with MeOH and heated to 100 C for 1 h. The mixture was cooled to −20 C overnight, then filtered to collect 25.8 g (48%) of a lavender solid. MS (ESI, pos. ion) m/z: 225 (M+1).

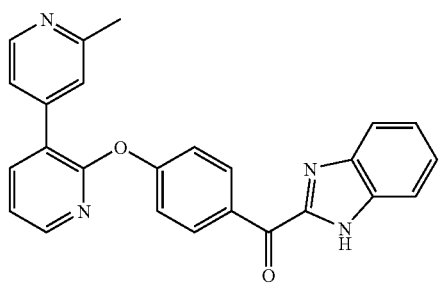

STEP 2. 2-(4-(3-(2-METHYLPYRIDIN-4-YL)PYRIDIN-2-YLOXY)BENZYL)-1H-BENZO[D]IMIDAZOLE

A mixture of 2-fluoro-3-(2-methylpyridin-4-yl)pyridine (1.00 g, 5.31 mmol), 4-((1H-benzo[d]imidazol-2-yl)methyl) phenol (1.43 g, 6.38 mmol) and cesium carbonate (2.60 g, 7.97 mmol) was heated to 80° C. for 16 h. After cooling to room temperature, the mixture was diluted with $H_2O$ and extracted with 25% i-PrOH/$CHCl_3$ (3×). The combined organics were dried over $Na_2SO_4$, filtered and concentrated. The residue was purified using column chromatography (Acetone/Hexanes=0→80%) to give the title compound. MS (ESI, pos. ion) m/z: 393 (M+1). IC50 (uM) ++++.

SCHEME 7

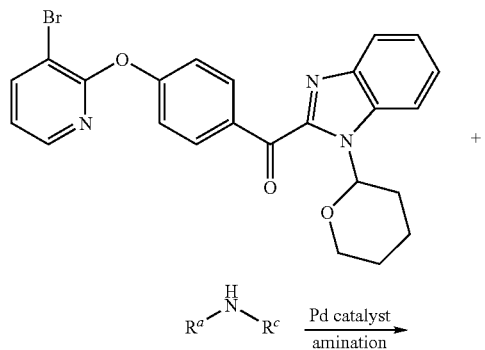

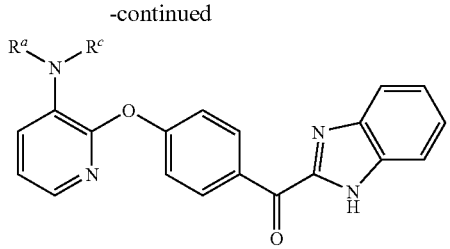

Example 8

(1H-BENZO[D]IMIDAZOL-2-YL)(4-(3-(PIPERIDIN-1-YL)PYRIDIN-2-YLOXY)PHENYL) METHANONE

A heavy-walled vial was charged with (4-(3-bromopyridin-2-yloxy)phenyl)(1-(tetrahydro-2H-pyran-2-yl)-1H-benzo[d]imidazol-2-yl)methanone (0.150 g, 0.314 mmol), piperidine (0.041 mL, 0.470 mmol), cesium carbonate (0.204 g, 0.627 mmol), (r)-binap (0.020 g, 0.031 mmol), Pd3 dba3 (0.014 g, 0.016 mmol) and Toluene (4 mL). Nitrogen was bubbled into the flask for 5 mins. The vial was capped and heated to 80° C. After 12 hours, the reaction was partitioned with ethyl acetate and water. The organic layer was washed (2×) with an aqueous saturated solution of sodium bicarbonate, then with water and then brine. The organic layer was then dried with sodium sulfate and purified by column chromatography on silica gel using a gradient of 20 to 60% EtOAc in hexanes to give a clear residue. The residue was dissolved in MeOH (10 mL) and treated with 1 mL of TFA. The mixture was allowed to stir at room temperature. 10 ml of 2N ammonia in MeOH was added to the reaction with was reduced in vacuo. The residue was partitioned in water and EtOAc. The organic layer was washed (2×) with an aqueous saturated solution of sodium bicarbonate, then with water and then brine. The organic layer was then dried with sodium sulfate and reduced. The residue obtained was triturated in 1:1 ethyl acetate:ether and then dried in a vacuum oven to give product as solid. MS (ESI, pos. ion) m/z: 398.8 (M+1). IC50 (uM) ++++.

TABLE IA

EXAMPLES 9 TO 71 ARE TABULATED BELOW:

| Ex # | Structure | IC50 (uM) | IUPAC names | MS |
|---|---|---|---|---|
| 9 | 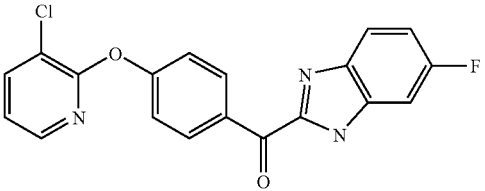 | + | (4-(3-chloropyridin-2-yloxy)phenyl)(6-fluoro-1H-benzo[d]imidazol-2-yl)methanone | 368 |
| 10 | 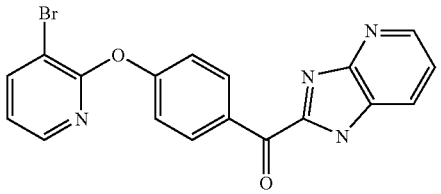 | + | (4-(3-bromopyridin-2-yloxy)phenyl)(1H-imidazo[4,5-b]pyridin-2-yl)methanone | 396.8 |
| 11 | 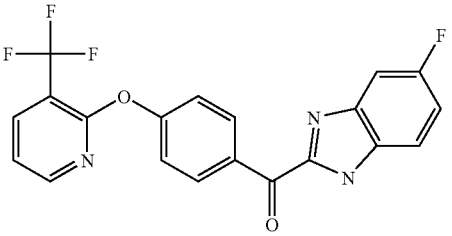 | ++ | (5-fluoro-1H-benzo[d]imidazol-2-yl)(4-(3-(trifluoromethyl)pyridin-2-yloxy)phenyl)methanone | 402 |
| 12 | 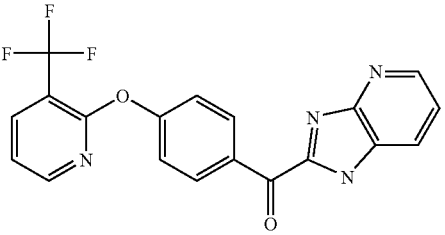 | + | (1H-imidazo[4,5-b]pyridin-2-yl)(4-(3-(trifluoromethyl)pyridin-2-yloxy)phenyl)methanone | 385 |
| 13 | 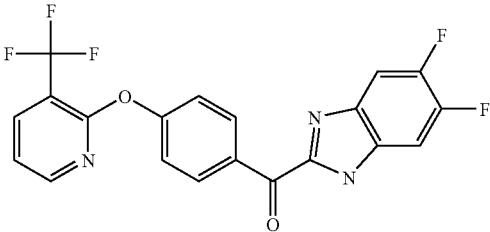 | ++ | (5,6-difluoro-1H-benzo[d]imidazol-2-yl)(4-(3-(trifluoromethyl)pyridin-2-yloxy)phenyl)methanone | 420 |

TABLE IA-continued

EXAMPLES 9 TO 71 ARE TABULATED BELOW:

| Ex # | Structure | IC50 (uM) | IUPAC names | MS |
|---|---|---|---|---|
| 14 | 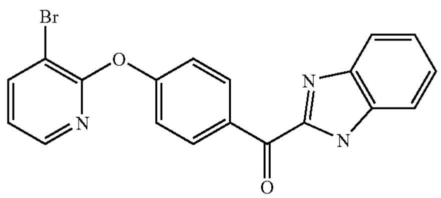 | ++++ | (1H-benzo[d]imidazol-2-yl)(4-(3-bromopyridin-2-yloxy)phenyl)methanone | 394.2 |
| 15 | 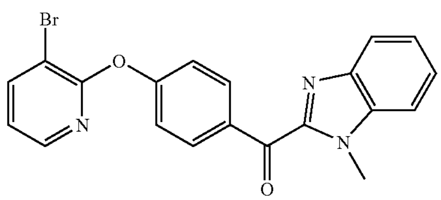 | ++++ | (4-(3-bromopyridin-2-yloxy)phenyl)(1-methyl-1H-benzo[d]imidazol-2-yl)methanone | 407.9 |
| 16 | 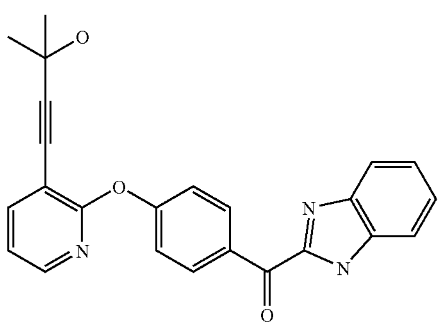 | ++++ | (1H-benzo[d]imidazol-2-yl)(4-(3-(3-hydroxy-3-methylbut-1-ynyl)pyridin-2-yloxy)phenyl)methanone | 398.0 |
| 17 | 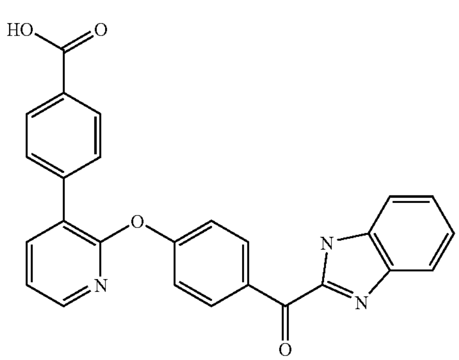 | +++++ | 4-(2-(4-(1H-benzo[d]imidazole-2-carbonyl)phenoxy)pyridin-3-yl)benzoic acid | 436.0 |

TABLE IA-continued

EXAMPLES 9 TO 71 ARE TABULATED BELOW:

| Ex # | Structure | IC50 (uM) | IUPAC names | MS |
|---|---|---|---|---|
| 18 | 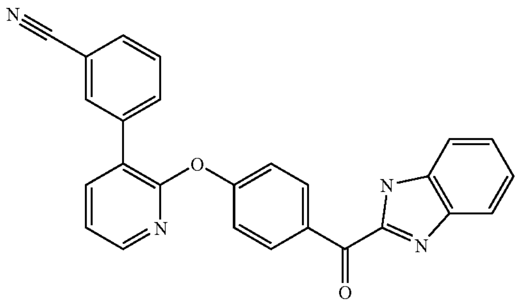 | +++++ | 3-(2-(4-(1H-benzo[d]imidazole-2-carbonyl)phenoxy)pyridin-3-yl)benzonitrile | 417.4 |
| 19 | 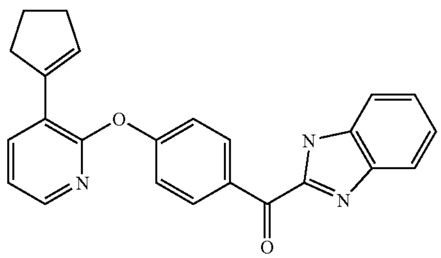 | +++++ | (1H-benzo[d]imidazol-2-yl)(4-(3-cyclopentenylpyridin-2-yloxy)phenyl)methanone | 382.0 |
| 20 | 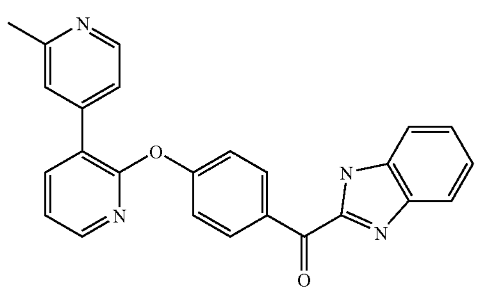 | +++++ | (1H-benzo[d]imidazol-2-yl)(4-(3-(2-methylpyridin-4-yl)pyridin-2-yloxy)phenyl)methanone | 407.5 |
| 21 | 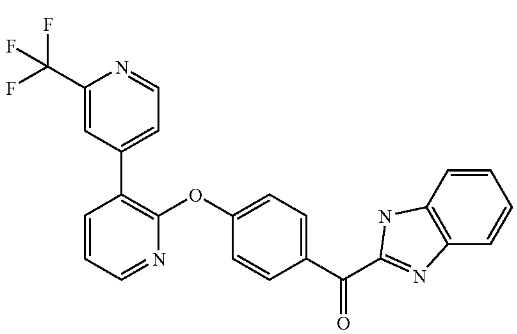 | +++++ | (1H-benzo[d]imidazol-2-yl)(4-(3-(2-(trifluoromethyl)pyridin-4-yl)pyridin-2-yloxy)phenyl)methanone | 461.5 |

TABLE IA-continued

EXAMPLES 9 TO 71 ARE TABULATED BELOW:

| Ex # | Structure | IC50 (uM) | IUPAC names | MS |
|---|---|---|---|---|
| 22 | 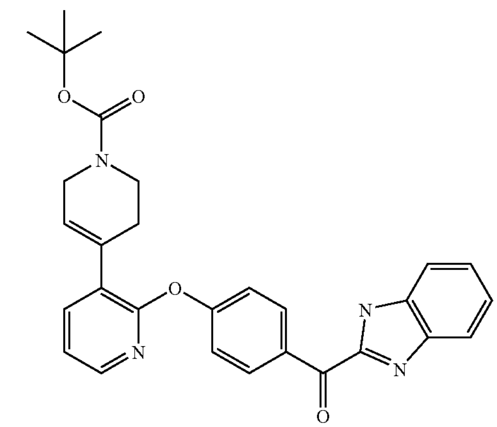 | +++++ | tert-butyl 4-(2-(4-(1H-benzo[d]imidazole-2-carbonyl)phenoxy)pyridin-3-yl)-5,6-dihydropyridine-1(2H)-carboxylate | 497.8 |
| 23 | 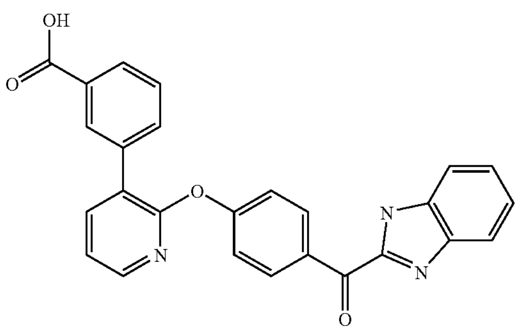 | +++++ | 3-(2-(4-(1H-benzo[d]imidazole-2-carbonyl)phenoxy)pyridin-3-yl)benzoic acid | 436.0 |
| 24 | 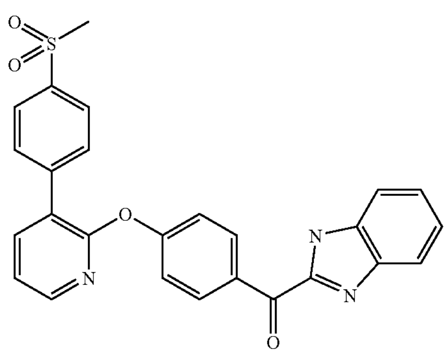 | +++ | (1H-benzo[d]imidazol-2-yl)(4-(3-(4-(methylsulfonyl)phenyl)pyridin-2-yloxy)phenyl)methanone' | 470.1 |
| 25 | 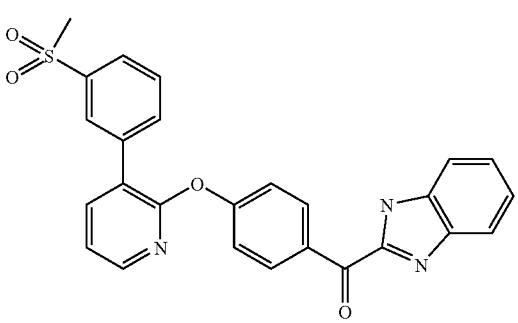 | +++ | (1H-benzo[d]imidazol-2-yl)(4-(3-(3-(methylsulfonyl)phenyl)pyridin-2-yloxy)phenyl)methanone | 470.5 |

TABLE IA-continued
EXAMPLES 9 TO 71 ARE TABULATED BELOW:
| Ex # | Structure | IC50 (uM) | IUPAC names | MS |
|---|---|---|---|---|
| 26 | 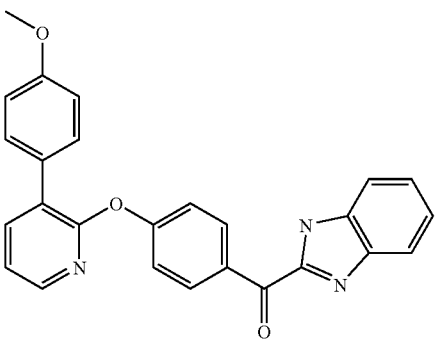 | +++++ | (1H-benzo[d]imidazol-2-yl)(4-(3-(4-methoxyphenyl)pyridin-2-yloxy)phenyl)methanone | 422.3 |
| 27 | 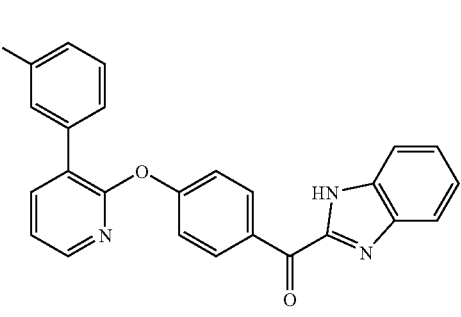 | +++++ | (1H-benzo[d]imidazol-2-yl)(4-(3-(3-methoxyphenyl)pyridin-2-yloxy)phenyl)methanone | 422.3 |
| 28 | 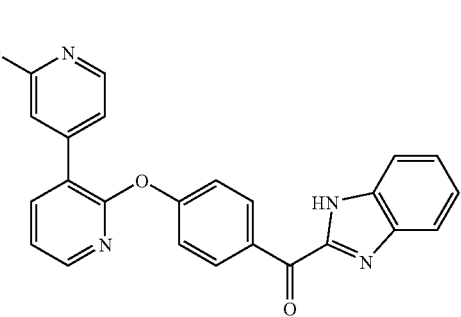 | +++++ | (1H-benzo[d]imidazol-2-yl)(4-(3-(2-methoxypyridin-4-yl)pyridin-2-yloxy)phenyl)methanone] | 423.0 |

TABLE IA-continued

EXAMPLES 9 TO 71 ARE TABULATED BELOW:

| Ex # | Structure | IC50 (uM) | IUPAC names | MS |
|---|---|---|---|---|
| 29 | 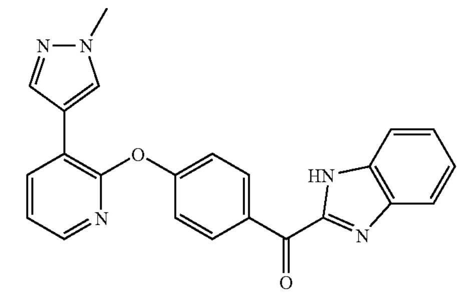 | +++++ | (1H-benzo[d]imidazol-2-yl)(4-(3-(1-methyl-1H-pyrazol-4-yl)pyridin-2-yloxy)phenyl)methanone | 396 |
| 30 | 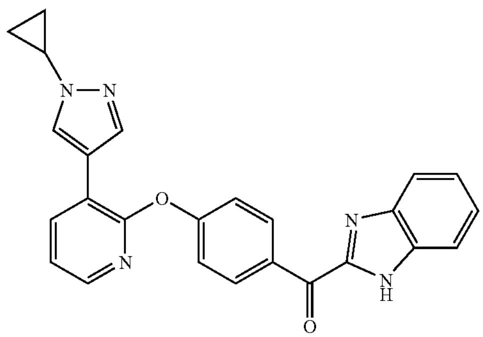 | ++++ | (1H-benzo[d]imidazol-2-yl)(4-(3-(1-cyclopropyl-1H-pyrazol-4-yl)pyridin-2-yloxy)phenyl)methanone | 422 |
| 31 | 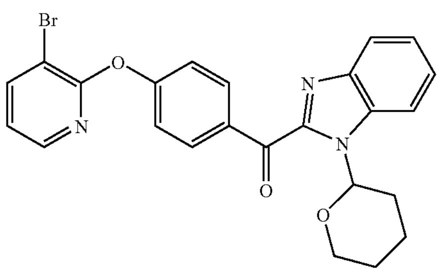 | + | (4-(3-bromopyridin-2-yloxy)phenyl)(1-(tetrahydro-2H-pyran-2-yl)-1H-benzo[d]imidazol-2-yl)methanone | 395.8 (M-84) |
| 32 | 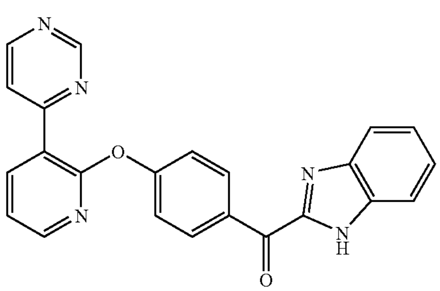 | ++++ | (1H-benzo[d]imidazol-2-yl)(4-(3-(pyrimidin-4-yl)pyridin-2-yloxy)phenyl)methanone | 393.9 |
| 33 | 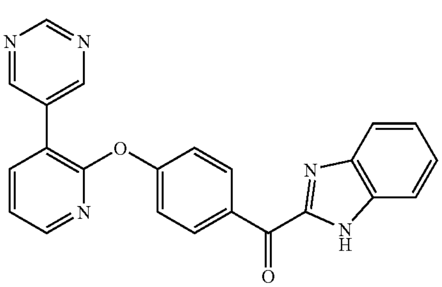 | +++++ | (1H-benzo[d]imidazol-2-yl)(4-(3-(pyrimidin-5-yl)pyridin-2-yloxy)phenyl)methanone | 393.9 |

TABLE IA-continued

EXAMPLES 9 TO 71 ARE TABULATED BELOW:

| Ex # | Structure | IC50 (uM) | IUPAC names | MS |
|---|---|---|---|---|
| 34 | 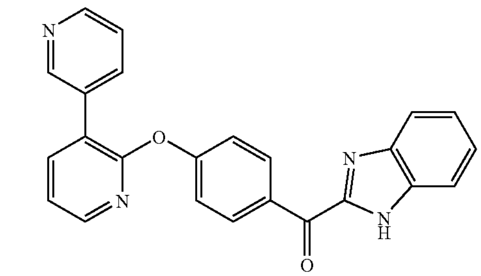 | +++++ | (4-(3,3'-bipyridin-2-yloxy)phenyl)(1H-benzo[d]imidazol-2-yl)methanone | 392.9 |
| 35 | 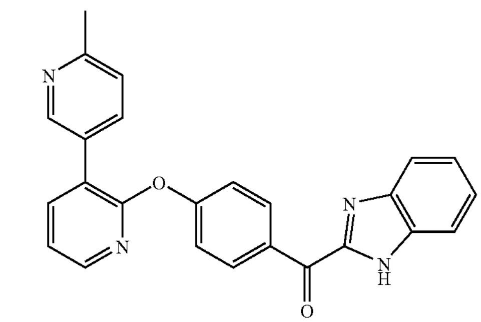 | +++++ | (1H-benzo[d]imidazol-2-yl)(4-(6'-methyl-3,3'-bipyridin-2-yloxy)phenyl)methanone | 406.9 |
| 36 | 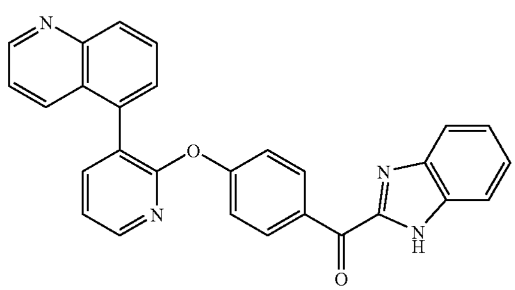 | ++++ | (1H-benzo[d]imidazol-2-yl)(4-(3-(quinolin-5-yl)pyridin-2-yloxy)phenyl)methanone | 443.0 |
| 37 | 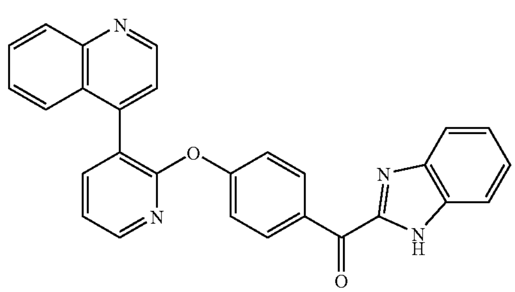 | +++++ | (1H-benzo[d]imidazol-2-yl)(4-(3-(quinolin-4-yl)pyridin-2-yloxy)phenyl)methanone | 443.0 |
| 38 | 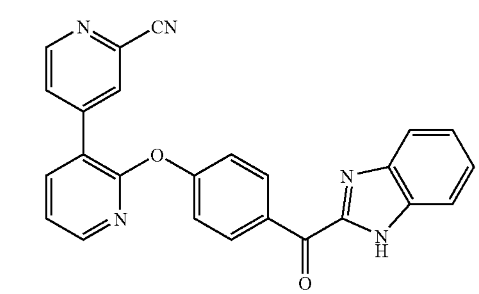 | +++++ | 2-(4-(1H-benzo[d]imidazole-2-carbonyl)phenoxy)-3,4'-bipyridine-2'-carbonitrile | 417.9 |

TABLE IA-continued

EXAMPLES 9 TO 71 ARE TABULATED BELOW:

| Ex # | Structure | IC50 (uM) | IUPAC names | MS |
|---|---|---|---|---|
| 39 | 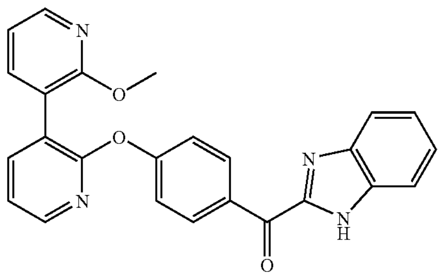 | +++++ | (1H-benzo[d]imidazol-2-yl)(4-(2'-methoxy-3,3'-bipyridin-2-yloxy)phenyl)methanone | 423.0 |
| 40 | 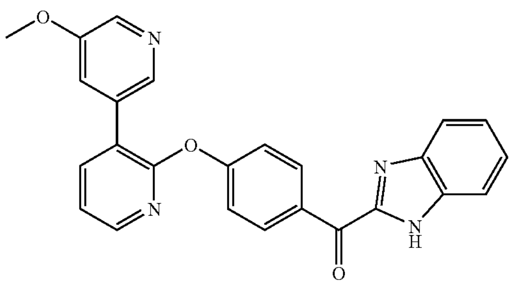 | +++++ | (1H-benzo[d]imidazol-2-yl)(4-(5'-methoxy-3,3'-bipyridin-2-yloxy)phenyl)methanone | 423.1 |
| 41 | 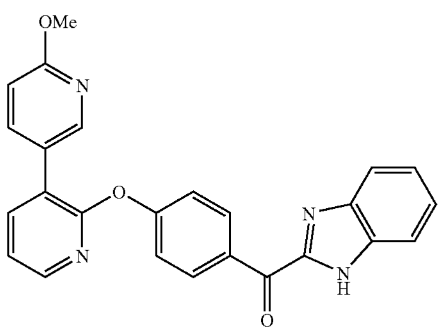 | +++++ | (1H-benzo[d]imidazol-2-yl)(4-(6'-methoxy-3,3'-bipyridin-2-yloxy)phenyl)methanone | 423.1 |
| 42 | 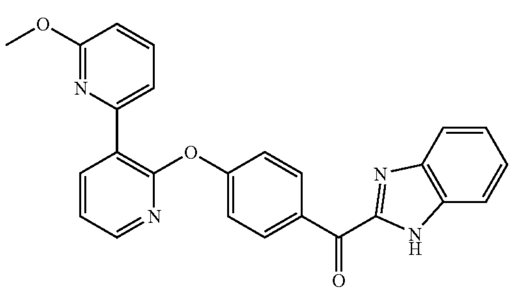 | +++++ | (1H-benzo[d]imidazol-2-yl)(4-(6-methoxy-2,3'-bipyridin-2'-yloxy)phenyl)methanone | 423.1 |
| 43 | 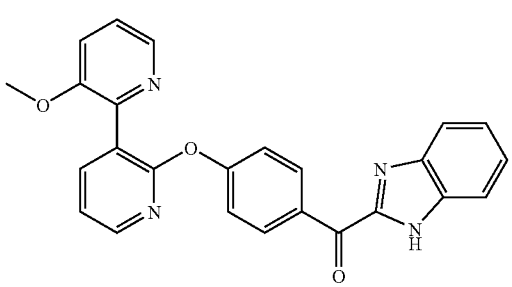 | +++++ | (1H-benzo[d]imidazol-2-yl)(4-(3-methoxy-2,3'-bipyridin-2'-yloxy)phenyl)methanone | 423.2 |

TABLE IA-continued

EXAMPLES 9 TO 71 ARE TABULATED BELOW:

| Ex # | Structure | IC50 (uM) | IUPAC names | MS |
|---|---|---|---|---|
| 44 | 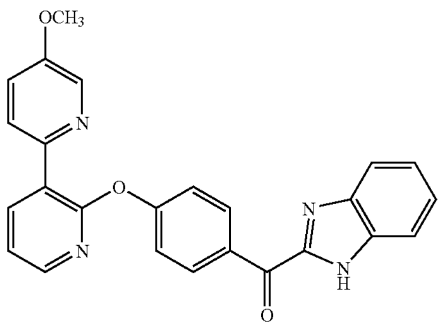 | +++++ | (1H-benzo[d]imidazol-2-yl)(4-(5-methoxy-2,3'-bipyridin-2'-yloxy)phenyl)methanone | 423.2 |
| 45 | 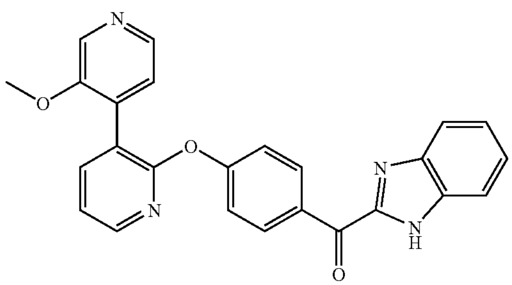 | +++++ | (1H-benzo[d]imidazol-2-yl)(4-(3'-methoxy-3,4'-bipyridin-2-yloxy)phenyl)methanone | 422.9 |
| 46 | 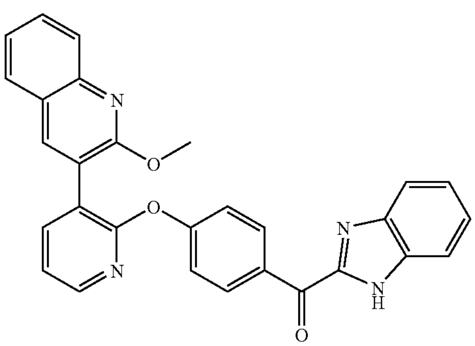 | ++++ | (1H-benzo[d]imidazol-2-yl)(4-(3-(2-methoxyquinolin-3-yl)pyridin-2-yloxy)phenyl)methanone | 473.2 |
| 47 | 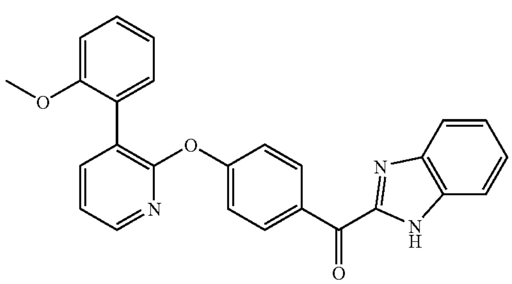 | ++++ | (1H-benzo[d]imidazol-2-yl)(4-(3-(2-methoxyphenyl)pyridin-2-yloxy)phenyl)methanone | 422.1 |
| 48 | 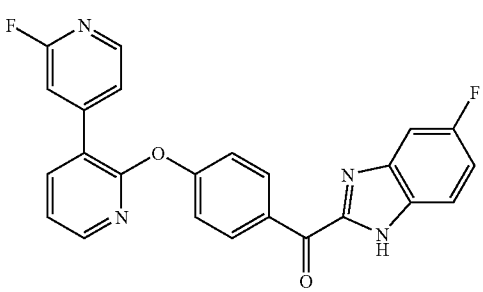 | ++++ | (5-fluoro-1H-benzo[d]imidazol-2-yl)(4-(2'-fluoro-3,4'-bipyridin-2-yloxy)phenyl)methanone | 429.9 |

TABLE IA-continued

EXAMPLES 9 TO 71 ARE TABULATED BELOW:

| Ex # | Structure | IC50 (uM) | IUPAC names | MS |
|---|---|---|---|---|
| 49 | 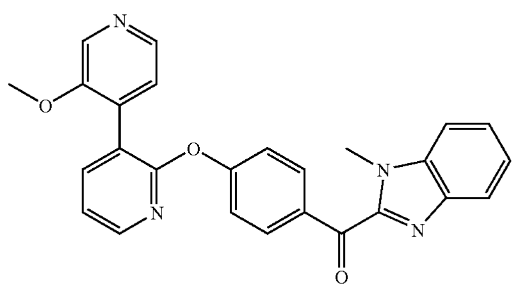 | +++++ | (4-(3'-methoxy-3,4'-bipyridin-2-yloxy)phenyl)(1-methyl-1H-benzo[d]imidazol-2-yl)methanone | 437.0 |
| 50 | 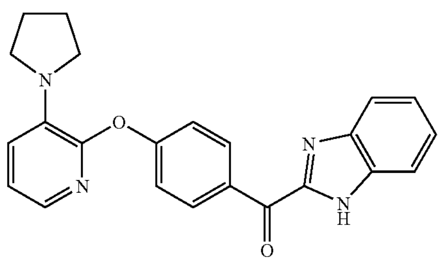 | ++++ | (1H-benzo[d]imidazol-2-yl)(4-(3-(pyrrolidin-1-yl)pyridin-2-yloxy)phenyl)methanone | 384.9 |
| 51 | 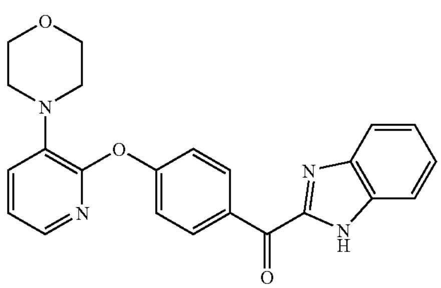 | +++++ | (1H-benzo[d]imidazol-2-yl)(4-(3-morpholinopyridin-2-yloxy)phenyl)methanone | 401.2 |
| 52 | 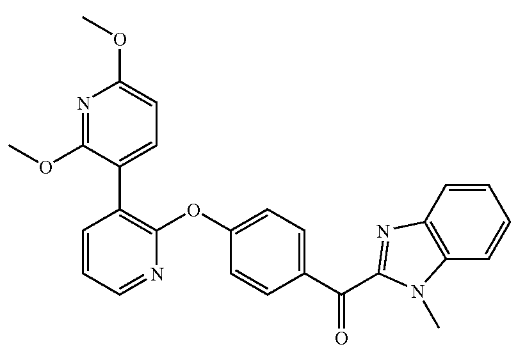 | ++++ | (4-(2',6'-dimethoxy-3,3'-bipyridin-2-yloxy)phenyl)(1-methyl-1H-benzo[d]imidazol-2-yl)methanone | 467.0 |
| 53 | 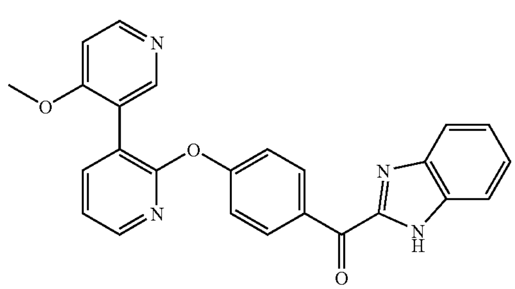 | +++++ | (1H-benzo[d]imidazol-2-yl)(4-(4'-methoxy-3,3'-bipyridin-2-yloxy)phenyl)methanone | 423.0 |

TABLE IA-continued

EXAMPLES 9 TO 71 ARE TABULATED BELOW:

| Ex # | Structure | IC50 (uM) | IUPAC names | MS |
|---|---|---|---|---|
| 54 | 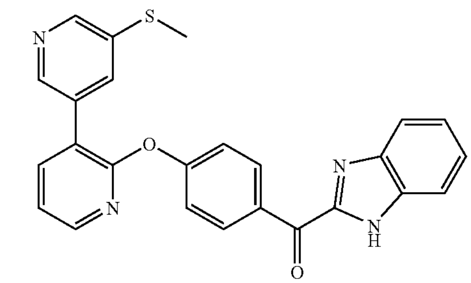 | +++++ | (1H-benzo[d]imidazol-2-yl)(4-(5'-(methylthio)-3,3'-bipyridin-2-yloxy)phenyl)methanone | 439.0 |
| 55 | 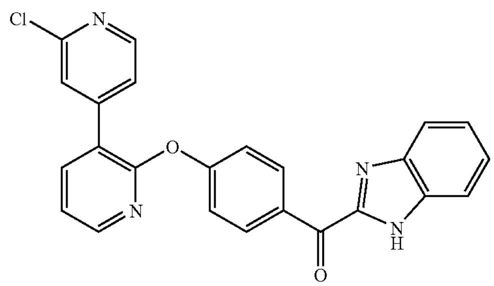 | +++++ | (1H-benzo[d]imidazol-2-yl)(4-(2'-chloro-3,4'-bipyridin-2-yloxy)phenyl)methanone | 427 |
| 56 | 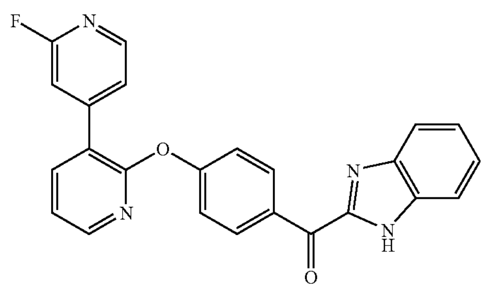 | +++++ | (1H-benzo[d]imidazol-2-yl)(4-(2'-fluoro-3,4'-bipyridin-2-yloxy)phenyl)methanone | 411 |
| 57 | 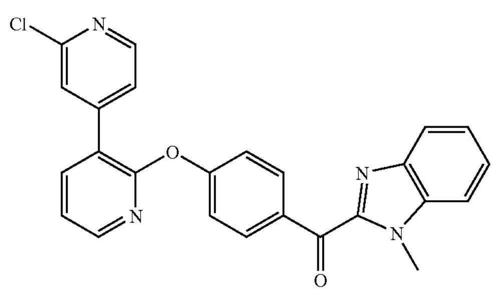 | ++++ | (4-(2'-chloro-3,4'-bipyridin-2-yloxy)phenyl)(1-methyl-1H-benzo[d]imidazol-2-yl)methanone | 441 |
| 58 | 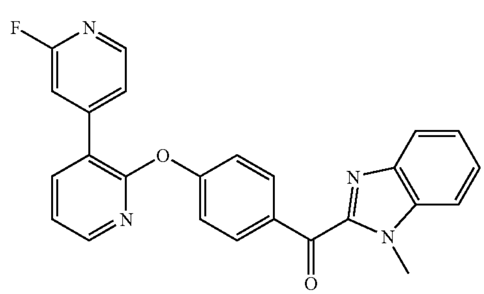 | +++++ | (4-(2'-fluoro-3,4'-bipyridin-2-yloxy)phenyl)(1-methyl-1H-benzo[d]imidazol-2-yl)methanone | 425 |

TABLE IA-continued

EXAMPLES 9 TO 71 ARE TABULATED BELOW:

| Ex # | Structure | IC50 (uM) | IUPAC names | MS |
|---|---|---|---|---|
| 59 | 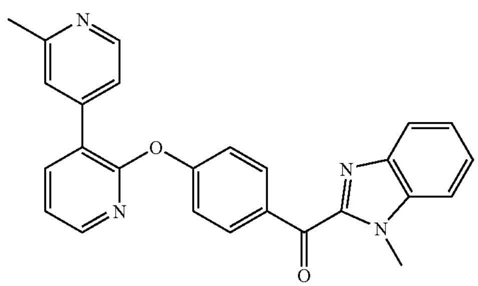 | +++++ | (1-methyl-1H-benzo[d]imidazol-2-yl)(4-(2'-methyl-3,4'-bipyridin-2-yloxy)phenyl)methanone | 421 |
| 60 | 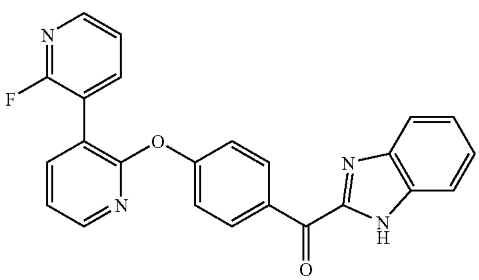 | +++++ | (1H-benzo[d]imidazol-2-yl)(4-(2'-fluoro-3,3'-bipyridin-2-yloxy)phenyl)methanone | 411 |
| 61 | 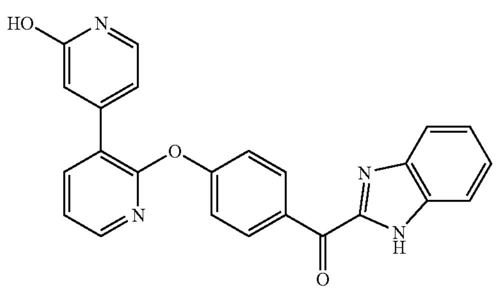 | ++++ | (1H-benzo[d]imidazol-2-yl)(4-(2'-hydroxy-3,4'-bipyridin-2-yloxy)phenyl)methanone | 409 |
| 62 | 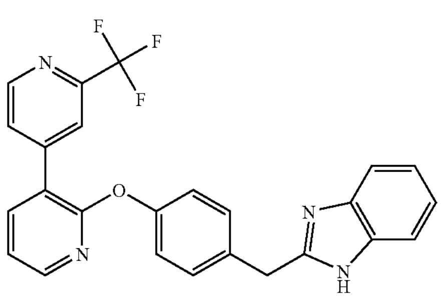 | +++ | 2-(4-(2'-(trifluoromethyl)-3,4'-bipyridin-2-yloxy)benzyl)-1H-benzo[d]imidazole | 447.0 |
| 63 | 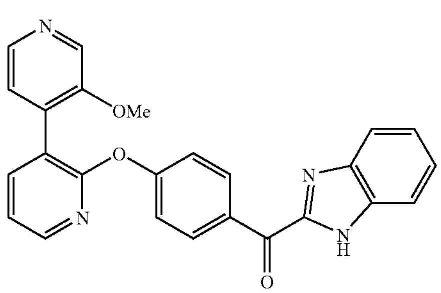 | +++++ | (1H-benzo[d]imidazol-2-yl)(4-(3'-methoxy-3,4'-bipyridin-2-yloxy)phenyl)methanone | 422.9 |

TABLE IA-continued

EXAMPLES 9 TO 71 ARE TABULATED BELOW:

| Ex # | Structure | IC50 (uM) | IUPAC names | MS |
|---|---|---|---|---|
| 64 | 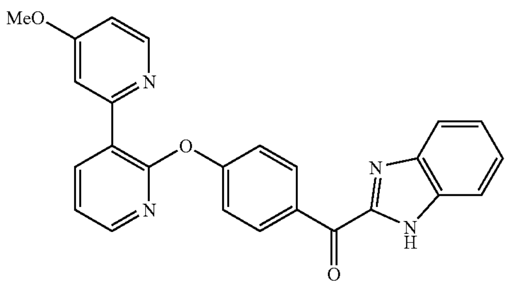 | +++++ | (1H-benzo[d]imidazol-2-yl)(4-(4-methoxy-2,3'-bipyridin-2'-yloxy)phenyl)methanone | 423.9 |
| 65 | 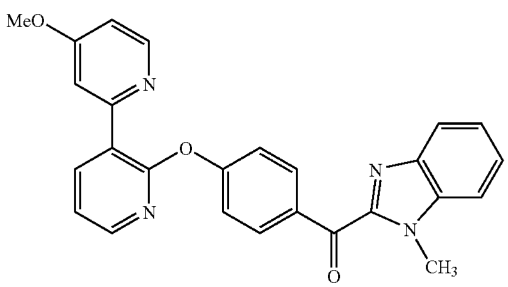 | +++++ | (4-(4-methoxy-2,3'-bipyridin-2'-yloxy)phenyl)(1-methyl-1H-benzo[d]imidazol-2-yl)methanone | 437.9 |
| 66 | 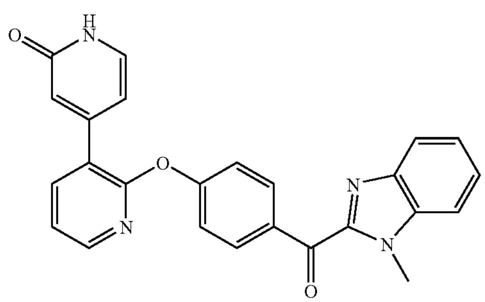 | +++++ | 4-(2-(4-(1-methyl-1H-benzo[d]imidazole-2-carbonyl)phenoxy)pyridin-3-yl)pyridin-2(1H)-one | 423 |
| 67 | | ++++ | (6-fluoro-1-methyl-1H-benzo[d]imidazol-2-yl)(4-(3-(tetrahydro-2H-pyran-4-yl)pyridin-2-yloxy)phenyl)methanone and (5-fluoro-1-methyl-1H-benzo[d]imidazol-2-yl)(4-(3-(tetrahydro-2H-pyran-4-yl)pyridin-2-yloxy)phenyl)methanone | 432 |

TABLE IA-continued

EXAMPLES 9 TO 71 ARE TABULATED BELOW:

| Ex # | Structure | IC50 (uM) | IUPAC names | MS |
|---|---|---|---|---|
| 68 | 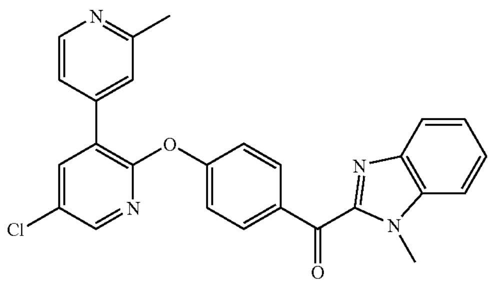 | ++++ | (4-(5-chloro-2'-methyl-3,4'-bipyridin-2-yloxy)phenyl)(1-methyl-1H-benzo[d]imidazol-2-yl)methanone | 455 |
| 69 | 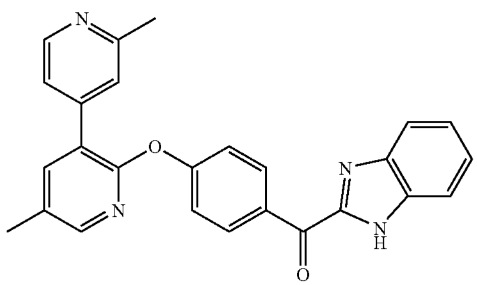 | +++++ | (1H-benzo[d]imidazol-2-yl)(4-(2',5-dimethyl-3,4'-bipyridin-2-yloxy)phenyl)methanone | 421 |
| 70 | 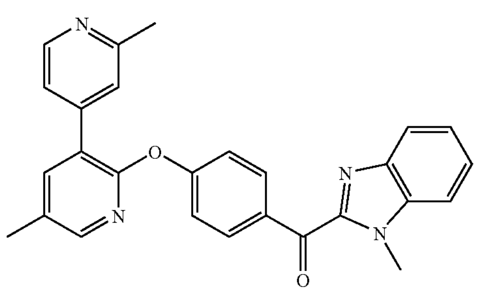 | +++++ | (4-(2',5-dimethyl-3,4'-bipyridin-2-yloxy)phenyl)(1-methyl-1H-benzo[d]imidazol-2-yl)methanone | 435 |
| 71 | 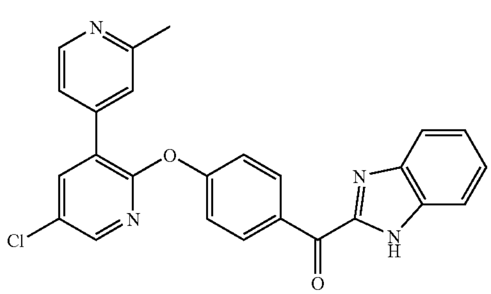 | +++++ | (1H-benzo[d]imidazol-2-yl)(4-(5-chloro-2'-methyl-3,4'-bipyridin-2-yloxy)phenyl)methanone | 441 |

TABLE IB
EXAMPLES 9 TO 71 WERE PREPARED AS FOLLOWS:
| Ex # | Synthetic Scheme | How Different From Main Route | Reagent Difference |
|---|---|---|---|
| 9 | 1 | same | 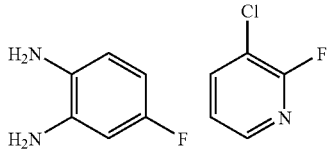 |
| 10 | 1 | same | 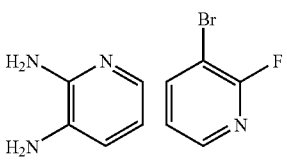 |
| 11 | 1 | same | 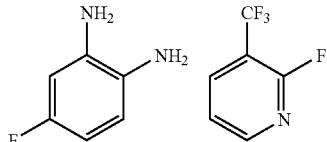 |
| 12 | 1 | same | 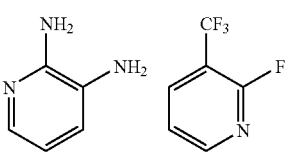 |
| 13 | 1 | same | 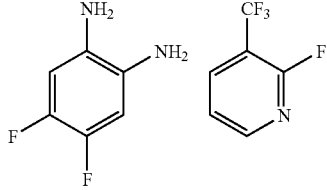 |
| 14 | 1 | same |  |
| 15 | 2 | Same | 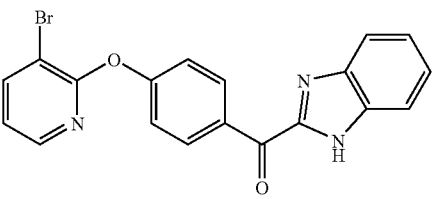 |
| 16 | 1 | PdCl$_2$(PPh$_3$)$_2$, CuI, TEA, 100° C. | 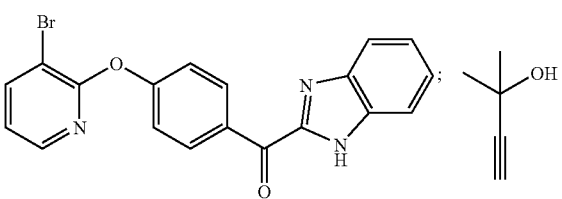 |

TABLE IB-continued

EXAMPLES 9 TO 71 WERE PREPARED AS FOLLOWS:

| Ex # | Synthetic Scheme | How Different From Main Route | Reagent Difference |
|---|---|---|---|
| 17 | 3 | same | 4-carboxyphenylboronic acid (COOH-C6H4-B(OH)2) |
| 18 | 3 | same | 3-cyanophenylboronic acid (CN-C6H4-B(OH)2) |
| 19 | 3 | same | cyclopent-1-enylboronic acid |
| 20 | 3 | same | 2-methylpyridin-4-ylboronic acid |
| 21 | 3 | same | 2-(trifluoromethyl)pyridin-4-ylboronic acid |
| 22 | 3 | same | N-Boc-1,2,3,6-tetrahydropyridin-4-ylboronic acid |
| 23 | 3 | same | 3-carboxyphenylboronic acid |

TABLE IB-continued
EXAMPLES 9 TO 71 WERE PREPARED AS FOLLOWS:
| Ex # | Synthetic Scheme | How Different From Main Route | Reagent Difference |
|---|---|---|---|
| 24 | 3 | same | 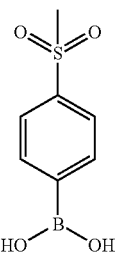 |
| 25 | 3 | same | 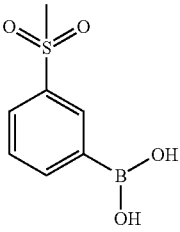 |
| 26 | 3 | same | 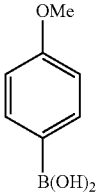 |
| 27 | 3 | same | 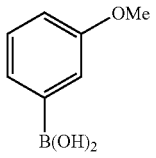 |
| 28 | 3 | same | 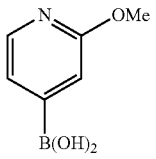 |
| 29 | 3 | same | 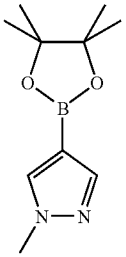 |

TABLE IB-continued
EXAMPLES 9 TO 71 WERE PREPARED AS FOLLOWS:
| Ex # | Synthetic Scheme | How Different From Main Route | Reagent Difference |
|---|---|---|---|
| 30 | 3 | same | 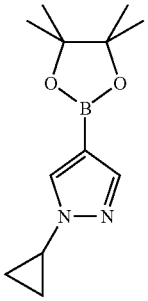 |
| 31 | 4 (step 1) | same | Same |
| 32 | 3 | same | 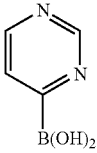 |
| 33 | 3 | same | 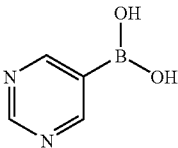 |
| 34 | 3 | same | 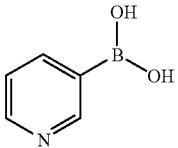 |
| 35 | 3 | same | 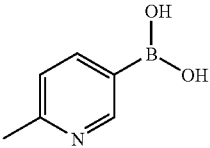 |
| 36 | 3 | KOAc, AmPhos, 140° C., microwave | 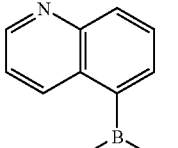 |
| 37 | 3 | KOAc, AmPhos, 140° C., microwave | 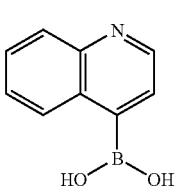 |

TABLE IB-continued

EXAMPLES 9 TO 71 WERE PREPARED AS FOLLOWS:

| Ex # | Synthetic Scheme | How Different From Main Route | Reagent Difference |
|---|---|---|---|
| 38 | 3 | KOAc, AmPhos, 140° C., microwave | (structure: 2-cyanopyridine-4-boronic acid pinacol ester) |
| 39 | 3 | K₃PO₄, AmPhos, 150° C., microwave | (structure: 2-methoxypyridine-3-boronic acid) |
| 40 | 3 | KOAc, AmPhos, 150° C., microwave | (structure: 5-methoxypyridine-3-boronic acid pinacol ester) |
| 41 | 3 | K₃PO₄, AmPhos, 150° C., microwave | (structure: 6-methoxypyridine-3-boronic acid) |
| 42 | 5 | Cs₂CO₃, 140° C. | (structure: 6-methoxy-2-(2-fluoropyridin-3-yl)pyridine) |
| 43 | 5 | Cs₂CO₃, 140° C. | (structure: 3-methoxy-2-(2-fluoropyridin-3-yl)pyridine) |

TABLE IB-continued

EXAMPLES 9 TO 71 WERE PREPARED AS FOLLOWS:

| Ex # | Synthetic Scheme | How Different From Main Route | Reagent Difference |
|---|---|---|---|
| 44 | 5 | Cs₂CO₃, 140° C. | 5-methoxy-2-(2-fluoropyridin-3-yl)pyridine |
| 45 | 3 | KOAc, AmPhos | 3-methoxypyridin-4-ylboronic acid |
| 46 | 3 | K₃PO₄, AmPhos, 150° C., microwave | 2-methoxyquinolin-3-ylboronic acid |
| 47 | 3 | K₃PO₄, AmPhos, 150° C., microwave | 2-methoxyphenylboronic acid |
| 48 | 3 | PdCl₂(PPh₃)₂, Na₂CO₃, DME/H₂O, 80° C. | 2-fluoropyridin-4-ylboronic acid |
| 49 | 3 | KOAc, AmPhos, 120° C. | 3-methoxypyridin-4-ylboronic acid |
| 50 | 7 | same | pyrrolidine |
| 51 | 7 | same | morpholine |

TABLE IB-continued
EXAMPLES 9 TO 71 WERE PREPARED AS FOLLOWS:
| Ex # | Synthetic Scheme | How Different From Main Route | Reagent Difference |
|---|---|---|---|
| 52 | 3 | PdCl$_2$(PPh$_3$)$_2$, Na$_2$CO$_3$, DME/H$_2$O, 80° C. | 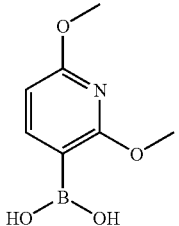 |
| 53 | 3 | Base: K$_2$CO$_3$ Solvent: DME/H$_2$O/EtOH T: 140-160° C. | 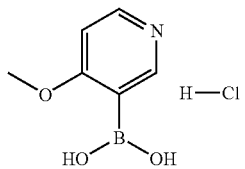 |
| 54 | 3 | Solvent: DME/H$_2$O/EtOH T: 140° C. | 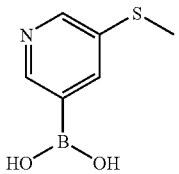 |
| 55 | 3 | Pd(PPh$_3$)$_2$Cl$_2$, Na$_2$CO$_3$ | 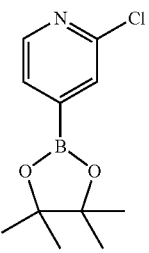 |
| 56 | 3 | Pd(PPh$_3$)$_2$Cl$_2$, Na$_2$CO$_3$ | 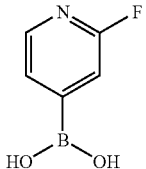 |
| 57 | 2 | same | 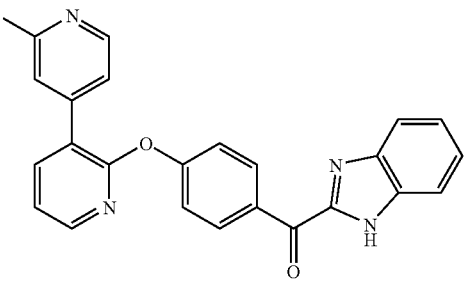 |

TABLE IB-continued
EXAMPLES 9 TO 71 WERE PREPARED AS FOLLOWS:
| Ex # | Synthetic Scheme | How Different From Main Route | Reagent Difference |
|---|---|---|---|
| 58 | 2 | same | 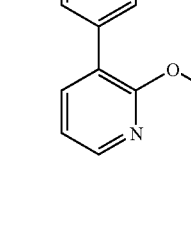 |
| 59 | 2 | same | 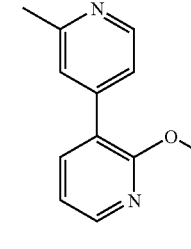 |
| 60 | 3 | same |  |
| 61 | | NaOH, DMSO, 80° C. | 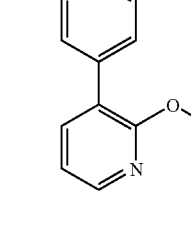 |
| 62 | 6 | same |  |

TABLE IB-continued
EXAMPLES 9 TO 71 WERE PREPARED AS FOLLOWS:
| Ex # | Synthetic Scheme | How Different From Main Route | Reagent Difference |
|---|---|---|---|
| 63 | 4 | same | 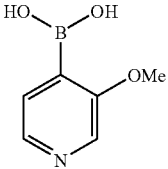 |
| 64 | 4 | same | 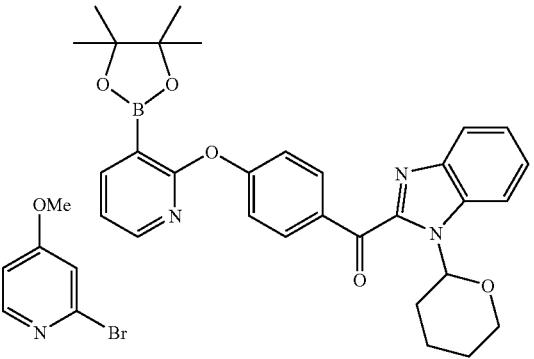 |
| 65 | 2 | same | 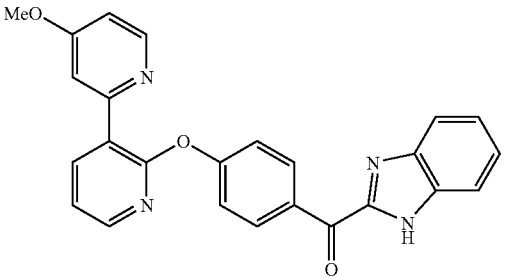 |
| 66 | 2 | same | 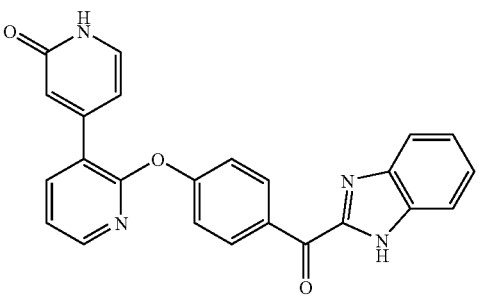 |
| 67 | 2 | same | 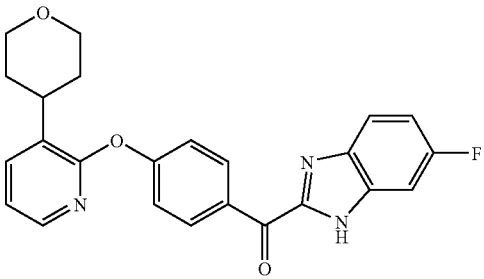 |

TABLE IB-continued
EXAMPLES 9 TO 71 WERE PREPARED AS FOLLOWS:
| Ex # | Synthetic Scheme | How Different From Main Route | Reagent Difference |
|---|---|---|---|
| 68 | 2 | same | |
| 69 | 5 | Used Pd(PPh$_3$)$_2$Cl$_2$, Na$_2$CO$_3$ @140° C. for Suzuki at last step | |
| 70 | 2 | same | |
| 71 | 5 | Used Pd(PPh$_3$)$_2$Cl$_2$, Na$_2$CO$_3$ @140° C. for Suzuki at last step | |
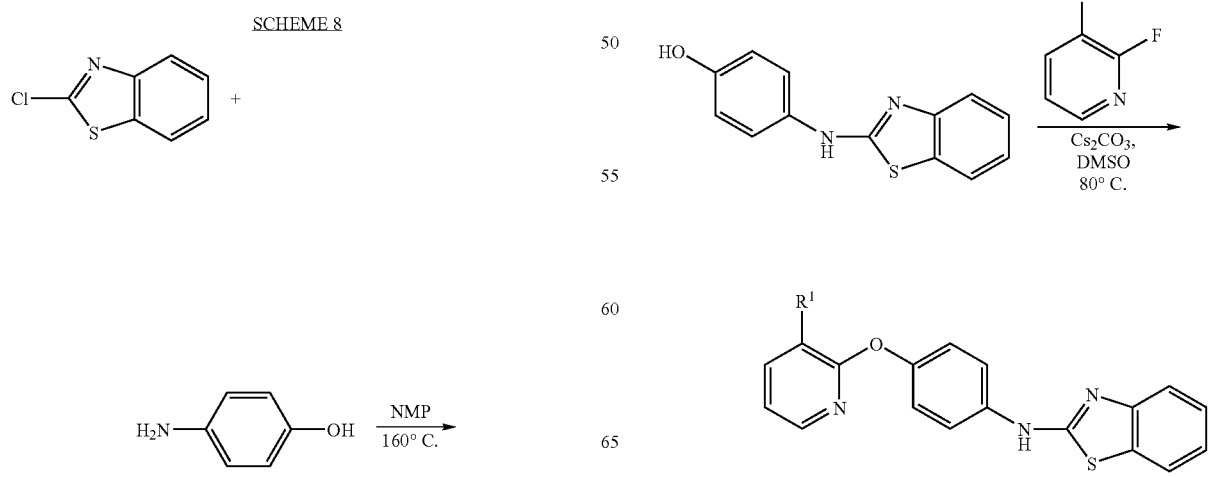

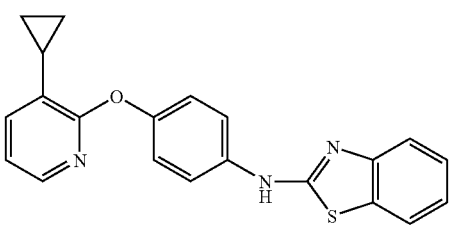

Example 72

N-(4-(3-CYCLOPROPYLPYRIDIN-2-YLOXY)
PHENYL)BENZO[D]THIAZOL-2-AMINE

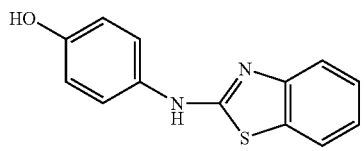

STEP 1.
4-(BENZO[D]THIAZOL-2-YLAMINO)PHENOL

The solution of 2-chlorobenzothiazole (2.47 mL, 20 mmol) and 4-aminophenol (2.18 g, 20.0 mmol) in N-methylpyrrolidone (16 mL) was heated at 160° C. for 7 h. The reaction mixture was quenched with aqueous 2N NaOH and then extracted with EtOAc. The organic layer was washed with 2N NaOH. To the combined aqueous layer was added aqueous 5N HCl until pH 6, then the product was extracted with EtOAc (2x), dried ($Na_2SO_4$) and concentrated. The crude product was dissolved in MeOH and treated with $SiO_2$. Chromatography through a Redi-Sep® pre-packed silica gel column (120 g), eluting with a gradient of 0% to 50% EtOAc in hexane, provided 4-(benzo[d]thiazol-2-ylamino)phenol as a tan solid.

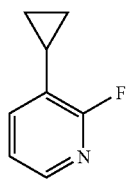

STEP 2.
3-CYCLOPROPYL-2-FLUOROPYRIDINE

To a solution of 3-bromo-2-fluoropyridine (1.56 g, 8.86 mmol), cyclopropylboronic acid (990 mg, 11.5 mmol), potassium phosphate (6.59 g, 31.0 mmol) and tricyclohexylphosphine (249 mg, 0.89 mmol) in a mixed solvent of toluene (40 mL) and water (2 mL) under a nitrogen atmosphere was added palladium(ii) acetate (99.5 mg, 0.443 mmol). The reaction mixture was heated at 100° C. for 3 h. The mixture was allowed to cool to RT, filtered through a pad of Celite™ and washed with EtOAc. The crude product was chromatographed through a Redi-Sep® pre-packed silica gel column (120 g), eluting with a gradient of 0% to 10% EtOAc in hexane, to provide 3-cyclopropyl-2-fluoropyridine as light-yellow oil.

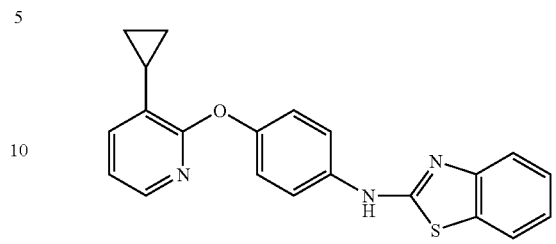

STEP 3. N-(4-(3-CYCLOPROPYLPYRIDIN-2-YLOXY)PHENYL)BENZO[D]THIAZOL-2-AMINE

To a solution of 4-(benzo[d]thiazol-2-ylamino)phenol (1.17 g, 4.81 mmol) in DMSO (40 mL) was added cesium carbonate (1.88 g, 5.78 mmol) and 3-cyclopropyl-2-fluoropyridine (660 mg, 4.81 mmol). The resulting mixture was heated to 125° C. for 16 h. After cooling to RT, the reaction mixture was diluted with EtOAc and washed with water and brine several times to remove DMSO. The aqueous layer was back extracted with EtOAc (3x) and the combined organic layer was dried ($Na_2SO_4$) and concentrated. The crude product was chromatographed through a Redi-Sep® pre-packed silica gel column (120 g), eluting with a gradient of 0% to 30% EtOAc in hexane, to provide N-(4-(3-cyclopropylpyridin-2-yloxy)phenyl)benzo[d]thiazol-2-amine as tan solid. MS (ESI, pos. ion) m/z: 360.0 (M+1). IC50 (uM) +++++.

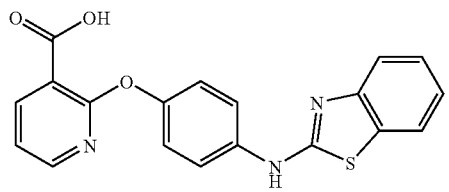

Example 73

2-(4-(BENZO[D]THIAZOL-2-YLAMINO)
PHENOXY)NICOTINIC ACID

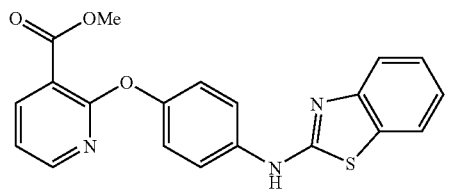

STEP 1. METHYL
2-(4-(BENZO[D]THIAZOL-2-YLAMINO)
PHENOXY)NICOTINATE

To a solution of 4-(benzo[d]thiazol-2-ylamino)phenol (900 mg, 3.71 mmol) and methyl 2-fluoronicotinate (576 mg, 3.71 mmol) in DMSO (15 mL) was added cesium carbonate (1.45 g, 4.46 mmol). The mixture was heated to 80° C. for 2 h.

The mixture was cooled to room temperature, diluted with EtOAc and brine, the layers were separated and the aqueous was extracted with EtOAc (3×). The combined organics were dried over Na$_2$SO$_4$, filtered and concentrated. The crude product was chromatographed through a Redi-Sep® prepacked silica gel column (40 g), eluting with a gradient of 0% to 50% EtOAc in hexane, to provide methyl 2-(4-(benzo[d]thiazol-2-ylamino)phenoxy)nicotinate as white solid. MS (ESI, pos. ion) m/z: 378.0 (M+1).

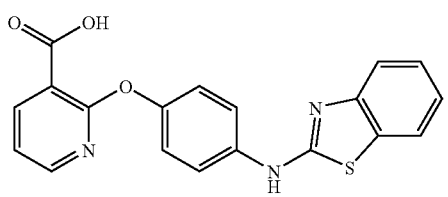

STEP 2. 2-(4-(BENZO[D]THIAZOL-2-YLAMINO)PHENOXY)NICOTINIC ACID

To a solution of methyl 2-(4-(benzo[d]thiazol-2-ylamino)phenoxy)nicotinate (0.70 g, 1.84 mmol) in a mixed solvent of THF (6 mL) and water (2 mL) was added lithium hydroxide monohydrate (0.39 mg, 9.2 mmol). The reaction mixture was stirred at RT for 16 h. The reaction was quenched with aqueous 2N HCl to pH 5. The precipitate formed was collected by filtration, washed with water, dried to provide 2-(4-(benzo[d]thiazol-2-ylamino)-phenoxy)nicotinic acid as off-white solid. MS (ESI, pos. ion) m/z: 364.0 (M+1). IC50 (uM) +.

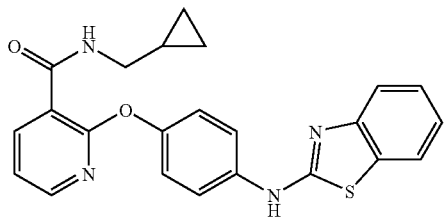

Example 74

2-(4-(BENZO[D]THIAZOL-2-YLAMINO)PHENOXY)-N-(CYCLOPROPYLMETHYL)NICOTINAMIDE

To a 100 mL round bottomed flask was added 2-(4-(benzo[d]thiazol-2-ylamino)phenoxy)nicotinic acid (0.3031 g, 0.834 mmol), cyclopropylmethanamine (0.0869 g, 1.22 mmol), and triethylamine (0.347 mL, 2.50 mmol) in N,N-dimethylformamide (3 mL) to stir for 5 min. HATU (0.3955 g, 0.917 mmol) was then added and allowed to stir overnight. The reaction mixture was diluted with water (10 mL) and extracted with DCM (3×10 mL). The organic extract was washed with water (1×10 mL), saturated sodium chloride (1×10 mL), saturated sodium bicarbonate (1×10 mL), dried with magnesium sulfate, filtered, and concentrated. The crude product was purified by reverse-phase preparative HPLC using a Phenomenex Gemini™ column, 5 micron, 150×30 mm, 0.1% trifluoroacetic acid in acetonitrile/water, gradient 10% to 100% over 15 min. The product was taken up in DCM and extracted with saturated sodium bicarbonate to remove TFA salts to provide 2-(4-(benzo[d]thiazol-2-ylamino)phenoxy)-N-(cyclopropylmethyl)nicotinamide as a white powder. MS (ESI, pos. ion) m/z: 417 (M+1). IC50 (uM) +++.

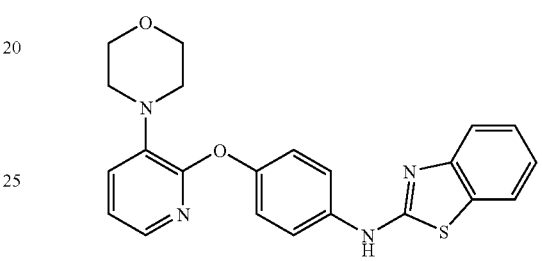

Example 75

N-(4-(3-MORPHOLINOPYRIDIN-2-YLOXY)PHENYL)BENZO[D]THIAZOL-2-AMINE

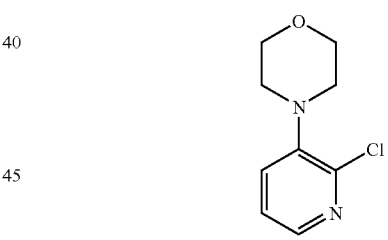

STEP 1. 4-(2-CHLOROPYRIDIN-3-YL)MORPHOLINE

To a glass microwave vial was added 3-bromo-2-chloropyridine (0.5489 g, 2.85 mmol), Pd$_2$(dba)$_3$ (0.131 g, 0.143 mmol), xantphos (0.165 g, 0.285 mmol), and sodium tert-butoxide (0.524 mL, 4.28 mmol). The vial was capped and placed under vacuum for 5 minutes. Morpholine (0.248 mL, 2.85 mmol) and toluene (2 mL) were added. The reaction was allowed to stir at 100° C. Upon completion, the reaction was allowed to cool to room temperature. Solvent was evaporated. The crude product was adsorbed onto a plug of silica gel and chromatographed through a Biotage pre-packed silica gel column (25M), eluting with a gradient of 10% to 80% EtOAc in hexane, to provide 4-(2-chloropyridin-3-yl)morpholine. MS: [M+H]=199.0.

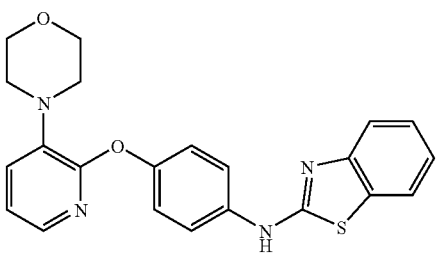

STEP 2. N-(4-(3-MORPHOLINOPYRIDIN-2-YLOXY)PHENYL)BENZO[D]THIAZOL-2-AMINE

To a round bottomed flask was added 4-(2-chloropyridin-3-yl)morpholine (0.2076 g, 1.045 mmol), 4-(benzo[d]thiazol-2-ylamino)phenol (0.304 g, 1.254 mmol), and cesium carbonate (0.409 g, 1.254 mmol) in DMSO (3.48 mL) at 80° C. for two days. The reaction was allowed to cool to room temperature. The reaction mixture was diluted with a 50% sodium chloride solution and extracted with DCM. The organic extract was washed with water, brine, dried with magnesium sulfate, filtered, and concentrated. The crude product was adsorbed onto a plug of silica gel and chromatographed through a Biotage pre-packed silica gel column (25M), eluting with a gradient of 10% to 100% EtOAc in hexane, to provide N-(4-(3-morpholinopyridin-2-yloxy)phenyl)benzo[d]thiazol-2-amine. MS (ESI, pos. ion) m/z: 405 (M+1). IC50 (uM) +++++.

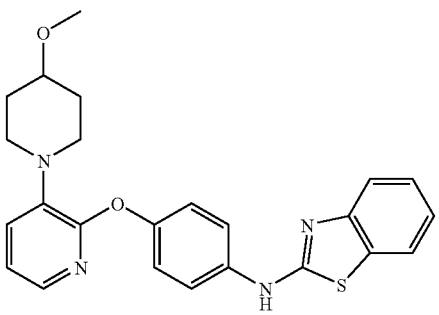

Example 76

N-(4-(3-(4-METHOXYPIPERIDIN-1-YL)PYRIDIN-2-YLOXY)PHENYL)BENZO[D]THIAZOL-2-AMINE

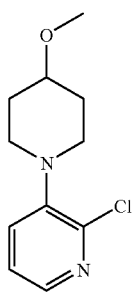

STEP 1. 2-CHLORO-3-(4-METHOXYPIPERIDIN-1-YL)PYRIDINE

A round-bottomed flask was charged with 3-bromo-2-chloropyridine (620 mg, 3.22 mmol), 4-methoxy-piperidine (371 mg, 3.22 mmol), tris(dibenzylideneacetone)dipalladium(0) (147 mg, 0.161 mmol), 9,9-dimethyl-4,5-bis(diphenylphosphino)xanthene (186 mg, 0.322 mmol), and sodium tert-butoxide (464 mg, 4.83 mmol) in toluene (6442 µL), sealed and then sparged with argon for 5 min. The reaction mixture was heated at 100° C. with stirring for 2 h. After cooling to RT, the reaction mixture was filtered through a pad of celite and purified by chromatography through a Redi-Sep pre-packed silica gel column (40 g), eluting with a gradient of 0% to 40% EtOAc in hexane, to provide 2-chloro-3-(4-methoxypiperidin-1-yl) as orange oil. MS (ESI, pos. ion) m/z: 226.8 (M+1).

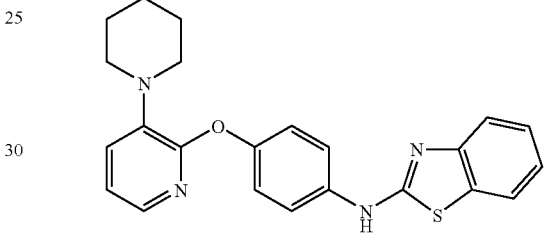

STEP 2. N-(4-(3-(4-METHOXYPIPERIDIN-1-YL)PYRIDIN-2-YLOXY)PHENYL)BENZO[D]THIAZOL-2-AMINE

The mixture of 2-chloro-3-(4-methoxypiperidin-1-yl)pyridine (25.0 mg, 0.11 mmol), 4-(benzo[d]thiazol-2-ylamino)phenol (32.1 mg, 0.132 mmol), $Pd_2(dba)_3$ (5.05 mg, 5.51 mmol), 2,2'-bis(diphenylphosphino)-1,1'-binaphthyl (5.15 mg, 8.27 µmol) and sodium 2-methylpropan-2-olate (26.5 mg, 0.276 mmol) in toluene (440 µL) was sparged under argon for 5 min. The mixture was heated to 120° C. in a microwave reactor for 10 min. More phenol (32 mg) was added and the reaction mixture was heated at 120° C. in microwave for another 25 min. After cooling to RT, the mixture was filtered through celite and washed with DCM. The crude product was purified by silica gel chromatography (12 g, 0-50% EtOAc-hexane) to give N-(4-(3-(4-methoxypiperidin-1-yl)pyridin-2-yloxy)phenyl)benzo[d]thiazol-2-amine as off-white solid. MS (ESI, pos. ion) m/z: 433.0 (M+1). IC50 (uM) +++++.

SCHEME 9

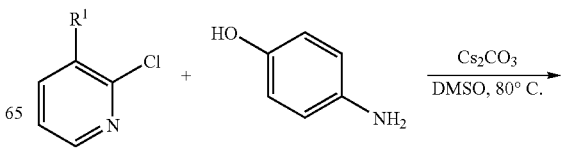

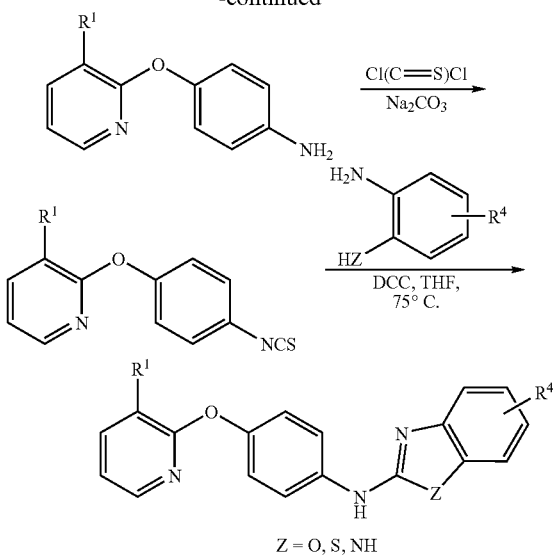

Z = O, S, NH

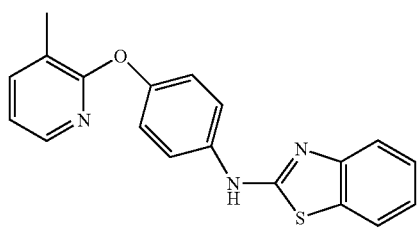

Example 77

N-(4-(3-METHYLPYRIDIN-2-YLOXY)PHENYL)
BENZO[D]THIAZOL-2-AMINE

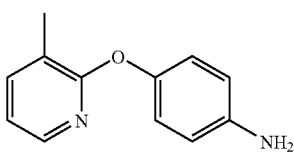

STEP 1.
4-(3-METHYLPYRIDIN-2-YLOXY)BENZENAMINE

To a solution of 4-aminophenol (0.87 g, 8.0 mmol) in DMSO (12 mL) was added cesium carbonate (3.1 g, 9.6 mmol) and 2-fluoro-3-picoline (0.89 g, 8.0 mmol). The resulting mixture was heated to 80° C. for 16 h. After cooling to RT, the reaction mixture was diluted with EtOAc and washed with water and brine several times to remove DMSO. The aqueous layer was back extracted with EtOAc and the combined organic layer was dried (Na$_2$SO$_4$) and concentrated. The crude product was chromatographed through a Redi-Sep® pre-packed silica gel column (120 g), eluting with a gradient of 0% to 30% EtOAc in hexane, to provide 4-(3-methylpyridin-2-yloxy)benzenamine as tan solid. MS (ESI, pos. ion) m/z: 201.2 (M+1).

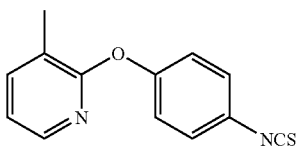

STEP 2. 2-(4-ISOTHIOCYANATOPHENOXY)-3-METHYLPYRIDINE

In a round bottomed flask were added 4-(3-methylpyridin-2-yloxy)benzenamine (100 mg, 0.5 mmol), O,O-dipyridin-2-yl carbonothioate (122 mg, 0.52 mmol) and DCM (2 mL). The reaction mixture was stirred at RT for 16 h. The reaction was partitioned between DCM and water, brine. The aqueous layer was extracted with DCM and the combined organics was dried (Na$_2$SO$_4$) and concentrated to give 2-(4-isothiocyanatophenoxy)-3-methylpyridine as tan solid. MS (ESI, pos. ion) m/z: 243.1 (M+1).

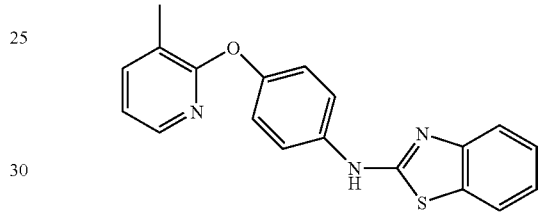

STEP 3. N-(4-(3-METHYLPYRIDIN-2-YLOXY)PHENYL)BENZO[D]THIAZOL-2-AMINE

A mixture of 2-(4-isothiocyanatophenoxy)-3-methylpyridine (136 mg, 0.56 mmol), 2-aminothiophenol (72 μL, 0.67 mmol), and N,N'-dicyclohexylcarbodiimide (174 mg, 0.84 mmol) in THF (5 mL) was heated at 75° C. for 16 h. The solvent was evaporated and the crude product was purified by reverse-phase preparative HPLC using a Phenomenex Gemini™ column (10 micron, C18, 110 Å, 150×30 mm), 0.1% TFA in CH$_3$CN/H$_2$O as eluent, a gradient 10% to 100% over 14 min., to provide the TFA salt of N-(4-(3-methylpyridin-2-yloxy)phenyl)benzo[d]thiazol-2-amine as off-white solid. MS (ESI, pos. ion) m/z: 334.1 (M+1). IC50 (uM) ++++.

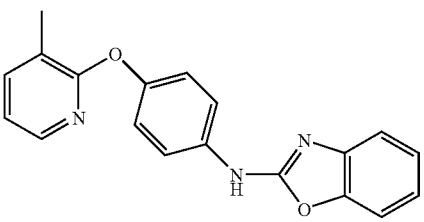

Example 78

N-(4-(3-METHYLPYRIDIN-2-YLOXY)PHENYL)BENZO[D]OXAZOL-2-AMINE

The mixture of 2-(4-isothiocyanatophenoxy)-3-methylpyridine (136 mg, 0.56 mmol), 2-aminophenol (74 mg, 0.67 mmol), and N,N'-dicyclohexylcarbodiimide (174 mg, 0.84 mmol) in THF (5 mL) was heated at 75° C. for 16 h. The solvent was evaporated and the crude product was chromatographed through a Redi-Sep® pre-packed silica gel column (40 g), eluting with a gradient of 0% to 30% EtOAc in hexane, to provide N-(4-(3-methylpyridin-2-yloxy)phenyl)benzo[d]oxazol-2-amine as white solid. MS (ESI, pos. ion) m/z: 318.1 (M+1).

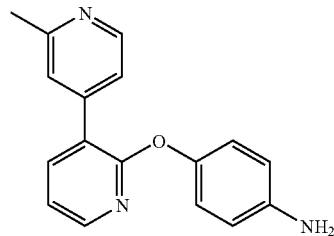

STEP 2. 4-(3-(2-METHYLPYRIDIN-4-YL)PYRIDIN-2-YLOXY)BENZENAMINE

To a 25 mL round bottomed flask was added 2-fluoro-3-(2-methylpyridin-4-yl)pyridine (0.7204 g, 3.828 mmol), 4-aminophenol (0.4254 g, 3.832 mmol), and cesium carbonate (1.6144 g, 4.593 mmol) in dimethyl sulfoxide at 90° C. Upon completion, the reaction was filtered through Celite™ and the filtrate was condensed. The reaction mixture was diluted with water (50 mL) and extracted with DCM (3×20 mL). The organic extract was washed with water (3×15 mL), brine (3×15 mL), dried with magnesium sulfate, filtered, and concentrated. The crude product was adsorbed onto a plug of silica gel and chromatographed through a Biotage™ pre-packed silica gel column (40M), eluting with a gradient of 1% to 5% methanol in DCM, to provide 4-(3-(2-methylpyridin-4-yl)pyridin-2-yloxy)benzenamine.

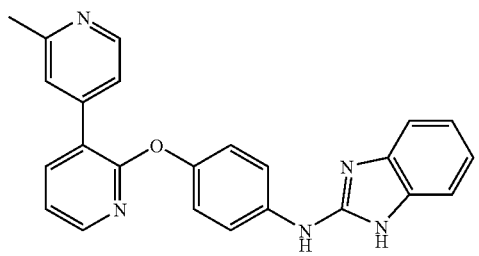

Example 79

N-(4-(3-(2-METHYLPYRIDIN-4-YL)PYRIDIN-2-YLOXY)PHENYL)-1H-BENZO[D]IMIDAZOL-2-AMINE

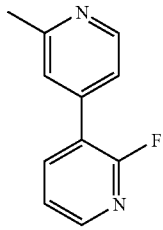

STEP 1. 4-(2-FLUOROPYRIDIN-3-YL)-2-METHYLPYRIDINE

To a round bottomed flask was added 3-bromo-2-fluoropyridine (1.0376 g, 5.9 mmol), 2-methylpyridin-4-ylboronic acid (1.6154 g, 12 mmol), tris(dibenzylideneacetone)dipalladium(o) (0.5501 g, 0.59 mmol), 2-dicyclohexylphosphino-2',6'-dimethoxy-1,1'-biphenyl (0.4846 g, 1.2 mmol), and sodium carbonate (0.74 mL, 18 mmol) in acetonitrile:water (5:1 ratio) at 85° C. to stir overnight. The reaction was monitored by LCMS. Upon completion, the solvents were evaporated. The crude product was adsorbed onto a plug of silica gel and chromatographed through a Biotage™ pre-packed silica gel column (40S), eluting with a gradient of 0.5% to 5% methanol in DCM, to provide 4-(2-fluoropyridin-3-yl)-2-methylpyridine. [M+1]=189.0.

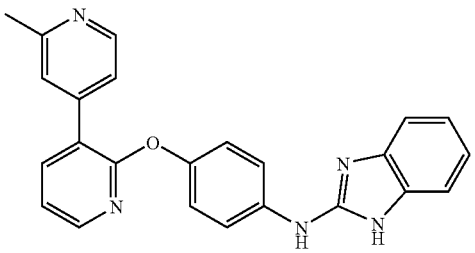

STEP 3. N-(4-(3-(2-METHYLPYRIDIN-4-YL)PYRIDIN-2-YLOXY)PHENYL)-1H-BENZO[D]IMIDAZOL-2-AMINE

To a 15 mL round bottomed flask was added 4-(3-(2-methylpyridin-4-yl)pyridin-2-yloxy)benzenamine (0.0978 g, 0.35 mmol) and sodium carbonate (0.0823 g, 0.78 mmol) in chloroform. Thiophosgene (0.030 mL, 0.39 mmol) was slowly added and allowed to stir overnight. The solution was filtered and concentrated to give 2-(4-isothiocyanatophenoxy)-3-(2-methylpyridin-4-yl)pyridine. To the flask was then added 1,2-phenylenediamine (0.0470 g, 0.410 mmol), and N,N'-dicyclohexylcarbodiimide (0.1032 g, 0.5200 mmol) in tetrahydrofuran at 75° C. to stir overnight. Upon completion, the solvent was evaporated. The crude product was adsorbed onto a plug of silica gel and chromatographed through a Biotage™ pre-packed silica gel column (25M), eluting with a gradient of 1% to 5% methanol in DCM, to provide N-(4-(3-(2-methylpyridin-4-yl)pyridin-2-yloxy)phenyl)-1H-benzo[d]imidazol-2-amine. MS (ESI, pos. ion) m/z: 394.1 (M+1). IC50 (uM) +++++.

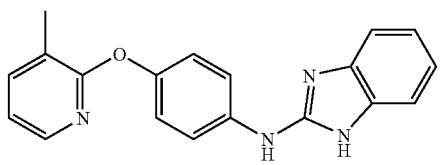

Example 80

N-(4-(3-METHYLPYRIDIN-2-YLOXY)PHENYL)-1H-BENZO[D]IMIDAZOL-2-AMINE

A mixture of 4-(3-methylpyridin-2-yloxy)benzenamine (1.00 g, 4.99 mmol) and 2-chlorobenzimidazole (0.860 g, 5.64 mmol) in 10 mL of iPrOH was heated at 170° C. for 30 min in the microwave. The reaction mixture was evaporated onto silica gel. Purification by flash chromatography (2M NH$_3$ in MeOH:CH$_2$Cl$_2$) afforded N-(4-(3-methylpyridin-2-yloxy)phenyl)-1H-benzo[d]imidazol-2-amine as solid. MS (ESI, pos. ion) m/z: 317.1 (M+1). IC50 (uM) ++++.

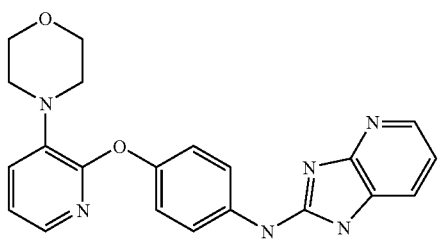

Example 81

N-(4-(3-MORPHOLINOPYRIDIN-2-YLOXY)PHENYL)-1H-IMIDAZO[4,5-B]PYRIDIN-2-AMINE

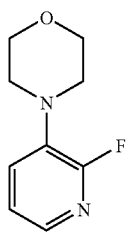

STEP 1. 4-(2-FLUOROPYRIDIN-3-YL)MORPHOLINE

A microwave reaction vessel was charged with 2-fluoro-3-iodopyridine (1.0211 g, 4.579 mmol), morpholine (0.3989 mL, 4.579 mmol), Pd$_2$(dba)$_3$ (0.2633 g, 0.2748 mmol), 2-dicyclohexylphosphino-2',6'-dimethoxy-1,1'-biphenyl (0.2232 g, 0.5495 mmol), and sodium t-butoxide (1.1363 g, 13.74 mmol) in toluene (15 mL). The reaction mixture was stirred and heated in a Discover® model microwave reactor (CEM, Matthews, N.C.) at 150° C. for 20 min (125 watts, Powermax™ feature on, ramp time 5 min). The solvent was evaporated. The crude product was adsorbed onto a plug of silica gel and chromatographed through a Biotage™ pre-packed silica gel column (40M), eluting with a gradient of 1% to 5% methanol in DCM, to provide 4-(2-fluoropyridin-3-yl)morpholine.

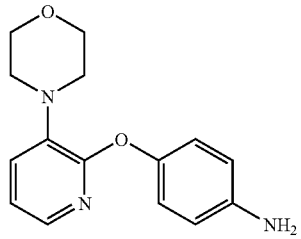

STEP 2. 4-(3-MORPHOLINOPYRIDIN-2-YLOXY)BENZENAMINE

To a 25 mL round-bottomed flask were added 4-(2-fluoropyridin-3-yl)morpholine (0.523 g, 2.87 mmol), 4-aminophenol (0.451 g, 2.88 mmol), cesium carbonate (1.18 g, 3.45 mmol) and DMSO (5 mL). The reaction mixture was heated at 120° C. for 8 h. After cooling to room temperature, the reaction mixture was filtered through SCX cartridges, and rinsed with DCM, MeOH, and 2.0 ammonia in MeOH. The ammonia rinses were combined and concentrated. The crude product was adsorbed onto a plug of silica gel and chromatographed through a Biotage pre-packed silica gel column (40M), eluting with a gradient of 1% to 5% MeOH in CH$_2$Cl$_2$, to provide 4-(3-morpholinopyridin-2-yloxy)benzenamine. MS: [M+1]=272.1

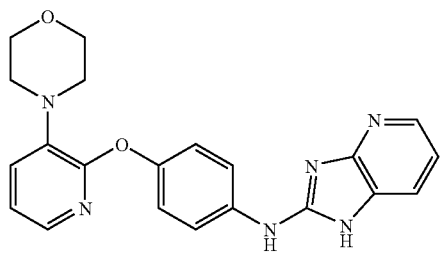

STEP 3. N-(4-(3-MORPHOLINOPYRIDIN-2-YLOXY)PHENYL)-1H-IMIDAZO[4,5-B]PYRIDIN-2-AMINE

To a 15 mL round-bottomed flask was added 4-(3-morpholinopyridin-2-yloxy)benzenamine (0.313 g, 1.15 mmol) and SODIUM CARBONATE (0.271 g, 2.54 mmol) in CHCl$_3$. Thiophosgene (0.098 ml, 1.27 mmol) was slowly added and the reaction was allowed to stir at RT for 16 h. The reaction mixture was filtered and the filtrate was concentrated to give the title compound. MS: [M+1]=314.0. IC50 (uM) ++++.

SCHEME 10

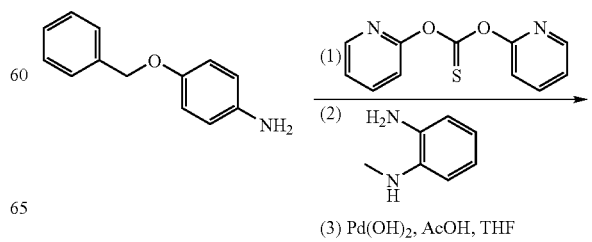

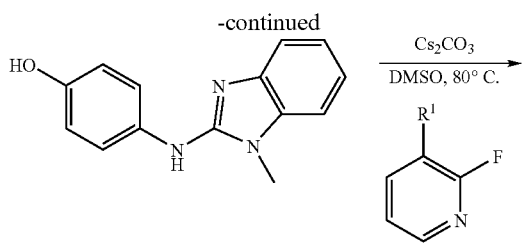

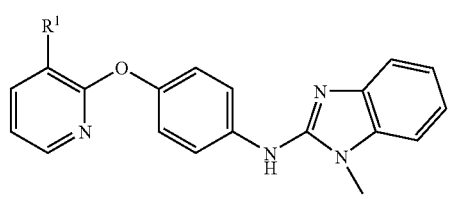

Example 82

2-(4-(1-METHYL-1H-BENZO[D]IMIDAZOL-2-YLAMINO)PHENOXY)NICOTINONITRILE

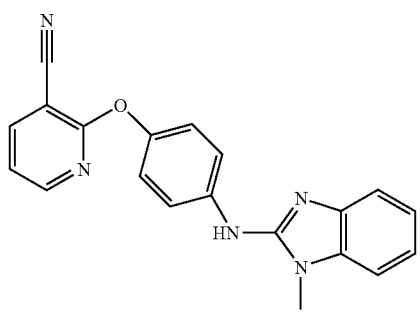

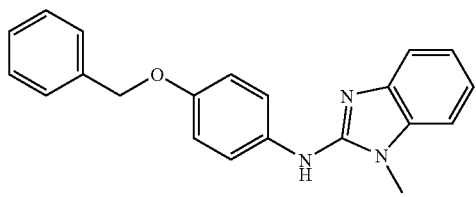

STEP 1. (4-BENZYLOXY-PHENYL)-(1-METHYL-1H-BENZOIMIDAZOL-2-YL)-AMINE

To a solution of 4-benzyloxy-phenylamine (2 g, 8.4 mmol) in 30 mL of DCM was added triethylamine (1 mL) and di-2-pyridylthionocarbonate (2.5 g, 8.4 mmol). The resulting mixture was stirred at RT for 2 h. The reaction mixture was diluted with DCM and washed with water and brine. The organic layer was then dried over $Na_2SO_4$, filtered and concentrated. The residue was dissolved in 30 mL DMF, N-me- thyl-benzene-1,2-diamine (1.5 g, 12.7 mmol) and EDCI (2 g, 10.5 mmol). The resulting mixture was heated at 70° C. for 4 h. The reaction was cooled to RT, diluted with ethyl acetate and washed with water and brine. Purification by silica gel chromatography (98:2 chlorforma/MeOH) afforded the desired product (4-benzyloxy-phenyl)-(1-methyl-1H-benzoimidazol-2-yl)-amine. [M+1]=330.1

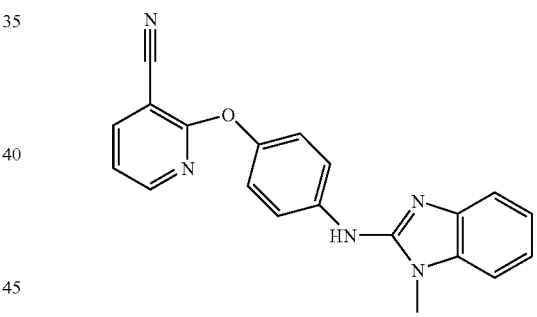

STEP 2. 4-(1-METHYL-1H-BENZOIMIDAZOL-2-YLAMINO)-PHENOL

To a solution of compound (4-benzyloxy-phenyl)-(1-methyl-1H-benzoimidazol-2-yl)-amine (1.8 g, 5.4 mmol) in 18 mL of THF and 18 mL of MeOH was added $Pd(OH)_2$ (0.36 g, 20%) and 9 mL of acetic acid. The resulting mixture was kept and kept at 50 psi $H_2$ atmosphere for 3 h. The reaction mixture was then filtered over a cake of Celite™. The filtrate was concentrated and purified by silica gel column chromatography (EtOAc/hexane) to get desired product 4-(1-methyl-1H-benzoimidazol-2-ylamino)-phenol. [M+1]=240

STEP 3. 2-(4-(1-METHYL-1H-BENZO[D]IMIDAZOL-2-YLAMINO)PHENOXY)NICOTINONITRILE

To a solution of 4-(1-methyl-1H-benzo[d]imidazol-2-ylamino)phenol (120 mg, 0.5 mmol) in DMSO (1 mL) was added cesium carbonate (196 mg, 0.6 mmol) and 2-fluoronicotinonitrile (61 mg, 0.5 mmol). The resulting mixture was heated to 80° C. for 16 h. After cooling to RT, the reaction mixture was diluted with EtOAc and washed with water and brine several times to remove DMSO. The aqueous layer was back extracted with EtOAc (3×) and the combined organic layer was dried ($Na_2SO_4$) and concentrated. The crude product was chromatographed through a Redi-Sep® pre-packed silica gel column (40 g), eluting with a gradient of 0% to 5% of MeOH in $CH_2Cl_2$, followed by trituration with ether, to provide 2-(4-(1-methyl-1H-benzo[d]imidazol-2-ylamino) phenoxy)nicotinonitrile as off-white solid. MS (ESI, pos. ion) m/z: 342.2 (M+1). IC50 (uM) +++++.

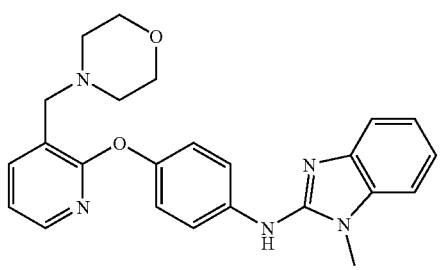

Example 83

1-METHYL-N-(4-(3-(MORPHOLINOMETHYL)PYRIDIN-2-YLOXY)PHENYL)-1H-BENZO[D]IMIDAZOL-2-AMINE

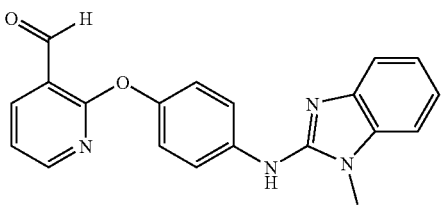

STEP 1. 2-(4-(1-METHYL-1H-BENZO[D]IMIDAZOL-2-YLAMINO)PHENOXY)NICOTINALDEHYDE

A solution of 2-chloropyridine-3-carboxaldehyde (3 g, 21 mmol), 4-(1-methyl-1H-benzo[d]imidazol-2-ylamino)phenol (5 g, 21 mmol), CESIUM CARBONATE (10 g, 32 mmol) in DMSO (60 mL) was heated to 80° C. overnight. Purification by aqueous workup (water, brine) and DCM extraction then Biotage (0-10% DCM/MeOH) produced product which partially solidified.

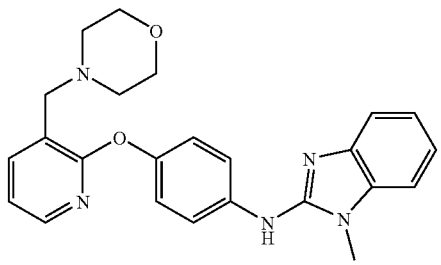

STEP 2. 1-METHYL-N-(4-(3-(MORPHOLINOMETHYL)PYRIDIN-2-YLOXY)PHENYL)-1H-BENZO[D]IMIDAZOL-2-AMINE

To a suspension of 2-(4-(1-methyl-1H-benzo[d]imidazol-2-ylamino)phenoxy)nicotinaldehyde (0.2 g, 0.6 mmol) in DCM (2 mL) was added morpholine (0.05 mL, 0.6 mmol). Sodium triacetoxyborohydride (0.1 g, 0.6 mmol) was added and the resulting mixture was stirred for 3 h at RT. LC/MS showed complete conversion. The reaction mixture was purified by silica gel chromatography (0-10% MeOH/DCM) to afford product 1-methyl-N-(4-(3-(morpholinomethyl)pyridin-2-yloxy)phenyl)-1H-benzo[d]imidazol-2-amine as solid. MS (ESI, pos. ion) m/z: 416.1 (M+1). IC50 (uM) +++++.

SCHEME 11

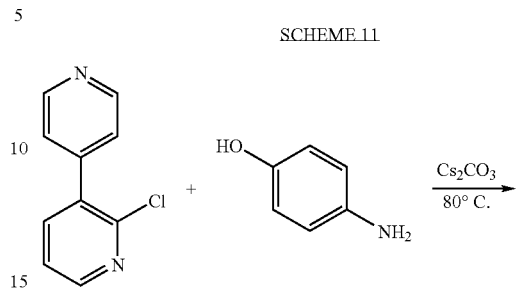

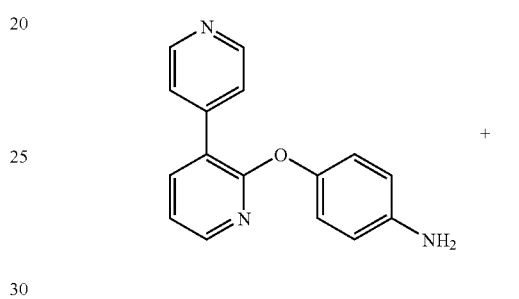

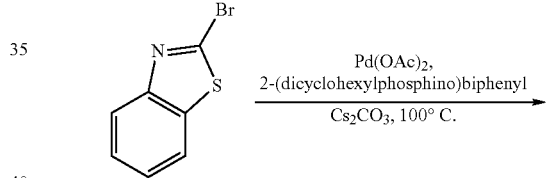

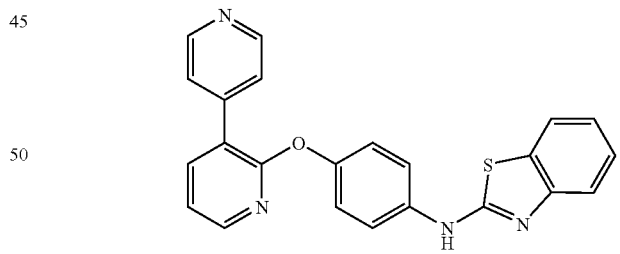

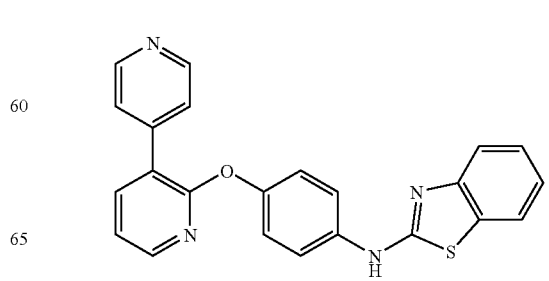

Example 84

N-(4-(3,4'-BIPYRIDIN-2-YLOXY)PHENYL)BENZO[D]THIAZOL-2-AMINE

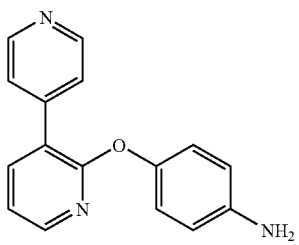

STEP 1. 4-(3,4'-BIPYRIDIN-2-YLOXY)ANILINE

To a 50 mL round-bottomed flask was added 2-chloro-3-(pyridin-4-yl)pyridine (0.75031 g, 3.9 mmol), 4-aminophenol (0.4302 g, 3.9 mmol), cesium carbonate (0.38 ml, 4.7 mmol) in DMSO at 80° C. Upon completion, the reaction was allowed to cool to room temperature. The reaction mixture was diluted with water (10 ml) and extracted with DCM (3 15 mL). The organic extract was washed with water (1 10 mL), brine (1 10 mL), dried with magnesium sulfate, filtered and concentrated. The residue was taken up in DCM and was loaded onto a SCX cartridge. The impurities were filtered off with DCM and MeOH. 4-(3,4'-Bipyridin-2-yloxy)aniline was filtered from cartridge using 2.0M ammonia in MeOH (MS 264.0).

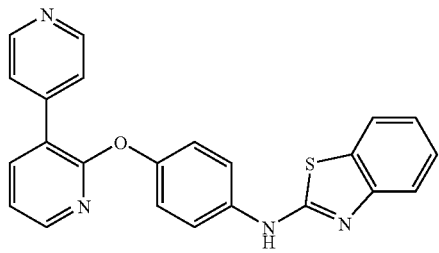

STEP 2. N-(4-(3,4'-BIPYRIDIN-2-YLOXY)PHENYL)BENZO[D]THIAZOL-2-AMINE

A 25 ml round bottomed flask was charged with 4-(3-(pyridin-4-yl)pyridin-2-yloxy)benzenamine (0.1531 g, 0.58 mmol), 2-bromobenzo[d]thiazole (0.1874 g, 0.88 mmol), Palladium acetate (0.0264 g, 0.12 mmol), 2-(dicyclohexylphosphino)biphenyl (0.0878 g, 0.23 mmol), and cesium carbonate (0.077 ml, 0.81 mmol) in toluene/t-BuOH (5/1) at 100° C. overnight. Upon completion, the reaction was allowed to cool to room temperature. The crude product was adsorbed onto a plug of silica gel and chromatographed through a Biotage pre-packed silica gel column (25M), eluting with a gradient of 1% to 5% MeOH in DCM. Further purification was performed by reverse-phase preparative HPLC using a Phenomenex Gemini column, 5 micron, 150× 30 mm, 0.1% TFA in ACN/H$_2$O, gradient 10% to 100% over 15 min. The product peak fractions were collected and organic solvents were removed. The aqueous solution was diluted with water (5 mL) and sodium bicarbonate was added until the pH ~10. The solution was extracted with DCM. The organic extract was washed with water, brine, dried with magnesium sulfate, filtered, and concentrated to provide N-(4-(3,4'-bipyridin-2-yloxy)phenyl)benzo[d]thiazol-2-amine. MS (ESI, pos. ion) m/z: 397.0 (M+1). IC50 (uM) +++++.

SCHEME 12

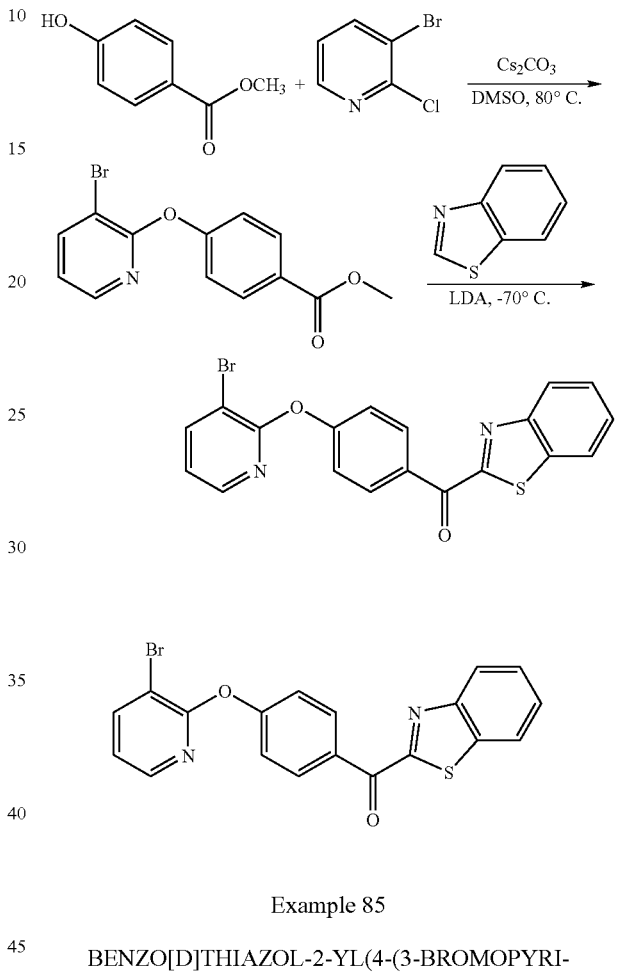

Example 85

BENZO[D]THIAZOL-2-YL(4-(3-BROMOPYRIDIN-2-YLOXY)PHENYL)METHANONE

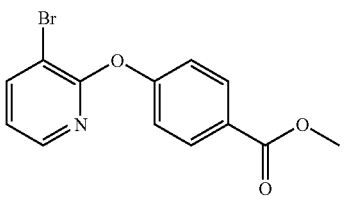

STEP 1. BENZOTHIAZOL-2-YL-[4-(3-BROMOPYRIDIN-2-YLOXY)-PHENYL]-METHANONE

In a 250 mL round-bottomed flask was added methyl 4-hydroxybenzoate (6 g, 38.7 mmol) and 100 ml of DMF. 3-Bromo-2-chloro-pyridine (7.43 g, 38.7 mmol) and cesium carbonate (20 g, 76.4 mmol) were added to the mixture and the reaction was stirred at 90° C. for 6 h. The reaction mixture was diluted with cold water to let the product precipitate out. The solid was collected by filtration and the crude product was purified by silica gel column chromatography with hexane and ethyl acetate to give the title compound.

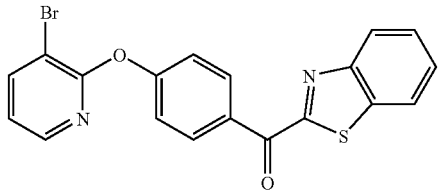

STEP-2. BENZOTHIAZOL-2-YL-[4-(3-BROMO-PYRIDIN-2-YLOXY)-PHENYL]-METHANONE

In a 250 ml round-bottomed flask were charged benzothiazol-2-yl-[4-(3-bromo-pyridin-2-yloxy)-phenyl]-methanone (4 g, 15.2 mmol), benzothiozole (2.06 g, 15.2 mmol) and 100 mL dry THF. The reaction mixture was cooled to −70° C., LDA (2.0 M, 45.6 mL) was added slowly for 5 min and the resulting mixture was stirred at −70° C. for 2 h. The reaction mixture was quenched with 1N HCl and extracted to ethyl acetate. The organic layer was washed with brine solution, dried over anhydrous sodium sulphate and concentrated. The crude product was recrystallized from hexane/ethyl acetate mixture to give the title compound. MS (ESI, pos. ion) m/z: 413 (M+1). IC50 (uM) +.

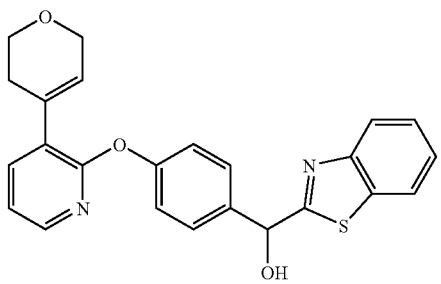

Example 86

BENZO[D]THIAZOL-2-YL(4-(3-(3,6-DIHYDRO-2H-PYRAN-4-YL)PYRIDIN-2-YLOXY)PHENYL)METHANOL

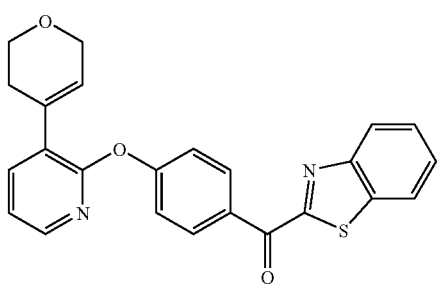

STEP 1. BENZO[D]THIAZOL-2-YL(4-(3-(3,6-DIHYDRO-2H-PYRAN-4-YL)PYRIDIN-2-YLOXY)PHENYL)METHANONE

To a glass microwave vial was added benzo[d]thiazol-2-yl (4-(3-bromopyridin-2-yloxy)phenyl)methanone (1.0902 g, 2.65 mmol), 2-(3,6-dihydro-2H-pyran-4-yl)-4,4,5,5-tetramethyl-1,3,2-dioxaborolane (1.114 g, 5.30 mmol), trans-dichlorobis(triphenylphosphine) palladium (II) (0.149 g, 0.212 mmol), and sodium carbonate (0.843 g, 7.95 mmol) in DMF (6.63 mL) and water (2.209 mL). The reaction mixture was stirred and heated in a Biotage Initiator microwave reactor at 120° C. for 20 min. Solvent was evaporated. The crude product was adsorbed onto a plug of silica gel and chromatographed through a Biotage pre-packed silica gel column (40S), eluting with a gradient of 5% to 50% EtOAc in hexane, to provide benzo[d]thiazol-2-yl(4-(3-(3,6-dihydro-2H-pyran-4-yl)pyridin-2-yloxy)phenyl)methanone. MS (ESI, pos. ion) m/z: 414.8 (M+1).

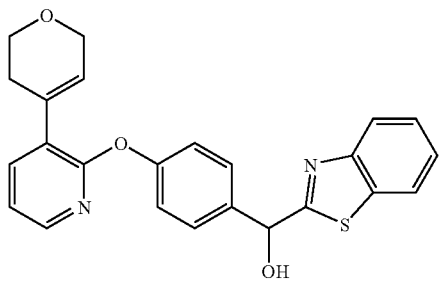

STEP 2. BENZO[D]THIAZOL-2-YL(4-(3-(3,6-DIHYDRO-2H-PYRAN-4-YL)PYRIDIN-2-YLOXY)PHENYL)METHANOL

To a round bottomed flask was added benzo[d]thiazol-2-yl (4-(3-(3,6-dihydro-2H-pyran-4-yl)pyridin-2-yloxy)phenyl) methanone (0.6000 g, 1.448 mmol) in THF (4.83 mL). Palladium hydroxide (0.051 g, 0.072 mmol) was added. The round bottomed flask was flushed with N₂(g) followed by vacuum repeating the process three times. A balloon of H₂(g) was then added to the reaction. Reaction was filtered through celite. The crude product was purified by reverse-phase preparative HPLC using a Phenomenex Synergi column, 4 micron, MAX-RP, 80 Å, 150×30 mM, 0.1% TFA in ACN/H₂O, gradient 50% to 100% over 15 min to provide benzo[d]thiazol-2-yl(4-(3-(3,6-dihydro-2H-pyran-4-yl)pyridin-2-yloxy)phenyl)methanol. MS (ESI, pos. ion) m/z: 416.9 (M+1). IC50 (uM) +++.

SCHEME 13

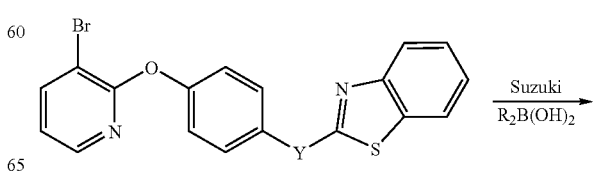

-continued

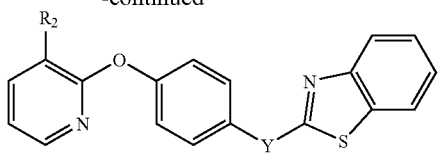

Y = NH, or CO

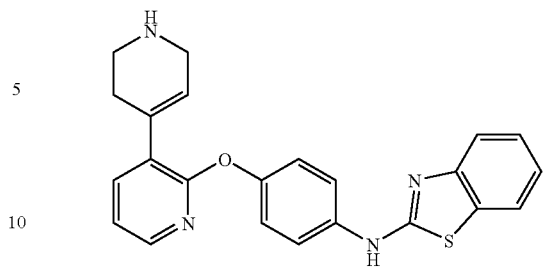

STEP 2. N-(4-(3-(1,2,3,6-TETRAHYDROPYRI-DIN-4-YL)PYRIDIN-2-YLOXY)PHENYL)BENZO[D]THIAZOL-2-AMINE

Tert-butyl 4-(2-(4-(benzo[d]thiazol-2-ylamino)phenoxy)pyridin-3-yl)-5,6-dihydropyridine-1(2H)-carboxylate (501.9 mg) was taken up in DCM and TFA was added. Upon completion, the solvent was evaporated. The residue was taken up in DCM and loaded onto an Agilent SCX cartridge. The impurities were washed from the cartridge with DCM and MeOH. N-(4-(3-(1,2,3,6-tetrahydropyridin-4-yl)pyridin-2-yloxy)phenyl)benzo[d]thiazol-2-amine was filtered from cartridge using 2.0M ammonia in MeOH. MS (ESI, pos. ion) m/z: 401.0 (M+1). IC50 (uM) +++++.

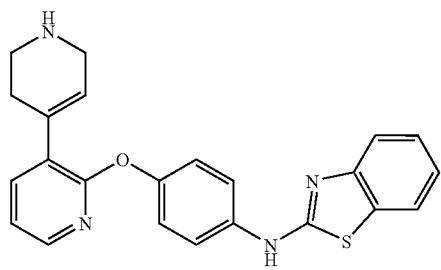

Example 87

N-(4-(3-(1,2,3,6-TETRAHYDROPYRIDIN-4-YL)PYRIDIN-2-YLOXY)PHENYL)BENZO[D]THIAZOL-2-AMINE

SCHEME 14

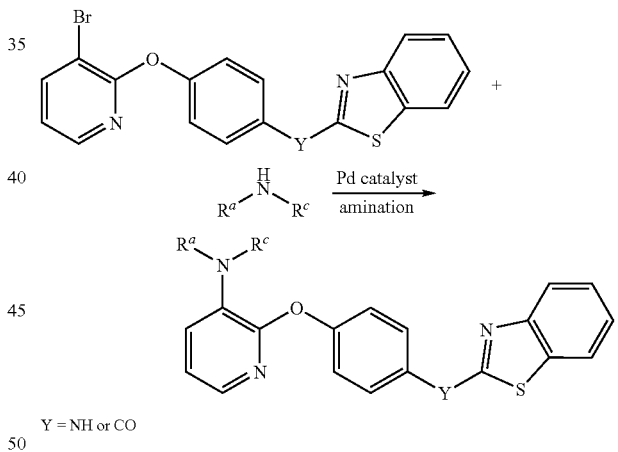

Y = NH or CO

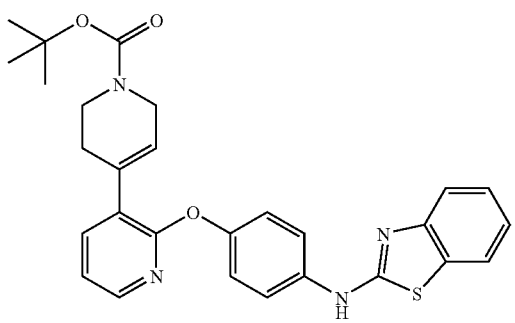

STEP 1. TERT-BUTYL 4-(2-(4-(BENZO[D]THIAZOL-2-YLAMINO)PHENOXY)PYRIDIN-3-YL)-5,6-DIHYDROPYRIDINE-1(2H)-CARBOXYLATE

To a round-bottomed flask was added N-(4-(3-bromopyridin-2-yloxy)phenyl)benzo[d]thiazol-2-amine (0.5770 g, 1.449 mmol), 1-(tert-butoxycarbonyl)-1,2,3,6-tetrahydropyridin-4-ylboronic acid (0.987 g, 4.35 mmol), PdCl$_2$(dppf) (0.080 g, 0.145 mmol), and sodium carbonate (0.768 g, 7.24 mmol) in DME (3.62 mL) and Water (1.207 mL) at 80° C. to stir overnight. Reaction allowed to cool to room temperature. Solvent was removed. The crude product was adsorbed onto a plug of silica gel and chromatographed through a Redi-Sep® pre-packed silica gel column (40 g), eluting with a gradient of 5% to 80% EtOAc in hexane, to provide tert-butyl 4-(2-(4-(benzo[d]thiazol-2-ylamino)phenoxy)pyridin-3-yl)-5,6-dihydropyridine-1(2H)-carboxylate. MS (ESI, pos. ion) m/z: 501.0 (M+1).

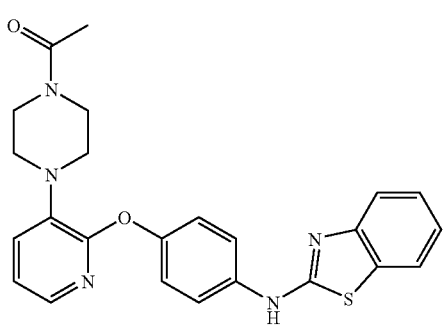

Example 88

1-(4-(2-(4-(BENZO[D]THIAZOL-2-YLAMINO) PHENOXY)PYRIDIN-3-YL)PIPERAZIN-1-YL) ETHANONE

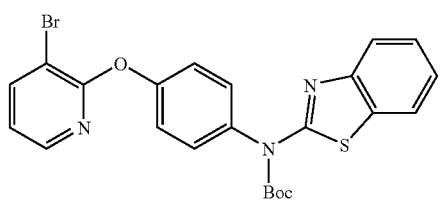

STEP 1. TERT-BUTYL BENZO[D]THIAZOL-2-YL(4-(3-BROMOPYRIDIN-2-YLOXY)PHENYL) CARBAMATE

To a round bottomed flask was added N-(4-(3-bromopyridin-2-yloxy)phenyl)benzo[d]thiazol-2-amine (4.41 g, 11.06 mmol), di-t-butyl dicarbonate (2.449 g, 11.22 mmol), and dmap (2.095 g, 17.14 mmol) to stir overnight in THF at 50° C. Upon completion, the solvent was evaporated. The crude product was taken up in water and extracted with DCM. The organic layer was washed with water, brine, dried with magnesium sulfate, filtered, and concentrated to provide tent-Butyl benzo[d]thiazol-2-yl(4-(3-bromopyridin-2-yloxy)phenyl)carbamate. MS (ESI, pos. ion) m/z: 499.9 (M+1).

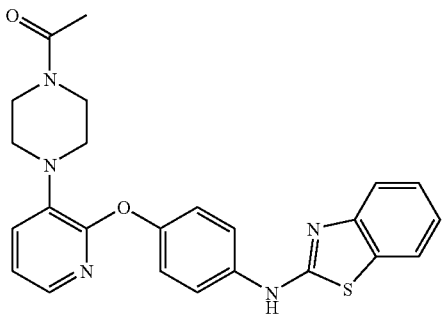

STEP 2. 1-(4-(2-(4-(BENZO[D]THIAZOL-2-YLAMINO)PHENOXY)PYRIDIN-3-YL)PIPERAZIN-1-YL)ETHANONE

To a round bottomed flask was added tert-butyl benzo[d]thiazol-2-yl(4-(3-bromopyridin-2-yloxy)phenyl)carbamate (0.2713 g, 0.544 mmol), 1-(piperazin-1-yl)ethanone (0.140 g, 1.089 mmol), Pd$_2$(dba)$_3$ (0.050 g, 0.054 mmol), binap (0.068 g, 0.109 mmol), and cesium carbonate (0.174 mL, 2.177 mmol) in toluene to stir at 100° C. overnight. Reaction was allowed to cool to room temperature. Solvent was evaporated. The crude product was purified by reverse-phase preparative HPLC using a Phenomenex Synergi column, 4 micron, MAX-RP, 80 Å, 150×30 mM, 0.1% TFA in ACN/H$_2$O, gradient 10% to 100% over 15 min to provide tert-butyl 4-(3-(4-acetylpiperazin-1-yl)pyridin-2-yloxy)phenyl(benzo[d]thiazol-2-yl)carbamate (MS 545.6). It was taken up in DCM and TFA was added. After purification the title compound was obtained. MS (ESI, pos. ion) m/z: 446.1 (M+1). IC50 (uM) +++++.

SCHEME 15

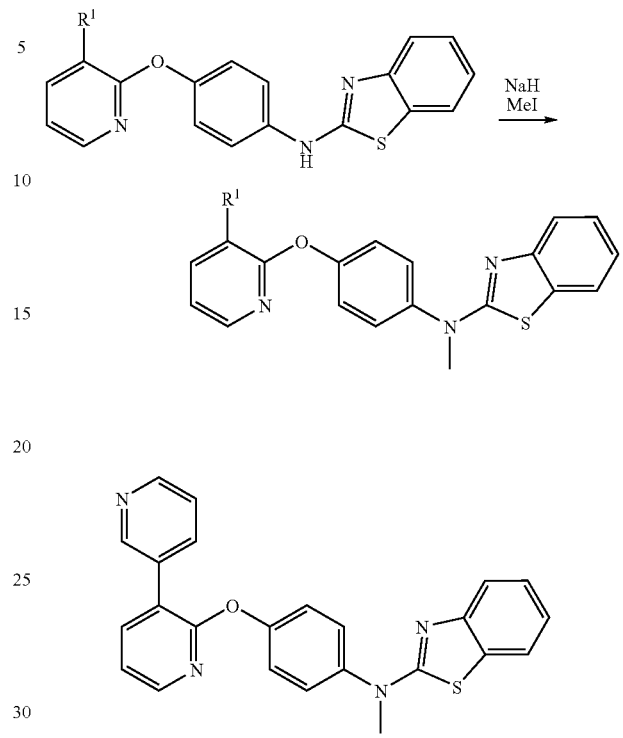

Example 89

N-(4-(3,3'-BIPYRIDIN-2-YLOXY)PHENYL)-N-METHYLBENZO[D]THIAZOL-2-AMINE

To a solution of N-(4-(3,3'-bipyridin-2-yloxy)phenyl)benzo[d]thiazol-2-amine (Example 4 from Table 1a; 0.377 g, 0.950 mmol) in DMF (3.17 mL) was added sodium hydride (0.095 g, 2.375 mmol). The reaction was allowed to stir for 10 minutes. Methyl iodide (0.059 mL, 0.950 mmol) was added and allowed to stir. The reaction mixture was diluted with water to quench and extracted with DCM. The organic extract was washed with water, brine, dried with magnesium sulfate, filtered, and concentrated. The crude product was purified by reverse-phase preparative HPLC using a Phenomenex Synergi column, 4 micron, MAX-RP, 80 Å, 150×30 mM, 0.1% TFA in ACN/H$_2$O, gradient 10% to 100% over 15 min to provide N-(4-(3,3'-Bipyridin-2-yloxy)phenyl)-N-methylbenzo[d]thiazol-2-amine. MS (ESI, pos. ion) m/z: 410.9 (M+1). IC50 (uM) +++++.

SCHEME 16

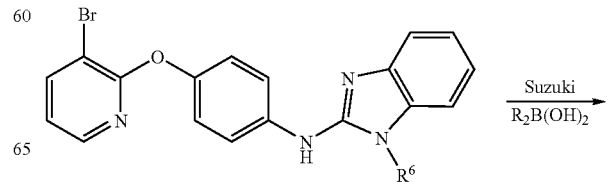

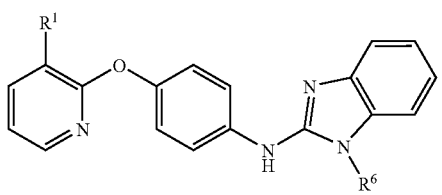

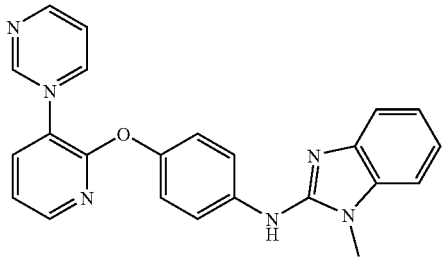

STEP 2. N-(4-(3,3'-BIPYRIDIN-2-YLOXY)PHENYL)-1-METHYL-1H-BENZO[D]IMIDAZOL-2-AMINE

To a microwave vial was added N-(4-(3-bromopyridin-2-yloxy)phenyl)-1-methyl-1H-benzo[d]imidazol-2-amine (0.2082 g, 0.527 mmol), pyridin-3-ylboronic acid (0.194 g, 1.580 mmol), PdCl$_2$(PPh$_2$iPr$_2$)$_2$ (0.020 g, 0.032 mmol), and sodium carbonate (0.279 g, 2.63 mmol) in DME (1.317 mL) and Water (0.439 mL). The reaction mixture was stirred and heated in a Discover® model microwave reactor (CEM, Matthews, N.C.) at 100° C. for 15 min (60 watts, Powermax feature on, ramp time 5 min). The crude product was adsorbed onto a plug of silica gel and chromatographed through a Redi-Sep® pre-packed silica gel column (40 g), eluting with a gradient of 1% to 5% MeOH in DCM, to provide N-(4-(3,3'-bipyridin-2-yloxy)phenyl)-1-methyl-1H-benzo[d]imidazol-2-amine. MS (ESI, pos. ion) m/z: 394.0 (M+1). IC50 (uM) +++++.

$R^6$ = H or Me

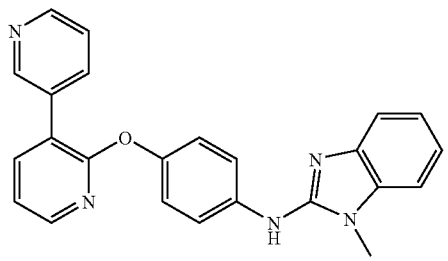

Example 90

N-(4-(3,3'-BIPYRIDIN-2-YLOXY)PHENYL)-1-METHYL-1H-BENZO[D]IMIDAZOL-2-AMINE

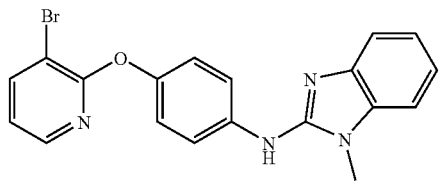

STEP 1. N-(4-(3-BROMOPYRIDIN-2-YLOXY)PHENYL)-1-METHYL-1H-BENZO[D]IMIDAZOL-2-AMINE

To a round bottomed flask was added 4-(1-methyl-1H-benzo[d]imidazol-2-ylamino)phenol (1.0058 g, 4.20 mmol), 3-bromo-2-chloropyridine (1.213 g, 6.31 mmol), and cesium carbonate (2.74 g, 8.41 mmol) in DMSO (14.01 mL) at 100° C. to stir. Upon completion, reaction was allowed to cool to room temperature. The reaction mixture was diluted with water (10 mL)/Brine (10 mL) and extracted with DCM (3×15 mL). A precipitate formed during extraction. The solid was filtered to provide N-(4-(3-bromopyridin-2-yloxy)phenyl)-1-methyl-1H-benzo[d]imidazol-2-amine.

Example 91

N-(4-(3-(TETRAHYDRO-2H-PYRAN-4-YL)PYRIDIN-2-YLOXY)PHENYL)-1H-BENZO[D]IMIDAZOL-2-AMINE

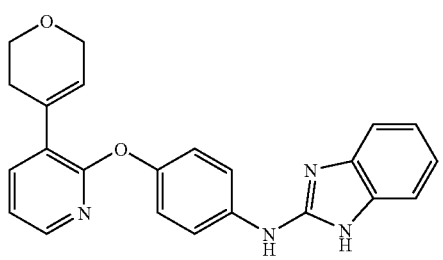

STEP 1. N-(4-(3-(3,6-DIHYDRO-2H-PYRAN-4-YL)PYRIDIN-2-YLOXY)PHENYL)-1H-BENZO[D]IMIDAZOL-2-AMINE

To a round bottomed flask was added N-(4-(3-bromopyridin-2-yloxy)phenyl)-1H-benzo[d]imidazol-2-amine (0.5674 g, 1.488 mmol), 2-(3,6-dihydro-2H-pyran-4-yl)-4,4,5,5-tetramethyl-1,3,2-dioxaborolane (0.938 g, 4.47 mmol), PdCl$_2$(PPhtBu$_2$)$_2$ (0.093 g, 0.149 mmol), and potassium acetate (0.698 mL, 11.16 mmol) in ACN (3.72 mL) and water (1.240 mL) at 100° C. to stir. Upon completion, reaction allowed to cool to room temperature. Solvent was evaporated. The crude product was purified by reverse-phase preparative HPLC using a Phenomenex Synergi column, 4 micron, MAX-RP, 80 Å, 150×30 mM, 0.1% TFA in ACN/H$_2$O, gradient 25% to 90% over 20 min to provide N-(4-(3-(3,6-dihydro-2H-pyran-4-yl)pyridin-2-yloxy)phenyl)-1H-benzo[d]imidazol-2-amine. MS (ESI, pos. ion) m/z: 385.0 (M+1).

STEP 2. N-(4-(3-(TETRAHYDRO-2H-PYRAN-4-YL)PYRIDIN-2-YLOXY)PHENYL)-1H-BENZO[D]IMIDAZOL-2-AMINE

To a round bottomed flask was added N-(4-(3-(3,6-dihydro-2H-pyran-4-yl)pyridin-2-yloxy)phenyl)-1H-benzo[d]imidazol-2-amine (0.0784 g, 0.204 mmol), palladium, 10% wt. on activated carbon (0.043 g, 0.041 mmol), and acetic acid (0.023 mL, 0.408 mmol) in THF (a few drops of MeOH was added to help solubility). To remove oxygen from the round bottomed flask, the flask was flushed by nitrogen and the placed under vacuum repeatedly. Hydrogen gas was then introduced to the reaction and allowed to stir. Upon completion, the reaction was filtered through celite. The crude product was run through a SCX cartridge. Impurities were removed from column using DCM and MeOH. The product was flushed from the cartridge using 2.0 ammonia in MeOH to provide N-(4-(3-(Tetrahydro-2H-pyran-4-yl)pyridin-2-yloxy)phenyl)-1H-benzo[d]imidazol-2-amine. MS (ESI, pos. ion) m/z: 387.0 (M+1). IC50 (uM) +++++.

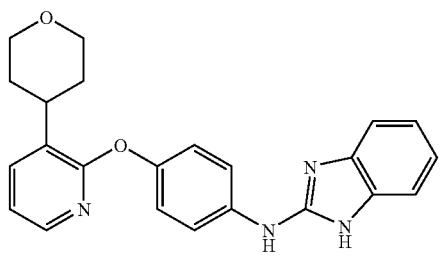

TABLE IIA

| Ex # | Structure | IC50 (uM) | IUPAC names | MS |
|---|---|---|---|---|
| 92 | 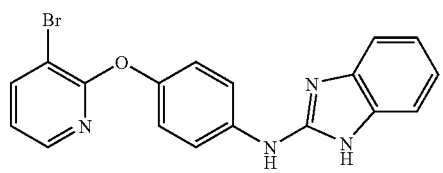 | ++++ | N-(4-(3-bromopyridin-2-yloxy)phenyl)-1H-benzo[d]imidazol-2-amine | 381.0 |
| 93 | 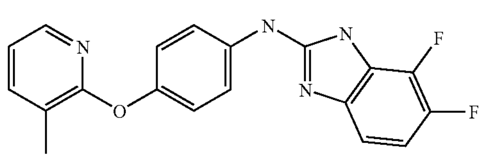 | +++ | 6,7-difluoro-N-(4-(3-methylpyridin-2-yloxy)phenyl)-1H-benzo[d]imidazol-2-amine | 353.1 |
| 94 | 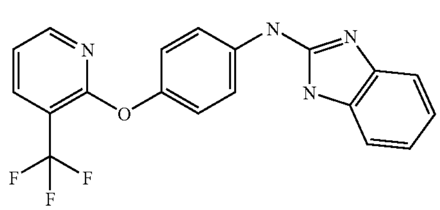 | +++++ | N-(4-(3-(trifluoromethyl)pyridin-2-yloxy)phenyl)-1H-benzo[d]imidazol-2-amine | 371.1 |

TABLE IIA-continued

| Ex # | Structure | IC50 (uM) | IUPAC names | MS |
|---|---|---|---|---|
| 95 | 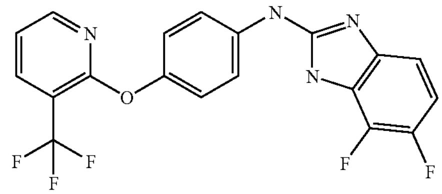 | ++ | 6,7-difluoro-N-(4-(3-(trifluoromethyl)pyridin-2-yloxy)phenyl)-1H-benzo[d]imidazol-2-amine | 407.1 |
| 96 | 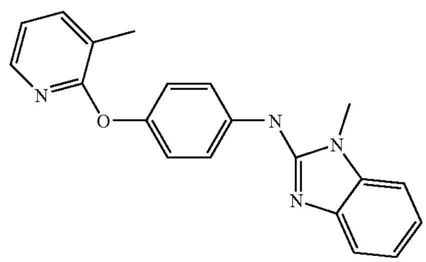 | ++++ | 1-methyl-N-(4-(3-methylpyridin-2-yloxy)phenyl)-1H-benzo[d]imidazol-2-amine | 331.1 |
| 97 | 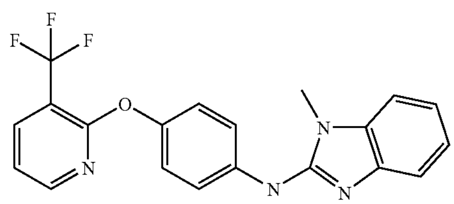 | ++++ | 1-methyl-N-(4-(3-(trifluoromethyl)pyridin-2-yloxy)phenyl)-1H-benzo[d]imidazol-2-amine | 385.1 |
| 98 | 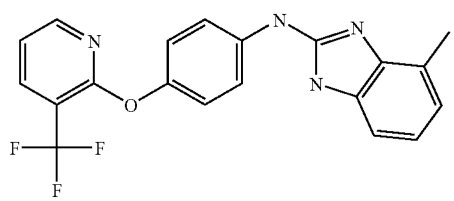 | +++ | 4-methyl-N-(4-(3-(trifluoromethyl)pyridin-2-yloxy)phenyl)-1H-benzo[d]imidazol-2-amine | 385.1 |
| 99 | 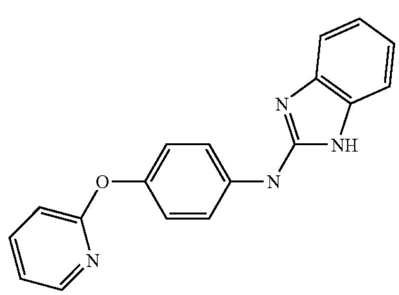 | ++++ | N-(4-(pyridin-2-yloxy)phenyl)-1H-benzo[d]imidazol-2-amine | 303.2 |
| 100 | 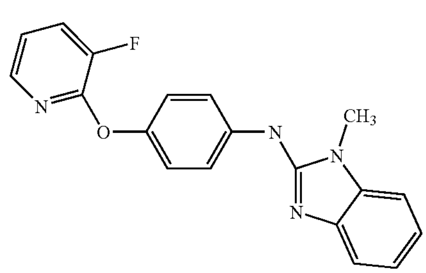 | +++ | N-(4-(3-fluoropyridin-2-yloxy)phenyl)-1-methyl-1H-benzo[d]imidazol-2-amine | 335.2 |

TABLE IIA-continued

| Ex # | Structure | IC50 (uM) | IUPAC names | MS |
|---|---|---|---|---|
| 101 | 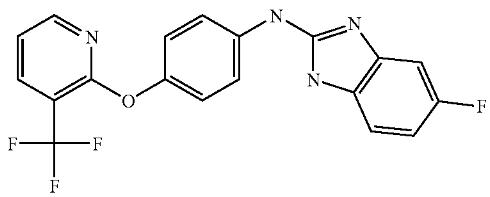 | ++++ | 5-fluoro-N-(4-(3-(trifluoromethyl)pyridin-2-yloxy)phenyl)-1H-benzo[d]imidazol-2-amine | 389.1 |
| 102 | 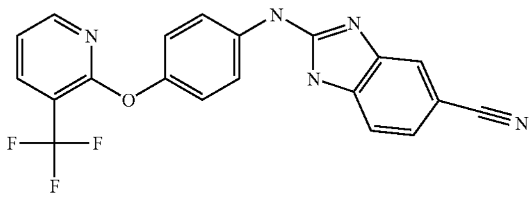 | +++ | 2-(4-(3-(trifluoromethyl)pyridin-2-yloxy)phenylamino)-1H-benzo[d]imidazol-5-carbonitrile | 396 |
| 103 | 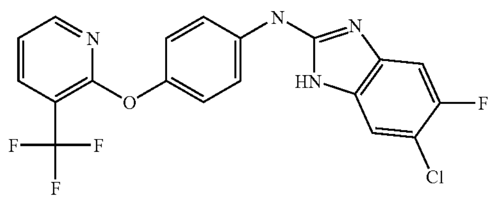 | + | 6-chloro-5-fluoro-N-(4-(3-(trifluoromethyl)pyridin-2-yloxy)phenyl)-1H-benzo[d]imidazol-2-amine | 423 |
| 104 | 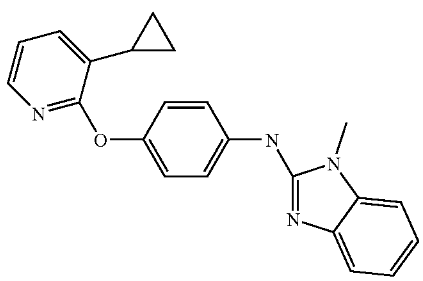 | ++++ | N-(4-(3-cyclopropylpyridin-2-yloxy)phenyl)-1-methyl-1H-benzo[d]imidazol-2-amine | 357.1 |
| 105 | 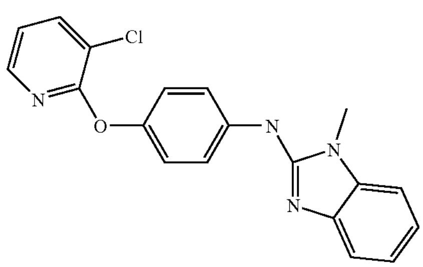 | +++ | N-(4-(3-chloropyridin-2-yloxy)phenyl)-1-methyl-1H-benzo[d]imidazol-2-amine | 351.1 |
| 106 | 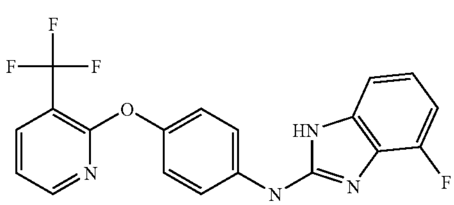 | +++ | 4-fluoro-N-(4-(3-(trifluoromethyl)pyridin-2-yloxy)phenyl)-1H-benzo[d]imidazol-2-amine | 389.1 |
| 107 | 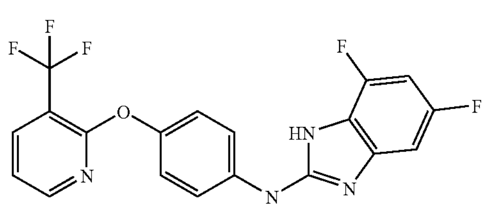 | ++ | 5,7-difluoro-N-(4-(3-(trifluoromethyl)pyridin-2-yloxy)phenyl)-1H-benzo[d]imidazol-2-amine | 407 |

TABLE IIA-continued

| Ex # | Structure | IC50 (uM) | IUPAC names | MS |
|---|---|---|---|---|
| 108 | 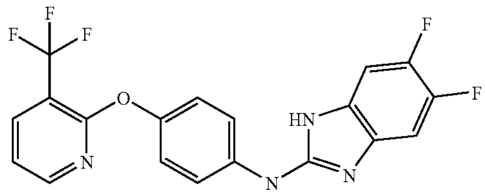 | + | 5,6-difluoro-N-(4-(3-(trifluoromethyl)pyridin-2-yloxy)phenyl)-1H-benzo[d]imidazol-2-amine | 407 |
| 109 | 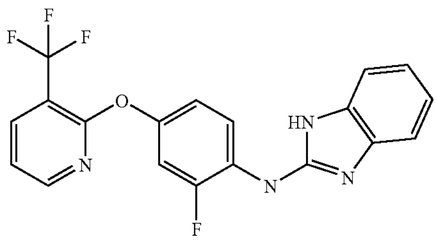 | ++++ | N-(2-fluoro-4-(3-(trifluoromethyl)pyridin-2-yloxy)phenyl)-1H-benzo[d]imidazol-2-amine | 389.1 |
| 110 | 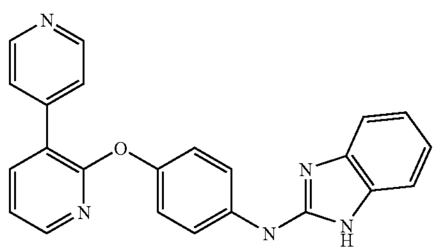 | +++++ | N-(4-(3-(pyridin-4-yl)pyridin-2-yloxy)phenyl)-1H-benzo[d]imidazol-2-amine | 380.0. |
| 111 | 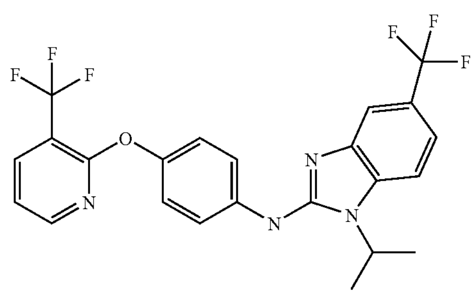 | + | 1-isopropyl-5-(trifluoromethyl)-N-(4-(3-(trifluoromethyl)pyridin-2-yloxy)phenyl)-1H-benzo[d]imidazol-2-amine | 481.1 |
| 112 | 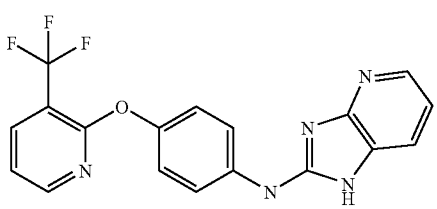 | ++++ | N-(4-(3-(trifluoromethyl)pyridin-2-yloxy)phenyl)-1H-imidazo[4,5-b]pyridin-2-amine | 372.1 |
| 113 | 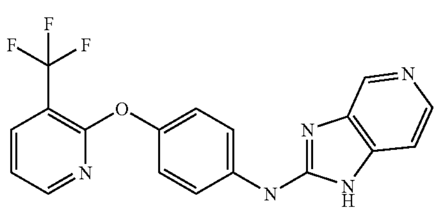 | +++++ | N-(4-(3-(trifluoromethyl)pyridin-2-yloxy)phenyl)-1H-imidazo[4,5-c]pyridin-2-amine | 372.1 |

TABLE IIA-continued

| Ex # | Structure | IC50 (uM) | IUPAC names | MS |
|---|---|---|---|---|
| 114 | 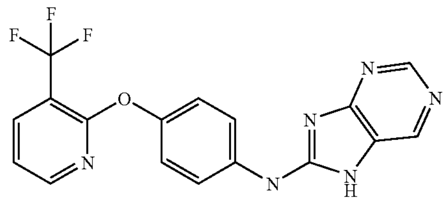 | +++ | N-(4-(3-(trifluoromethyl)pyridin-2-yloxy)phenyl)-7H-purin-8-amine | 373.1 |
| 115 | 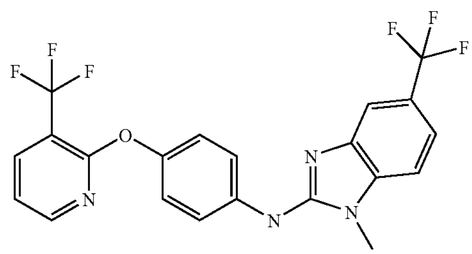 | + | 1-methyl-5-(trifluoromethyl)-N-(4-(3-(trifluoromethyl)pyridin-2-yloxy)phenyl)-1H-benzo[d]imidazol-2-amine | 453.1 |
| 116 | 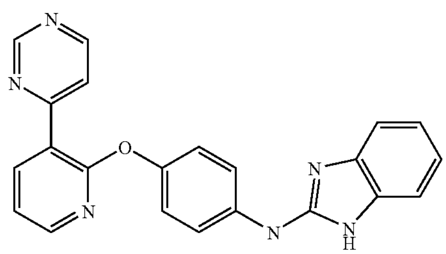 | +++++ | N-(4-(3-(pyrimidin-4-yl)pyridin-2-yloxy)phenyl)-1H-benzo[d]imidazol-2-amine | 381.1 |
| 117 | 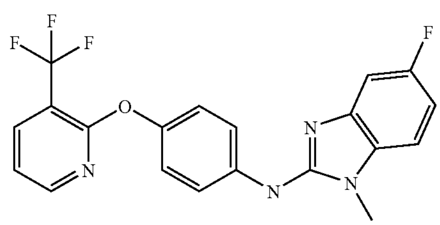 | +++ | 5-fluoro-1-methyl-N-(4-(3-(trifluoromethyl)pyridin-2-yloxy)phenyl)-1H-benzo[d]imidazol-2-amine | 403.1 |
| 118 | 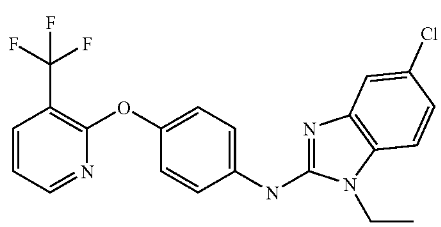 | + | 5-chloro-1-ethyl-N-(4-(3-(trifluoromethyl)pyridin-2-yloxy)phenyl)-1H-benzo[d]imidazol-2-amine | 433.1 |
| 119 | 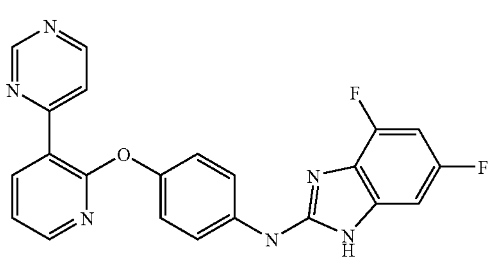 | ++++ | 4,6-difluoro-N-(4-(3-(pyrimidin-4-yl)pyridin-2-yloxy)phenyl)-1H-benzo[d]imidazol-2-amine | 417 |

TABLE IIA-continued

| Ex # | Structure | IC50 (uM) | IUPAC names | MS |
|---|---|---|---|---|
| 120 | 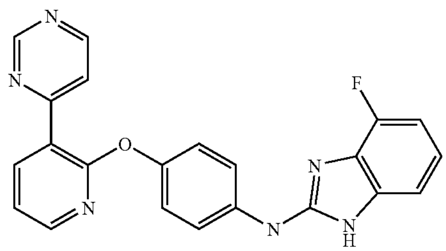 | +++++ | 4-fluoro-N-(4-(3-(pyrimidin-4-yl)pyridin-2-yloxy)phenyl)-1H-benzo[d]imidazol-2-amine | 398.8 |
| 121 | 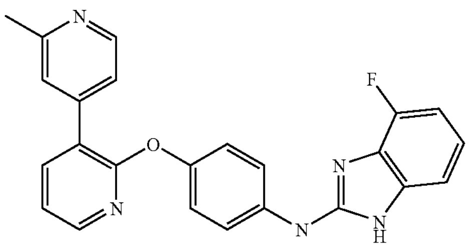 | +++++ | 4-fluoro-N-(4-(3-(2-methylpyridin-4-yl)pyridin-2-yloxy)phenyl)-1H-benzo[d]imidazol-2-amine | 412.1 |
| 122 | 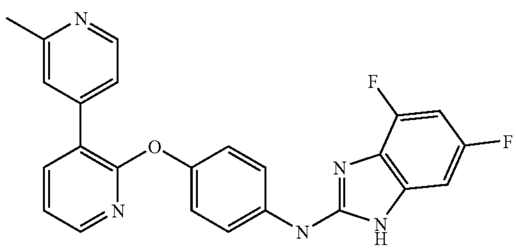 | +++++ | 4,6-difluoro-N-(4-(3-(2-methylpyridin-4-yl)pyridin-2-yloxy)phenyl)-1H-benzo[d]imidazol-2-amine | 430 |
| 123 | 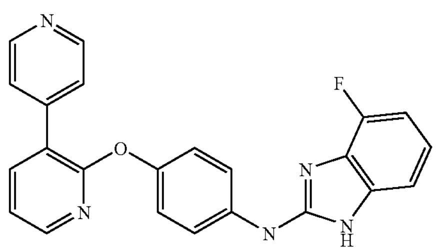 | +++++ | 4-fluoro-N-(4-(3-(pyridin-4-yl)pyridin-2-yloxy)phenyl)-1H-benzo[d]imidazol-2-amine | 398 |
| 124 | 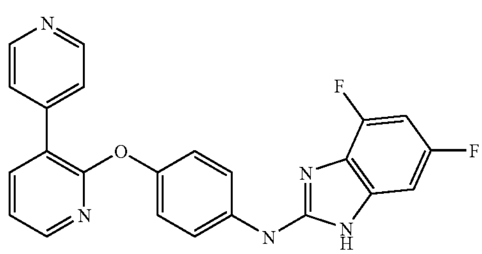 | +++++ | 4,6-difluoro-N-(4-(3-(pyridin-4-yl)pyridin-2-yloxy)phenyl)-1H-benzo[d]imidazol-2-amine | 416 |
| 125 | 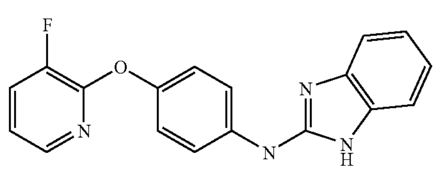 | ++++ | N-(4-(3-fluoropyridin-2-yloxy)phenyl)-1H-benzo[d]imidazol-2-amine | 321.1 |

| Ex # | Structure | IC50 (uM) | IUPAC names | MS |
|---|---|---|---|---|
| 126 | 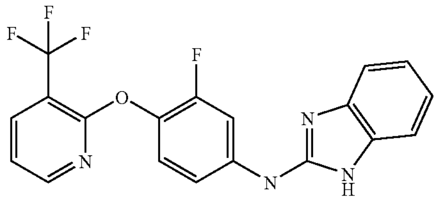 | +++ | N-(3-fluoro-4-(3-(trifluoromethyl)pyridin-2-yloxy)phenyl)-1H-benzo[d]imidazol-2-amine | 389.1 |
| 127 | 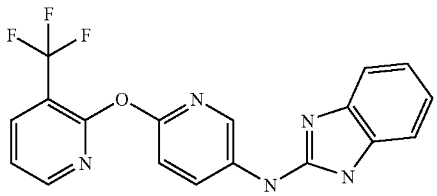 | +++ | N-(6-(3-(trifluoromethyl)pyridin-2-yloxy)pyridin-3-yl)-1H-benzo[d]imidazol-2-amine | 372.1 |
| 128 | 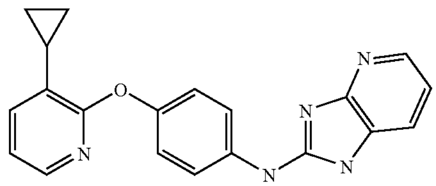 | +++++ | N-(4-(3-cyclopropylpyridin-2-yloxy)phenyl)-1H-imidazo[4,5-b]pyridin-2-amine | 344.1 |
| 129 | 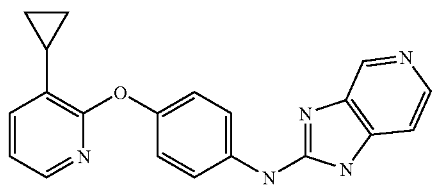 | ++++ | N-(4-(3-cyclopropylpyridin-2-yloxy)phenyl)-1H-imidazo[4,5-c]pyridin-2-amine | 344.1 |
| 130 | 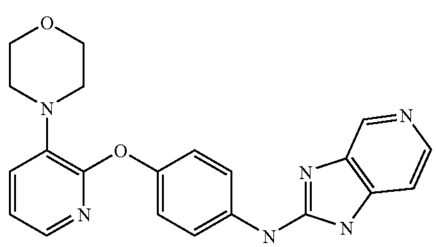 | ++++ | N-(4-(3-morpholinopyridin-2-yloxy)phenyl)-1H-imidazo[4,5-c]pyridin-2-amine | 389.1 |
| 131 | 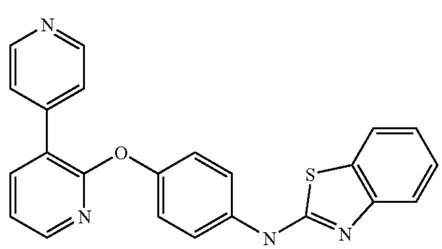 | +++ | N-(4-(3-(pyridin-4-yl)pyridin-2-yloxy)phenyl)benzo[d]thiazol-2-amine | 397 |
| 132 | 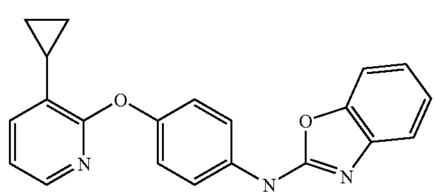 | +++ | N-(4-(3-cyclopropylpyridin-2-yloxy)phenyl)benzo[d]oxazol-2-amine | 344.1 |

TABLE IIA-continued

| Ex # | Structure | IC50 (uM) | IUPAC names | MS |
|---|---|---|---|---|
| 133 | 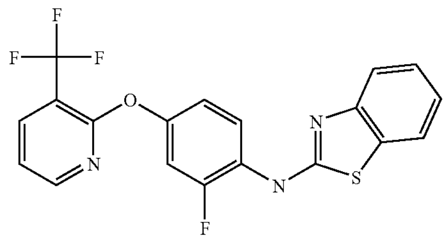 | +++ | N-(2-fluoro-4-(3-(trifluoromethyl)pyridin-2-yloxy)phenyl)benzo[d]thiazol-2-amine | 406 |
| 134 | 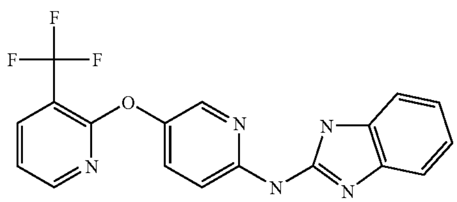 | + | N-(5-(3-(trifluoromethyl)pyridin-2-yloxy)pyridin-2-yl)-1H-benzo[d]imidazol-2-amine | 372.1 |
| 135 | 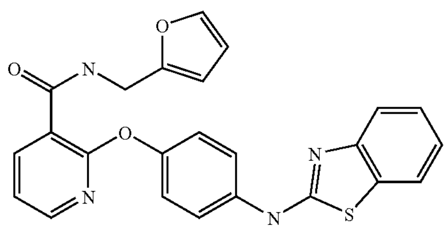 | ++++ | 2-(4-(benzo[d]thiazol-2-ylamino)phenoxy)-N-(furan-2-ylmethyl)nicotinamide | 443 |
| 136 | 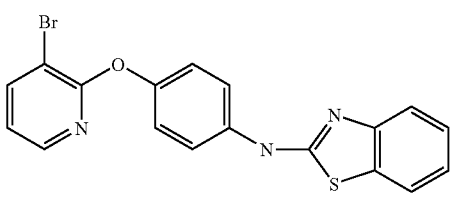 | ++ | N-(4-(3-bromopyridin-2-yloxy)phenyl)benzo[d]thiazol-2-amine | 399.9 |
| 137 | 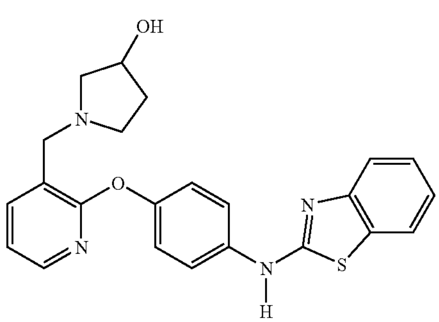 | +++ | 1-((2-(4-(benzo[d]thiazol-2-ylamino)phenoxy)pyridin-3-yl)methyl)pyrrolidin-3-ol | 419 |

TABLE IIA-continued

| Ex # | Structure | IC50 (uM) | IUPAC names | MS |
|---|---|---|---|---|
| 138 | 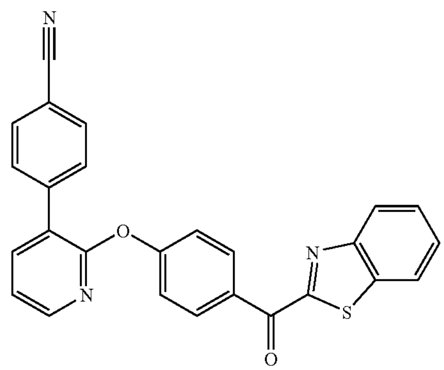 | +++++ | 4-(2-(4-(benzo[d]thiazole-2-carbonyl)phenoxy)pyridin-3-yl)benzonitrile | 434 |
| 139 | 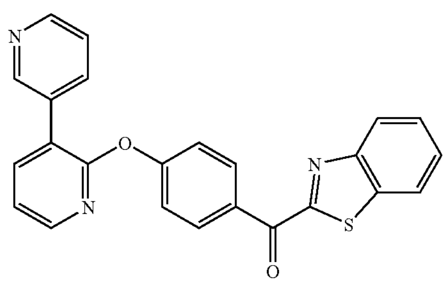 | +++++ | (4-(3,3'-bipyridin-2-yloxy)phenyl)(benzo[d]thiazol-2-yl)methanone | 410 |
| 140 | 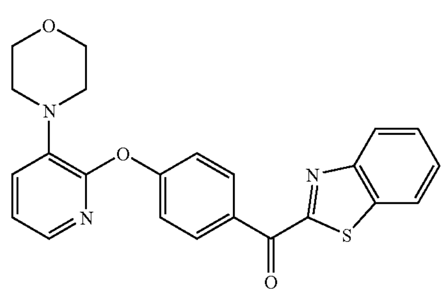 | +++ | benzo[d]thiazol-2-yl(4-(3-morpholinopyridin-2-yloxy)phenyl)methanone | 418 |
| 141 | 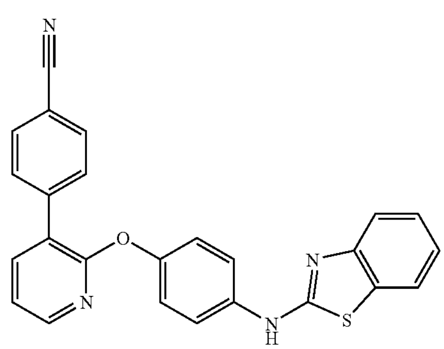 | +++++ | 4-(2-(4-(benzo[d]thiazol-2-ylamino)phenoxy)pyridin-3-yl)benzonitrile | 421.0 |

TABLE IIA-continued

| Ex # | Structure | IC50 (uM) | IUPAC names | MS |
|---|---|---|---|---|
| 142 | 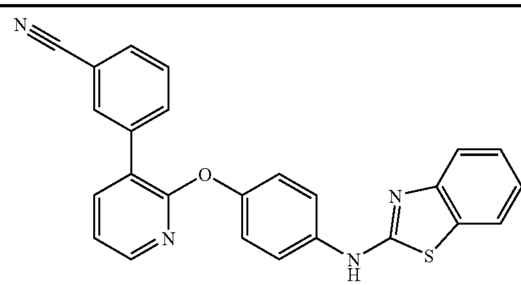 | +++++ | 3-(2-(4-(benzo[d]thiazol-2-ylamino)phenoxy)pyridin-3-yl)benzonitrile | 421.0 |
| 143 | 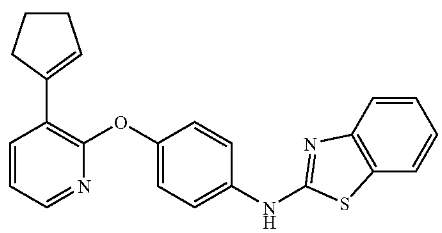 | +++ | N-(4-(3-cyclopentenylpyridin-2-yloxy)phenyl)benzo[d]thiazol-2-amine | 386.0 |
| 144 | 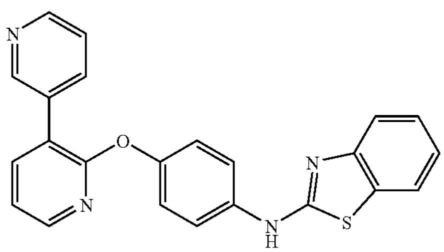 | +++++ | N-(4-(3,3'-bipyridin-2-yloxy)phenyl)benzo[d]thiazol-2-amine | 397.0 |
| 145 | 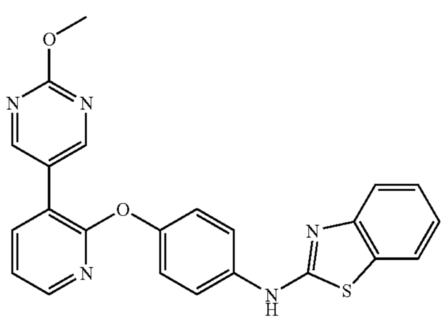 | +++++ | N-(4-(3-(2-methoxypyrimidin-5-yl)pyridin-2-yloxy)phenyl)benzo[d]thiazol-2-amine | 428.0 |
| 146 | 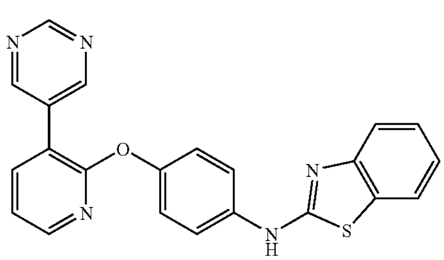 | +++++ | N-(4-(3-pyrimidin-5-yl)pyridin-2-yloxy)phenyl)benzo[d]thiazol-2-amine | 398.0 |

| Ex # | Structure | IC50 (uM) | IUPAC names | MS |
|---|---|---|---|---|
| 147 | 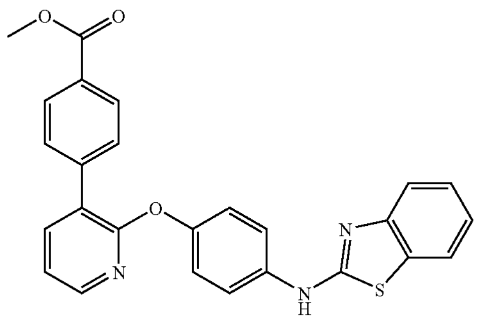 | ++++ | methyl 4-(2-(4-(benzo[d]thiazol-2-ylamino)phenoxy)pyridin-3-yl)benzoate | 454.0 |
| 148 | 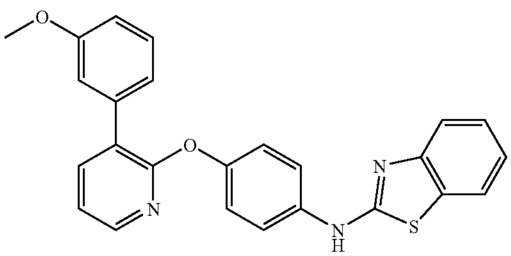 | ++++ | N-(4-(3-(3-methoxyphenyl)pyridin-2-yloxy)phenyl)benzo[d]thiazol-2-amine | 426.0 |
| 149 | 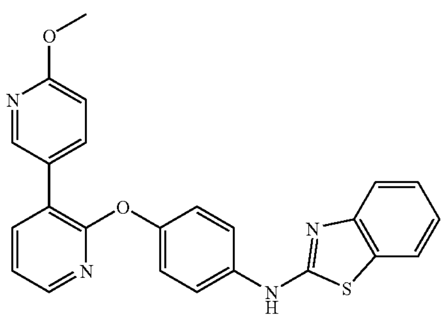 | +++++ | N-(4-(6'-methoxy-3,3'-bipyridin-2-yloxy)phenyl)benzo[d]thiazol-2-amine | 427.0 |
| 150 | 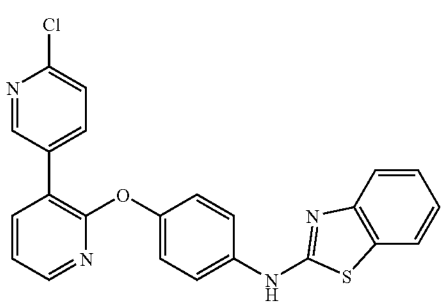 | +++++ | N-(4-(6'-chloro-3,3'-bipyridin-2-yloxy)phenyl)benzo[d]thiazol-2-amine | 431.0 |
| 151 | 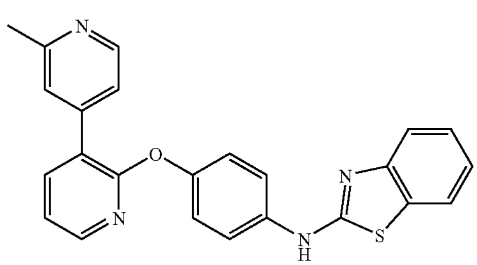 | +++++ | N-(4-(2'-methyl-3,4'-bipyridin-2-yloxy)phenyl)benzo[d]thiazol-2-amine | 411.0 |

TABLE IIA-continued

| Ex # | Structure | IC50 (uM) | IUPAC names | MS |
|---|---|---|---|---|
| 152 | 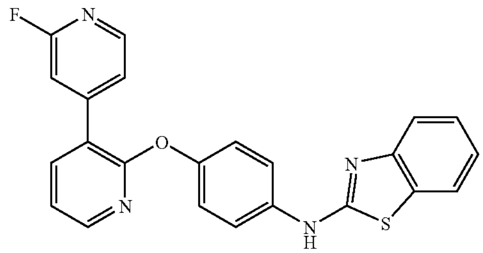 | +++++ | N-(4-(2'-fluoro-3,4'-bipyridin-2-yloxy)phenyl)benzo[d]thiazol-2-amine | 415.0 |
| 153 | 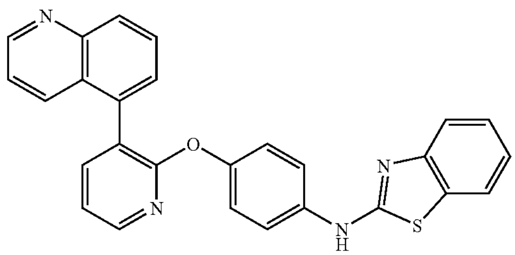 | +++++ | N-(4-(3-(quinolin-5-yl)pyridin-2-yloxy)phenyl)benzo[d]thiazol-2-amine | 447.0 |
| 154 | 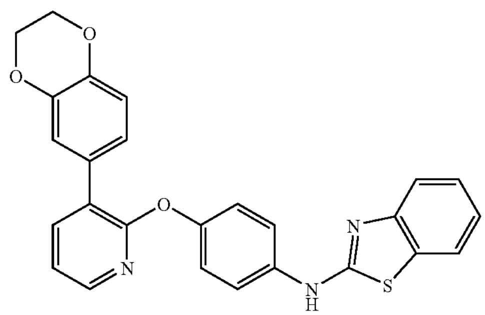 | ++++ | N-(4-(3-(2,3-dihydrobenzo[b][1,4]dioxin-6-yl)pyridin-2-yloxy)phenyl)benzo[d]thiazol-2-amine | 453.9 |
| 155 | 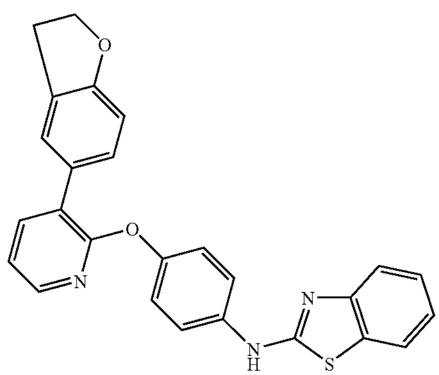 | ++++ | N-(4-(3-(2,3-dihydrobenzofuran-5-yl)pyridin-2-yloxy)phenyl)benzo[d]thiazol-2-amine | 437.9 |
| 156 | 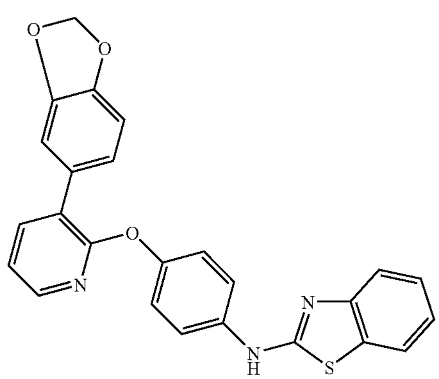 | ++++ | N-(4-(3-(benzo[d][1,3]dioxol-5-yl)pyridin-2-yloxy)phenyl)benzo[d]thiazol-2-amine | 439.9 |

TABLE IIA-continued

| Ex # | Structure | IC50 (uM) | IUPAC names | MS |
|---|---|---|---|---|
| 157 | 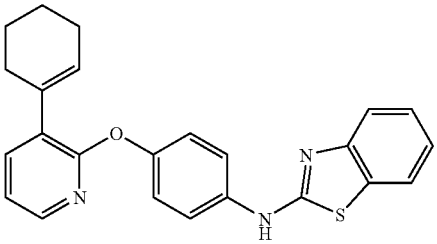 | ++++ | N-(4-(3-cyclohexenylpyridin-2-yloxy)phenyl)benzo[d]thiazol-2-amine | 400.0 |
| 158 | 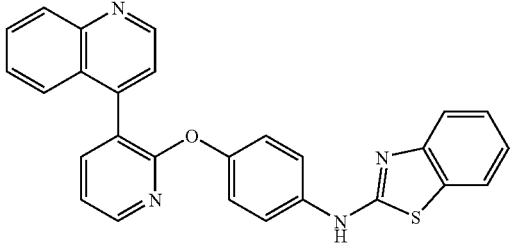 | +++++ | N-(4-(3-(quinolin-4-yl)pyridin-2-yloxy)phenyl)benzo[d]thiazol-2-amine | 447.0 |
| 159 | 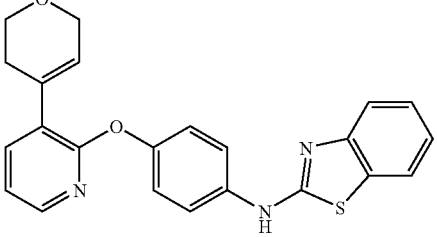 | +++++ | N-(4-(3-(3,6-dihydro-2H-pyran-4-yl)pyridin-2-yloxy)phenyl)benzo[d]thiazol-2-amine | 402.0 |
| 160 | 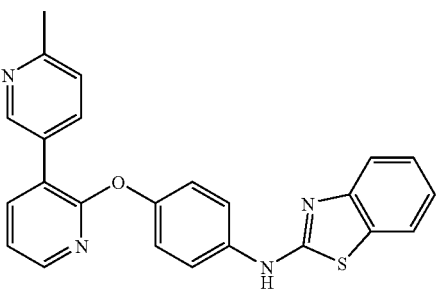 | +++++ | N-(4-(6'-methyl-3,3'-bipyridin-2-yloxy)phenyl)benzo[d]thiazol-2-amine | 411.0 |
| 161 | 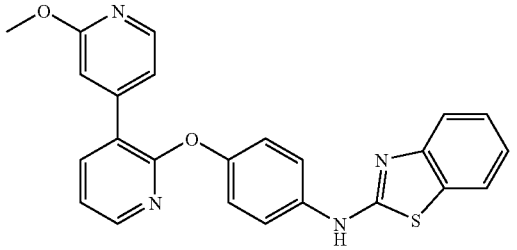 | +++++ | N-(4-(2'-methoxy-3,4'-bipyridin-2-yloxy)phenyl)benzo[d]thiazol-2-amine | 427.0 |

TABLE IIA-continued

| Ex # | Structure | IC50 (uM) | IUPAC names | MS |
|---|---|---|---|---|
| 162 | 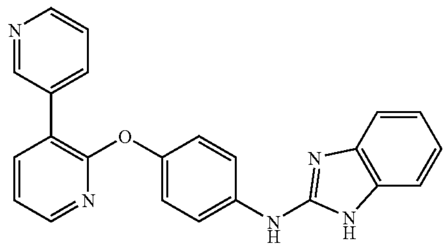 | +++++ | N-(4-(3,3'-bipyridin-2-yloxy)phenyl)-1H-benzo[d]imidazol-2-amine | 380.0 |
| 163 | 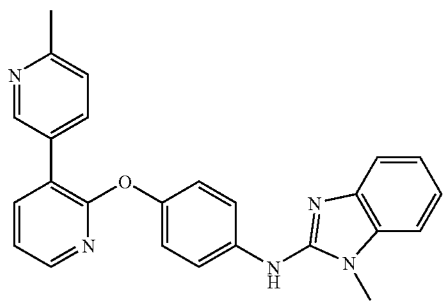 | +++++ | 1-methyl-N-(4-(6'-methyl-3,3'-bipyridin-2-yloxy)phenyl)-1H-benzo[d]imidazol-2-amine | 408.0 |
| 164 | 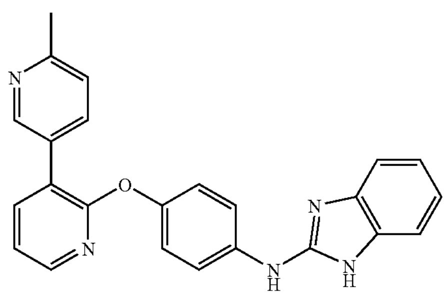 | +++++ | N-(4-(6'-methyl-3,3'-bipyridin-2-yloxy)phenyl)-1H-benzo[d]imidazol-2-amine | 394.0 |
| 165 | 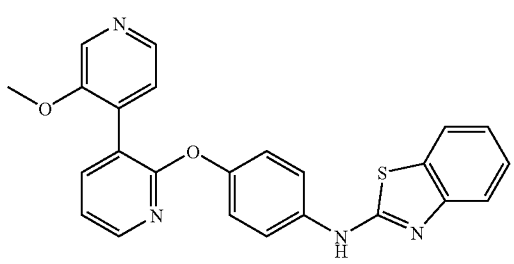 | +++++ | N-(4-(3'-methoxy-3,4'-bipyridin-2-yloxy)phenyl)benzo[d]thiazol-2-amine | 427.0 |
| 166 | 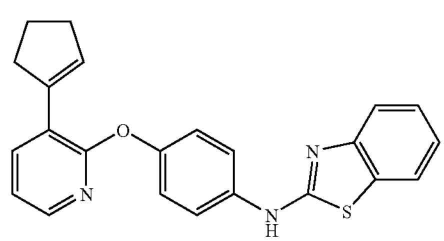 | ++++ | N-(4-(3-cyclopentenylpyridin-2-yloxy)phenyl)benzo[d]thiazol-2-amine | 386.0 |

TABLE IIA-continued

| Ex # | Structure | IC50 (uM) | IUPAC names | MS |
|---|---|---|---|---|
| 167 | 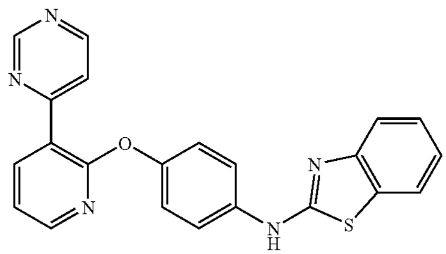 | +++++ | N-(4-(3-(pyrimidin-4-yl)pyridin-2-yloxy)phenyl)benzo[d]thiazol-2-amine | 398.0 |
| 168 | 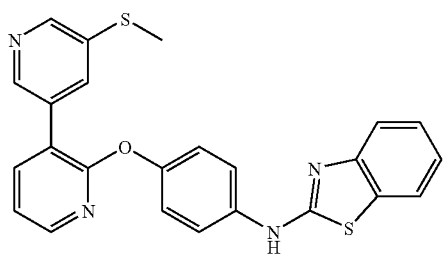 | +++++ | N-(4-(5'-(methylthio)-3,3'-bipyridin-2-yloxy)phenyl)benzo[d]thiazol-2-amine | 443.0 |
| 169 | 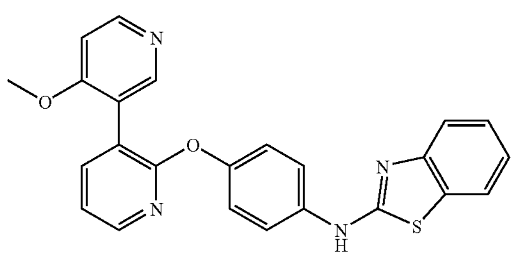 | +++++ | N-(4-(4'-methoxy-3,3'-bipyridin-2-yloxy)phenyl)benzo[d]thiazol-2-amine | 427.1 |
| 170 | 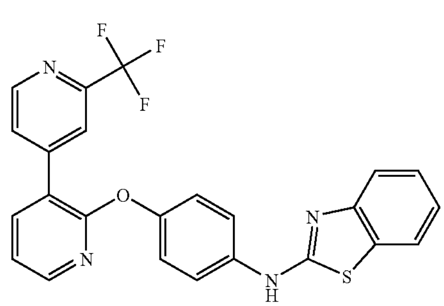 | +++++ | N-(4-(2'-(trifluoromethyl)-3,4'-bipyridin-2-yloxy)phenyl)benzo[d]thiazol-2-amine | 465.0 |

TABLE IIB
EXAMPLES 92 TO 170 WERE PREPARED AS FOLLOWS:
| Ex # | Synthetic Scheme | How Different From Main Route | Reagent Difference |
|---|---|---|---|
| 92 | 9 | Same | 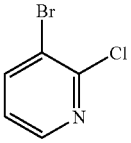 |
| 93 | 9 | Same | 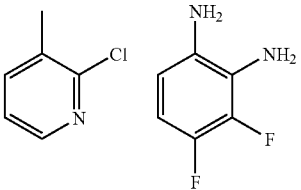 |
| 94 | 9 | Same | 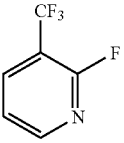 |
| 95 | 9 | Same | 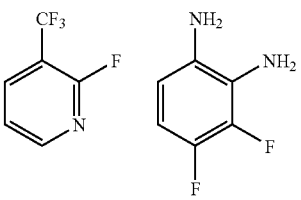 |
| 96 | 9 | Same | 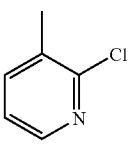 |
| 97 | 9 | Same | 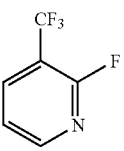 |
| 98 | 9 | Same | 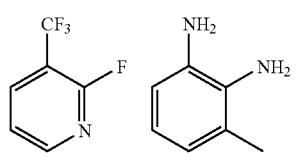 |
| 99 | 9 | Same | 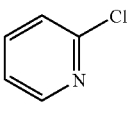 |
| 100 | 9 | Same | 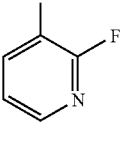 |

TABLE IIB-continued
EXAMPLES 92 TO 170 WERE PREPARED AS FOLLOWS:
| Ex # | Synthetic Scheme | How Different From Main Route | Reagent Difference |
|---|---|---|---|
| 101 | 9 | Same | 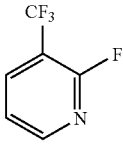 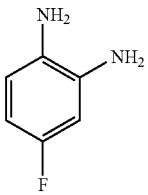 |
| 102 | 9 | Same | 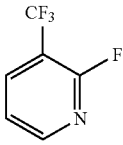 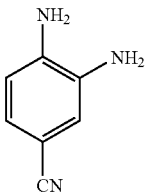 |
| 103 | 9 | Same | 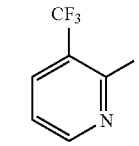 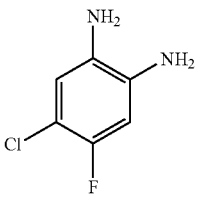 |
| 104 | 9 | (note: the pyridyl piece came from 1st step of route II-B) |  |
| 105 | 10 | Same | 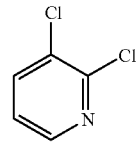 |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 106 | 9 | Same | 2-fluoro-3-(trifluoromethyl)pyridine; 3-fluorobenzene-1,2-diamine |
| 107 | 9 | Same | 2-fluoro-3-(trifluoromethyl)pyridine; 3,5-difluorobenzene-1,2-diamine |
| 108 | 9 | Same | 2-fluoro-3-(trifluoromethyl)pyridine; 4,5-difluorobenzene-1,2-diamine |
| 109 | 9 | Same | 2-fluoro-3-(trifluoromethyl)pyridine; 4-amino-3-fluorophenol |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 110 | 9 | Same | pyridin-4-yl boronic acid |
| 111 | 9 | Same | N-isopropyl-4-(trifluoromethyl)-2-(pyridin-2-yl)aniline derivative; 2-fluoro-3-(trifluoromethyl)pyridine |
| 112 | 9 | Same | 2-fluoro-3-(trifluoromethyl)pyridine; pyridine-2,3-diamine |
| 113 | 9 | Same | 2-fluoro-3-(trifluoromethyl)pyridine; pyridine-3,4-diamine |
| 114 | 9 | Same | 2-fluoro-3-(trifluoromethyl)pyridine; pyrimidine-4,5-diamine |
| 115 | 9 | Same | N-methyl-2-amino-4-(trifluoromethyl)aniline; 2-fluoro-3-(trifluoromethyl)pyridine |
| 116 | 9 | Same | 2-chloro-3-(pyrimidin-4-yl)pyridine |

TABLE IIB-continued
EXAMPLES 92 TO 170 WERE PREPARED AS FOLLOWS:
| Ex # | Synthetic Scheme | How Different From Main Route | Reagent Difference |
|---|---|---|---|
| 117 | 9 | Same | 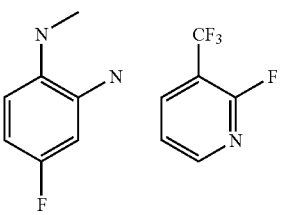 |
| 118 | 9 | Same | 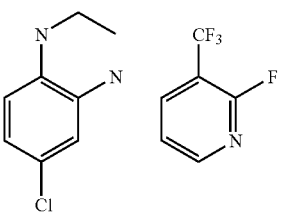 |
| 119 | 9 | Same | 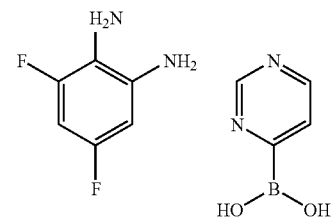 |
| 120 | 9 | Same | 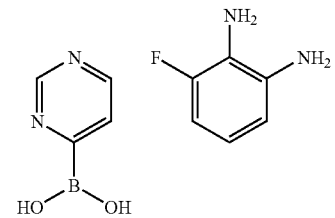 |
| 121 | 9 | Same | 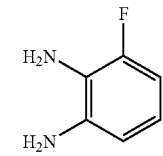 |
| 122 | 9 | Same | 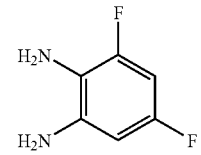 |
| 123 | 9 | Same | 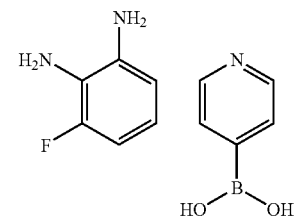 |

TABLE IIB-continued
EXAMPLES 92 TO 170 WERE PREPARED AS FOLLOWS:
| Ex # | Synthetic Scheme | How Different From Main Route | Reagent Difference |
|---|---|---|---|
| 124 | 9 | Same | 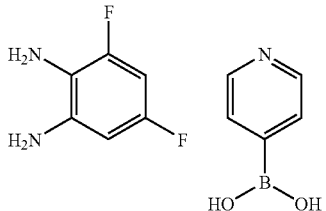 |
| 125 | 9 | Same |  |
| 126 | 9 | Same | 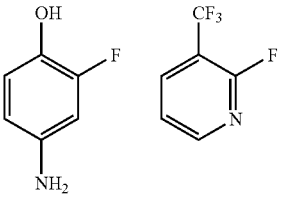 |
| 127 | 9 | Same | 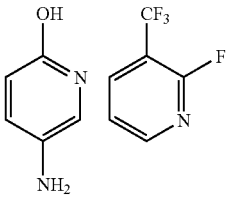 |
| 128 | 9 | Same | 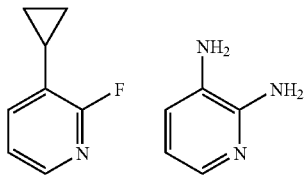 |
| 129 | 9 | Same | 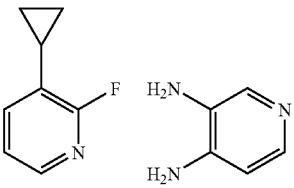 |
| 130 | 9 | Same | 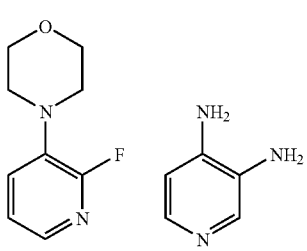 |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 131 | 9 | Same | 4-(2-fluorophenyl)pyridine |
| 132 | 9 | Same | 3-cyclopropyl-2-fluoropyridine |
| 133 | 9 | Same | 4-amino-3-fluorophenol; 2-fluoro-3-(trifluoromethyl)pyridine |
| 134 | 9 | Same | 6-amino-3-hydroxypyridine; 2-fluoro-3-(trifluoromethyl)pyridine |
| 135 | 8 | Same | furan-2-ylmethanamine |
| 136 | 8 | Same | 3-bromo-2-fluoropyridine |
| 137 | 8 | Same | pyrrolidin-3-ol |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 138 | 13 | Same | |
| 139 | 13 | Same | |
| 140 | 14 | Same | |
| 141 | 13 | Same | |
| 142 | 13 | Same | |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 143 | 13 | Same | cyclopent-1-enyl-B(OH)₂ |
| 144 | 13 | Same | pyridin-3-yl-B(OH)₂ |
| 145 | 13 | Same | 2-methoxypyrimidin-5-yl-B(OH)₂ |
| 146 | 13 | Same | pyrimidin-5-yl pinacol boronate |
| 147 | 13 | Same | 4-(methoxycarbonyl)phenyl-B(OH)₂ |
| 148 | 13 | Same | 3-methoxyphenyl pinacol boronate |
| 149 | 13 | Same | 6-methoxypyridin-3-yl-B(OH)₂ |

TABLE IIB-continued
EXAMPLES 92 TO 170 WERE PREPARED AS FOLLOWS:
| Ex # | Synthetic Scheme | How Different From Main Route | Reagent Difference |
|---|---|---|---|
| 150 | 13 | Same | 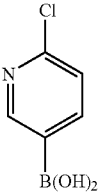 |
| 151 | 13 | Same | 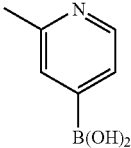 |
| 152 | 13 | Same | 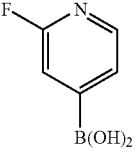 |
| 153 | 13 | Same | 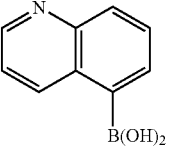 |
| 154 | 13 | Same | 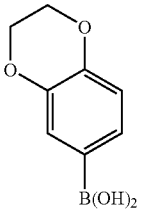 |
| 155 | 13 | Same | 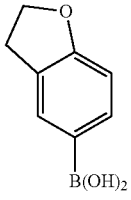 |
| 156 | 13 | PdCl$_2$(dppf)$_2$ | 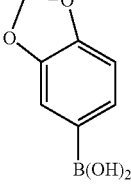 |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 157 | 13 | PdCl$_2$(dppf)$_2$ | cyclohex-1-enyl-B(OH)$_2$ |
| 158 | 13 | PdCl$_2$(dppf)$_2$ | quinolin-4-yl-B(OH)$_2$ |
| 159 | 13 | PdCl$_2$(dppf)$_2$ | 3,6-dihydro-2H-pyran-4-yl pinacol boronate |
| 160 | 13 | PdCl$_2$(dppf)$_2$ | 6-methylpyridin-3-yl boronic acid · H$_2$O |
| 161 | 13 | microwave | 2-methoxypyridin-4-yl boronic acid |
| 162 | 13 | Same | pyridin-3-yl-B(OH)$_2$ |
| 163 | 13 | Same | 6-methylpyridin-3-yl boronic acid · H$_2$O |

TABLE IIB-continued

EXAMPLES 92 TO 170 WERE PREPARED AS FOLLOWS:

| Ex # | Synthetic Scheme | How Different From Main Route | Reagent Difference |
|---|---|---|---|
| 164 | 13 | PdCl$_2$(dppf)$_2$ | 6-methylpyridin-3-yl boronic acid, hydrate |
| 165 | 13 | KOAc, AmPhos | 3-methoxypyridin-4-yl boronic acid |
| 166 | 13 | PdCl$_2$(PPh$_3$)$_2$ | cyclopent-1-enyl boronic acid |
| 167 | 8 | Same | 4-(2-chloropyridin-3-yl)pyrimidine |
| 168 | 13 | Base: K$_2$CO$_3$<br>Solvent: DME/H$_2$O/EtOH<br>T: 140° C., microwave | 5-(methylthio)pyridin-3-yl boronic acid |
| 169 | 13 | Base: K$_2$CO$_3$<br>Solvent: DME/H$_2$O/EtOH<br>T: 140° C., microwave | 4-methoxypyridin-3-yl boronic acid, HCl |
| 170 | 8 | Same | 2-fluoro-3-(2-(trifluoromethyl)pyridin-4-yl)pyridine |

SCHEME 17

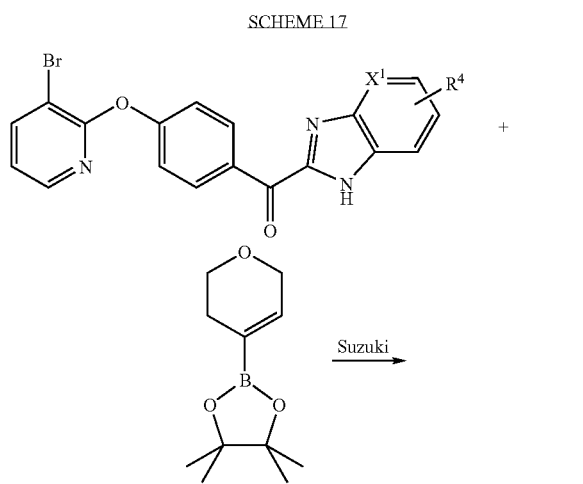

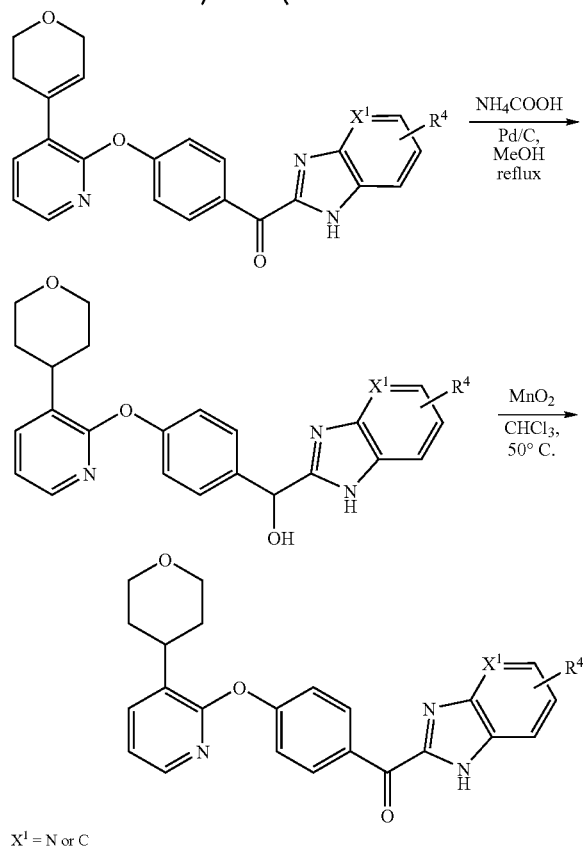

X¹ = N or C

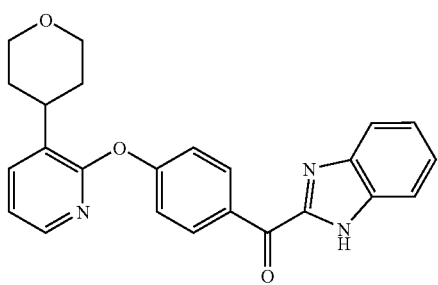

Example 171

(1H-BENZO[D]IMIDAZOL-2-YL)(4-(3-(TETRAHYDRO-2H-PYRAN-4-YL)PYRIDIN-2-YLOXY)PHENYL)METHANONE

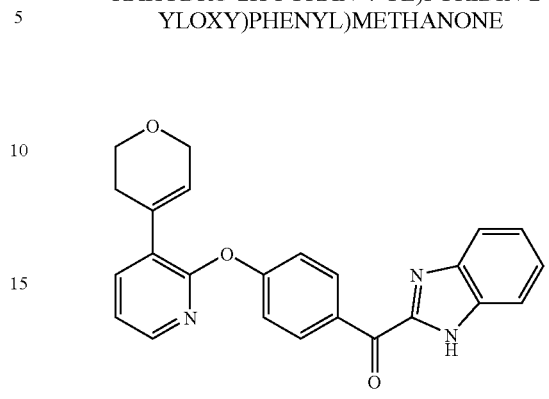

STEP 1. (1H-BENZO[D]IMIDAZOL-2-YL)(4-(3-(3,6-DIHYDRO-2H-PYRAN-4-YL)PYRIDIN-2-YLOXY)PHENYL)METHANONE

A clear 150 ml pressure tube was charged with (1H-benzo[d]imidazol-2-yl)(4-(3-bromopyridin-2-yloxy)phenyl)methanone (1.5 g, 3.80 mmol), 2-(3,6-dihydro-2H-pyran-4-yl)-4,4,5,5-tetramethyl-1,3,2-dioxaborolane (0.959 g, 4.57 mmol), Bis-[4-(di-tert-butylphosphino)-N,N-dimethylbenzenamine]Palladium dichloride (2.69 g, 3.80 mmol), potassium acetate (0.373 g, 3.80 mmol), Dioxane (9 mL) and Water (1.000 mL). The reaction flask was flushed with nitrogen and capped. The reaction was heated to 100° C. for 16 hours. The reaction was then cooled down to RT and partitioned with ethyl acetate (50 ml) and water (50 ml). The organic layer was washed (2x) with an aqueous saturated solution of sodium bicarbonate, then with water and then brine. The organic layer was then dried with sodium sulfate and then filtered. The volatile were reduced to a smaller volume and the solid that precipitated out was filtered off. The cake obtained was suspended in hot MeOH, filtered and dried to give (1H-benzo[d]imidazol-2-yl)(4-(3-(3,6-dihydro-2H-pyran-4-yl)pyridin-2-yloxy)phenyl)methanone as a yellow solid. MS (ESI, pos. ion) m/z: 397.9 (M+1).

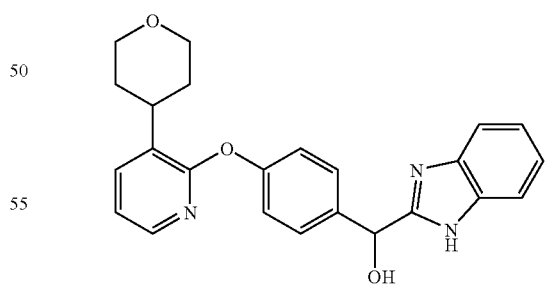

STEP 2. (1H-BENZO[D]IMIDAZOL-2-YL)(4-(3-(TETRAHYDRO-2H-PYRAN-4-YL)PYRIDIN-2-YLOXY)PHENYL)METHANOL

A 350 ml heavy-walled vessel was charged with (1H-benzo[d]imidazol-2-yl)(4-(3-(3,6-dihydro-2H-pyran-4-yl)pyridin-2-yloxy)phenyl)methanone (1.2 g, 3.02 mmol) and ammonium formate (5.71 g, 91 mmol) in THF (20 mL) and MeOH (20.00 mL). The reaction was evacuated 2× and treated with palladium on carbon 10% (0.321 g, 0.302 mmol) under nitrogen. The vessel was capped and the mixture was heated to 70° C. After 6 hours, the reaction was allowed to cool down to RT and filtered through celite. The filtrate was reduced under vacuum and the resulting residue was partition with DCM and water. The DCM layer was washed (2×) with an aqueous saturated solution of sodium bicarbonate, then with water and then brine. The organic layer was then dried with sodium sulfate and purified by column chromatography on silica gel using a gradient of 2 to 12% MeOH in DCM to give (1H-benzo[d]imidazol-2-yl)(4-(3-(tetrahydro-2H-pyran-4-yl)pyridin-2-yloxy)phenyl)methanol as a white solid. MS (ESI, pos. ion) m/z: 401.9 (M+1).

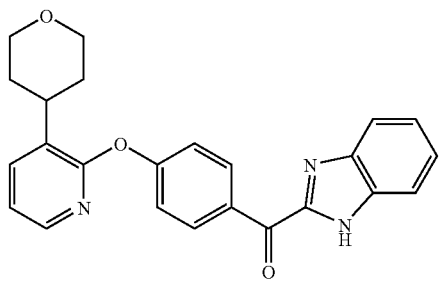

STEP 3. (1H-BENZO[D]IMIDAZOL-2-YL)(4-(3-(TETRAHYDRO-2H-PYRAN-4-YL)PYRIDIN-2-YLOXY)PHENYL)METHANONE

A suspension of (1H-benzo[d]imidazol-2-yl)(4-(3-(tetrahydro-2H-pyran-4-yl)pyridin-2-yloxy)phenyl)methanol (0.500 g, 1.245 mmol) in Chloroform (50 mL) and THF (50.0 mL) was treated with manganese dioxide (1.083 g, 12.45 mmol) at RT under nitrogen. The mixture was heated to 50° C. while stirring. After 40 mins, the reaction was filtered while warm through a small pad of celite. The filtrate was reduced and purified by column chromatography on silica gel using a gradient of 0 to 10% MeOH is DCM. The pure fractions were reduced and the residue was triturated in ethyl ether to give (1H-benzo[d]imidazol-2-yl)(4-(3-(tetrahydro-2H-pyran-4-yl)pyridin-2-yloxy)phenyl)methanone as an off-white solid. MS (ESI, pos. ion) m/z: 399.9 (M+1). IC50 (uM) +++++.

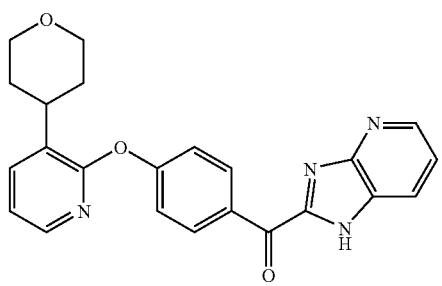

Example 172

(1H-IMIDAZO[4,5-B]PYRIDIN-2-YL)(4-(3-(TETRAHYDRO-2H-PYRAN-4-YL)PYRIDIN-2-YLOXY)PHENYL)METHANOL

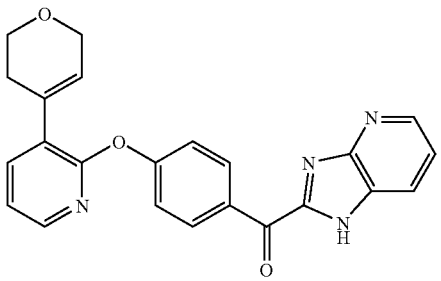

STEP 1. (4-(3-(3,6-DIHYDRO-2H-PYRAN-4-YL)PYRIDIN-2-YLOXY)PHENYL)(1H-IMIDAZO[4,5-B]PYRIDIN-2-YL)METHANONE

To a glass microwave vial was added (4-(3-bromopyridin-2-yloxy)phenyl)(1H-imidazo[4,5-b]pyridin-2-yl)methanone (1.1099 g, 2.81 mmol), 2-(3,6-dihydro-2H-pyran-4-yl)-4,4,5,5-tetramethyl-1,3,2-dioxaborolane (1.180 g, 5.62 mmol), trans-dichlorobis(triphenylphosphine) palladium (II) (0.158 g, 0.225 mmol), and sodium carbonate (0.893 g, 8.43 mmol) in DMF (7.02 mL) and water (2.340 mL). The reaction mixture was stirred and heated in a Biotage Initiator microwave reactor at 120° C. for 20 min. The reaction mixture was diluted with water and extracted with DCM. The organic extract was washed with water, brine, dried with magnesium sulfate, filtered, and concentrated. The crude product was adsorbed onto a plug of silica gel and chromatographed through a Biotage pre-packed silica gel column (40M), eluting with a gradient of 1% to 5% MeOH in DCM, to provide (4-(3-(3,6-dihydro-2H-pyran-4-yl)pyridin-2-yloxy)phenyl)(1H-imidazo[4,5-b]pyridin-2-yl)methanone. MS (ESI, pos. ion) m/z: 398.9 (M+1).

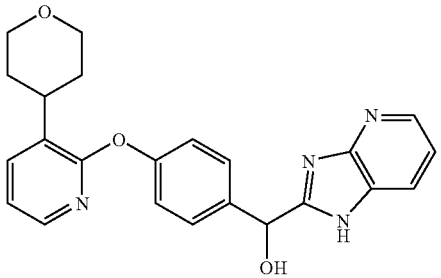

STEP 2. (1H-IMIDAZO[4,5-B]PYRIDIN-2-YL)(4-(3-(TETRAHYDRO-2H-PYRAN-4-YL)PYRIDIN-2-YLOXY)PHENYL)METHANOL

To a round bottomed flask was added (4-(3-(3,6-dihydro-2H-pyran-4-yl)pyridin-2-yloxy)phenyl)(1H-imidazo[4,5-b]pyridin-2-yl)methanone (0.3642 g, 0.914 mmol) in THF (3.05 mL). Palladium hydroxide (0.032 g, 0.046 mmol) was added. The round bottomed flask was flushed with $N_2(g)$ followed by vacuum repeating the process three times. A balloon of H₂(g) was then added to the reaction. Upon completion, reaction was filtered. The crude product was adsorbed onto a plug of silica gel and chromatographed through a Biotage pre-packed silica gel column (40S), eluting with a gradient of 0.5% to 10% MeOH in DCM, to provide (1H-imidazo[4,5-b]pyridin-2-yl)(4-(3-(tetrahydro-2H-pyran-4-yl)pyridin-2-yloxy)phenyl)methanol. MS (ESI, pos. ion) m/z: 403.0 (M+1).

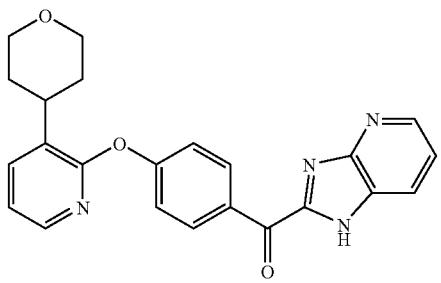

STEP 3. (1H-IMIDAZO[4,5-B]PYRIDIN-2-YL)(4-(3-(TETRAHYDRO-2H-PYRAN-4-YL)PYRIDIN-2-YLOXY)PHENYL)METHANONE

To a round bottomed flask was added (1H-imidazo[4,5-b]pyridin-2-yl)(4-(3-(tetrahydro-2H-pyran-4-yl)pyrazin-2-yloxy)phenyl)methanol (0.992 g, 2.459 mmol) and manganese dioxide (1.069 g, 12.29 mmol) to stir in chloroform (8.20 mL) for 1 hr. Reaction was filtered through celite. The crude product was purified by reverse-phase preparative HPLC using a Phenomenex Synergi column, 4 micron, MAX-RP, 80 Å, 150×30 mM, 0.1% TFA in ACN/H₂O, gradient 40% to 80% over 18 min to provide (1H-Imidazo[4,5-b]pyridin-2-yl)(4-(3-(tetrahydro-2H-pyran-4-yl)pyridin-2-yloxy)phenyl)methanone. MS (ESI, pos. ion) m/z: 401.9 (M+1). IC50 (uM) +++++.

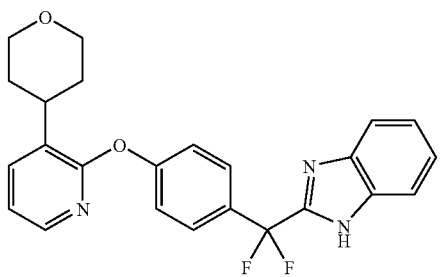

Example 173

2-(DIFLUORO(4-(3-(TETRAHYDRO-2H-PYRAN-4-YL)PYRIDIN-2-YLOXY)PHENYL)METHYL)-1H-BENZO[D]IMIDAZOLE

A solution of (1H-benzo[d]imidazol-2-yl)(4-(3-(tetrahydro-2H-pyran-4-yl)pyridin-2-yloxy)phenyl)methanone (0.100 g, 0.250 mmol) was treated with (diethylamino)sulfur trifluoride (DAST) (0.662 mL, 5.01 mmol) at RT. After 6 hours, the reaction was partitioned with water and DCM. The organic layer was washed (2×) with an aqueous saturated solution of sodium bicarbonate, then with water and then brine. The organic layer was then dried with sodium sulfate and purified by column chromatography on silica gel using a gradient of 20 to 70% EtOAc in hexanes to give 2-(difluoro (4-(3-(tetrahydro-2H-pyran-4-yl)pyridin-2-yloxy)phenyl) methyl)-1H-benzo[d]imidazole as white solid. MS (ESI, pos. ion) m/z: 421.9 (M+1). IC50 (uM) +++++.

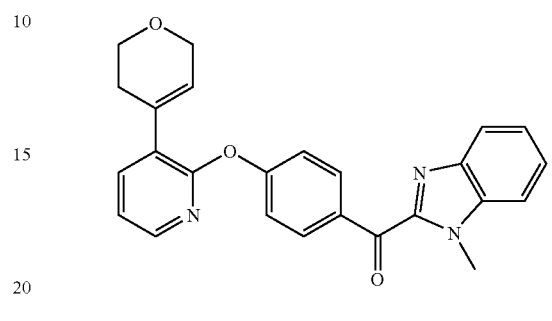

Example 174

(4-(3-(3,6-DIHYDRO-2H-PYRAN-4-YL)PYRIDIN-2-YLOXY)PHENYL)(1-METHYL-1H-BENZO[D]IMIDAZOL-2-YL)METHANONE

A solution of (1H-benzo[d]imidazol-2-yl)(4-(3-(3,6-dihydro-2H-pyran-4-yl)pyridin-2-yloxy)phenyl)methanone (0.350 g, 0.881 mmol) in DMF (5 mL) was treated with iodomethane (0.083 mL, 1.321 mmol). The mixture was stirred at RT and after 4 hours, it was diluted with water and extracted (2×) with DCM. The organic portions were combined and washed (2×) with an aqueous saturated solution of sodium bicarbonate, then with water and then brine. The organic layer was then dried with sodium sulfate, reduced and purified by column chromatography on silica gel using a gradient of 30 to 80% EtOAc in hexanes to afford (4-(3-(3,6-dihydro-2H-pyran-4-yl)pyridin-2-yloxy)phenyl)(1-methyl-1H-benzo[d]imidazol-2-yl)methanone as white solid. MS (ESI, pos. ion) m/z: 411.9 (M+1). IC50 (uM) +++++.

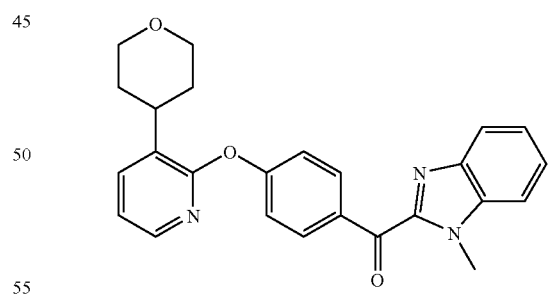

Example 175

(1-METHYL-1H-BENZO[D]IMIDAZOL-2-YL)(4-(3-(TETRAHYDRO-2H-PYRAN-4-YL)PYRIDIN-2-YLOXY)PHENYL)METHANONE

A solution of (4-(3-(3,6-dihydro-2H-pyran-4-yl)pyridin-2-yloxy)phenyl)(1-methyl-1H-benzo[d]imidazol-2-yl) methanone (0.120 g, 0.292 mmol) in THF (10 mL) was evacuated and treated with Pd(OH)₂ (20 mg) under nitrogen. The reaction was stirred under a hydrogen atmosphere with a balloon. After 24 hours, the reaction was filtered through a small plug of celite and the filtrate was treated with manganese dioxide (0.254 g, 2.92 mmol). The reaction was stirred at 50° C. for 1 hour and filtered through celite. The filtered was reduced under vacuum. The residue was taken up in DCM and washed (2×) with an aqueous saturated solution of sodium bicarbonate, then with water and then brine. The organic layer was then dried with sodium sulfate and purified by column chromatography on silica gel using a gradient of 30 to 80% EtOAc in hexanes to give (1-methyl-1H-benzo[d]imidazol-2-yl)(4-(3-(tetrahydro-2H-pyran-4-yl)pyridin-2-yloxy)phenyl)methanone as a white solid. MS (ESI, pos. ion) m/z: 414.0. IC50 (uM) +++++.

SCHEME 18

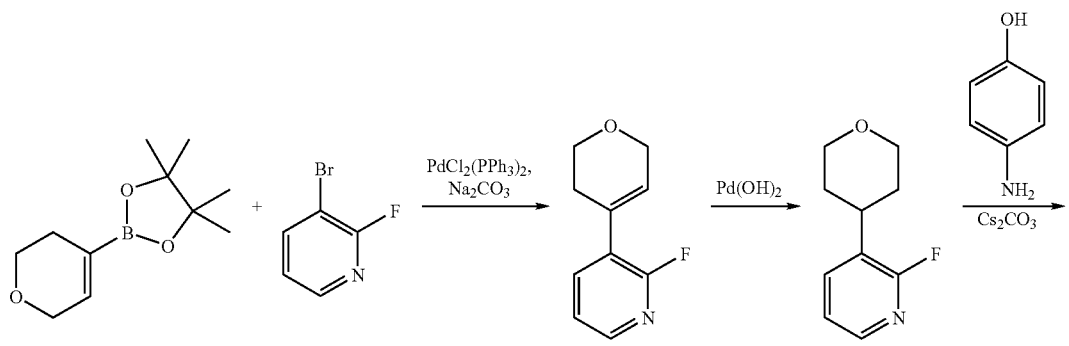

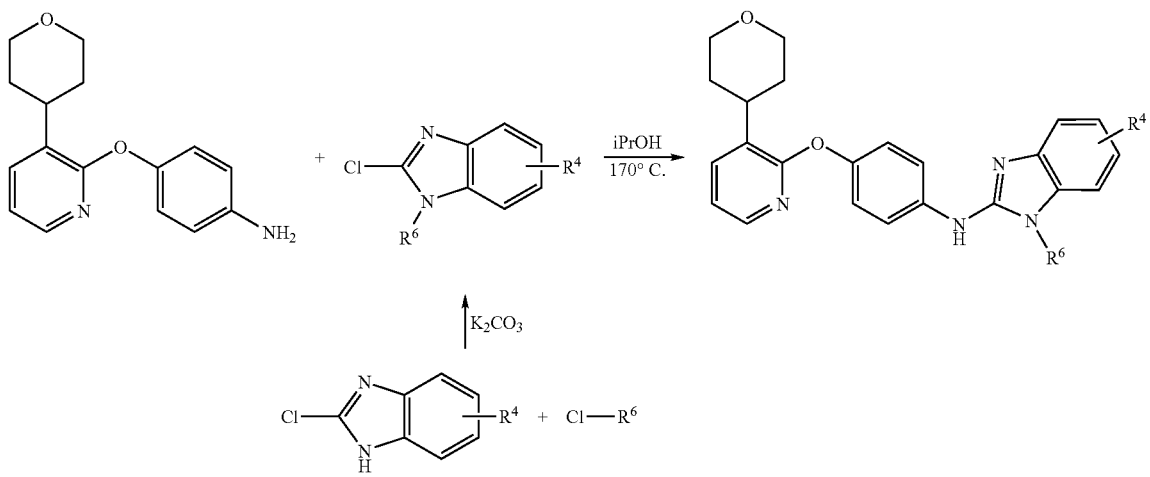

Example 176

1-(4-METHOXYBENZYL)-N-(4-(3-(TETRAHY-DRO-2H-PYRAN-4-YL)PYRIDIN-2-YLOXY) PHENYL)-1H-BENZO[D]IMIDAZOL-2-AMINE

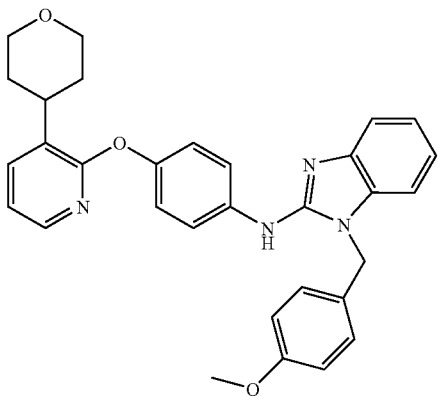

STEP 1. 3-(3,6-DIHYDRO-2H-PYRAN-4-YL)-2-FLUOROPYRIDINE

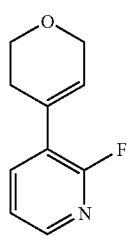

To a round bottomed flask was added 3-bromo-2-fluoropyridine (5.2201 g, 29.7 mmol), 2-(3,6-dihydro-2H-pyran-4-yl)-4,4,5,5-tetramethyl-1,3,2-dioxaborolane (7.79 g, 37.1 mmol), trans-dichlorobis(triphenylphosphine) palladium (II) (1.666 g, 2.373 mmol), and sodium carbonate (15.72 g, 148 mmol) in DME (47.5 mL) and Water (11.86 mL) to stir at 80° C. overnight. Reaction was allowed to cool to room temperature. The reaction mixture was diluted with water and extracted with DCM. The organic extract was washed with water, brine, dried with magnesium sulfate, filtered, and concentrated. The crude product was adsorbed onto a plug of silica gel and chromatographed through a Biotage pre-packed silica gel column (40M), eluting with a gradient of 10% to 100% EtOAc in hexane, to provide 3-(3,6-dihydro-2H-pyran-4-yl)-2-fluoropyridine. MS (ESI, pos. ion) m/z: 180.1 (M+1).

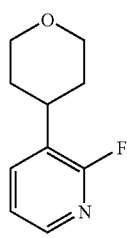

STEP 2. 2-FLUORO-3-(TETRAHYDRO-2H-PYRAN-4-YL) PYRIDINE

To a round bottomed flask was added 3-(3,6-dihydro-2H-pyran-4-yl)-2-fluoropyridine (3.5962 g, 20.07 mmol) and palladium hydroxide on carbon (1.409 g, 2.007 mmol) in EtOAc (66.9 mL). The round bottomed flask was flushed with argon and then placed under vacuum three times. A hydrogen balloon was then attached to the reaction. Upon completion, the reaction was filtered through celite to produce 2-Fluoro-3-(tetrahydro-2H-pyran-4-yl)pyridine. MS (ESI, pos. ion) m/z: 182.1 (M+1).

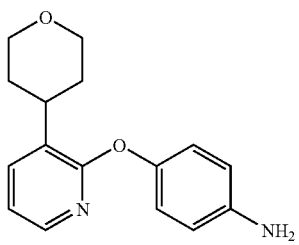

STEP 3. 4-(3-(TETRAHYDRO-2H-PYRAN-4-YL) PYRIDIN-2-YLOXY)ANILINE

To a round bottomed flask was added 2-fluoro-3-(tetrahydro-2H-pyran-4-yl)pyridine (3.4590 g, 19.09 mmol), 4-aminophenol (3.12 g, 28.6 mmol), and cesium carbonate (18.66 g, 57.3 mmol) in DMSO (63.6 mL) at 110° C. to stir overnight. Reaction was allowed to cool to room temperature. The reaction mixture was diluted with water and extracted with DCM. The organic extract was washed 50% sodium chloride solution, dried with magnesium sulfate, filtered, and concentrated. The crude product was adsorbed onto a plug of silica gel and chromatographed through a Biotage pre-packed silica gel column (40M), eluting with a gradient of 1% to 5% MeOH in DCM, to provide 4-(3-(tetrahydro-2H-pyran-4-yl)pyridin-2-yloxy)aniline. MS (ESI, pos. ion) m/z: 271.1 (M+1).

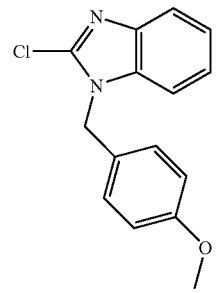

STEP 4. 2-CHLORO-1-(4-METHOXYBENZYL)-1H-BENZO[D]IMIDAZOLE

To a round bottomed flask was added 2-chloro-1H-benzo[d]imidazole (1.000 g, 6.55 mmol), 1-(chloromethyl)-4-methoxybenzene (1.540 g, 9.83 mmol), and potassium carbonate (1.359 g, 9.83 mmol) in DMF (21.85 mL) to stir overnight. Reaction was allowed to cool to room temperature. The reaction mixture was diluted with water and extracted with DCM. The organic extract was washed with water, brine, dried with magnesium sulfate, filtered, and concentrated to provide 2-Chloro-1-(4-methoxybenzyl)-1H-benzo[d]imidazole. MS (ESI, pos. ion) m/z: 273.2 (M+1).

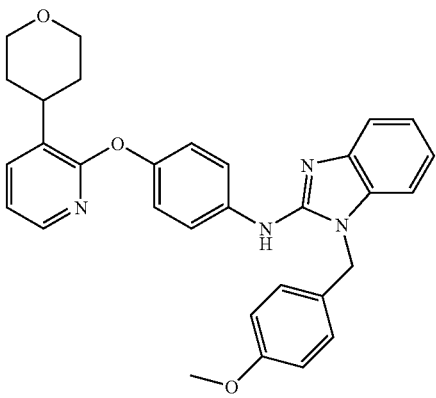

STEP 5. 1-(4-METHOXYBENZYL)-N-(4-(3-(TETRAHYDRO-2H-PYRAN-4-YL)PYRIDIN-2-YLOXY)PHENYL)-1H-BENZO[D]IMIDAZOL-2-AMINE

A glass microwave reaction vessel was charged with 4-(3-(tetrahydro-2H-pyran-4-yl)pyridin-2-yloxy)aniline (0.2573 g, 0.952 mmol) and 2-chloro-1-(4-methoxybenzyl)-1H-benzo[d]imidazole (0.312 g, 1.142 mmol) in IPA. The reaction mixture was stirred and heated in a Biotage Initiator microwave reactor at 170° C. for 30 min. Solvent was evaporated. The crude product was adsorbed onto a plug of silica gel and chromatographed through a Biotage pre-packed silica gel column (40S), eluting with a gradient of 10% to 80% EtOAc in hexane, to provide 1-(4-methoxybenzyl)-N-(4-(3-(tetrahydro-2H-pyran-4-yl)pyridin-2-yloxy)phenyl)-1H-benzo[d]imidazol-2-amine. IC50 (uM) +++++.

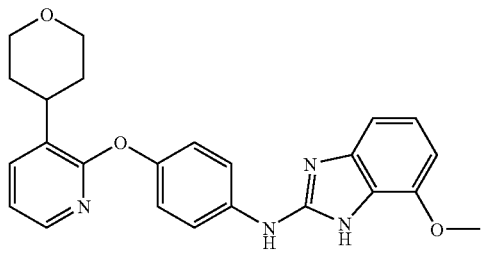

Example 177

7-METHOXY-N-(4-(3-(TETRAHYDRO-2H-PYRAN-4-YL)PYRIDIN-2-YLOXY)PHENYL)-1H-BENZO[D]IMIDAZOL-2-AMINE

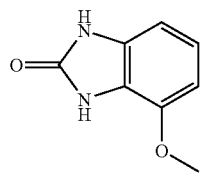

STEP 1.
4-METHOXY-1H-BENZO[D]IMIDAZOL-2(3H)-ONE

To a round bottomed flask was added 2-amino-3-methoxybenzoic acid (2.2705 g, 13.58 mmol), diphenyl phosphorazidate (3.51 mL, 16.30 mmol), and triethylamine (3.79 mL, 27.2 mmol) in THF to stir at 80° C. Upon completion the reaction was allowed to cool to room temperature. Solvent was evaporated. The residue was taken up in DCM. The reaction mixture was diluted with water and extracted with DCM. A white precipitate was noted to form during extraction The solid was filtered to provide 4-methoxy-1H-benzo[d]imidazol-2(3H)-one. MS (ESI, pos. ion) m/z: 165.0 (M+1).

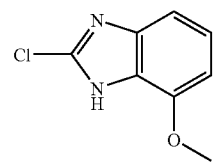

STEP 2.
2-CHLORO-7-METHOXY-1H-BENZO[D]IMIDAZOLE

To a round bottomed flask was added 4-methoxy-1H-benzo[d]imidazol-2(3H)-one (1.8163 g, 11.06 mmol). POCl₃ (1.031 mL, 11.06 mmol) was added and the reaction was brought to reflux. Upon completion, POCL₃ was evaporated off. The residue was taken up in DCM. The reaction mixture was diluted with water and saturated sodium bicarbonate and extracted with DCM. The organic extract was washed with sat. sodium bicarbonate solution, water, brine, dried with magnesium sulfate, filtered, and concentrated to provide 2-Chloro-7-methoxy-1H-benzo[d]imidazole. MS (ESI, pos. ion) m/z: 182.9 (M+1).

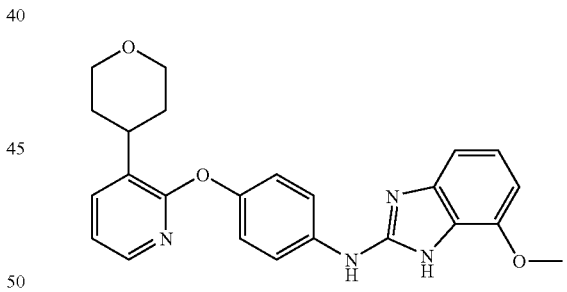

STEP 3. 7-METHOXY-N-(4-(3-(TETRAHYDRO-2H-PYRAN-4-YL)PYRIDIN-2-YLOXY)PHENYL)-1H-BENZO[D]IMIDAZOL-2-AMINE

A glass microwave reaction vessel was charged with 4-(3-(tetrahydro-2H-pyran-4-yl)pyridin-2-yloxy)aniline (0.1130 g, 0.418 mmol) and 2-chloro-7-methoxy-1H-benzo[d]imidazole (0.092 g, 0.502 mmol) in IPA. The reaction mixture was stirred and heated in a Biotage Initiator microwave reactor at 170° C. for 30 min. The reaction mixture was diluted with water and extracted with DCM. The organic extract was washed with water, brine, dried with magnesium sulfate, filtered, and concentrated. The crude product was adsorbed onto a plug of silica gel and chromatographed through a Biotage pre-packed silica gel column (40S), eluting with a gradient of 1% to 5% MeOH in DCM, to provide 7-methoxy-N-(4-(3-(tetrahydro-2H-pyran-4-yl)pyridin-2-yloxy)phenyl)-1H-benzo[d]imidazol-2-amine. MS (ESI, pos. ion) m/z: 417.0 (M+1). IC50 (uM) +++++.

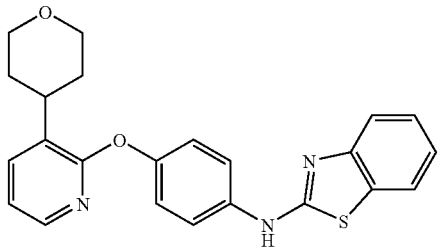

Example 178

N-(4-(3-(TETRAHYDRO-2H-PYRAN-4-YL)PYRIDIN-2-YLOXY)PHENYL)BENZO[D]THIAZOL-2-AMINE

A glass microwave reaction vessel was charged with 2-fluoro-3-(tetrahydro-2H-pyran-4-yl)pyridine (0.3904 g, 2.154 mmol), 4-(benzo[d]thiazol-2-ylamino)phenol (0.783 g, 3.23 mmol), and cesium carbonate (2.106 g, 6.46 mmol) in N-Methyl-2-pyrrolidinone (7.18 mL). The reaction mixture was stirred and heated in a Biotage Initiator microwave reactor at 180° C. for 30 min. Reaction was worked up via seperatory funnel. The crude product was purified by reverse-phase preparative HPLC using a Phenomenex Synergi column, 4 micron, MAX-RP, 80 Å, 150×30 mM, 0.1% TFA in ACN/H$_2$O, gradient 15% to 100% over 15 min. Further purification was pursued by absorbing crude product onto a plug of silica gel and chromatographed through a Biotage pre-packed silica gel column (25M), eluting with a gradient of 5% to 60% EtOAc in hexane, to provide N-(4-(3-(tetrahydro-2H-pyran-4-yl)pyridin-2-yloxy)phenyl)benzo[d]thiazol-2-amine. MS (ESI, pos. ion) m/z: 404.0 (M+1). IC50 (uM) +++++.

SCHEME 19

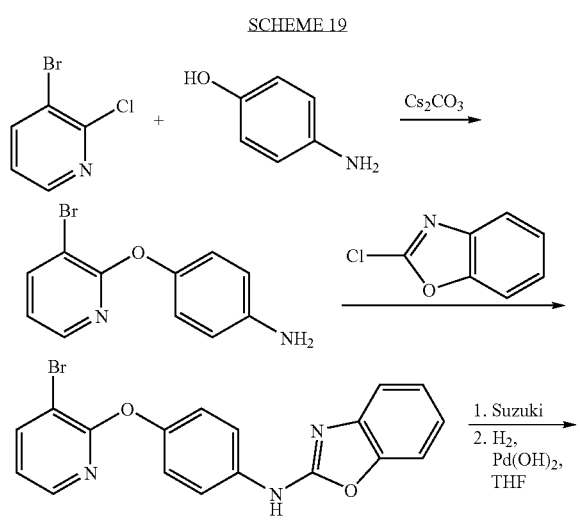

-continued

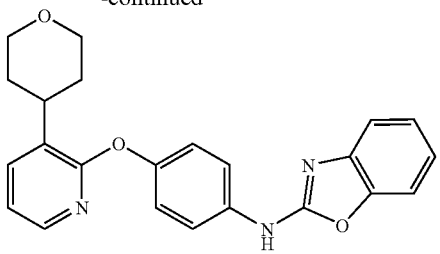

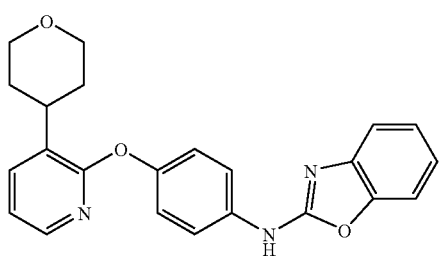

Example 179

N-(4-(3-(TETRAHYDRO-2H-PYRAN-4-YL)PYRIDIN-2-YLOXY)PHENYL)BENZO[D]OXAZOL-2-AMINE

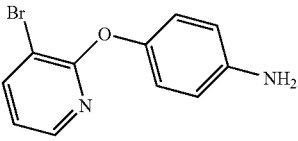

STEP 1.
4-(3-BROMOPYRIDIN-2-YLOXY)BENZENAMINE

A mixture of 3-bromo-2-chloropyridine (75.50 g, 392.3 mmol, Aldrich), 4-aminophenol (51.46 g, 471.6 mmol, TCI America) and cesium carbonate (256.80 g, 788.2 mmol, Strem) in DMSO (400 mL) in a 1 L flask and heated at 80° C. overnight. The reaction was cooled (0° C.) and diluted with water. After stirring for 30 min the mixture was filtered and the solid was partitioned between 50% EtOAc/hexane (1 L) and water (300 mL). The organic layer was washed with water (3×300 mL) and with brine (1×200 mL) then dried over Na$_2$SO$_4$. Filtration and concentration in vacuo gave a brown amorphous solid. MS (ESI, pos. ion) m/z: 264.9, 266.9 (M+1).

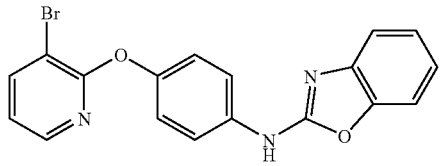

STEP 2. N-(4-(3-BROMOPYRIDIN-2-YLOXY) PHENYL)BENZO[D]OXAZOL-2-AMINE

A mixture of 4-(3-bromopyridin-2-yloxy)aniline (1.73 g, 6.53 mmol) and 2-chlorobenzoxazole (1.00 g, 6.51 mmol, TCI America) in NMP (3 mL) was sealed in a screw-cap flask and heated at 170° C. for 20 h. The reaction was cooled to rt and partitioned with water/EtOAc. The aqueous layer was extracted with EtOAc (3×) and the combined organic layers were evaporated onto silica gel and purified by flash chromatography (Isco (80 gram)) eluting with EtOAc:hexanes (0:1→1:2) a tan amorphous solid. MS (ESI, pos. ion) m/z: 382.0, 383.9 (M+1).

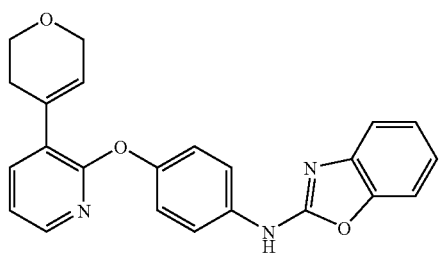

STEP 3. N-(4-(3-(3,6-DIHYDRO-2H-PYRAN-4-YL)PYRIDIN-2-YLOXY)PHENYL)BENZO[D]OXAZOL-2-AMINE

A glass microwave reaction vessel was charged with N-(4-(3-bromopyridin-2-yloxy)phenyl)benzo[d]oxazol-2-amine (0.500 g, 1.308 mmol), 2-(3,6-dihydro-2H-pyran-4-yl)-4,4,5,5-tetramethyl-1,3,2-dioxaborolane (0.414 g, 1.971 mmol), sodium carbonate anhydrous (0.700 g, 6.60 mmol) and trans-dichlorobis(triphenyl-phosphine)palladium (II) (0.092 g, 0.131 mmol, Strem). A mixture of 7:3:2 DME:H₂O:EtOH (11 mL) was added and the reaction mixture was sealed under argon and heated in a Emrys Optmizer microwave reactor (Personal Chemistry, Biotage AB, Inc., Upssala, Sweden) at 140° C. for 15 min. The reaction mixture was partitioned between EtOAc/water and the aqueous layer was extracted with EtOAc (3×). The combined organic layers were evaporated onto silica gel and purified by flash chromatography (Isco (80 gram)) eluting with EtOAc:hexanes (0:1→1:2) to give a light-orange amorphous solid. MS (ESI, pos. ion) m/z: 386.0 (M+1). IC50 (uM) +++++.

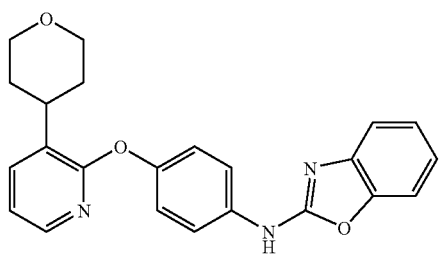

STEP 4. N-(4-(3-(TETRAHYDRO-2H-PYRAN-4-YL)PYRIDIN-2-YLOXY)PHENYL)BENZO[D]OXAZOL-2-AMINE

A flask containing a mixture of N-(4-(3-(3,6-dihydro-2H-pyran-4-yl)pyridin-2-yloxy)phenyl)benzo[d]oxazol-2-amine (0.277 g, 0.719 mmol) and palladium hydroxide, 20 wt % Pd (dry basis) on carbon, wet (0.505 g, 0.719 mmol) in THF (6 mL) was equipped with a vacuum adapter and evacuated/purged with hydrogen (1 atm). The mixture was continued to stir at rt overnight and the mixture was filtered and concentrated to dryness to give a tan solid. The material was dissolved in DCM and loaded onto an SCX II cartridge eluting with DCM then 2M NH₃ in MeOH/DCM (1:9) to give a tan crystalline solid. MS (ESI, pos. ion) m/z: 388.1 (M+1). IC50 (uM) +++++.

SCHEME 20

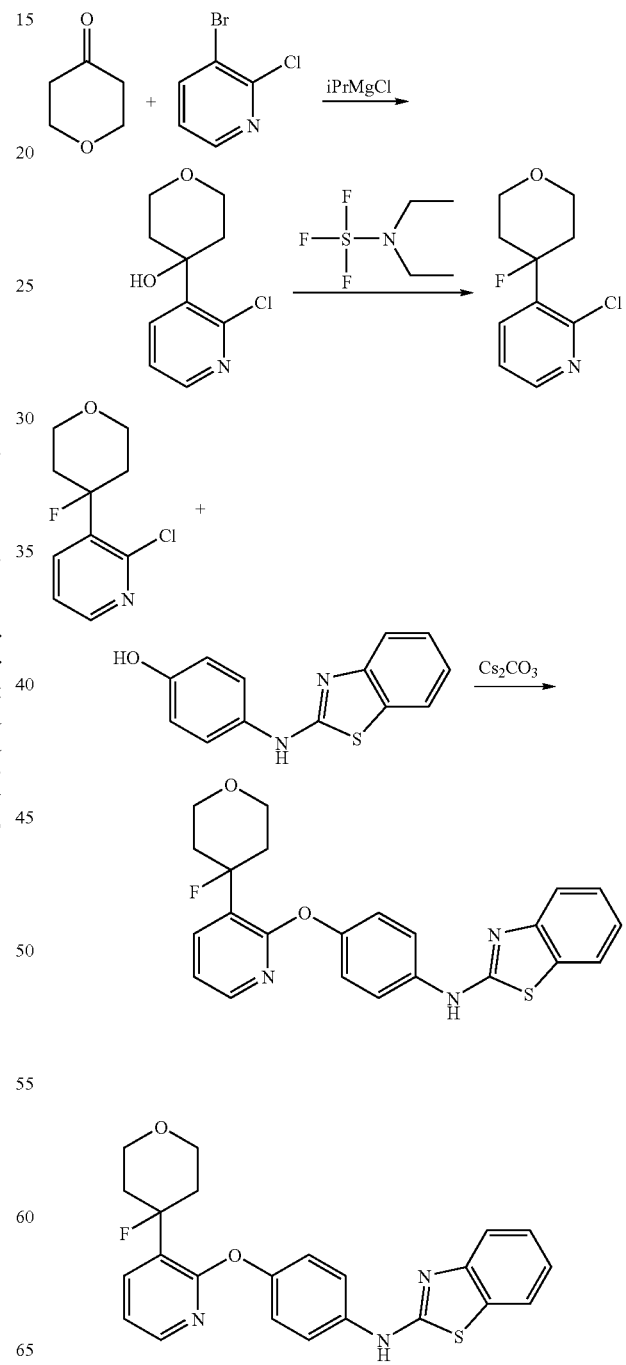

Example 180

N-(4-(3-(4-FLUOROTETRAHYDRO-2H-PYRAN-4-YL)PYRIDIN-2-YLOXY)PHENYL)BENZO[D]THIAZOL-2-AMINE

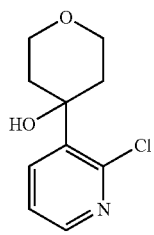

STEP 1: 4-(2-CHLOROPYRIDIN-3-YL)TETRAHYDRO-2H-PYRAN-4-OL

To a solution of 3-bromo-2-chloropyridine (0.33 g, 1.715 mmol) in THF (2 mL) at room temperature was added isopropylmagnesium chloride (0.857 mL, 1.715 mmol, 2M solution). Reaction mixture was stirred for 1 hr at room temperature before addition of dihydro-2H-pyran-4(3H)-one (0.158 mL, 1.715 mmol). After overnight stirring, reaction mixture was quenched with saturated NH₄Cl solution followed by aqueous workup. Purification by Prep-plate TLC (10% MeOH/DCM) produced product that was advanced to the next step.

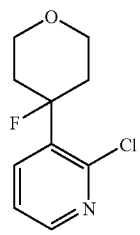

STEP 2: 2-CHLORO-3-(4-FLUOROTETRAHYDRO-2H-PYRAN-4-YL)PYRIDINE

To a solution of 4-(2-chloropyridin-3-yl)tetrahydro-2H-pyran-4-ol (0.11 g, 0.515 mmol) in DCM (1 mL, 15.54 mmol) was added dropwise DAST (0.102 mL, 0.772 mmol) at room temperature, followed by one drop of MeOH. The resulting mixture was stirred at room temperature for 3 hr. Reaction was quenched with water and extracted with DCM. The recovered residue was advanced to the next step.

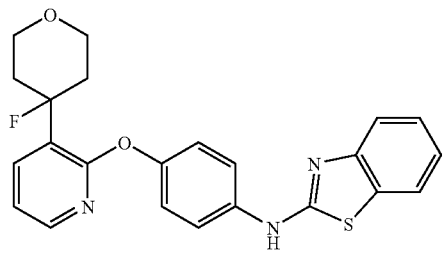

STEP 3: N-(4-(3-(4-FLUOROTETRAHYDRO-2H-PYRAN-4-YL)PYRIDIN-2-YLOXY)PHENYL)BENZO[D]THIAZOL-2-AMINE

To 2-chloro-3-(4-fluorotetrahydro-2H-pyran-4-yl)pyridine (0.11 g, 0.510 mmol) was added to 4-(benzo[d]thiazol-2-ylamino)phenol (0.124 g, 0.510 mmol) with cesium carbonate (0.332 g, 1.020 mmol) in DMSO (1 mL). The resulting mixture was heated to 90° C. overnight. Aqeuous work up and purification by prep-plate TLC (3% MeOH/DCM) produced desired product. MS (ESI, pos. ion) m/z: 422 (M+1). IC50 (uM) +++++.

SCHEME 21

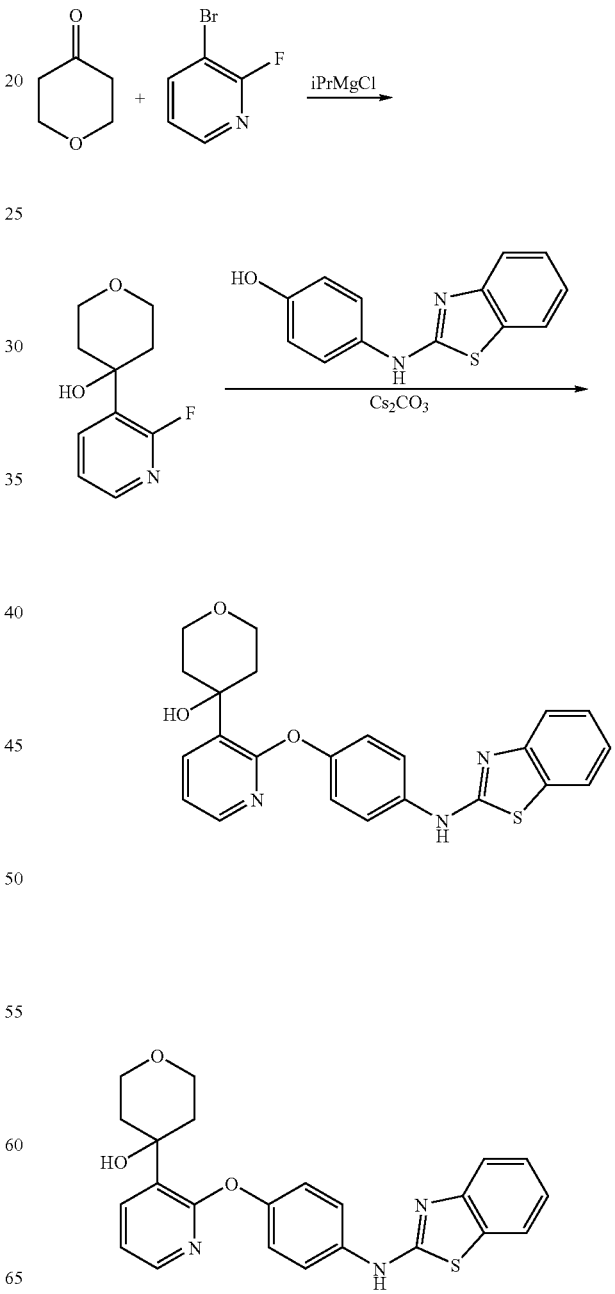

Example 181

4-(2-(4-(BENZO[D]THIAZOL-2-YLAMINO)PHE-NOXY)PYRIDIN-3-YL)TETRAHYDRO-2H-PY-RAN-4-OL

SCHEME 22

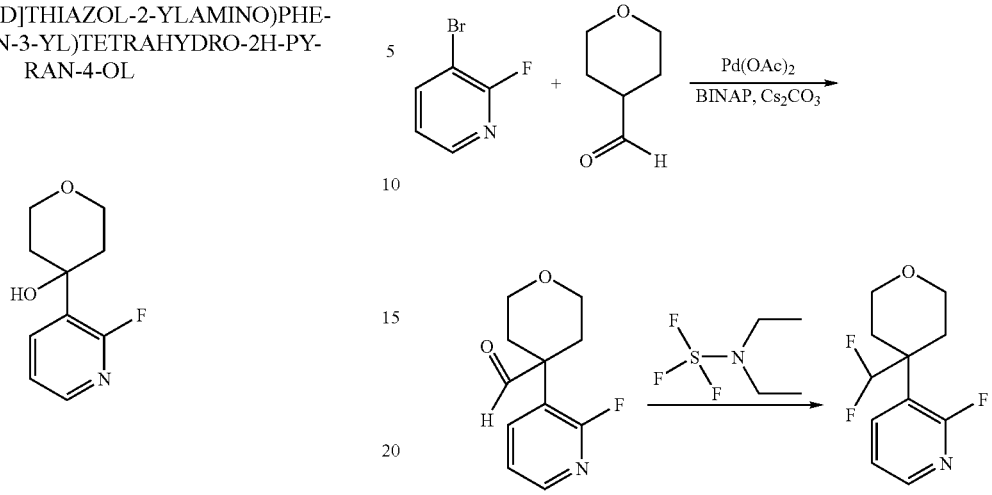

STEP 1: 4-(2-FLUOROPYRIDIN-3-YL)TETRAHYDRO-2H-PYRAN-4-OL

To a solution of 3-bromo-2-fluoropyridine (0.93 g, 5.28 mmol) in THF (5 mL) was added dropwise isopropylmagnesium chloride (2.64 mL, 5.28 mmol, 2M solution) at room temperature. After overnight stirring, dihydro-2H-pyran-4(3H)-one (0.486 mL, 5.28 mmol) was added dropwise. Reaction was quenched with saturated $NH_4Cl$ solution and extracted with DCM. Purification by Biotage (0-10% MeOH/DCM) produced the desired product.

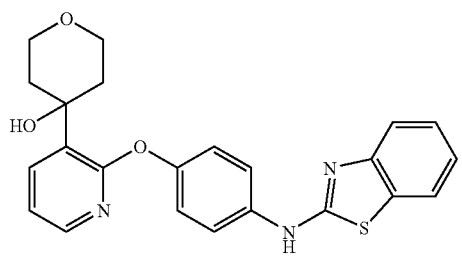

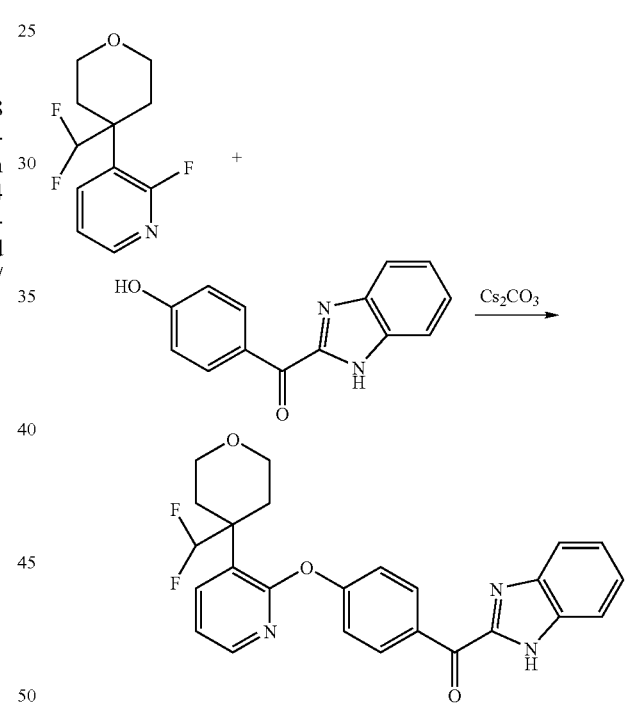

STEP 2: 4-(2-(4-(BENZO[D]THIAZOL-2-YLAMINO)PHENOXY)PYRIDIN-3-YL)TETRAHYDRO-2H-PYRAN-4-OL

To a solution of 4-(benzo[d]thiazol-2-ylamino)phenol (0.123 g, 0.507 mmol) and 4-(2-fluoropyridin-3-yl)tetrahydro-2H-pyran-4-ol (0.1 g, 0.507 mmol) in DMSO (1 mL) was added cesium carbonate (0.330 g, 1.014 mmol). The resulting mixture was heated to 100° C. and stirred overnight. Aqueous work up with multiple water and brine washes to remove DMSO and extraction with DCM. Purification by Biotage (0-10% MeOH/DCM) produced product. MS (ESI, pos. ion) m/z: 420 (M+1). IC50 (uM) +++++.

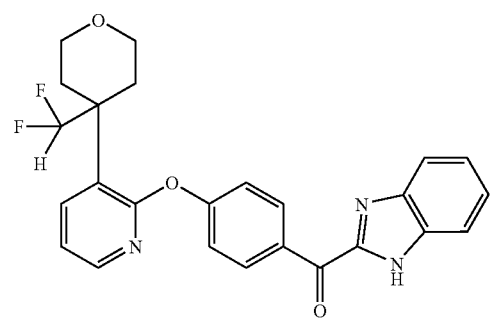

Example 182

(1H-BENZO[D]IMIDAZOL-2-YL)(4-(3-(4-(DIFLUOROMETHYL)TETRAHYDRO-2H-PYRAN-4-YL)PYRIDIN-2-YLOXY)PHENYL)METHANONE

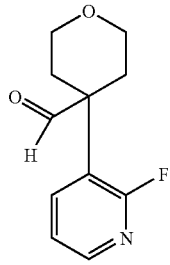

STEP 1: 4-(2-FLUOROPYRIDIN-3-YL)TETRAHYDRO-2H-PYRAN-4-CARBALDEHYDE

Into a sealed tube was added tetrahydro-2H-pyran-4-carbaldehyde (0.25 g, 2.190 mmol), 3-bromo-2-fluoropyridine (0.321 g, 1.825 mmol), palladium(ii) acetate (0.016 g, 0.073 mmol), cesium carbonate (0.714 g, 2.190 mmol), water (1.644 µL, 0.091 mmol), BINAP (0.068 g, 0.110 mmol) in Dioxane (7.30 mL). The resulting mixture was heated to 100° C. overnight. More catalyst and ligand (palladium(ii) acetate (0.016 g, 0.073 mmol), binap (0.068 g, 0.110 mmol)) were added and the resulting mixture was heated to 113° C. until the starting material was completely consumed. Aqueous work up followed by DCM extraction. Purification by Biotage (0-100% MeOH/DCM) & prep-plate TLC (5% MeOH/DCM) produced product which was advanced to the next step.

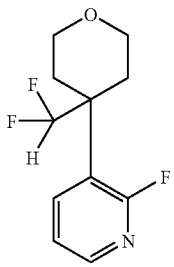

STEP 2: 3-(4-(DIFLUOROMETHYL)TETRAHYDRO-2H-PYRAN-4-YL)-2-FLUOROPYRIDINE

To a solution of 4-(2-fluoropyridin-3-yl)tetrahydro-2H-pyran-4-carbaldehyde (0.1 g, 0.478 mmol) in DCM (2 mL) at 0° C. was added DAST (0.126 mL, 0.956 mmol). The mixture was gradually warmed to room temperature overnight. Reaction mixture was quenched with saturated bicarbonate solution and extracted with DCM. The recovered residue was advanced to next step.

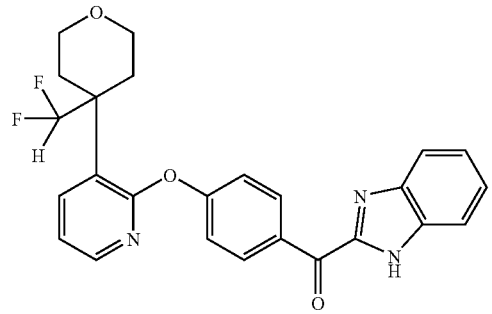

STEP 3: (1H-BENZO[D]IMIDAZOL-2-YL)(4-(3-(4-(DIFLUOROMETHYL)TETRAHYDRO-2H-PYRAN-4-YL)PYRIDIN-2-YLOXY)PHENYL)METHANONE

To a solution of 3-(4-(difluoromethyl)tetrahydro-2H-pyran-4-yl)-2-fluoropyridine (0.1 g, 0.432 mmol) in NMP was added cesium carbonate (0.282 g, 0.865 mmol) and (1H-benzo[d]imidazol-2-yl)(4-hydroxyphenyl)methanone (0.155 g, 0.649 mmol). The resulting mixture was heated to 175° C. overnight. Purification by prep-plate TLC (5% MeOH/DCM & 75% EtOAc/hexane) produced product. MS (ESI, pos. ion) m/z: 450 (M+1). IC50 (uM) +++++.

SCHEME 23

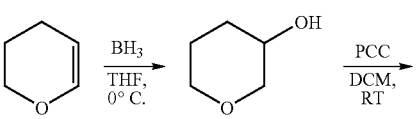

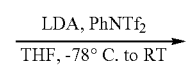

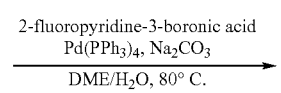

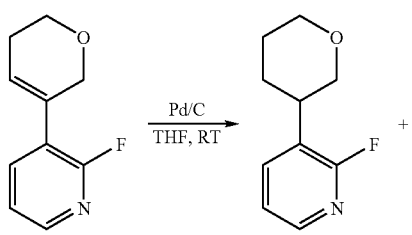

-continued

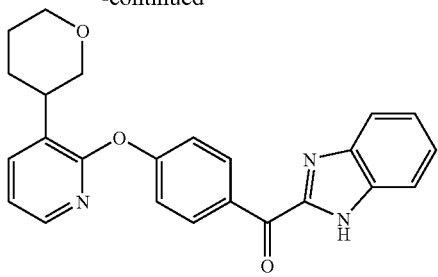

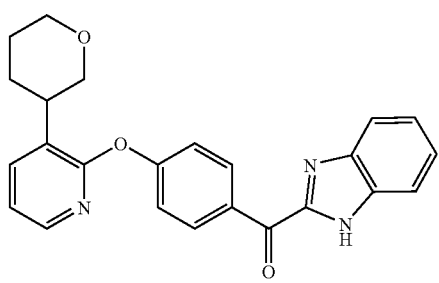

Example 183

(1H-BENZO[D]IMIDAZOL-2-YL)(4-(3-(TET-RAHYDRO-2H-PYRAN-3-YL)PYRIDIN-2-YLOXY)PHENYL)METHANONE

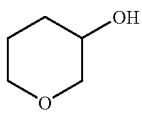

STEP 1. TETRAHYDRO-2H-PYRAN-3-OL

To a stirred solution of 3,4-dihydro-2H-pyran (5.42 mL, 59.4 mmol) in THF (100 mL) at 0° C. under a nitrogen atmosphere was added borane tetrahydrofuran complex, (29.7 mL, 29.7 mmol, 1.0 M in THF) via syringe. The reaction mixture was stirred at 0° C. for 3 h before a mixture of 5 M aqueous sodium hydroxide (40 mL) and 30% aqueous hydrogen peroxide (20 mL) was added. The reaction mixture was warmed to room temperature and stirred for 3 h. Sat. aqueous sodium bicarbonate was added, and the mixture was extracted with EtOAc (2×). The combined organic layers were washed with sat. aqueous sodium chloride, dried over magnesium sulfate, filtered, and concentrated in vacuo to give tetrahydro-2H-pyran-3-ol.

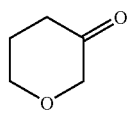

STEP 2. DIHYDRO-2H-PYRAN-3(4H)-ONE

To a stirred mixture of pyridinium chlorochromate (11.02 g, 51.1 mmol) and 3 Å molecular sieves (10.0 g) in DCM (100 mL) was added a solution of tetrahydro-2H-pyran-3-ol (3.48 g, 34.1 mmol) in DCM (100 mL). The reaction mixture was refluxed for 3 h before being cooled to room temperature and partially concentrated in vacuo. The mixture was then diluted with EtOAc and filtered through Celite. The filtrate was concentrated in vacuo and purified by silica gel chromatography to give dihydro-2H-pyran-3(4H)-one.

STEP 3. 5,6-DIHYDRO-2H-PYRAN-3-YL TRIFLUOROMETHANESULFONATE

To a stirred solution of diisopropylamine (3.06 mL, 21.8 mmol) in THF (50 mL) at −78° C. under an argon atmosphere was added butyllithium (8.73 mL, 21.8 mmol, 2.5 M in hexanes). The mixture was stirred for 5 min before dihydro-2H-pyran-3(4H)-one (1.82 g, 18.2 mmol) in THF (15 mL) was added slowly via syringe. The mixture was stirred for an additional 15 min before n-phenyltrifluoromethanesulfonimide (7.14 g, 20.0 mmol) in THF (15 mL) was added slowly via syringe. The reaction mixture was then stirred at −78° C. for an additional 15 min before being allowed to warm to room temperature and stirred for 1 h. Sat. aqueous sodium bicarbonate was added, and the mixture was extracted with EtOAc (2×). The combined organic layers were washed with sat. sodium chloride, dried over magnesium sulfate, filtered, and concentrated in vacuo. The resulting crude oil was purified by silica gel chromatography to give 5,6-dihydro-2H-pyran-3-yl trifluoromethanesulfonate.

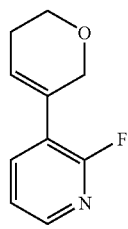

STEP 4. 3-(5,6-DIHYDRO-2H-PYRAN-3-YL)-2-FLUOROPYRIDINE

Sodium carbonate (29.0 mL, 58.0 mmol, 2.0 M in water) was added via syringe to a stirred mixture of 5,6-dihydro-2H-pyran-3-yl trifluoromethanesulfonate (4.49 g, 19.3 mmol), 2-fluoropyridine-3-boronic acid (2.72 g, 19.3 mmol), and tetrakis(triphenylphosphine)palladium (1.12 g, 0.97 mmol) in DME (82 mL) under an argon atmosphere. The reaction mixture was stirred at 80° C. for 17 h. The reaction mixture was then cooled to room temperature before being diluted with EtOAc and water. The organic layer was separated, washed with sat. aqueous sodium chloride, dried over magnesium sulfate, filtered, and concentrated in vacuo. The resulting crude product was purified by silica gel chromatography to give 3-(5,6-dihydro-2H-pyran-3-yl)-2-fluoropyridine. MS (ESI, pos. ion) m/z: 180.0.

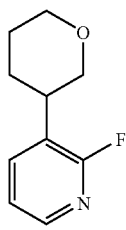

STEP 5. 2-FLUORO-3-(TETRAHYDRO-2H-PYRAN-3-YL) PYRIDINE

Palladium (0.005 g, 0.005 mmol, 10% wt. on activated carbon) was added to a stirred solution of 3-(5,6-dihydro-2H-pyran-3-yl)-2-fluoropyridine (0.10 g, 0.558 mmol) in THF (2 mL). The reaction mixture was placed under a hydrogen atmosphere (balloon) and stirred at room temperature for 4 h. The reaction mixture was filtered through Celite, and the filtrate was concentrated in vacuo to give 2-fluoro-3-(tetrahydro-2H-pyran-3-yl)pyridine. MS (ESI, pos. ion) m/z: 182.1 (M+1).

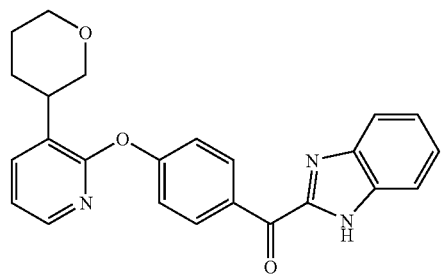

STEP 6. (1H-BENZO[D]IMIDAZOL-2-YL)(4-(3-(TETRAHYDRO-2H-PYRAN-3-YL)PYRIDIN-2-YLOXY)PHENYL)METHANONE

2-Fluoro-3-(tetrahydro-2H-pyran-3-yl)pyridine (0.10 g, 0.55 mmol), (1H-benzo[d]imidazol-2-yl)(4-hydroxyphenyl) methanone (0.33 g, 1.38 mmol), and cesium carbonate (0.54 g, 1.66 mmol) were mixed in NMP (2 mL). The reaction mixture was placed under a nitrogen atmosphere and stirred at 140° C. for 72 h. The reaction mixture was cooled to room temperature, diluted with water, and extracted with EtOAc (2×). The combined organic layers were washed with 1 M aqueous sodium hydroxide (1×), sat. sodium chloride (1×), dried over magnesium sulfate, filtered, and concentrated in vacuo. The resulting crude product was purified by silica gel chromatography to give (1H-benzo[d]imidazol-2-yl)(4-(3-(tetrahydro-2H-pyran-3-yl)pyridin-2-yloxy)phenyl)methanone. MS (ESI, pos. ion) m/z: 400.1 (M+1). IC50 (uM) +++++.

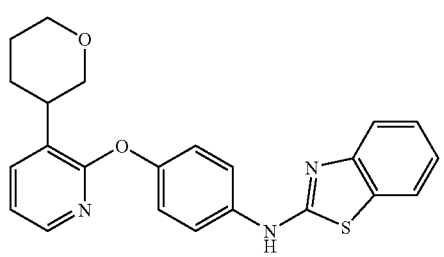

Example 184

N-(4-(3-(TETRAHYDRO-2H-PYRAN-3-YL)PYRIDIN-2-YLOXY)PHENYL)BENZO[D]THIAZOL-2-AMINE

2-Fluoro-3-(tetrahydro-2H-pyran-3-yl)pyridine (0.10 g, 0.55 mmol), 4-(benzo[d]thiazol-2-ylamino)phenol (0.33 g, 1.38 mmol), and cesium carbonate (0.54 g, 1.66 mmol) were mixed in NMP (2 mL). The reaction mixture was placed under a nitrogen atmosphere and stirred at 120° C. for 16 h. The reaction mixture was cooled to room temperature, diluted with water, and extracted with EtOAc (2×). The combined organic layers were washed with 1 M aqueous sodium hydroxide, sat. sodium chloride, dried over magnesium sulfate, filtered, and concentrated in vacuo. The resulting crude product was purified by silica gel chromatography to give N-(4-(3-(tetrahydro-2H-pyran-3-yl)pyridin-2-yloxy)phenyl) benzo[d]thiazol-2-amine. MS (ESI, pos. ion) m/z: 404.1 (M+1). IC50 (uM) +++++.

SCHEME 24

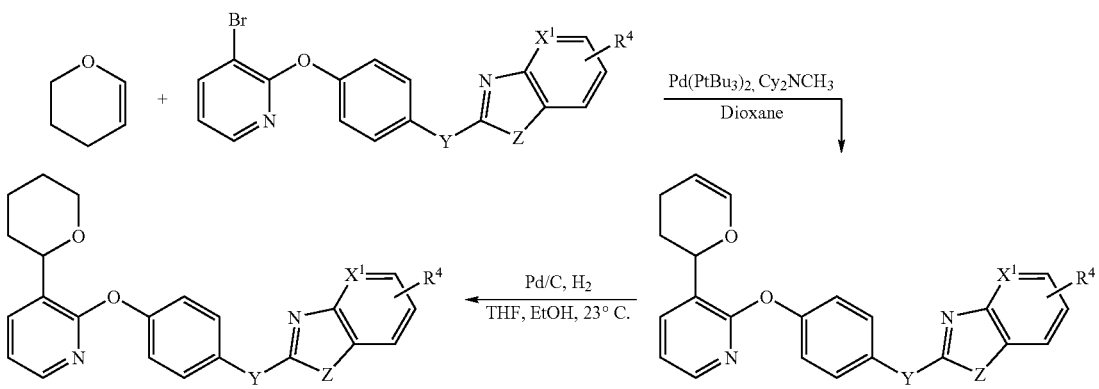

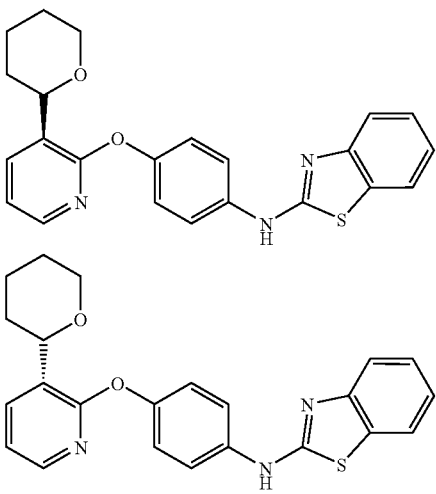

Example 185

(±)-N-(4-(3-(TETRAHYDRO-2H-PYRAN-2-YL)
PYRIDIN-2-YLOXY)PHENYL)BENZO[D]THIA-
ZOL-2-AMINE

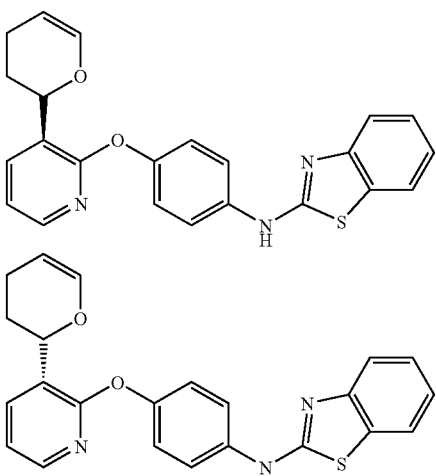

STEP 1. (±)-N-(4-(3-(3,4-DIHYDRO-2H-PYRAN-
2-YL)PYRIDIN-2-YLOXY)PHENYL)BENZO[D]
THIAZOL-2-AMINE

A 25 mL reseable vial was charged with bis(tri-tert-butylphosphine) palladium (0) (83 mg, 0.163 mmol) and N-(4-(3-bromopyridin-2-yloxy)phenyl)benzo[d]thiazol-2-amine (650 mg, 1.632 mmol). The vial was sealed and placed under an atmosphere of nitrogen. After addition of dioxane (5.38 ml), N-cyclohexyl-N-methylcyclohexanamine (1.072 ml, 4.90 mmol) and 3,4-dihydro-2H-pyran (549 mg, 6.53 mmol) were added and the mixture was heated to 105° C. Following complete consumption of the starting material, the reaction mixture was cooled to room temperature and transferred to a 100 mL round bottom flask, and the solvent was removed under reduced pressure. Following purification by silica gel chromatography the desired product was obtained as a racemic mixture. MS (ESI, pos. ion) m/z: 402.0 (M+1).

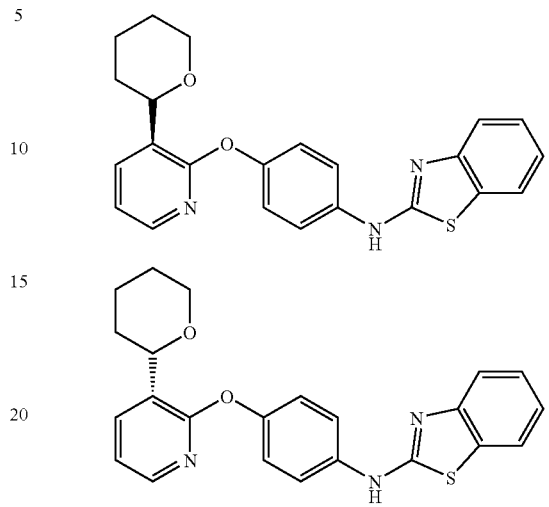

STEP 2. (±)-N-(4-(3-(TETRAHYDRO-2H-PYRAN-
2-YL)PYRIDIN-2-YLOXY)PHENYL)BENZO[D]
THIAZOL-2-AMINE

A mixture of N-(4-(3-(3,4-dihydro-2H-pyran-2-yl)pyridin-2-yloxy)phenyl)benzo[d]thiazol-2-amine (357 mg, 0.889 mmol) and palladium on carbon, wet (95 mg, 0.089 mmol) in ethanol (0.15M) was placed under an atmosphere of hydrogen (g) and stirred at room temperature. After the starting material was completely consumed, the mixture was filtered through a cake of celite, washed with MeOH & THF and filtrate was concentrated to dryness. The residue was purified by silica gel chromatography to give the desired product as a racemic mixture. MS (ESI, pos. ion) m/z: 404.0 (M+1). IC50 (uM) +++++.

SCHEME 25

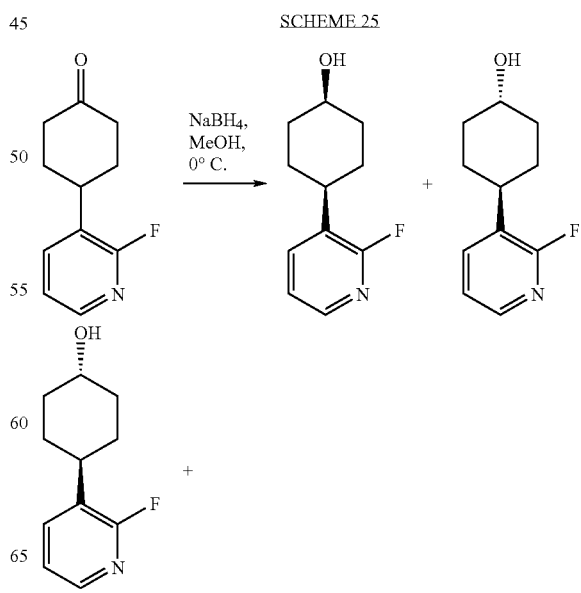

-continued

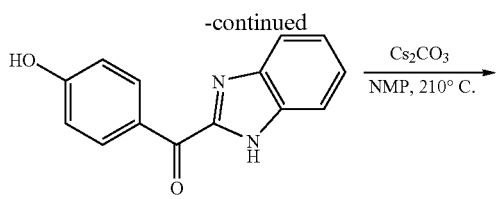

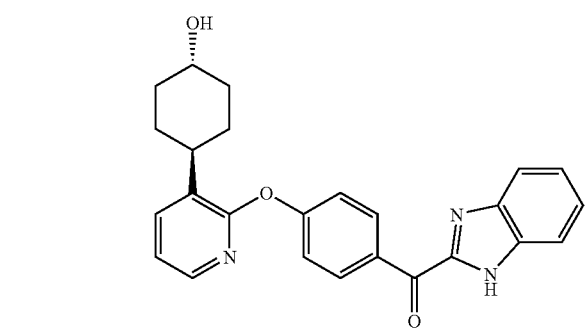

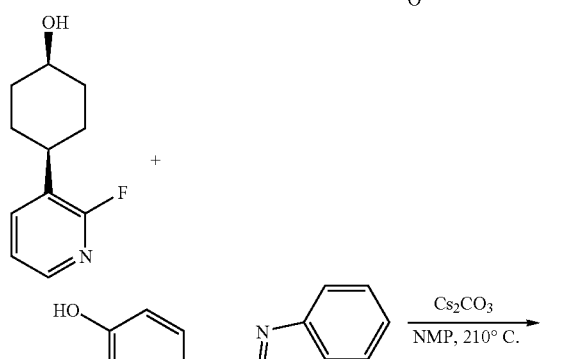

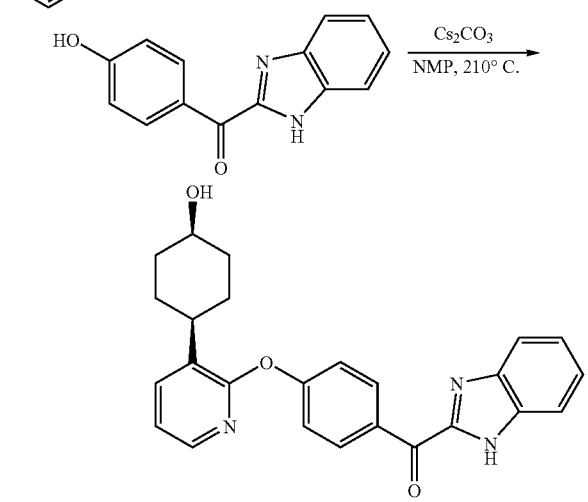

Example 186

(1H-BENZO[D]IMIDAZOL-2-YL)(4-(3-((1R,4R)-4-HYDROXYCYCLOHEXYL)PYRIDIN-2-YLOXY)PHENYL)METHANONE

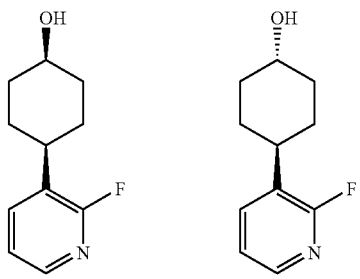

STEP 1. (1R,4R)-4-(2-FLUOROPYRIDIN-3-YL)CYCLOHEXANOL; (1S,4S)-4-(2-FLUOROPYRIDIN-3-YL)CYCLOHEXANOL 4-(2-fluoropyridin-3-yl)cyclohexanone (0.420 g, 2.174 mmol) was dissolved in 20 mL MeOH and cooled to 0° C. Sodium boron hydrate (0.123 g, 3.26 mmol) was added slowly portion wise and stirring was continued for 7 h. The mixture was evaporated and 3 mL of DCM was added to the residue. The mixture was purified and separated via glass column chromatography (10-100% EtOAc in hexanes) providing (1R,4R)-4-(2-fluoropyridin-3-yl)cyclohexanol and (1S,4S)-4-(2-fluoropyridin-3-yl)cyclohexanol as white solids.

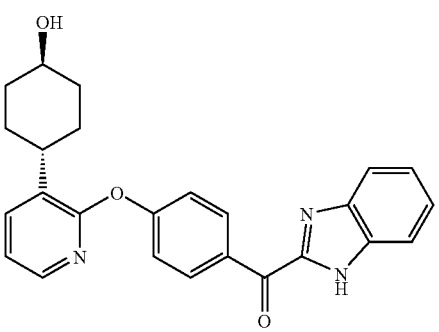

STEP 2. (1H-BENZO[D]IMIDAZOL-2-YL)(4-(3-((1R,4R)-4-HYDROXYCYCLOHEXYL) PYRIDIN-2-YLOXY)PHENYL)METHANONE (1R,4R)-4-(2-fluoropyridin-3-yl)cyclohexanol (75 mg, 0.384 mmol) and (1H-benzo[d]imidazol-2-yl)(4-hydroxyphenyl)methanone (183 mg, 0.768 mmol) were dissolved in 1 mL NMP and cesium carbonate (250 mg, 0.768 mmol) was added. The reaction was heated to 210° C. for 1 h in a sealed reaction vessel. After cooling to room temperature, the mixture was diluted with 1 mL DMF and filtered. The filtrate was injected w/o further work up procedure onto the HPLC for product purification purposes. The collected HPLC fractions were combined and K₂CO₃ was added (aq. phase pH 9). The mixture was extracted 3 times with EtOAc (3×100 mL) and the combined organic phases were dried over MgSO₄ and evaporated to give (1H-benzo[d]imidazol-2-yl)(4-(3-((1r,4r)-4-hydroxycyclohexyl)pyridin-2-yloxy)phenyl)methanone as a white solid. MS (ESI, pos. ion) m/z: 414.0 (M+1). IC50 (uM) +++++.

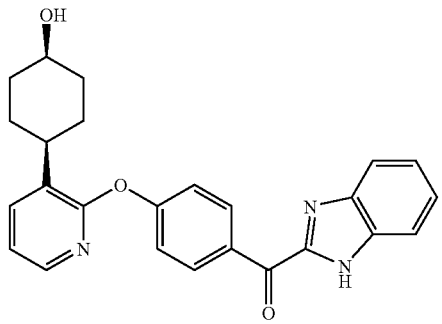

Example 187

(1H-BENZO[D]IMIDAZOL-2-YL)(4-(3-((1S,4S)-4-HYDROXYCYCLOHEXYL)PYRIDIN-2-YLOXY)PHENYL)METHANONE (1s,4s)-4-(2-fluoropyridin-3-yl)cyclohexanol (0.058 g, 0.297 mmol) and (1H-benzo[d]imidazol-2-yl)(4-hydroxyphenyl)methanone (0.142 g, 0.594 mmol) were dissolved in 1 ml NMP and cesium carbonate (0.194 g, 0.594 mmol) was added. The reaction was heated to 210° C. for 1 h in a sealed reaction vessel. After cooling to room temperature, the mixture was diluted with 1 ml DMF and filtered. The filtrate was injected w/o further work up procedure onto the HPLC for product purification purposes. The collected HPLC fractions were combined and K2CO3 was added (aq. phase pH 9). The mixture was extracted 3 times with EtOAc (3×100 ml) and the combined organic phases were dried over MgSO4 and evaporated to give (1H-benzo[d]imidazol-2-yl)(4-(3-((1S,4S)-4-hydroxycyclohexyl)pyridin-2-yloxy)phenyl)methanone as a white solid. MS (ESI, pos. ion) m/z: 414.0 (M+1). IC50 (uM) +++++.

SCHEME 26

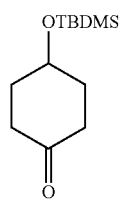

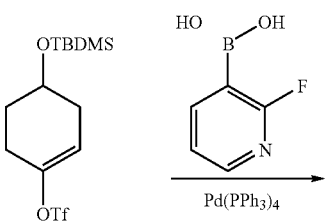

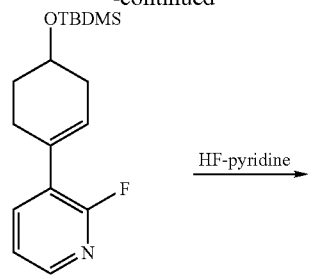

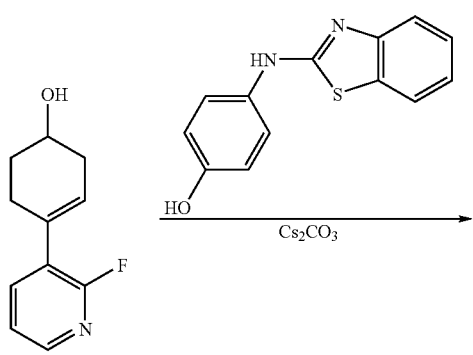

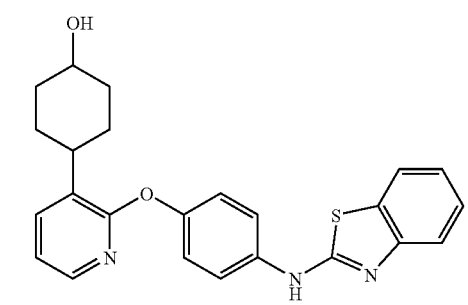

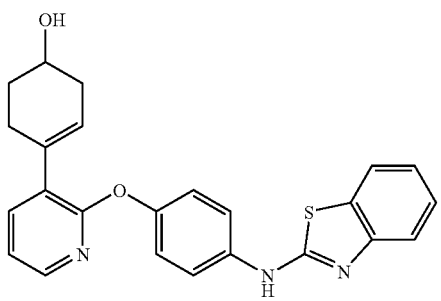

Example 188

4-(2-(4-(BENZO[D]THIAZOL-2-YLAMINO)PHE-NOXY)PYRIDIN-3-YL)CYCLOHEX-3-ENOL

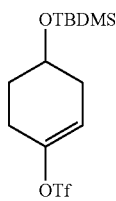

STEP 1: 4-(TERT-BUTYLDIMETHYLSILYLOXY)CYCLOHEX-1-ENYL TRIFLUOROMETHANESULFONATE

To a 500 mL round bottom was added 4-(tert-butyldimethylsilyloxy)cyclohexanone (7.71 g, 33.8 mmol). A 1M solution of NaHMDS (35.4 mL, 35.4 mmol) in THF was added dropwise after cooling the reaction to −20° C. The resulting orange solution was stirred for 1 h before adding trifluoromethanesulfonic anhydride (10 mL, 35.4 mmol) dropwise over 10 minutes. The yellow suspension was allowed to warm to room temperature with stirring over 12 h. It was diluted with saturated aqueous NaHCO$_3$ before extracting with diethyl ether, drying over sodium sulfate, filtering, and drying under reduced pressure to an orange oil, which was purified by column chromatography (ethyl acetate/hexanes), affording 4-(tert-butyldimethylsilyloxy)cyclohex-1-enyl trifluoromethanesulfonate as a pale yellow oil.

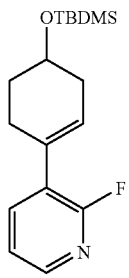

STEP 2: 3-(4-(TERT-BUTYLDIMETHYLSILYLOXY)CYCLOHEX-1-ENYL)-2-FLUOROPYRIDINE

To a sealable vessel was added 4-(tert-butyldimethylsilyloxy)cyclohex-1-enyl trifluoromethanesulfonate (1.90 g, 5.27 mmol), sodium carbonate as a 2N solution in water (7.91 mL, 15.81 mmol), and 2-fluoropyridin-3-ylboronic acid (0.891 g, 6.33 mmol) before adding tetrakis(triphenylphosphine)palladium(0) (0.305 g, 0.264 mmol) under argon. The reaction mixture was sealed and set stirring at 80° C. After complete consumption of starting material, the black mixture was diluted with water before extracting with dichloromethane, drying over sodium sulfate, filtering, and concentrating under reduced pressure to an orange oil, which was used without purification. MS (ESI, pos. ion) m/z: 308.0 (M+1).

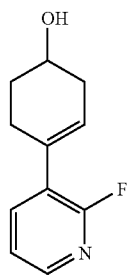

STEP 3: 4-(2-FLUOROPYRIDIN-3-YL)CYCLOHEX-3-ENOL

To a flask containing 3-(4-(tert-butyldimethylsilyloxy)cyclohex-1-enyl)-2-fluoropyridine (1.5 g, 4.88 mmol) was added anhydrous dichloromethane (48.8 mL) under nitrogen. After cooling to 0° C., hydrogen fluoride-pyridine complex (1.696 mL, 19.51 mmol) was added dropwise. The reaction mixture was warmed to room temperature and stirred until the starting material had been consumed. The reaction mixture was quenched with saturated aqueous sodium bicarbonate and extracted with dichloromethane before drying over magnesium sulfate, filtering, and concentrating to a clear oil under reduced pressure. The material was used without purification.

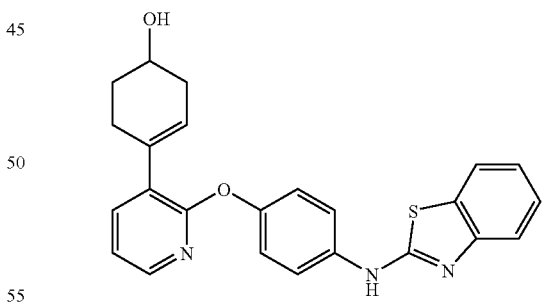

STEP 4: 4-(2-(4-(BENZO[D]THIAZOL-2-YLAMINO)PHENOXY)PYRIDIN-3-YL)CYCLOHEX-3-ENOL

To a vial containing cesium carbonate (1391 mg, 4.27 mmol) was added 4-(benzo[d]thiazol-2-ylamino)phenol (1035 mg, 4.27 mmol), and 4-(2-fluoropyridin-3-yl)cyclohex-3-enol (330 mg, 1.708 mmol) followed by NMP (2.2 mL). The reaction was heated at 200° C. for 2 h with microwave irradiation. The black mixture was diluted with ethyl acetate and washed with 5N NaOH before drying over sodium sulfate, filtering, and concentrating under reduced pressure to a brown residue. Purification by column chromatography (ethyl acetate/dichlormethane) afforded 4-(2-(4-(benzo[d]thiazol-2-ylamino)phenoxy)pyridin-3-yl)cyclohex-3-enol (44.8 mg, 0.108 mmol, 3, steps, 6.31% yield) as a pale brown oil. MS (ESI, pos. ion) m/z: 416.1 (M+1). IC50 (uM) +++++.

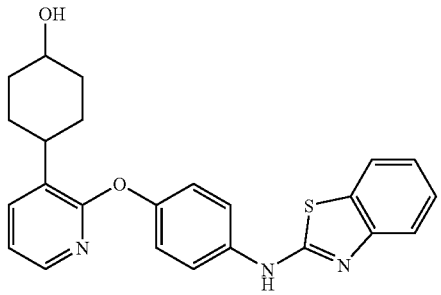

Example 189

4-(2-(4-(BENZO[D]THIAZOL-2-YLAMINO)PHENOXY)PYRIDIN-3-YL)CYCLOHEXANOL

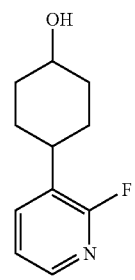

STEP 1: 4-(2-FLUOROPYRIDIN-3-YL)CYCLOHEXANOL

To a flask containing 4-(2-fluoropyridin-3-yl)cyclohex-3-enol (750 mg, 3.88 mmol) and Ethanol (31.100 ml):Tetrahydrofuran (7.78 ml) was added 10% palladium on carbon, (240 mg, 2.255 mmol) before purging the reaction of air and backfilling with hydrogen. It was stirred for 3 h at room temperature before adding an additional 30 mol % Pd/C and stirring at 40° C. for 16 h. The reaction mixture was cooled and filtered through Celite before concentrating under reduced pressure to yield 4-(2-fluoropyridin-3-yl)cyclohexanol as a pale yellow oil that was used without purification. MS (ESI, pos. ion) m/z: 196.1 (M+1).

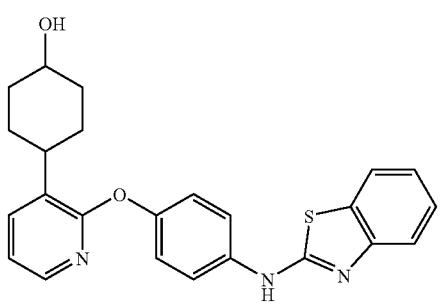

STEP 2: 4-(2-(4-(BENZO[D]THIAZOL-2-YLAMINO)PHENOXY)PYRIDIN-3-YL)CYCLOHEXANOL

To a vial containing 4-(benzo[d]thiazol-2-ylamino)phenol (819 mg, 3.38 mmol) was added cesium carbonate (918 mg, 2.82 mmol) followed by 4-(2-fluoropyridin-3-yl)cyclohexanol (220 mg, 1.127 mmol) as a solution in NMP (7.5 mL). The reaction mixture was heated to 200° C. for 2.5 h with microwave irradiation. The reaction mixture was diluted with water and extracted with 15% IPA:chloroform before drying over magnesium sulfate, filtering, and concentrating to a dark brown residue under reduced pressure.

The dark brown residue was adsorbed onto a plug of silica and purified by column chromatography (methanol/dichloromethane) to yield a clear oil that was a mixture of cis and trans compounds. The oil was purified by SFC to yield two compounds. Chirality was arbitrarily assigned. IC50 (uM) +++++.

SCHEME 27

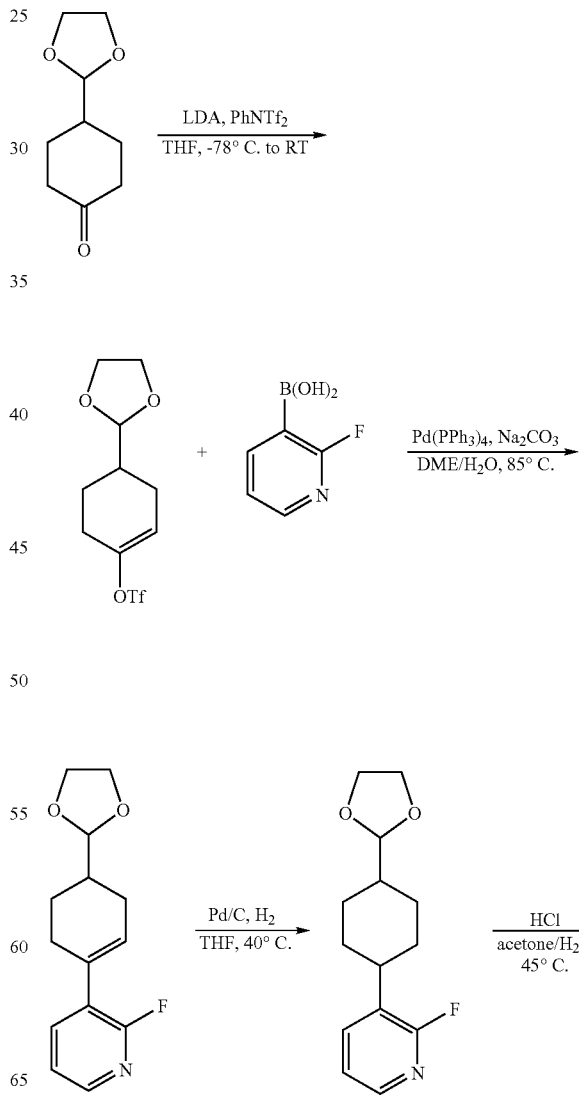

-continued

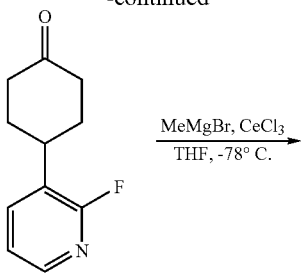

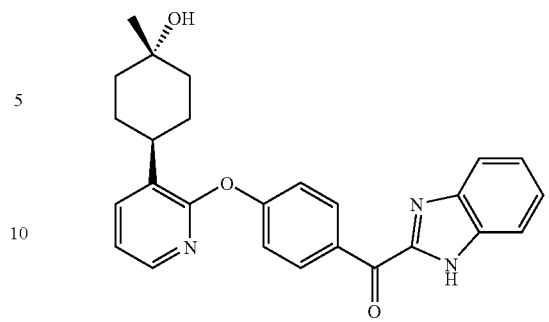

Example 190

(1H-BENZO[D]IMIDAZOL-2-YL)(4-(3-((1R,4R)-4-HYDROXY-4-METHYLCYCLOHEXYL)PYRIDIN-2-YLOXY)PHENYL)METHANONE

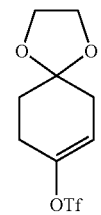

STEP 1. 1,4-DIOXASPIRO[4.5]DEC-7-EN-8-YL TRIFLUOROMETHANESULFONATE

To a solution of diisopropylamine, (6.24 mL, 44.2 mmol) in THF (60 mL) at −78° C. under argon was slowly added n-butyllithium (17.7 mL, 44.2 mmol, 2.5 M in hexanes). The mixture was stirred for 30 min at that temperature before 1,4-cyclohexanedione mono-ethylene ketal (6.00 g, 38.4 mmol) was added slowly as a solution in THF (20 mL). The mixture was stirred for an additional 30 min at −78° C. and then n-phenyltriflimide (13.7 g, 38.4 mmol) was slowly added as a suspension in THF (50 mL). This mixture was stirred overnight with gradual warming to room temperature. The solvent was removed in vacuo and the remaining oil was partitioned between 3:1 ethyl acetate/hexane and water. The layers were separated and the organic layer was washed with water (3×), dried over anhydrous magnesium sulfate, filtered, and concentrated in vacuo to give 1,4-dioxaspiro[4.5]dec-7-en-8-yl trifluoromethanesulfonate.

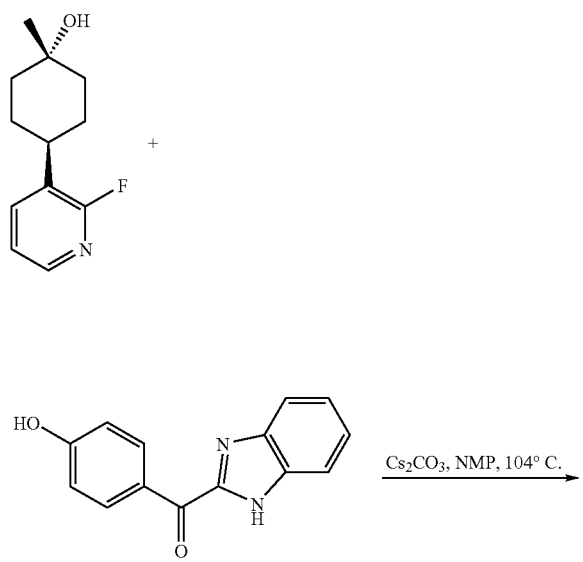

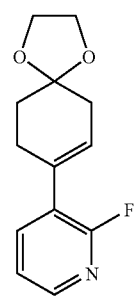

STEP 2. 2-FLUORO-3-(1,4-DIOXASPIRO[4.5]DEC-7-EN-8-YL)PYRIDINE

To a mixture of 1,4-dioxaspiro[4.5]dec-7-en-8-yl trifluoromethanesulfonate (10.2 g, 35.4 mmol) and 2-fluoropyridin-3-ylboronic acid (5.00 g, 35.5 mmol) in 1,2-dimethoxyethane (200 mL) and aqueous sodium carbonate (53.2 mL, 106 mmol, 2N) under argon atmosphere was added palladium tetrakis(triphenylphosphine) (1.23 g, 1.06 mmol). The mixture was heated and stirred at 85° C. for 1 h., then cooled to room temperature. Ethyl acetate was added and the mixture was washed with water, saturated sodium chloride, dried over anhydrous magnesium sulfate, filtered, and concentrated in vacuo. The resulting oil was purified by silica gel chromatography to give 2-fluoro-3-(1,4-dioxaspiro[4.5]dec-7-en-8-yl)pyridine. MS (ESI, pos. ion) m/z: 236.1 (M+1).

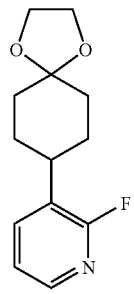

STEP 3. 2-FLUORO-3-(1,4-DIOXASPIRO[4.5]DECAN-8-YL)PYRIDINE

To a solution of 2-fluoro-3-(1,4-dioxaspiro[4.5]dec-7-en-8-yl)pyridine (7.99 g, 34.0 mmol) in THF (40 mL) under argon atmosphere was added palladium on carbon (10% activated, 0.80 g). The mixture was placed under 1 atmosphere of hydrogen and stirred for 5 h at 40° C. After placing the mixture back under argon atmosphere, the mixture was filtered through celite and the filtrate was concentrated in vacuo to give 2-fluoro-3-(1,4-dioxaspiro[4.5]decan-8-yl)pyridine. MS (ESI, pos. ion) m/z: 238.1 (M+1).

STEP 4. 4-(2-FLUOROPYRIDIN-3-YL)CYCLOHEXANONE

To a solution of 2-fluoro-3-(1,4-dioxaspiro[4.5]decan-8-yl)pyridine (7.88 g, 33.2 mmol) in acetone (350 mL) was added aqueous hydrochloric acid (39.9 mL, 39.9 mmol, 1N). The mixture was heated to 45° C. for 5 h, then cooled to room temperature. Most of the organic solvent was removed in vacuo and ethyl acetate (200 mL) was added. The resulting solution was washed with saturated aqueous sodium bicarbonate (2×), water (1×), saturated aqueous sodium chloride (1×), dried over anhydrous magnesium sulfate, filtered, and concentrated in vacuo to give 4-(2-fluoropyridin-3-yl)cyclohexanone. MS (ESI, pos. ion) m/z: 194.1 (M+1).

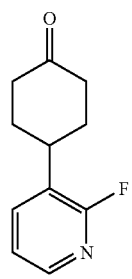

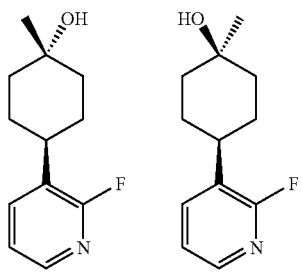

STEP 5. (1R,4R)-4-(2-FLUOROPYRIDIN-3-YL)-1-METHYLCYCLOHEXANOL AND (1S,4S)-4-(2-FLUOROPYRIDIN-3-YL)-1-METHYLCYCLOHEXANOL

A suspension of dry cerium(III) chloride (1.61 g, 6.52 mmol) in THF (15 mL) under argon was stirred at 40° C. for 2 h, then cooled to −78° C. Methylmagnesium bromide (2.17 mL, 6.52 mmol, 3M in diethyl ether) was added dropwise over 3 minutes and the mixture was stirred an additional 30 minutes at −78° C. A solution of 4-(2-fluoropyridin-3-yl)cyclohexanone (1.05 g, 5.43 mmol) in THF (3 mL) was added dropwise and the mixture was stirred at −78° C. for 1 h. The reaction was then quenched with saturated aqueous ammonium chloride, warmed to room temperature, and extracted with ethyl acetate several times. The combined organic extracts were dried over anhydrous magnesium sulfate, filtered, and concentrated in vacuo. The resulting oil was purified by silica gel chromatography to give (1r,4r)-4-(2-Fluoropyridin-3-yl)-1-methylcyclohexanol and (1s,4s)-4-(2-fluoropyridin-3-yl)-1-methylcyclohexanol as pure stereoisomeric compounds. MS (ESI, pos. ion) m/z: 210.1 (M+1) for each compound.

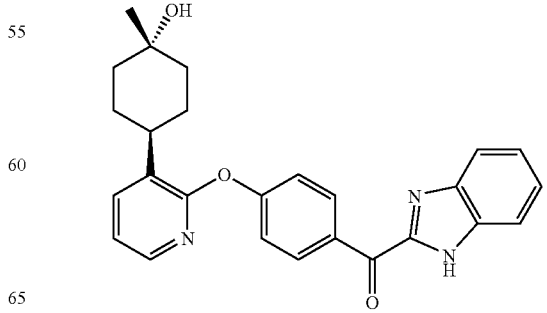

249

STEP 6. (1H-BENZO[D]IMIDAZOL-2-YL)(4-(3-((1R,4R)-4-HYDROXY-4-METHYLCYCLO-HEXYL)PYRIDIN-2-YLOXY)PHENYL)METHA-NONE

A mixture of cesium carbonate (0.51 g, 1.56 mmol), (1H-benzo[d]imidazol-2-yl)(4-hydroxyphenyl)methanone (0.37 g, 1.563 mmol), and (1r,4r)-4-(2-fluoropyridin-3-yl)-1-methylcyclohexanol (0.11 g, 0.52 mmol) in NMP (2 mL) was heated to 160° C. for 3 d, cooled to room temperature, and partitioned between ethyl acetate and water. The layers were separated and the organic layer was washed with 1N aqueous sodium hydroxide (2×), water (1×), saturated aqueous sodium chloride (1×), dried over magnesium sulfate, filtered, and concentrated in vacuo. The resulting oil was purified by silica gel chromatography to give (1H-benzo[d]imidazol-2-yl)(4-(3-((1r,4r)-4-hydroxy-4-methylcyclohexyl)pyridin-2-yloxy)phenyl)methanone. MS (ESI, pos. ion) m/z: 428.1 (M+1). IC50 (uM) +++++.

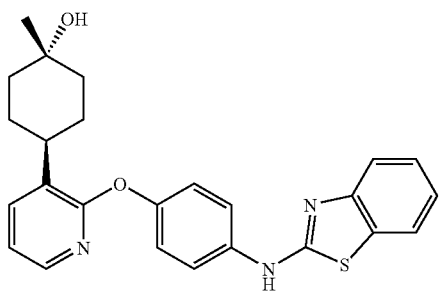

250

Example 191

(1R,4R)-4-(2-(4-(BENZO[D]THIAZOL-2-YLAMINO)PHENOXY)PYRIDIN-3-YL)-1-METHYLCYCLOHEXANOL

A mixture of cesium carbonate (0.50 g, 1.52 mmol), 4-(benzo[d]thiazol-2-ylamino)phenol (0.37 g, 1.52 mmol), and (1r,4r)-4-(2-fluoropyridin-3-yl)-1-methylcyclohexanol (0.11 g, 0.51 mmol) in NMP (1 mL) in a sealed tube was heated to 120° C. for 24 h, cooled to room temperature and partitioned between ethyl acetate and water. The layers were separated and the organic layer was washed with 1N aqueous sodium hydroxide (2×), water (1×), saturated aqueous sodium chloride (1×), dried over anhydrous magnesium sulfate, filtered, and concentrated in vacuo. The resulting oil was purified by silica gel chromatography to give (1r,4r)-4-(2-(4-(benzo[d]thiazol-2-ylamino)phenoxy)pyridin-3-yl)-1-methylcyclohexanol. MS (ESI, pos. ion) m/z: 432.1 (M+1). IC50 (uM) +++++.

SCHEME 28

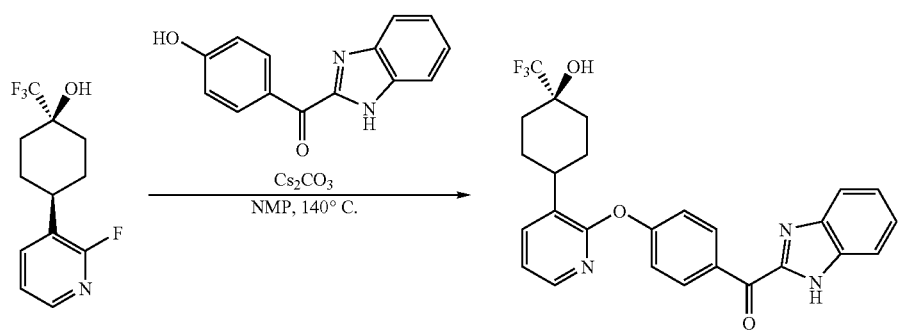

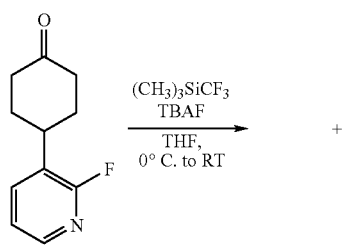

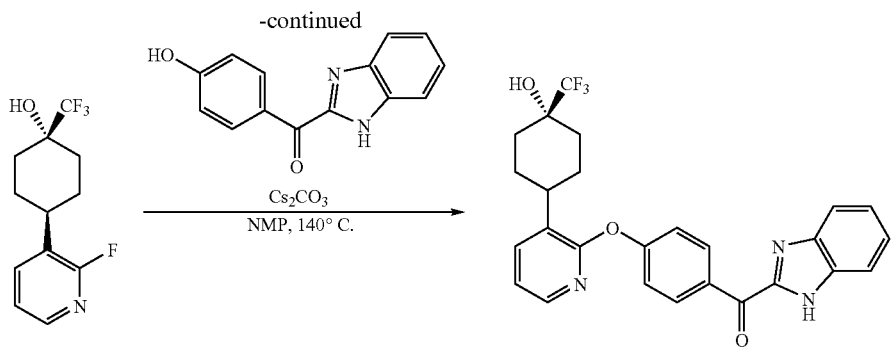

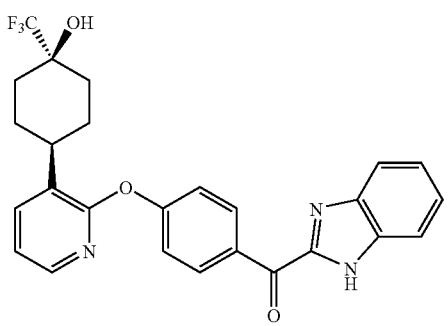

Example 192

(1H-BENZO[D]IMIDAZOL-2-YL)(4-(3-((1S,4S)-4-HYDROXY-4-(TRIFLUOROMETHYL)CYCLOHEXYL)PYRIDIN-2-YLOXY)PHENYL)METHANONE

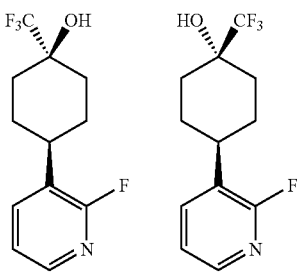

STEP 1. (1S,4S)-4-(2-FLUOROPYRIDIN-3-YL)-1-(TRIFLUOROMETHYL)CYCLOHEXANOL AND (1R,4R)-4-(2-FLUOROPYRIDIN-3-YL)-1-(TRIFLUOROMETHYL)CYCLOHEXANOL

To a stirred mixture of 4-(2-fluoropyridin-3-yl)cyclohexanone (1.00 g, 5.18 mmol) and trimethyl(trifluoromethyl)silane (12.4 mL, 6.21 mmol, 0.5 M solution in THF) at 0° C. under a nitrogen atmosphere was added tetrabutylammonium fluoride (0.26 mL, 0.26 mmol, 1.0 M in THF) via syringe. The reaction mixture was brought to room temperature and stirred for 1 h. 10% Aqueous hydrochloric acid was added, and the mixture was stirred for an additional 1.5 h before being extracted with EtOAc. The organic layer was separated, washed with water (1×), sat. aqueous sodium chloride (1×), dried over magnesium sulfate, filtered, and concentrated in vacuo. The resulting crude product was purified by silica gel column chromatography to give approximately a 10:1 mixture of (1r,4r)-4-(2-fluoropyridin-3-yl)-1-(trifluoromethyl)cyclohexanol to (1s,4s)-4-(2-fluoropyridin-3-yl)-1-(trifluoromethyl)cyclohexanol. The isomers were then separated by reverse phase HPLC. The separated isomers were then each individually partitioned between DCM and sat. aqueous sodium bicarbonate. The organic layers were separated, dried over magnesium sulfate, filtered, and concentrated in vacuo to give (1s,4s)-4-(2-fluoropyridin-3-yl)-1-(trifluoromethyl)cyclohexanol and (1r,4r)-4-(2-fluoropyridin-3-yl)-1-(trifluoromethyl)cyclohexanol as separate white solids. [M+1]=264.1 for both isomers.

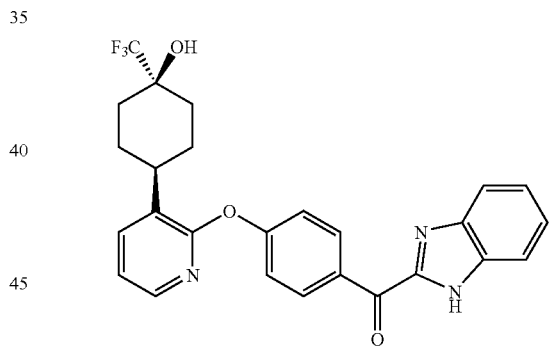

STEP 2. (1H-BENZO[D]IMIDAZOL-2-YL)(4-(3-((1S,4S)-4-HYDROXY-4-(TRIFLUOROMETHYL)CYCLOHEXYL)PYRIDIN-2-YLOXY)PHENYL)METHANONE (1s,4s)-4-(2-Fluoropyridin-3-yl)-1-(trifluoromethyl)cyclohexanol (0.05 g, 0.19 mmol), (1H-benzo[d]imidazol-2-yl)(4-hydroxyphenyl)methanone (0.14 mg, 0.57 mmol), and cesium carbonate (0.19 g, 0.57 mmol) were mixed in NMP (0.5 mL). The reaction mixture was placed under a nitrogen atmosphere and stirred at 140° C. for 72 h. The reaction mixture was cooled to room temperature, diluted with water, and extracted with EtOAc (4×). The combined organic layers were washed with 1 M aqueous sodium hydroxide, washed with sat. sodium chloride, dried over magnesium sulfate, filtered, and concentrated in vacuo. The resulting crude product was purified by silica gel chromatography to give (1H-- benzo[d]imidazol-2-yl)(4-(3-((1s,4s)-4-hydroxy-4-(trifluoromethyl)cyclohexyl)pyridin-2-yloxy)phenyl)methanone. MS (ESI, pos. ion) m/z: 482.1 (M+1). IC50 (uM) +++++.

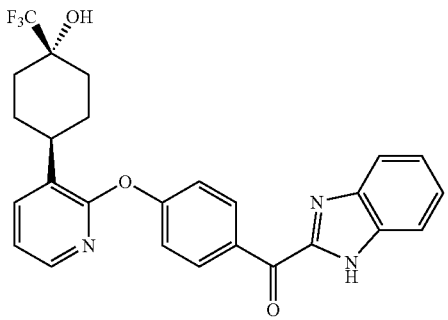

Example 193
(1H-BENZO[D]IMIDAZOL-2-YL)(4-(3-((1R,4R)-4-HYDROXY-4-(TRIFLUOROMETHYL)CYCLOHEXYL)PYRIDIN-2-YLOXY)PHENYL)METHANONE (1r,4r)-4-(2-Fluoropyridin-3-yl)-1-(trifluoromethyl)cyclohexanol (0.10 g, 0.40 mmol), (1H-benzo[d]imidazol-2-yl)(4-hydroxyphenyl)methanone (0.28 g, 1.19 mmol), and cesium carbonate (0.39 g, 1.19 mmol) were mixed in NMP (1 mL). The reaction mixture was placed under a nitrogen atmosphere and stirred at 140° C. for 72 h. The reaction mixture was cooled to room temperature, diluted with water, and extracted with EtOAc (4×). The combined organic layers were washed with 1 M aqueous sodium hydroxide, washed with sat. sodium chloride, dried over magnesium sulfate, filtered, and concentrated in vacuo. The resulting crude product was purified by silica gel chromatography to give (1H-benzo[d]imidazol-2-yl)(4-(3-((1r,4r)-4-hydroxy-4-(trifluoromethyl)cyclohexyl)pyridin-2-yloxy)phenyl)methanone. MS (ESI, pos. ion) m/z: 482.1 (M+1). IC50 (uM) +++++.

SCHEME 29

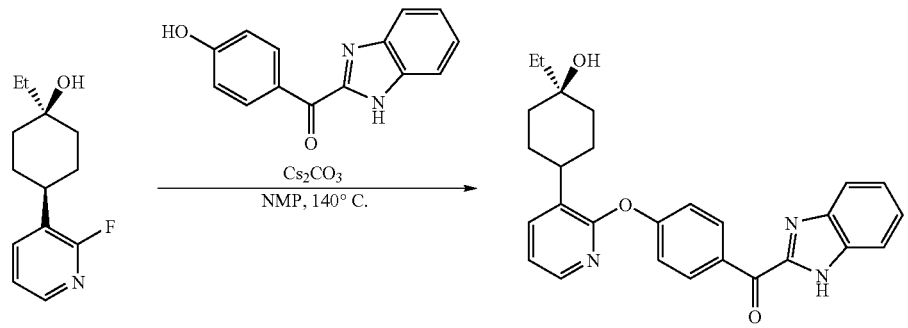

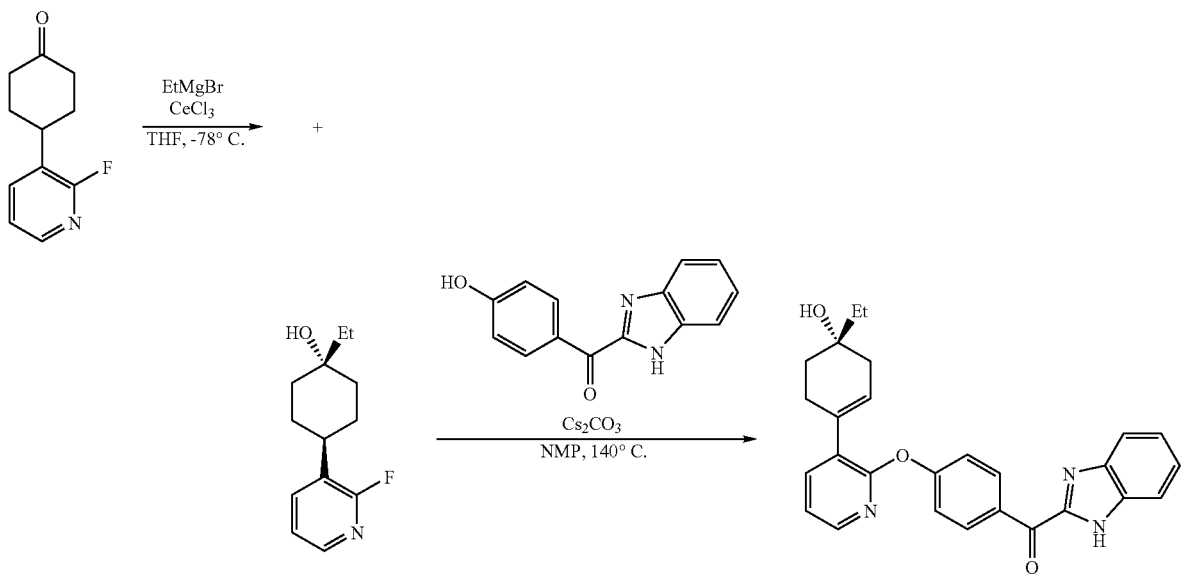

255

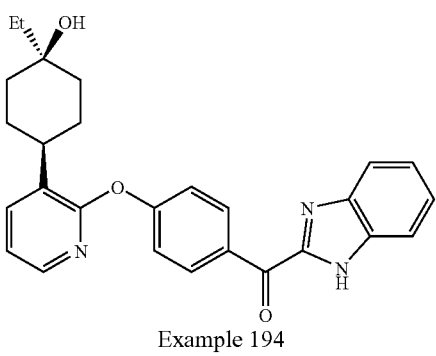

Example 194

(1H-BENZO[D]IMIDAZOL-2-YL)(4-(3-((1S,4S)-4-ETHYL-4-HYDROXYCYCLOHEXYL)PYRIDIN-2-YLOXY)PHENYL)METHANONE

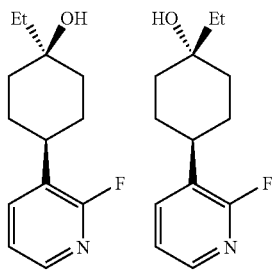

STEP 1. (1S,4S)-1-ETHYL-4-(2-FLUOROPYRIDIN-3-YL)CYCLOHEXANOL AND (1R,4R)-1-ETHYL-4-(2-FLUOROPYRIDIN-3-YL)CYCLOHEXANOL

A suspension of dry cerium(III) chloride (0.31 g, 1.24 mmol) in THF (3 mL) was stirred at 40° C. for 2 h under an argon atmosphere. The suspension was cooled to −78° C., and ethylmagnesium bromide (1.24 mL, 1.24 mmol, 1.0 M in MTBE) was added dropwise via syringe. The reaction mixture was stirred for 30 min before 4-(2-fluoropyridin-3-yl)cyclohexanone (0.20 g, 1.04 mmol) in THF (0.5 mL) was added dropwise via syringe. The reaction mixture was stirred at −78° C. for an additional 1 h before being quenched with sat. ammonium chloride and extracted with EtOAc (2×). The combined organic layers were washed with sat. aqueous sodium chloride, dried over magnesium sulfate, filtered, and concentrated in vacuo. The resulting crude product was purified by silica gel chromatography to give the separated isomers (1S,4S)-1-ethyl-4-(2-fluoropyridin-3-yl)cyclohexanol and (1R,4R)-1-ethyl-4-(2-fluoropyridin-3-yl)cyclohexanol. [M+1]=224.1 for both isomers.

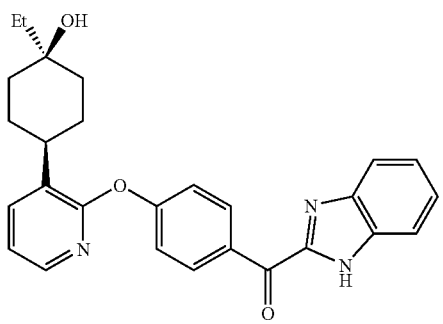

256

STEP 2. (1H-BENZO[D]IMIDAZOL-2-YL)(4-(3-((1S,4S)-4-ETHYL-4-HYDROXYCYCLOHEXYL)PYRIDIN-2-YLOXY)PHENYL)METHANONE (1S,4S)-1-Ethyl-4-(2-fluoropyridin-3-yl)cyclohexanol (0.056 g, 0.26 mmol), (1H-benzo[d]imidazol-2-yl)(4-hydroxyphenyl)methanone (0.19 g, 0.78 mmol), and cesium carbonate (0.25 g, 0.78 mmol) were mixed in NMP (0.75 mL). The reaction mixture was placed under a nitrogen atmosphere and stirred at 140° C. for 72 h. The reaction mixture was cooled to room temperature, diluted with water, and extracted with EtOA. The combined organic layers were washed with 1 M aqueous sodium hydroxide, washed with sat. sodium chloride, dried over magnesium sulfate, filtered, and concentrated in vacuo. The resulting crude product was purified by silica gel chromatography to give (1H-benzo[d]imidazol-2-yl)(4-(3-((1S,4S)-4-ethyl-4-hydroxycyclohexyl)pyridin-2-yloxy)phenyl)methanone. MS (ESI, pos. ion) m/z: 442.2 (M+1). IC50 (uM) +++++.

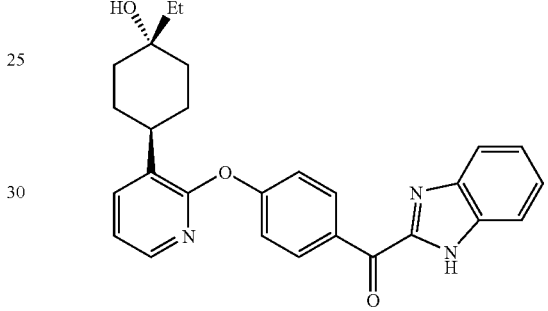

Example 195

(1H-BENZO[D]IMIDAZOL-2-YL)(4-(3-((1R,4R)-4-ETHYL-4-HYDROXYCYCLOHEXYL)PYRIDIN-2-YLOXY)PHENYL)METHANONE (1R,4R)-1-Ethyl-4-(2-fluoropyridin-3-yl)cyclohexanol (0.04 g, 0.16 mmol), (1H-benzo[d]imidazol-2-yl)(4-hydroxyphenyl)methanone (0.11 g, 0.47 mmol), and cesium carbonate (0.15 mL, 0.47 mmol) were mixed in NMP (0.5 mL). The reaction mixture was placed under a nitrogen atmosphere and stirred at 140° C. for 72 h. The reaction mixture was cooled to room temperature, diluted with water, and extracted with EtOAc (4×). The combined organic layers were washed with 1 M aqueous sodium hydroxide, washed with sat. sodium chloride, dried over magnesium sulfate, filtered, and concentrated in vacuo. The resulting crude product was purified by silica gel chromatography to give (1H-benzo[d]imidazol-2-yl)(4-(3-((1r,4r)-4-ethyl-4-hydroxycyclohexyl)pyridin-2-yloxy)phenyl)methanone. MS (ESI, pos. ion) m/z: 442.2 (M+1). IC50 (uM) +++++.

SCHEME 30

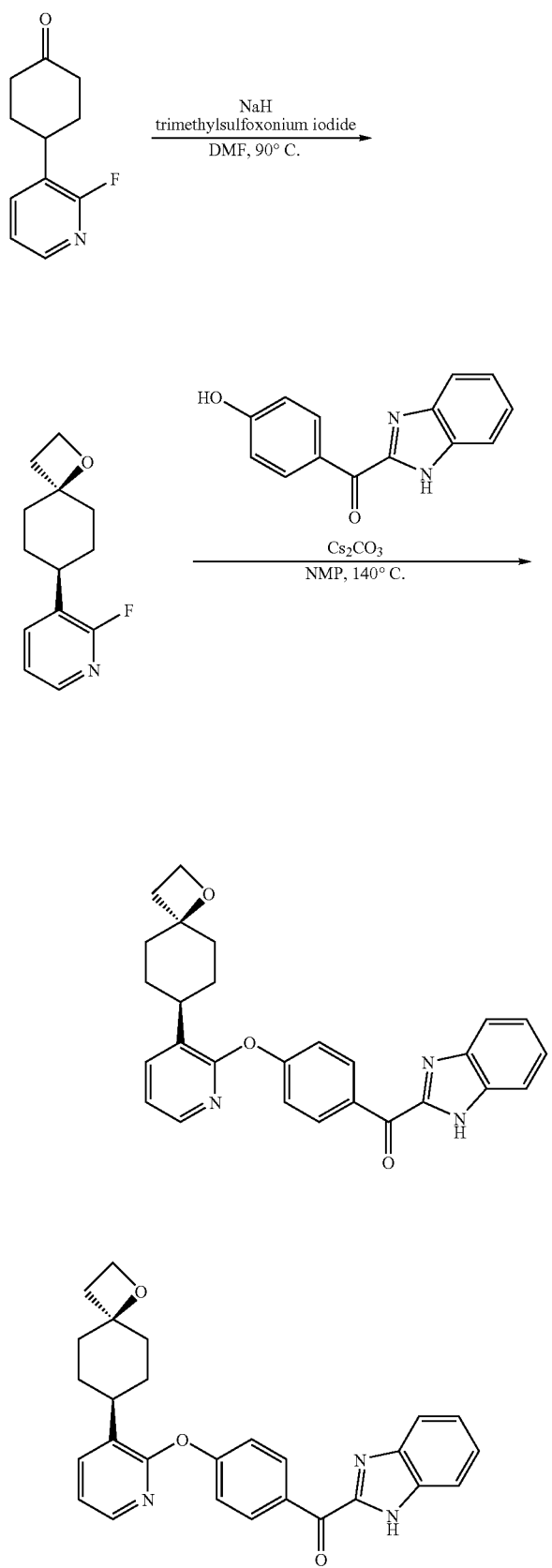

Example 196

(4-(3-((4S,7S)-1-OXASPIRO[3.5]NONAN-7-YL)PYRIDIN-2-YLOXY)PHENYL)(1H-BENZO[D]IMIDAZOL-2-YL)METHANONE

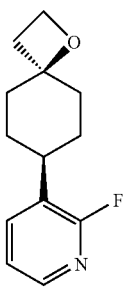

STEP 1. 2-FLUORO-3-((4S,7S)-1-OXASPIRO[3.5]NONAN-7-YL)PYRIDINE

A mixture of sodium hydride (0.31 g, 7.76 mmol, 60% dispersion in mineral oil) and trimethylsulfoxonium iodide (1.82 g, 8.28 mmol) was stirred in DMF (10 mL) under an argon atmosphere at room temperature for 1 h. The mixture was heated to 90° C. and then 4-(2-fluoropyridin-3-yl)cyclohexanone (0.50 g, 2.59 mmol) was added. The reaction mixture was stirred at 90° C. for 16 h. The reaction mixture was cooled to room temperature, diluted with water, and extracted with EtOAc. The organic layer was separated, washed with sat. aqueous sodium chloride, dried over magnesium sulfate, filtered, and concentrated in vacuo. The resulting crude product was purified by silica gel chromatography to give 2-fluoro-3-((4S,7S)-1-oxaspiro[3.5]nonan-7-yl)pyridine. MS (ESI, pos. ion) m/z: 222.1 (M+1).

STEP 2. (4-(3-((4S,7S)-1-OXASPIRO[3.5]NONAN-7-YL)PYRIDIN-2-YLOXY)PHENYL)(1H-BENZO[D]IMIDAZOL-2-YL)METHANONE

2-Fluoro-3-((4s,7s)-1-oxaspiro[3.5]nonan-7-yl)pyridine (0.070 g, 0.32 mmol), (1H-benzo[d]imidazol-2-yl)(4-hydroxyphenyl)methanone (0.23 g, 0.95 mmol), and cesium carbonate (0.31 g, 0.95 mmol) were mixed in NMP (1 mL). The reaction mixture was placed under a nitrogen atmosphere and stirred at 100° C. for 2 h, 120° C. for 2 h, 140° C. for 72 h, and 150° C. for 24 h. The reaction mixture was cooled to room temperature, diluted with water, and extracted with EtOAc (2x). The combined organic layers were washed with 1 M aqueous sodium hydroxide, washed with sat. sodium chloride, dried over magnesium sulfate, and concentrated in vacuo. The resulting crude product was purified by silica gel chromatography to give (4-(3-((4s,7s)-1-oxaspiro[3.5]nonan-7-yl)pyridin-2-yloxy)phenyl)(1H-benzo[d]imidazol-2-yl)methanone. MS (ESI, pos. ion) m/z: 440.1 (M+1). IC50 (uM) +++++.

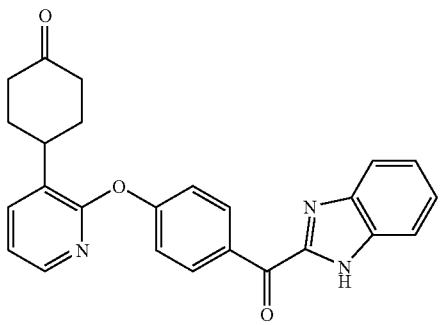

Example 197

4-(2-(4-(1H-BENZO[D]IMIDAZOLE-2-CARBONYL)PHENOXY)PYRIDIN-3-YL)CYCLOHEXANONE 4-(2-Fluoropyridin-3-yl)cyclohexanone (0.05 g, 0.26 mmol), (1H-benzo[d]imidazol-2-yl)(4-hydroxyphenyl)methanone (0.19 g, 0.78 mmol), and cesium carbonate (0.25 g, 0.78 mmol) were mixed in NMP (1 mL). The reaction mixture was placed under a nitrogen atmosphere and stirred at 140° C. for 48 h. The reaction mixture was cooled to room temperature, diluted with water, and extracted with EtOAc (3x). The combined organic layers were washed with 1 M aqueous sodium hydroxide, washed with sat. sodium chloride, dried over magnesium sulfate, and concentrated in vacuo. The resulting crude product was partially purified by silica gel chromatography. The impure product was then dissolved in a minimal amount of DCM, and hexanes were added until a precipitate formed. The resulting suspension was partially concentrated and filtered to give 4-(2-(4-(1H-benzo[d]imidazole-2-carbonyl)phenoxy)pyridin-3-yl)cyclohexanone. MS (ESI, pos. ion) m/z: 412.1 (M+1). IC50 (uM) +++++.

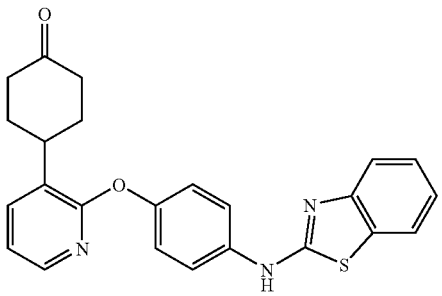

Example 198

4-(2-(4-(BENZO[D]THIAZOL-2-YLAMINO)PHENOXY)PYRIDIN-3-YL)CYCLOHEXANONE 4-(2-Fluoropyridin-3-yl)cyclohexanone (0.05 g, 0.26 mmol), 4-(benzo[d]thiazol-2-ylamino)phenol (0.19 g, 0.78 mmol) and cesium carbonate (0.25 g, 0.78 mmol) were mixed in NMP (1 mL). The reaction mixture was placed under a nitrogen atmosphere and stirred at 120° C. for 16 h. The reaction mixture was cooled to room temperature, diluted with water, and extracted with EtOAc (4x). The combined organic layers were washed with 1 M aqueous sodium hydroxide, washed with sat. sodium chloride, dried over magnesium sulfate, and concentrated in vacuo. The resulting crude product was purified by silica gel chromatography to give 4-(2-(4-(benzo[d]thiazol-2-ylamino)phenoxy)pyridin-3-yl)cyclohexanone. MS (ESI, pos. ion) m/z: 416.1 (M+1). IC50 (uM) +++++.

SCHEME 31

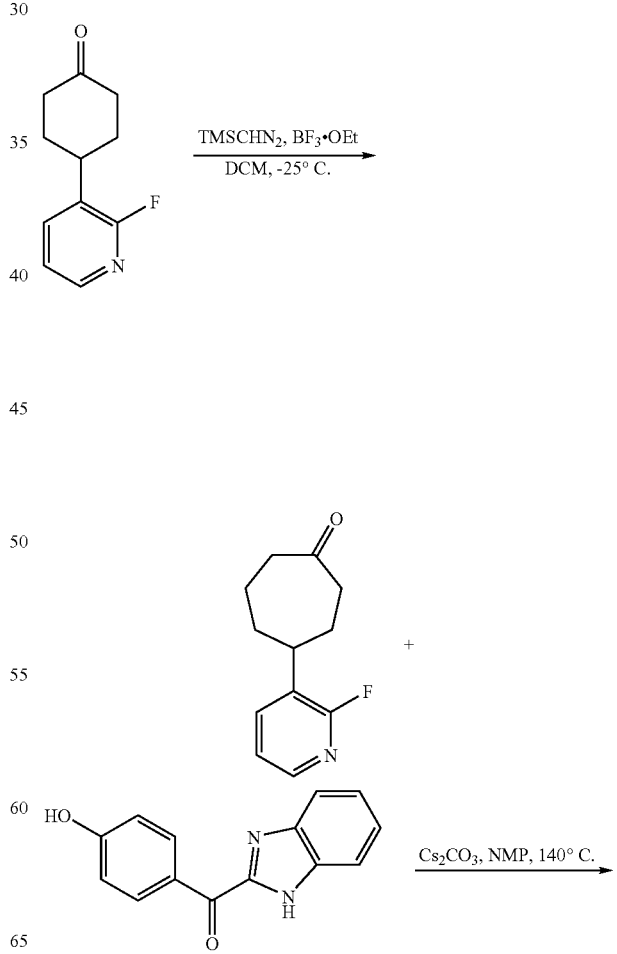

-continued

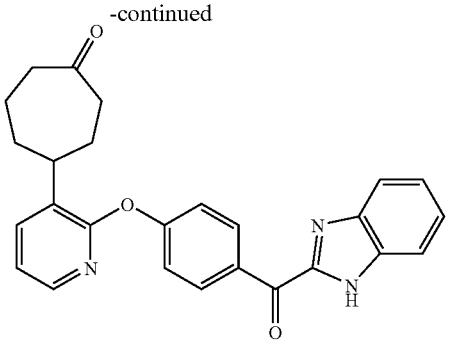

Example 199

4-(2-(4-(1H-BENZO[D]IMIDAZOLE-2-CARBO-
NYL)PHENOXY)PYRIDIN-3-YL)CYCLOHEP-
TANONE

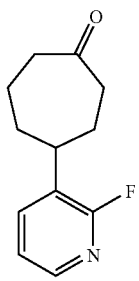

STEP 1.
4-(2-FLUOROPYRIDIN-3-YL)CYCLOHEPTANONE

To a solution of boron trifluoride-diethyl etherate (0.64 g, 4.50 mmol) and 4-(2-fluoropyridin-3-yl)cyclohexanone (0.79 g, 4.09 mmol) in DCM (8 mL) at −25° C. under argon was added (trimethylsilyl)diazomethane (2.25 mL, 5.18 mmol, 2.0 M in hexanes). The reaction was stirred for 2 h at that temperature, water was added, and the mixture was extracted with DCM (2×). The combined organic extracts were washed with 10:1 saturated ammonium chloride/ammonium hydroxide mixture (1×), water (1×), saturated aqueous sodium chloride (1×), and dried over anhydrous magnesium sulfate. The mixture was filtered and the filtrate concentrated in vacuo. The resulting oil was purified by silica gel chromatography to give 4-(2-fluoropyridin-3-yl)cycloheptanone. MS (ESI, pos. ion) m/z: 208.1 (M+1).

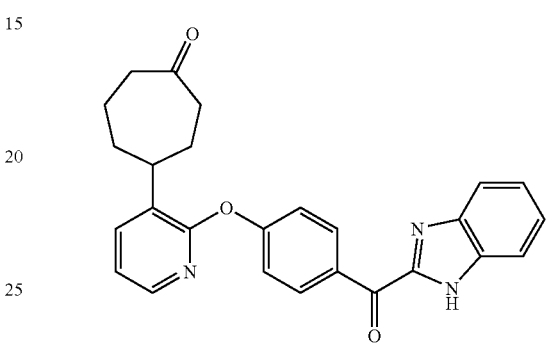

STEP 2. 4-(2-(4-(1H-BENZO[D]IMIDAZOLE-2-
CARBONYL)PHENOXY)PYRIDIN-3-YL)CY-
CLOHEPTANONE

A mixture of cesium carbonate (0.34 g, 1.03 mmol), (1H-benzo[d]imidazol-2-yl)(4-hydroxyphenyl)methanone (0.25 g, 1.03 mmol), and 4-(2-fluoropyridin-3-yl)cycloheptanone (0.071 g, 0.343 mmol) in NMP (0.3 mL) under argon was heated to 140° C. for 36 h, then cooled to room temperature. The resulting mixture was partitioned between ethyl acetate and water, the layers were separated, and the organic layer was washed 1N aqueous sodium hydroxide (2×), saturated aqueous sodium chloride (1×), dried over anhydrous magnesium sulfate, filtered, and concentrated in vacuo. The oil was purified by silica gel chromatography to give 4-(2-(4-(1H-benzo[d]imidazole-2-carbonyl)phenoxy)pyridin-3-yl)cycloheptanone. MS (ESI, pos. ion) m/z: 426.1 (M+1). IC50 (uM) +++++.

SCHEME 32

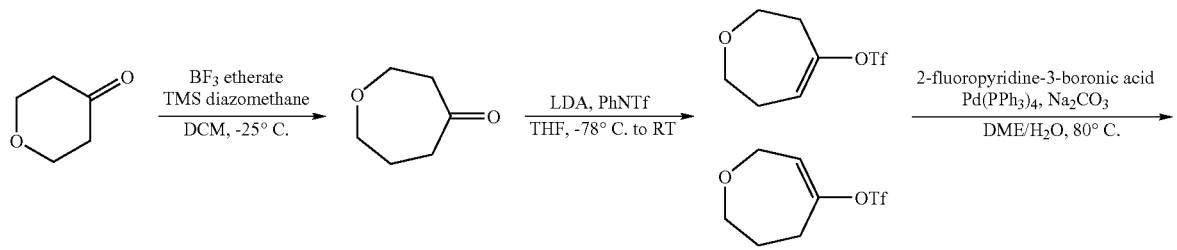

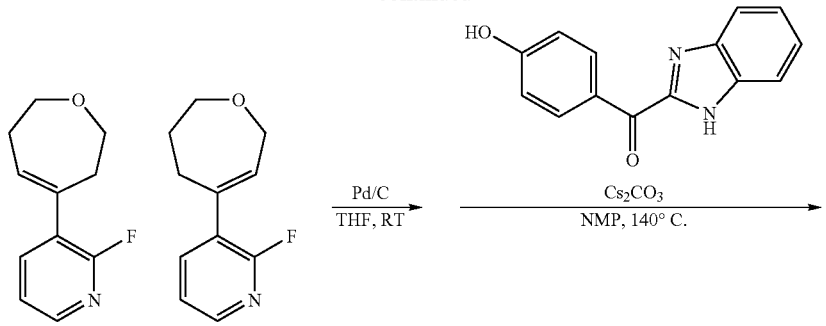

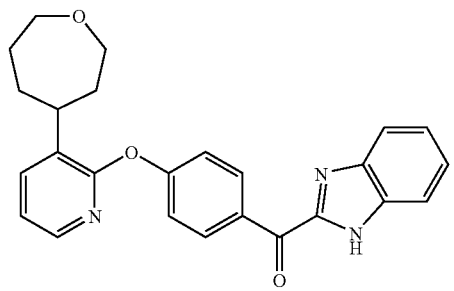

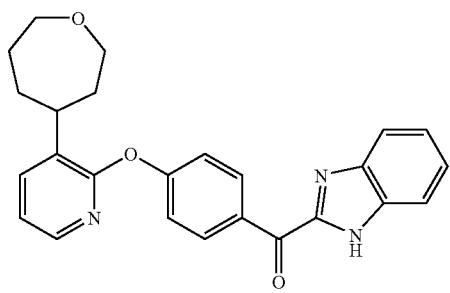

Example 200

(1H-BENZO[D]IMIDAZOL-2-YL)(4-(3-(OXEPAN-4-YL)PYRIDIN-2-YLOXY)PHENYL)METHA-NONE

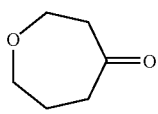

STEP 1. OXEPAN-4-ONE

To a stirred solution of dihydro-2H-pyran-4(3H)-one (9.23 mL, 100 mmol) and boron trifluoride diethyl etherate (13.80 mL, 110 mmol) in DCM (400 mL) at −25° C. was added (trimethylsilyl)diazomethane (54.90 mL, 110 mmol, 2.0 M in hexanes) slowly via syringe. The reaction mixture was stirred at −25° C. for 2.5 h. The reaction mixture was diluted with water and extracted with DCM. The organic layer was separated, washed with 10:1 sat. ammonium chloride:ammonium hydroxide, washed with sat. sodium chloride, dried over magnesium sulfate, filtered, and concentrated in vacuo. The resulting crude product was purified by silica gel chromatography to give oxepan-4-one.

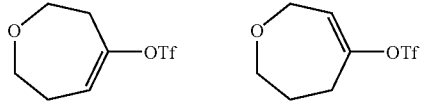

STEP 2. (E)-2,3,6,7-TETRAHYDROOXEPIN-4-YL TRIFLUOROMETHANESULFONATE AND (E)-2, 5,6,7-TETRAHYDROOXEPIN-4-YL TRIFLUO-ROMETHANESULFONATE

To a stirred solution of diisopropylamine (1.97 mL, 14.1 mmol) in THF (20 mL) at −78° C. under an argon atmosphere was added n-butyllithium (5.40 mL, 13.50 mmol, 2.5 M in hexanes). The mixture was stirred for approximately 35 min before oxepan-4-one (1.34 g, 11.74 mmol) in THF (7 mL) was added slowly via syringe. The mixture was stirred for an additional 30 min at −78° C. before n-phenyltrifluoromethanesulfonimide (4.19 g, 11.74 mmol) in THF (10 mL) was added slowly via syringe. The reaction mixture was then stirred overnight with gradual warming to room temperature. The mixture was partially concentrated in vacuo and then partitioned between 3:1 EtOAc:hexanes and water. The organic layer was separated, washed with water, washed once with sat. sodium chloride, dried over magnesium sulfate, and concentrated in vacuo to yield approximately a 7:3 mixture of (E)-2,3,6,7-tetrahydrooxepin-4-yl trifluoromethane-sulfonate:(E)-2,5,6,7-tetrahydrooxepin-4-yl trifluo-romethanesulfonate. The crude material was taken on to the next step without further purification.

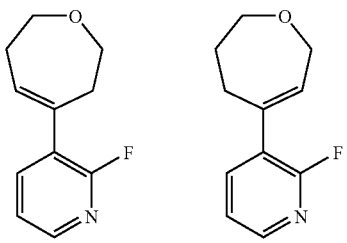

STEP 3. (E)-2-FLUORO-3-(2,3,6,7-TETRAHYDROOXEPIN-4-YL)PYRIDINE AND (E)-2-FLUORO-3-(2,5,6,7-TETRAHYDROOXEPIN-4-YL)PYRIDINE

Sodium carbonate (15.2 mL, 30.3 mmol. 2.0 M in water) was added via syringe to a stirred mixture of an approximately 7:3 mixture of (E)-2,3,6,7-tetrahydrooxepin-4-yl trifluoromethanesulfonate:(E)-2,5,6,7-tetrahydrooxepin-4-yl trifluoromethanesulfonate (2.49 g, 10.11 mmol), 2-fluoro-3-pyridineboronic acid (1.43 g, 10.11 mmol), and tetrakis(triphenylphosphine)palladium (0.58 g, 0.51 mmol) in 1,2-dimethoxyethane (40 mL) under an argon atmosphere. The reaction mixture was stirred at 80° C. for 3 h. The reaction mixture was cooled to room temperature, diluted with water, and extracted with EtOAc. The organic layer was separated, washed with sat. sodium chloride, dried over magnesium sulfate, filtered, and concentrated in vacuo. The resulting crude product was purified by silica gel chromatography to give approximately a 7:3 mixture of (E)-2-fluoro-3-(2,3,6,7-tetrahydrooxepin-4-yl)pyridine and (E)-2-fluoro-3-(2,5,6,7-tetrahydrooxepin-4-yl)pyridine. [M+1]=194.1.

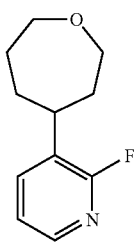

STEP 4. 2-FLUORO-3-(OXEPAN-4-YL)PYRIDINE

Palladium (0.20 g, 0.0188 mmol, 10% wt. on activated carbon) was added to a stirred solution of an approximately 7:3 mixture of (E)-2-fluoro-3-(2,3,6,7-tetrahydrooxepin-4-yl)pyridine:(E)-2-fluoro-3-(2,5,6,7-tetrahydrooxepin-4-yl)pyridine (0.75 g, 3.88 mmol) in THF (15 mL). The reaction mixture was placed under a hydrogen atmosphere (balloon) and stirred at room temperature for 4.5 h. The reaction mixture was filtered through Celite, and the filtrate was concentrated in vacuo to give 2-fluoro-3-(oxepan-4-yl)pyridine. [M+1]=196.1.

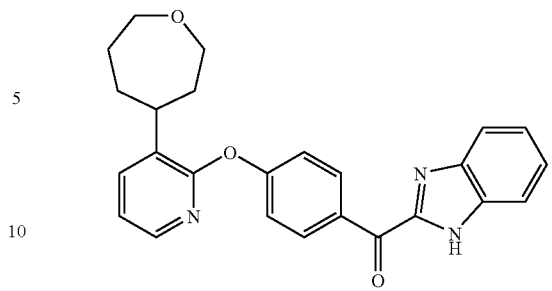

STEP 5. (1H-BENZO[D]IMIDAZOL-2-YL)(4-(3-(OXEPAN-4-YL)PYRIDIN-2-YLOXY)PHENYL)METHANONE

2-Fluoro-3-(oxepan-4-yl)pyridine (0.10 g, 0.51 mmol), (1H-benzo[d]imidazol-2-yl)(4-hydroxyphenyl)methanone (0.37 g, 1.54 mmol), and cesium carbonate (0.50 g, 1.54 mmol) were mixed in NMP (1.5 mL). The reaction mixture was placed under a nitrogen atmosphere and stirred at 140° C. for 96 h. The reaction mixture was cooled to room temperature, diluted with water, and extracted with EtOAc (2x). The combined organic layers were washed with 1 M aqueous sodium hydroxide, washed with sat. sodium chloride, dried over magnesium sulfate, and concentrated in vacuo. The resulting crude product was purified by silica gel chromatography (EtOAc/hexanes) to give (1H-benzo[d]imidazol-2-yl)(4-(3-(oxepan-4-yl)pyridin-2-yloxy)phenyl)methanone. MS (ESI, pos. ion) m/z: 414.1 (M+1). IC50 (uM) +++++.

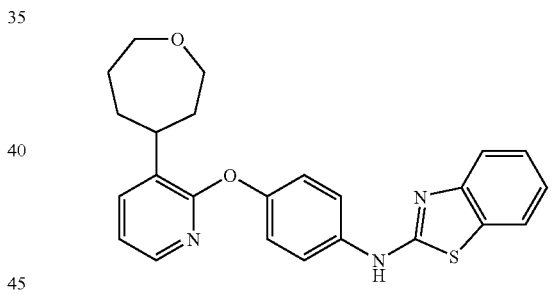

Example 201

N-(4-(3-(OXEPAN-4-YL)PYRIDIN-2-YLOXY)PHENYL)BENZO[D]THIAZOL-2-AMINE

2-Fluoro-3-(oxepan-4-yl)pyridine (0.055 g, 0.28 mmol), 4-(benzo[d]thiazol-2-ylamino)phenol (0.20 g, 0.85 mmol), and cesium carbonate (0.28 mL, 0.85 mmol) were mixed in NMP (0.75 mL). The reaction mixture was placed under a nitrogen atmosphere and stirred at 120° C. for 17 h. The reaction mixture was cooled to room temperature, diluted with water, and extracted with EtOAc (2x). The combined organic layers were washed with 1 M aqueous sodium hydroxide, washed with sat. sodium chloride, dried over magnesium sulfate, and concentrated in vacuo. The resulting crude product was purified by silica gel chromatography to yield an orange solid. The solid was slurried in MeOH and filtered to give N-(4-(3-(oxepan-4-yl)pyridin-2-yloxy)phenyl)benzo[d]thiazol-2-amine. MS (ESI, pos. ion) m/z: 418.1 (M+1). IC50 (uM) +++++.

SCHEME 33
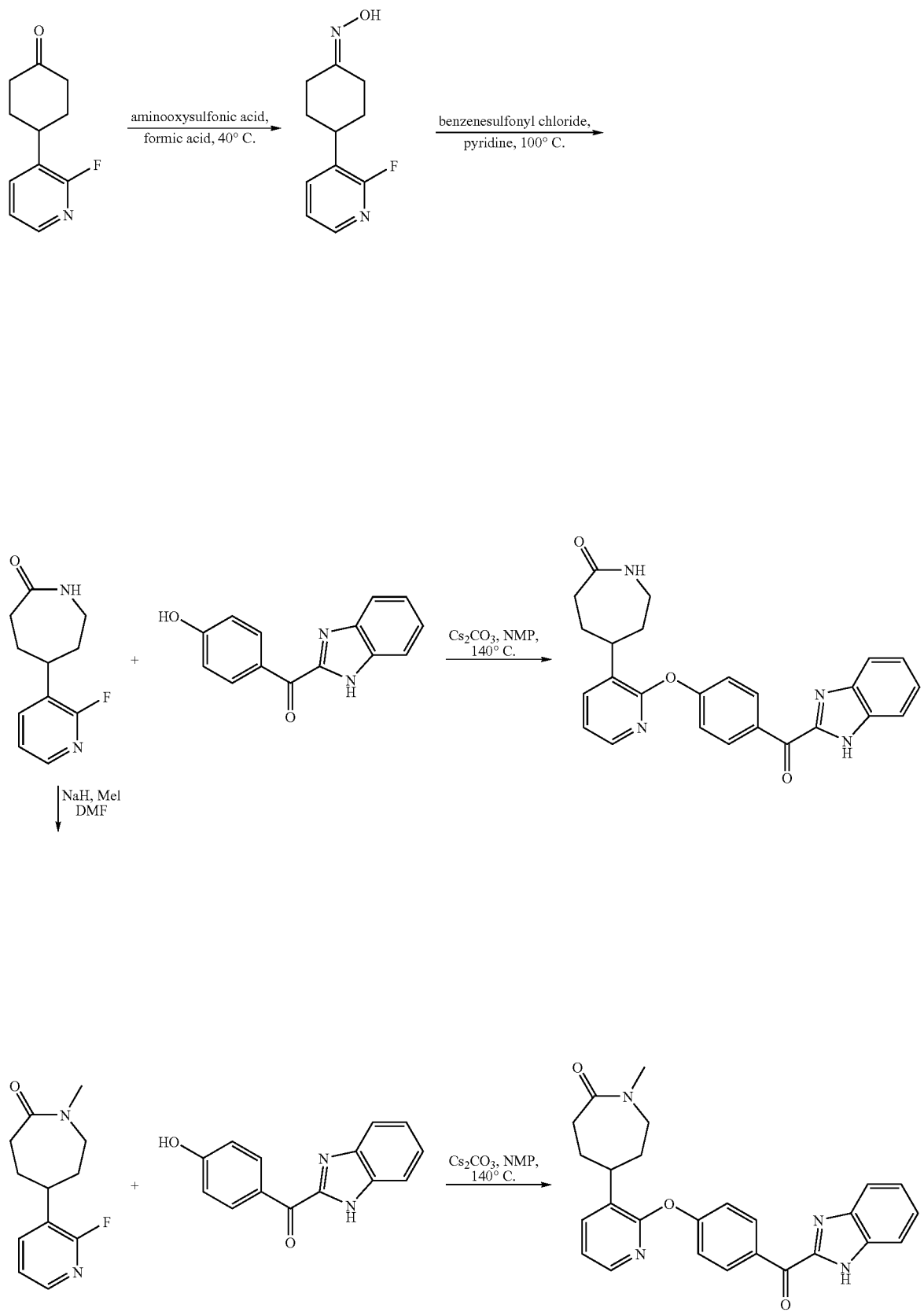

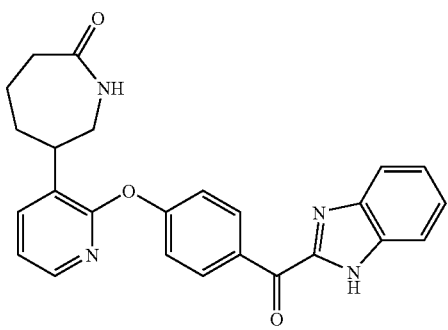

Example 202

5-(2-(4-(1H-BENZO[D]IMIDAZOLE-2-CARBO-
NYL)PHENOXY)PYRIDIN-3-YL)AZEPAN-2-
ONE

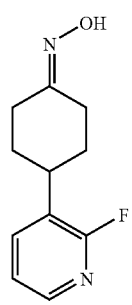

STEP 1.
4-(2-FLUOROPYRIDIN-3-YL)CYCLOHEXANONE
OXIME

A suspension of aminooxysulfonic acid (0.35 g, 3.11 mmol) in 96% formic acid (2.5 mL) was added dropwise to a solution of 4-(2-fluoropyridin-3-yl)cyclohexanone (0.50 g, 2.59 mmol) in 96% formic acid (2.5 mL) at room temperature. The solution was stirred for 15 min, then warmed to 40° C. for 2 h, then cooled 0° C. Ethyl acetate (10 mL) was added and the mixture was neutralized by the dropwise addition of 10 N aqueous sodium hydroxide solution (10 mL) followed by saturated aqueous sodium bicarbonate. The resulting biphasic mixture was separated, the aqueous layer was extracted with ethyl acetate (2×), and the combined extracts were dried over anhydrous magnesium sulfate, filtered and concentrated in vacuo. The resulting oil was purified by silica gel chromatography to give 4-(2-fluoropyridin-3-yl)cyclohexanone oxime. [M+1]=209.1.

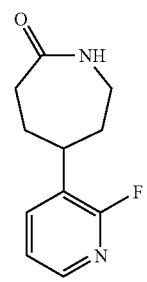

STEP 2.
5-(2-FLUOROPYRIDIN-3-YL)AZEPAN-2-ONE

Benzenesulfonyl chloride (0.05 mL, 0.40 mmol) was added to a solution of 4-(2-fluoropyridin-3-yl)cyclohexanone oxime (0.075 g, 0.36 mmol) in pyridine (1 mL) at 0° C. The ice bath was removed and the mixture was stirred for 45 min before being heated to 100° C. for 30 minutes. After cooling to room temperature the pyridine was removed in vacuo and the residue was dissolved in 1:1 dioxane/water (5 mL) and stirred overnight. Ammonium chloride (50 mg) was added and stirring continued for 30 minutes. The mixture was extracted with ethyl acetate (3×), the combined extracts were dried over anhydrous magnesium sulfate, filtered, and concentrated in vacuo. The resulting oil was purified by silica gel chromatography to 5-(2-fluoropyridin-3-yl)azepan-2-one. [M+1]=209.1.

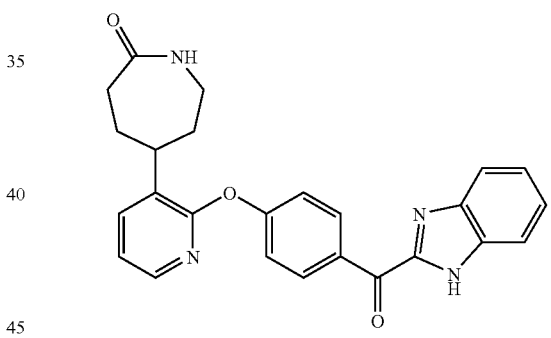

STEP 3. 5-(2-(4-(1H-BENZO[D]IMIDAZOLE-2-
CARBONYL)PHENOXY)PYRIDIN-3-YL)
AZEPAN-2-ONE

A mixture of cesium carbonate (0.24 g, 0.72 mmol), (1H-benzo[d]imidazol-2-yl)(4-hydroxyphenyl)methanone (0.17 g, 0.72 mmol), and 5-(2-fluoropyridin-3-yl)azepan-2-one (0.050 g, 0.24 mmol) in NMP (0.25 mL) under argon was heated to 140° C. for 36 h. After cooling to room temperature, the mixture was partitioned between ethyl acetate and water. The layers were separated and the organic layer was washed with water several times, dried over anhydrous magnesium sulfate, filtered, and concentrated in vacuo. The resulting oil was purified by reversed phase HPLC, and the resulting oil was dissolved in DCM and washed with saturated aqueous sodium bicarbonate (2×), dried over anhydrous magnesium sulfate, filtered, and concentrated in vacuo to give 4-(2-(4-(1H-benzo[d]imidazole-2-carbonyl)phenoxy)pyridin-3-yl) cycloheptanone. MS (ESI, pos. ion) m/z: 427.1 (M+1). IC50 (uM) +++++.

Example 203

5-(2-(4-(1H-BENZO[D]IMIDAZOLE-2-CARBO-NYL)PHENOXY)PYRIDIN-3-YL)-1-METHY-LAZEPAN-2-ONE

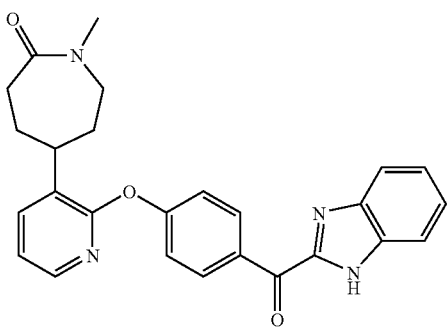

STEP 1. 5-(2-FLUOROPYRIDIN-3-YL)-1-METHYLAZEPAN-2-ONE

To a solution of 5-(2-fluoropyridin-3-yl)azepan-2-one (0.15 g, 0.72 mmol) in DMF (2.5 mL) under argon was added sodium hydride (0.021 g, 0.86 mmol). The mixture was stirred at room temperature for 15 min before iodomethane (0.054 mL, 0.86 mmol) was added via syringe. This mixture was stirred for 4 h at room temperature before saturated aqueous ammonium chloride was added. The mixture was extracted with ethyl acetate (2×) and the combined extracts were washed with water (3×), saturated aqueous sodium chloride (1×), dried over anhydrous magnesium sulfate, filtered, and concentrated in vacuo to give 5-(2-fluoropyridin-3-yl)-1-methylazepan-2-one. [M+1]=223.1.

STEP 2. 5-(2-(4-(1H-BENZO[D]IMIDAZOLE-2-CARBONYL)PHENOXY)PYRIDIN-3-YL)-1-METHYLAZEPAN-2-ONE

A mixture of cesium carbonate (0.29 g, 0.88 mmol), (1H-benzo[d]imidazol-2-yl)(4-hydroxyphenyl)methanone (0.21 g, 0.878 mmol), and 5-(2-fluoropyridin-3-yl)-1-methylazepan-2-one (0.07 g, 0.29 mmol) in 1-methyl-2-pyrrolidinone (0.5 mL) under argon was heated to 140° C. for 48 h, then cooled to room temperature. The resulting mixture was partitioned between ethyl acetate and water, the layers were separated, and the organic layer was washed with 1N aqueous sodium hydroxide (2×), saturated aqueous sodium chloride (1×), dried over anhydrous magnesium sulfate, filtered, and concentrated in vacuo. The oil was purified by silica gel chromatography 5-(2-(4-(1H-benzo[d]imidazole-2-carbonyl)phenoxy)pyridin-3-yl)-1-methylazepan-2-one. MS (ESI, pos. ion) m/z: 441.1 (M+1). IC50 (uM) +++++.

SCHEME 34

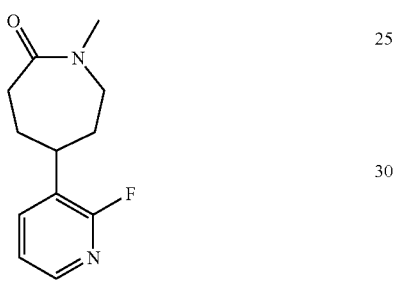

273
-continued

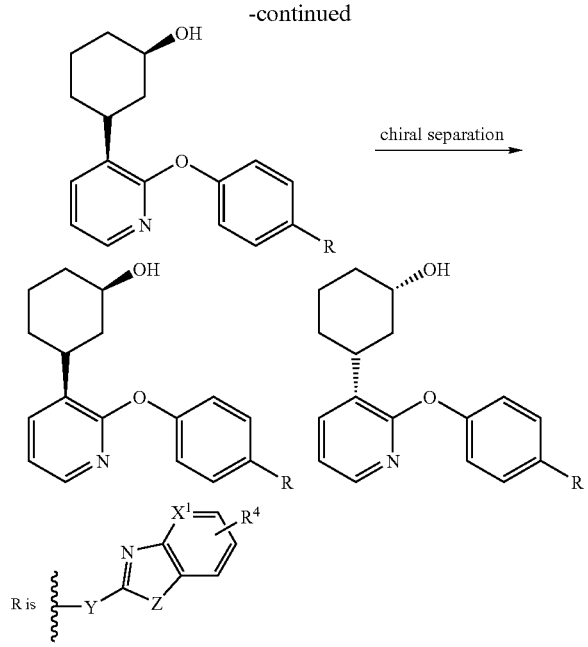

274
STEP 2. (RAC)-3-(2-FLUOROPYRIDIN-3-YL) CYCLOHEX-2-ENOL AND (RAC)-CIS-3-(2-FLUOROPYRIDIN-3-YL)CYCLOHEXANOL

Sodium borohydrate (1.055 g, 27.9 mmol) was added to a solution of 3-(2-fluoropyridin-3-yl)cyclohex-2-enone (4 g, 20.9 mmol) in MeOH (20 ml). The mixture was stirred for 10 min, cooled in ice-water bath, and saturated aqueous ammonium chloride (5 ml) was added. The mixture was diluted with water (100 ml) and extracted with EtOAc (2×100 ml). The organic layer was washed with brine, dried over sodium sulfate, filtered and concentrated. The mixture of products was directly used in the next step.

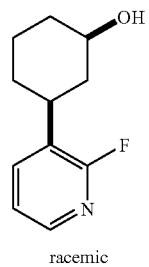

racemic

STEP 3. (RAC)-CIS-3-(2-FLUOROPYRIDIN-3-YL)CYCLOHEXANOL

A suspension of the mixture of products from the previous step (1.8 g) and 10 wt. % palladium on carbon (0.20 g, 0.19 mmol) in THF (20 ml) was stirred at RT under 50 psi of hydrogen gas for 1 h. The mixture was filtered through a Celite pad that was washed with THF. The combined filtrates and washings were concentrated under reduced pressure to deliver (rac)-cis-3-(2-fluoropyridin-3-yl)cyclohexanol as an off-white solid. MS (ESI, pos. ion) m/z: 196.1 (M+1). IC50 (uM) +++++.

STEP 1. 3-(2-FLUOROPYRIDIN-3-YL)CYCLOHEX-2-ENONE

A solution of 3-bromo-2-fluoropyridine (11 g, 62.5 mmol), 2-cyclohexen-1-one (24.03 g, 250 mmol), N,N-dicyclohexylmethylamine (30.5 g, 156 mmol) and bis(tri-t-butylphosphine)palladium (o) (0.958 g, 1.875 mmol) in dioxane (80 mL) was heated to 105° C. for 6 h. The mixture was cooled to RT and the dioxane was evaporated under reduced pressure. Water (200 ml) was added and the mixture layer was extracted with EtOAc (2×200 ml). The combined organic layers were washed with brine and dried over sodium sulfate. Filtration and concentration under reduced pressure, followed by flash chromatography on silica gel (20% to 50% EtOAc in hexanes) afforded 3-(2-fluoropyridin-3-yl)cyclohex-2-enone as colorless crystals. MS (ESI, pos. ion) m/z: 191.9 (M+1).

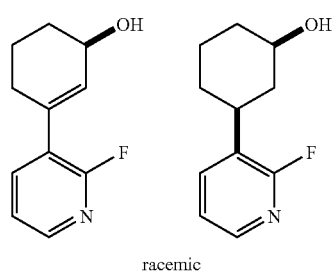

racemic

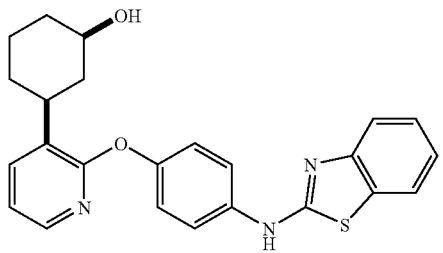

racemic

Example 204

(RAC)-CIS-3-(2-(4-(BENZO[D]THIAZOL-2-YLAMINO)PHENOXY)PYRIDIN-3-YL)CYCLO-HEXANOL

A mixture of (rac)-cis-3-(2-fluoropyridin-3-yl)cyclohexanol (60 mg, 0.307 mmol), 4-(benzo[d]thiazol-2-ylamino)phenol (149 mg, 0.615 mmol), and potassium carbonate (85 mg, 0.615 mmol) in NMP (2 ml) was heated in a Biotage™ microwave reactor at 150° C. for 0.5 h and at 180° C. for 0.5 h. Additional cesium carbonate (200 mg, 0.615 mmol) was added and the mixture was heated in a Biotage™ microwave reactor at 180° C. two times for 1 h and once for 2 h. The mixture was partitioned between H₂O (10 ml) and CH₂Cl₂ (20 ml), the layers were separated, and the aqueous layer was extracted with CH₂Cl₂ (3×20 ml). The combined organic layers were dried (MgSO₄), concentrated under reduced pressure, to deliver a brown oil that was purified by reversed phase HPLC (Gilson Gemini-NX 10u C18 110 A, 100×50.0 mm, 10% to 95% H₂O/MeCN, 0.1% TFA). The product containing fractions were combined, neutralized by the addition of solid Na₂CO₃, and extracted with CH₂Cl₂ (3×20 mL). The combined organic layers were dried (MgSO₄) and concentrated under reduced pressure to deliver (rac)-cis-3-(2-(4-(benzo[d]thiazol-2-ylamino)phenoxy)pyridin-3-yl)cyclohexanol as a tan solid. MS (ESI, pos. ion) m/z: 418.0 (M+1). IC50 (uM) +++++.

SCHEME 35

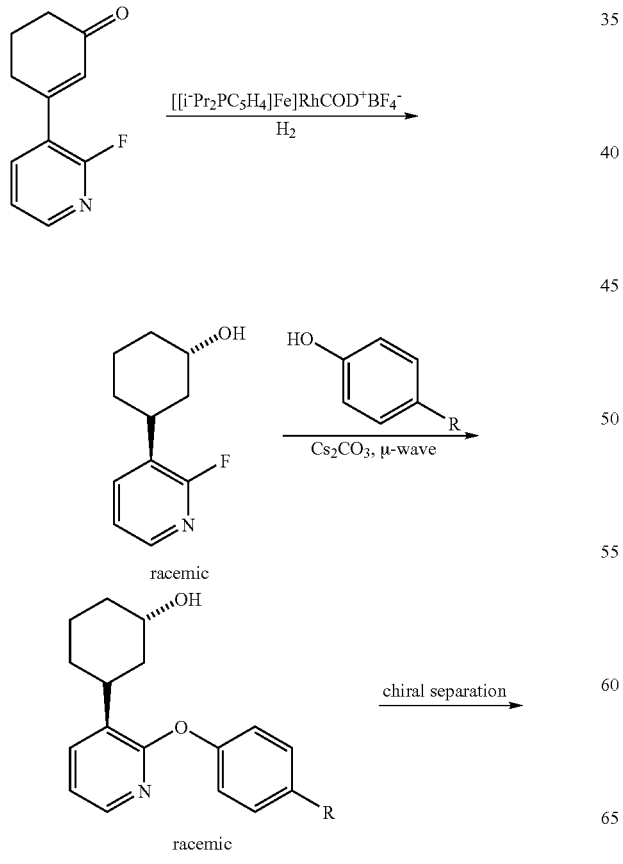

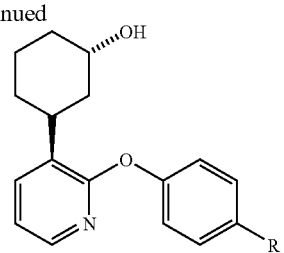

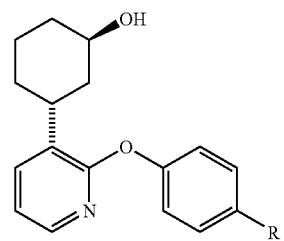

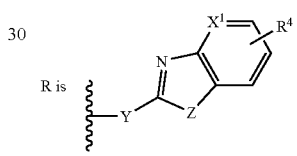

R is

STEP 1: (RAC)-TRANS-3-(2-FLUOROPYRIDIN-3-YL) CYCLOHEXANOL

A mixture of 3-(2-fluoropyridin-3-yl)cyclohex-2-enone (1100 mg, 5.75 mmol) and 1,1'-bis(di-1-propylphosphino)ferrocene(1,5-cyclooctadiene)rhodium (i) tetrafluoroborate (412 mg, 0.575 mmol) in THF (40 mL) was stirred at 45° C. under an atmosphere of hydrogen gas for 5 h. The mixture was filtered through a Celite pad that was washed with THF. Concentration of the combined filtrated and washings under reduced pressure, followed by flash chromatography on silica gel (0% to 50% EtOAc in hexanes) afforded (rac)-trans-3-(2-fluoropyridin-3-yl)cyclohexanol as a colorless oil together with its cis-isomer. MS (ESI, pos. ion) m/z: 196.1 (M+1). IC50 (uM) +++++.

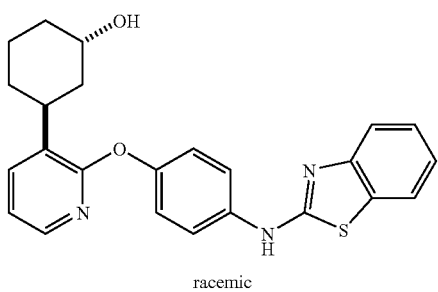

racemic

Example 205

(RAC)-TRANS-3-(2-(4-(BENZO[D]THIAZOL-2-YLAMINO)PHENOXY)PYRIDIN-3-YL)CYCLO-HEXANOL

A mixture of (rac)-trans-3-(2-fluoropyridin-3-yl)cyclohexanol (70 mg, 0.359 mmol), 4-(benzo[d]thiazol-2-ylamino)phenol (174 mg, 0.717 mmol), and cesium carbonate (234 mg, 0.717 mmol) in NMP (2.5 ml) was heated in a Biotage™ microwave reactor at 180° C. for 1 h and at 180° C. for 20 min. The mixture was partitioned between $H_2O$ (10 ml) and $CH_2Cl_2$ (20 ml), the layers were separated, and the aqueous layer was extracted with $CH_2Cl_2$ (3×20 ml). The combined organic layers were dried ($MgSO_4$), concentrated under reduced pressure, and the resulting brown oil was purified by reversed phase HPLC (Gilson Gemini-NX 10u C18 110 A, 100×50.0 mm, 10% to 95% $H_2O$/MeCN, 0.1% TFA). The product containing fractions were combined, neutralized by the addition of solid $Na_2CO_3$, and extracted with $CH_2Cl_2$ (3×20 mL). The combined organic layers were dried ($MgSO_4$) and concentrated under reduced pressure to deliver (rac)-trans-3-(2-(4-(benzo[d]thiazol-2-ylamino)phenoxy)pyridin-3-yl)cyclohexanol as a tan solid. MS (ESI, pos. ion) m/z: 418.1 (M+1). IC50 (uM) +++++.

SCHEME 36

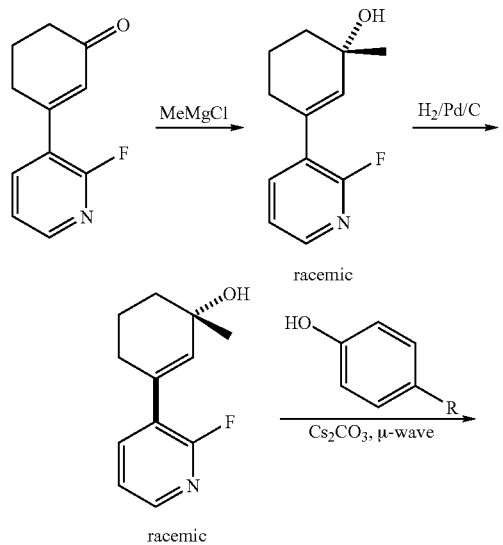

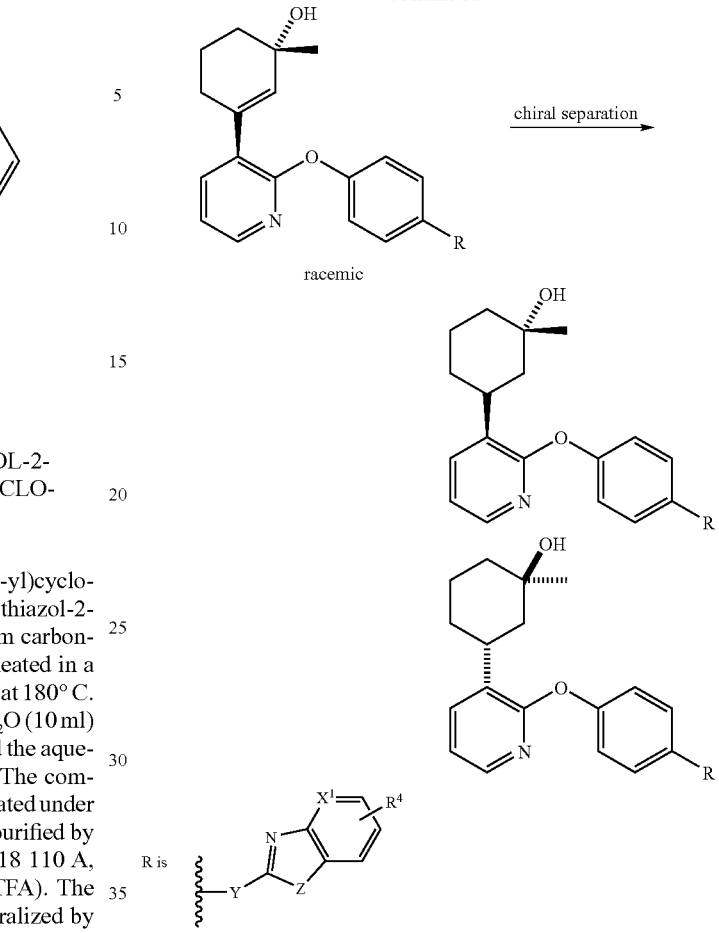

STEP 1. (RAC)-3-(2-FLUOROPYRIDIN-3-YL)-1-METHYLCYCLOHEX-2-ENOL

A 3.0 M solution of methylmagnesium chloride in tetrahydrofuran (4.88 mL, 14.64 mmol) was added slowly to a solution of 3-(2-fluoropyridin-3-yl)cyclohex-2-enone (2.00 g, 10.46 mmol) in THF (20 ml) at −78° C. After completion of the addition the reaction mixture was stirred overnight while it gradually warmed up to RT. It was cooled in an ice water bath and distilled water (5 ml) was added slowly. The mixture was concentrated under reduced pressure, saturated aqueous sodium bicarbonate (200 ml) was added, and it was extracted EtOAc (3×100 ml). The combined organic layers were washed by brine and dried over sodium sulfate. Filtration and concentration under reduced pressure gave (rac)-3-(2-fluoro-pyridin-3-yl)-1-methylcyclohex-2-enol as a light yellow liquid. MS (ESI, pos. ion) m/z: 208.0 (M+1).

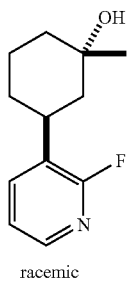

racemic

STEP 2: (RAC)-E-3-(2-FLUOROPYRIDIN-3-YL)-1-METHYLCYCLOHEXANOL

A suspension of (rac)-3-(2-fluoropyridin-3-yl)-1-methyl-cyclohex-2-enol (1.8 g, 8.7 mmol) and 10 wt. % palladium on carbon (0.277 g, 2.61 mmol) in THF (20 ml) was stirred in a pressure reactor under 50 psi of hydrogen gas for 7 h. The mixture was filtered through a pad of Celite that was washed with THF. Concentration of the combined filtrates and washings under reduced pressure, followed by flash chromatography on silica gel (20% to 50% EtOAc in hexanes) afforded (rac)-E-3-(2-fluoropyridin-3-yl)-1-methylcyclohexanol (530 mg, 2.53 mmol) as a white solid. MS (ESI, pos. ion) m/z: 210.0 (M+1). IC50 (uM) +++++.

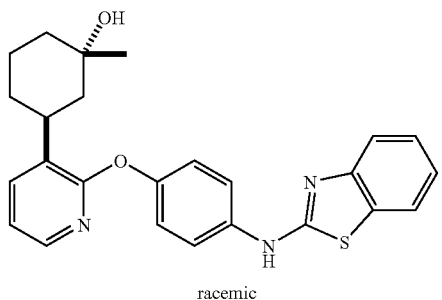

racemic

Example 206

(RAC)-E-3-(2-(4-(BENZO[D]THIAZOL-2-YLAMINO)PHENOXY)PYRIDIN-3-YL)-1-METHYLCYCLOHEXANOL

A mixture of (rac)-E-3-(2-fluoropyridin-3-yl)-1-methyl-cyclohexanol (156 mg, 0.745 mmol), 4-(benzo[d]thiazol-2-ylamino)phenol (361 mg, 1.491 mmol), and cesium carbonate (486 mg, 1.491 mmol) in NMP (2 ml) was heated in a microwave reactor at 180° C. for 1.5 h. The mixture was partitioned between H₂O (10 ml) and CH₂Cl₂ (20 ml), the layers were separated, and the aqueous layer was extracted with CH₂Cl₂ (3×20 ml). The combined organic layers were dried (MgSO₄) and concentrated under reduced pressure. The resulting brown oil was purified by reversed phase HPLC (Gilson Gemini-NX 10u C18 110 A, 100×50.0 mm, 10% to 95% H₂O/MeCN, 0.1% TFA). The product containing fractions were combined, neutralized by the addition of solid Na₂CO₃, and extracted with CH₂Cl₂ (3×20 mL). The combined organic layers were dried (MgSO₄) and concentrated under reduced pressure to deliver (rac)-E-3-(2-(4-(benzo[d]thiazol-2-ylamino)phenoxy)pyridin-3-yl)-1-methylcyclo-hexanol as a white solid. MS (ESI, pos. ion) m/z: 432.1 (M+1). IC50 (uM) +++++.

SCHEME 37

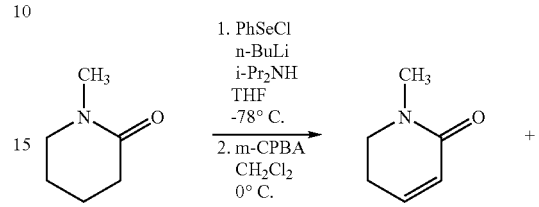

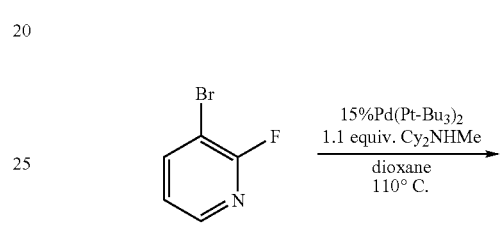

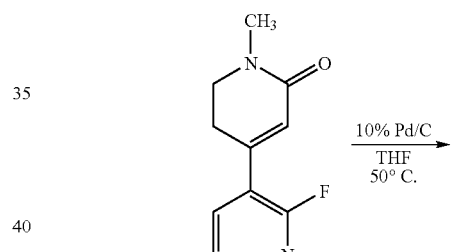

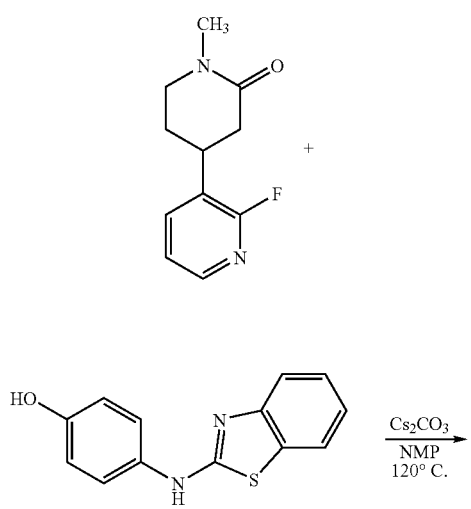

281
-continued

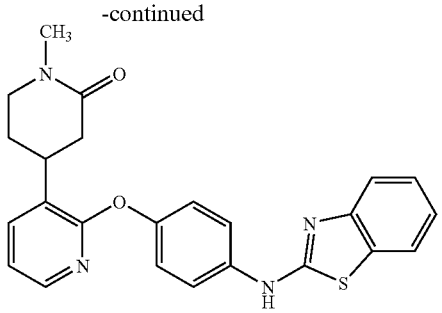

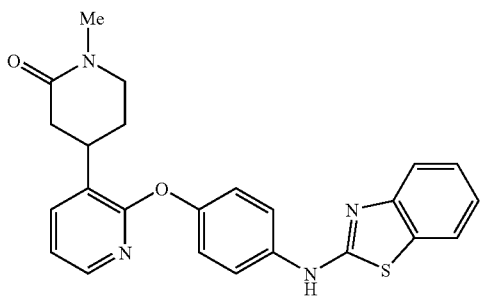

Example 207

4-(2-(4-(BENZO[D]THIAZOL-2-YLAMINO)PHE-NOXY)PYRIDIN-3-YL)-1-METHYLPIPERIDIN-2-ONE

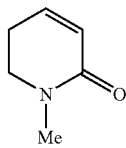

STEP 1.
1-METHYL-5,6-DIHYDROPYRIDIN-2(1H)-ONE

A solution of diisopropylamine (3.02 mL, 21.21 mmol) in tetrahydrofuran (44.2 mL) under argon was cooled to −78° C. and added butyllithium solution, 2.5M in hexanes (8.48 mL, 21.21 mmol). After 5 min, a solution of 1-methylpiperidin-2-one (2 g, 17.67 mmol) in tetrahydrofuran (2 mL) was added dropwise. After stirring for 10 min, a solution of phenylselenenyl chloride (4.06 g, 21.21 mmol) in 16 mL of tetrahydrofuran was added, and the reaction was stirred at −78° C. for 2 h. The reaction was quenched with aqueous saturated NH₄Cl solution and diluted with CH₂Cl₂; the aqueous layer was back-extracted with CH₂Cl₂ (1×). The combined organic extracts were dried (MgSO₄), filtered, and concentrated in vacuo to afford a crude crop of 1-methyl-3-(phenylselanyl)piperidin-2-one in dichloromethane. To the crude 1-methyl-3-(phenylselanyl)piperidin-2-one in dichloromethane (50

282 mL) at 0° C. under argon was added 3-chlorobenzoperoxoic acid (7.92 g, 35.3 mmol). The resulting mixture was allowed to gradually warm to room temperature overnight. The orange suspension was filtered, and the filtrate was concentrated in vacuo and partitioned between CH₂Cl₂ and aqueous saturated NaHCO₃ solution; the aqueous layer was back-extracted with CH₂Cl₂ (5×). The combined organic extracts were dried (MgSO₄), filtered, and concentrated in vacuo. Flash column chromatography (20% EtOAc/Hexanes to 100% EtOAc) afforded 1-methyl-5,6-dihydropyridin-2(1H)-one (1.33 g, 67.7% yield) as a brown oil. [M+1]=112.2.

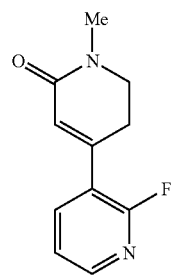

STEP 2. 4-(2-FLUOROPYRIDIN-3-YL)-1-METHYL-5,6-DIHYDROPYRIDIN-2(1H)-ONE

Into a sealed tube were placed 3-bromo-2-fluoropyridine (0.106 g, 0.602 mmol), 1-methyl-5,6-dihydropyridin-2(1H)-one (0.134 g, 1.205 mmol), bis(tri-tert-butylphosphine)palladium (0) (0.046 g, 0.090 mmol), N,N-dicyclohexylmethylamine (0.129 mL, 0.663 mmol), and 1,4-dioxane (0.5 mL). After the mixture was degassed for 5 min, the reaction was heated at 100° C. for 3 h. The cooled reaction was concentrated in vacuo, and the brown residue was directly purified via flash column chromatography (20% EtOAc/Hexanes to 100% EtOAc) to give 4-(2-fluoropyridin-3-yl)-1-methyl-5,6-dihydropyridin-2(1H)-one (0.0153 g, 12.32% yield) as a tan solid. [M+1]=207.1.

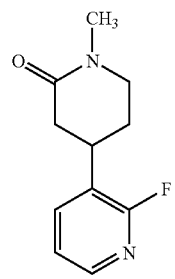

STEP 3. 4-(2-FLUOROPYRIDIN-3-YL)-1-METHYLPIPERIDIN-2-ONE

A solution of 4-(2-fluoropyridin-3-yl)-1-methyl-5,6-dihydropyridin-2(1H)-one (0.067 g, 0.325 mmol) in tetrahydrofuran (1.6 mL) was added palladium, 10 wt. % on activated carbon (0.035 g, 0.032 mmol) and hydrogenated (double-walled balloon pressure) at 40° C. for 3 h. The mixture was filtered via a pad of Celite, and the filtrate was concentrated in vacuo to give a relatively pure crop of 4-(2-fluoropyridin-3-yl)-1-methylpiperidin-2-one as a milky oil. [M+1]=209.0.

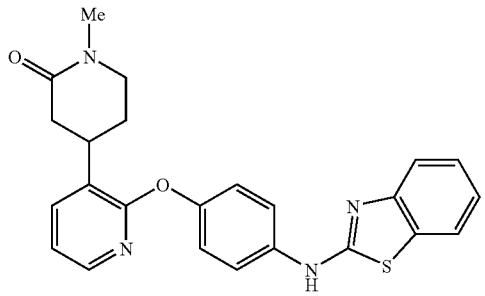

STEP 4. 4-(2-(4-(BENZO[D]THIAZOL-2-YLAMINO)PHENOXY)PYRIDIN-3-YL)-1-METHYLPIPERIDIN-2-ONE

Into a sealed tube were added 4-(2-fluoropyridin-3-yl)-1-methylpiperidin-2-one (0.06 g, 0.288 mmol), 4-(benzo[d]thiazol-2-ylamino)phenol (0.223 g, 0.922 mmol), cesium carbonate (0.310 g, 0.951 mmol), and 1-methyl-2-pyrrolidinone (1 mL). After degassing for 5 min, the reaction was heated at 120° C. for 14 h. The cooled mixture was diluted with EtOAc and washed with water; the aqueous layer was back-washed with EtOAc (1×). The combined organic extracts were washed with aqueous 1N NaOH solution, dried (MgSO$_4$), filtered, and concentrated in vacuo. Flash column chromatography (20% to 100% EtOAc/Hexanes) afforded 4-(2-(4-(benzo[d]thiazol-2-ylamino)phenoxy)pyridin-3-yl)-1-methylpiperidin-2-one (0.046 g, 37.1% yield) as a tan amorphous solid. MS (ESI, pos. ion) m/z: 431.9 (M+1). IC50 (uM) +++++.

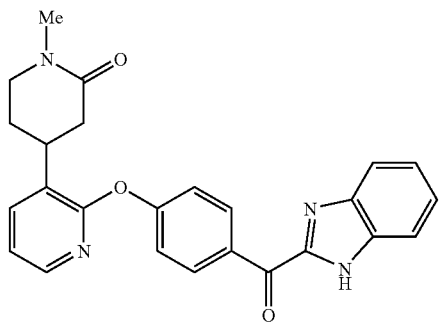

Example 208

4-(2-(4-(1H-BENZO[D]IMIDAZOLE-2-CARBONYL)PHENOXY)PYRIDIN-3-YL)-1-METHYLPIPERIDIN-2-ONE

The title compound was prepared from 4-(2-fluoropyridin-3-yl)-1-methylpiperidin-2-one (Step 3, Example 1) and (1H-benzo[d]imidazol-2-yl)(4-hydroxyphenyl)methanone by following the procedure described in Step 4 of Example 1. MS (ESI, pos. ion) m/z: 427.1 (M+1). IC50 (uM) +++++.

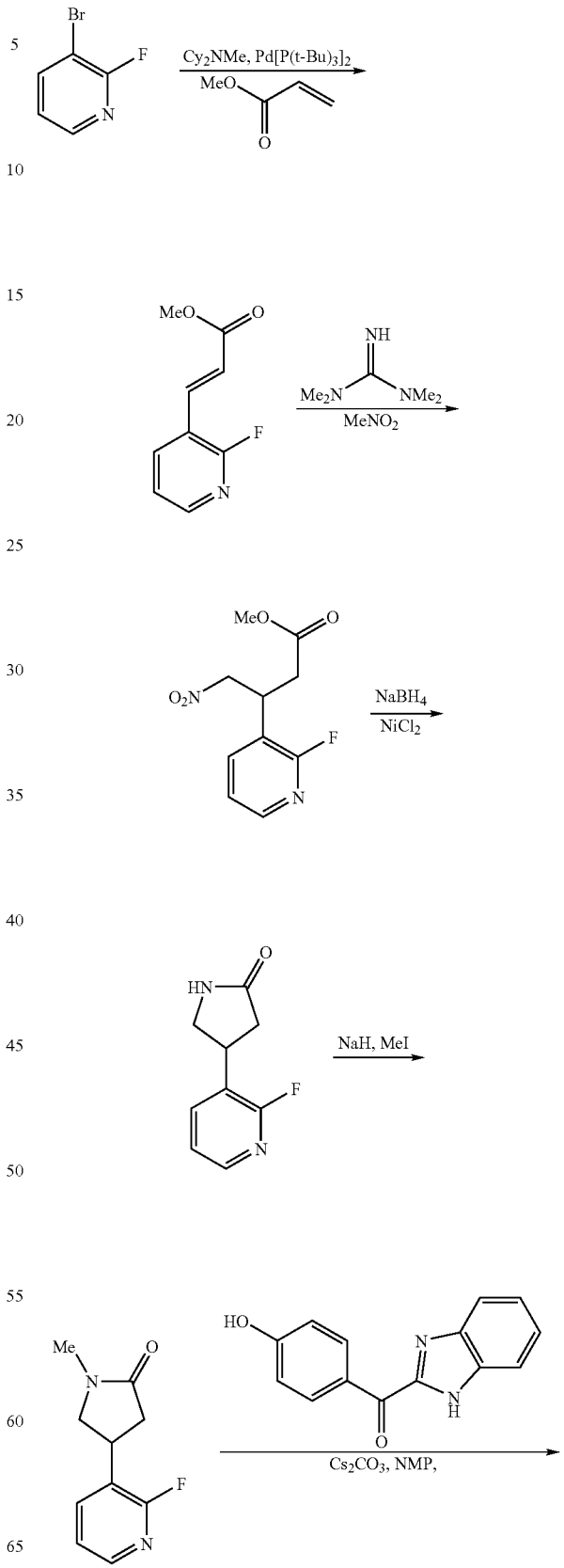

SCHEME 38

-continued

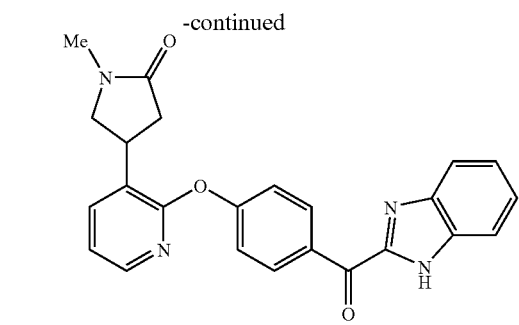

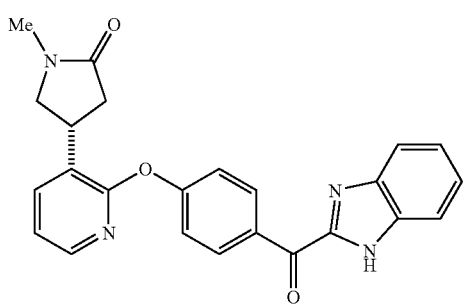

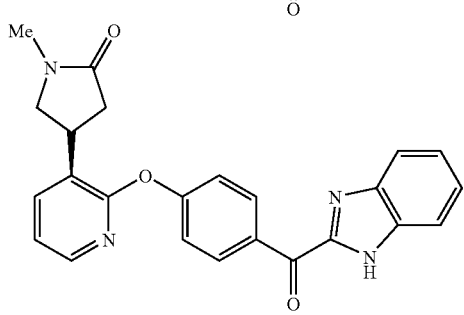

Example 209

(R)-4-(2-(4-(1H-BENZO[D]IMIDAZOLE-2-CAR-BONYL)PHENOXY)PYRIDIN-3-YL)-1-METH-YLPYRROLIDIN-2-ONE AND (S)-4-(2-(4-(1H-BENZO[D]IMIDAZOLE-2-CARBONYL)PHENOXY)PYRIDIN-3-YL)-1-METHYLPYRROLIDIN-2-ONE

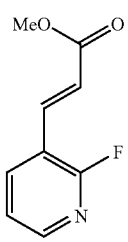

STEP 1. (E)-METHYL 3-(2-FLUOROPYRIDIN-3-YL)ACRYLATE

To Pd[P(t-Bu)$_3$]$_2$ (0.210 g, 0.411 mmol) was added dioxane (6 mL), methyl acrylate (2.00 mL, 22.2 mmol), N,N-dicyclohexylmethylamine (3.60 mL, 17.0 mmol), and 3-bromo-2-fluoropyridine (1.02 g, 5.80 mmol). The reaction mixture was degassed and heated to 110° C. for 5 min. The reaction was cooled to room temperature and diluted with EtOAc. The organic phase was washed with water (1×), brine (1×), dried over MgSO$_4$, filtered, and concentrated. Purification by flash column chromatography on silica gel (10% to 50% EtOAc in hexanes) gave the product which contained Cy$_2$NMe. The Cy$_2$NMe was removed by dissolving the mixture in DCM (5 mL) and diluting with hexanes (10 mL). The solution was concentrated to a volume of 5 mL and the solid precipitate was collected by filtration and dried under high vacuum to give (E)-methyl 3-(2-fluoropyridin-3-yl)acrylate (0.995 g, 5.49 mmol, 95% yield) as a white solid. MS (ESI, pos. ion) m/z: 182.1 (M+1).

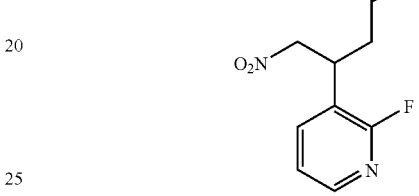

STEP 2. METHYL 3-(2-FLUOROPYRIDIN-3-YL)-4-NITROBUTANOATE

To (E)-methyl 3-(2-fluoropyridin-3-yl)acrylate (0.945 g, 5.22 mmol) was added nitromethane (10.0 mL, 186 mmol) and 1,1,3,3-tetramethylguanidine (0.120 mL, 0.956 mmol). The reaction mixture was stirred at room temperature for 30 min, heated to 50° C. for 1 h, and diluted with EtOAc and water. The aqueous phase was extracted with EtOAc (2×) and the combined organic extracts were washed with brine (1×), dried over MgSO$_4$, filtered, and concentrated. Purification by flash column chromatography on silica gel (20% to 60% EtOAc in hexanes) gave methyl 3-(2-fluoropyridin-3-yl)-4-nitrobutanoate (0.996 g, 4.11 mmol, 79% yield) as a colorless oil. MS (ESI, pos. ion) m/z: 243.1 (M+1).

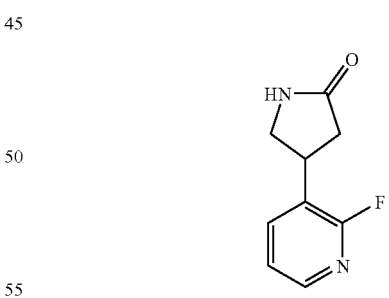

STEP 3. 4-(2-FLUOROPYRIDIN-3-YL)PYRROLIDIN-2-ONE

To a solution of methyl 3-(2-fluoropyridin-3-yl)-4-nitrobutanoate (0.991 g, 4.09 mmol) in EtOH (20 mL) at 0° C. was added nickel chloride (0.532 g, 4.10 mmol) and sodium borohydride (1.60 g, 42.3 mmol). The reaction mixture was stirred at 0° C. for 30 min, warmed to room temperature over 30 min, and stirred at room temperature for 30 min. The reaction mixture was quenched with saturated aqueous KH$_2$PO$_4$ and diluted with water and EtOAc. The mixture was filtered through a pad of Celite. The filtrate was extracted with EtOAc (6×) and the combined organic extracts were washed with brine (1×), dried over MgSO$_4$, filtered, and concentrated. Purification by flash column chromatography on silica gel (5% to 10% MeOH in DCM) gave 4-(2-fluoropyridin-3-yl)pyrrolidin-2-one (0.168 g, 0.932 mmol, 23% yield) as a colorless oil. MS (ESI, pos. ion) m/z: 181.1 (M+1).

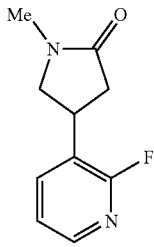

STEP 4. 4-(2-FLUOROPYRIDIN-3-YL)-1-METHYLPYRROLIDIN-2-ONE

To a solution of 4-(2-fluoropyridin-3-yl)pyrrolidin-2-one (0.254 g, 1.41 mmol) in DMF (5 mL) at 0° C. was added iodomethane (0.090 mL, 1.4 mmol) and sodium hydride (60% weight dispersion in mineral oil, 0.056 g, 1.4 mmol). The reaction mixture was stirred at 0° C. for 30 min, warmed to room temperature, and stirred for 30 min. The reaction mixture was diluted with EtOAc, quenched with water, and diluted with brine and water. The aqueous phase was extracted with EtOAc (6×) and the combined organic extracts were washed with brine (1×), dried over MgSO$_4$, filtered, and concentrated. Purification by flash column chromatography on silica gel (50% to 100% EtOAc (10% MeOH) in hexanes) gave 4-(2-fluoropyridin-3-yl)-1-methylpyrrolidin-2-one (0.226 g, 1.16 mmol, 83% yield) as a pale yellow oil. MS (ESI, pos. ion) m/z: 195.1 (M+1).

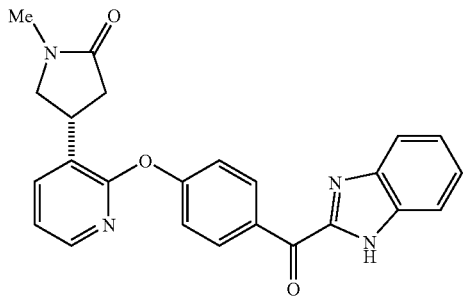

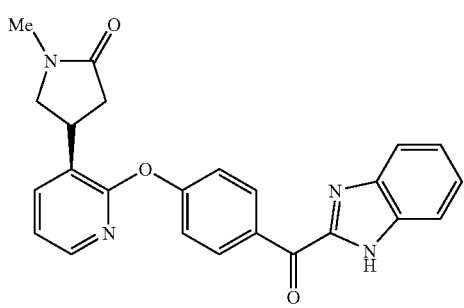

STEP 5. (R)-4-(2-(4-(1H-BENZO[D]IMIDAZOLE-2-CARBONYL)PHENOXY)PYRIDIN-3-YL)-1-METHYLPYRROLIDIN-2-ONE AND (S)-4-(2-(4-(1H-BENZO[D]IMIDAZOLE-2-CARBONYL)PHENOXY)PYRIDIN-3-YL)-1-METHYLPYRROLIDIN-2-ONE

To a mixture of cesium carbonate (563 mg, 1.73 mmol), (1H-benzo[d]imidazol-2-yl)(4-hydroxyphenyl)methanone (0.381 g, 1.60 mmol), and 4-(2-fluoropyridin-3-yl)-1-methylpyrrolidin-2-one (0.131 g, 0.675 mmol) was added NMP (2 mL). The reaction mixture was degassed and heated to 140° C. for 11 h. The mixture was cooled to room temperature and diluted with EtOAc and water. The aqueous phase was extracted with EtOAc (4×) and the combined organic extracts were washed with brine (1×), dried over MgSO$_4$, filtered, and concentrated. Purification by flash column chromatography on silica gel (20% to 60% EtOAc in hexanes) gave 4-(2-(4-(1H-benzo[d]imidazole-2-carbonyl)phenoxy)pyridin-3-yl)-1-methylpyrrolidin-2-one (0.169 g, 0.410 mmol, 61% yield) as an off-white solid. MS m/z: 413.1 (M+1). The mixture of enantiomers was separated by preparatory SFC (Chiralcel OJH (21×250 mm), 25% EtOH/0.2% diethylamine) to afford the individual enantiomers (R)-4-(2-(4-(1H-benzo[d]imidazole-2-carbonyl)phenoxy)pyridin-3-yl)-1-methylpyrrolidin-2-one and (S)-4-(2-(4-(1H-benzo[d]imidazole-2-carbonyl)phenoxy)pyridin-3-yl)-1-methylpyrrolidin-2-one. MS (ESI, pos. ion) m/z: 413.1 (M+1). IC50 (uM) +++++.

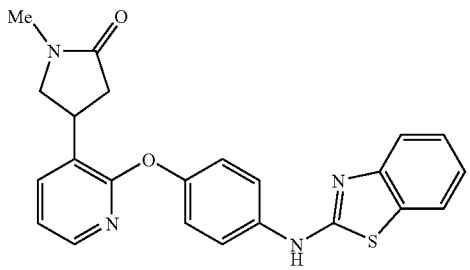

Example 210

4-(2-(4-(BENZO[D]THIAZOL-2-YLAMINO)PHENOXY)PYRIDIN-3-YL)-1-METHYLPYRROLIDIN-2-ONE

To a mixture of cesium carbonate (0.625 g, 1.92 mmol), 4-(benzo[d]thiazol-2-ylamino)phenol (0.445 g, 1.84 mmol), and 4-(2-fluoropyridin-3-yl)-1-methylpyrrolidin-2-one (0.111 g, 0.572 mmol) was added NMP (2 mL). The reaction mixture was degassed and heated to 100° C. for 30 min, heated to 120° C. for 3.5 h, and diluted with EtOAc and water. The aqueous phase was extracted with EtOAc (3×), and the combined organic extracts were washed with 1 M NaOH (1×), brine (1×), dried over MgSO$_4$, filtered, and concentrated. Purification by flash column chromatography on silica gel (20% to 80% EtOAc (10% MeOH) in hexanes) gave 4-(2-(4-(benzo[d]thiazol-2-ylamino)phenoxy)pyridin-3-yl)-1-methylpyrrolidin-2-one (0.174 g, 0.418 mmol, 73% yield) as a white solid and a 1:1 mixture of enantiomers. MS (ESI, pos. ion) m/z: 417.1 (M+1). IC50 (uM) +++++.

SCHEME 39
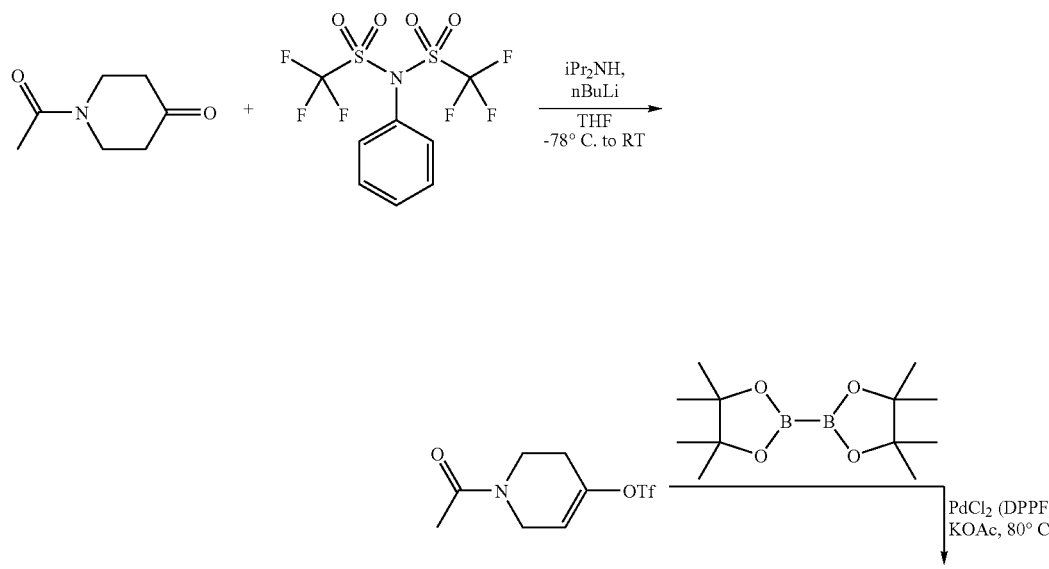
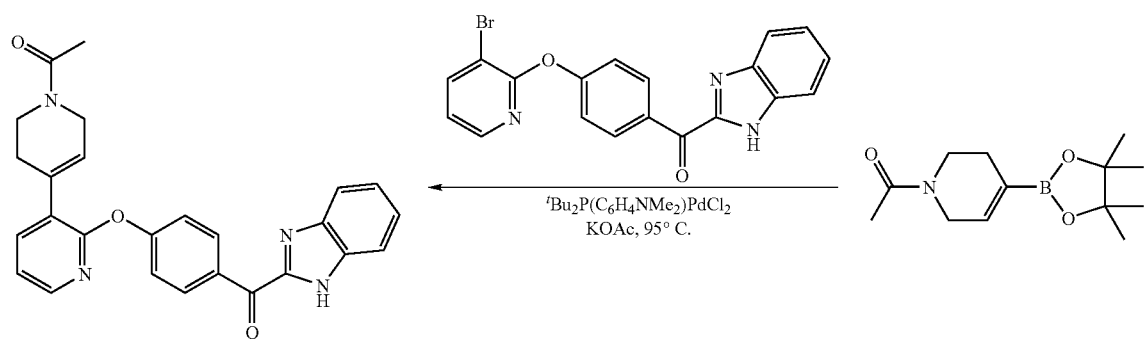
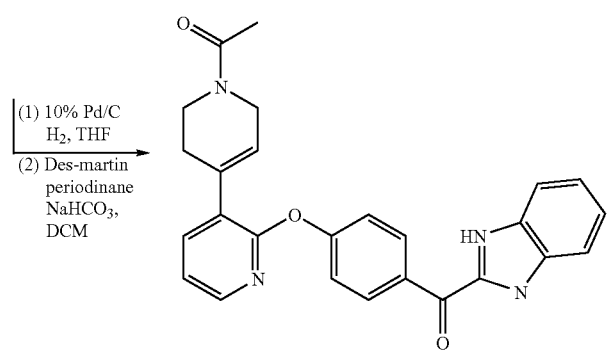

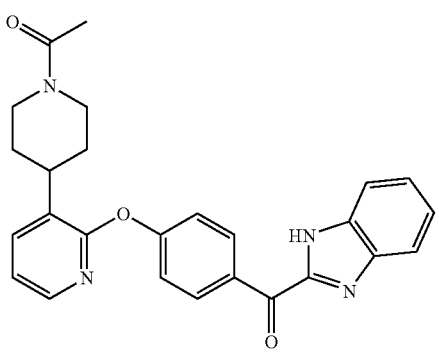

Example 211

1-(4-(2-(4-(1H-BENZO[D]IMIDAZOLE-2-CAR-BONYL)PHENOXY)PYRIDIN-3-YL)PIPERIDIN-1-YL)ETHANONE

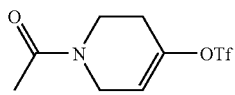

STEP 1. 1-ACETYL-1,2,3,6-TETRAHYDROPYRIDIN-4-YL TRIFLUOROMETHANESULFONATE

Diisopropylamine (18.0 mL, 128 mmol) was taken up in 50 mL of THF and chilled to −78° C. Butyllithium, 2.5 M in hexanes (51.0 mL, 128 mmol) was added dropwise. After 10 min, 1-acetylpiperidin-4-one (15.0 g, 106 mmol) was added in 60 mL of THF with rigorous stirring. After 30 min, n-phenyltriflimide (41.8 g, 117 mmol) was added in 120 mL of THF. The reaction mixture was stirred at −78° C. to RT for 16 h. The reaction mixture was quenched by saturated NaHCO₃, followed by extraction with EtOAc and 5% citric acid. The organic layer was washed with 1 N NaOH (2×), water (2×), and brine, then dried over MgSO₄. Filtration and concentration under reduced pressure, followed by flash chromatography on silica gel (0% to 60% EtOAc/hexanes) afforded 1-acetyl-1,2,3,6-tetrahydropyridin-4-yl trifluoromethanesulfonate as a yellow oil.

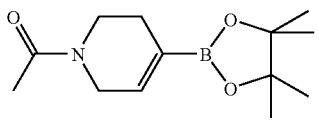

STEP 2. 1-(4-(4,4,5,5-TETRAMETHYL-1,3,2-DIOXABOROLAN-2-YL)-5,6-DIHYDROPYRIDIN-1(2H)-YL)ETHANONE 1-acetyl-1,2,3,6-tetrahydropyridin-4-yl trifluoromethanesulfonate (6.77 g, 24.8 mmol), bis(pinacolato)diboron (6.92 g, 27.3 mmol), potassium acetate (2.93 g, 49.6 mmol), and 1,1'-bis(diphenylphosphino)ferrocene]dichloride palladium (ii)complex with dichlormethane (1.01 g, 1.24 mmol) were taken up in dioxane (83 mL). The mixture was purged with nitrogen and then was heated to 80° C. After 16 h, the reaction mixture was cooled to RT, and was diluted with 150 mL of EtOAc and washed with 50 mL of water and 50 mL of brine, then dried over MgSO₄. Filtration and concentration under reduced pressure, followed by flash chromatography on silica gel (0% to 90% EtOAc/hexanes) afforded 1-(4-(4,4,5,5-tetramethyl-1,3,2-dioxaborolan-2-yl)-5,6-dihydropyridin-1(2H)-yl)ethanone as an orange oil.

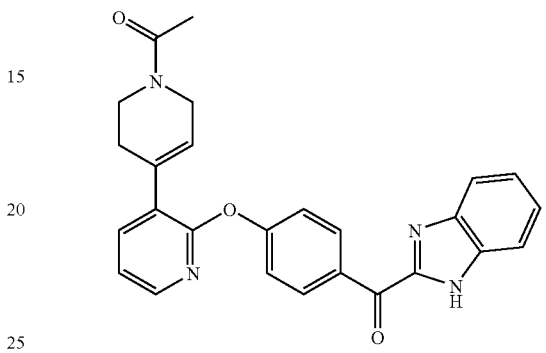

STEP 3. 1-(4-(2-(4-(1H-BENZO[D]IMIDAZOLE-2-CARBONYL)PHENOXY)PYRIDIN-3-YL)-5,6-DIHYDROPYRIDIN-1(2H)-YL)ETHANONE (1H-benzo[d]imidazol-2-yl)(4-(3-bromopyridin-2-yloxy)phenyl)methanone (0.895 g, 2.270 mmol), 1-(4-(4,4,5,5-tetramethyl-1,3,2-dioxaborolan-2-yl)-5,6-dihydropyridin-1(2H)-yl)ethanone (0.60 g, 2.39 mmol), potassium acetate (1.06 g, 17.9 mmol), and palladium catalyst (0.13 g, 0.18 mmol) were taken up in 24 mL of 3:1 MeCN:water. The mixture was purged with nitrogen and heated to 90° C. for 15 h. The reaction mixture was diluted with water and extracted with EtOAc (3×). The organics were washed with 30 mL of brine and dried over MgSO₄. Filtration and concentration under reduced pressure, followed by flash chromatography on silica gel [10 to 100% EtOAc (contains 5% MeOH)/hexane] afforded 1-(4-(2-(4-(1H-benzo[d]imidazole-2-carbonyl)phenoxy)pyridin-3-yl)-5,6-dihydropyridin-1(2H)-yl)ethanone as a yellow solid.

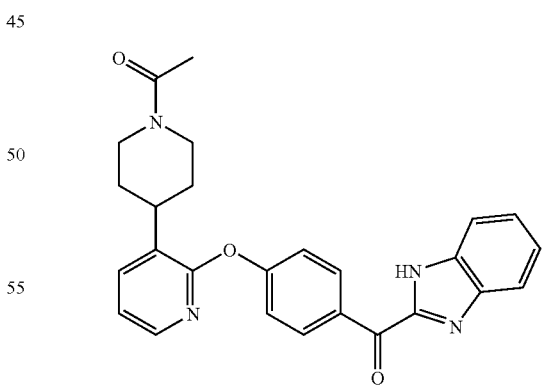

STEP 4. 1-(4-(2-(4-(1H-BENZO[D]IMIDAZOLE-2-CARBONYL)PHENOXY)PYRIDIN-3-YL)PIPERIDIN-1-YL)ETHANONE 1-(4-(2-(4-(1H-benzo[d]imidazole-2-carbonyl)phenoxy)pyridin-3-yl)-5,6-dihydropyridin-1(2H)-yl)ethanone (0.42 g, 0.96 mmol), acetic acid, glacial (0.11 mL, 1.92 mmol) and palladium on carbon, 10% (0.20 g, 0.19 mmol) were suspended in tetrahydrofuran (10 mL) in a pressure reactor. The mixture was hydrogenated at 50 psi for 16 h. The catalyst was filtered off and washed with THF. To the solution was added palladium on carbon, 10% (0.204 g, 0.192 mmol) and acetic acid, glacial (0.111 mL, 1.916 mmol) and the mixture was hydrogenated at 50 psi for another 24 h. The mixture was filtered through celite and washed with THF. The solvent was removed under reduced pressure and the residue was partitioned between DCM and saturated NaHCO₃. The organic layer was dried and concentrated to give 1-(4-(2-(4-((1H-benzo[d]imidazol-2-yl)(hydroxy)methyl)phenoxy)pyridin-3-yl)piperidin-1-yl)ethanone as off-white solid.

The material (0.24 g, 0.54 mmol) was taken up in DCM (5.4 mL). Sodium bicarbonate (0.33 g, 5.4 mmol) was added, followed by dess-martin periodinane (0.35 g, 0.81 mmol). After 20 min, the reaction was quenched with 5 mL of aq. Na₂S₂O₃ and 5 mL of aq. NaHCO₃. The mixture was diluted with 5 mL of water and stirred for 15 min. The aqueous layer was extracted with 9:1 CHCl₃/IPA (3×). The combined organics were dried (Na₂SO₄) and concentrated. The crude material was chromatographed through a Redi-Sep pre-packed silica gel column (40 g), eluting with a gradient of 10% to 100% EtOAc in hexane, then 5% MeOH in EtOAc, to provide 1-(4-(2-(4-(1H-benzo[d]imidazole-2-carbonyl)phenoxy)pyridin-3-yl)piperidin-1-yl)ethanone as light-yellow solid. MS (ESI, pos. ion) m/z: 441.0 (M+1). IC50 (uM) +++++.

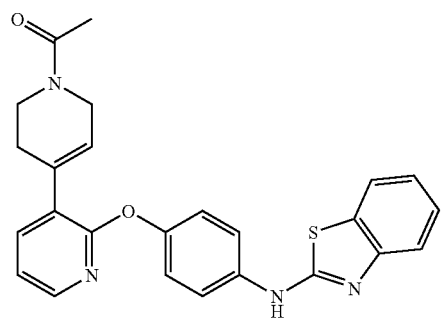

Example 212

1-(4-(2-(4-(BENZO[D]THIAZOL-2-YLAMINO)PHENOXY)PYRIDIN-3-YL)-5,6-DIHYDROPYRIDIN-1(2H)-YL)ETHANONE

Same procedure as step 3 of example 2 using 4-(benzo[d]thiazol-2-ylamino)phenol to produce desired product. MS (ESI, pos. ion) m/z: 443.0 (M+1). IC50 (uM) +++++.

SCHEME 40

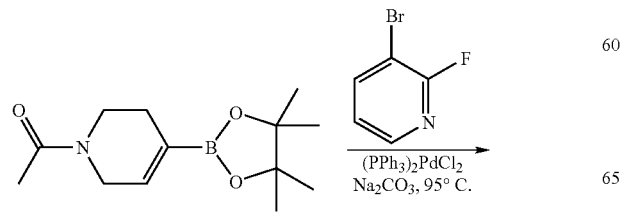

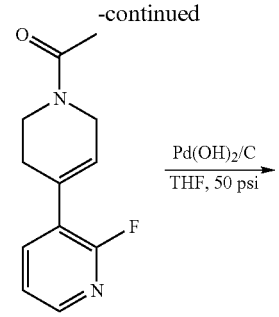

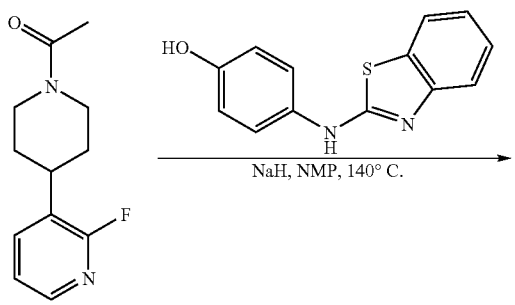

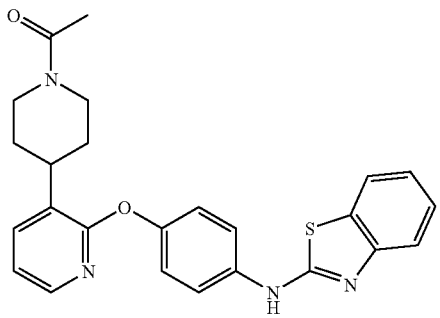

Example 213

1-(4-(2-(4-(BENZO[D]THIAZOL-2-YLAMINO)PHENOXY)PYRIDIN-3-YL)PIPERIDIN-1-YL)ETHANONE

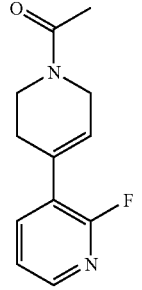

STEP 1. 1-(4-(2-FLUOROPYRIDIN-3-YL)-5,6-DIHYDROPYRIDIN-1(2H)-YL)ETHANONE

To a round-bottomed flask was added 3-bromo-2-fluoropyridine (0.54 g, 3.1 mmol), 1-(4-(4,4,5,5-tetramethyl-1,3,2-dioxaborolan-2-yl)-5,6-dihydropyridin-1(2H)-yl)ethanone (0.96 g, 3.8 mmol), trans-dichlorobis(triphenylphosphine) palladium (II) (0.17 g, 0.25 mmol), and sodium carbonate (0.97 g, 9.2 mmol) in DME (7.5 mL) and Water (2.5 mL). The reaction mixture was stirred at 100° C. for 16 h. After cooling to RT, the reaction mixture was diluted with water (15 mL) and extracted with EtOAc (3×50 mL). The organic extract was washed with water, brine, dried with $Na_2SO_4$, filtered, and concentrated. The crude product was chromatographed through a Redi-Sep pre-packed silica gel column (40 g), eluting with a gradient of 10% to 100% EtOAc in hexane, to provide 1-(4-(2-fluoropyridin-3-yl)-5,6-dihydropyridin-1(2H)-yl)ethanone (0.14 g, 21% yield) as a yellow oil. MS (ESI, pos. ion) m/z: 221.0 (M+1).

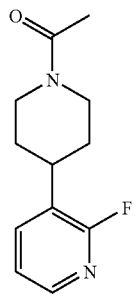

STEP 2. 1-(4-(2-(4-(BENZO [D]THIAZOL-2-YLAMINO)PHENOXY)PYRIDIN-3-YL)PIPERIDIN-1-YL)ETHANONE 1-(4-(2-fluoropyridin-3-yl)-5,6-dihydropyridin-1(2H)-yl)ethanone (0.14 g, 0.65 mmol), palladium hydroxide, 20 wt % pd (dry basis) on carbon, wet, degussa type e101 new (91 mg, 0.13 mmol) and acetic acid, glacial (19 uL, 0.32 mmol) were suspended in THF (13 mL) in a pressure tube. The reaction mixture was hydrogenated at 50 psi for 5 h then filtered through a pad of celite and washed with THF. The filtrate was concentrated to give 1-(4-(2-fluoropyridin-3-yl)piperidin-1-yl)ethanone as clear oil.

STEP 3. 1-(4-(2-(4-(BENZO [D]THIAZOL-2-YLAMINO)PHENOXY)PYRIDIN-3-YL)PIPERIDIN-1-YL)ETHANONE

To 4-(benzo[d]thiazol-2-ylamino)phenol (0.327 g, 1.35 mmol) dissolved in N-Methyl-2-pyrrolidinone (3 mL) was added sodium hydride, 60% dispersion in mineral oil (54 mg, 1.4 mmol). After stirring at RT for 10 min, 1-(4-(2-fluoropyridin-3-yl)piperidin-1-yl)ethanone (0.15 g, 0.68 mmol) was added and the reaction mixture was stirred at 140° C. for 16 h. After cooling to RT, the reaction mixture was partitioned between EtOAc and brine. The aqueous layer was back extracted with EtOAc (3×) and the combined organics were dried ($Na_2SO_4$) and concentrated. The crude material was purified by chromatography through a Redi-Sep pre-packed silica gel column (40 g), eluting with a gradient of 10% to 100% EtOAc in hexane, followed by trituration with $Et_2O$ and hexane to provide 1-(4-(2-(4-(benzo[d]thiazol-2-ylamino)phenoxy)pyridin-3-yl)piperidin-1-yl)ethanone (0.137 g, 0.308 mmol, 45.7% yield) as off-white solid. MS (ESI, pos. ion) m/z: 445.0 (M+1). IC50 (uM) +++++.

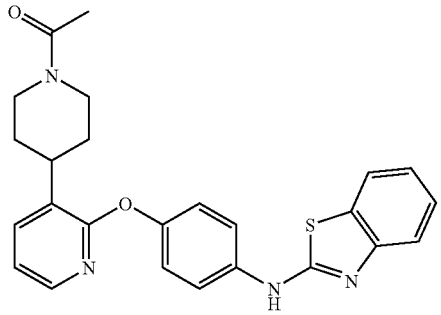

SCHEME 41

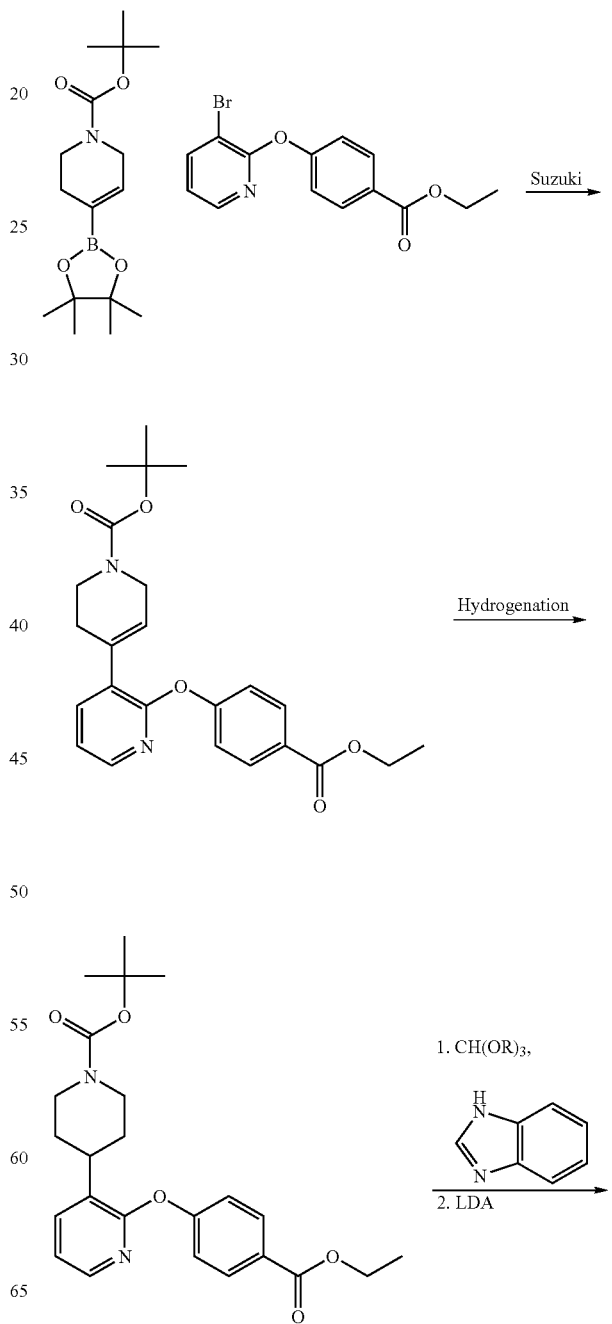

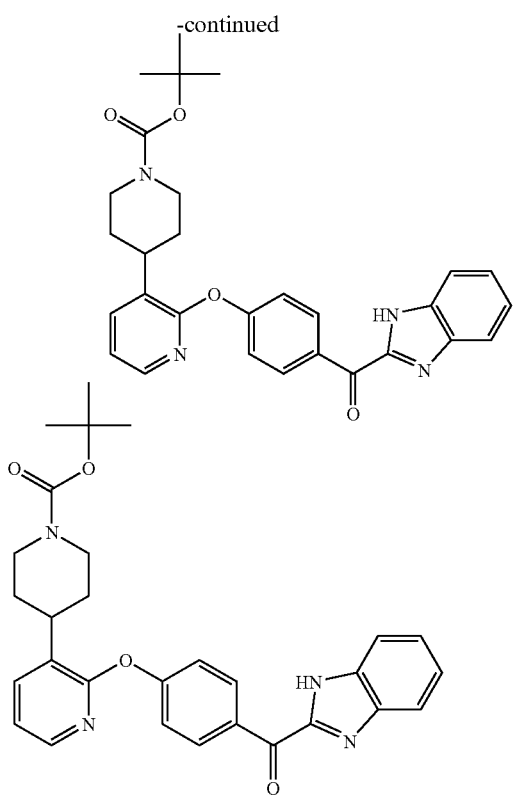

Example 214

TERT-BUTYL 4-(2-(4-(1H-BENZO[D]IMIDAZOLE-2-CARBONYL)PHENOXY)PYRIDIN-3-YL)PIPERIDINE-1-CARBOXYLATE

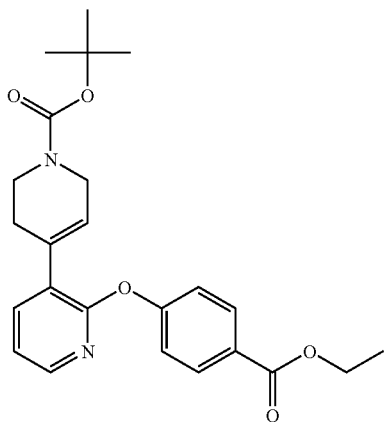

STEP 1. TERT-BUTYL 4-(2-(4-(ETHOXYCARBONYL)PHENOXY)PYRIDIN-3-YL)-5,6-DIHYDROPYRIDINE-1(2H)-CARBOXYLATE

Four glass microwave reaction vessels were charged with ethyl 4-(3-bromopyridin-2-yloxy)benzoate (1.025 g, 3.18 mmol), tert-butyl 4-(4,4,5,5-tetramethyl-1,3,2-dioxaborolan-2-yl)-5,6-dihydropyridine-1(2H)-carboxylate (1.195 g, 3.86 mmol), sodium carbonate (1.725 g, 16.28 mmol) and trans-dichlorobis(triphenyl-phosphine)palladium (II) (0.140 g, 0.199 mmol). DME (6 mL), Water (3 mL) and Ethanol (2 mL) were added and the reaction mixtures were sealed under argon and heated in a Emrys Optimizer microwave reactor (Personal Chemistry, Biotage AB, Inc., Upssala, Sweden) at 135° C. for 15 min. The reaction mixtures were combined and partitioned between EtOAc/water. The aqueous layer was extracted with EtOAc (3×) and the combined organic layers were evaporated onto silica gel and purified by flash chromatography (Isco (120 gram)) eluting with EtOAc:hexanes (0:1→1:4) to give a light-yellow crystalline solid. MS m/z: 425.1 [M+1].

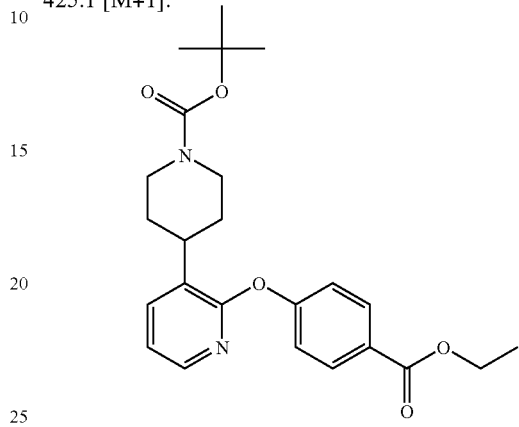

STEP 2. TERT-BUTYL 4-(2-(4-(ETHOXYCARBONYL)PHENOXY)PYRIDIN-3-YL)PIPERIDINE-1-CARBOXYLATE

A mixture of tert-butyl 4-(2-(4-(ethoxycarbonyl)phenoxy)pyridin-3-yl)-5,6-dihydropyridine-1(2H)-carboxylate (5.89 g, 13.87 mmol) and palladium hydroxide on carbon (0.950 g, 1.353 mmol) in EtOH (50 mL) was evacuated/purged with hydrogen (1 atm, 3×). After stirring at rt overnight. The mixture was filtered through a pad of Celite and the filtrate was concentrated to dryness to give a light-yellow oil. MS m/z: 427.1 [M+1].

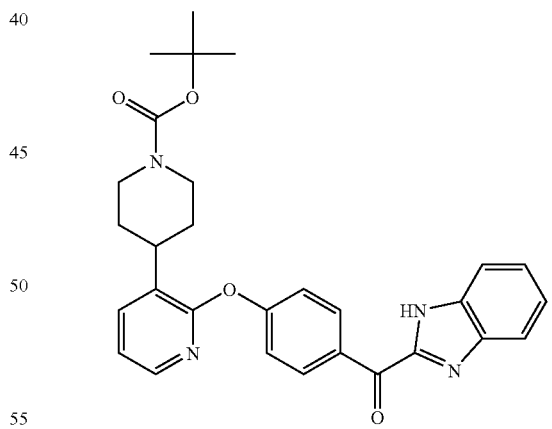

STEP 3. TERT-BUTYL 4-(2-(4-(1H-BENZO[D]IMIDAZOLE-2-CARBONYL)PHENOXY)PYRIDIN-3-YL)PIPERIDINE-1-CARBOXYLATE

A mixture of benzimidazole (0.351 g, 2.97 mmol) and triisopropyl orthoformate (3.9 mL, 17.61 mmol) in toluene (25 mL) was heated in a 100 mL round bottom flask equipped with a Dean-Stark trap and reflux condenser under an atmosphere of nitrogen. After 1 h the solvent was removed in vacuo. The residue was dissolved in THF (8 mL) and to the solution was added a solution of tert-butyl 4-(2-(4-(ethoxycarbonyl)phenoxy)pyridin-3-yl)piperidine-1-carboxylate (1.07 g, 2.509 mmol) in THF (8 mL). The mixture was cooled (−78° C.) and lithium diisopropylamide (2.0M solution in heptane/THF/ethylbenzene, 1.80 mL, 3.60 mmol) was added dropwise resulting in a reddish solution. After 2 h the reaction was quenched with saturated NH$_4$Cl and allowed to warm to rt. The mixture was partitioned between EtOAc/saturated NaHCO$_3$. The organic layer was washed with brine and dried over Na$_2$SO$_4$. The solution was filtered and the filtrate was evaporated onto silica gel and purified by flash chromatography (Isco, (120 gram)) eluting with 2M NH$_3$ in MeOH:CH$_2$Cl$_2$ (0:1→3:97) to give a white amorphous solid. MS (ESI, pos. ion) m/z: 499.1 (M+1). IC50 (uM) +++++.

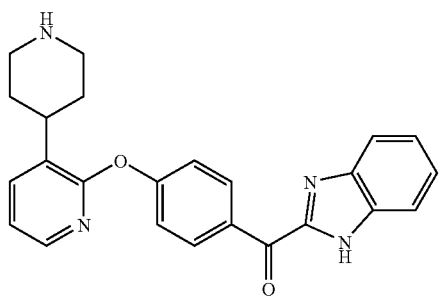

Example 215

(1H-BENZO[D]IMIDAZOL-2-YL)(4-(3-(PIPERIDIN-4-YL)PYRIDIN-2-YLOXY)PHENYL)METHANONE tert-butyl 4-(2-(4-(1H-benzo[d]imidazole-2-carbonyl)phenoxy)pyridin-3-yl)piperidine-1-carboxylate (300 mg, 0.601 mmol) was dissolved in MeOH (10 mL) and HCl (4.0 M in dioxane, 5 mL) was added and the reaction stirred 16 h at rt. The solution was concentrated to give the crude HCl salt. The product was purified by reverse-phase preparative HPLC, 10% to 80% MeCN (0.1% TFA) in water (0.1% TFA) over 20 minutes to give the trifluoroacetic acid salt as a yellow solid. The salt was freebased by dissolving in MeOH and application to a 5 g Bondesil-SCX ion exchange column. Elution of the product with NH$_3$ in MeOH (2.0 M) and concentration of the product containing fractions gives (1H-benzo[d]imidazol-2-yl)(4-(3-(piperidin-4-yl)pyridin-2-yloxy)phenyl)methanone as a yellow solid. MS (ESI, pos. ion) m/z: 399.0 (M+1). IC50 (uM) +++++.

SCHEME 42

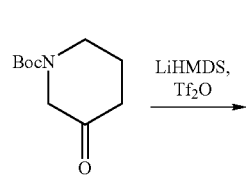

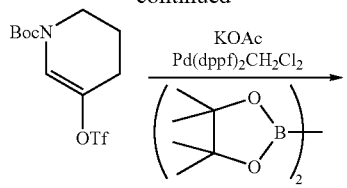

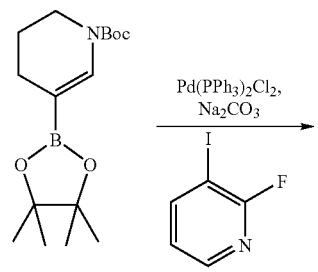

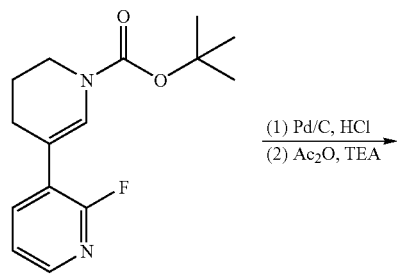

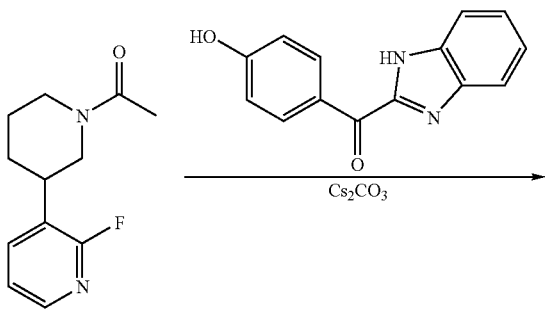

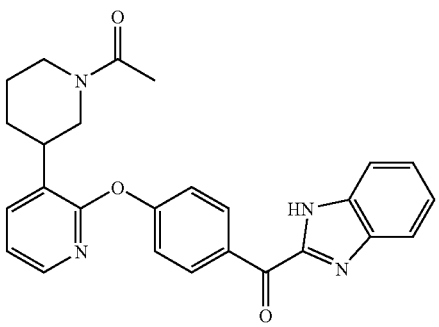

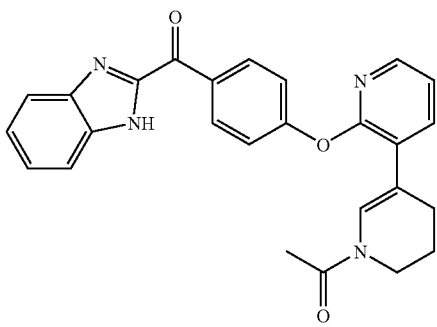

Example 216

1-(5-(2-(4-(1H-BENZO[D]IMIDAZOLE-2-CAR-
BONYL)PHENOXY)PYRIDIN-3-YL)-3,4-DIHY-
DROPYRIDIN-1(2H)-YL)ETHANONE

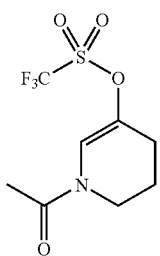

STEP 1.
1-ACETYL-1,4,5,6-TETRAHYDROPYRIDIN-3-YL TRIFLUOROMETHANESULFONATE

To a −78° C. solution of diisopropylamine (3.60 mL, 25.5 mmol) in THF (30 mL) was added butyllithium (9.35 mL, 23.38 mmol) dropwise. After the addition was complete the reaction was allowed to stir at −78° C. for 15 minutes, then a solution of 1-acetylpiperidin-3-one (3.0 g, 21.25 mmol) in THF (5 mL) was added dropwise. After a further 20 minutes, a solution of 1,1,1-trifluoro-N-phenyl-N-(trifluoromethylsulfonyl)methanesulfonamide (8.35 g, 23.38 mmol) in THF (15 mL) was added dropwise to the reaction. The solution was allowed to slowly warm to room temperature. After 16 hours, the reaction was quenched with sat'd NH$_4$Cl and the diluted with water (20 mL). The aqueous solution was basified and extracted with EtOAc (4×30 mL). The combined organics were washed with brine and concentrated in vacuo. The crude product was adsorbed onto a plug of silica gel and chromatographed through a Redi-Sep® pre-packed silica gel column (40 g), eluting with 0% to 70% EtOAc in hexane, to provide 1-acetyl-1,4,5,6-tetrahydropyridin-3-yl trifluoromethanesulfonate (2.0 g, 7.32 mmol) as a golden oil. [M+1]=274.0.

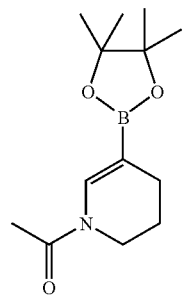

STEP 2. 1-(5-(4,4,5,5-TETRAMETHYL-1,3,2-DI-
OXABOROLAN-2-YL)-3,4-DIHYDROPYRIDIN-1
(2H)-YL)ETHANONE

To a solution of 1-acetyl-1,4,5,6-tetrahydropyridin-3-yl trifluoromethanesulfonate (2.5 g, 9.15 mmol), bis(pinacolato)diboron (2.88 g, 11.34 mmol), potassium acetate (1.91 g, 19.46 mmol), and dioxane (60 mL) was added 1,1'-bis(diphenylphosphino)ferrocenedichloro palladium(ii) dichloromethane complex (400 mg, 0.547 mmol). The mixture was purged with nitrogen and then was heated to 80° C. After 16 hours, the reaction was cooled to room temperature. The mixture was diluted with 150 mL of EtOAc and washed with 50 mL of water and 50 mL of brine, dried over MgSO$_4$, and concentrated in vacuo. The crude product was adsorbed onto a plug of silica gel and chromatographed through a Redi-Sep® pre-packed silica gel column (40 g), eluting with 0% to 40% EtOAc in hexane, to provide 1-(5-(4,4,5,5-tetramethyl-1,3,2-dioxaborolan-2-yl)-3,4-dihydropyridin-1(2H)-yl)ethanone (1.2 g, 4.78 mmol) as an orange oil. [M+1]=252.1.

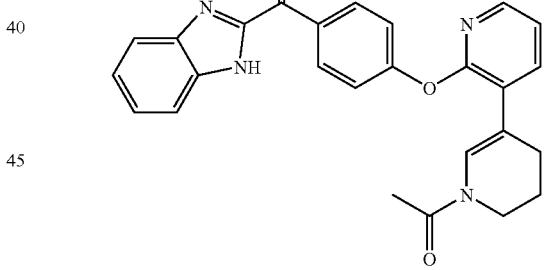

STEP 3. 1-(5-(2-(4-(1H-BENZO[D]IMIDAZOLE-2-
CARBONYL)PHENOXY)PYRIDIN-3-YL)-3,4-
DIHYDROPYRIDIN-1(2H)-YL)ETHANONE

To a degassed solution of (1H-benzo[d]imidazol-2-yl)(4-(3-bromopyridin-2-yloxy)phenyl)methanone (706 mg, 1.791 mmol), 1-(5-(4,4,5,5-tetramethyl-1,3,2-dioxaborolan-2-yl)-3,4-dihydropyridin-1(2H)-yl)ethanone (0.5 g, 1.991 mmol), potassium acetate (1.5 g, 15.28 mmol), and dioxane (10 mL) was added A-Phos (140 mg, 0.198 mmol). The solution was stirred at 80° C. After 16 hours, the reaction was allowed to cool to room temperature, diluted with H$_2$O (10 mL), and the aqueous layer extracted with DCM (5 mL). The combined organic layers were concentrated in vacuo and purified by Prep TLC (1:1 hexanes/EtOAc) to give 1-(5-(2-(4-(1H-benzo[d]imidazole-2-carbonyl)phenoxy)pyridin-3-yl)-3,4-dihydropyridin-1(2H)-yl)ethanone (1.6 mg, 3.65 µmol) as a light yellow film. MS (ESI, pos. ion) m/z: 439.0 (M+1). IC50 (uM) +++++.

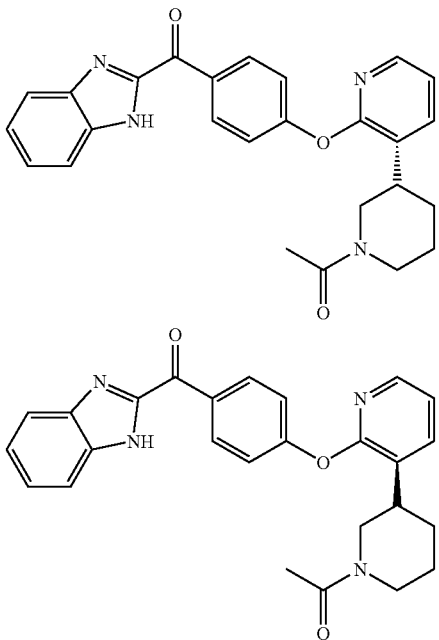

Example 217

(S)-1-(3-(2-(4-(1H-BENZO[D]IMIDAZOLE-2-CARBONYL)PHENOXY)PYRIDIN-3-YL)PIPERIDIN-1-YL)ETHANONE AND (R)-1-(3-(2-(4-(1H-BENZO[D]IMIDAZOLE-2-CARBONYL)PHENOXY)PYRIDIN-3-YL)PIPERIDIN-1-YL)ETHANONE

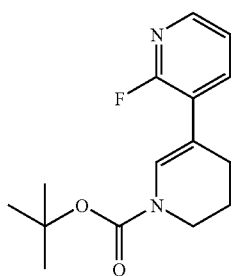

STEP 1. TERT-BUTYL 5-(2-FLUOROPYRIDIN-3-YL)-3,4-DIHYDROPYRIDINE-1(2H)-CARBOXYLATE

A microwave vial was charged with 2-fluoro-3-iodopyridine (1.325 g, 5.94 mmol), tert-butyl 5-(4,4,5,5-tetramethyl-1,3,2-dioxaborolan-2-yl)-3,4-dihydropyridine-1(2H)-carboxylate (1.8 g, 5.82 mmol), sodium carbonate hydrate (2166 mg, 17.46 mmol), catalyst (211 mg, 0.301 mmol), DME (3 mL), Ethanol (0.857 mL) and Water (1.286 mL). The vial was capped and heated in a Biotage Initiator to 140° C. for 15 minutes. The reaction was diluted with water (20 ml) and ethyl acetate (30 ml). The organic layer was washed with water (2×10 mL), brine (10 mL), and concentrated in vacuo. The crude product was adsorbed onto a plug of silica gel and chromatographed through a Redi-Sep® pre-packed silica gel column (40 g), eluting with 0% to 50% EtOAc in hexane, to provide tert-butyl 5-(2-fluoropyridin-3-yl)-3,4-dihydropyridine-1(2H)-carboxylate (673 mg, 2.418 mmol) as a colorless syrup. [M+Na]=332.1

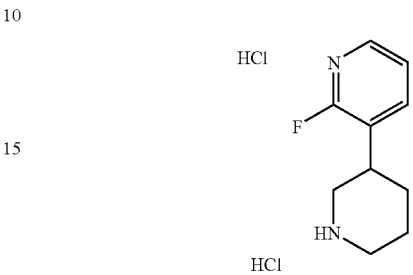

STEP 2.
2-FLUORO-3-(PIPERIDIN-3-YL)PYRIDINE DIHYDROCHLORIDE

To a $N_2$ purged round bottomed flask containing tert-butyl 5-(2-fluoropyridin-3-yl)-3,4-dihydropyridine-1(2H)-carboxylate (673 mg, 2.418 mmol) was added 10% Pd/C (50 mg, 0.470 mmol) and EtOH (15 mL). After stirring for 5 minutes, 5N HCl in iPrOH (4.0 mL, 20.00 mmol) was added and the flask capped with a balloon of $H_2$. After 16 hours, LC-MS shows ~30% conversion. The balloon was refilled. After a further 5 days, LC-MS shows complete consumption of starting material. The reaction was filtered through a celite cartridge and the cartridge rinsed with DCM:10% EtOH (50 mL). The filtrate was concentrated in vacuo to give 2-fluoro-3-(piperidin-3-yl)pyridine dihydrochloride as a yellow foam. The material was carried forward without further purification.

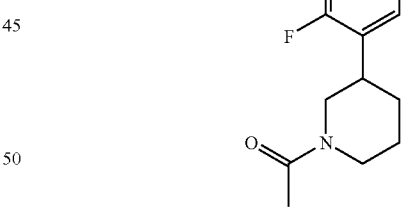

STEP 3. 1-(3-(2-FLUOROPYRIDIN-3-YL)PIPERIDIN-1-YL)ETHANONE

To an ice cooled solution of 2-fluoro-3-(piperidin-3-yl)pyridine dihydrochloride (612 mg, 2.418 mmol), DCM (20 mL) and triethylamine (2022 µL, 14.51 mmol) was added acetic anhydride (229 µL, 2.418 mmol) dropwise. After 1 hour, the reaction was poured into water and the aqueous mixture back extracted once with DCM (10 mL). The combined organics were washed with 0.5M NaOH and concentrated in vacuo. The crude product was adsorbed onto a plug of silica gel and chromatographed through a Redi-Sep® pre-packed silica gel column (12 g), eluting with 0% to 100%

EtOAc in hexane, to provide 1-(3-(2-fluoropyridin-3-yl)piperidin-1-yl)ethanone (100 mg, 0.450 mmol) as a light yellow syrup. [M+1]=223.1.

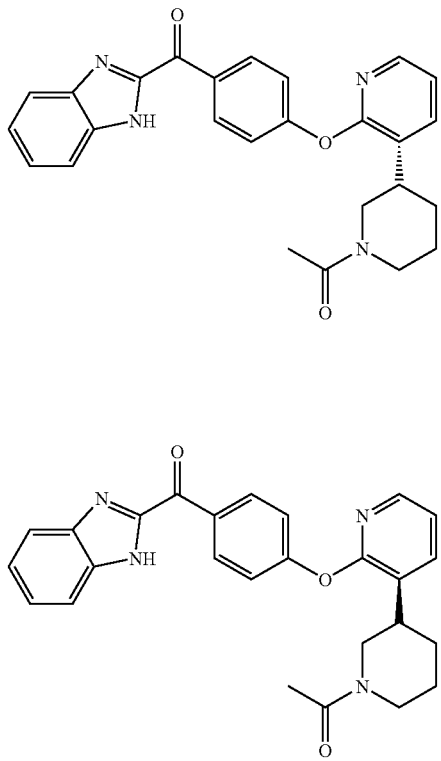

STEP 4. (S)-1-(3-(2-(4-(1H-BENZO[D]IMIDAZOLE-2-CARBONYL)PHENOXY)PYRIDIN-3-YL)PIPERIDIN-1-YL)ETHANONE AND (R)-1-(3-(2-(4-(1H-BENZO[D]IMIDAZOLE-2-CARBONYL)PHENOXY)PYRIDIN-3-YL)PIPERIDIN-1-YL)ETHANONE

To a solution of (1H-benzo[d]imidazol-2-yl)(4-hydroxyphenyl)methanone (107 mg, 0.450 mmol), NMP (2 mL) and 1-(3-(2-fluoropyridin-3-yl)piperidin-1-yl)ethanone (50 mg, 0.225 mmol) was added cesium carbonate (147 mg, 0.450 mmol). The reaction mixture was stirred and heated in a Biotage Initiator at 160° C. for 60 minutes, then at 180° C. for 2 hours, then at 200° C. for 2 hours and finally at 200° C. for 1 hour. The starting material has been consumed, but the reaction became messier the longer it was heated. The reaction was filtered through a Acrodisc syringe filter 0.2 mm ultipor nylon membrane. The filtrate was purified by reverse-phase preparative HPLC (Shimadzu) on a Phenomenex Gemini column (5 micron, C18, 110 Å, Axia, 100×50 mm) eluting at 90 mL/min with an linear gradient of 10% to 80% MeCN (0.1% TFA) in water (0.1% TFA) over 20 minutes to give the product as a TFA salt. The desired fractions were poured into 10% Na$_2$CO$_3$ (aq)/DCM, and the DCM layer separated, dried over MgSO$_4$, and concentrated in vacuo to give a mixture of (S)-1-(3-(2-(4-(1H-benzo[d]imidazole-2-carbonyl)phenoxy)pyridin-3-yl)piperidin-1-yl)ethanone and (R)-1-(3-(2-(4-(1H-benzo[d]imidazole-2-carbonyl)phenoxy)pyridin-3-yl)piperidin-1-yl)ethanone as a light yellow solid. MS (ESI, pos. ion) m/z: 441.0 (M+1). IC50 (uM) +++++.

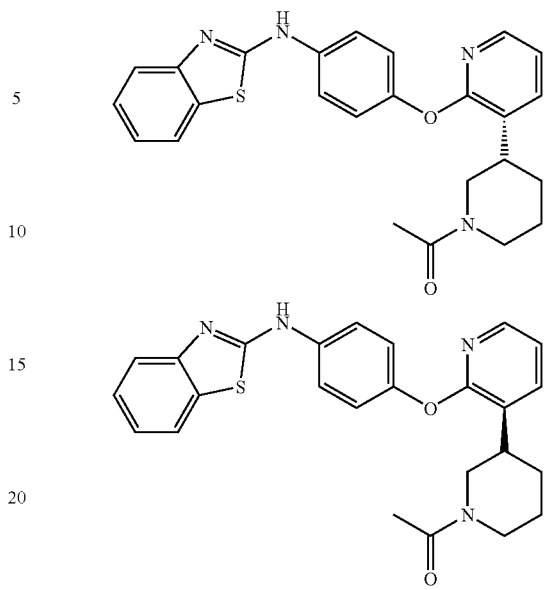

Example 218

(S)-1-(3-(2-(4-(BENZO[D]THIAZOL-2-YLAMINO)PHENOXY)PYRIDIN-3-YL)PIPERIDIN-1-YL)ETHANONE AND (R)-1-(3-(2-(4-(BENZO[D]THIAZOL-2-YLAMINO)PHENOXY)PYRIDIN-3-YL)PIPERIDIN-1-YL)ETHANONE

To a solution of 4-(benzo[d]thiazol-2-ylamino)phenol (109 mg, 0.450 mmol), NMP (2 mL) and 1-(3-(2-fluoropyridin-3-yl)piperidin-1-yl)ethanone (50 mg, 0.225 mmol) was added cesium carbonate (147 mg, 0.450 mmol). The reaction mixture was stirred and heated in a Biotage Initiator at 160° C. for 60 minutes. LC-MS shows complete conversion. The reaction was filtered through a Acrodisc syringe filter 0.2 mm ultipor nylon membrane. The filtrate was purified by reverse-phase preparative HPLC (Shimadzu) on a Phenomenex Gemini column (5 micron, C18, 110 Å, Axia, 100×50 mm) eluting at 90 mL/min with an linear gradient of 10% to 80% MeCN (0.1% TFA) in water (0.1% TFA) over 20 minutes to give the product as a TFA salt. The desired fractions were poured into 10% Na$_2$CO$_3$ (aq)/DCM, and the DCM layer separated, dried over MgSO$_4$, and concentrated in vacuo to give a mixture of (S)-1-(3-(2-(4-(benzo[d]thiazol-2-ylamino)phenoxy)pyridin-3-yl)piperidin-1-yl)ethanone (13.5 mg, 0.030 mmol, 27.0% yield) and (R)-1-(3-(2-(4-(benzo[d]thiazol-2-ylamino)phenoxy)pyridin-3-yl)piperidin-1-yl)ethanone (13.5 mg, 0.030 mmol) as a off white solid. MS (ESI, pos. ion) m/z: 445.1 (M+1). IC50 (uM) +++++.

SCHEME 43

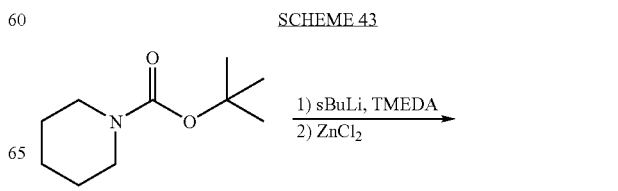

-continued

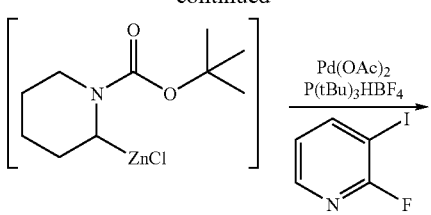

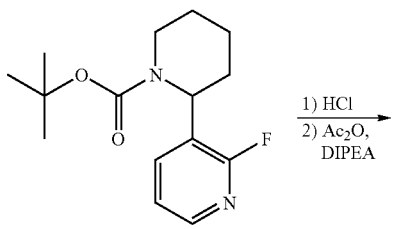

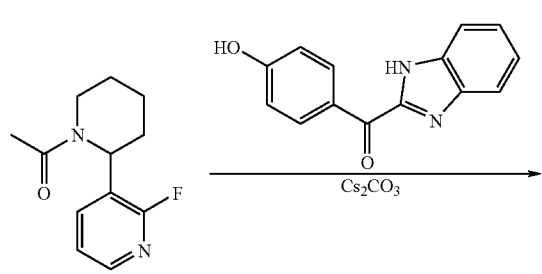

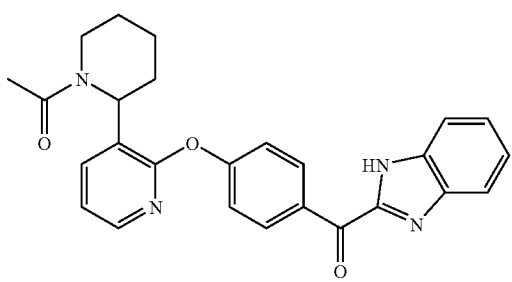

-continued

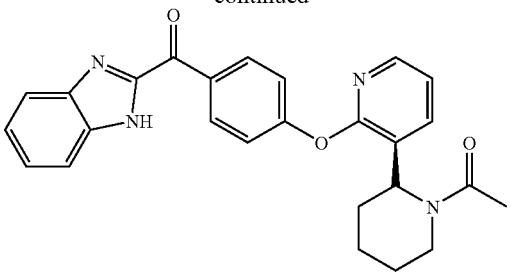

Example 219

(R)-1-(2-(2-(4-(1H-BENZO[D]IMIDAZOLE-2-CARBONYL)PHENOXY)PYRIDIN-3-YL)PIPERIDIN-1-YL)ETHANONE AND (S)-1-(2-(2-(4-(1H-BENZO[D]IMIDAZOLE-2-CARBONYL)PHENOXY)PYRIDIN-3-YL)PIPERIDIN-1-YL)ETHANONE

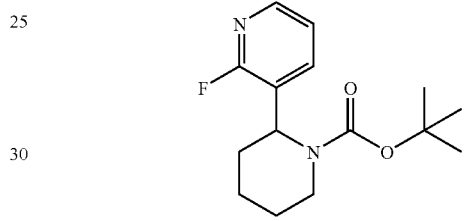

STEP 1. TERT-BUTYL 2-(2-FLUOROPYRIDIN-3-YL)PIPERIDINE-1-CARBOXYLATE

To a −78° C. solution of tert-butyl piperidine-1-carboxylate (1.0 mL, 5.20 mmol), dry ether (20 mL) and TMEDA (0.82 mL, 5.47 mmol) was added sec-butyllithium, 1.4M in cyclohexane (3.90 mL, 5.46 mmol) dropwise over 5 minutes. After 2 hours, a solution of zinc chloride, 0.5M in ether (6.8 mL, 6.80 mmol) was added over 7 minutes. After 30 minutes, the mixture was warmed to ambient temperature and stirred for a further 30 minutes then 2-fluoro-3-iodopyridine (1511 mg, 6.78 mmol), palladium(ii) acetate (127 mg, 0.566 mmol), tri-t-butylphosphonium tetrafluoroborate (268 mg, 0.924 mmol) was added in one portion. After 18 hours, NH4OH (10 mL, 10% aqueous solution) was added dropwise, followed by Et2O (10 mL). The organic layer was extracted, washed with brine, dried (MgSO$_4$) and concentrated in vacuo. The crude product was adsorbed onto a plug of silica gel and chromatographed through a Redi-Sep® pre-packed silica gel column (40 g), eluting with 0% to 40% EtOAc in hexane, to provide tert-butyl 2-(2-fluoropyridin-3-yl)piperidine-1-carboxylate (70 mg, 0.250 mmol) as a colorless oil. [M+Na]=303.2.

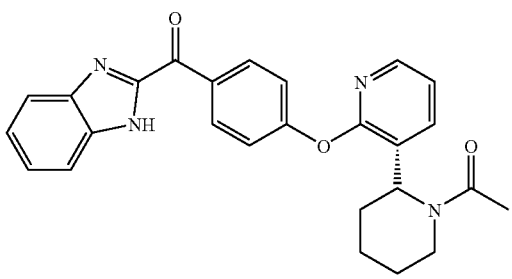

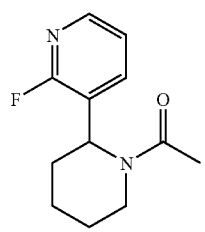

STEP 2. 1-(2-(2-FLUOROPYRIDIN-3-YL)PIPERIDIN-1-YL)ETHANONE

To a solution of tert-butyl 2-(2-fluoropyridin-3-yl)piperidine-1-carboxylate (70 mg, 0.250 mmol) and DCM (5 mL) was added TFA (0.50 mL, 6.49 mmol). After 1 hour, the reaction was washed with 10% $Na_2CO_3$. The organic layer was treated with TEA (0.070 mL, 0.499 mmol), then acetic anhydride (0.024 mL, 0.250 mmol). After 15 minutes, LC-MS shows conversion to the desired product [M+1=223]. The reaction was washed with water and concentrated in vacuo to give 1-(2-(2-fluoropyridin-3-yl)piperidin-1-yl)ethanone as a yellow oil.

(R)-1-(2-(2-(4-(1H-BENZO[D]IMIDAZOLE-2-CARBONYL)PHENOXY)PYRIDIN-3-YL)PIPERIDIN-1-YL)ETHANONE AND (S)-1-(2-(2-(4-(1H-BENZO[D]IMIDAZOLE-2-CARBONYL)PHENOXY)PYRIDIN-3-YL)PIPERIDIN-1-YL)ETHANONE

To a solution of 1-(2-(2-fluoropyridin-3-yl)piperidin-1-yl)ethanone (20 mg, 0.090 mmol), NMP (0.5 mL) was added cesium carbonate (55 mg, 0.169 mmol) and (1H-benzo[d]imidazol-2-yl)(4-hydroxyphenyl)methanone (35 mg, 0.147 mmol). The reaction mixture was stirred and heated in a Biotage Initiator at 200° C. for 60 minutes. The reaction was filtered through a Acrodisc syringe filter 0.2 mm ultipor nylon membrane. The filtrate was purified by reverse-phase preparative HPLC (Shimadzu) on a Phenomenex Gemini column (10 micron, C18, 110 Å, Axia, 100×30 mm) eluting at 45 mL/min with an linear gradient of 10% to 80% MeCN (0.1% TFA) in water (0.1% TFA) over 20 minutes to give the product as a TFA salt. The desired fractions were poured into 10% $Na_2CO_3$ (aq)/DCM, and the DCM layer separated, dried over $MgSO_4$, and concentrated in vacuo to give a mixture of (R)-1-(2-(2-(4-(1H-benzo[d]imidazole-2-carbonyl)phenoxy)pyridin-3-yl)piperidin-1-yl)ethanone and (S)-1-(2-(2-(4-(1H-benzo[d]imidazole-2-carbonyl)phenoxy)pyridin-3-yl)piperidin-1-yl)ethanone as a brown film. MS (ESI, pos. ion) m/z: 441.0 (M+1). IC50 (uM) +++++.

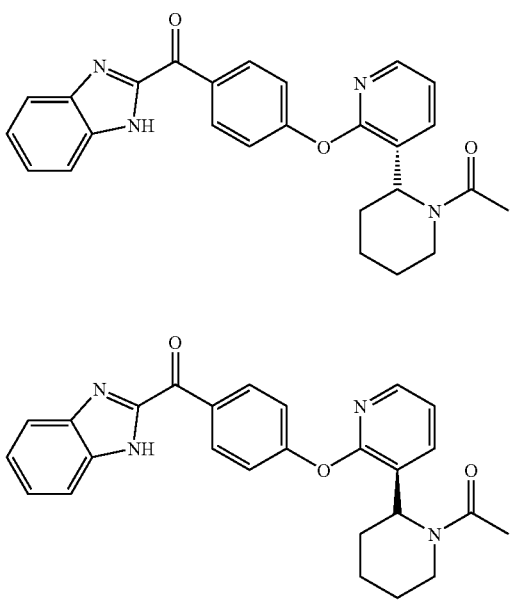

SCHEME 44

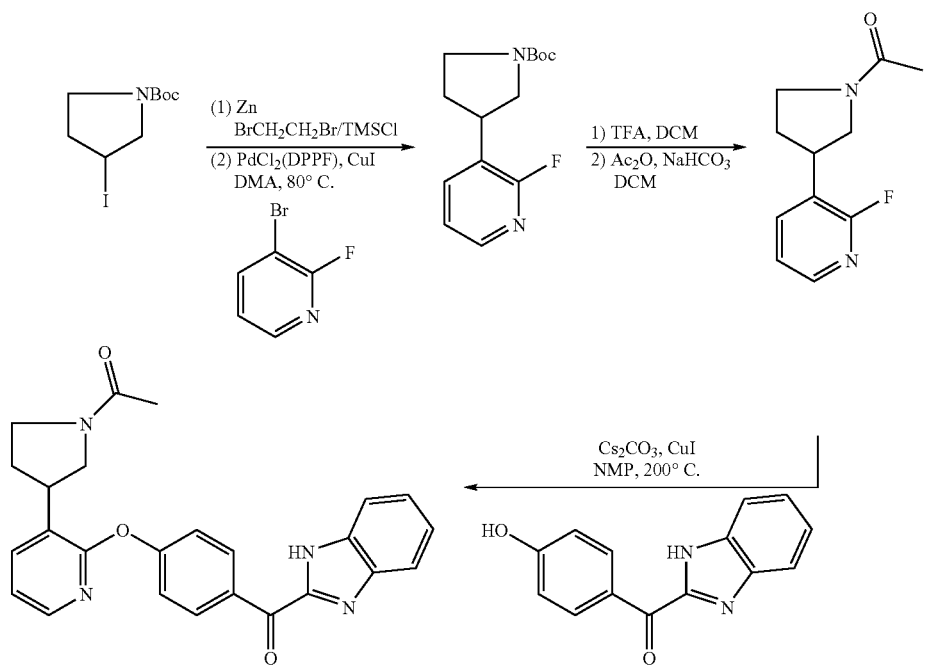

Example 220

1-(3-(2-(4-(1H-BENZO[D]IMIDAZOLE-2-CARBONYL)PHENOXY)PYRIDIN-3-YL)PYRROLIDIN-1-YL)ETHANONE

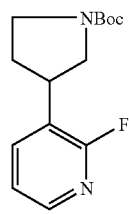

STEP 1. TERT-BUTYL 3-(2-FLUOROPYRIDIN-3-YL)PYRROLIDINE-1-CARBOXYLATE

Into an oven-dried 25 mL round bottomed flask was charged dry DMA (2 mL), zinc dust (0.843 g, 12.9 mmol). The mixture was stirred at RT while the mixture of chlorotrimethylsilane (0.132 mL, 1.04 mmol) and 1,2-dibromoethane (0.09 mL, 1.040 mmol) was added slowly. The resulting slurry was aged for 15 min. A solution of tert-butyl 3-iodopyrrolidine-1-carboxylate (3.09 g, 10.4 mmol) in DMA (5.2 mL) was added slowly to the above mixture. Zinc slurry reacted exothermically with the gradual addition of the iodide. After stirring for 30 min, the resulting milky solution was cooled to RT and used directly in the next step.

Into an oven-dried flask were charged 3-bromo-2-fluoropyridine (1.3 g, 7.39 mmol), Pd catalyst (0.181 g, 0.222 mmol), copper(i) iodide (0.084 g, 0.443 mmol), and DMA (10 mL). The resulting mixture was degassed with alternating vacuum/nitrogen purges. The (1-(tert-butoxycarbonyl)pyrrolidin-3-yl)zinc(II) iodide (3.75 g, 10.34 mmol) solution from previous step was filtered into the mixture. It was degassed one more time and then heated to 80° C. with stirring for 16 h. After cooling to RT, the reaction mixture was partitioned between EtOAc and 1 N NH₄Cl. The aqueous layer was back extracted with EtOAc (2×) and the combined EtOAc layer was washed once again with 1 N NH4Cl, then with brine, dried (Na₂SO₄) and concentrated. The crude material as chromatography through a Redi-Sep pre-packed silica gel column (120 g), eluting with a gradient of 0% to 40% EtOAc in hexane, to provide tert-butyl 3-(2-fluoropyridin-3-yl)pyrrolidine-1-carboxylate as dark-red oil. [M−56]=211.2.

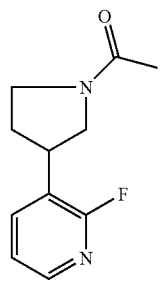

STEP 2. 1-(3-(2-FLUOROPYRIDIN-3-YL)PYRROLIDIN-1-YL)ETHANONE

To tert-butyl 3-(2-fluoropyridin-3-yl)pyrrolidine-1-carboxylate (0.25 g, 0.939 mmol) dissolved in DCM (3.1 mL) was added trifluoroacetic acid (1.05 mL, 14.1 mmol). The reaction mixture was stirred at RT for 1 h. The solvent was evaporated in vacuo and to the residue dissolved in DCM (1 mL) was added acetic anhydride (0.44 mL, 4.7 mmol) and sodium bicarbonate (0.4 g, 4.7 mmol). The reaction mixture was stirred at RT under N2 for 3 h. The reaction mixture was partitioned between 1N NaOH and DCM. The aqueous layer was back extracted with DCM (3×) and the combined DCM layer was dried (Na₂SO₄) and concentrated. The crude material was purified by chromatography through a Redi-Sep pre-packed silica gel column (40 g), eluting with a gradient of 0% to 100% EtOAc in hexane, then 10% MeOH in EtOAc, to provide 1-(3-(2-fluoropyridin-3-yl)pyrrolidin-1-yl)ethanone as tan oil. [M+H]=209.2.

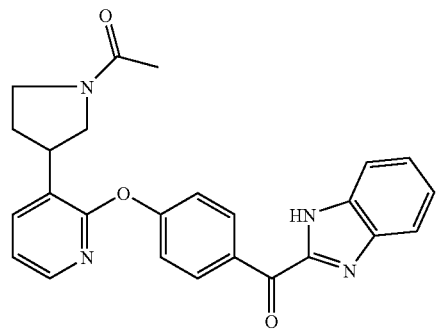

STEP 3. 1-(3-(2-(4-(1H-BENZO[D]IMIDAZOLE-2-CARBONYL)PHENOXY)PYRIDIN-3-YL)PYRROLIDIN-1-YL)ETHANONE

A glass microwave reaction vessel was charged with 1-(3-(2-fluoropyridin-3-yl)pyrrolidin-1-yl)ethanone (86 mg, 0.41 mmol), (1H-benzo[d]imidazol-2-yl)(4-hydroxyphenyl)methanone (197 mg, 0.826 mmol), cesium carbonate (309 mg, 0.95 mmol), copper(i) iodide (79 mg, 0.413 mmol), and NMP (1.4 mL). The reaction mixture was degassed and flushed with N₂ and heated in a Emrys Optmizer microwave reactor (Personal Chemistry, Biotage AB, Inc., Upssala, Sweden) at 200° C. for 1 h. After cooling to RT, the reaction mixture was partitioned between EtOAc and 1 N NH₄Cl. The aqeuous layer was back extracted with EtOAc (2×) and the combined organic layer was washed with water, brine, dried (Na₂SO₄) and concentrated. The crude material was chromatographed through a Redi-Sep pre-packed silica gel column (40 g), eluting with a gradient of 0% to 100% EtOAc in hexane, then 5% MeOH in EtOAc, followed by trituration with ether, dried to provide 1-(3-(2-(4-(1H-benzo[d]imidazole-2-carbonyl)phenoxy)pyridin-3-yl)pyrrolidin-1-yl)ethanone as off-white solid. MS (ESI, pos. ion) m/z: 427.1 (M+1). IC50 (uM) +++++.

SCHEME 45

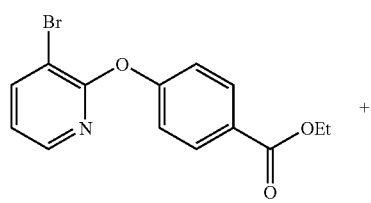

+

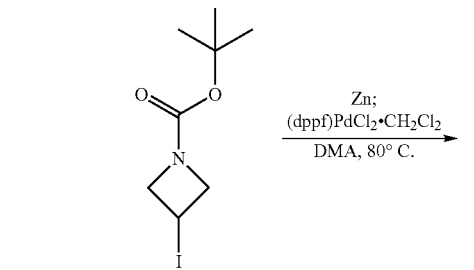

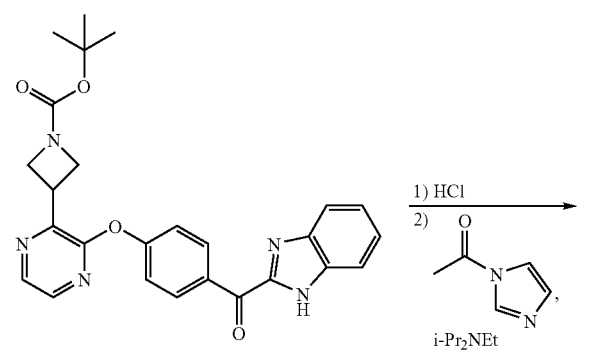

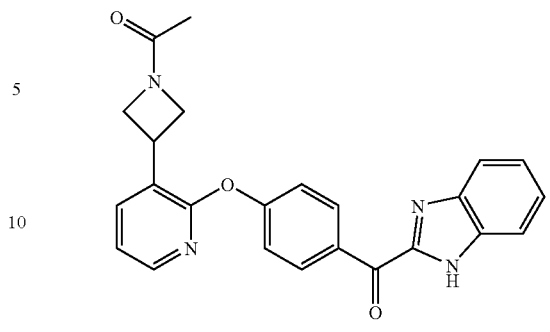

Example 221

1-(3-(3-(4-(1H-BENZO[D]IMIDAZOLE-2-CAR-
BONYL)PHENOXY)PYRAZIN-2-YL)PIPERIDIN-
1-YL)ETHANONE

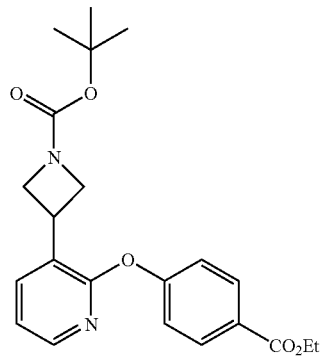

STEP 1. TERT-BUTYL 3-(2-(4-(ETHOXYCARBO-
NYL)PHENOXY)PYRIDIN-3-YL)AZETIDINE-1-
CARBOXYLATE

To a suspension of zinc dust (217 mg, 3.31 mmol) in DMA (2 mL) at rt was added chlorotrimethylsilane (67.3 µL, 0.532 mmol) and 1,2-dibromoethane (45.9 µL, 0.532 mmol) slowly. The resulting slurry was stirred 15 min, then tert-butyl 3-iodoazetidine-1-carboxylate (753 mg, 2.66 mmol) was added to the above mixture (mild exotherm). The suspension was stirred at rt 30 min.

The zinc solution was added via syringe to a solution of ethyl 4-(3-bromopyridin-2-yloxy)benzoate (600 mg, 1.862 mmol), Pd(dppf)Cl$_2$.CH$_2$Cl$_2$ (65.2 mg, 0.080 mmol), and copper(I) iodide (30.4 mg, 0.160 mmol) in DMA (1.0 mL) that was degassed with Ar sparging. The solution was heated to 80° C. and stirred 1 h. The reaction was quenched with half saturated NH$_4$Cl and extracted with EtOAc (3×10 mL). The combined organic fractions were dried (MgSO$_4$), concentrated, and purified by ISCO (40 g SiO$_2$, 0-100% EtOAc/

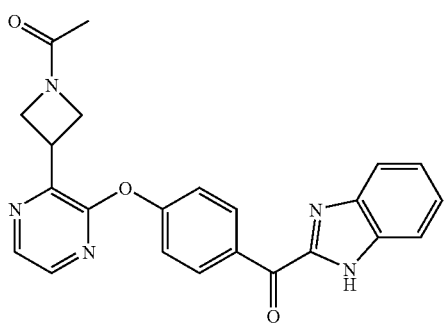

Hexane) to give tert-butyl 3-(2-(4-(ethoxycarbonyl)phenoxy)pyridin-3-yl)azetidine-1-carboxylate as a light brown oil.

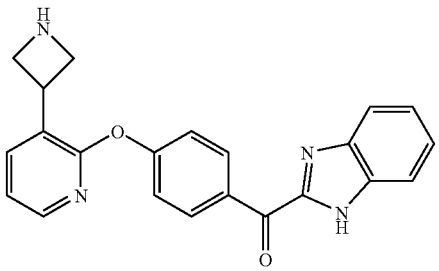

STEP 2. (4-(3-(AZETIDIN-3-YL)PYRIDIN-2-YLOXY)PHENYL)(1H-BENZO[D]IMIDAZOL-2-YL)METHANONE

To a solution of 1-(diisopropoxymethyl)-1H-benzo[d]imidazole (318 mg, 1.280 mmol) in THF (5 mL) at 0° C. is added LiHMDS (0.753 mL, 0.753 mmol) over 1 min. The reaction was stirred 5 min., then 3.5 mL of the 6 mL solution (1.0 theoretical equivalent of the lithium benzoimidazole) was added to a solution of tert-butyl 3-(2-(4-(ethoxycarbonyl)phenoxy)pyridin-3-yl)azetidine-1-carboxylate (300 mg, 0.753 mmol) in THF (3 mL) at 0° C. The reaction was stirred at 0° C. 30 min. LCMS showed only 5% conversion. The remaining solution of benzoimidazole was added and the reaction stirred 1 h at 0° C. LCMS shows 2:1 ratio of starting material to desired product. The reaction was quenched with 2 N HCl (15 mL) and warmed to rt and stirred overnight. The aqueous layer was neutralized with solid $Na_2CO_3$ and the aqueous layer extracted with $CH_2Cl_2$ (2×25 mL). The combined organic fractions were washed with saturated NaCl, dried ($MgSO_4$), and concentrated. The crude material was then taken up in MeOH (3 mL) and 4.0 M HCl in dioxane was added. The reaction was stirred at rt 2 h, then concentrated to give the crude amine hydrochloride, which was taken on to the next step without purification.

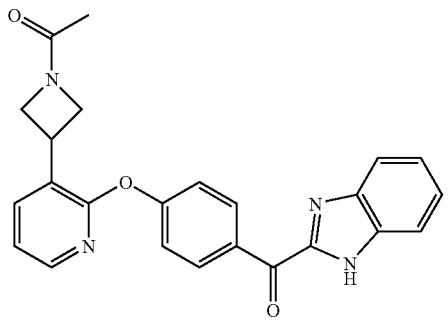

STEP 3. 1-(3-(2-(4-(1H-BENZO[D]IMIDAZOLE-2-CARBONYL)PHENOXY)PYRIDIN-3-YL)AZETIDIN-1-YL)ETHANONE

To a solution of (4-(3-(azetidin-3-yl)pyridin-2-yloxy)phenyl)(1H-benzo[d]imidazol-2-yl)methanone (279 mg, 0.753 mmol) in DMF (1.0 mL) is added triethylamine (0.386 mL, 3.01 mmol) and 1-(1H-imidazol-1-yl)ethanone (100 mg, 0.904 mmol). A solid crashed out, so THF (2 mL) was added to give a homogeneous solution and the reaction was stirred at rt 2 h. The reaction mixture was quenched with saturated $NaHCO_3$ and extracted with $CH_2Cl_2$ (3×5 mL). The combined organic layers were dried ($MgSO_4$) and concentrated, then purified by RPHPLC to give 1-(3-(2-(4-(1H-benzo[d]imidazole-2-carbonyl)phenoxy)pyridin-3-yl)azetidin-1-yl)ethanone (35 mg, 0.085 mmol, 11.27% yield over 2 steps) as a white solid. MS (ESI, pos. ion) m/z: 413.0 (M+1). IC50 (uM) +++++.

SCHEME 46

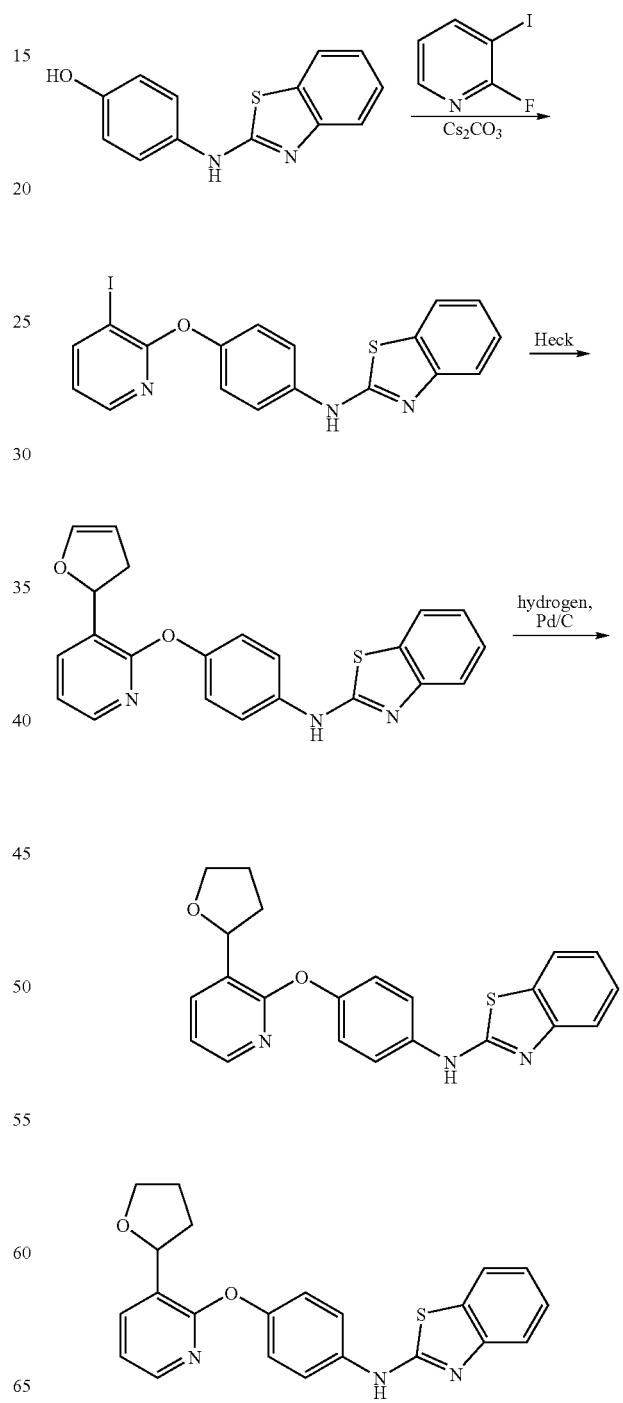

Example 222

N-(4-(3-(TETRAHYDROFURAN-2-YL)PYRIDIN-2-YLOXY)PHENYL)BENZO[D]THIAZOL-2-AMINE

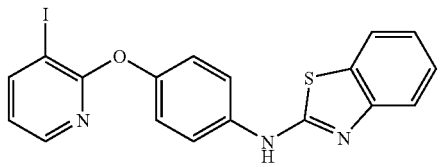

STEP 1. N-(4-(3-IODOPYRIDIN-2-YLOXY)PHENYL)BENZO[D]THIAZOL-2-AMINE

A mixture of 2-fluoro-3-iodopyridine (4.93 g, 22.11 mmol), 4-(benzo[d]thiazol-2-ylamino)phenol (6.16 g, 25.4 mmol), and cesium carbonate (10.81 g, 33.2 mmol) in DMSO (50 mL) was heated at 80° C. overnight. The reaction was cooled to rt and poured into water (200 mL). The solution was extracted with EtOAc (3×) and the combined organic layers were washed with brine, evaporated onto silica gel and purified by flash chromatography (Isco (240 gram)) eluting with EtOAc:hexanes (0:1→1:1) to give a white crystalline solid. MS (ESI, pos. ion) m/z: 445.8 (M+1).

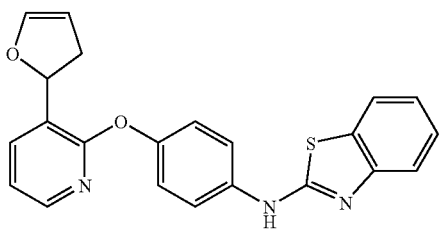

STEP 2. N-(4-(3-(2,3-DIHYDROFURAN-2-YL)PYRIDIN-2-YLOXY)PHENYL)BENZO[D]THIAZOL-2-AMINE

A mixture of N-(4-(3-iodopyridin-2-yloxy)phenyl)benzo[d]thiazol-2-amine (0.403 g, 0.905 mmol), N-methyldicyclohexylamine (0.400 mL, 1.886 mmol, Aldrich), bis(tri-tert-butylphosphine)palladium (0) (0.045 g, 0.088 mmol, Strem) and 2,5-dihydrofuran (0.500 mL, 6.78 mmol, Aldrich) in 5 mL of dioxane was capped under an atmosphere of argon and stirred at rt for 3 h and then heated at 45° C. overnight. The reaction mixture was diluted with MeOH, evaporated onto silica gel and purified by flash chromatography (Isco, (40 gram)) eluting with 2M $NH_3$ in MeOH:$CH_2Cl_2$ (0:1→3:97) to give a white amorphous solid. MS (ESI, pos. ion) m/z: 386.0 (M+1).

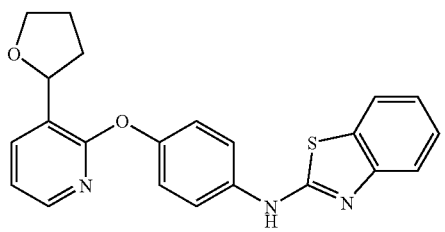

STEP 3. N-(4-(3-(TETRAHYDROFURAN-2-YL)PYRIDIN-2-YLOXY)PHENYL)BENZO[D]THIAZOL-2-AMINE

A mixture of N-(4-(3-(2,3-dihydrofuran-3-yl)pyridin-2-yloxy)phenyl)benzo[d]thiazol-2-amine (0.258 g, 0.666 mmol) and 10% palladium on carbon (0.060 g, 0.564 mmol) in EtOH (5 mL) was evacuated and purged with hydrogen. After 6 h the reaction was diluted with MeOH, evaporated onto silica gel and purified by flash chromatography (Isco (40 gram)) eluting with EtOAc:hexanes (0:1→1:1) to give a white crystalline solid. MS (ESI, pos. ion) m/z: 390.0 (M+1). IC50 (uM) +++++.

SCHEME 47

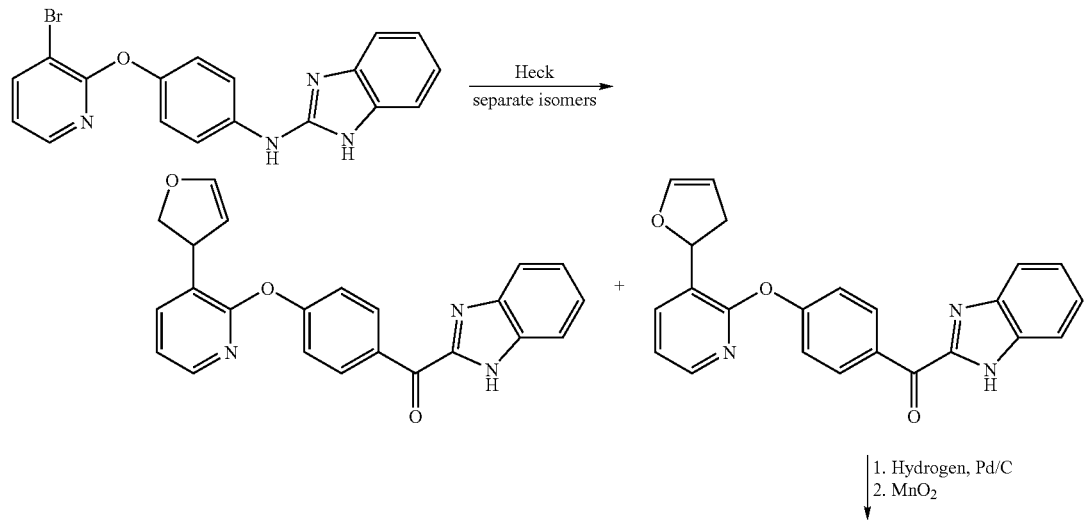

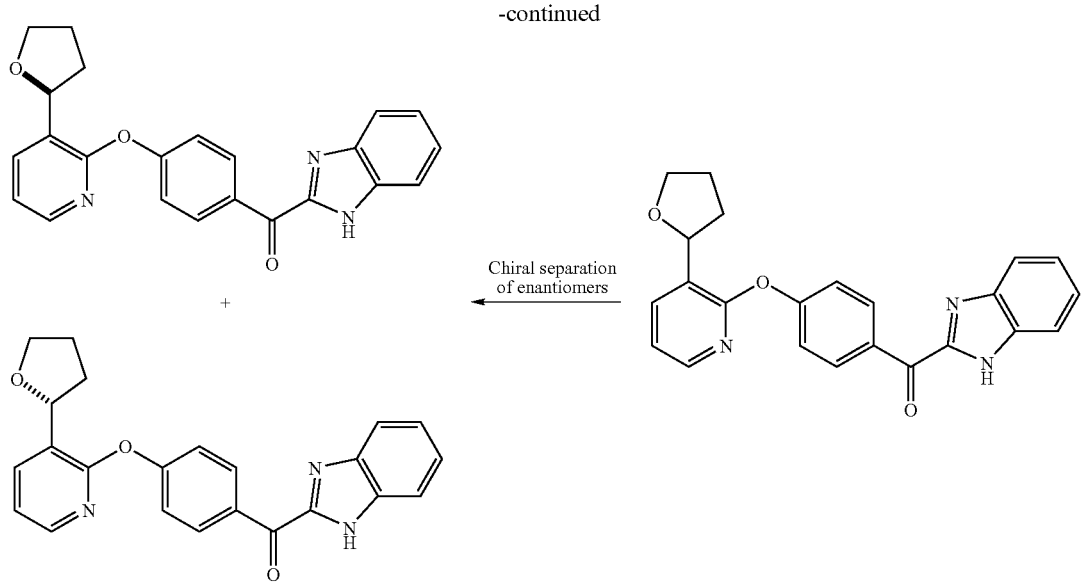

Example 223
(R)-(1H-BENZO[D]IMIDAZOL-2-YL)(4-(3-(TETRAHYDROFURAN-2-YL)PYRIDIN-2-YLOXY)PHENYL)METHANONE AND (S)-(1H-BENZO[D]IMIDAZOL-2-YL)(4-(3-(TETRAHYDROFURAN-2-YL)PYRIDIN-2-YLOXY)PHENYL)METHANONE

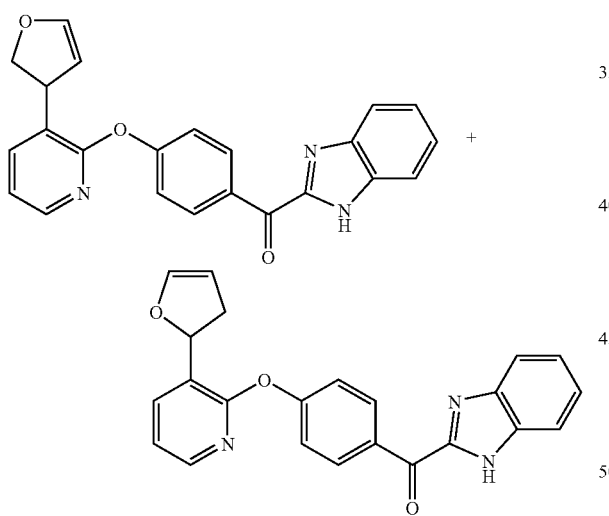

STEP 1. (1H-BENZO[D]IMIDAZOL-2-YL)(4-(3-(2,3-DIHYDROFURAN-3-YL)PYRIDIN-2-YLOXY)PHENYL)METHANONE AND (1H-BENZO[D]IMIDAZOL-2-YL)(4-(3-(2,3-DIHYDROFURAN-2-YL)PYRIDIN-2-YLOXY)PHENYL)METHANONE

A mixture of (1H-benzo[d]imidazol-2-yl)(4-(3-bromopyridin-2-yloxy)phenyl)methanone (1.522 g, 3.86 mmol), 2,5-dihydrofuran (1.400 mL, 18.98 mmol, Aldrich), N-cyclohexyl-N-methylcyclohexanamine (1.600 mL, 7.54 mmol, Aldrich) and bis(tri-tert-butylphosphine)palladium (0) (0.194 g, 0.380 mmol, Strem) in dioxane (10 mL) was sealed in a microwave vessel under an atmosphere of argon and heated thermally at 80° C. for 6 h. The reaction was diluted with EtOAc and the mixture was extracted with water (1×) and brine (1×). The organic mixture was evaporated onto silica gel and purified by flash chromatography (Isco (120 gram)) eluting with EtOAc:hexanes (0:1→1:2) to give 650 mg of (1H-benzo[d]imidazol-2-yl)(4-(3-(2,3-dihydrofuran-2-yl)pyridin-2-yloxy)phenyl)methanone and 325 mg of (1H-benzo[d]imidazol-2-yl)(4-(3-(2,3-dihydro furan-3-yl)pyridin-2-yloxy)phenyl)methanone.

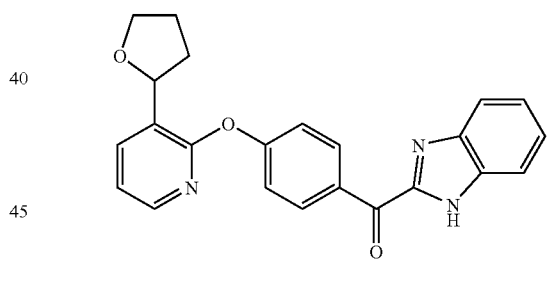

STEP 2. (1H-BENZO[D]IMIDAZOL-2-YL)(4-(3-(TETRAHYDROFURAN-2-YL)PYRIDIN-2-YLOXY)PHENYL)METHANONE

A mixture of (1H-benzo[d]imidazol-2-yl)(4-(3-(2,3-dihydrofuran-2-yl)pyridin-2-yloxy)phenyl)methanone (0.650 g, 1.695 mmol) and palladium hydroxide, 20 wt % pd (dry basis) on carbon, wet, degussa type e101 new (0.210 g, 0.299 mmol, Aldrich) in dioxane (10 mL) was evacuated/purged with hydrogen (1 atm, 3×) at rt for 6 h. The reaction was filtered and the filtrate was concentrated to dryness. The material was taken onto the next step without further purification.

A mixture of (1H-benzo[d]imidazol-2-yl)(4-(3-(tetrahydrofuran-2-yl)pyridin-2-yloxy)phenyl)methanol (0.659 g, 1.7 mmol) and (1H-benzo[d]imidazol-2-yl)(4-(3-(tetrahydrofuran-2-yl)pyridin-2-yloxy)phenyl)methanone (0.655 g, 1.700 mmol) and manganese(IV) oxide activated (1.37 g, 15.76 mmol, Strem) in CHCl₃ (50 mL) was heated under argon at 50° C. for 1 h. The reaction was cooled to rt, filtered through Celite and concentrated in vacuo to give the desired product. MS (ESI, pos. ion) m/z: 386.0 (M+1). IC50 (uM) +++++.

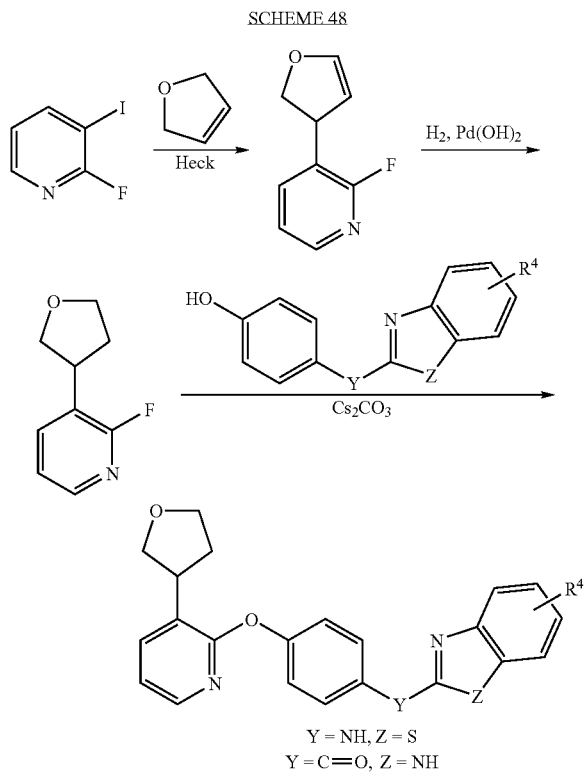

Example 224

N-(4-(3-(TETRAHYDROFURAN-3-YL)PYRIDIN-2-YLOXY)PHENYL)BENZO[D]THIAZOL-2-AMINE

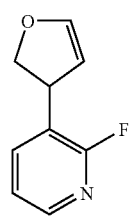

STEP 1. 3-(2,3-DIHYDROFURAN-3-YL)-2-FLUOROPYRIDINE

To a 500 mL round bottomed flask charged with 2-fluoro-3-iodopyridine (15.05 g, 67.5 mmol, Asymchem), tetrabutylammonium chloride (18.80 g, 67.6 mmol, Alfa Aesar), potassium carbonate (28.60 g, 207 mmol, Aldrich) and palladium (ii) acetate (1.48 g, 6.59 mmol, Strem) was added DMF (75 mL) followed by 2,5-dihydrofuran (50.00 mL, 678 mmol, Aldrich) and the reaction mixture was stirred vigorously at 25° C. for 2 h. The mixture was poured into 500 mL of water and the mixture was extracted with EtOAc (3×). The combined organic layers were evaporated onto silica gel and purified by flash chromatography (Isco (330 gram)) eluting with EtOAc:hexanes (0:1→1:2) to give a clear colorless oil. MS (ESI, pos. ion) m/z: 166.1 (M+1).

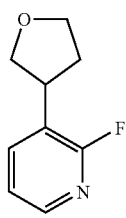

STEP 2. 2-FLUORO-3-(TETRAHYDROFURAN-3-YL)PYRIDINE

A mixture of 3-(2,3-dihydrofuran-3-yl)-2-fluoropyridine (5.26 g, 31.8 mmol) and palladium hydroxide, 20 wt % pd (dry basis) on carbon, wet (2.500 g, 3.56 mmol) in THF (50 mL) was evacuated/purged with hydrogen (3×). The mixture was stirred vigorously under hydrogen (1 atm) at rt overnight. The mixture was filtered through a pad of Celite and the filtrate was concentrated to dryness to give a clear colorless oil. MS (ESI, pos. ion) m/z: 168.1 (M+1).

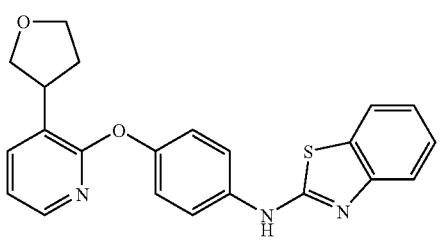

STEP 3. N-(4-(3-(TETRAHYDROFURAN-3-YL)PYRIDIN-2-YLOXY)PHENYL)BENZO[D]THIAZOL-2-AMINE

A glass microwave reaction vessel was charged with 2-fluoro-3-(tetrahydrofuran-3-yl)pyridine (1.00 g, 5.98 mmol), 4-(benzo[d]thiazol-2-ylamino)phenol (1.56 g, 6.44 mmol) and cesium carbonate (4.88 g, 14.98 mmol) in DMSO (10 mL). The reaction mixture was sealed under argon and was heated thermally at 100° C. for 24 h. The reaction was cooled to rt and diluted with water. The product turned into a gum and the aqueous solution was decanted. The gum was stirred over MeOH for 1 h resulting in a precipitate that was filtered, washed with MeOH and dried in vacuo to give the title compound as a white crystalline solid. MS (ESI, pos. ion) m/z: 389.9 (M+1). IC50 (uM) +++++.

SCHEME 49

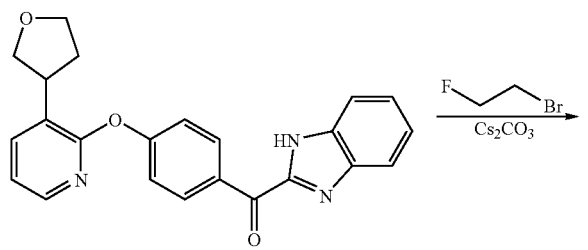

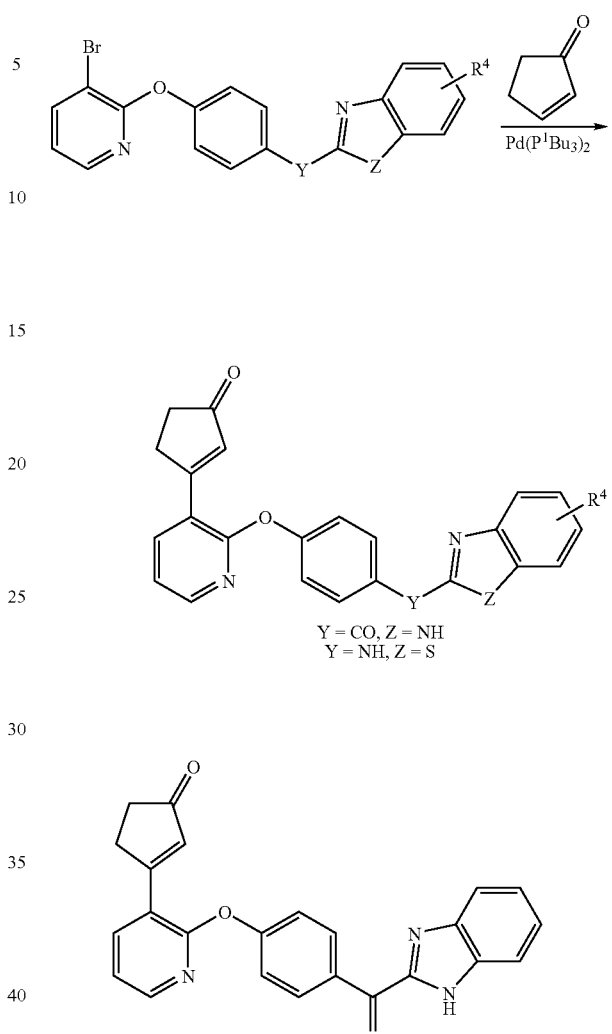

Example 225

(1-(2-FLUOROETHYL)-1H-BENZO[D]IMIDA-ZOL-2-YL)(4-(3-(TETRAHYDROFURAN-3-YL)PYRIDIN-2-YLOXY)PHENYL)METHANONE

To a slurry of cesium carbonate (0.441 g, 1.354 mmol) and (1H-benzo[d]imidazol-2-yl)(4-(3-(tetrahydrofuran-3-yl)pyridin-2-yloxy)phenyl)methanone (0.350 g, 0.908 mmol) in DMF (5 mL) was added 1-bromo-2-fluoroethane (0.090 mL, 1.21 mmol) at rt. After 1.5 h the mixture was partitioned between DCM/water. The aqueous layer was extracted with DCM (3×) and the combined organic layers were washed with water and dried over $Na_2SO_4$. The solution was filtered and concentrated in vacuo. The residue was dissolved in DMSO/MeOH and purified by reverse-phase HPLC (Gilson; Gemini-NX 10 μm C18 110 A AXIA, 100×50 mm column) eluting with 0.1% TFA-$H_2O$:0.1% TFA $CH_3CN$ (9:1→1:9). The fractions containing the desired product were combined and concentrated in vacuo. The residue was dissolved in MeOH and loaded onto an SCX II cartridge eluting with MeOH then 2M $NH_3$ in MeOH to give an off-white crystalline solid. MS (ESI, pos. ion) m/z: 432.0 (M+1). IC50 (uM) +++++.

SCHEME 50

Example 226

3-(2-(4-(1H-BENZO[D]IMIDAZOLE-2-CARBO-NYL)PHENOXY)PYRIDIN-3-YL)CYCLOPENT-2-ENONE

A suspension of (1H-benzo[d]imidazol-2-yl)(4-(3-bromopyridin-2-yloxy)phenyl)methanone (500 mg, 1.268 mmol), 2-cyclopenten-1-one (0.410 mL, 5.07 mmol), 105° C. and bis(tri-tert-butylphosphine)palladium (0) (64.8 mg, 0.127 mmol) in Dioxane (4 mL) was capped, degassed and backfilled with argon. The reaction was heated at 105° C. After 6 h, the reaction was cooled to 23° C., concentrated in vacuo and purified by silica gel chromatography (eluant: 40-100% EtOAc/hexane), affording the product as a yellow solid. MS (ESI, pos. ion) m/z: 396.1 (M+1). IC50 (uM) +++++.

SCHEME 51

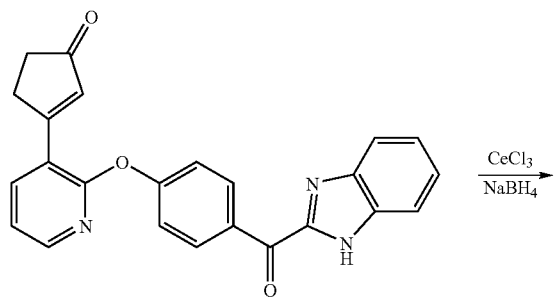

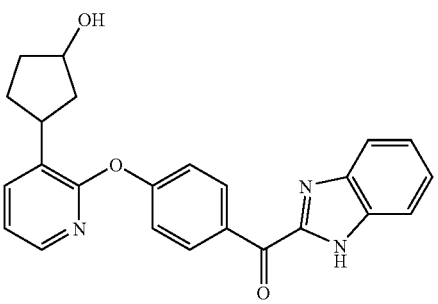

Example 227

(1H-BENZO[D]IMIDAZOL-2-YL)(4-(3-(3-HY-DROXYCYCLOPENTYL)PYRIDIN-2-YLOXY)PHENYL)METHANONE

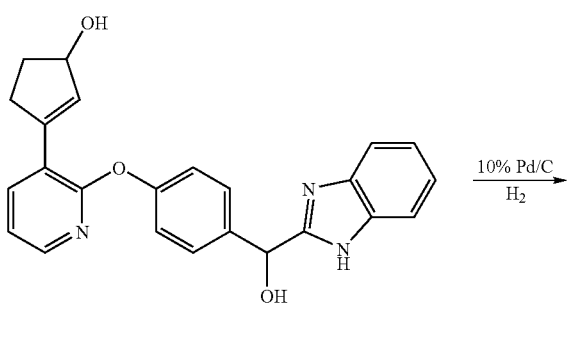

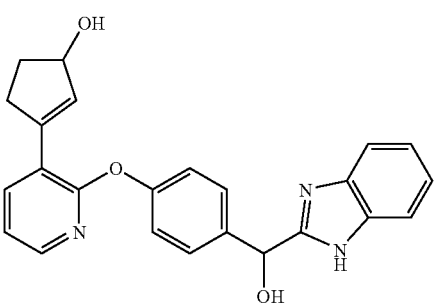

STEP 1. 3-(2-(4-((1H-BENZO[D]IMIDAZOL-2-YL)(HYDROXY)METHYL)PHENOXY)PYRIDIN-3-YL)CYCLOPENT-2-ENOL

A suspension of 3-(2-(4-(1H-benzo[d]imidazole-2-carbonyl)phenoxy)pyridin-3-yl)cyclopent-2-enone (2125 mg, 5.37 mmol) and cerium (iii) chloride (1325 mg, 5.37 mmol) in tetrahydrofuran (300 mL) and methanol (30.0 mL) was cooled to 0° C. under nitrogen. Sodium borohydrate (813 mg, 21.50 mmol) was added in 4 lots over 20 min. The reaction was warmed to 23° C. over 2 h. After a total reaction time of 4 h, the reaction was quenched with saturated ammonium chloride solution (10 ml, slowly—effervescence). The solution was diluted with EtOAc (500 mL) and washed with saturated ammonium chloride solution (100 mL) and brine (100 mL), dried over MgSO₄, concentrated in vacuo and purified by silica gel chromatography (eluant: 1-8% methanol/dichloromethane), affording the product as a yellow film.

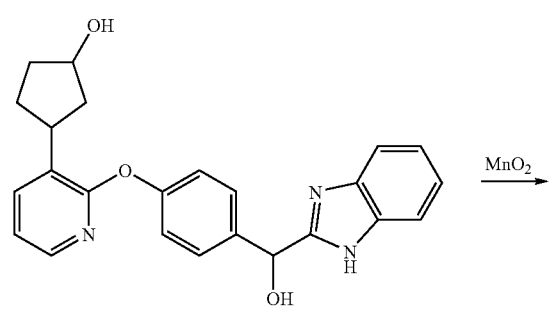

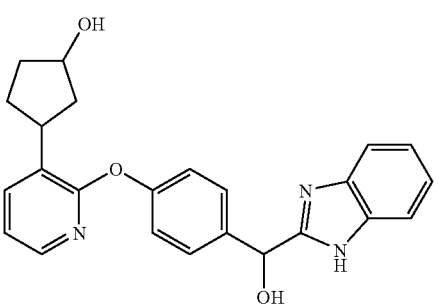

STEP 2. 3-(2-(4-((1H-BENZO[D]IMIDAZOL-2-YL)(HYDROXY)METHYL)PHENOXY)PYRIDIN-3-YL)CYCLOPENTANOL

A solution of 3-(2-(4-((1H-benzo[d]imidazol-2-yl)(hydroxy)methyl)phenoxy)pyridin-3-yl)cyclopent-2-enol (780 mg, 1.953 mmol) in Tetrahydrofuran (50 mL) was treated with palladium, 10% wt. on activated carbon (208 mg, 0.195 mmol) under nitrogen. The reaction flask was equipped with a hydrogen balloon and cycled through vacuum-hydrogen cycles (3×). The reaction was heated to 40° C. under hydrogen. After 5 h, the reaction was cooled to 23° C., and filtered through celite. The filter cake was washed with tetrahydrofuran (200 mL), the filtrates combined and concentrated, affording the product as a white solid. MS (ESI, pos. ion) m/z: 402.1 (M+1).

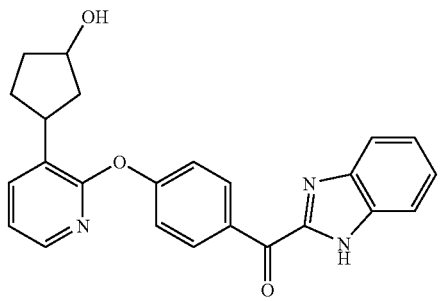

STEP 3. (1H-BENZO[D]IMIDAZOL-2-YL)(4-(3-(3-HYDROXYCYCLOPENTYL)PYRIDIN-2-YLOXY)PHENYL)METHANONE

A solution of 3-(2-(4-((1H-benzo[d]imidazol-2-yl)(hydroxy)methyl)phenoxy)pyridin-3-yl)cyclopentanol (780 mg, 1.943 mmol) in tetrahydrofuran (20 mL) and dichloromethane (50 mL) was treated with manganese dioxide (1351 mg, 15.54 mmol). The reaction was stirred at 23° C. under nitrogen. After 3 h, the reaction was filtered through celite, the filter cake washed with tetrahydrofuran (200 mL), the filtrates combined, concentrated in vacuo and purified by silica gel chromatography (eluant: 1-5% methanol/dichloromethane), affording the product as a white solid. MS (ESI, pos. ion) m/z: 400.1 (M+1). IC50 (uM) +++++.

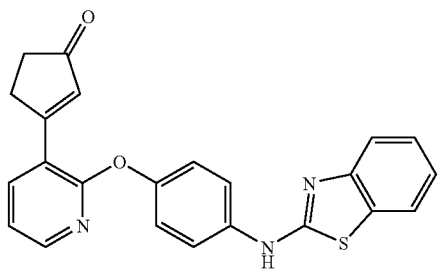

Example 228

3-(2-(4-(BENZO[D]THIAZOL-2-YLAMINO)PHENOXY)PYRIDIN-3-YL)CYCLOPENT-2-ENONE

A solution of N-(4-(3-bromopyridin-2-yloxy)phenyl)benzo[d]thiazol-2-amine (600 mg, 1.506 mmol), 2-cyclopenten-1-one (0.609 mL, 7.53 mmol), n-methyldicyclohexylamine (0.959 mL, 4.52 mmol) and bis(tri-tert-butylphosphine)palladium (0) (77 mg, 0.151 mmol) in Dioxane (4 mL) was capped, degassed and backfilled with argon. The reaction was heated to 90° C. After 6 h, the reaction was heated to 110° C. After 36 h, the reaction was cooled to 23° C., diluted with EtOAc (150 mL) and washed with water (100 mL) and brine (100 mL), dried over MgSO$_4$, concentrated in vacuo and purified by silica gel chromatography (eluant: 0.5-3% methanol/dichloromethane), affording the product as a yellow solid. MS (ESI, pos. ion) m/z: 400.1 (M+1).

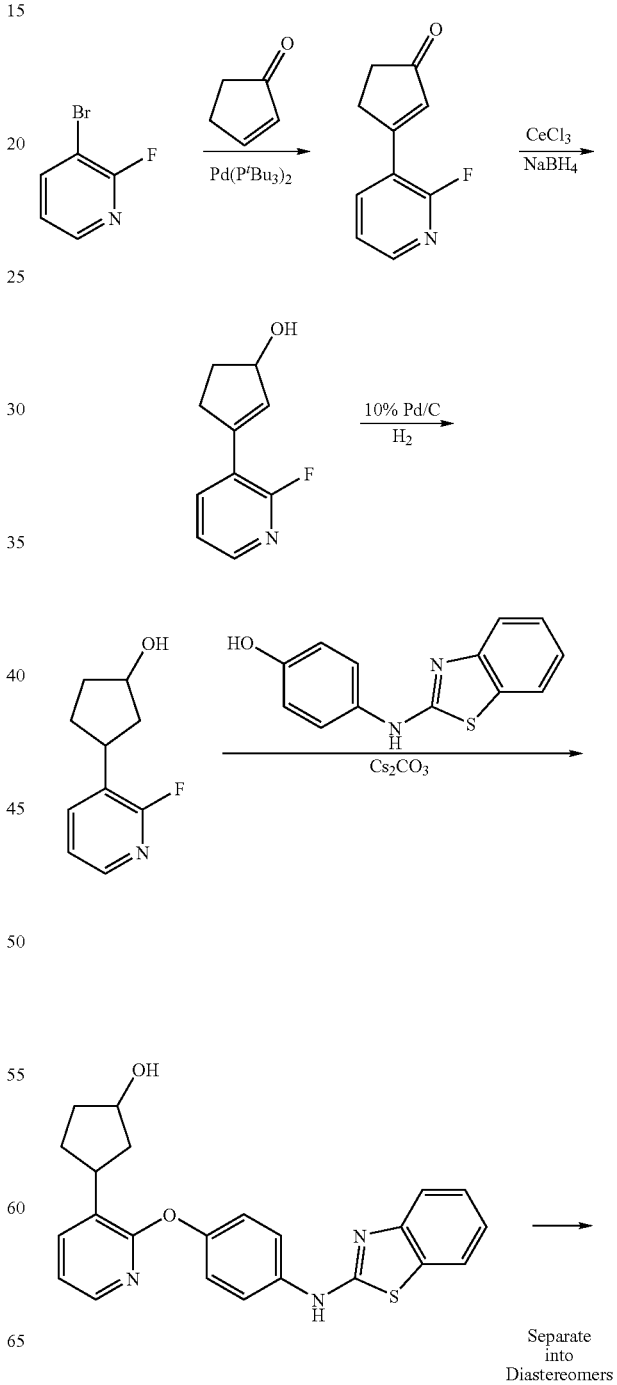

SCHEME 52

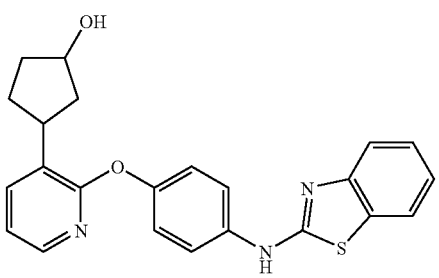

Example 229

3-(2-(4-(BENZO[D]THIAZOL-2-YLAMINO)PHENOXY)PYRIDIN-3-YL)CYCLOPENTANOL

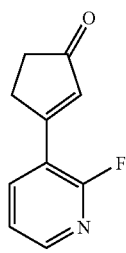

STEP 1.
3-(2-FLUOROPYRIDIN-3-YL)CYCLOPENT-2-ENONE

A solution of 3-bromo-2-fluoropyridine (4 g, 22.73 mmol), 2-cyclopenten-1-one (7.35 mL, 91 mmol), n-methyldicyclohexylamine (12.05 mL, 56.8 mmol) and bis(tri-tert-butylphosphine)palladium (0) (0.581 g, 1.136 mmol) in 1,4-dioxane (50 mL) was heated to 105° C. in a capped vessel. After 21 h, the reaction was cooled to 23° C., diluted with EtOAc (400 mL) and washed with water (150 mL) and brine (150 mL), dried over MgSO$_4$, concentrated in vacuo and purified by silica gel chromatography (eluant: 15-50% EtOAc/hexane), affording the product as a yellow solid. MS (ESI, pos. ion) m/z: 178.0 (M+1).

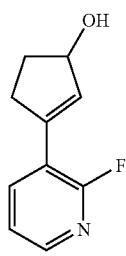

STEP 2.
3-(2-FLUOROPYRIDIN-3-YL)CYCLOPENT-2-ENOL

A solution of 3-(2-fluoropyridin-3-yl)cyclopent-2-enone (1582 mg, 8.93 mmol) in Tetrahydrofuran (20 mL) and Methanol (20 mL) was cooled to 0° C. under nitrogen. Cerium (III) chloride (2201 mg, 8.93 mmol) was added, followed by sodium borohydrate (676 mg, 17.86 mmol) in 4 lots, over 15 min. After 30 min, the reaction was quenched with saturated ammonium chloride solution (20 mL—effervescence!), and partitioned between dichloromethane (100 mL) and saturated ammonium chloride solution (30 mL). The organic layer was separated, and the aqueous layer was extracted with dichloromethane (50 mL). The organic layers were combined, dried over MgSO$_4$, and concentrated, affording the product as a yellow oil. MS (ESI, pos. ion) m/z: 180.1 (M+1).

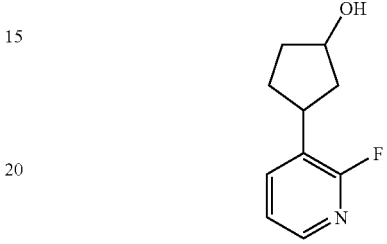

STEP 3.
3-(2-FLUOROPYRIDIN-3-YL)CYCLOPENTANOL

A solution of 3-(2-fluoropyridin-3-yl)cyclopent-2-enol (1184 mg, 6.61 mmol) in tetrahydrofuran (40 mL) was treated with palladium, 10% wt. on activated carbon (703 mg, 0.661 mmol). The reaction mixture was evacuated under vacuum and backfilled with hydrogen (3×), and stirred under hydrogen at 23° C. After 4 h, the reaction was filtered through celite, the filter cake washed with 1:1 methanol:dichloromethane (50 mL), the filtrates combined and concentrated, affording the product as a yellow oil. MS (ESI, pos. ion) m/z: 182.0 (M+1).

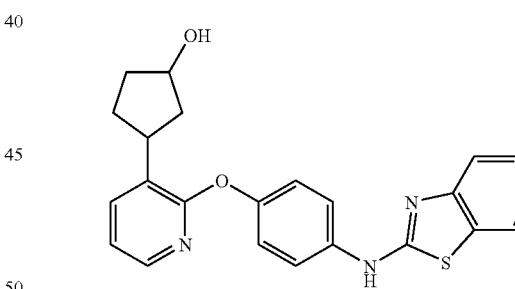

STEP 4. 3-(2-(4-(BENZO[D]THIAZOL-2-YLAMINO)PHENOXY)PYRIDIN-3-YL)CYCLOPENTANOL

A suspension of 3-(2-fluoropyridin-3-yl)cyclopentanol (869 mg, 4.80 mmol), 4-(benzo[d]thiazol-2-ylamino)phenol (2324 mg, 9.59 mmol) and cesium carbonate (3281 mg, 10.07 mmol) in N-methyl-2-pyrrolidinone (8 mL) was heated to 130° C. under nitrogen. After 9 h, the reaction was cooled to 23° C., diluted with EtOAc (500 mL) and washed with 1N NaOH solution (6×150 mL) and brine (150 mL), dried over MgSO$_4$, concentrated in vacuo and purified by silica gel chromatography (eluant: 1-4% methanol/dichloromethane), affording the product as a tan solid. MS (ESI, pos. ion) m/z: 404.1 (M+1). IC50 (uM) +++++.

SCHEME 53

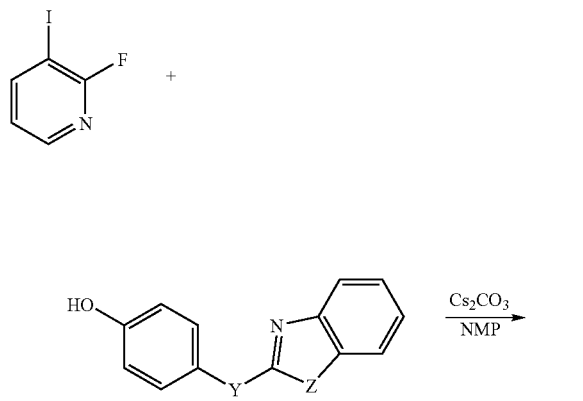

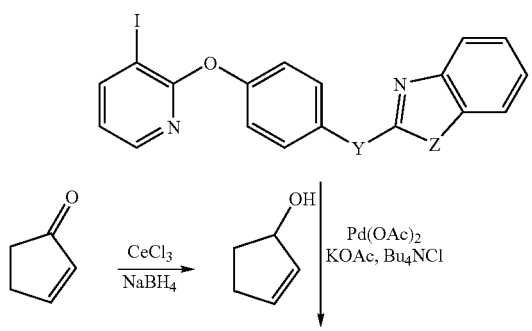

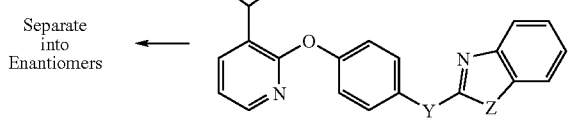

Separate into Enantiomers ←

Y = CO, Z = NH
Y = NH, Z = S

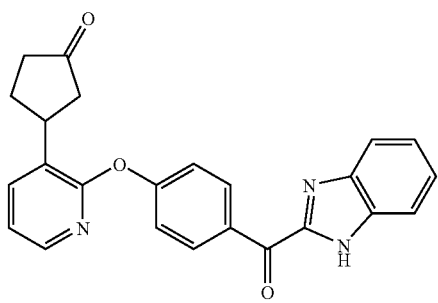

Example 230

3-(2-(4-(1H-BENZO[D]IMIDAZOLE-2-CARBO-NYL)PHENOXY)PYRIDIN-3-YL)CYCLOPEN-TANONE

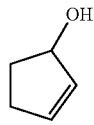

STEP 1. (1H-BENZO[D]IMIDAZOL-2-YL)(4-(3-IODOPYRIDIN-2-YLOXY)PHENYL)METHA-NONE

A solution of 2-fluoro-3-iodopyridine (3.052 g, 13.69 mmol), (1H-benzo[d]imidazol-2-yl)(4-hydroxyphenyl)methanone (4.89 g, 20.53 mmol) and cesium carbonate (7.58 g, 23.27 mmol) in N-Methyl-2-pyrrolidinone (20 mL) was degassed and heated to 115° C. After 64 h, the reaction was cooled to 23° C., diluted with EtOAc (250 mL) and washed with water (100 mL) and brine (75 mL), dried over MgSO$_4$, concentrated in vacuo and purified by silica gel chromatography (eluant: 0.5-1.5% methanol/dichloromethane), affording the product as a yellow solid. MS (ESI, pos. ion) m/z: 404.1 (M+1).

STEP 2. CYCLOPENT-2-ENOL

To a round bottom flask was added 2-cyclopenten-1-one (18.73 mL, 224 mmol), Methanol (559 mL), and cerium(iii) chloride heptahydrate (83 g, 224 mmol) with stirring at 0° C. before adding sodium borohydrate (15.75 mL, 447 mmol) portionwise over 2 h. Each addition of the hydride gave a large exotherm. Upon complete addition, off-white suspension was allowed to stir at room temperature for 16 h before removing the solvent under reduced pressure, yielding a light purple solid. The crude solid was solubilized with ethyl acetate and washed with a saturated solution of NH$_4$OH in water. The combined organics were dried over sodium sulfate and concentrated to a clear oil. The oil was diluted with water and extracted with ethyl acetate (3×40 mL), dried over sodium sulfate, filtered, and concentrated under high vacuum, affording cyclopent-2-enol as a clear oil.

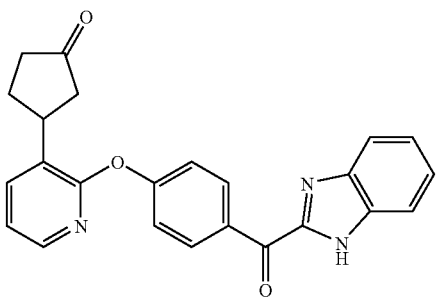

STEP 3. 3-(2-(4-(1H-BENZO[D]IMIDAZOLE-2-CARBONYL)PHENOXY)PYRIDIN-3-YL)CYCLOPENTANONE

A suspension of (1H-benzo[d]imidazol-2-yl)(4-(3-iodopyridin-2-yloxy)phenyl)methanone (4.138 g, 9.38 mmol), cyclopent-2-enol (3.16 g, 37.5 mmol), tetrabutylammonium chloride (2.87 g, 10.32 mmol), potassium acetate (1.841 g, 18.76 mmol) and palladium (II) acetate (0.211 g, 0.938 mmol) in acetonitrile (30 mL) (argon bubbled through for 30 min) and water (3.00 mL) in a round bottom flask was capped with a septum, degassed, backfilled with argon and heated to 85° C. After 23 h, the reaction was cooled to 23° C., diluted with dichloromethane (200 mL) and washed with brine (2×150 mL), dried over MgSO$_4$, concentrated in vacuo and purified by silica gel chromatography (eluant: 35-50% EtOAc/hexane), affording the product as an off-white solid. MS (ESI, pos. ion) m/z: 398.1 (M+1). IC50 (uM) +++++.

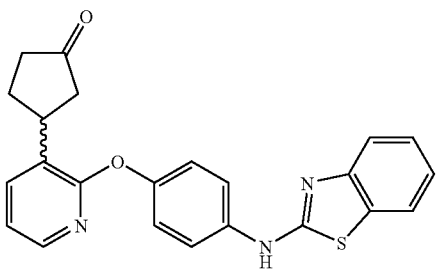

Example 231

3-(2-(4-(BENZO[D]THIAZOL-2-YLAMINO)PHENOXY)PYRIDIN-3-YL)CYCLOPENTANONE

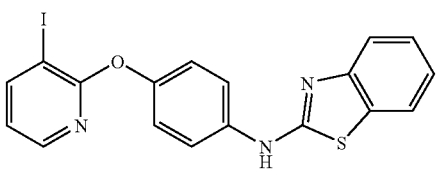

STEP 1. N-(4-(3-IODOPYRIDIN-2-YLOXY)PHENYL)BENZO[D]THIAZOL-2-AMINE

A suspension of 2-fluoro-3-iodopyridine (1.674 g, 7.51 mmol), 4-(benzo[d]thiazol-2-ylamino)phenol (2.73 g, 11.26 mmol) and cesium carbonate (4.16 g, 12.76 mmol) in N-methyl-2-pyrrolidinone (10 mL) was degassed and heated to 120° C. After 3 h 30 min, the reaction was cooled to 23° C., diluted with EtOAc (200 mL) and washed with water (100 mL) and brine (100 mL), dried over MgSO$_4$, concentrated in vacuo and purified by silica gel chromatography (eluant: 0-1% methanol/dichloromethane), affording the product as an off-white solid. MS (ESI, pos. ion) m/z: 445.9 (M+1).

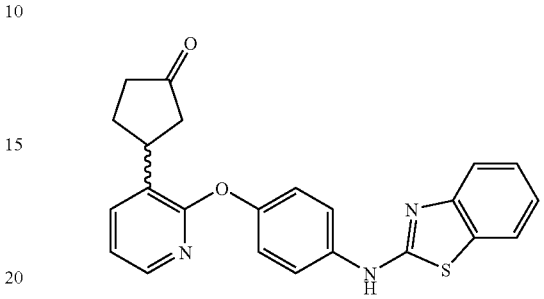

STEP 2. 3-(2-(4-(BENZO[D]THIAZOL-2-YLAMINO)PHENOXY)PYRIDIN-3-YL)CYCLOPENTANONE

A suspension of N-(4-(3-iodopyridin-2-yloxy)phenyl)benzo[d]thiazol-2-amine (493 mg, 1.107 mmol), cyclopent-2-enol (373 mg, 4.43 mmol), potassium acetate (217 mg, 2.214 mmol), tetrabutylammonium chloride (338 mg, 1.218 mmol) and Palladium (II) acetate (24.86 mg, 0.111 mmol) in acetonitrile (3 mL) and water (0.300 mL) was degassed and backfilled with argon. The reaction was heated to 90° C. for 18 h. Palladium (II) acetate (24.86 mg, 0.111 mmol) was added, and the reaction was capped, degassed and filled with argon, and heated to 135° C. in a microwave for 1 h. The crude reaction mixture was diluted with dichloromethane (75 mL) and washed with brine (75 mL), dried over MgSO$_4$, concentrated in vacuo and purified by silica gel chromatography (eluant: 35-50% EtOAc/hexane), affording a white solid. It was further purified on a prep HPLC system (and free-based by partitioning between dichloromethane and saturated sodium bicarbonate solution), affording the product as a white solid. MS (ESI, pos. ion) m/z: 402.1 (M+1). IC50 (uM) +++++.

SCHEME 54

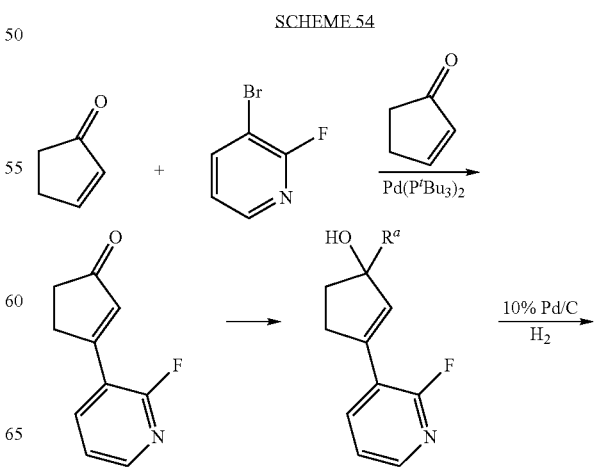

-continued

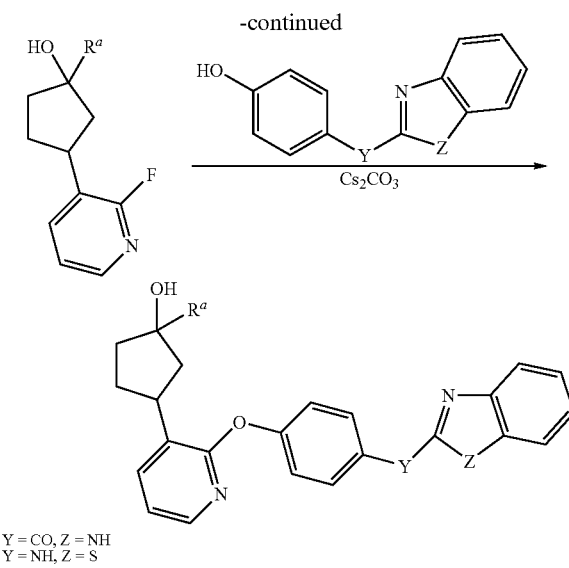

Y = CO, Z = NH
Y = NH, Z = S

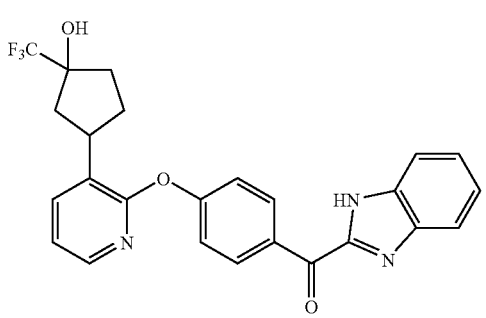

Example 232

(1H-BENZO[D]IMIDAZOL-2-YL)(4-(3-((1S,3S)-3-HYDROXY-3-(TRIFLUOROMETHYL)CYCLOPENTYL)PYRIDIN-2-YLOXY)PHENYL)METHANONE

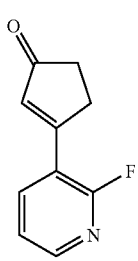

STEP 1:
3-(2-FLUOROPYRIDIN-3-YL)CYCLOPENT-2-ENONE

To a round bottom flask was added bis(tri-t-butyl)phosphine palladium (0.591 g, 1.156 mmol) before sealing and evacuating and backfilling with nitrogen. Subsequently, cyclopent-2-enone (7.48 mL, 93 mmol), N-cyclohexyl-N-methylcyclohexanamine (14.73 mL, 69.4 mmol), and 3-bromo-2-fluoropyridine (4.07 g, 23.13 mmol) were added before adding dioxane (25 mL). The reaction mixture was stirred under nitrogen at 110° C. for 16 h. The reaction mixture was cooled to room temperature and diluted with water and extracted with ethyl acetate before drying over magnesium sulfate, filtering, and concentrating under reduced pressure. The crude compound was purified by column chromatography (ethyl acetate/dichloromethane) to give 3-(2-fluoropyridin-3-yl)cyclopent-2-enone as an orange solid. MS (ESI, pos. ion) m/z: 178.0 (M+1).

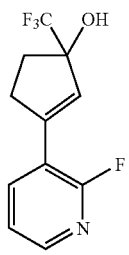

STEP 2. 3-(2-FLUOROPYRIDIN-3-YL)-1-(TRIFLUOROMETHYL)CYCLOPENT-2-ENOL

A solution of 3-(2-fluoropyridin-3-yl)cyclopent-2-enone (1.9 g, 10.72 mmol) in tetrahydrofuran (30 mL) was treated with (trifluoromethyl)trimethylsilane (1.906 g, 13.40 mmol), followed by tetra-n-butylammonium fluoride, 1.0M in THF (0.536 mL, 0.536 mmol). The reaction turned dark, and was stirred under nitrogen at 23° C.

After 2 h, more (trifluoromethyl)trimethylsilane (1.906 g, 13.40 mmol) and tetra-n-butylammonium fluoride, 1.0M in THF (0.536 mL, 0.536 mmol) were added. After a total of 4 h, 10% hydrochloric acid solution (50 ml) was added, and the reaction was stirred for 15 min. The solution was diluted with EtOAc (200 ml) and washed with 10% hydrochloric acid solution (50 ml), water (50 ml) and brine (50 ml), dried over MgSO$_4$, concentrated in vacuo and purified by silica gel chromatography (eluant: 10-45% EtOAc/hexane), affording the product as a yellow oil. MS (ESI, pos. ion) m/z: 248.0 (M+1).

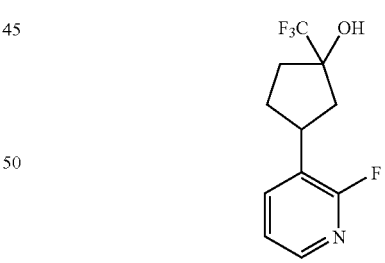

STEP 3. 3-(2-FLUOROPYRIDIN-3-YL)-1-(TRIFLUOROMETHYL)CYCLOPENTANOL

A solution of 3-(2-fluoropyridin-3-yl)-1-(trifluoromethyl)cyclopent-2-enol (940 mg, 3.80 mmol) in tetrahydrofuran (35 mL) was treated with palladium, 10% wt. on activated carbon (202 mg, 0.190 mmol). The reaction mixture was purged through 3 vacuum-hydrogen cycles, and was stirred under hydrogen at 23° C. After 18 h, the reaction was filtered through celite and the filter cake was washed with tetrahydrofuran (50 mL). The combined filtrates were concentrated, affording the product as a yellow oil. MS (ESI, pos. ion) m/z: 250.0 (M+1).

337

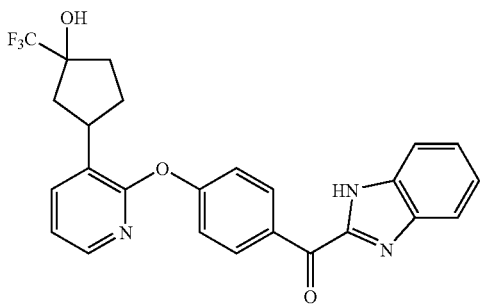

STEP 4. (1H-BENZO[D]IMIDAZOL-2-YL)(4-(3-((1S,3S)-3-HYDROXY-3-(TRIFLUOROMETHYL)CYCLOPENTYL)PYRIDIN-2-YLOXY)PHENYL)METHANONE

To a vial containing cesium carbonate (1634 mg, 5.02 mmol), (1H-benzo[d]imidazol-2-yl)(4-hydroxyphenyl)methanone (717 mg, 3.01 mmol), and 3-(2-fluoropyridin-3-yl)-1-(trifluoromethyl)cyclopentanol (500 mg, 2.006 mmol) was added NMP (13.400 ml). The mixture was heated at 200° C. for 5 h with microwave irradiation. The reaction mixture was diluted with ethyl acetate and washed with 5N NaOH before drying the organic layer over magnesium sulfate, filtering, and concentrating under reduced pressure. The resulting orange oil was purified by column chromatography (ethyl acetate/dichloromethane) to give a pale orange oil. The material was diluted with ethyl acetate and washed with water and 10 N NaOH before separating the mixture by SFC into its components, which consisted of two products identified as enantiomers by NMR. MS (ESI, pos. ion) m/z: 468.2 (M+1). IC50 (uM) +++++.

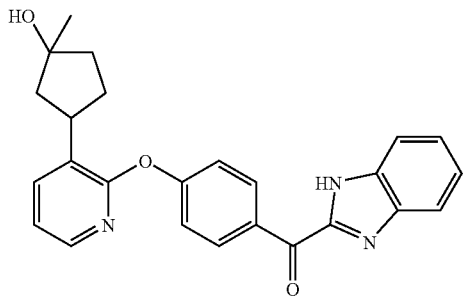

Example 233

(1H-BENZO[D]IMIDAZOL-2-YL)(4-(3-((1S,3R)-3-HYDROXY-3-METHYLCYCLOPENTYL)PYRIDIN-2-YLOXY)PHENYL)METHANONE

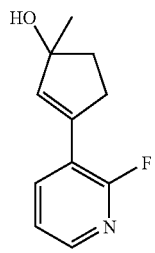

338

STEP 1: 3-(2-FLUOROPYRIDIN-3-YL)-1-METHYLCYCLOPENT-2-ENOL

To a solution of 3-(2-fluoropyridin-3-yl)cyclopent-2-enone (1 g, 5.64 mmol) in THF (28.2 mL) was added methylmagnesium bromide (4.70 mL, 14.11 mmol) dropwise over 5 minutes. The dark brown solution was stirred for 3 h at room temperature before. slowly quenching with aqueous ammonium chloride. The crude reaction was diluted with water and extracted with ethyl acetate, drying over magnesium sulfate, filtering, and concentrating to a dark brown oil under reduced pressure. The crude compound was purified by column chromatography (ethyl acetate/dichloromethane) to afford 3-(2-fluoropyridin-3-yl)-1-methylcyclopent-2-enol as a clear oil. MS (ESI, pos. ion) m/z: 194.1 (M+1).

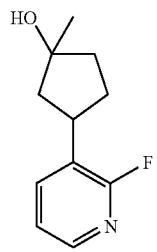

STEP 2: 3-(2-FLUOROPYRIDIN-3-YL)-1-METHYLCYCLOPENTANOL

To a 150 mL round bottom flask was added 3-(2-fluoropyridin-3-yl)-1-methylcyclopent-2-enol (282.8 mg, 1.449 mmol, 78% yield) and ethanol (14.900 ml) before adding palladium on carbon, 10% by weight (150 mg, 1.410 mmol) followed by a tetrahydrofuran (3.73 ml) rinse. The reaction vessel was purged of air and backfilled with hydrogen before stirring at room temperature for 2 h. The reaction mixture was filtered through a pad of Celite with ethyl acetate and concentrated under reduced pressure to a pale yellow oil. MS (ESI, pos. ion) m/z: 196.2 (M+1).

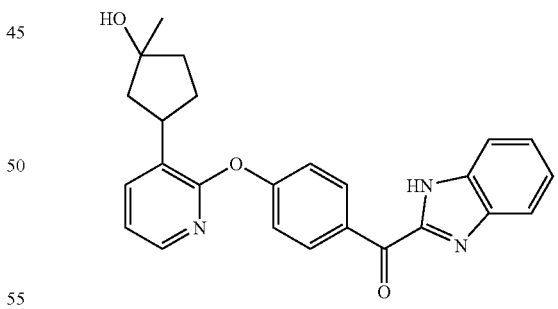

STEP 3: (1H-BENZO[D]IMIDAZOL-2-YL)(4-(3-((1S,3R)-3-HYDROXY-3-METHYLCYCLOPENTYL)PYRIDIN-2-YLOXY)PHENYL)METHANONE

To a vial containing 3-(2-fluoropyridin-3-yl)-1-methylcyclopentanol (570 mg, 2.92 mmol), (1H-benzo[d]imidazol-2-yl)(4-hydroxyphenyl)methanone (1043 mg, 4.38 mmol), and cesium carbonate (2378 mg, 7.30 mmol) was added NMP (5.389 mL) before sealing and purging the vessel of air with nitrogen. The reaction mixture was set to heated at 180° C. for 5 h with microwave irradiation. It was diluted with ethyl acetate and washed with 5 N NaOH. The organic layer was dried over magnesium sulfate, filtered, and concentrated under reduced pressure to a brown oil. The crude mixture of diastereomers was purified by SFC to yield four compounds. MS (ESI, pos. ion) m/z: 414.2 (M+1). IC50 (uM) +++++.

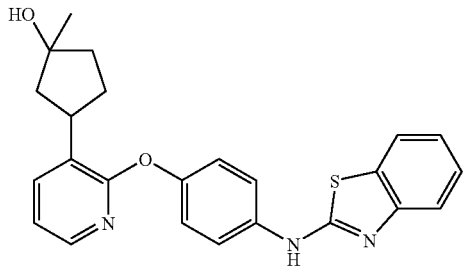

Example 234

3-(2-(4-(BENZO[D]THIAZOL-2-YLAMINO)PHE-NOXY)PYRIDIN-3-YL)-1-METHYLCYCLOPENTANOL

To a 20 mL microwave vial was added cesium carbonate (1460 mg, 4.48 mmol), 4-(benzo[d]thiazol-2-ylamino)phenol (565 mg, 2.331 mmol), and 3-(2-fluoropyridin-3-yl)-1-methylcyclopentanol (350 mg, 1.793 mmol) as a solution in NMP (3585 µL). The reaction mixture was heated to 180° C. for 3 h with microwave irradiation. The reaction was diluted with water and extracted with ethyl acetate before drying over magnesium sulfate, filtering, and concentrating under reduced pressure to a dark brown oil. Three purifications of the diastereomeric mixture by SFC gave four compounds. MS (ESI, pos. ion) m/z: 418.2 (M+1). IC50 (uM) +++++.

SCHEME 55

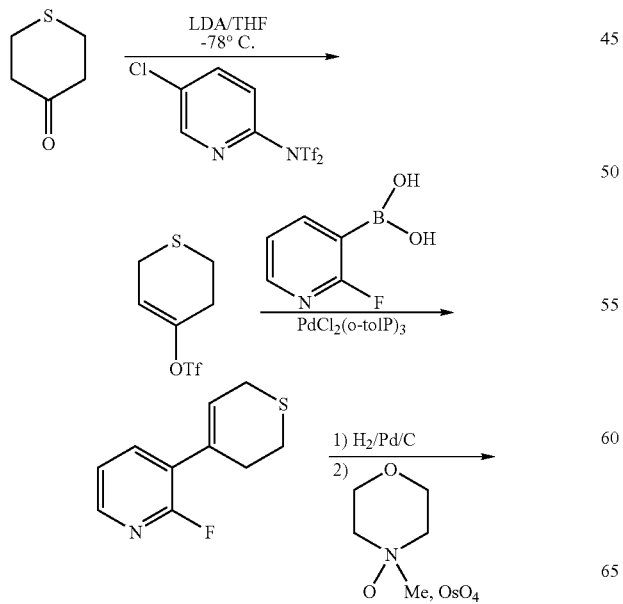

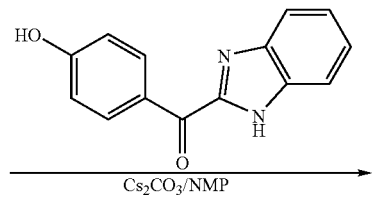

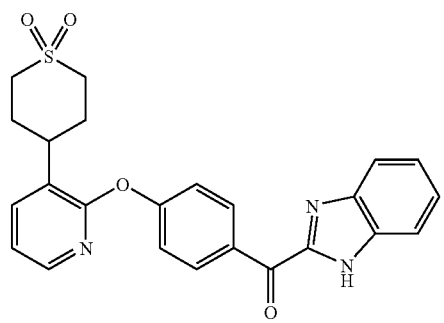

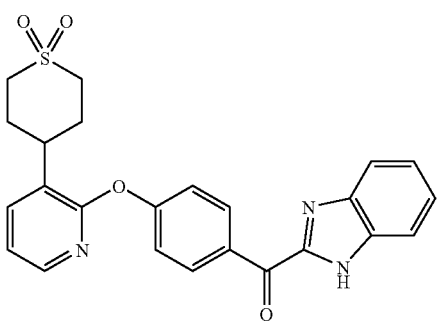

Example 235

1H-BENZIMIDAZOL-2-YL(4-((3-(1,1-DIOXIDOTETRAHYDRO-2H-THIOPYRAN-4-YL)-2-PYRIDINYL)OXY)PHENYL)METHANONE

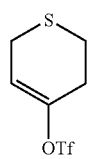

STEP 1: 3,6-DIHYDRO-2H-THIOPYRAN-4-YL-TRIFLUOROMETHANESULFONATE

To a stirred solution of dihydro-2H-thiopyran-4(3H)-one (5.0 g, 43.0 mmol) in THF (30 mL) at −78° C. was added LDA (25.8 mL, 51.6 mmol) dropwise. After stirring for 1 h, a solution of 2-(n,n-bis(trifluoromethylsulfonyl)amino)-5-chloropyridine (17.74 g, 45.2 mmol) in THF (50 mL) was added. The reaction mixture was then warmed to RT and stirred overnight, quenched by saturated NH₄Cl, extracted with ether (3×), dried over MgSO₄, concentrated and purified by ISCO (0-10% EtOAc/Hexanes) to give the yellow oil. MS (M+1): 249.2.

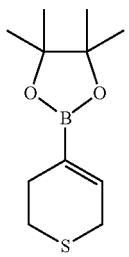

STEP 2: 2-(3,6-DIHYDRO-2H-THIOPYRAN-4-YL)-4,4,5,5-TETRAMETHYL-1,3,2-DIOX-ABOROLANE

A mixture of 3,6-dihydro-2H-thiopyran-4-yl trifluoromethanesulfonate (4.5 g, 18.13 mmol), 4,4,4',4',5,5,5',5'-octamethyl-2,2'-bi(1,3,2-dioxaborolane) (6.90 g, 27.2 mmol), potassium acetate (5.34 g, 54.4 mmol), and PdCl₂(dppf)₂ (1.480 g, 1.813 mmol) in p-dioxane/H₂O (10:1, 22 ml) was heated at 100° C. for 24 h, cooled, diluted with EtOAc, washed with H₂O, dried over MgSO₄, concentrated and purified by ISCO (0-10% EtOAc/Hexanes) to give the yellow oil. MS (M+1): 227.1.

STEP 3: 3-(3,6-DIHYDRO-2H-THIOPYRAN-4-YL)-2-FLUOROPYRIDINE

A mixture of 3,6-dihydro-2H-thiopyran-4-yl trifluoromethanesulfonate (4.0 g, 16.11 mmol), 2-fluoropyridin-3-ylboronic acid (2.498 g, 17.72 mmol), sodium carbonate (5.12 g, 48.3 mmol), and dichlorobis(tri-o-tolylphosphine)palladium(ii) (0.633 g, 0.806 mmol) in p-dioxane/H₂O (10:1, 22 mL) was heated at 135° C. in 30 min. by microwave. The reaction mixture was cooled, diluted with H₂O, extracted with EtOAc (3×), dried over MgSO₄, concentrated and purified by ISCO (0-40% EtOAc/Hexanes) to give the expected product was a light brown oil. MS (M+1): 196.2.

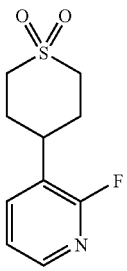

STEP 4: 3-(1,1-DIOXIDOTETRAHYDRO-2H-THIOPYRAN-4-YL)-2-FLUOROPYRIDINE

A solution of 3-(3,6-dihydro-2H-thiopyran-4-yl)-2-fluoropyridine (1.30 g, 6.66 mmol) in EtOH (15 ml) was hydrogenated at RT in palladium on carbon (0.709 g, 0.666 mmol) for 14 h. The solid was filtered and the filtrate was concentrated to give the light yellow oil.

To a stirred mixture of 2-fluoro-3-(tetrahydro-2H-thiopyran-4-yl)pyridine (1.2 g, 6.08 mmol), 4-methylmorpholine 4-oxide (1.781 g, 15.21 mmol) in acetone/water (7:3, 30 mL) was added osmium(VIII) oxide (0.631 mL, 0.304 mmol). Stirring was continued at RT overnight. A saturated solution of sodium hydrogensulfite (10 mL) was added and stirred in 15 min., extracted with EtOAc (3×), dried over MgSO₄, concentrated to give the tan solid. MS (M+1): 230.2.

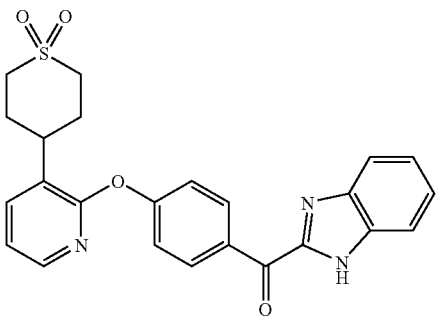

STEP 5: 1H-BENZIMIDAZOL-2-YL(4-((3-(1,1-DIOXIDOTETRAHYDRO-2H-THIOPYRAN-4-YL)-2-PYRIDINYL)OXY)PHENYL)METHANONE

A mixture of (1H-benzo[d]imidazol-2-yl)(4-hydroxyphenyl)methanone (0.485 g, 2.035 mmol), 3-(1,1-dioxidotetrahydro-2H-thiopyran-4-yl)-2-fluoropyridine (0.311 g, 1.356 mmol), and cesium carbonate (1.326 g, 4.07 mmol) in NMP (5 mL) in a sealed tube was heated at 200° C. in 2 h. The reaction mixture was cooled, taken in H₂O, filtered the dark brown solid, purified by ISCO (50% EtOAc/Hexanes) to give the expected product as a tan solid. MS (ESI, pos. ion) m/z: 448.1 (M+1). IC50 (uM) +++++.

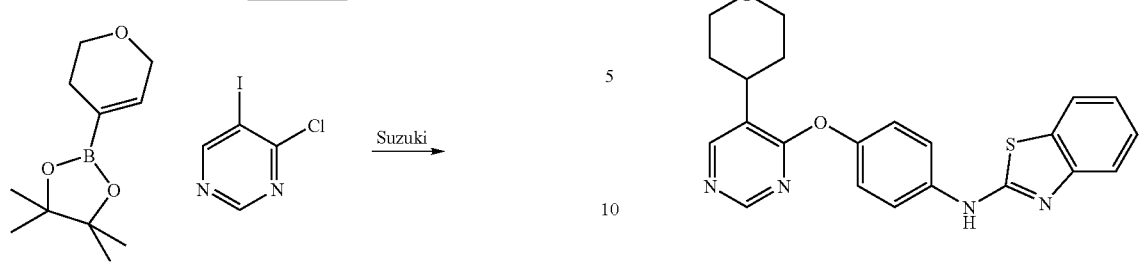

Example 236

N-(4-(5-(TETRAHYDRO-2H-PYRAN-4-YL)PYRI-MIDIN-4-YLOXY)PHENYL)BENZO[D]THIA-ZOL-2-AMINE

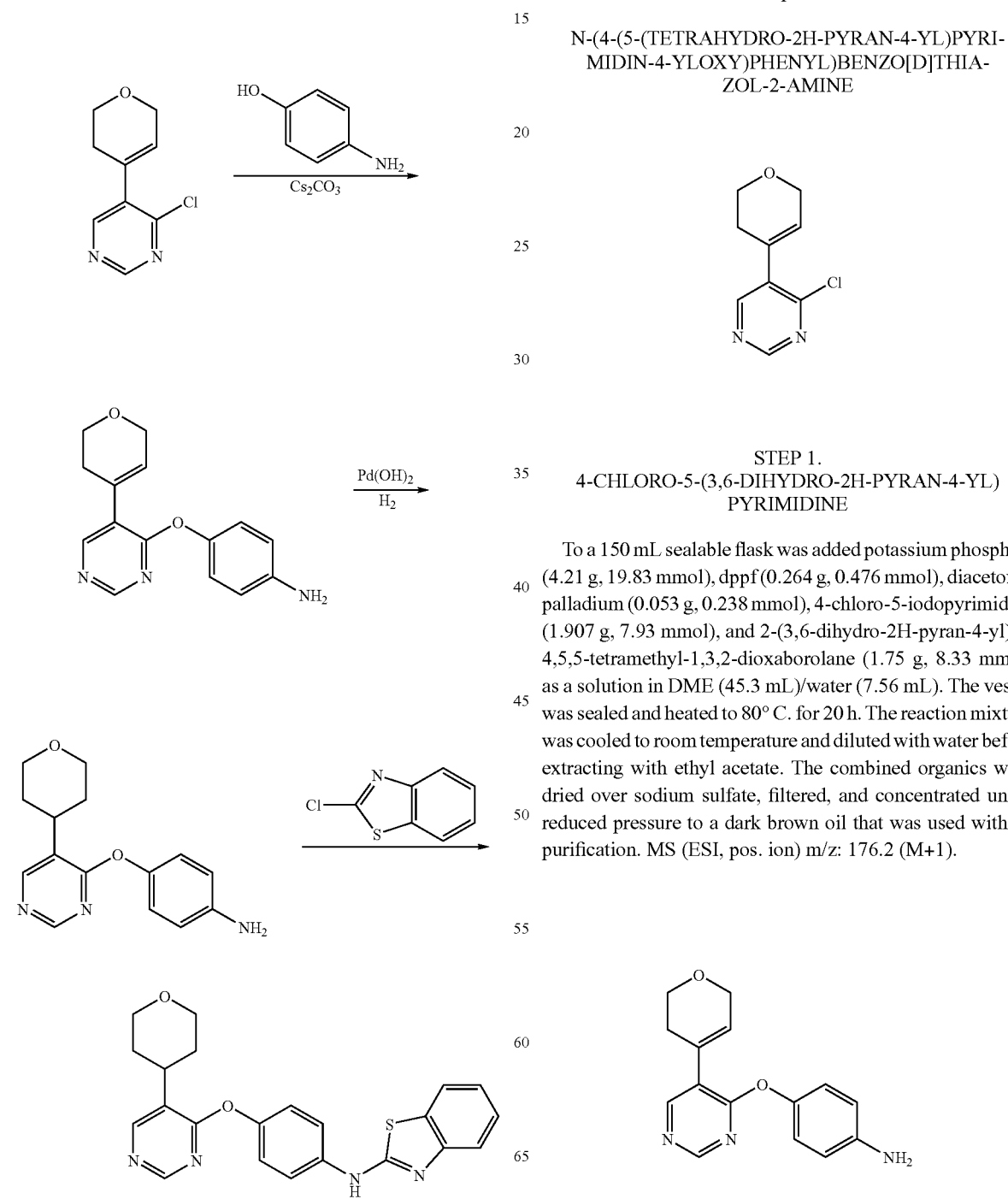

STEP 1.
4-CHLORO-5-(3,6-DIHYDRO-2H-PYRAN-4-YL)PYRIMIDINE

To a 150 mL sealable flask was added potassium phosphate (4.21 g, 19.83 mmol), dppf (0.264 g, 0.476 mmol), diacetoxy-palladium (0.053 g, 0.238 mmol), 4-chloro-5-iodopyrimidine (1.907 g, 7.93 mmol), and 2-(3,6-dihydro-2H-pyran-4-yl)-4,4,5,5-tetramethyl-1,3,2-dioxaborolane (1.75 g, 8.33 mmol) as a solution in DME (45.3 mL)/water (7.56 mL). The vessel was sealed and heated to 80° C. for 20 h. The reaction mixture was cooled to room temperature and diluted with water before extracting with ethyl acetate. The combined organics were dried over sodium sulfate, filtered, and concentrated under reduced pressure to a dark brown oil that was used without purification. MS (ESI, pos. ion) m/z: 176.2 (M+1).

STEP 2: 4-(5-(3,6-DIHYDRO-2H-PYRAN-4-YL)PYRIMIDIN-4-YLOXY)ANILINE

To a 150 mL sealable tube was added 4-aminophenol (388 mg, 3.56 mmol), 4-chloro-5-(3,6-dihydro-2H-pyran-4-yl)pyrimidine (700 mg, 3.56 mmol), and cesium carbonate (1218 mg, 3.74 mmol) with DMSO (23.700 ml). The vessel was sealed and heated to 100° C. for 2 h. The reaction mixture was cooled to room temperature and diluted with water before extracting with ethyl acetate. The combined organics were dried over sodium sulfate, filtered, and concentrated under reduced pressure to a dark brown oil that was used without purification. MS (ESI, pos. ion) m/z: 270.0 (M+1).

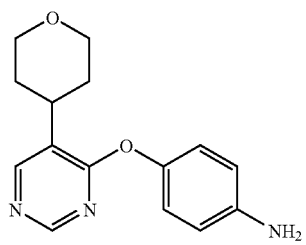

STEP 3: 4-(5-(TETRAHYDRO-2H-PYRAN-4-YL)PYRIMIDIN-4-YLOXY)ANILINE

To a pressure vessel was added palladium hydroxide, palladium on carbon (396 mg, 2.82 mmol), ethanol (18.800 ml), and 4-(5-(3,6-dihydro-2H-pyran-4-yl)pyrimidin-4-yloxy)aniline (760 mg, 2.82 mmol). The vessel was purged of air and backfilled with hydrogen (45 psi) before heating to 50° C. for 60 h. It was cooled to room temperature, filtered through Celite, and concentrated under reduced pressure to afford the product as a dark yellow oil. MS (ESI, pos. ion) m/z: 272.1 (M+1).

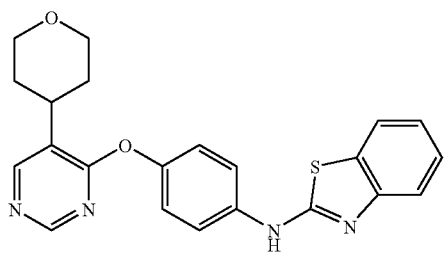

STEP 4: N-(4-(5-(TETRAHYDRO-2H-PYRAN-4-YL)PYRIMIDIN-4-YLOXY)PHENYL)BENZO[D]THIAZOL-2-AMINE

To a microwave vial was added 2-chlorobenzo[d]thiazole (68.5 µL, 0.553 mmol) and 4-(5-(tetrahydro-2H-pyran-4-yl)pyrimidin-4-yloxy)aniline (150 mg, 0.553 mmol) with isopropanol (1.1 mL). The reaction was irradiated at 120° C. for 3 h with microwave irradiation. The crude reaction was concentrated under reduced pressure. Preparative HPLC afforded the target compound as a salt. The material was washed with sat. aq. sodium bicarbonate and extracted with dichloromethane before concentrating the combined organics under reduced pressure to a pale yellow oil. MS (ESI, pos. ion) m/z: 405.0 (M+1). IC50 (uM) +++++.

SCHEME 57

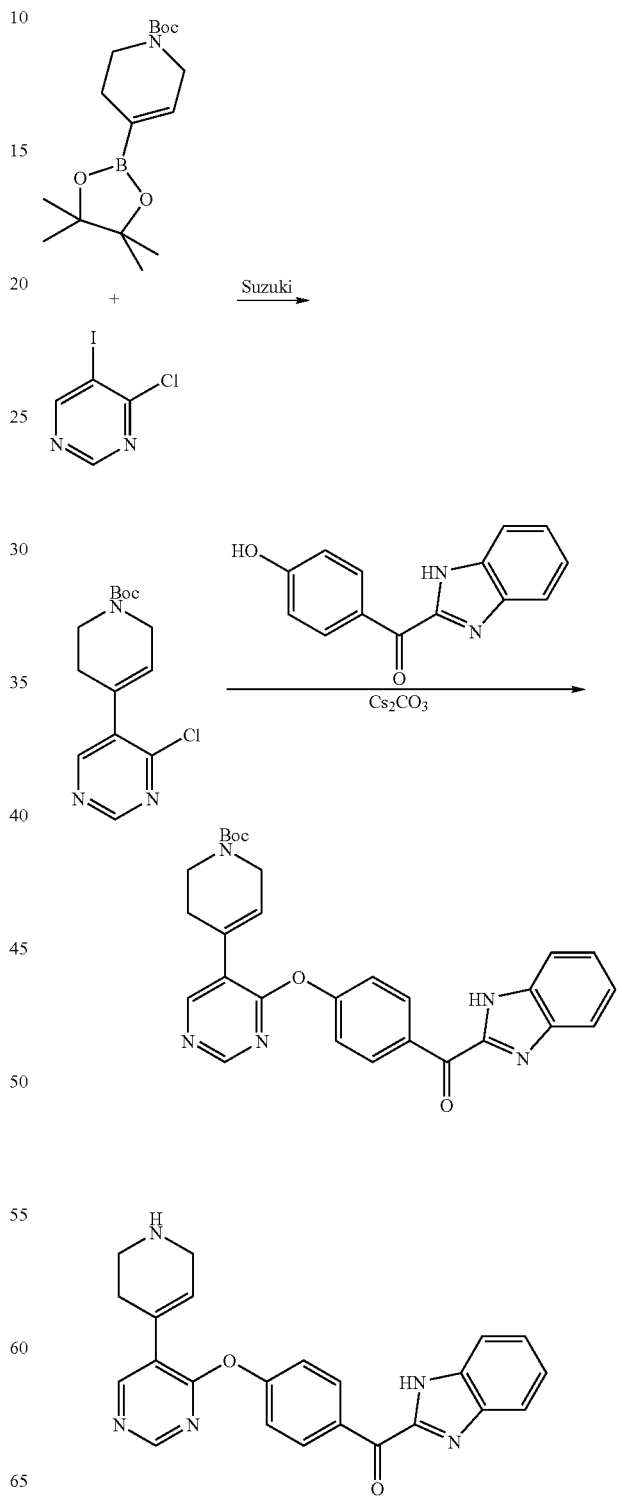

Example 237

(1H-BENZO[D]IMIDAZOL-2-YL)(4-(5-(1,2,3,6-TETRAHYDROPYRIDIN-4-YL)PYRIMIDIN-4-YLOXY)PHENYL)METHANONE

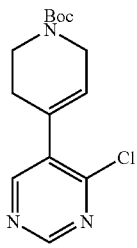

STEP 1: TERT-BUTYL 4-(4-CHLOROPYRIMIDIN-5-YL)-5,6-DIHYDROPYRIDINE-1(2H)-CARBOXYLATE

To a sealable tube was added potassium phosphate (1.308 g, 6.16 mmol), dppf (0.051 g, 0.092 mmol), palladium (II) acetate (0.014 g, 0.062 mmol), 4-chloro-5-iodopyrimidine (0.741 g, 3.08 mmol), and tert-butyl 4-(4,4,5,5-tetramethyl-1,3,2-dioxaborolan-2-yl)-5,6-dihydropyridine-1(2H)-carboxylate (1 g, 3.23 mmol) followed by DME (17.60 mL) and water (2.93 mL) before sealing the reaction under argon and stirring at 85° C. for 4 h. It was cooled to room temperature and diluted with water before extracting with dichloromethane drying over magnesium sulfate, filtering, and concentrating under reduced pressure to a dark brownish-orange residue that was used without purification. MS (ESI, pos. ion) m/z: 296.2 (M+1).

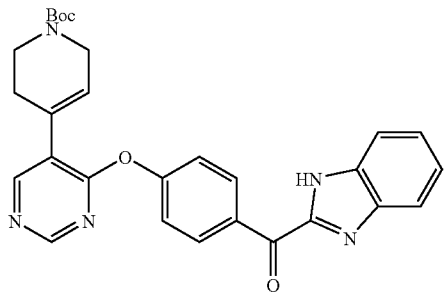

STEP 2: TERT-BUTYL 4-(4-(4-(1H-BENZO[D]IMIDAZOLE-2-CARBONYL)PHENOXY)PYRIMIDIN-5-YL)-5,6-DIHYDROPYRIDINE-1(2H)-CARBOXYLATE

To a vial was added tert-butyl 4-(4-chloropyrimidin-5-yl)-5,6-dihydropyridine-1(2H)-carboxylate (320 mg, 1.082 mmol), DMSO (5.4 mL), cesium carbonate (370 mg, 1.136 mmol), and (1H-benzo[d]imidazol-2-yl)(4-hydroxyphenyl)methanone (258 mg, 1.082 mmol) before sealing and heating to 100° C. for 45 minutes. The reaction mixture was diluted with water and extracted with ethyl acetate before drying over magnesium sulfate, filtering, and concentrating under reduced pressure. The crude material was taken after purifying by column chromatography (10% methanol/dichloromethane), affording tert-butyl 4-(4-(4-(1H-benzo[d]imidazole-2-carbonyl)phenoxy)pyrimidin-5-yl)-5,6-dihydropyridine-1(2H)-carboxylate. MS (ESI, pos. ion) m/z: 498.3 (M+1).

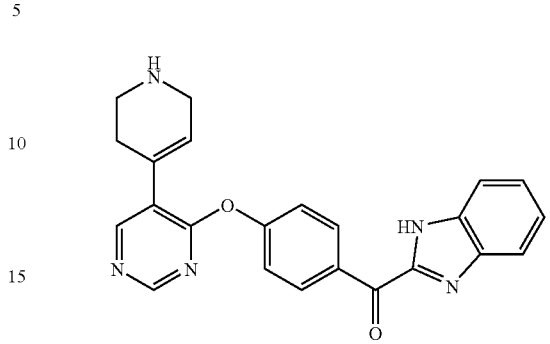

STEP 3: (1H-BENZO[D]IMIDAZOL-2-YL)(4-(5-(1,2,3,6-TETRAHYDROPYRIDIN-4-YL)PYRIMIDIN-4-YLOXY)PHENYL)METHANONE

To a round bottom was added tert-butyl 4-(4-(4-(1H-benzo[d]imidazole-2-carbonyl)phenoxy)pyrimidin-5-yl)-5,6-dihydropyridine-1(2H)-carboxylate (500 mg, 1.005 mmol), formic acid (10 ml), and hydrochloric acid, 5.0N (0.256 ml, 7.03 mmol) with stirring. The reaction was quenched after 15 minutes with saturated aqueous sodium bicarbonate and extracted with dichloromethane before drying over sodium sulfate, filtering, and concentrating under reduced pressure, affording (1H-benzo[d]imidazol-2-yl)(4-(5-(1,2,3,6-tetrahydropyridin-4-yl)pyrimidin-4-yloxy)phenyl)methanone as a pale yellow solid. IC50 (uM) +++++.

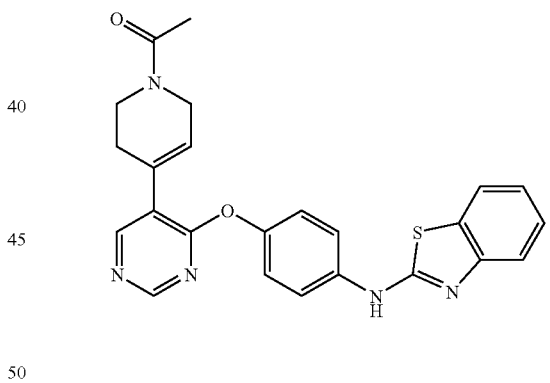

Example 238

1-(4-(4-(4-(BENZO[D]THIAZOL-2-YLAMINO)PHENOXY)PYRIMIDIN-5-YL)-5,6-DIHYDROPYRIDIN-1(2H)-YL)ETHANONE

To a round bottom flask was added (1H-benzo[d]imidazol-2-yl)(4-(5-(1,2,3,6-tetrahydropyridin-4-yl)pyrimidin-4-yloxy)phenyl)methanone (60.8 mg, 0.153 mmol) with DCM (1 mL) under nitrogen. With stirring, acetyl chloride (12 μL, 0.168 mmol) was added dropwise to a yield a suspension that quickly became a solution. After complete addition of the chloride, triethylamine (32.0 μL, 0.229 mmol) was added in one aliquot. The reaction was diluted with water after 10 minutes and extracted with dichloromethane before drying over sodium sulfate, filtering, and concentrating under reduced pressure to a yellow oil. It was purified by column chromatography (2M NH₃/MeOH/DCM). The resulting oil was resolubilized in dichloromethane and flushed through a plug of silica to yield 1-(4-(4-(4-(1H-benzo[d]imidazole-2-carbonyl)phenoxy)pyrimidin-5-yl)-5,6-dihydropyridin-1(2H)-yl)ethanone as a pale yellow oil. MS (ESI, pos. ion) m/z: 440.2 (M+1). IC50 (uM) ++++.

SCHEME 58

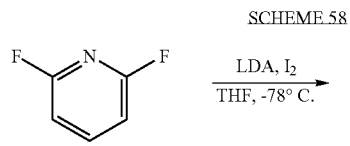

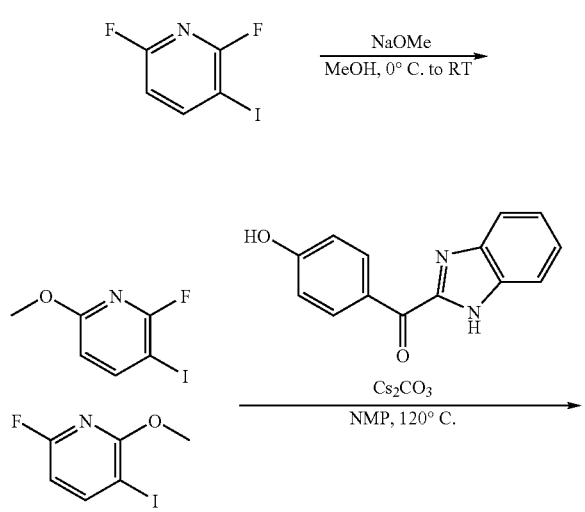

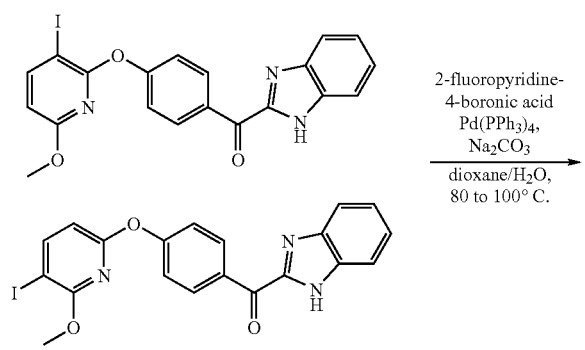

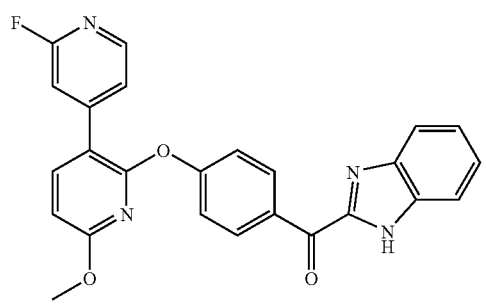

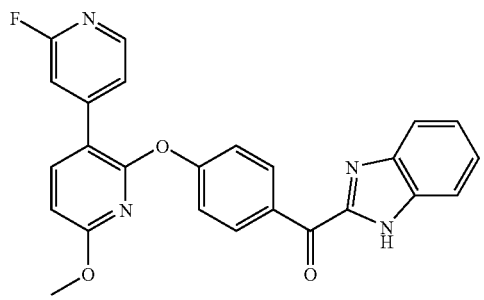

Example 239

(1H-BENZO[D]IMIDAZOL-2-YL)(4-(2'-FLUORO-6-METHOXY-3,4'-BIPYRIDIN-2-YLOXY)PHENYL)METHANONE

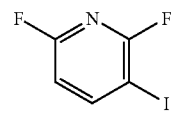

STEP 1. 2,6-DIFLUORO-3-IODOPYRIDINE

To a stirred solution of lithium diisopropylamide (4.34 mL, 8.69 mmol, 2.0 M solution in heptane/THF/ethylbenzene) in THF (20 mL) at −78° C. under a nitrogen atmosphere was added 2,6-difluoropyridine (0.79 mL, 8.69 mmol). The mixture was stirred at −78° C. for 45 min before iodine (2.21 g, 8.69 mmol) in THF (10 mL) was added via syringe. The reaction was stirred for an additional 30 min at −78° C. The reaction mixture was diluted with EtOAc and washed with 10% aqueous sodium sulfite. The organic layer was separated, dried over magnesium sulfate, filtered, and concentrated. The resulting crude product was purified by silica gel chromatography to give 2,6-difluoro-3-iodopyridine.

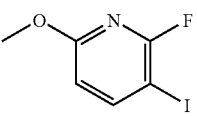 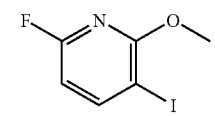

STEP 2.
2-FLUORO-3-IODO-6-METHOXYPYRIDINE
AND
6-FLUORO-3-IODO-2-METHOXYPYRIDINE

Sodium metal (0.14 g, 5.89 mmol) was dissolved in MeOH (3 mL) under a nitrogen atmosphere. The solution was cooled to 0° C. before 2,6-difluoro-3-iodopyridine (1.42 g, 5.89 mmol) in MeOH (3 mL) was added via syringe. The reaction mixture was stirred at 0° C. for 3 h before being allowed to warm to room temperature gradually overnight. The reaction mixture was concentrated and then partitioned between EtOAc and water. The organic layer was separated, washed with sat. sodium chloride, dried over magnesium sulfate, filtered, and concentrated to give a mixture of 2-fluoro-3-iodo-6-methoxypyridine and 6-fluoro-3-iodo-2-methoxypyridine.

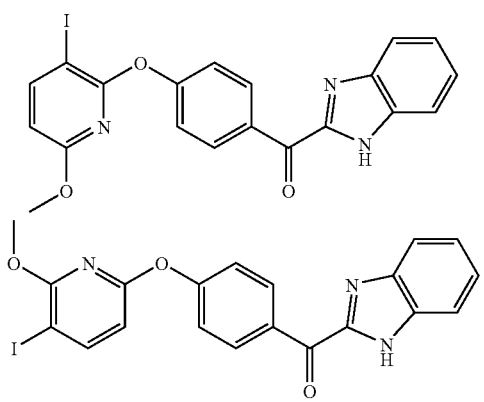

STEP 3. (1H-BENZO[D]IMIDAZOL-2-YL)(4-(3-IODO-6-METHOXYPYRIDIN-2-YLOXY)PHENYL)METHANONE AND (1H-BENZO[D]IMIDAZOL-2-YL)(4-(5-IODO-6-METHOXYPYRIDIN-2-YLOXY)PHENYL)METHANONE

A mixture of 2-fluoro-3-iodo-6-methoxypyridine and 6-fluoro-3-iodo-2-methoxypyridine (0.40 g, 1.59 mmol), (1H-benzo[d]imidazol-2-yl)(4-hydroxyphenyl)methanone (0.76 g, 3.18 mmol), and cesium carbonate (1.04 g, 3.18 mmol) were mixed in NMP (4 mL). The reaction mixture was placed under a nitrogen atmosphere and stirred at 120° C. for 5 h. The reaction mixture was cooled to room temperature, diluted with water, and extracted with EtOAc (2×). The combined organic layers were washed with sat. sodium chloride, dried over magnesium sulfate, filtered, and concentrated. The resulting crude product was purified by silica gel chromatography to give a mixture of (1H-benzo[d]imidazol-2-yl)(4-(3-iodo-6-methoxypyridin-2-yloxy)phenyl)methanone and (1H-benzo[d]imidazol-2-yl)(4-(5-iodo-6-methoxypyridin-2-yloxy)phenyl)methanone. [M+1]=472.0 for both isomers.

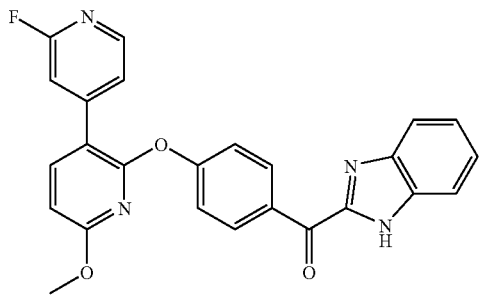

STEP 4. (1H-BENZO[D]IMIDAZOL-2-YL)(4-(2'-FLUORO-6-METHOXY-3,4'-BIPYRIDIN-2-YLOXY)PHENYL)METHANONE

A mixture of (1H-benzo[d]imidazol-2-yl)(4-(3-iodo-6-methoxypyridin-2-yloxy)phenyl)methanone and (1H-benzo[d]imidazol-2-yl)(4-(5-iodo-6-methoxypyridin-2-yloxy)phenyl)methanone (0.22 g, 0.45 mmol), 2-fluoropyridine-4-boronic acid (0.077 g, 0.55 mmol), and tetrakis(triphenylphosphine)palladium (0.053 g, 0.046 mmol) were mixed in dioxane (2 mL) under an argon atmosphere. Sodium carbonate (0.64 mL, 1.28 mmol, 2.0 M in water) was added via syringe, and the reaction mixture was stirred at 80° C. for 16 h. The reaction mixture was then stirred at 100° C. for an additional 24 h before being cooled to room temperature. The reaction mixture was diluted with water and extracted with EtOAc (2×). The combined organic layers were washed with sat. sodium chloride, dried over magnesium sulfate, filtered, and concentrated. The resulting crude product was purified by silica gel chromatography to give a mixture of (1H-benzo[d]imidazol-2-yl)(4-(2'-fluoro-6-methoxy-3,4'-bipyridin-2-yloxy)phenyl)methanone and (1H-benzo[d]imidazol-2-yl)(4-(2'-fluoro-2-methoxy-3,4'-bipyridin-6-yloxy)phenyl)methanone. The regioisomers were then separated by reverse phase HPLC. The desired regioisomer was then partitioned between DCM and sat. aqueous sodium bicarbonate. The organic layers were separated, dried over magnesium sulfate, filtered, and concentrated to give (1H-benzo[d]imidazol-2-yl)(4-(2'-fluoro-6-methoxy-3,4'-bipyridin-2-yloxy)phenyl)methanone. MS (ESI, pos. ion) m/z: 440.9 (M+1). IC50 (uM) ++++.

SCHEME 59

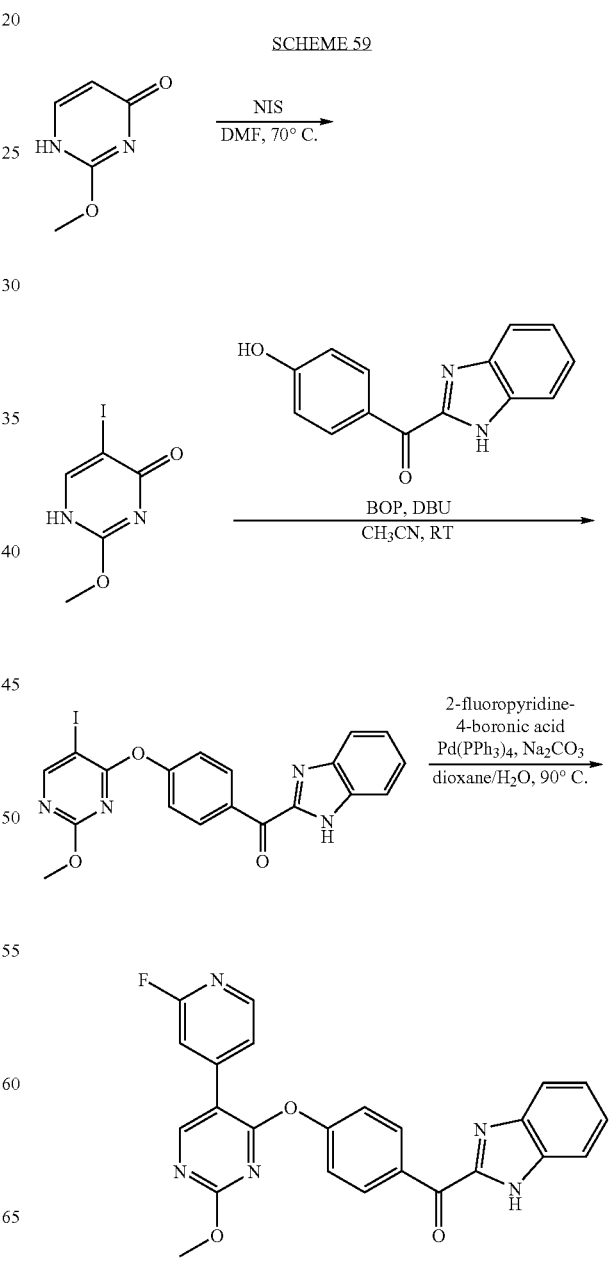

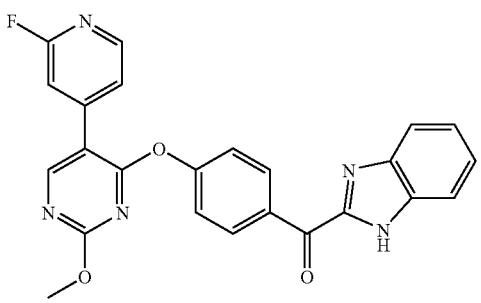

Example 240

(1H-BENZO[D]IMIDAZOL-2-YL)(4-(5-(2-FLUO-ROPYRIDIN-4-YL)-2-METHOXYPYRIMIDIN-4-YLOXY)PHENYL)METHANONE

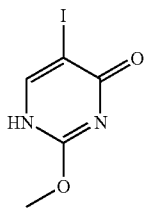

STEP 1.

5-IODO-2-METHOXYPYRIMIDIN-4(1H)-ONE

2-Methoxypyrimidin-4(1H)-one (1.00 g, 7.93 mmol) and n-iodosuccinimide (3.57 g, 15.86 mmol) were mixed in DMF (8 mL) under a nitrogen atmosphere. The reaction mixture was stirred at 70° C. for 2.5 h. The reaction mixture was cooled to room temperature, diluted with water, and extracted with EtOAc (3×). The combined organic layers were washed with sat. sodium chloride, dried over magnesium sulfate, filtered, and concentrated. The resulting solid was suspended in DCM, filtered, and washed with DCM to give 5-iodo-2-methoxypyrimidin-4(1H)-one. [M+1]=252.9.

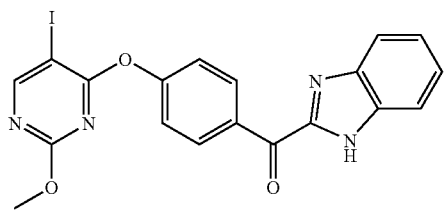

STEP 2. (1H-BENZO[D]IMIDAZOL-2-YL)(4-(5-IODO-2-METHOXYPYRIMIDIN-4-YLOXY)PHE-NYL)METHANONE

To a stirred mixture of 5-iodo-2-methoxypyrimidin-4(1H)-one (0.25 g, 0.99 mmol) and (1H-benzo[d][1,2,3]triazol-1-yloxy)tris(dimethylamino)phosphonium hexafluorophosphate(V) (0.53 g, 1.19 mmol) in acetonitrile (8 mL) was added 1,8-diazabicyclo[5.4.0]undec-7-ene (0.30 mL, 1.98 mmol). The reaction mixture was stirred at room temperature for 30 min before (1H-benzo[d]imidazol-2-yl)(4-hydroxyphenyl)methanone (0.47 g, 1.98 mmol) was added. The reaction mixture was stirred at room temperature for an additional 19 h. The reaction mixture was concentrated. The resulting crude product was purified by silica gel chromatography to give (1H-benzo[c]imidazol-2-yl)(4-(5-iodo-2-methoxypyrimidin-4-yloxy)phenyl)methanone. [M+1]=473.1.

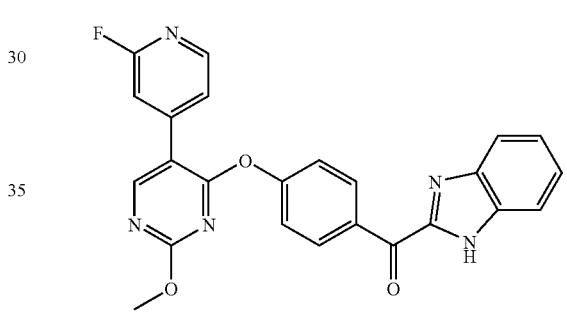

STEP 3. (1H-BENZO[D]IMIDAZOL-2-YL)(4-(5-(2-FLUOROPYRIDIN-4-YL)-2-METHOXYPYRI-MIDIN-4-YLOXY)PHENYL)METHANONE (1H-benzo[c]imidazol-2-yl)(4-(5-iodo-2-methoxypyrimidin-4-yloxy)phenyl)methanone (0.095 g, 0.20 mmol), 2-fluoropyridine-4-boronic acid (0.043 g, 0.30 mmol), and tetrakis(triphenylphosphine)palladium (0.023 g, 0.020 mmol) were mixed in dioxane (0.8 mL) under an argon atmosphere. Sodium carbonate (0.30 mL, 0.60 mmol, 2.0 M in water) was added via syringe, and the reaction mixture was stirred at 90° C. for 44 h. The reaction mixture was cooled to room temperature, diluted with water, and extracted with EtOAc. The organic layer was separated, washed with sat. sodium chloride, dried over magnesium sulfate, filtered, and concentrated. The resulting crude product was purified by silica gel chromatography to give (1H-benzo[c]imidazol-2-yl)(4-(5-(2-fluoropyridin-4-yl)-2-methoxypyrimidin-4-yloxy)phenyl)methanone. MS (ESI, pos. ion) m/z: 442.2 (M+1). IC50 (uM) ++++.

TABLE IIIA

EXAMPLES 241 TO 255 ARE TABULATED BELOW.

| Ex # | structure | IC50 (uM) | IUPAC names | MS |
|---|---|---|---|---|
| 241 | 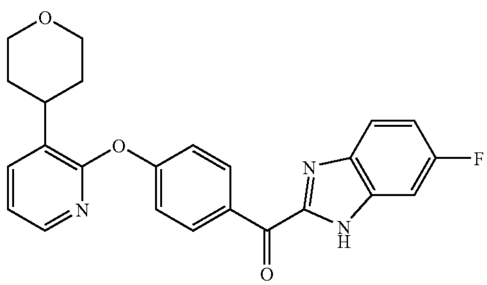 | +++++ | (6-fluoro-1H-benzo[d]imidazol-2-yl)(4-(3-(tetrahydro-2H-pyran-4-yl)pyridin-2-yloxy)phenyl)methanone | 418.0 |
| 242 | 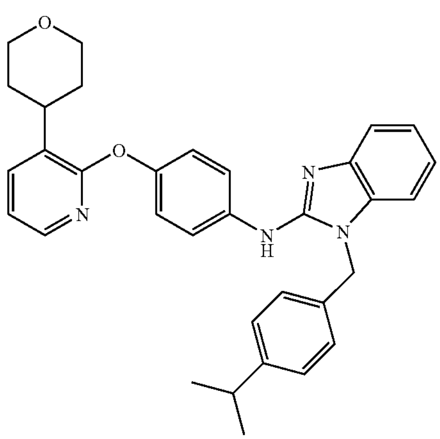 | ++++ | 1-(4-isopropylbenzyl)-N-(4-(3-(tetrahydro-2H-pyran-4-yl)pyridin-2-yloxy)phenyl)-1H-benzo[d]imidazol-2-amine | 519.2 |
| 243 | 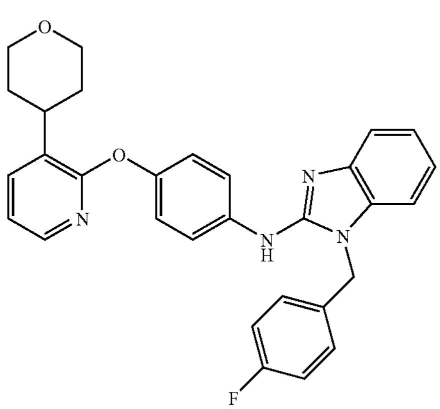 | +++++ | 1-(4-fluorobenzyl)-N-(4-(3-(tetrahydro-2H-pyran-4-yl)pyridin-2-yloxy)phenyl)-1H-benzo[d]imidazol-2-amine | 495.0 |

TABLE IIIA-continued

EXAMPLES 241 TO 255 ARE TABULATED BELOW.

| Ex # | structure | IC50 (uM) | IUPAC names | MS |
|---|---|---|---|---|
| 244 | 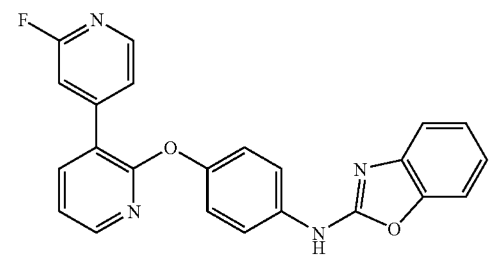 | +++++ | N-(4-(2'-fluoro-3,4'-bipyridin-2-yloxy)phenyl)benzo[d]oxazol-2-amine | 399.0 |
| 245 | 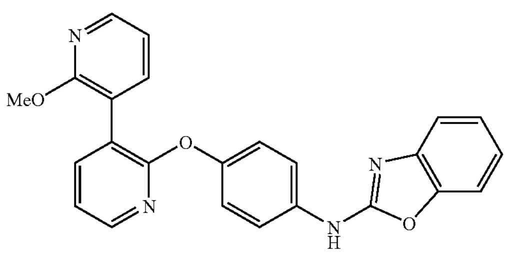 | +++++ | N-(4-(2'-methoxy-3,3'-bipyridin-2-yloxy)phenyl)benzo[d]oxazol-2-amine | 411.0 |
| 246 | 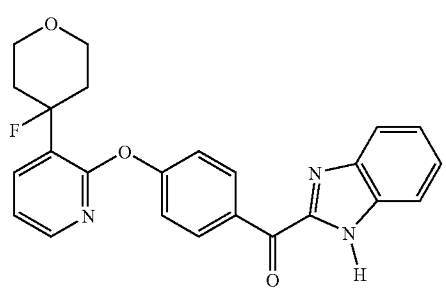 | +++++ | (1H-benzo[d]imidazol-2-yl)(4-(3-(4-fluorotetrahydro-2H-pyran-4-yl)pyridin-2-yloxy)phenyl)methanone | 418 |
| 247 | 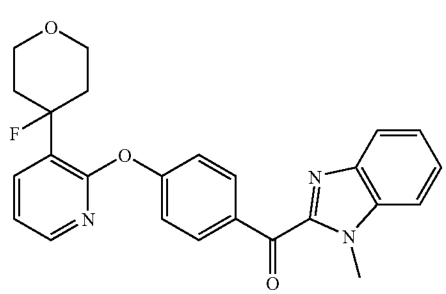 | +++++ | (4-(3-(4-fluorotetrahydro-2H-pyran-4-yl)pyridin-2-yloxy)phenyl)(1-methyl-1H-benzo[d]imidazol-2-yl)methanone | 432 |

TABLE IIIA-continued

EXAMPLES 241 TO 255 ARE TABULATED BELOW.

| Ex # | structure | IC50 (uM) | IUPAC names | MS |
|---|---|---|---|---|
| 248 | 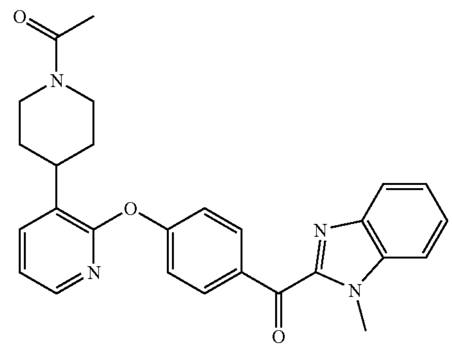 | +++++ | 1-(4-(2-(4-(1-methyl-1H-benzo[d]imidazole-2-carbonyl)phenoxy)pyridin-3-yl)piperidin-1-yl)ethanone | 455.1 |
| 249 | 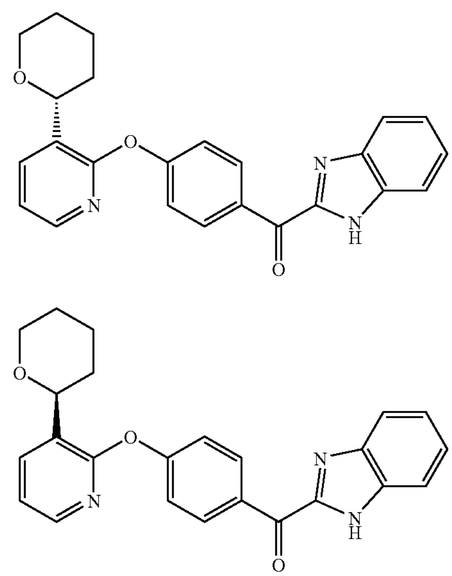 | +++++ | (±)-(1H-benzo[d]imidazol-2-yl)(4-(3-(tetrahydro-2H-pyran-2-yl)pyridin-2-yloxy)phenyl)methanone | 400.0 |
| 250 | 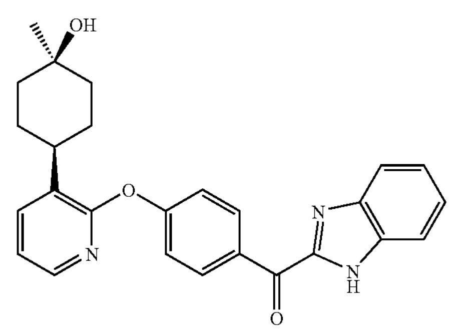 | +++++ | (1H-benzo[d]imidazol-2-yl)(4-(3-((1s,4s)-4-hydroxy-4-methylcyclohexyl)pyridin-2-yloxy)phenyl)methanone | 428.1 |
| 251 | 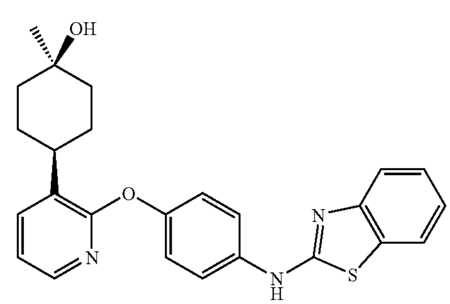 | +++++ | (1s,4s)-4-(2-(4-(benzo[d]thiazol-2-ylamino)phenoxy)pyridin-3-yl)-1-methylcyclohexanol | 432.1 |

TABLE IIIA-continued

EXAMPLES 241 TO 255 ARE TABULATED BELOW.

| Ex # | structure | IC50 (uM) | IUPAC names | MS |
|---|---|---|---|---|
| 252 | | +++++ | (rac)-cis-(1H-benzo[d]imidazol-2-yl)(4-(3-(3-hydroxycyclohexyl)pyridin-2-yloxy)phenyl)methanone | 414.0 |
| 253 | | +++++ | (rac)-trans-(1H-benzo[d]imidazol-2-yl)(4-(3-(3-hydroxycyclohexyl)pyridin-2-yloxy)phenyl)methanone | 414.0 |
| 254 | 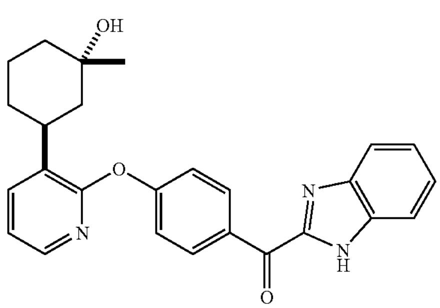 | +++++ | (rac)-E-(1H-benzo[d]imidazol-2-yl)(4-(3-(3-hydroxy-3-methylcyclohexyl)pyridin-2-yloxy)phenyl)methanone | 428.1 |

TABLE IIIA-continued

EXAMPLES 241 TO 255 ARE TABULATED BELOW.

| Ex # | structure | IC50 (uM) | IUPAC names | MS |
|---|---|---|---|---|
| 255 | 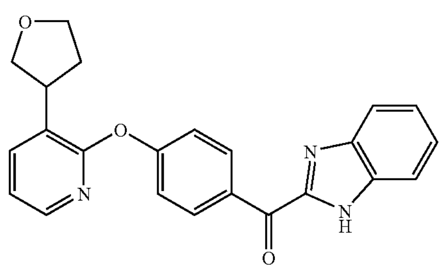 | +++++ | (1H-benzo[d]imidazol-2-yl)(4-(3-(tetrahydrofuran-3-yl)pyridin-2-yloxy)phenyl)methanone | 386.0 |

TABLE IIIB

EXAMPLES 241 TO 255 WERE PREPARED AS FOLLOWS:

| Ex # | Synthetic Scheme | How Different From Main Route | Reagent Difference |
|---|---|---|---|
| 241 | 17 | Same | |

TABLE IIIB-continued
EXAMPLES 241 TO 255 WERE PREPARED AS FOLLOWS:
| Ex # | Synthetic Scheme | How Different From Main Route | Reagent Difference |
|---|---|---|---|
| 242 | 18 | Same | 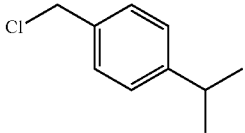 |
| 243 | 18 | Step 4 was not needed due to commercially available starting material. | 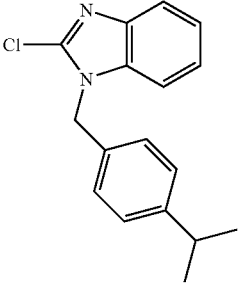 |
| 244 | 19 | Step 4 omitted | 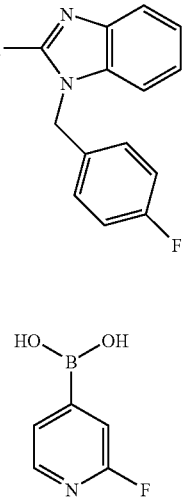 |
| 245 | 19 | Step 4 omitted | 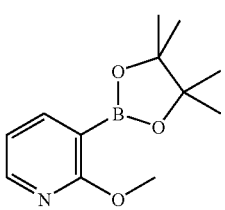 |
| 246 | 20 | Same | 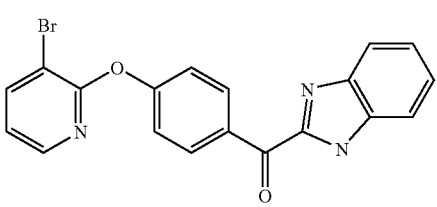 |

TABLE IIIB-continued

EXAMPLES 241 TO 255 WERE PREPARED AS FOLLOWS:

| Ex # | Synthetic Scheme | How Different From Main Route | Reagent Difference |
|---|---|---|---|
| 247 | 2 | Same | (structure) |
| 248 | 2 | Same | (structure) |
| 249 | 24 | Same | (structure) |
| 250 | 27 | Use other stereoisomer | (structure) |
| 251 | 27 | Use other stereoisomer | (structure) |
| 252 | 35 | Same | (structure) |
| 253 | 35 | Same | (structure) |

TABLE IIIB-continued

EXAMPLES 241 TO 255 WERE PREPARED AS FOLLOWS:

| Ex # | Synthetic Scheme | How Different From Main Route | Reagent Difference |
|------|------------------|-------------------------------|--------------------|
| 254  | 36               | Same                          | 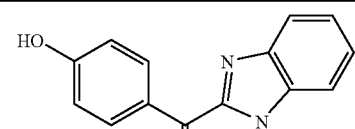 |
| 255  | 48               | Same                          | 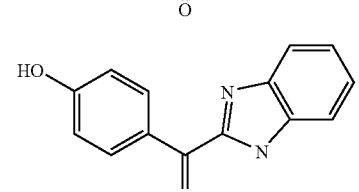 |

SCHEME 60

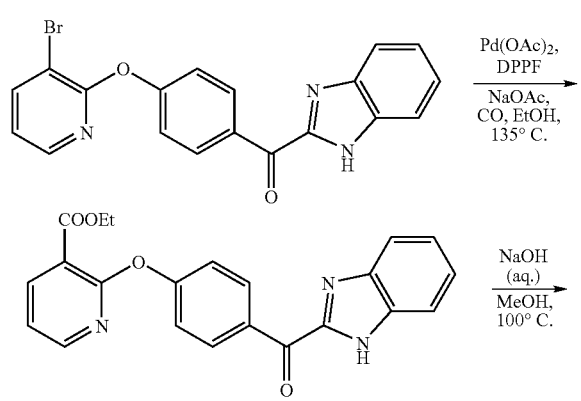

Example 256

2-(4-(1H-BENZO[D]IMIDAZOLE-2-CARBONYL)PHENOXY)-N-(2-(PYRIDIN-2-YL)ETHYL)NICOTINAMIDE

STEP 1:—ETHYL 2-(4-(1H-BENZO[D]IMIDAZOLE-2-CARBONYL) PHENOXY) NICOTINATE

To the solution of (1H-benzo[d]imidazol-2-yl)(4-(3-bromopyridin-2-yloxy)phenyl)methanone. (17.0 g, 43.1 mmol) in ethanol (600 mL) was added dppf (0.716 g, 1.29 mmol) and Pd(OAc)$_2$ (77 mg, 0.344 mmol) and sodium acetate (14.13 g, 172 mmol) in 2.0 L. autoclave and apply CO(g) 15 kg/cm2 pressure. Then the reaction mixture was heated up to 135° C. and maintained at that temperature for 1 h. The reaction mass was concentrated under vacuum and diluted with water, then extracted by ethyl acetate(3×500 mL). The combined organic extracts were dried over sodium sulfate and concentrate under vacuum to give the title compound as dark brown solid. MS (ESI, pos. ion) m/z: 389.1 (M+1).

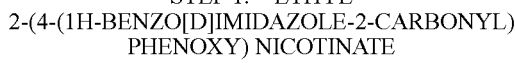

STEP 2:—2-(4-(1H-BENZO[D]IMIDAZOLE-2-CARBONYL)PHENOXY)NICOTINIC ACID

To the solution of ethyl 2-(4-(1H-benzo[d]imidazole-2-carbonyl)Phenoxy)nicotinate (12.0 g, 30.9 mmol) in methanol (100 mL) was added aqueous solution of NaOH (1.85 g, 46.3 mmol, 30 mL). The reaction mixture was heated up to reflux for 1 h. The reaction mixture was concentrated, diluted with water and filtered. The aqueous layer was washed with ethyl acetate and acidified by addition of 2N HCl to pH 6. The brown precipitate was collected by filtration, dried to give the title compound. MS (ESI, pos. ion) m/z: 360.1 (M+1).

STEP 3. 2-(4-(1H-BENZO[D]IMIDAZOLE-2-CARBONYL)PHENOXY)-N-(2-(PYRIDIN-2-YL)ETHYL)NICOTINAMIDE

HATU (122 mg, 0.321 mmol) was added to a mixture of 2-(4-(1H-benzo[d]imidazole-2-carbonyl)phenoxy)nicotinic acid (105 mg, 0.292 mmol) and diisopropylethylamine (102 μL, 0.584 mmol) in DMF (1 mL) and the mixture was stirred at RT for 10 min. 2-Phenethylamine (55.4 μL, 0.438 mmol) was added, and the mixture was stirred at RT for 1 h. The mixture was purified by chromatography on silica gel to deliver 2-(4-(1H-benzo[d]imidazole-2-carbonyl)phenoxy)-N-phenethylnicotinamide as an off-white solid. MS (ESI, pos. ion) m/z: 463.1 (M+1). IC50 (uM) +.

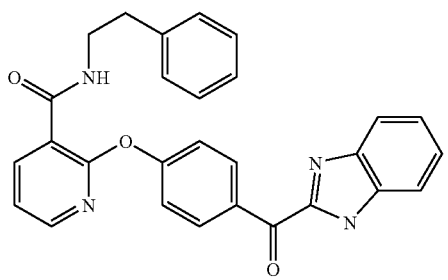

TABLE IVA

EXAMPLES 257 TO 276 ARE TABULATED BELOW:

| Ex # | structure | IC50 (uM) | IUPAC names | MS |
|---|---|---|---|---|
| 257 | 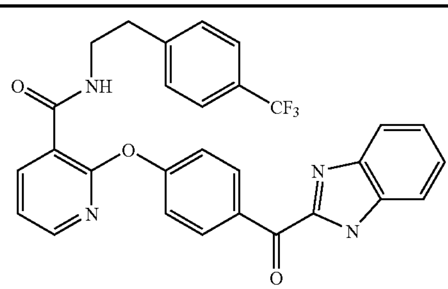 | +++++ | 2-(4-(1H-benzo[d]imidazole-2-carbonyl)phenoxy)-N-(4-(trifluoromethyl)phenethyl)nicotinamide | 531.0 |
| 258 | 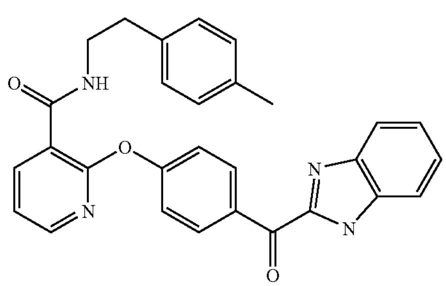 | +++++ | 2-(4-(1H-benzo[d]imidazole-2-carbonyl)phenoxy)-N-(4-methylphenethyl)nicotinamide | 477.0 |
| 259 | 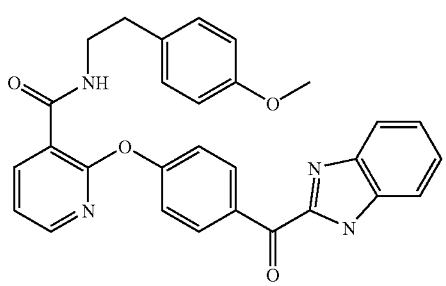 | +++++ | 2-(4-(1H-benzo[d]imidazole-2-carbonyl)phenoxy)-N-phenethylnicotinamide | 493.0 |

TABLE IVA-continued

EXAMPLES 257 TO 276 ARE TABULATED BELOW:

| Ex # | structure | IC50 (uM) | IUPAC names | MS |
|---|---|---|---|---|
| 260 | 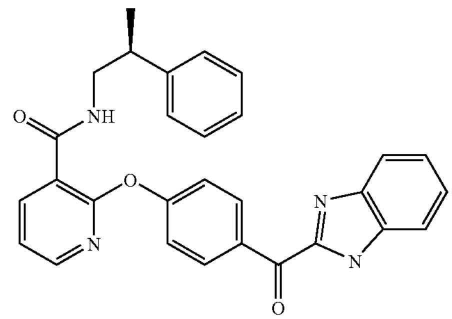 | +++++ | (S)-2-(4-(1H-benzo[d]imidazole-2-carbonyl)phenoxy)-N-(2-phenylpropyl)nicotinamide | 477.1 |
| 261 | 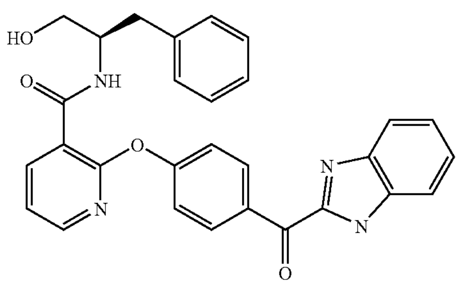 | +++++ | (R)-2-(4-(1H-benzo[d]imidazole-2-carbonyl)phenoxy)-N-(1-hydroxy-3-phenylpropan-2-yl)nicotinamide | 493.0 |
| 262 | 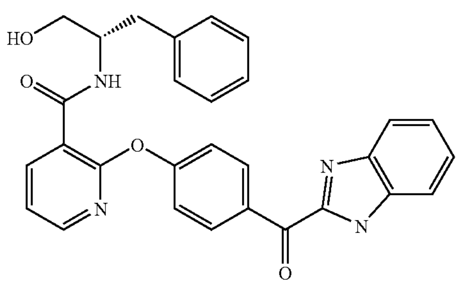 | +++++ | (S)-2-(4-(1H-benzo[d]imidazole-2-carbonyl)phenoxy)-N-(1-hydroxy-3-phenylpropan-2-yl)nicotinamide | 493.0 |
| 263 | 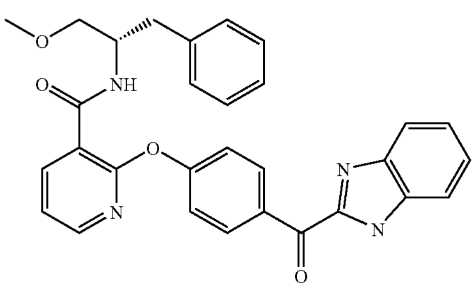 | +++++ | (S)-2-(4-(1H-benzo[d]imidazole-2-carbonyl)phenoxy)-N-(1-methoxy-3-phenylpropan-2-yl)nicotinamide | 507.1 |
| 264 | 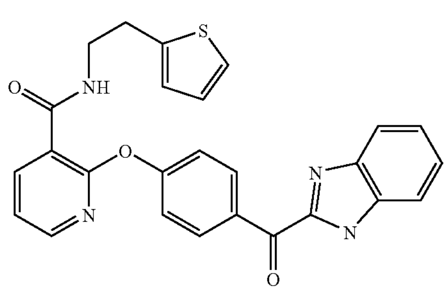 | ++++ | 2-(4-(1H-benzo[d]imidazole-2-carbonyl)phenoxy)-N-(2-(thiophen-2-yl)ethyl)nicotinamide | 469.0 |

TABLE IVA-continued

EXAMPLES 257 TO 276 ARE TABULATED BELOW:

| Ex # | structure | IC50 (uM) | IUPAC names | MS |
|---|---|---|---|---|
| 265 | 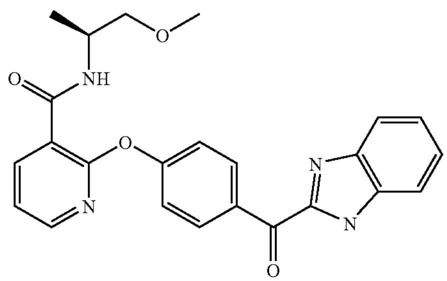 | +++ | (S)-2-(4-(1H-benzo[d]imidazole-2-carbonyl)phenoxy)-N-(1-methoxypropan-2-yl)nicotinamide | 431.0 |
| 266 | 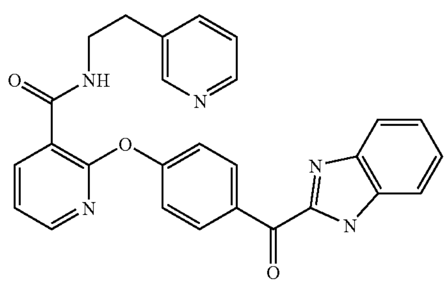 | +++++ | 2-(4-(1H-benzo[d]imidazole-2-carbonyl)phenoxy)-N-(2-(pyridin-2-yl)ethyl)nicotinamide | 464.1 |
| 267 | 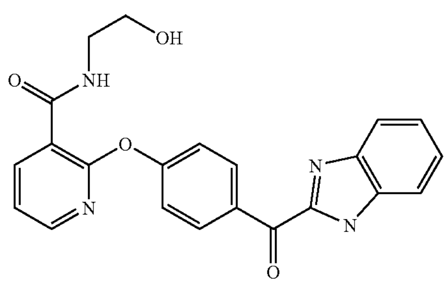 | +++ | 2-(4-(1H-benzo[d]imidazole-2-carbonyl)phenoxy)-N-(2-hydroxyethyl)nicotinamide | 403.0 |
| 268 | 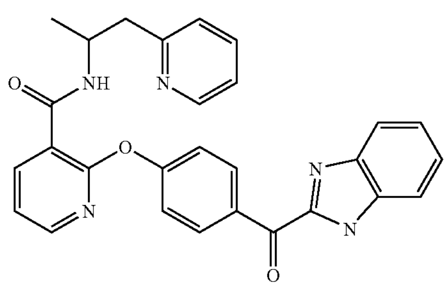 | +++++ | (rac)-2-(4-(1H-benzo[d]imidazole-2-carbonyl)phenoxy)-N-(1-(pyridin-2-yl)propan-2-yl)nicotinamide | 478.1 |
| 269 | 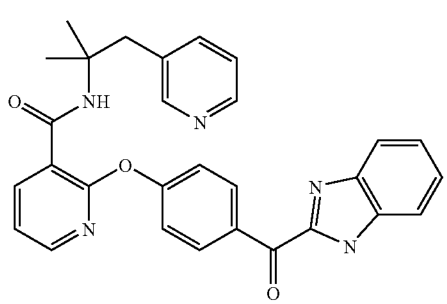 | +++++ | 2-(4-(1H-benzo[d]imidazole-2-carbonyl)phenoxy)-N-(2-methyl-2-(pyridin-2-yl)propyl)nicotinamide | 492 |

TABLE IVA-continued

EXAMPLES 257 TO 276 ARE TABULATED BELOW:

| Ex # | structure | IC50 (uM) | IUPAC names | MS |
|---|---|---|---|---|
| 270 | 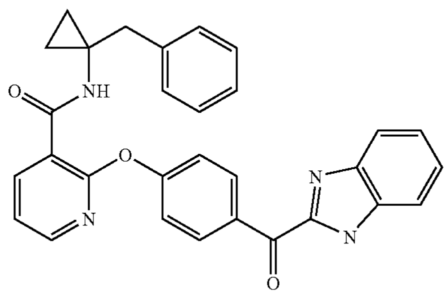 | +++++ | 2-(4-(1H-benzo[d]imidazole-2-carbonyl)phenoxy)-N-(1-benzylcyclopropyl)nicotinamide | 489 |
| 271 | 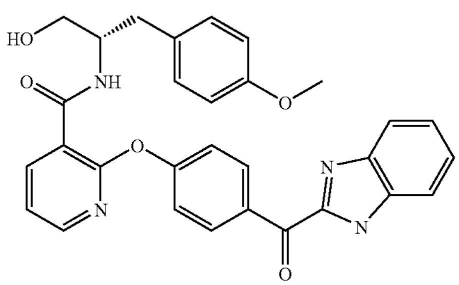 | +++++ | (S)-2-(4-(1H-benzo[d]imidazole-2-carbonyl)phenoxy)-N-(1-hydroxy-3-(4-methoxyphenyl)propan-2-yl)nicotinamide | 523.1 |
| 272 | 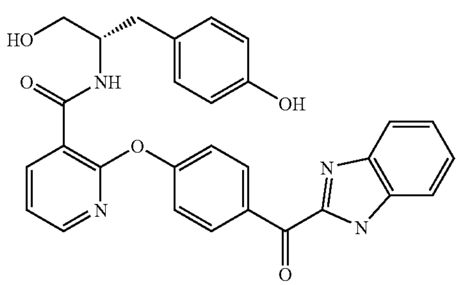 | +++++ | (S)-2-(4-(1H-benzo[d]imidazole-2-carbonyl)phenoxy)-N-(1-hydroxy-3-(4-hydroxyphenyl)propan-2-yl)nicotinamide | 509.0 |
| 273 | 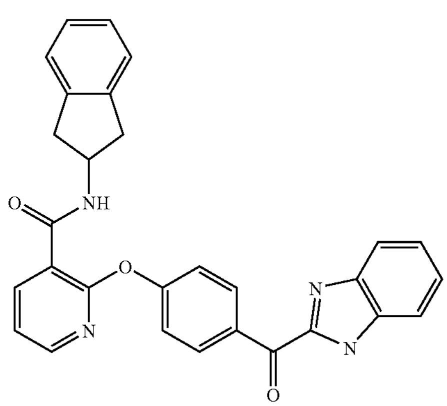 | +++ | 2-(4-(1H-benzo[d]imidazole-2-carbonyl)phenoxy)-N-(2,3-dihydro-1H-inden-2-yl)nicotinamide | 475.1 |

TABLE IVA-continued

EXAMPLES 257 TO 276 ARE TABULATED BELOW:

| Ex # | structure | IC50 (uM) | IUPAC names | MS |
|---|---|---|---|---|
| 274 | 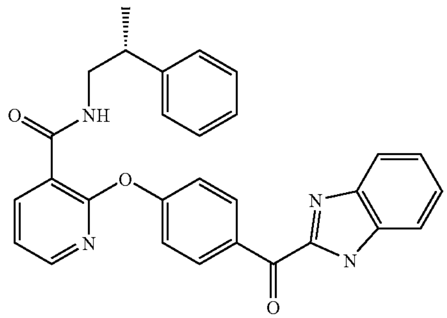 | +++++ | (R)-2-(4-(1H-benzo[d]imidazole-2-carbonyl)phenoxy)-N-(2-phenylpropyl)nicotinamide | 477.0 |
| 275 | 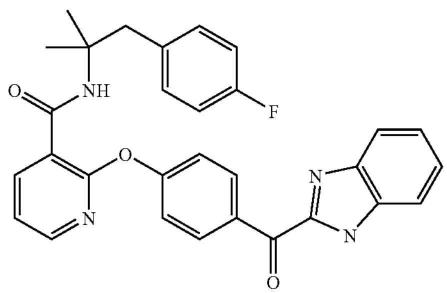 | +++++ | 2-(4-(1H-benzo[d]imidazole-2-carbonyl)phenoxy)-N-(1-(4-fluorophenyl)-2-methylpropan-2-yl)nicotinamide | 509.1 |
| 276 | 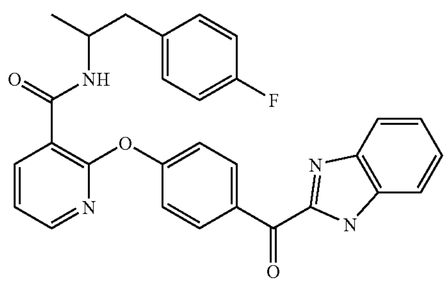 | +++++ | (rac)-2-(4-(1H-benzo[d]imidazole-2-carbonyl)phenoxy)-N-(1-(4-fluorophenyl)propan-2-yl)nicotinamide | 495.1 |

TABLE IVB

EXAMPLES 258 TO 277 WERE PREPARED AS FOLLOWS:

| Ex # | Synthetic Scheme | How Different From Main Route | Reagent Difference |
|---|---|---|---|
| 257 | 57 | Same | |
| 258 | 57 | Same | |
| 259 | 57 | Same | |
| 260 | 57 | Same | |

TABLE IVB-continued

EXAMPLES 258 TO 277 WERE PREPARED AS FOLLOWS:

| Ex # | Synthetic Scheme | How Different From Main Route | Reagent Difference |
|------|------------------|-------------------------------|---------------------|
| 261 | 57 | Same | 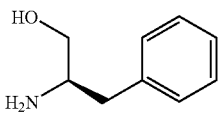 |
| 262 | 57 | Same | 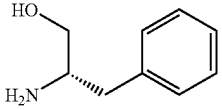 |
| 263 | 57 | Same | 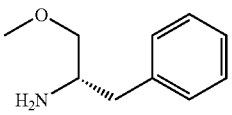 |
| 264 | 57 | Same | 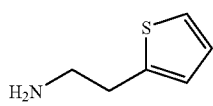 |
| 265 | 57 | Same | 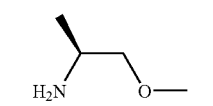 |
| 266 | 57 | Same | 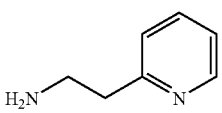 |
| 267 | 57 | Same | 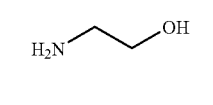 |
| 268 | 57 | Same | 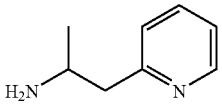 |
| 269 | 57 | Same | 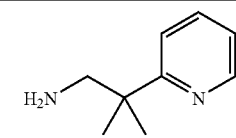 |
| 270 | 57 | Same | 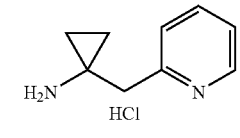 |
| 271 | 57 | Same | 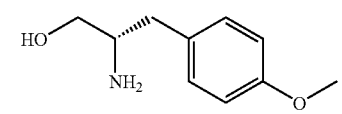 |
| 272 | 57 | Same | 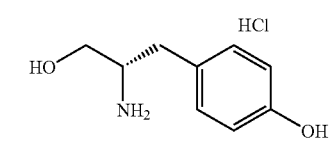 |
| 273 | 57 | Same | 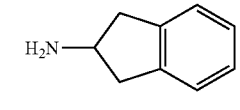 |
| 274 | 57 | Same | 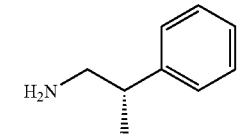 |
| 275 | 57 | Same | 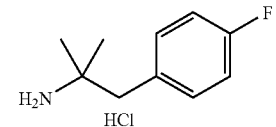 |
| 276 | 57 | Same | 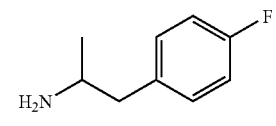 |

The racemic mixtures were/can be separated by chiral HPLC to give the following chiral compounds by known methods. Prep* means preparative experiment was performed according to the tabulated previous examples or schemes.

TABLE (V)

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 277 | +++++ | 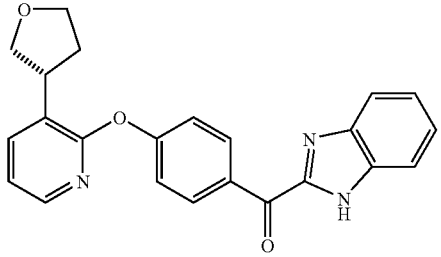 | (R)-(1H-benzo[d]imidazol-2-yl)(4-(3-(tetrahydrofuran-3-yl)pyridin-2-yloxy)phenyl)methanone | 386.0 | Ex. 255 |
| 278 | +++++ | 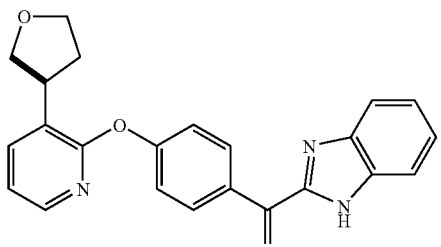 | (S)-(1H-benzo[d]imidazol-2-yl)(4-(3-(tetrahydrofuran-3-yl)pyridin-2-yloxy)phenyl)methanone | 386.0 | Ex. 255 |
| 279 | +++++ | 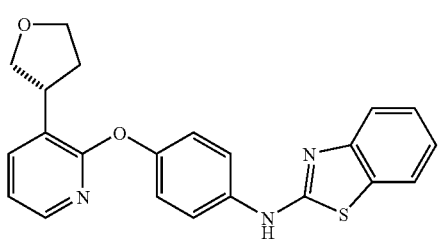 | (R)-N-(4-(3-(tetrahydrofuran-3-yl)pyridin-2-yloxy)phenyl)benzo[d]thiazol-2-amine | 390.0 | Ex. 224 |
| 280 | +++++ | 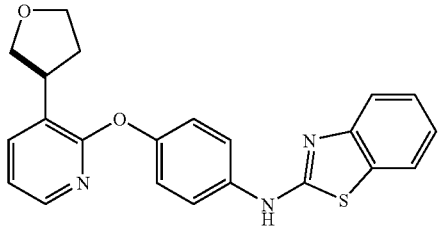 | (S)-N-(4-(3-(tetrahydrofuran-3-yl)pyridin-2-yloxy)phenyl)benzo[d]thiazol-2-amine | 389.9 | Ex. 224 |
| 281 | +++++ | 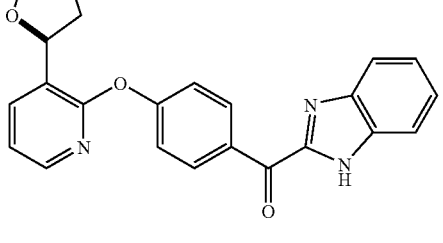 | (S)-(1H-benzo[d]imidazol-2-yl)(4-(3-(tetrahydrofuran-2-yl)pyridin-2-yloxy)phenyl)methanone | 386.0 | Ex. 223 |
| 282 | +++++ | 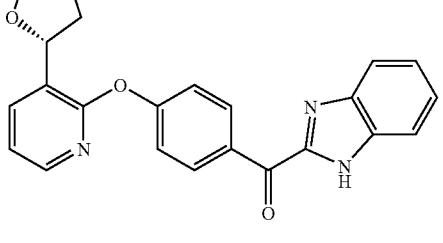 | (R)-(1H-benzo[d]imidazol-2-yl)(4-(3-(tetrahydrofuran-2-yl)pyridin-2-yloxy)phenyl)methanone | 386.0 | Ex. 223 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 283 | +++++ | 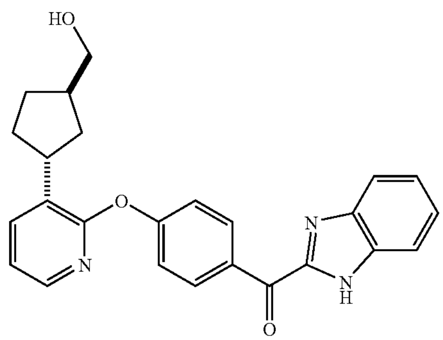 | (1H-benzo[d]imidazol-2-yl)(4-(3-((1R,3R)-3-(hydroxymethyl)cyclopentyl)pyridin-2-yloxy)phenyl)methanone | 413.9 | Scheme 47 |
| 284 | +++++ | 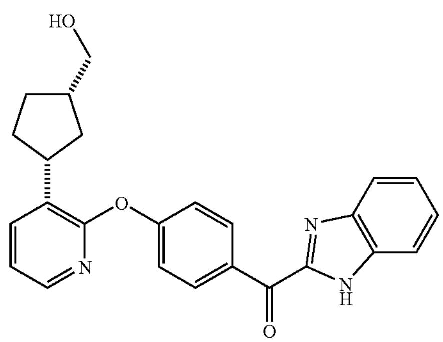 | (1H-benzo[d]imidazol-2-yl)(4-(3-((1R,3S)-3-(hydroxymethyl)cyclopentyl)pyridin-2-yloxy)phenyl)methanone | 414.0 | Scheme 47 |
| 285 | +++++ | 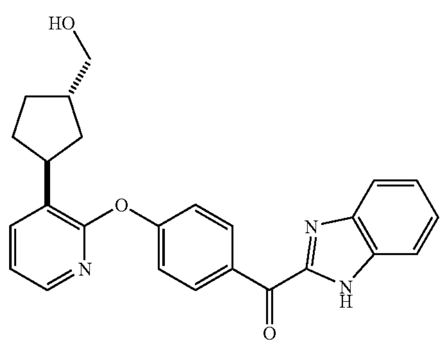 | (1H-benzo[d]imidazol-2-yl)(4-(3-((1S,3S)-3-(hydroxymethyl)cyclopentyl)pyridin-2-yloxy)phenyl)methanone | 414.0 | Scheme 47 |
| 286 | +++++ | 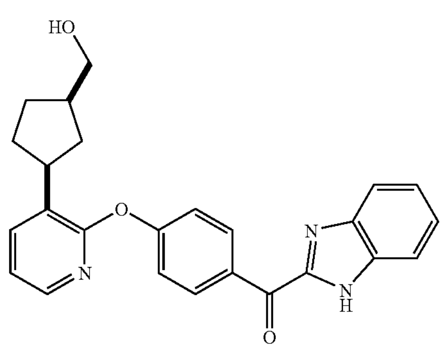 | (1H-benzo[d]imidazol-2-yl)(4-(3-((1S,3R)-3-(hydroxymethyl)cyclopentyl)pyridin-2-yloxy)phenyl)methanone | 414.0 | Scheme 47 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 287 | +++++ | 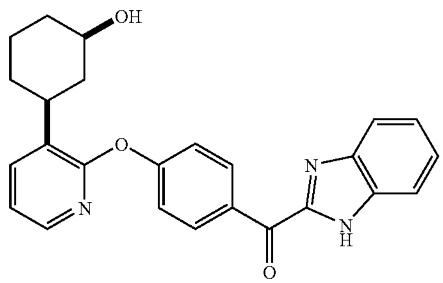 | (1H-benzo[d]imidazol-2-yl)(4-(3-((1S,3R)-3-(hydroxycyclohexyl)pyridin-2-yloxy)phenyl)methanone | 414.0 | Ex. 252 |
| 288 | +++++ | 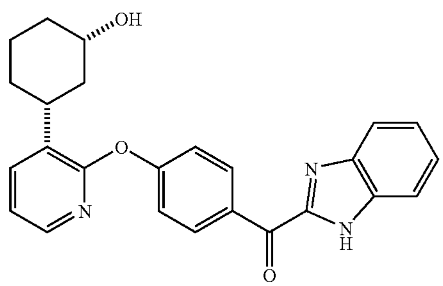 | (1H-benzo[d]imidazol-2-yl)(4-(3-((1R,3S)-3-(hydroxycyclohexyl)pyridin-2-yloxy)phenyl)methanone | 414.0 | Ex. 252 |
| 289 | +++++ | 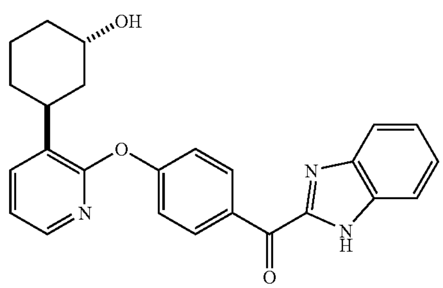 | (1H-benzo[d]imidazol-2-yl)(4-(3-((1S,3S)-3-(hydroxycyclohexyl)pyridin-2-yloxy)phenyl)methanone | 414.0 | Ex. 253 |
| 290 | +++++ | 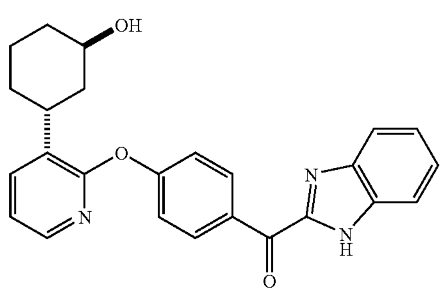 | (1H-benzo[d]imidazol-2-yl)(4-(3-((1R,3R)-3-(hydroxycyclohexyl)pyridin-2-yloxy)phenyl)methanone | 414.0 | Ex. 253 |
| 291 | +++++ | 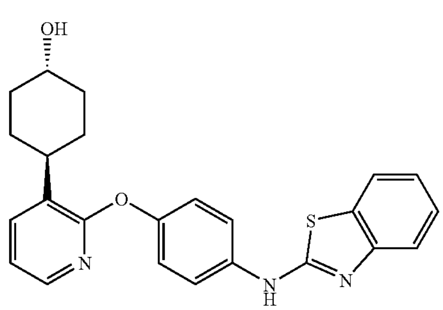 | (1r,4r)-4-(2-(4-(benzo[d]thiazol-2-ylamino)phenoxy)pyridin-3-yl)cyclohexanol | 418.2 | Ex. 189 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 292 | +++++ | 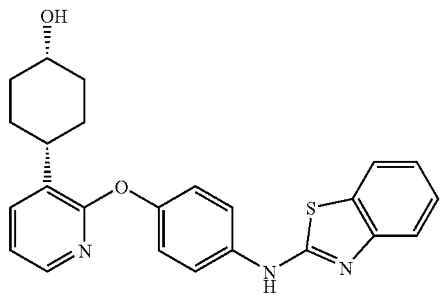 | (1r,4s)-4-(2-(4-(benzo[d]thiazol-2-ylamino)phenoxy)pyridin-3-yl)cyclohexanol | 418.2 | Ex. 189 |
| 293 | +++++ | 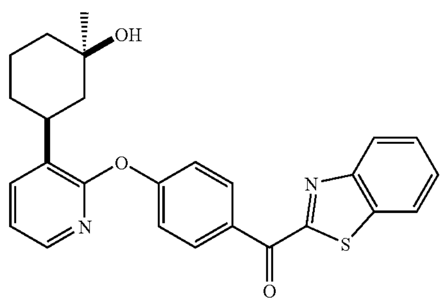 | (1R,3S)-3-(2-(4-(benzo[d]thiazol-2-ylamino)phenoxy)pyridin-3-yl)cyclohexanol | 418.0 | Ex. 204 |
| 294 | +++++ | 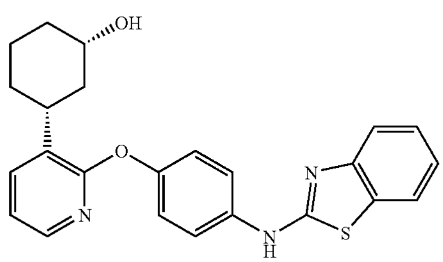 | (1S,3R)-3-(2-(4-(benzo[d]thiazol-2-ylamino)phenoxy)pyridin-3-yl)cyclohexanol | 418.0 | Ex. 204 |
| 295 | +++++ | 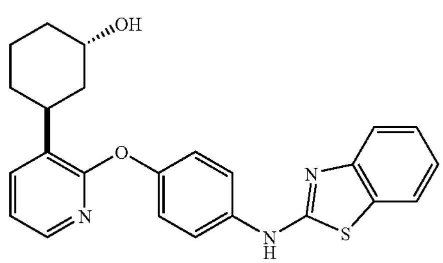 | (1S,3S)-3-(2-(4-(benzo[d]thiazol-2-ylamino)phenoxy)pyridin-3-yl)cyclohexanol | 418.0 | Ex. 205 |
| 296 | +++++ | 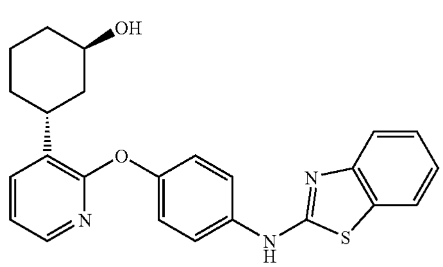 | (1R,3R)-3-(2-(4-(benzo[d]thiazol-2-ylamino)phenoxy)pyridin-3-yl)cyclohexanol | 418.0 | Ex. 205 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 297 | +++++ | 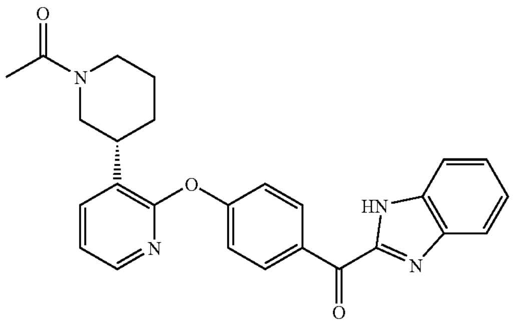 | (R)-1-(3-(2-(4-(1H-benzo[d]imidazole-2-carbonyl)phenoxy)pyridin-3-yl)piperidin-1-yl)ethanone | 441.0 | Ex. 217 |
| 298 | +++++ | 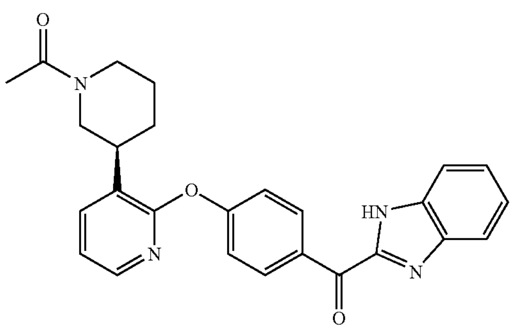 | (S)-1-(3-(2-(4-(1H-benzo[d]imidazole-2-carbonyl)phenoxy)pyridin-3-yl)piperidin-1-yl)ethanone | 441.0 | Ex. 217 |
| 299 | +++++ | 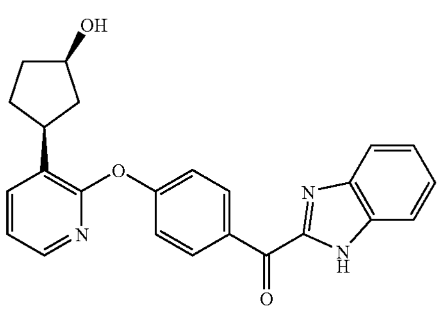 | ((1H-benzo[d]imidazol-2-yl)(4-(3-((1S,3R)-3-hydroxycyclopentyl)pyridin-2-yloxy)phenyl)methanone | 400.1 | Ex. 227 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 300 | +++++ | 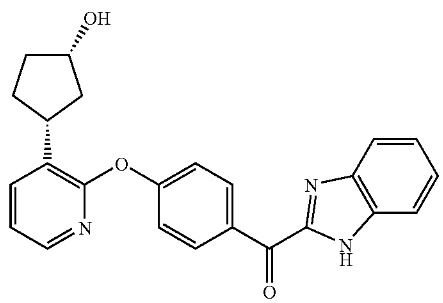 | ((1H-benzo[d]imidazol-2-yl)(4-(3-((1R,3S)-3-hydroxycyclopentyl)pyridin-2-yloxy)phenyl)methanone | 400.1 | Ex. 227 |
| 301 | +++++ | 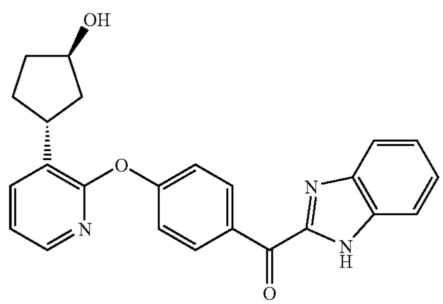 | ((1H-benzo[d]imidazol-2-yl)(4-(3-((1S,3S)-3-hydroxycyclopentyl)pyridin-2-yloxy)phenyl)methanone | 400.1 | Ex. 227 |
| 302 | +++++ | 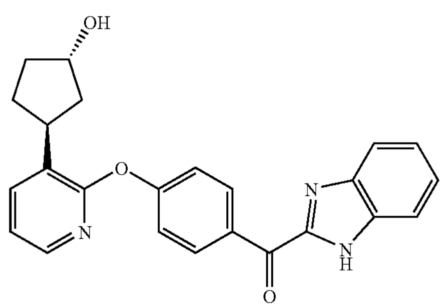 | ((1H-benzo[d]imidazol-2-yl)(4-(3-((1R,3R)-3-hydroxycyclopentyl)pyridin-2-yloxy)phenyl)methanone | 400.1 | Ex. 227 |
| 303 | +++++ | 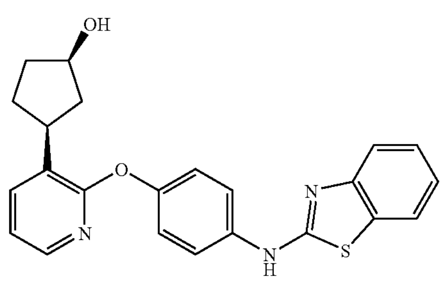 | (1R,3S)-3-(2-(4-(benzo[d]thiazol-2-ylamino)phenoxy)pyridin-3-yl)cyclopentanol | 404.1 | Ex. 229 |
| 304 | +++++ | 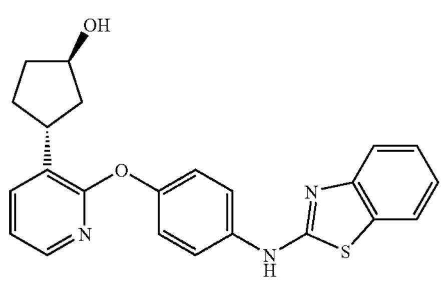 | (1R,3R)-3-(2-(4-(benzo[d]thiazol-2-ylamino)phenoxy)pyridin-3-yl)cyclopentanol | 404.1 | Ex. 229 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 305 | +++++ | 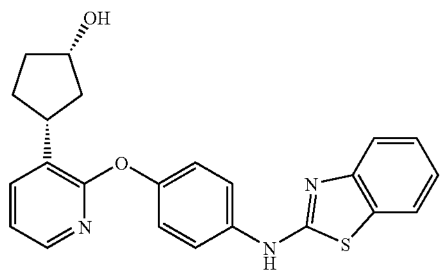 | (1S,3R)-3-(2-(4-(benzo[d]thiazol-2-ylamino)phenoxy)pyridin-3-yl)cyclopentanol | 404.1 | Ex. 229 |
| 306 | +++++ | 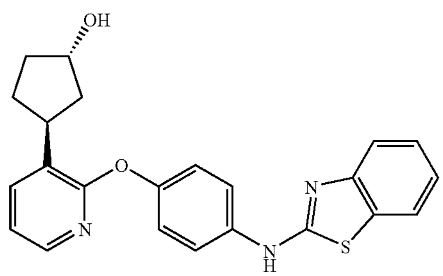 | (1S,3S)-3-(2-(4-(benzo[d]thiazol-2-ylamino)phenoxy)pyridin-3-yl)cyclopentanol | 404.1 | Ex. 229 |
| 307 | +++++ | 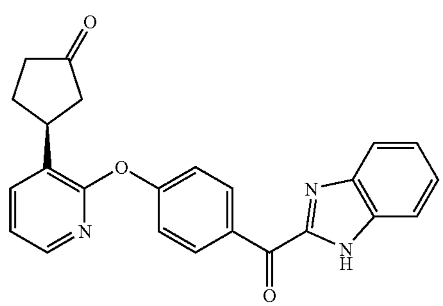 | (S)-3-(2-(4-(1H-benzo[d]imidazole-2-carbonyl)phenoxy)pyridin-3-yl)cyclopentanone | 398.1 | Ex. 230 |
| 308 | +++++ | 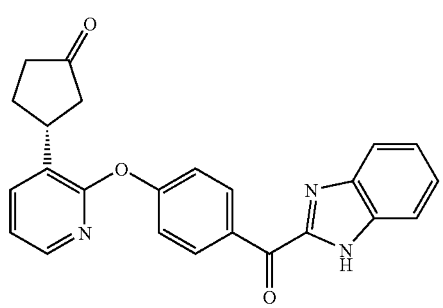 | (R)-3-(2-(4-(1H-benzo[d]imidazole-2-carbonyl)phenoxy)pyridin-3-yl)cyclopentanone | 398.1 | Ex. 230 |
| 309 | +++++ | 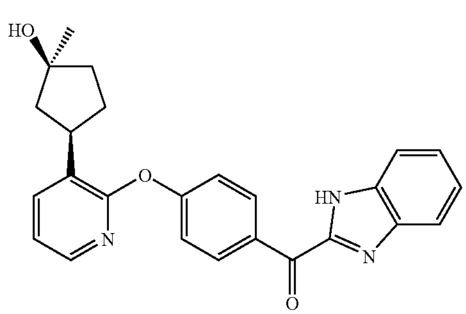 | (1H-benzo[d]imidazol-2-yl)(4-(3-((1R,3S)-3-hydroxy-3-methylcyclopentyl)pyridin-2-yloxy)phenyl)methanone | 414.2 | Ex. 233 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 310 | +++++ | 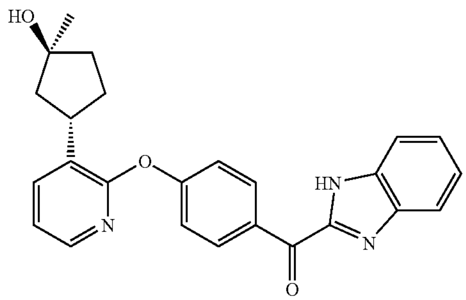 | (1H-benzo[d]imidazol-2-yl)(4-(3-((1S,3S)-3-hydroxy-3-methylcyclopentyl)pyridin-2-yloxy)phenyl)methanone | 414.2 | Ex. 233 |
| 311 | +++++ | 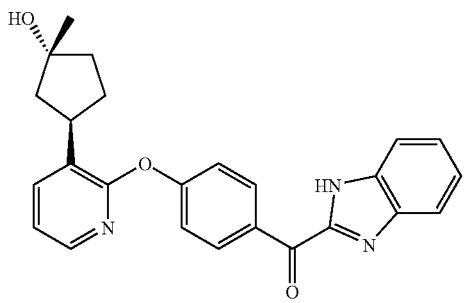 | (1H-benzo[d]imidazol-2-yl)(4-(3-((1R,3R)-3-hydroxy-3-methylcyclopentyl)pyridin-2-yloxy)phenyl)methanone | 414.2 | Ex. 234 |
| 312 | +++++ | 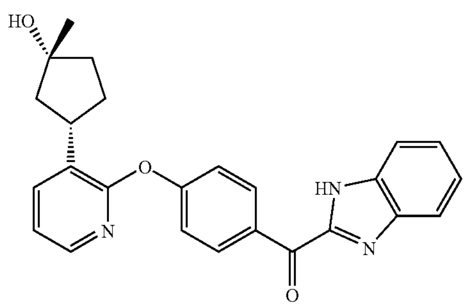 | (1H-benzo[d]imidazol-2-yl)(4-(3-((1S,3R)-3-hydroxy-3-methylcyclopentyl)pyridin-2-yloxy)phenyl)methanone | 414.2 | Ex. 233 |
| 313 | +++++ | 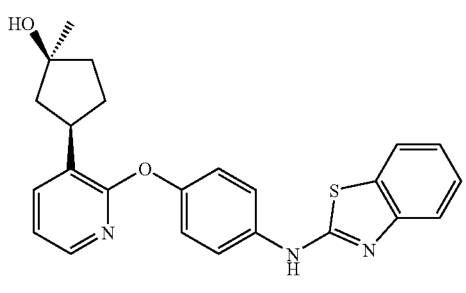 | (1S,3R)-3-(2-(4-(benzo[d]thiazol-2-ylamino)phenoxy)pyridin-3-yl)-1-methylcyclopentanol | 418.2 | Ex. 234 |
| 314 | +++++ | 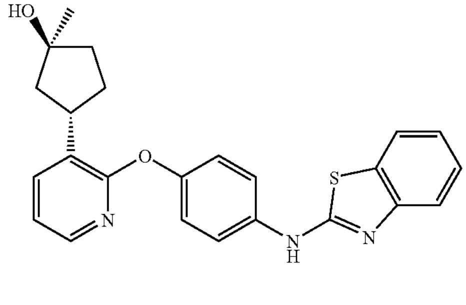 | (1R,3R)-3-(2-(4-(benzo[d]thiazol-2-ylamino)phenoxy)pyridin-3-yl)-1-methylcyclopentanol | 418.2 | Ex. 234 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 315 | +++++ | 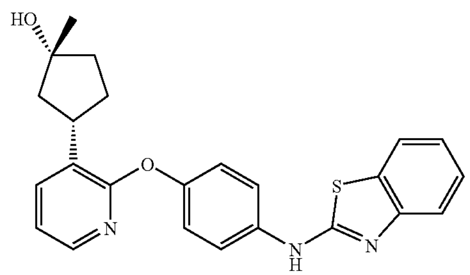 | (1R,3S)-3-(2-(4-(benzo[d]thiazol-2-ylamino)phenoxy)pyridin-3-yl)-1-methylcyclopentanol | 418.2 | Ex. 234 |
| 316 | +++++ | 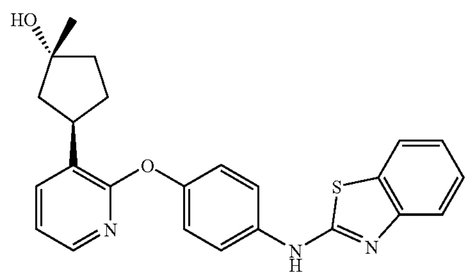 | (1S,3S)-3-(2-(4-(benzo[d]thiazol-2-ylamino)phenoxy)pyridin-3-yl)-1-methylcyclopentanol | 418.2 | Ex. 234 |
| 317 | +++++ | 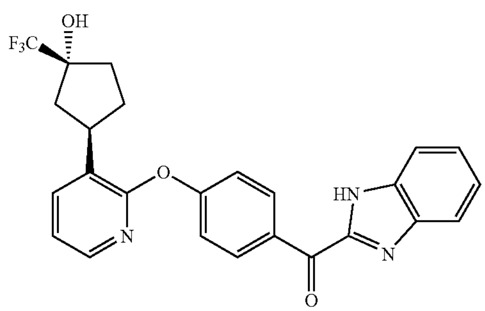 | (1H-benzo[d]imidazol-2-yl)(4-(3-((1R,3R)-3-hydroxy-3-(trifluoromethyl)cyclopentyl)pyridin-2-yloxy)phenyl)methanone | 468.2 | Ex. 232 |
| 318 | +++++ | 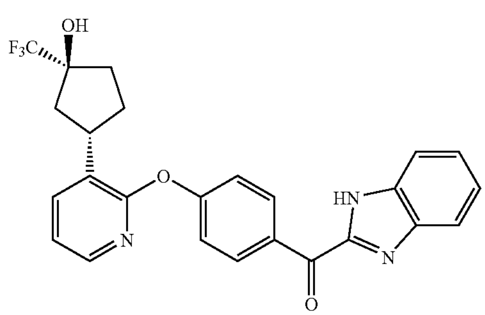 | (1H-benzo[d]imidazol-2-yl)(4-(3-((1S,3S)-3-hydroxy-3-(trifluoromethyl)cyclopentyl)pyridin-2-yloxy)phenyl)methanone | 468.2 | Ex. 232 |
| 319 | +++++ | 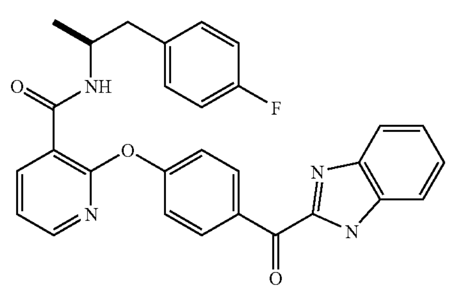 | (S)-2-(4-(1H-benzo[d]imidazole-2-carbonyl)phenoxy)-N-(1-(4-fluorophenyl)propan-2-yl)nicotinamide | 495.0 | Ex. 276 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 320 | +++++ | 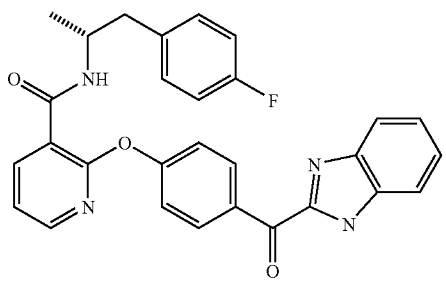 | (R)-2-(4-(1H-benzo[d]imidazole-2-carbonyl)phenoxy)-N-(1-(4-fluorophenyl)propan-2-yl)nicotinamide | 495.0 | Ex. 276 |
| 321 | +++++ | 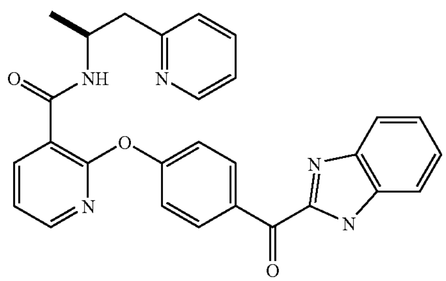 | (S)-2-(4-(1H-benzo[d]imidazole-2-carbonyl)phenoxy)-N-(1-(pyridin-2-yl)propan-2-yl)nicotinamide | 478.1 | Ex. 268 |
| 322 | +++++ | 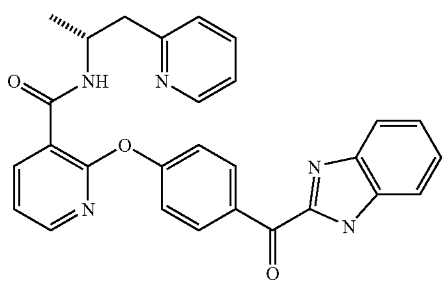 | (R)-2-(4-(1H-benzo[d]imidazole-2-carbonyl)phenoxy)-N-(1-(pyridin-2-yl)propan-2-yl)nicotinamide. | 478.1 | Ex. 268 |
| 323 | +++++ | 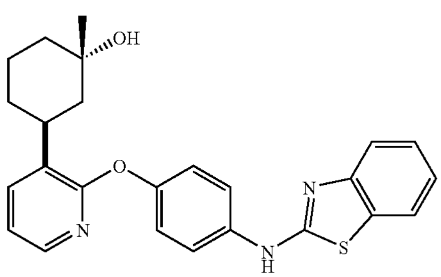 | (1S,3S)-3-(2-(4-(benzo[d]thiazol-2-ylamino)phenoxy)pyridin-3-yl)-1-methylcyclohexanol | 432.1 | Ex. 206 |
| 324 | +++++ | 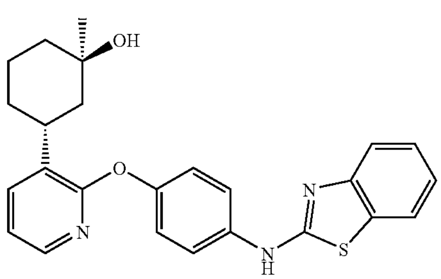 | (1R,3R)-3-(2-(4-(benzo[d]thiazol-2-ylamino)phenoxy)pyridin-3-yl)-1-methylcyclohexanol | 432.1 | Ex. 206 |

TABLE (V)-continued

EXAMPLES 277 TO 326 AND THEIR PREPARATIONS ARE TABULATED BELOW.

| Ex # | IC50 (uM) | structure | IUPAC names | MS | Prep* |
|---|---|---|---|---|---|
| 325 | +++++ | 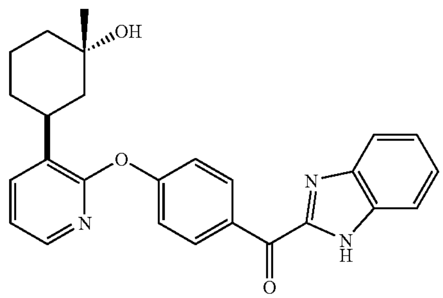 | (1H-benzo[d]imidazol-2-yl)(4-(3-((1S,3S)-3-hydroxy-3-methylcyclohexyl)pyridin-2-yloxy)phenyl)methanone | 428.1 | Ex. 254 |
| 326 | +++++ | 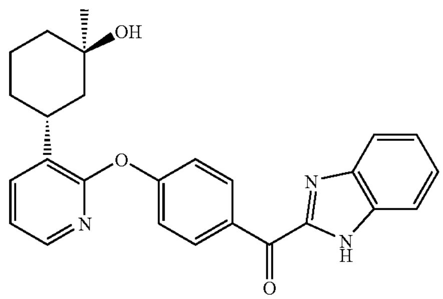 | (1H-benzo[d]imidazol-2-yl)(4-(3-((1R,3R)-3-hydroxy-3-methylcyclohexyl)pyridin-2-yloxy)phenyl)methanone | 428.1 | Ex. 254 |

BIOLOGICAL EXAMPLES

Example 1

MPDE10A7 ENZYME ACTIVITY AND INHIBITION

Enzyme Activity. An IMAP TR-FRET assay was used to analyze the enzyme activity (Molecular Devices Corp., Sunnyvale Calif.). 5 μL of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 μL of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).

Enzyme Inhibition. To check the inhibition profile, 5 μL of serial diluted compounds were incubated with 5 μL of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 μL of diluted fluorescein labeled cAMP or cGMP substrate were added and incubated for 60 min at room temperature. The reaction was stopped by adding 60 μL of diluted binding reagents and plates were read on an Envision (Perkin Elmer, Waltham, Mass.) for time resolved fluorescence resonance energy transfer. The data were analyzed with GraphPad Prism (La Jolla, Calif.).

Exemplary compounds of the invention having useful activity as measured by IC50 are shown in Table VI below. The tabulated IC50 data represent an average IC50 data for each compound.

TABLE VI

Average IC50 for representative compounds of the invention:

| Structure | MS | Average IC50 (μM) |
|---|---|---|
| 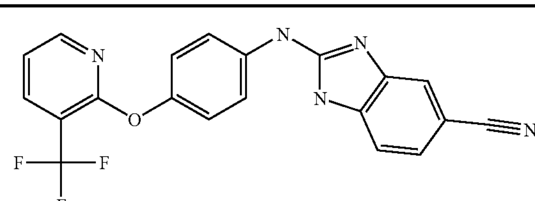 | 395.343 | 0.112 |

TABLE VI-continued

Average IC50 for representative compounds of the invention:

| Structure | MS | Average IC50 (μM) |
|---|---|---|
| 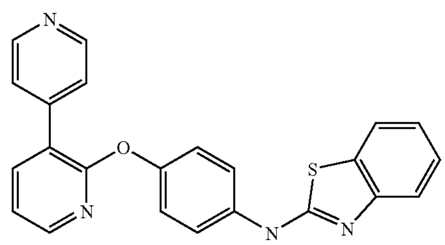 | 396.472 | 0.00399 |
| 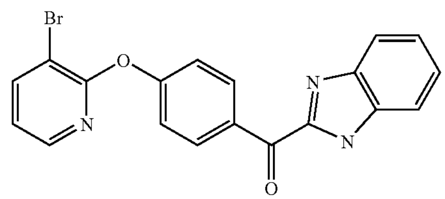 | 394.227 | 0.0447 |
| 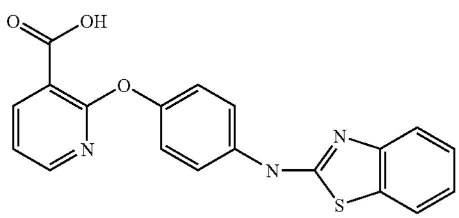 | 363.396 | 0.651 |
| 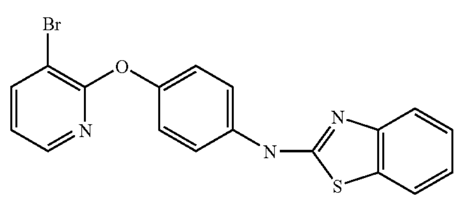 | 398.283 | 0.691 |
| 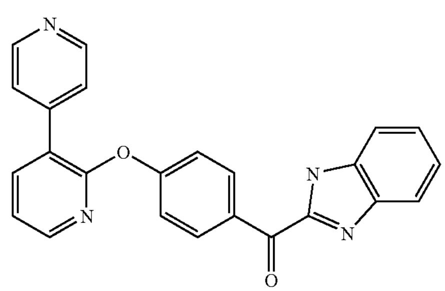 | 392.416 | 0.000256 |
| 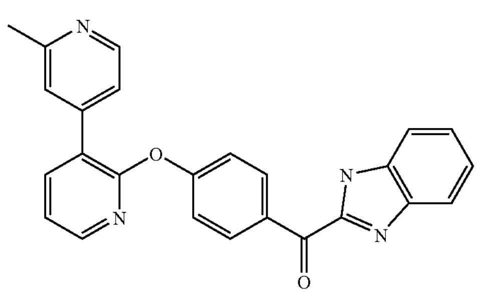 | 406.443 | 0.00076 |

TABLE VI-continued

Average IC50 for representative compounds of the invention:

| Structure | MS | Average IC50 (μM) |
|---|---|---|
| 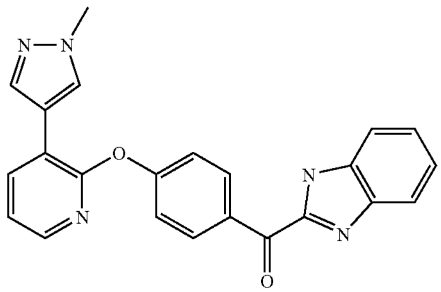 | 395.42 | 0.00628 |
| 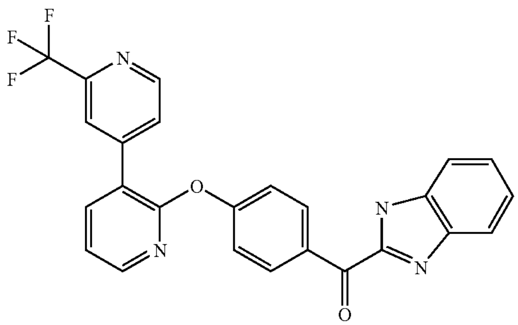 | 460.414 | 0.00617 |
| 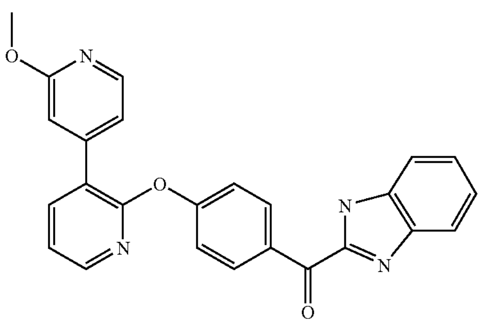 | 422.442 | 0.00161 |
| 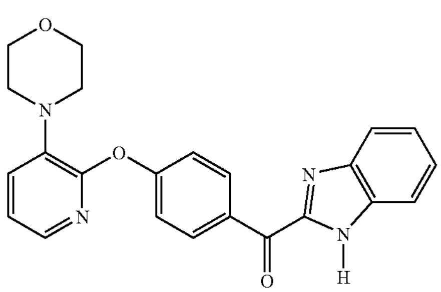 | 400.436 | 0.00159 |

TABLE VI-continued

Average IC50 for representative compounds of the invention:

| Structure | MS | Average IC50 (μM) |
|---|---|---|
| | 420.494 | 0.0069 |
| | 420.494 | 0.0183 |
| 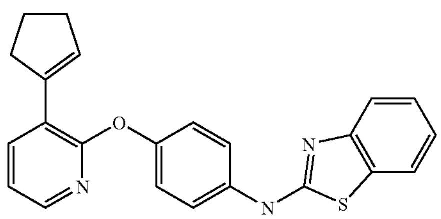 | 385.489 | 0.112 |
| 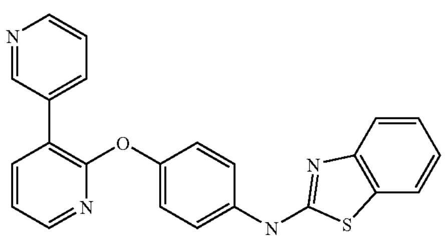 | 396.472 | 0.00129 |
| 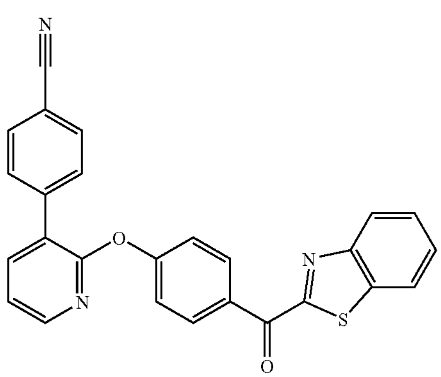 | 433.49 | 0.245 |

TABLE VI-continued
Average IC50 for representative compounds of the invention:
| Structure | MS | Average IC50 (μM) |
|---|---|---|
| 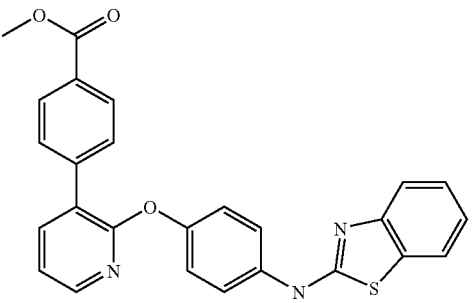 | 453.52 | 0.0723 |
| 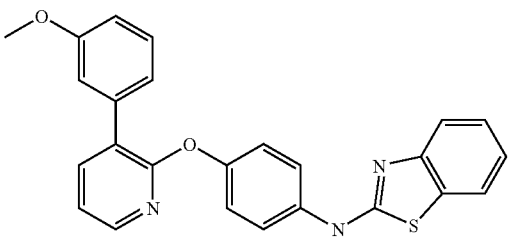 | 425.51 | 0.0389 |
| 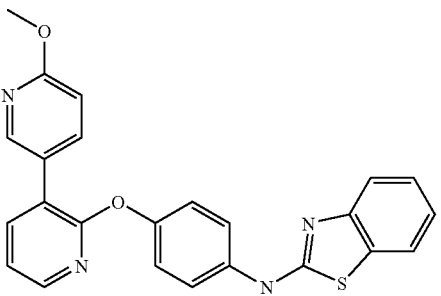 | 426.498 | 0.0237 |
| 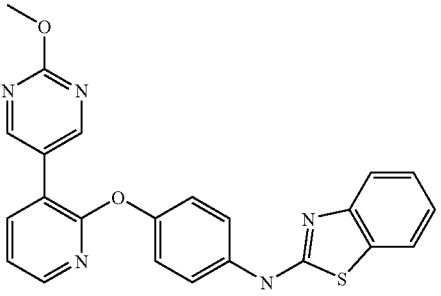 | 427.486 | 0.00187 |
| 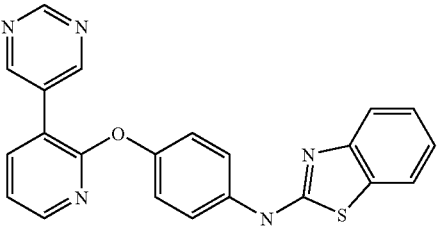 | 397.461 | 0.000303 |

TABLE VI-continued

Average IC50 for representative compounds of the invention:

| Structure | MS | Average IC50 (μM) |
|---|---|---|
| (structure) | 409.468 | 0.032 |
| (structure) | 430.918 | 0.00104 |
| (structure) | 392.46 | 0.0266 |
| (structure) | 410.499 | 0.005 |
| (structure) | 414.463 | 0.0102 |

TABLE VI-continued

Average IC50 for representative compounds of the invention:

| Structure | MS | Average IC50 (μM) |
|---|---|---|
| (structure) | 445.545 | 0.00663 |
| (structure) | 446.43 | 0.118 |
| (structure) | 464.47 | 0.0367 |
| (structure) | 421.458 | 0.023 |
| (structure) | 478.344 | 1.61 |

TABLE VI-continued
Average IC50 for representative compounds of the invention:
| Structure | MS | Average IC50 (μM) |
|---|---|---|
| 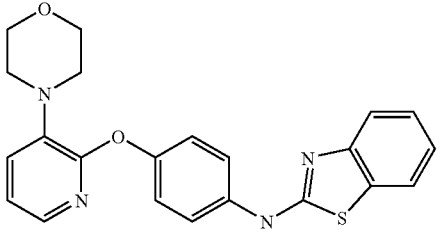 | 404.492 | 0.000962 |
| 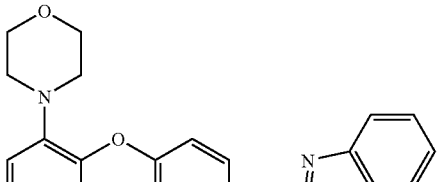 | 417.487 | 0.0988 |
| 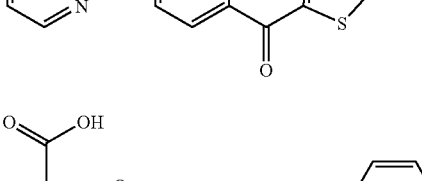 | 359.34 | 0.273 |
| 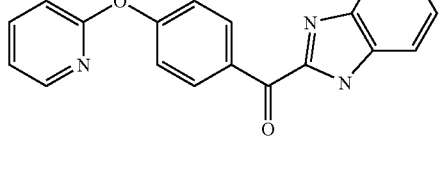 | 397.461 | 0.0224 |
| 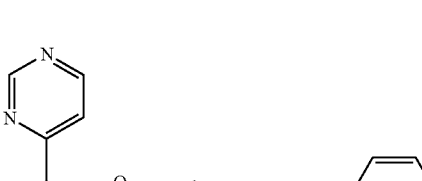 | 463.495 | 0.00174 |

TABLE VI-continued

Average IC50 for representative compounds of the invention:

| Structure | MS | Average IC50 (μM) |
|---|---|---|
| 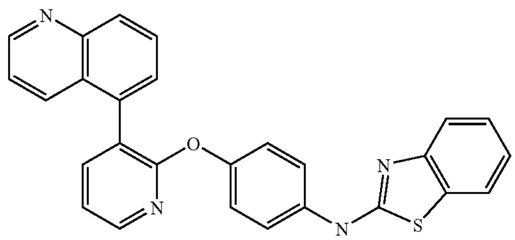 | 446.532 | 0.00691 |
| 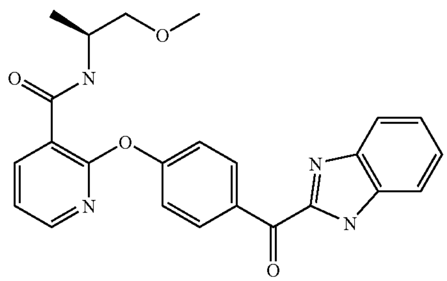 | 430.462 | 0.0128 |
| 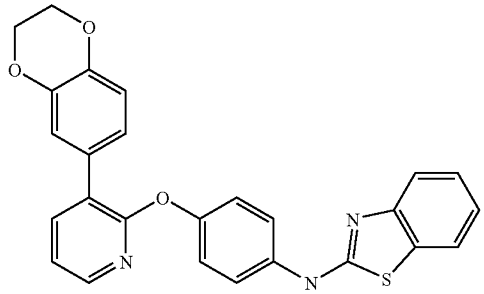 | 453.52 | 0.0439 |
| 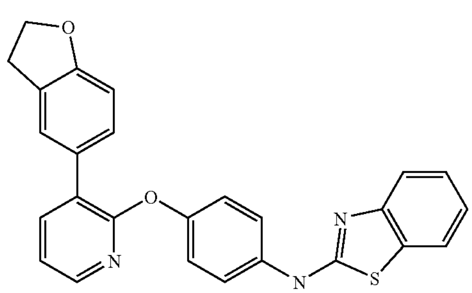 | 437.521 | 0.0424 |

TABLE VI-continued

Average IC50 for representative compounds of the invention:

| Structure | MS | Average IC50 (μM) |
|---|---|---|
| 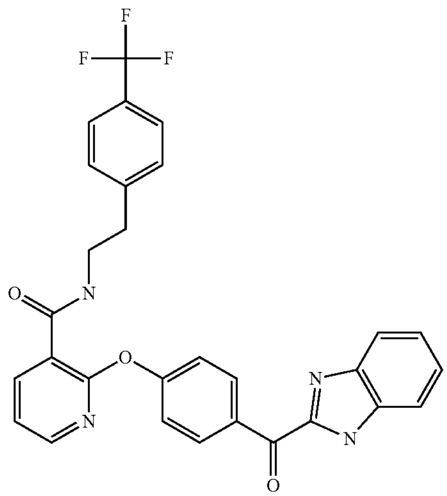 | 530.504 | 0.0101 |
| 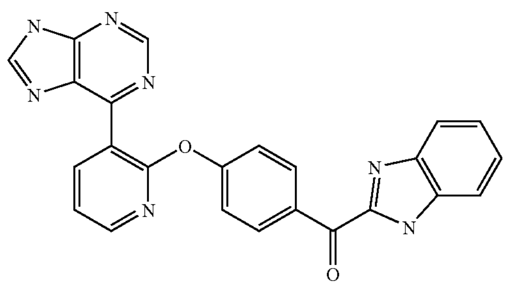 | 433.43 | 0.0327 |
| | 393.405 | 0.00745 |
| | 393.405 | 0.000271 |

TABLE VI-continued

Average IC50 for representative compounds of the invention:

| Structure | MS | Average IC50 (μM) |
|---|---|---|
| (structure) | 392.416 | 0.00026 |
| (structure) | 406.443 | 0.000177 |
| (structure) | 367.766 | 0.0556 |
| (structure) | 412.217 | 0.0746 |
| (structure) | 395.215 | 0.0143 |
| (structure) | 411.278 | 3.94 |

TABLE VI-continued

Average IC50 for representative compounds of the invention:

| Structure | MS | Average IC50 (μM) |
|---|---|---|
| 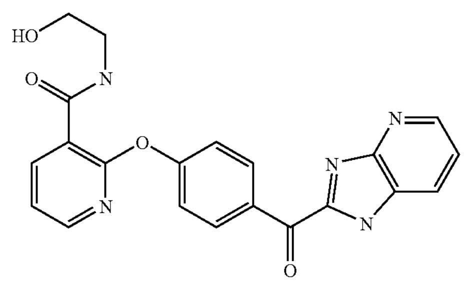 | 402.408 | 0.0274 |
| 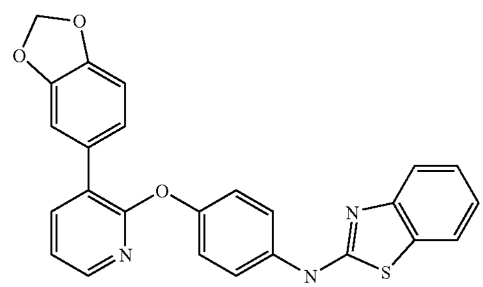 | 439.493 | 0.0591 |
| 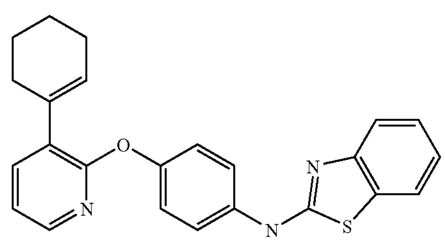 | 399.516 | 0.072 |
| 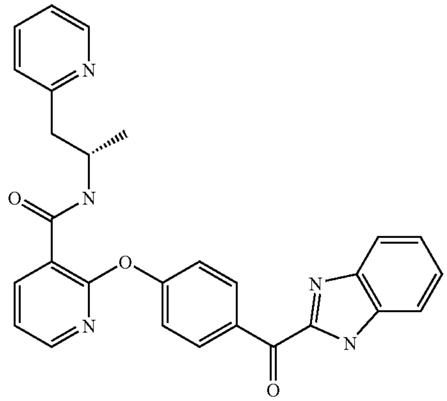 | 477.522 | 0.000971 |

TABLE VI-continued

Average IC50 for representative compounds of the invention:

| Structure | MS | Average IC50 (μM) |
|---|---|---|
| | | |
| 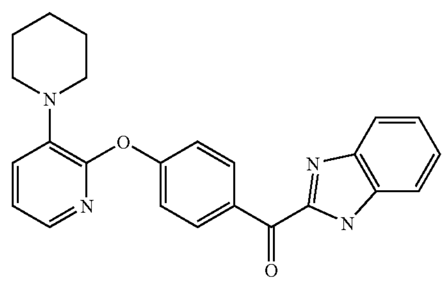 | 398.464 | 0.0133 |
| 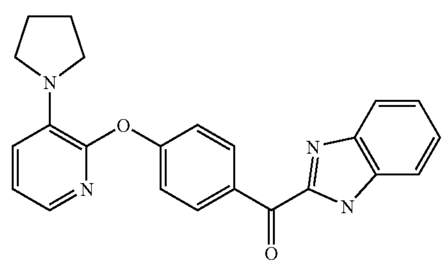 | 384.437 | 0.014 |
| 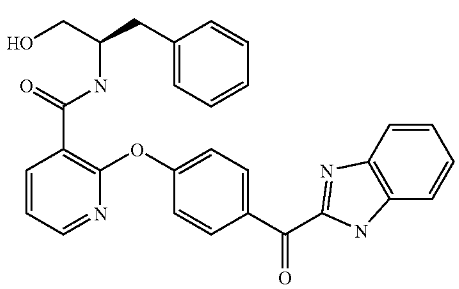 | 492.533 | 0.0128 |

TABLE VI-continued
Average IC50 for representative compounds of the invention:
| Structure | MS | Average IC50 (μM) |
|---|---|---|
| 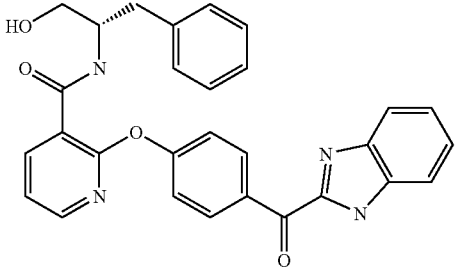 | 492.533 | 0.000839 |
| 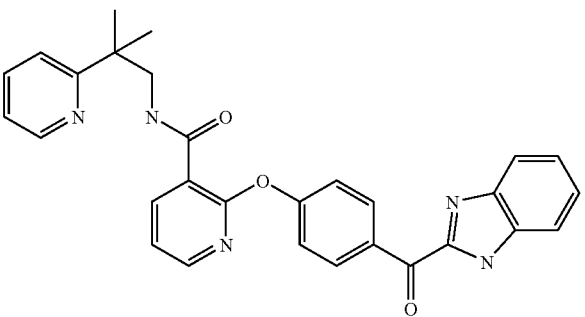 | 491.549 | 0.00148 |
| 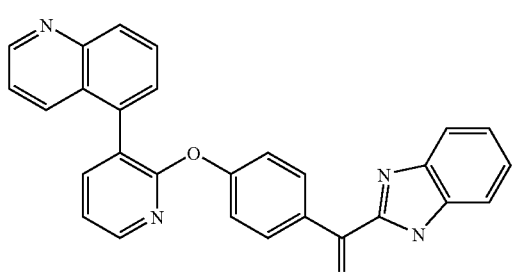 | 442.476 | 0.000342 |
| 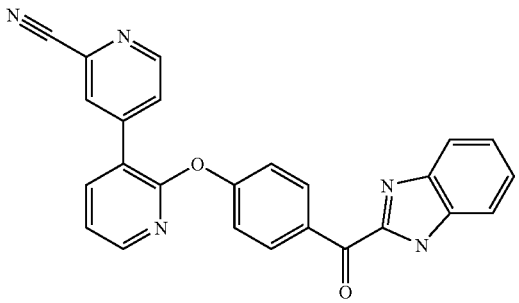 | 417.427 | 0.00278 |

TABLE VI-continued

Average IC50 for representative compounds of the invention:

| Structure | MS | Average IC50 (μM) |
|---|---|---|
| 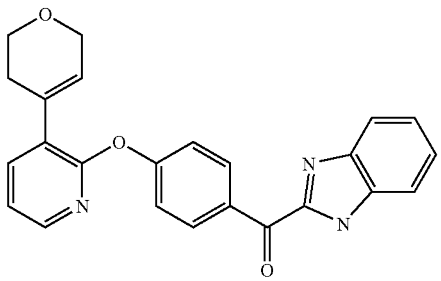 | 397.432 | 0.000752 |
| 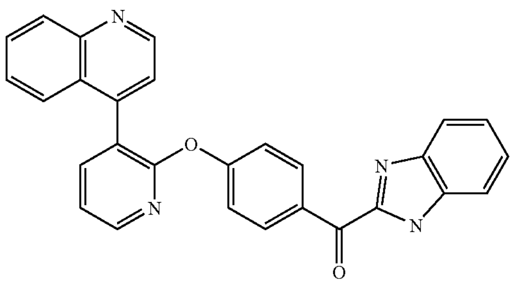 | 442.476 | 0.00067 |
| 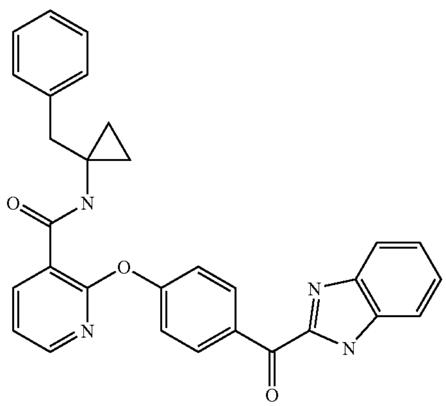 | 488.545 | 0.000168 |
| 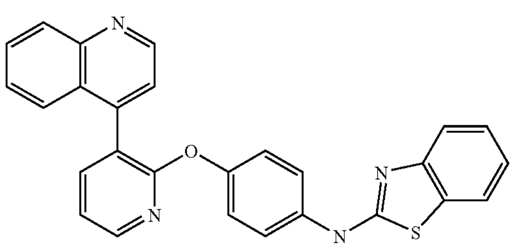 | 446.532 | 0.00722 |
| 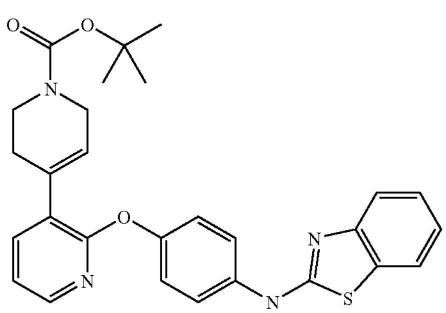 | 500.62 | 0.0444 |

TABLE VI-continued

Average IC50 for representative compounds of the invention:

| Structure | MS | Average IC50 (μM) |
|---|---|---|
| 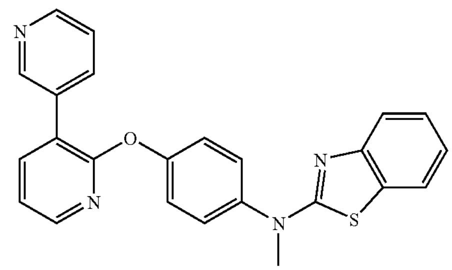 | 410.499 | 0.0152 |
| 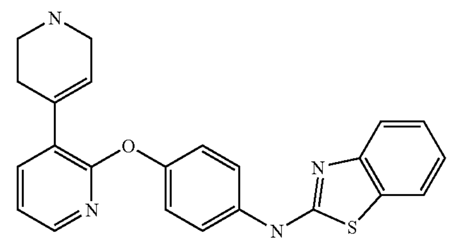 | 400.504 | 0.00168 |
| 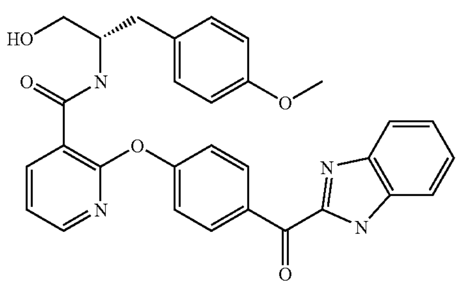 | 522.558 | 0.0014 |
| 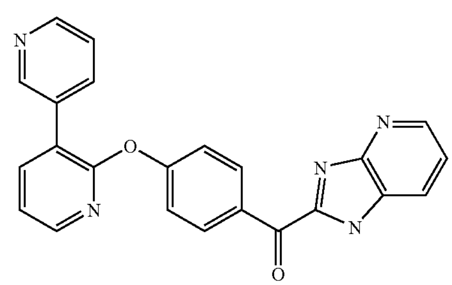 | 393.405 | 0.00481 |
| 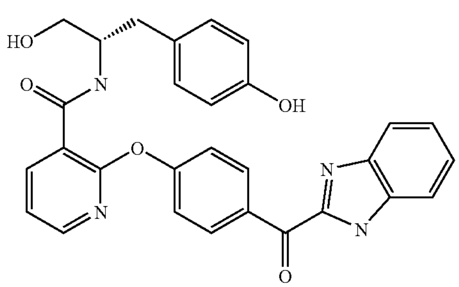 | 508.532 | 0.00365 |

TABLE VI-continued

Average IC50 for representative compounds of the invention:

| Structure | MS | Average IC50 (μM) |
|---|---|---|
| (structure) | 418.519 | 0.0242 |
| (structure) | 462.507 | 0.00272 |
| (structure) | 401.488 | 0.00221 |
| (structure) | 393.448 | 0.000219 |

TABLE VI-continued

Average IC50 for representative compounds of the invention:

| Structure | MS | Average IC50 (μM) |
|---|---|---|
| 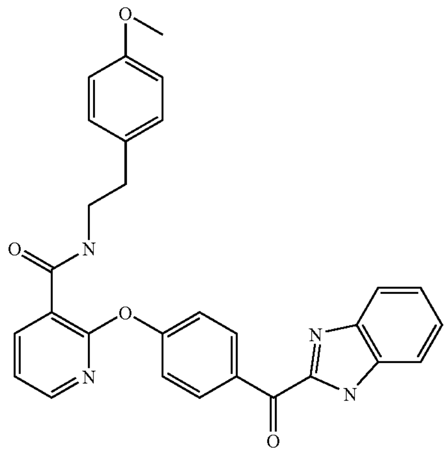 | 492.533 | 0.00247 |
| 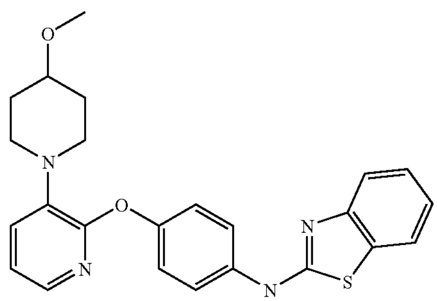 | 432.546 | 0.00316 |
| 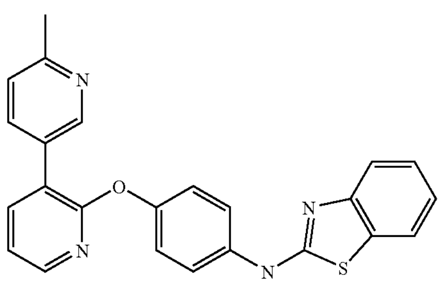 | 410.499 | 0.00287 |
| 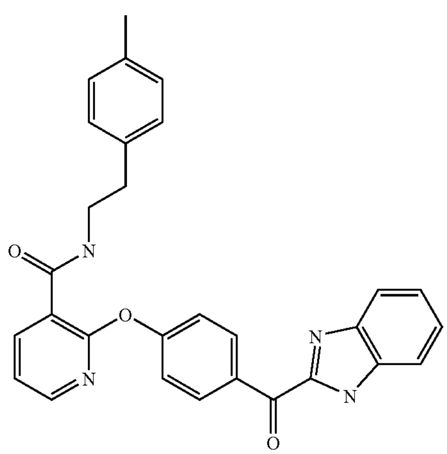 | 476.534 | 0.00311 |

TABLE VI-continued
Average IC50 for representative compounds of the invention:
| Structure | MS | Average IC50 (μM) |
|---|---|---|
| 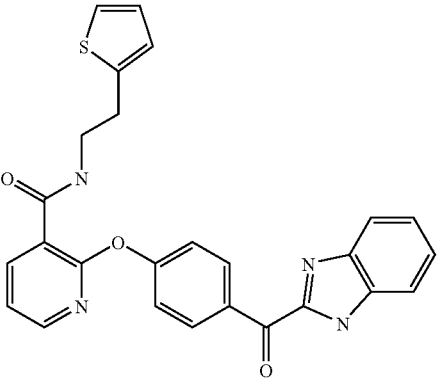 | 468.535 | 0.00295 |
| 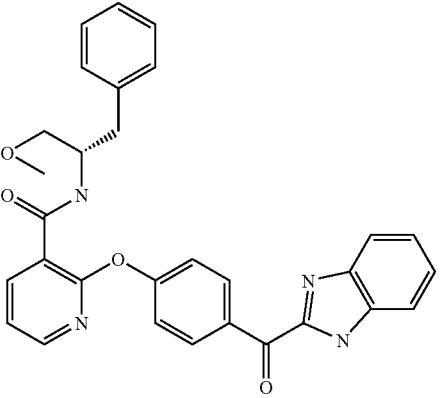 | 506.559 | 0.00164 |
| 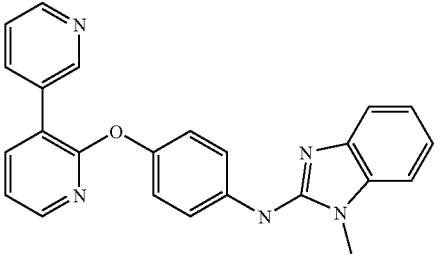 | 393.448 | 0.000249 |
| 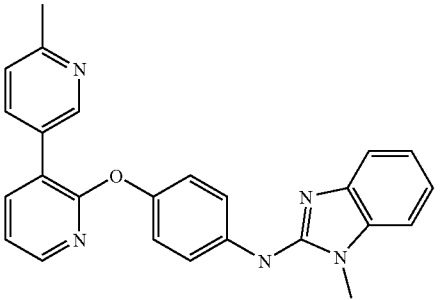 | 407.475 | 0.000338 |

TABLE VI-continued

Average IC50 for representative compounds of the invention:

| Structure | MS | Average IC50 (μM) |
|---|---|---|
| 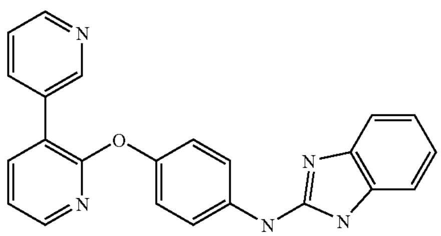 | 379.421 | 0.000179 |
| 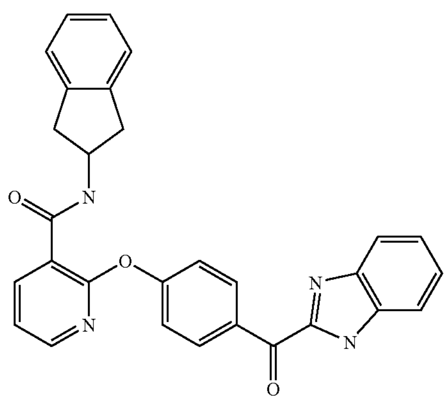 | 474.518 | 0.0567 |
| 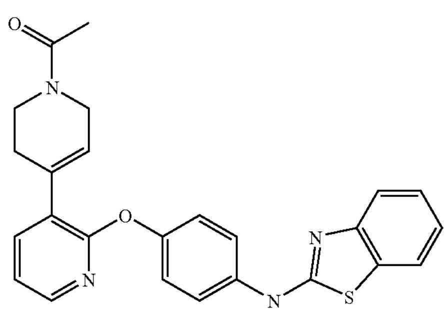 | 442.541 | 0.000363 |
| 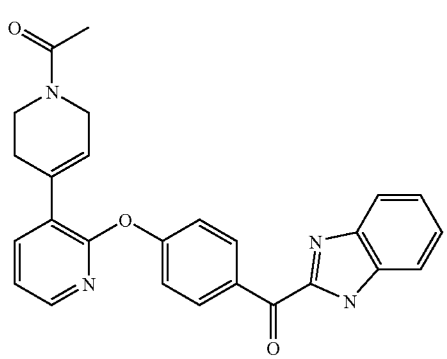 | 438.485 | 0.000194 |

TABLE VI-continued

Average IC50 for representative compounds of the invention:

| Structure | MS | Average IC50 (μM) |
|---|---|---|
| 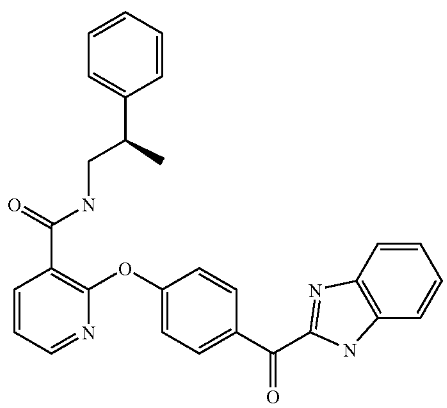 | 476.534 | 0.00269 |
| 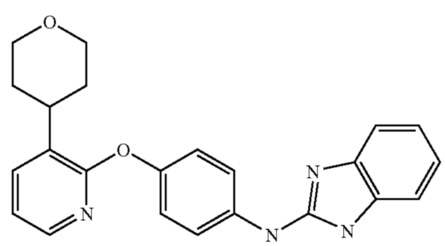 | 386.453 | 0.000267 |
| 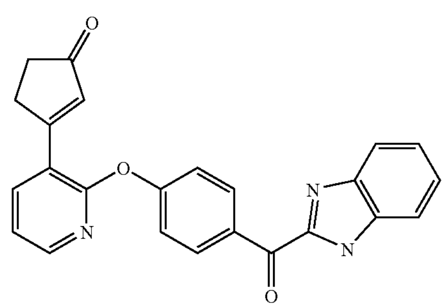 | 395.416 | 0.00101 |
| 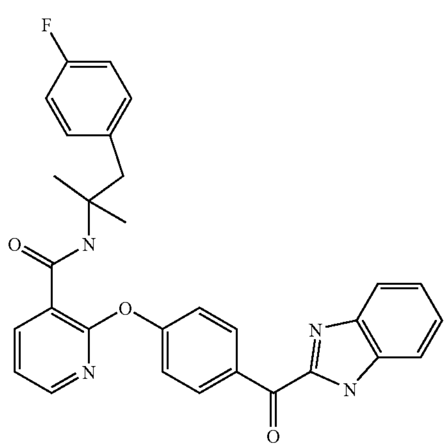 | 508.551 | 0.00997 |

TABLE VI-continued
Average IC50 for representative compounds of the invention:
| Structure | MS | Average IC50 (μM) |
|---|---|---|
| 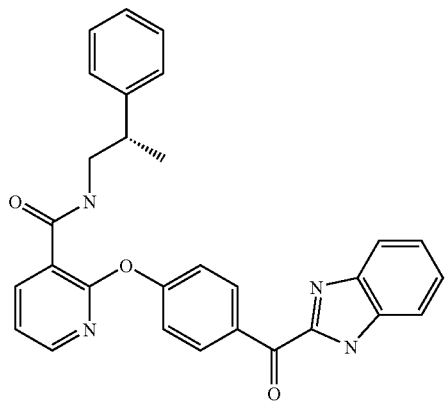 | 476.534 | 0.00881 |
| 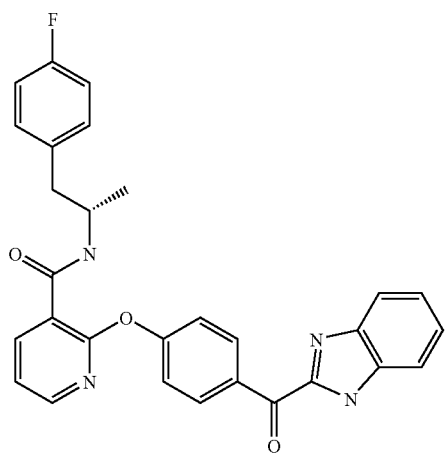 | 494.524 | 0.00134 |
| 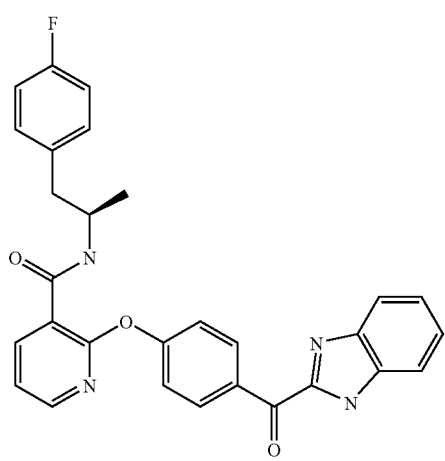 | | |

TABLE VI-continued

Average IC50 for representative compounds of the invention:

| Structure | MS | Average IC50 (μM) |
|---|---|---|
| (acetyl-piperidinyl-pyridinyl-O-phenyl-CH(OH)-benzimidazole) | 442.516 | 0.0042 |
| (acetyl-piperidinyl-pyridinyl-O-phenyl-CH(OH)-benzimidazole, stereoisomer) | | |
| (tetrahydropyranyl-pyridinyl-O-phenyl-CH(OH)-benzimidazole) | 401.464 | 0.0457 |
| (tetrahydropyranyl-pyridinyl-O-phenyl-C(=O)-benzimidazole) | 399.448 | 0.00017 |
| (cyclopentenone-pyridinyl-O-phenyl-NH-benzothiazole) | 399.472 | 0.00284 |

TABLE VI-continued

Average IC50 for representative compounds of the invention:

| Structure | MS | Average IC50 (μM) |
|---|---|---|
| 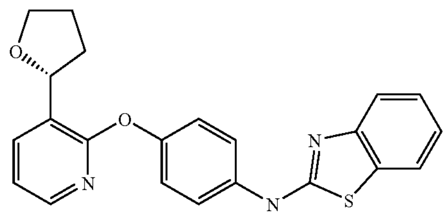 | 389.477 | 0.0542 |
| 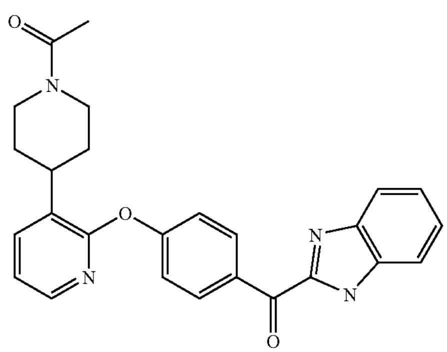 | 440.501 | 0.000158 |
| 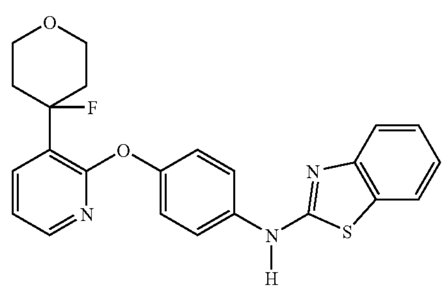 | 421.494 | 0.00212 |
| 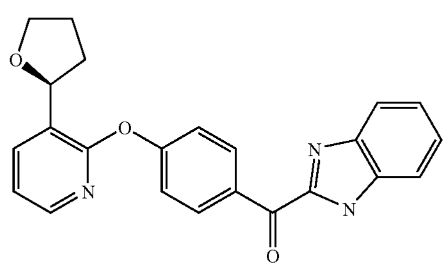 | 385.421 | 0.00497 |

TABLE VI-continued

Average IC50 for representative compounds of the invention:

| Structure | MS | Average IC50 (μM) |
|---|---|---|
| | | |
| 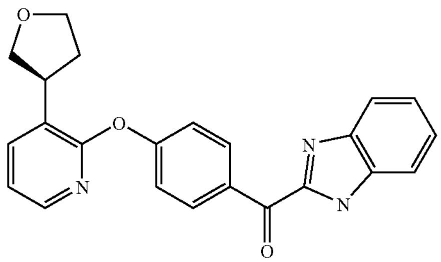 | 385.421 | 0.000232 |
| | | |
| 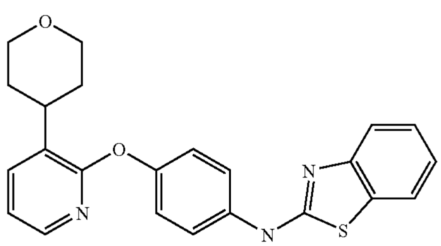 | 403.504 | 0.000436 |
| 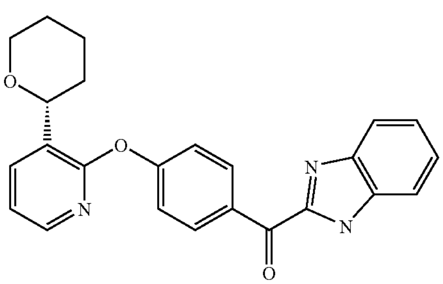 | 399.448 | 0.00879 |

TABLE VI-continued

Average IC50 for representative compounds of the invention:

| Structure | MS | Average IC50 (μM) |
|---|---|---|
| | | |
| 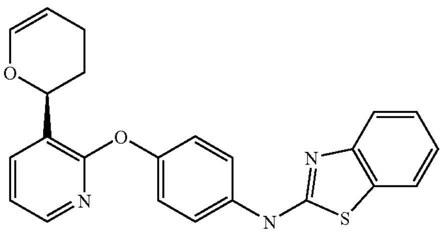 | 401.488 | 0.0223 |
| 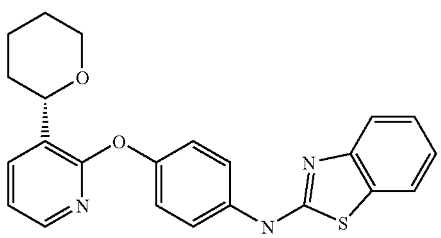 | 403.504 | 0.0313 |
| 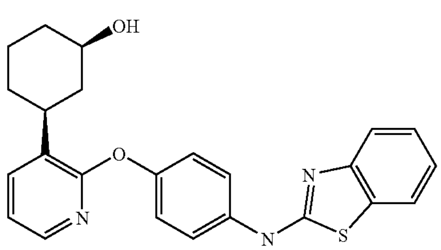 | 417.531 | 0.00104 |

TABLE VI-continued
Average IC50 for representative compounds of the invention:
| Structure | MS | Average IC50 (μM) |
|---|---|---|
| 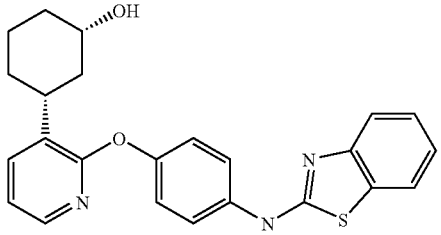 | | |
| 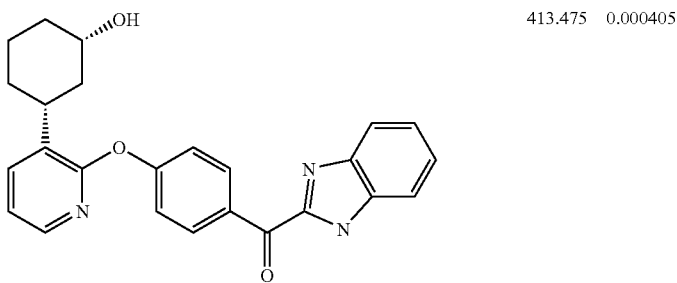 | 413.475 | 0.000405 |
| 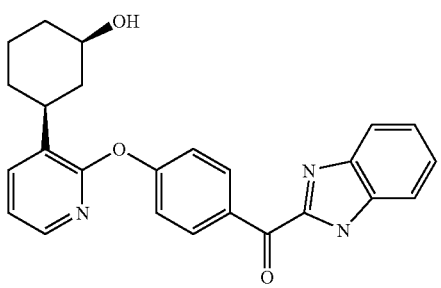 | | |
| 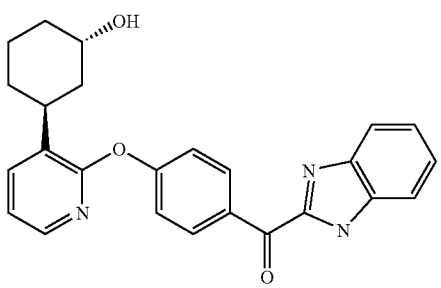 | | |

TABLE VI-continued

Average IC50 for representative compounds of the invention:

| Structure | MS | Average IC50 (μM) |
|---|---|---|
| | | |
| 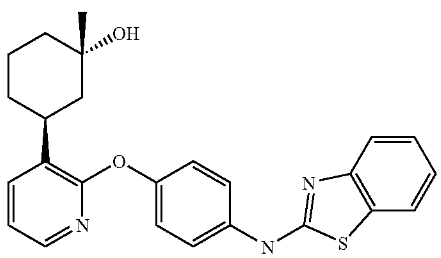 | 431.558 | 0.00687 |
| | | |
| 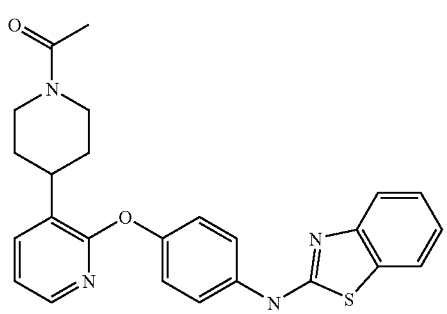 | 444.557 | 0.000175 |
| 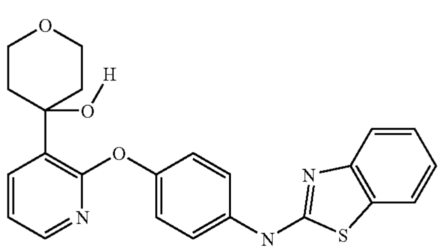 | 419.503 | 0.00049 |

TABLE VI-continued

| Structure | MS | Average IC50 (μM) |
|---|---|---|
| 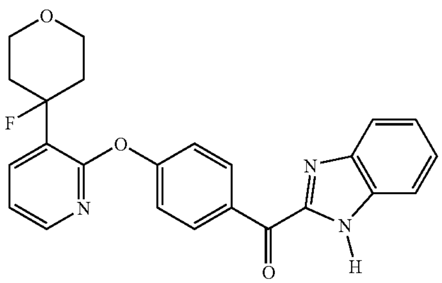 | 417.438 | 0.000311 |
| 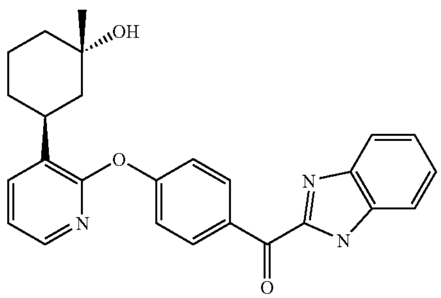 | 427.502 | 0.00114 |
| | | |
| 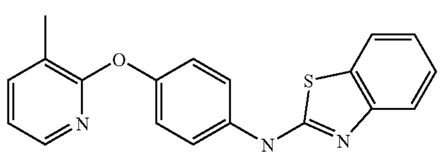 | 445.279 | 0.04 |
| 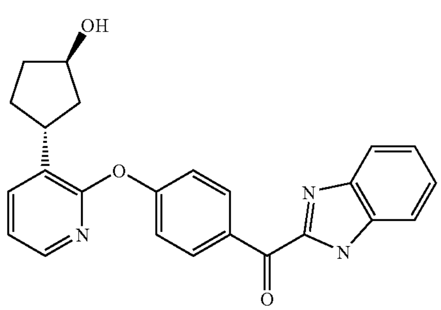 | 399.448 | 0.000167 |

TABLE VI-continued

Average IC50 for representative compounds of the invention:

| Structure | MS | Average IC50 (μM) |
|---|---|---|
| 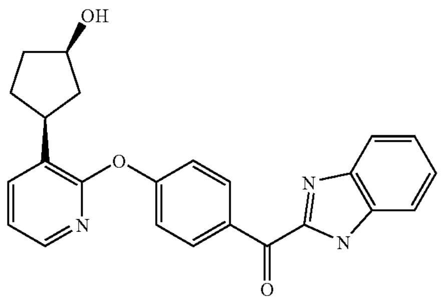 | 399.448 | 0.000405 |
| 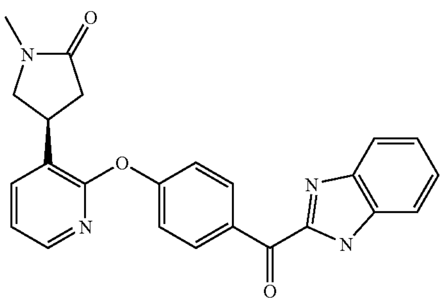 | 412.447 | 0.000207 |
| | | |
| 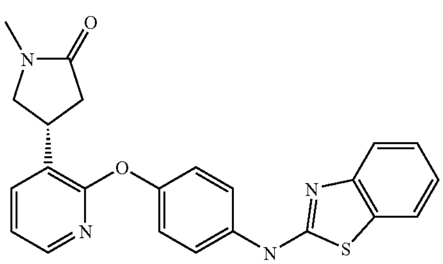 | 416.503 | 0.000195 |
| | | |

TABLE VI-continued

Average IC50 for representative compounds of the invention:

| Structure | MS | Average IC50 (μM) |
|---|---|---|
| 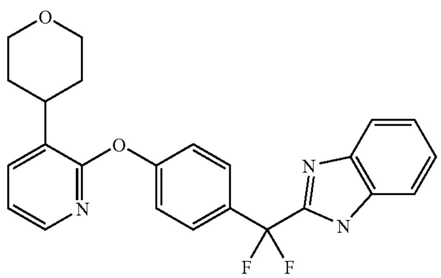 | 421.445 | 0.0116 |
| 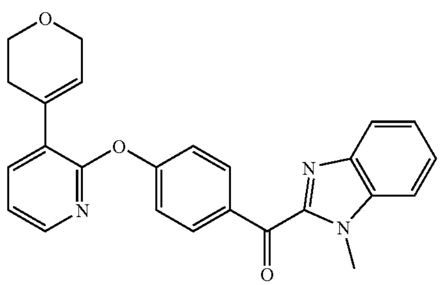 | 411.459 | 0.000692 |
| 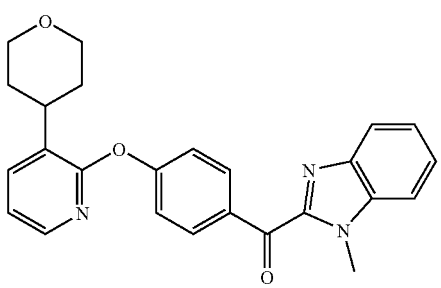 | 413.475 | 0.000509 |
| 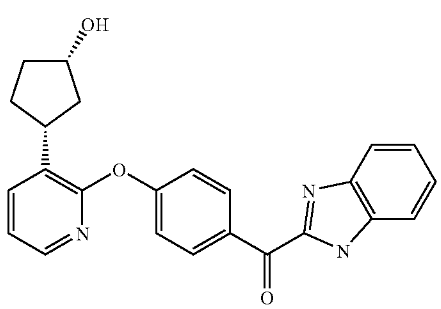 | 399.448 | 0.000675 |
| 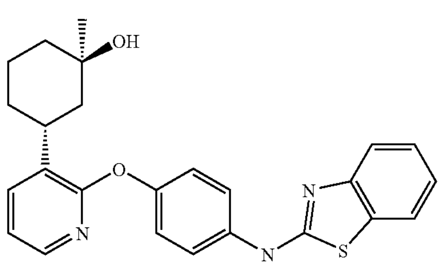 | 431.558 | 0.00366 |

TABLE VI-continued

Average IC50 for representative compounds of the invention:

| Structure | MS | Average IC50 (μM) |
|---|---|---|
| 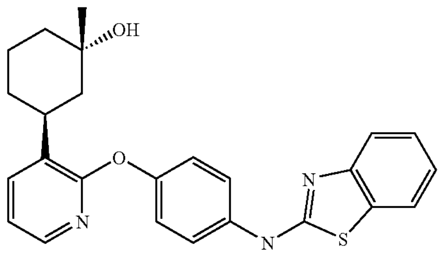 | 431.558 | 0.00382 |
| 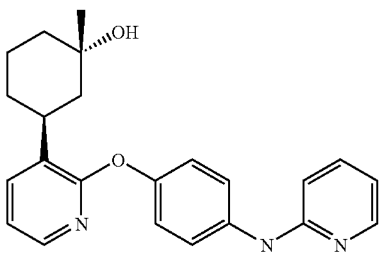 | 375.47 | 0.0242 |
| 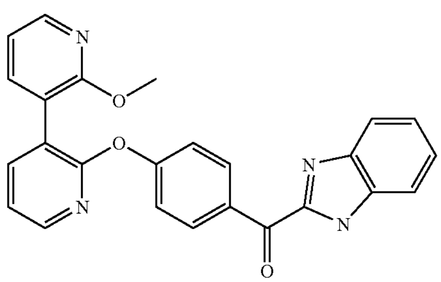 | 422.442 | 0.00116 |
| 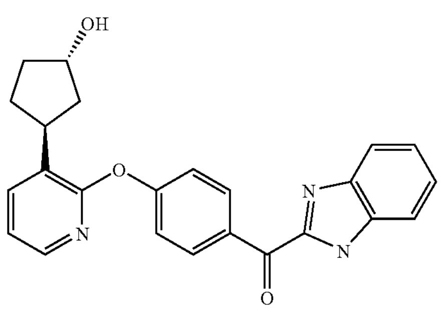 | 399.448 | 0.000551 |

TABLE VI-continued

Average IC50 for representative compounds of the invention:

| Structure | MS | Average IC50 (μM) |
|---|---|---|
| [structure] | 494.524 | 0.013 |
| [structure] | 494.524 | 0.000135 |
| [structure] | 415.515 | 0.00129 |
| [structure] | 422.442 | 0.000622 |

TABLE VI-continued

Average IC50 for representative compounds of the invention:

| Structure | MS | Average IC50 (μM) |
|---|---|---|
| 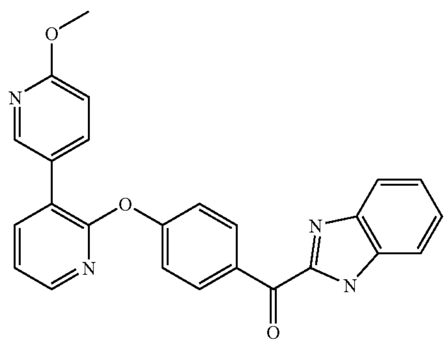 | 422.442 | 0.00127 |
| | 477.522 | 0.000541 |
| | 477.522 | 0.00683 |
| 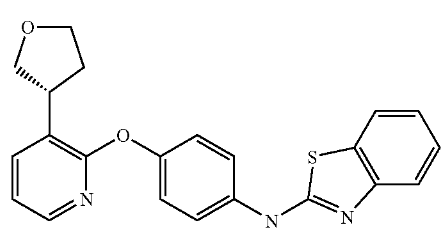 | 389.477 | 0.000814 |

TABLE VI-continued

Average IC50 for representative compounds of the invention:

| Structure | MS | Average IC50 (μM) |
|---|---|---|
| | | |
| | 413.475 | 0.000547 |
| | 413.475 | 0.00099 |
| | 427.502 | 0.00162 |
| | 427.502 | 0.00122 |

TABLE VI-continued

Average IC50 for representative compounds of the invention:

| Structure | MS | Average IC50 (μM) |
|---|---|---|
| | 431.558 | 0.0126 |
| | 427.502 | 0.00163 |
| | 427.502 | 0.00142 |
| | 431.558 | 0.00451 |
| 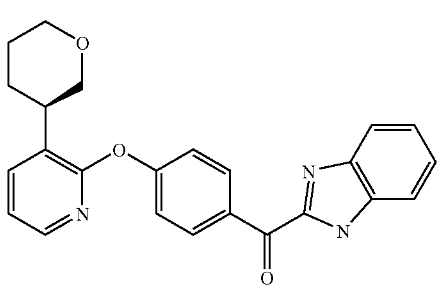 | 399.448 | 0.000521 |

TABLE VI-continued

Average IC50 for representative compounds of the invention:

| Structure | MS | Average IC50 (μM) |
|---|---|---|
| 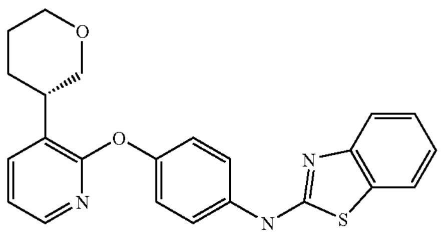 | 403.504 | 0.00249 |
| 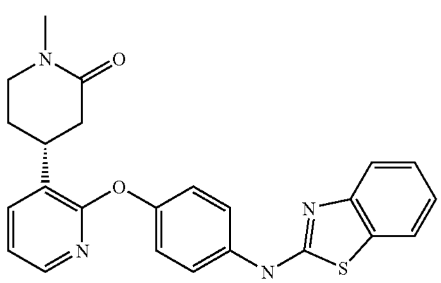 | 430.53 | 0.00101 |

TABLE VI-continued

Average IC50 for representative compounds of the invention:

| Structure | MS | Average IC50 (μM) |
|---|---|---|
| 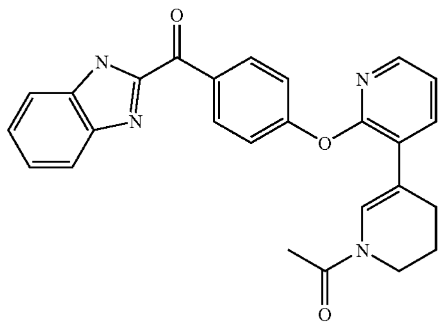 | 438.485 | 0.000214 |
| 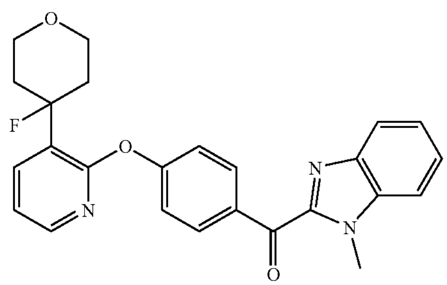 | 431.465 | 0.000749 |
| 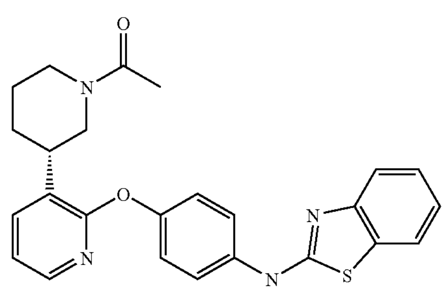 | 444.557 | 0.000268 |
| | | |
| 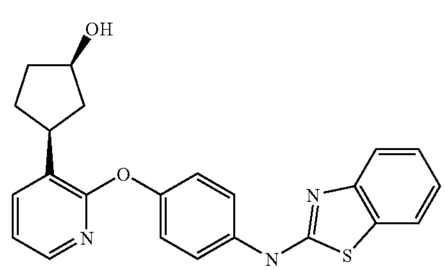 | 403.504 | 0.00264 |

TABLE VI-continued
Average IC50 for representative compounds of the invention:
| Structure | MS | Average IC50 (μM) |
|---|---|---|
| 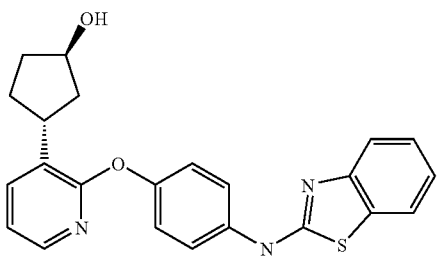 | 403.504 | 0.000286 |
| 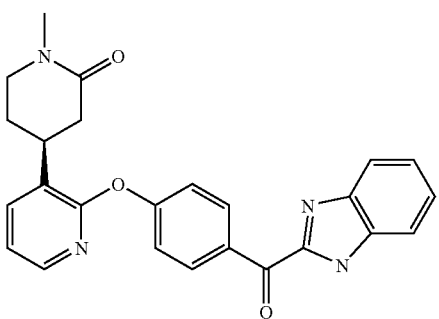 | 426.474 | 0.000644 |
| 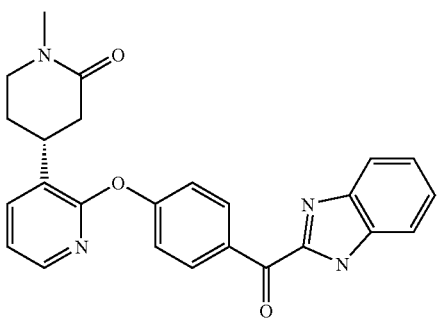 | | |
| 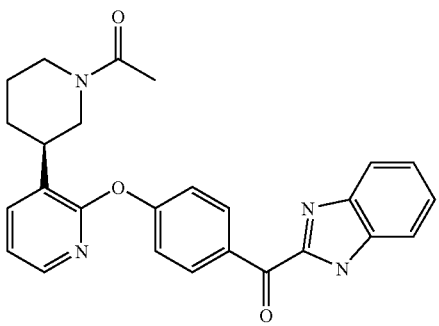 | 440.501 | 0.0000503 |

TABLE VI-continued
Average IC50 for representative compounds of the invention:
| Structure | MS | Average IC50 (μM) |
|---|---|---|
| 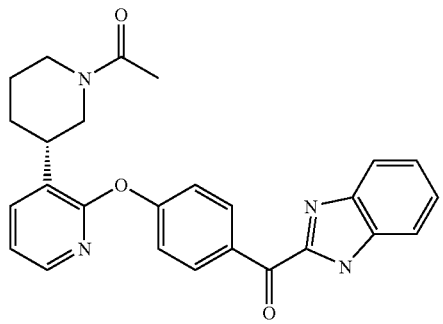 | | |
| 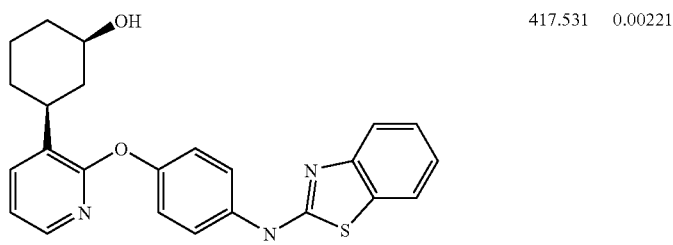 | 417.531 | 0.00221 |
| 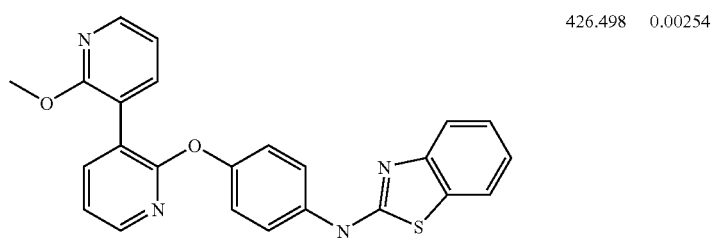 | 426.498 | 0.00254 |
| 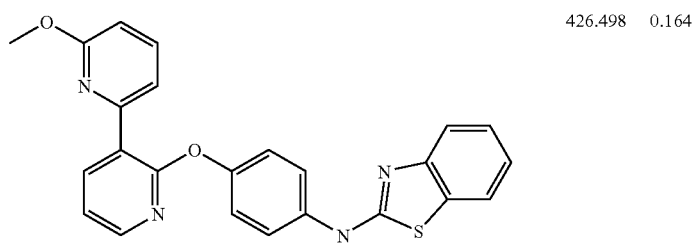 | 426.498 | 0.164 |

TABLE VI-continued
Average IC50 for representative compounds of the invention:
| Structure | MS | Average IC50 (μM) |
|---|---|---|
| 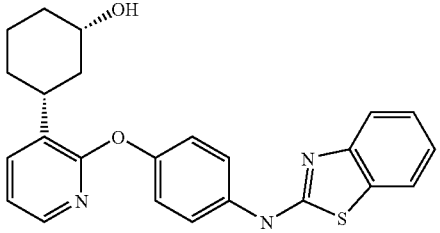 | 417.531 | 0.00375 |
| 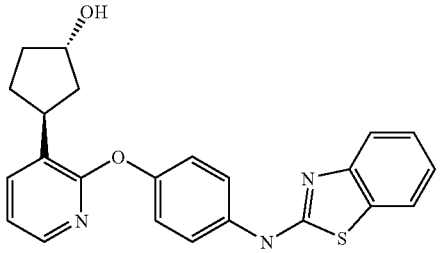 | 403.504 | 0.00121 |
| 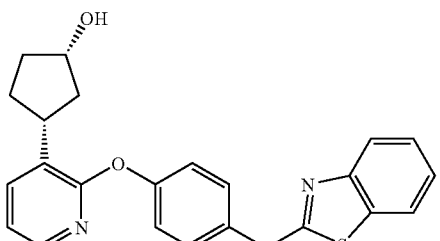 | 403.504 | 0.00254 |
| 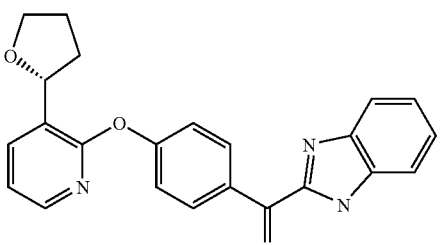 | 385.421 | 0.00683 |
| 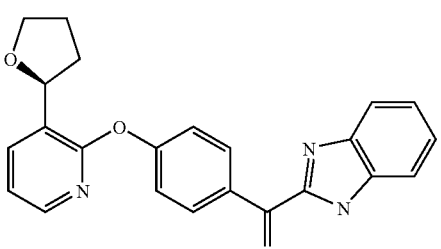 | 385.421 | 0.0133 |

TABLE VI-continued

Average IC50 for representative compounds of the invention:

| Structure | MS | Average IC50 (μM) |
|---|---|---|
| | 385.421 | 0.000582 |
| | 385.421 | 0.00092 |
| | 417.531 | 0.00638 |
| | 417.531 | 0.00163 |

TABLE VI-continued

Average IC50 for representative compounds of the invention:

| Structure | MS | Average IC50 (μM) |
|---|---|---|
|  | 389.477 | 0.000865 |
|  | 389.477 | 0.00045 |
| 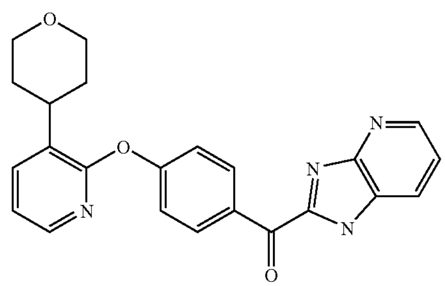 | 400.436 | 0.00134 |
| 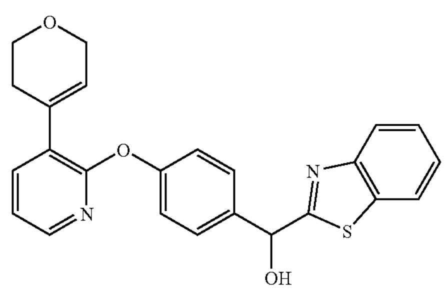 | 416.499 | 0.516 |
| 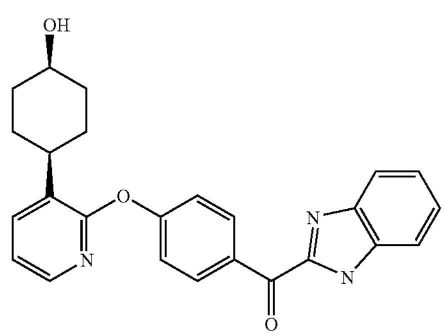 | 413.475 | 0.000308 |

TABLE VI-continued

Average IC50 for representative compounds of the invention:

| Structure | MS | Average IC50 (μM) |
|---|---|---|
| 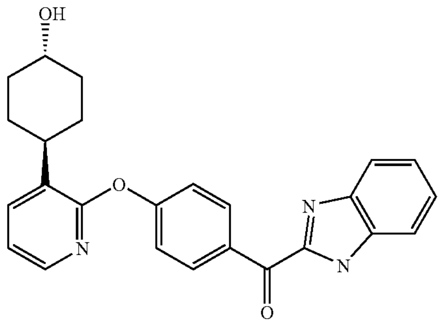 | 413.475 | 0.000101 |
| | 481.472 | 0.00149 |
| | 481.472 | 0.0127 |
| 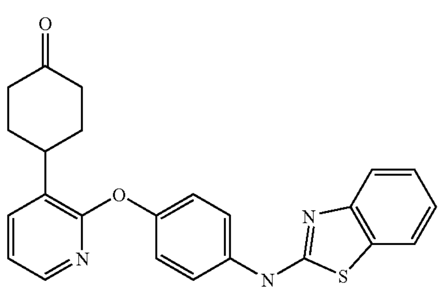 | 415.515 | 0.000123 |

TABLE VI-continued

Average IC50 for representative compounds of the invention:

| Structure | MS | Average IC50 (μM) |
|---|---|---|
| 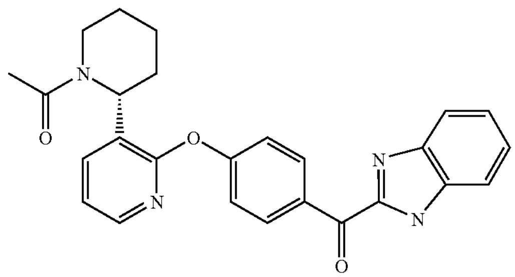 | 440.501 | 0.0000645 |
| | | |
| 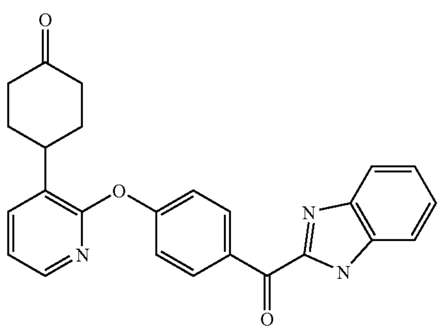 | 411.459 | 0.0000285 |
| 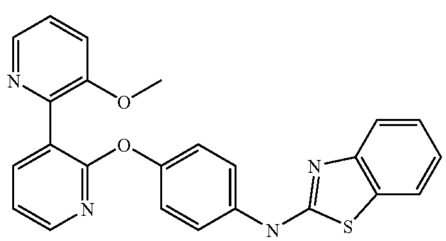 | 426.498 | 0.232 |
| 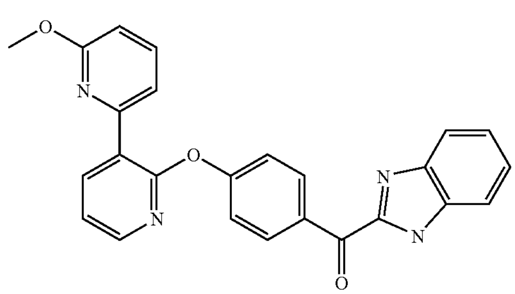 | 422.442 | 0.00232 |

TABLE VI-continued

Average IC50 for representative compounds of the invention:

| Structure | MS | Average IC50 (μM) |
|---|---|---|
| | 467.445 | 0.000728 |
| | 441.528 | 0.00258 |
| | 441.528 | 0.000679 |
| | 467.445 | 0.00159 |

TABLE VI-continued

Average IC50 for representative compounds of the invention:

| Structure | MS | Average IC50 (μM) |
|---|---|---|
| | 412.447 | 0.0000748 |
| | 412.447 | 0.000534 |
| 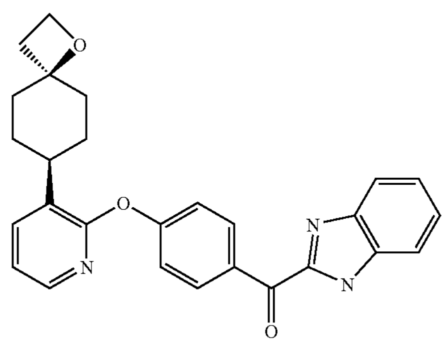 | 439.513 | 0.000641 |
| 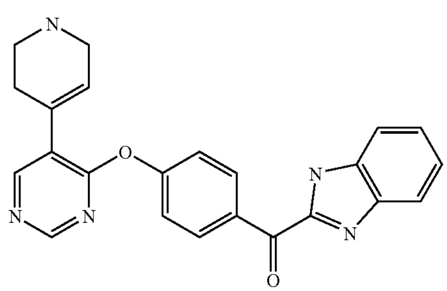 | 397.436 | 0.00958 |
| 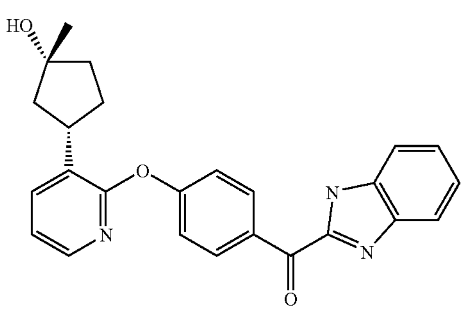 | 413.475 | 0.00192 |

TABLE VI-continued

Average IC50 for representative compounds of the invention:

| Structure | MS | Average IC50 (μM) |
|---|---|---|
| (structure) | 413.475 | 0.000662 |
| (structure) | 413.475 | 0.000763 |
| (structure) | 413.475 | 0.000524 |
| (structure) | 422.442 | 0.0171 |
| (structure) | 413.475 | 0.000315 |

TABLE VI-continued
Average IC50 for representative compounds of the invention:
| Structure | MS | Average IC50 (µM) |
|---|---|---|
| 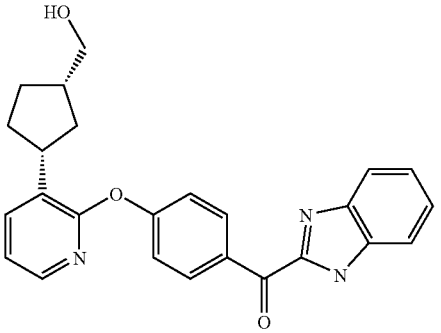 | 413.475 | 0.000312 |
| 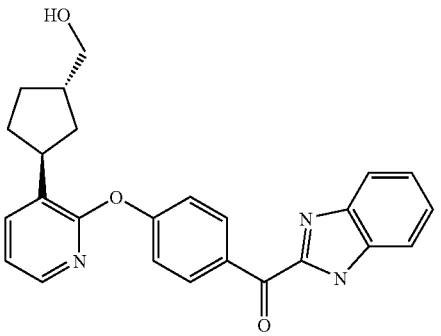 | 413.475 | 0.000199 |
| 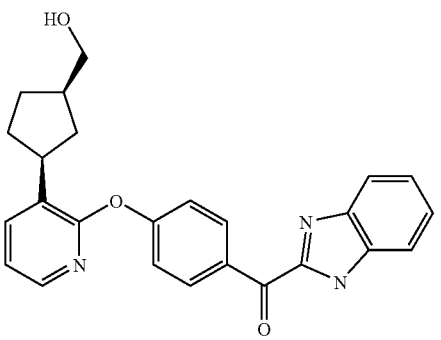 | 413.475 | 0.000212 |
| 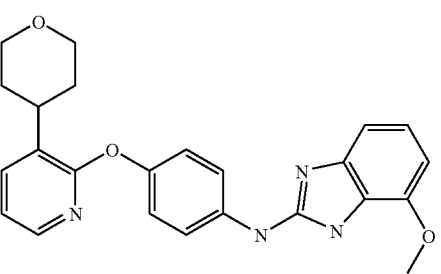 | 416.479 | 0.000418 |

TABLE VI-continued

Average IC50 for representative compounds of the invention:

| Structure | MS | Average IC50 (μM) |
|---|---|---|
| | 440.501 | 0.00161 |
| | 440.501 | 0.000024 |
| 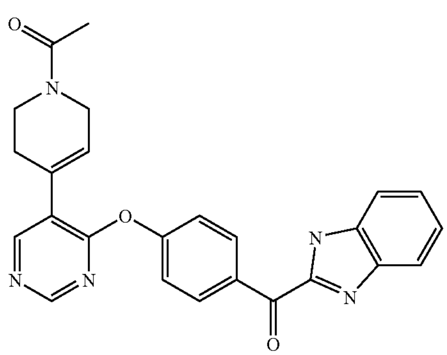 | 439.473 | 0.00156 |
| 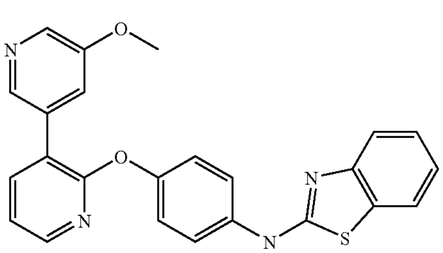 | 426.498 | 0.00408 |

TABLE VI-continued
Average IC50 for representative compounds of the invention:
| Structure | MS | Average IC50 (μM) |
|---|---|---|
| 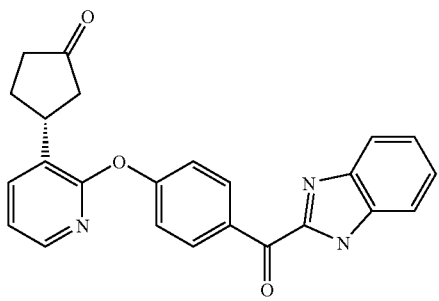 | 397.432 | 0.000021 |
| 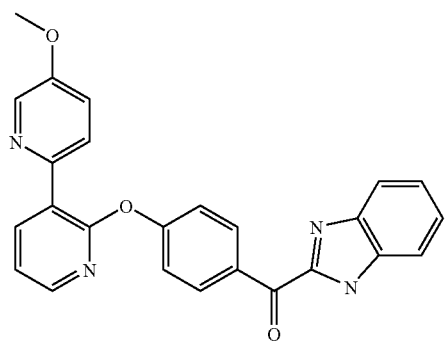 | 422.442 | 0.00877 |
| 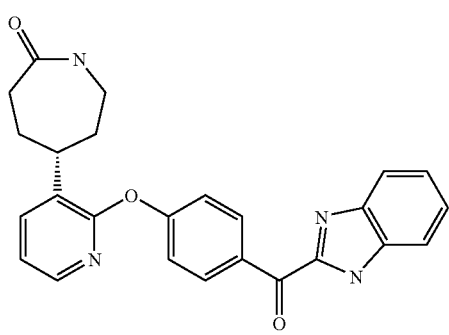 | 426.474 | 0.0000595 |

TABLE VI-continued

Average IC50 for representative compounds of the invention:

| Structure | MS | Average IC50 (μM) |
|---|---|---|
| | | |
| 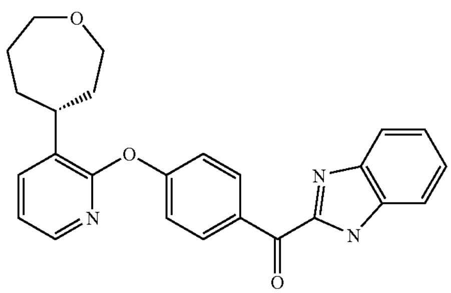 | 413.475 | 0.0000505 |
| | | |
| 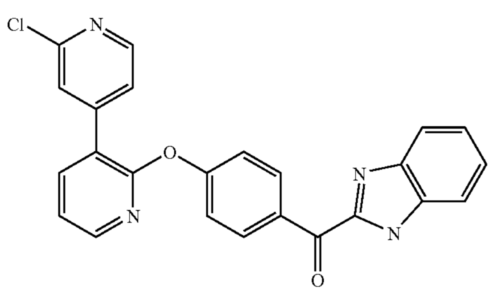 | 426.862 | 0.00163 |
| 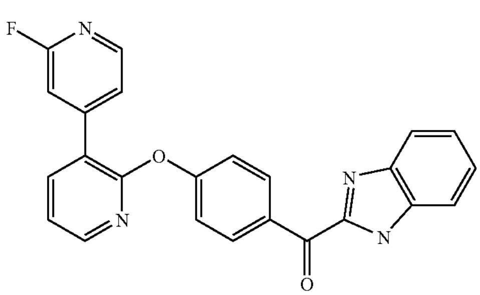 | 410.407 | 0.0008 |

TABLE VI-continued

Average IC50 for representative compounds of the invention:

| Structure | MS | Average IC50 (μM) |
|---|---|---|
| | 417.531 | 0.00286 |
| | 417.531 | 0.0107 |
| | 417.531 | 0.00231 |
| | 417.531 | 0.000897 |
| | 417.531 | 0.000737 |

TABLE VI-continued
Average IC50 for representative compounds of the invention:
| Structure | MS | Average IC50 (μM) |
|---|---|---|
| 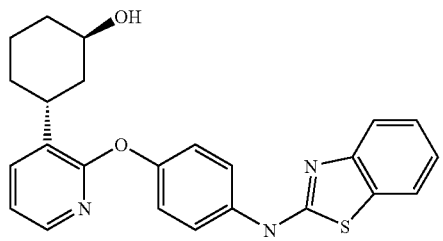 | | |
| 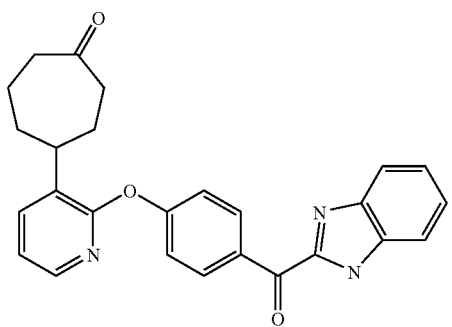 | 425.486 | 0.000077 |
| 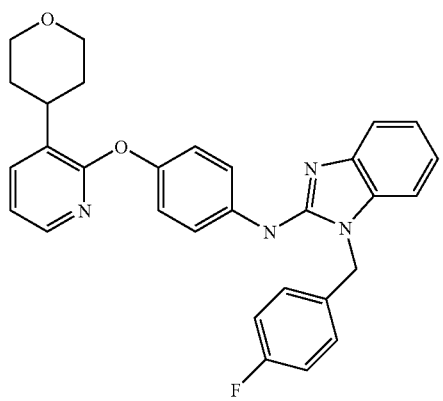 | 494.567 | 0.00912 |
| 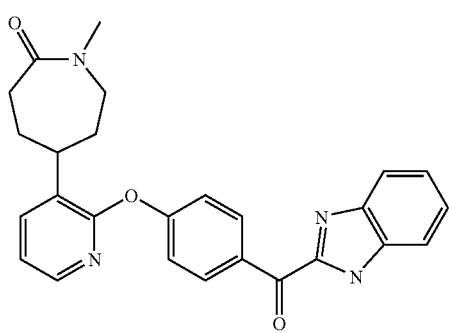 | 440.501 | 0.000218 |

TABLE VI-continued
Average IC50 for representative compounds of the invention:
| Structure | MS | Average IC50 (μM) |
|---|---|---|
| 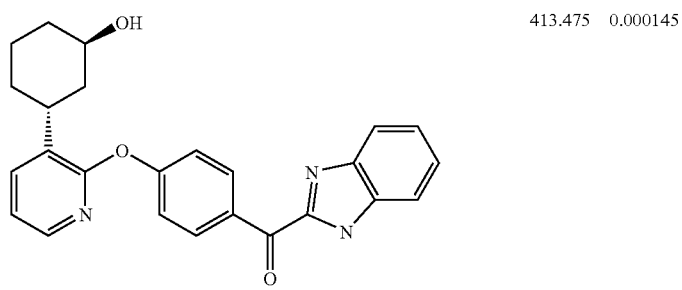 | 413.475 | 0.000145 |
| 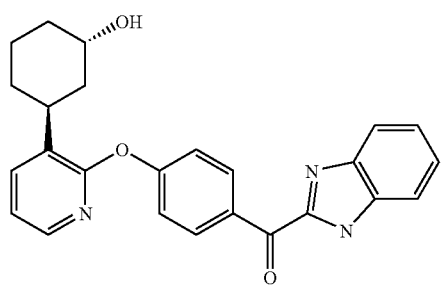 | | |
| 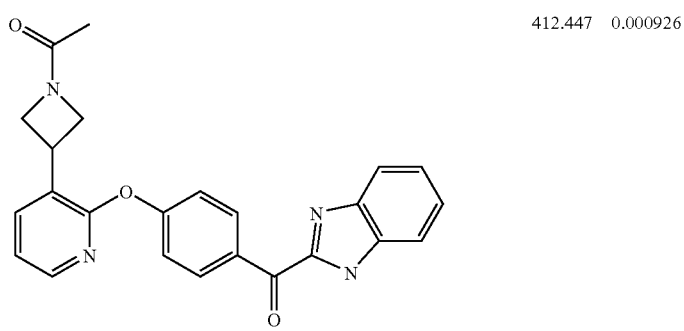 | 412.447 | 0.000926 |
| 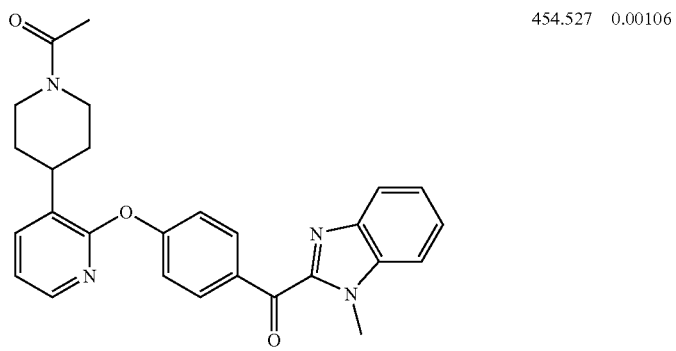 | 454.527 | 0.00106 |

TABLE VI-continued
Average IC50 for representative compounds of the invention:
| Structure | MS | Average IC50 (μM) |
|---|---|---|
| 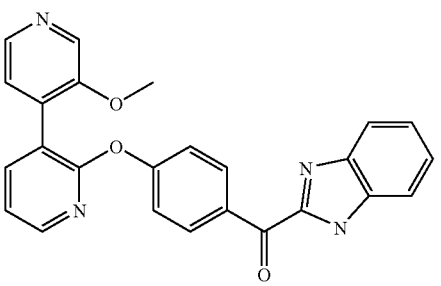 | 422.442 | 0.000261 |
| 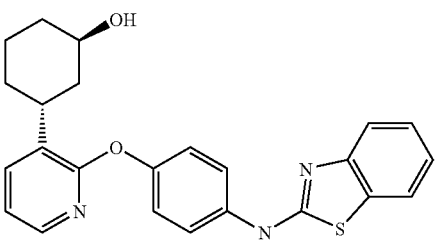 | 417.531 | 0.00286 |
| 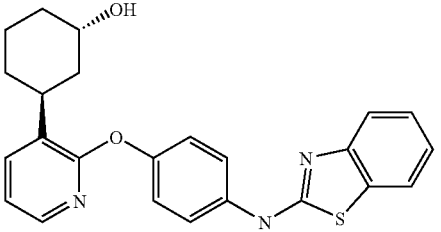 | 417.531 | 0.00993 |
| 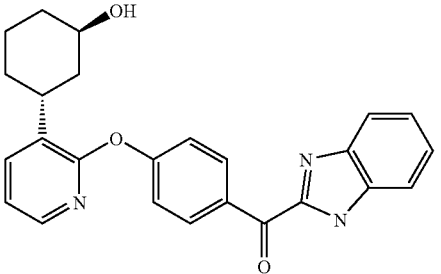 | 413.475 | 0.000585 |
| 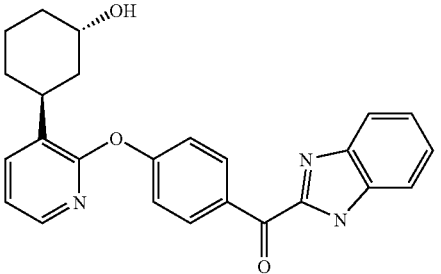 | 413.475 | 0.00171 |

TABLE VI-continued
Average IC50 for representative compounds of the invention:
| Structure | MS | Average IC50 (μM) |
|---|---|---|
| 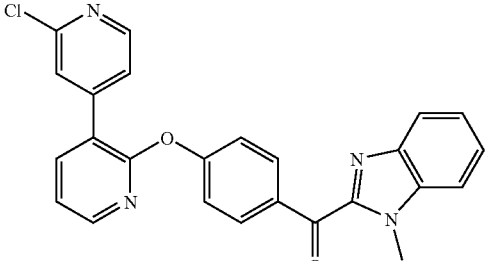 | 440.888 | 0.0102 |
| 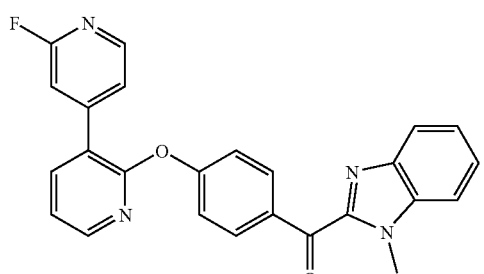 | 424.433 | 0.0103 |
| 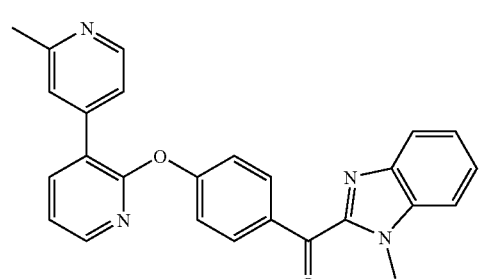 | 420.47 | 0.00617 |
| 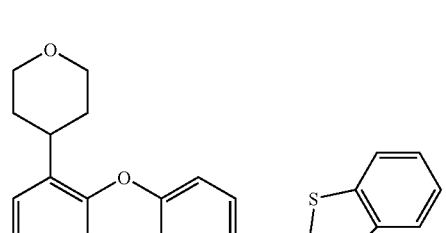 | 404.492 | 0.00828 |
| 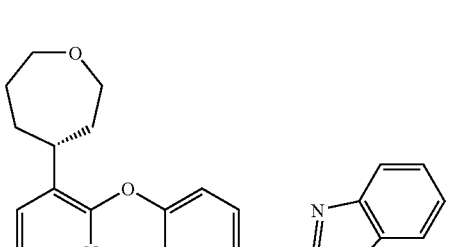 | 417.531 | 0.00279 |

TABLE VI-continued

Average IC50 for representative compounds of the invention:

| Structure | MS | Average IC50 (μM) |
|---|---|---|
| | | |
| 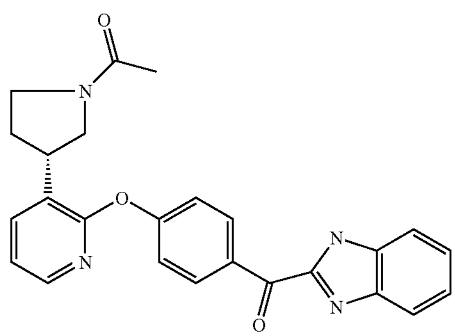 | 426.474 | 0.000528 |
| | | |
| 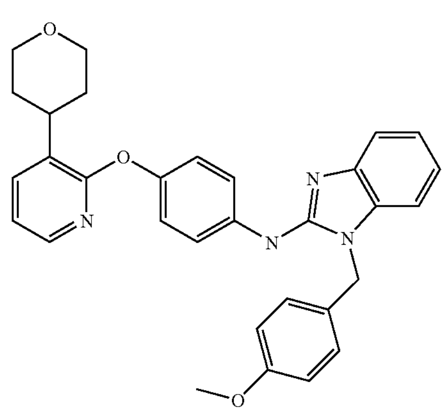 | 506.603 | 0.0017 |

TABLE VI-continued

Average IC50 for representative compounds of the invention:

| Structure | MS | Average IC50 (μM) |
|---|---|---|
| 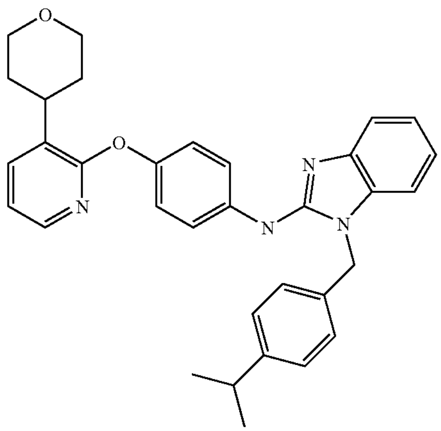 | 518.658 | 0.0319 |
| 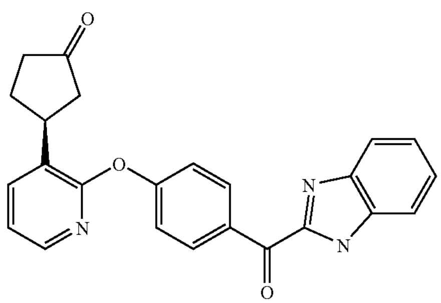 | 397.432 | 0.0000957 |
| 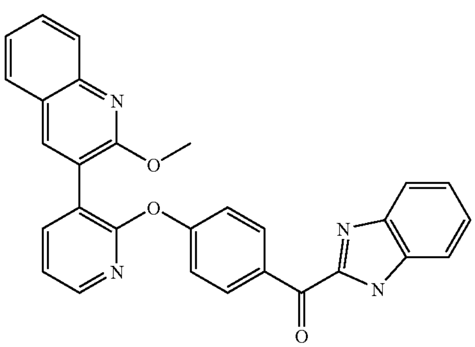 | 472.502 | 0.419 |
| 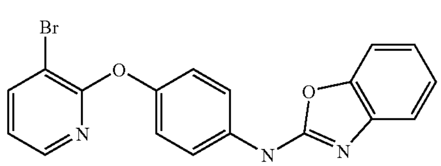 | 382.216 | 0.119 |

TABLE VI-continued

Average IC50 for representative compounds of the invention:

| Structure | MS | Average IC50 (μM) |
|---|---|---|
| 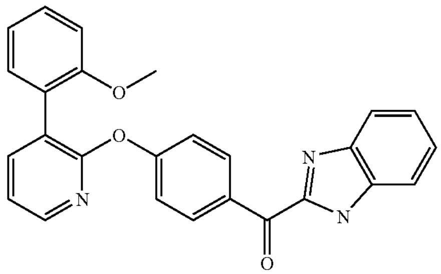 | 421.454 | 0.00251 |
| 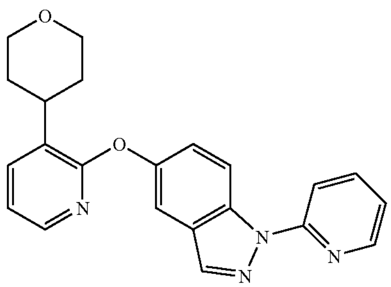 | 372.426 | 0.417 |
| 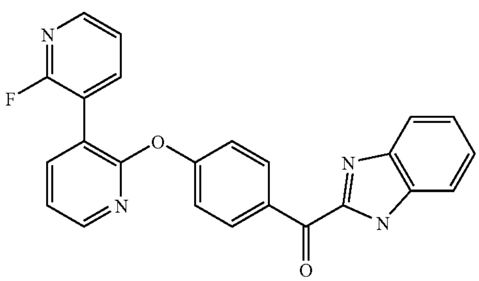 | 410.407 | 0.000162 |
| 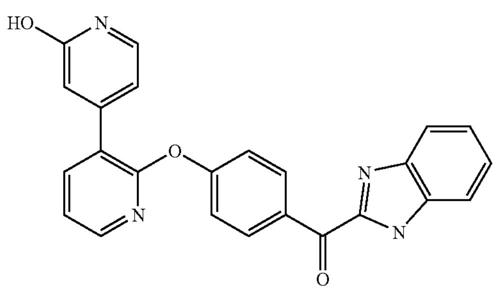 | 408.415 | 0.00117 |
| 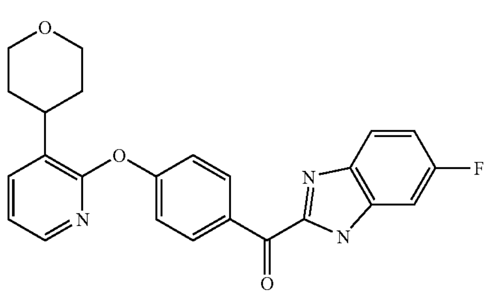 | 417.438 | 0.000475 |

TABLE VI-continued
Average IC50 for representative compounds of the invention:
| Structure | MS | Average IC50 (µM) |
|---|---|---|
| 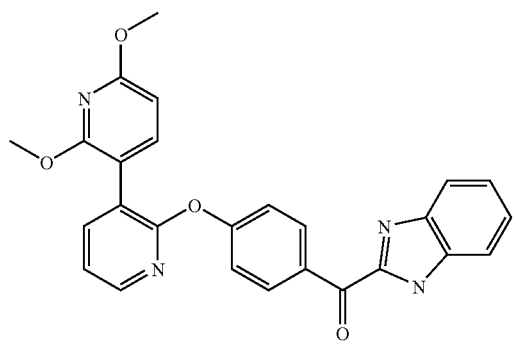 | 452.468 | 0.000694 |
| 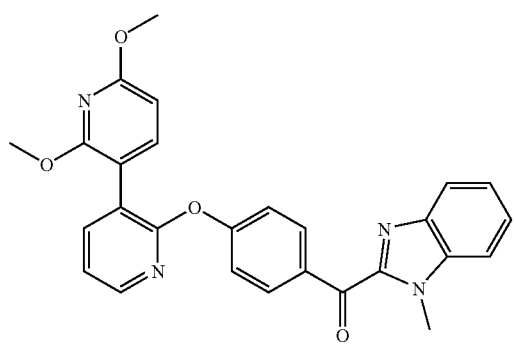 | 466.495 | 0.00115 |
| 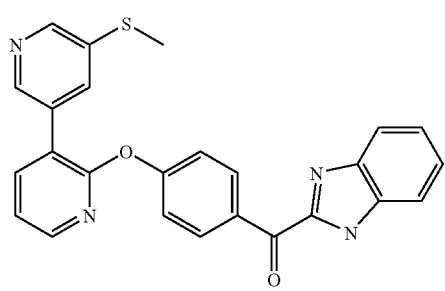 | 438.509 | 0.00106 |
| 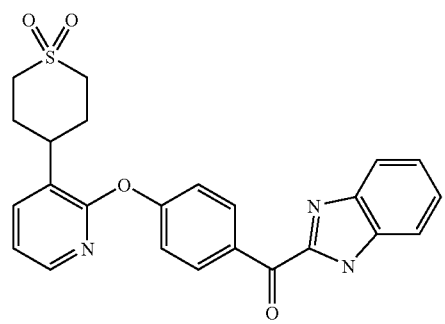 | 447.513 | 0.000631 |

TABLE VI-continued
Average IC50 for representative compounds of the invention:
| Structure | MS | Average IC50 (μM) |
|---|---|---|
| 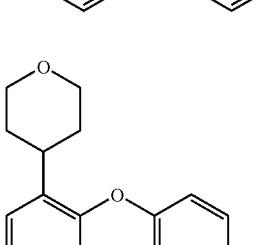 | 426.498 | 0.0119 |
| 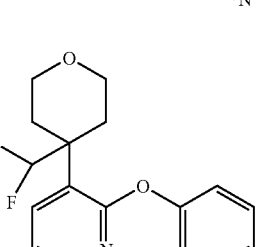 | 428.514 | 0.0579 |
| 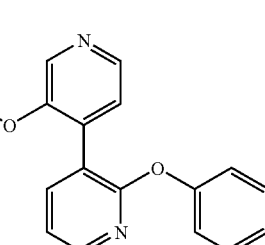 | 449.455 | 0.00207 |
| 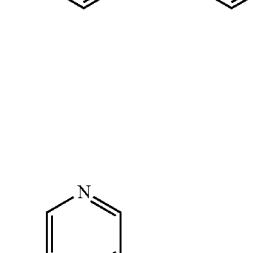 | 436.469 | 0.000121 |
| 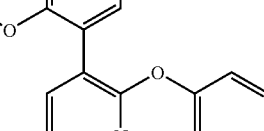 | 326.498 | 0.000747 |

TABLE VI-continued
Average IC50 for representative compounds of the invention:
| Structure | MS | Average IC50 (μM) |
|---|---|---|
| 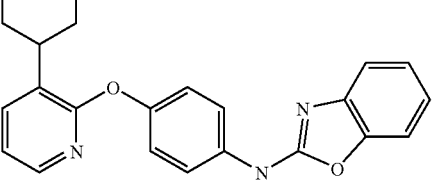 | 487.437 | 0.00037 |
| 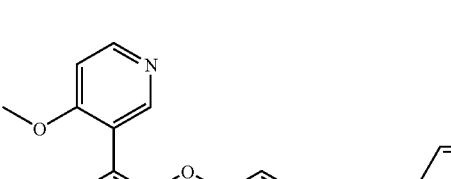 | 422.442 | 0.0000725 |
| 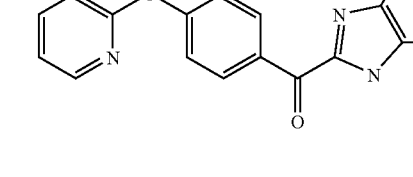 | 431.465 | 0.00229 |
| 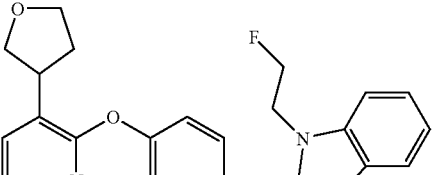 | 426.498 | 0.000902 |
| 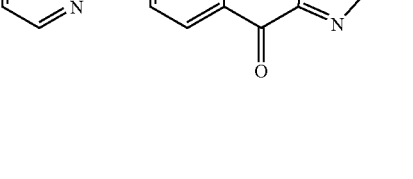 | 442.565 | 0.00326 |

TABLE VI-continued
Average IC50 for representative compounds of the invention:
| Structure | MS | Average IC50 (μM) |
|---|---|---|
| 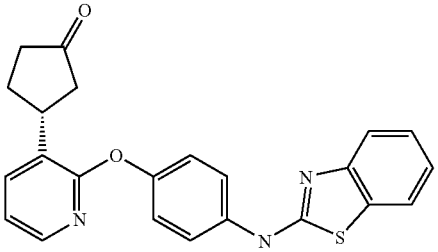 | 401.488 | 0.000169 |
| 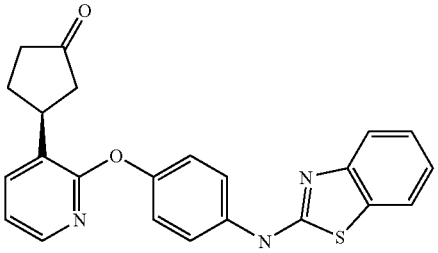 | | |
| 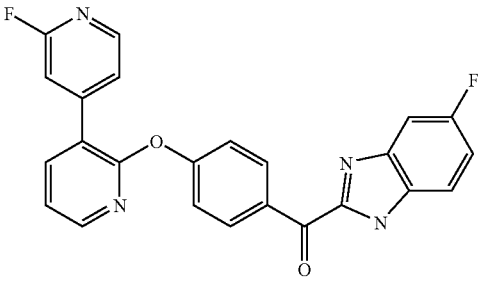 | 428.397 | 0.00154 |
| 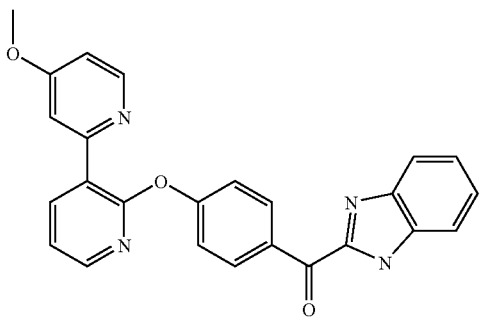 | 422.442 | 0.00411 |

TABLE VI-continued
Average IC50 for representative compounds of the invention:
| Structure | MS | Average IC50 (μM) |
|---|---|---|
| 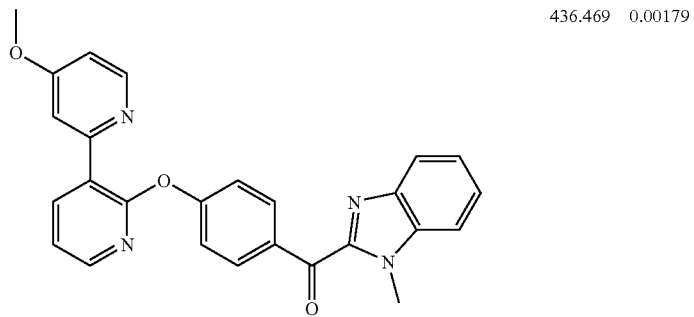 | 436.469 | 0.00179 |
| 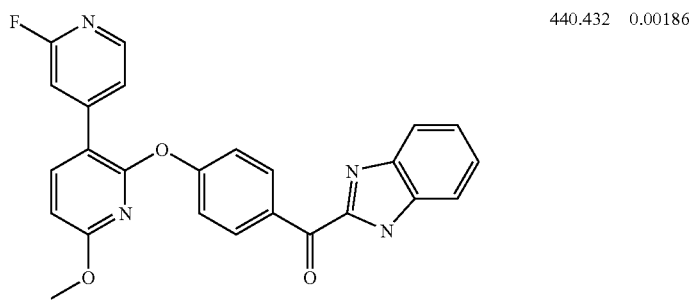 | 440.432 | 0.00186 |
| 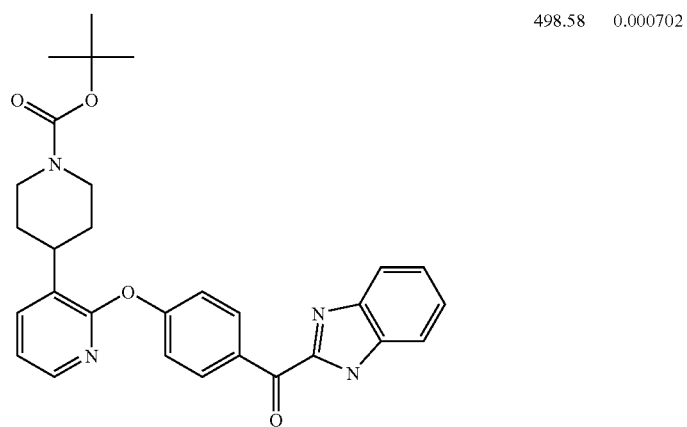 | 498.58 | 0.000702 |

TABLE VI-continued

Average IC50 for representative compounds of the invention:

| Structure | MS | Average IC50 (μM) |
|---|---|---|
| 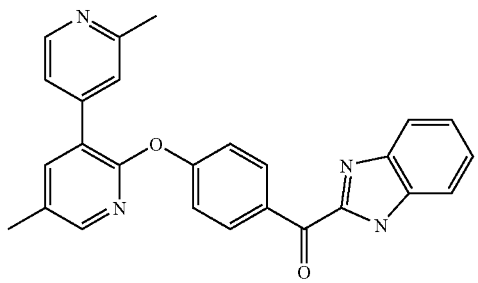 | 420.47 | 0.00138 |
| 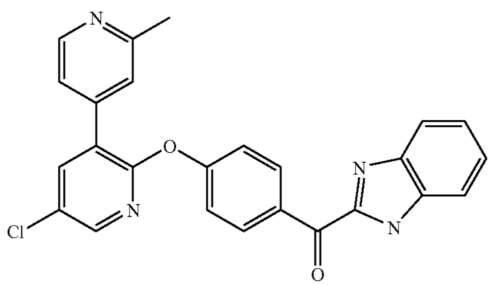 | 440.888 | 0.000814 |
| 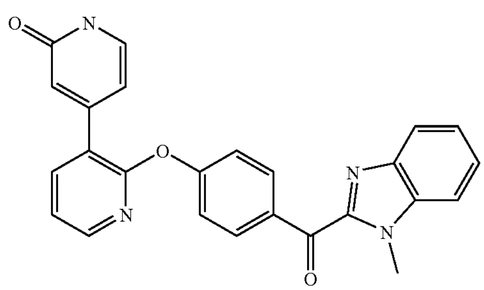 | 422.442 | 0.0013 |
| 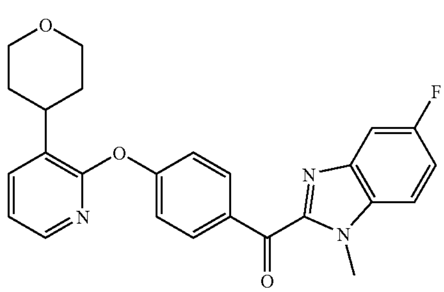 | 431.465 | 0.000943 |

TABLE VI-continued

Average IC50 for representative compounds of the invention:

| Structure | MS | Average IC50 (µM) |
|---|---|---|
| 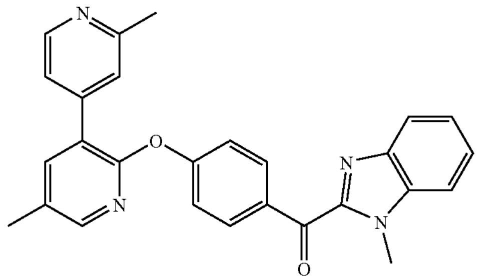 | 434.497 | 0.00114 |
| 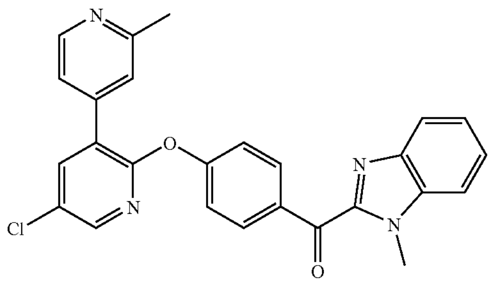 | 454.915 | 0.000738 |
| 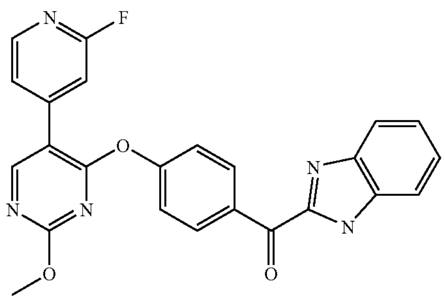 | 441.42 | 0.0229 |
| 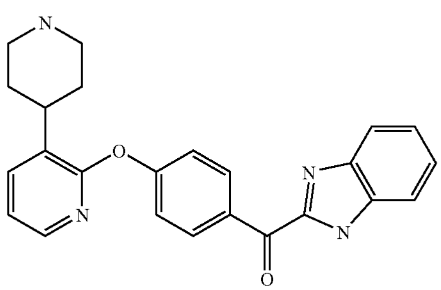 | 398.464 | 0.00207 |

Example 2

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats are exposed to a sudden burst of noise, at a level of 120 db for 40 msec, e.g., the reflex activity of the rats is measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example 3

Conditioned Avoidance Responding (Car) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal is placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal is free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training is conducted using a shuttle box (Med Associates, St. Albans, Vt.). The shuttle box is divided into 2 equal compartments that each contain a light source, a speaker that emits an 85 dB tone when activated and an electrified grid that can deliver a scrambled foot shock. Sessions consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and is recorded as an escape response. If an animal does not leave the conditioning chamber during the delivery of the shock it is recorded as an escape failure. Training is continued daily until the avoidance of 16 or more shocks out of 20 trials (80% avoidance) on 2 consecutive days is achieved. After this criterion is reached the rats are given one day of pharmacological testing. On test day, rats are randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds are injected at 1.0 ml/kg for i.p. and 10 mL/kg for p.o. administration. Compounds can be administered either acutely or chronically. For testing, each rat is placed in the shuttle box, and given 20 trials with the same parameters as described above for training trials. The number of avoidances, escapes, and escape failures are recorded.

Example 4

PCP-Induced Hyperactivity (PCP-LMA)

Equipment Used: 4×8 home cage photobeam activity system (PAS) frame from San Diego Instruments. Open PAS program and prepare an experimental session using the following variables:
Multiphase Experiment
300 sec/interval (5 min)
12 intervals (1 h)
Individual on screen switches.
Start recording after first beam break.
End session after end of interval.
Cage Preparation:
Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.
Animal Preparation:
Mark Rats and Record their Weights. Bring Rats to Testing Room.
Phase I: Habituation
Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g ½ needle or oral gavage needle) with Amgen compound solution (5 mL/kg) or risperidone (1 mL syringe with 23 g ½ needle) control (1 mL/kg) s.c.
Phase II: Compound Pre-Treatment
Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.
During phase II, prepare pcp: Dissolve pcp in saline to a concentration of 5 mg/mL.
Fill syringes (1 mL syringes with 26 g ⅜ needle) with pcp solution (1 mL/kg).
Phase III: Pcp Administration.
Make sure phase II is ended. Remove rat from enclosure, start the next phase using on-screen individual switch, administer pcp s.c. and place rat back in the enclosure. The computer will record for 1 h.
Clean-Up:
End-session to terminate experiment and so that computer will compile data. Export raw data to excel file for data analysis. Euthanize rats and take necessary tissue/sample for PK.
Data Generation:
Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The compounds of the present invention may be administered orally, parentally, by inhalation spray, rectally, or topically in dosage unit formulations containing conventional pharmaceutically acceptable carriers, adjuvants, and vehicles, for the treatment of PDE10-related diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating PDE10-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions).

The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure of formula I:

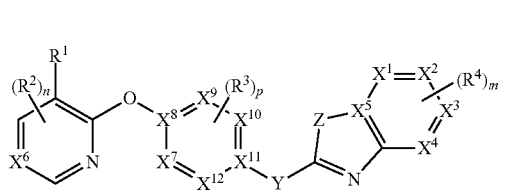

(I)

or any pharmaceutically-acceptable salt thereof, wherein:
Each of $X^1$, $X^2$, $X^3$, and $X^4$ is independently N or CH, and $X^5$ is independently N, CH, or C; wherein no more than two of $X^1$, $X^2$, $X^3$ and $X^4$ are N;
$X^6$ is CH;
Each of $X^7$, $X^9$, $X^{10}$, and $X^{12}$ is independently N or CH; each of $X^8$ and $X^{11}$ is C; wherein no more than three of $X^7$, $X^9$, $X^{10}$, and $X^{12}$ are N;
Y is NH, $NR^5$, CH(OH), C(=O), $-CR^aR^b$, or $CF_2$; or alternatively Y and $R^3$ form a 5- to 6-membered ring fused to the ring containing both said Y and $R^3$;
Z is NH, $NR^6$, S, SO, $SO_2$, O, CH, or —CH—; wherein Z is only CH when $X^5$ is N;
m is 0, 1, 2, 3 or 4;
n is 0, 1 or 2;
p is 0, 1 or 2;
$R^1$ is selected from the group consisting of
(a) H, F, Cl, Br, I, $C_{1-8}$alk, $C_{1-4}$haloalk, $-OR^a$, $-NR^aR^a$, $-N(R^a)C(=O)R^b$, $-C(=O)NR^aR^a$, $-C(=O)R^d$, $-C(=O)-O-R^a$, $-OR^c$, $-NR^aR^c$, $-N(R^c)C(=O)R^b$, $-N(R^a)C(=O)R^c$, $-C(=O)NR^aR^c$, or $-C(=O)NR^aR^c$;
(b) a saturated, partially-saturated or unsaturated 3-, 4-, 5-, 6-, or 7-membered monocyclic ring or a saturated 8-, 9-, 10-, 11-, or 12-membered bicyclic ring, partially-saturated 8-, 9-, 10-, 11-, or 12-membered bicyclic ring, or unsaturated 8-, 9-, 10-, 11-, or 12-membered bicyclic ring, wherein each said ring contains 0, 1, 2, 3, or 4 N atoms and 0, 1, or 2 atoms selected from O and S, and wherein each said ring is substituted by 0, 1, 2 or 3 groups selected from F, Cl, Br, $C_{1-6}$alk, $C_{1-6}$haloalk, $-OR^a$, $-OC_{1-4}$haloalk, CN, $-C(=O)R^b$, $-C(=O)OR^a$, $-C(=O)NR^aR^a$, $-C(=NR^a)NR^aR^a$, $-OC(=O)R^b$, $-OC(=O)NR^aR^a$, $-OC_{2-6}$alkNR^aR^a$, $-OC_{2-6}$alkOR^a$, $-SR^a$, $-S(=O)R^b$, $-S(=O)_2R^b$, $-S(=O)_2NR^aR^a$, $-NR^aR^a$, $-NR^aR^c$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkNR^aR^a$, $-NR^aC_{2-6}$alkOR^a$, $-C_{1-6}$alkNR^aR^a$, $-C_{1-6}$alkOR^a$, $-C_{1-6}$alkN(R^a)C(=O)R^b$, $-C_{1-6}$alkOC(=O)R^b$, $-C_{1-6}$alkC(=O)NR^aR^a$, $-C_{1-6}$alkC(=O)OR^a$, $R^7$, $R^8$ and oxo;
with a proviso that said unsaturated 6-membered monocyclic ring is not of formula:

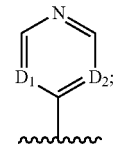

wherein each $D_1$ and $D_2$ are independently N or CH; and said partially unsaturated 5-membered monocyclic ring is not of formula:

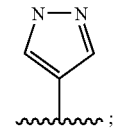

(c) group -L-$R^7$, wherein L is $CH_2$, NH, $N(C_{1-4}$alk), $-C(=O)NR^aR^a(C_{1-4}$alk), O, S, S=O, or $S(=O)_2$; or
(d) $C_{1-6}$alk substituted by 0, 1, 2 or 3 groups selected from F, Cl, Br, $C_{1-6}$alk, $C_{1-4}$haloalk, $-OR^a$, $-OC_{1-4}$haloalk, CN, $-C(=O)R^b$, $-C(=O)OR^b$, $-C(=O)NR^aR^a$, $-C(=NR^a)NR^aR^a$, $-OC(=O)R^b$, $-OC(=O)NR^aR^a$, $-OC_{2-6}$alkNR^aR^a$, $-OC_{2-6}$alkOR^a$, $-SR^a$, $-S(=O)R^b$, $-S(=O)_2R^b$, $-S(=O)_2NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkNR^aR^a$, $-NR^aC_{2-6}$alkOR^a$, $-C_{1-6}$alkNR^aR^a$, $-C_{1-6}$alkOR^a$, $R^8$ and oxo;
$R^2$ is, independently in each instance, F, Cl, Br, CN, OH, $OC_{1-4}$alk, $C_{1-4}$alk or $C_{1-4}$haloalk;
$R^3$ is, independently in each instance, F, Cl, Br, CN, OH, $OC_{1-4}$alk, $C_{1-4}$alk, $C_{1-4}$haloalk, or $-NR^aC_{1-4}$alk;
$R^4$ is independently in each instance, F, Cl, $CH_3$, CN, $CF_3$, $CHF_2$, $CH_2F$, $OR^a$, or $NR^aR^a$;
$R^5$ is $C_{1-8}$alk, $C_{1-4}$haloalk, $-C(=O)R^b$, or $R^c$;
$R^6$ is $C_{1-8}$alk, $C_{1-4}$haloalk, or $-C(=O)R^b$, or $R^c$;
$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, $-OR^a$, $-OC_{1-4}$haloalk, CN, $-C(=O)R^b$, $-C(=O)OR^a$, $-C(=O)NR^aR^a$, $-C(=NR^a)NR^aR^a$, $-OC(=O)R^b$, $-OC(=O)NR^aR^a$, $-OC_{2-6}$alkNR^aR^a$, $-OC_{2-6}$alkOR^a$, $-SR^a$, $-S(=O)R^b$, $-S(=O)_2R^b$, $-S(=O)_2NR^aR^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$ alkOC(=O)R$^b$, —C$_{1-6}$alkC(=O)NR$^a$R$^a$, —C$_{1-6}$ alkC(=O)OR$^a$, R$^8$ and oxo;

R$^8$ is a C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$ alkOC(=O)R$^b$, —C$_{1-6}$alkC(=O)NR$^a$R$^a$, —C$_{1-6}$ alkC(=O)OR$^a$ and oxo;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk;

R$^c$ is a C$_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, wherein said C$_{0-4}$alk and said ring moiety may be substituted by 0, 1, 2 or 3 groups selected from F, Cl, Br, C$_{1-6}$alk, C$_{1-4}$haloalk, R$^7$, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$ alkOC(=O)R$^b$, —C$_{1-6}$alkC(=O)NR$^a$R$^a$, —C$_{1-6}$alkC(=O)OR$^a$, R$^7$, R$^8$, and oxo; and R$^d$ is a nitrogen-linked saturated, partially-saturated, or unsaturated 5-, 6- or 7-membered ring heterocycle containing the linking nitrogen and 0, 1 or 2 additional nitrogen atoms and containing 0 or 1 sulfur or oxygen atom, the heterocycle being substituted by 0, 1, 2 or 3 substituents selected from oxo, halo, C$_{1-4}$alk, C$_{1-3}$haloalk, —OC$_{1-4}$alk, —NH$_2$, —NHC$_{1-4}$alk, and —N(C$_{1-4}$alk)C$_{1-4}$alk.

2. The compound of claim 1 wherein the group

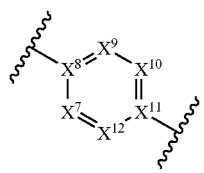

is selected from the group consisting of;

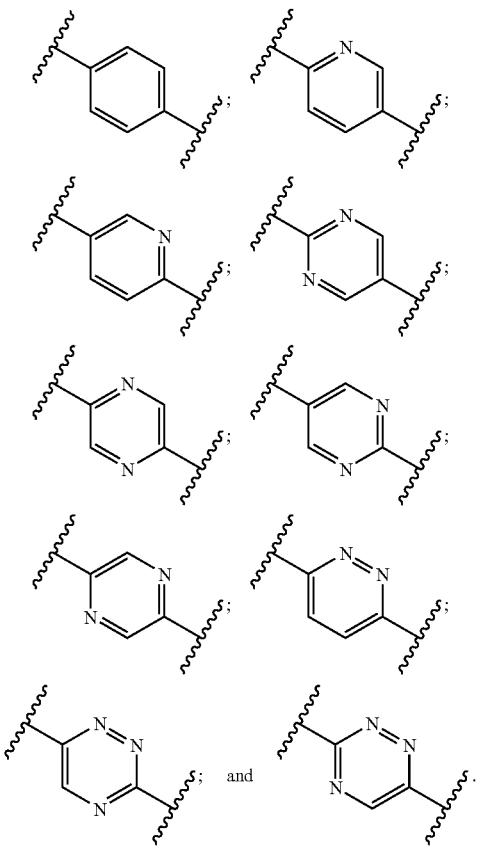

3. The compound of claim 1 wherein the group

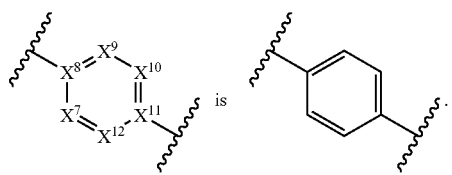

4. The compound of claim 1 wherein the group

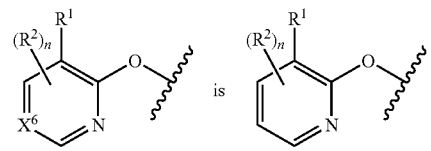

5. The compound of claim 1 wherein Y is NH, N—CH$_3$, NR$^C$, or —C(=O).

6. The compound of claim 1 wherein Y is NH.

7. The compound of claim 1 wherein Y is —C(=O).

8. The compound of claim 1 wherein Y is —N—CH$_2$—C$_6$C$_5$—F.

9. The compound of claim 1 wherein Y is —CH$_2$—.

10. The compound of claim 1 wherein Y and R$^3$ form a 5- to 6-membered ring fused to the ring containing both said Y and R$^3$.

11. The compound of claim 1 wherein $X^1$ is N or CH, and each of $X^2$, $X^3$, and $X^4$ is CH.

12. The compound of claim 1 wherein $X^5$ is N.

13. The compound of claim 1 wherein Z is NH, N—$C_{1-4}$alk, N-halo$C_{1-4}$alk, S, or CH.

14. The compound of claim 1 wherein m is 0 or 1.

15. The compound of claim 1 wherein n is 0 or 1.

16. The compound of claim 1 wherein p is 0.

17. The compound of claim 1 wherein $R^1$ is selected from the group consisting of H, F, Cl, Br, I, —$OR^a$, $C_{1-8}$alk, $C_{1-4}$haloalk, —C(=O)—O—$R^a$, —C(=O)$NR^aR^a$, —$OR^c$, and —C(=O)$NR^aR^c$.

18. The compound of claim 1 wherein $R^1$ is selected from the group consisting of a saturated 4-, 5-, 6-, or 7-membered monocyclic ring, wherein each said ring contains 0, 1, 2, or 3 N atoms and 0, 1, or 2 O atoms, and wherein each said ring is substituted by 0, 1 or 2 groups selected from F, Cl, Br, $C_{1-6}$alk, $C_{1-4}$haloalk, —$OR^a$, —CN, —C(=O)$R^b$, —C(=O)$OR^a$, and oxo.

19. The compound of claim 1 wherein $R^1$ is selected from the group consisting of a partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1 or 2 groups selected from F, Cl, Br, $C_{1-6}$alk, $C_{1-4}$haloalk, —$OR^a$, —CN, —C(=O)$R^b$, —C(=O)$OR^a$, and oxo; with a proviso that said unsaturated 6-membered monocyclic ring and said unsaturated 5-membered monocyclic ring is not of formula:

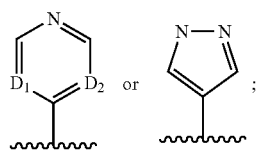

wherein each $D_1$ and $D_2$ are independently N or CH.

20. The compound of claim 1 wherein $R^1$ is selected from the group consisting of a saturated 9- or 10-membered bicyclic ring, partially-saturated 9- or 10-membered bicyclic ring, or unsaturated 10-membered bicyclic ring, wherein each said ring contains 0, 1, 2, 3 or 4 N atoms and 0, 1, or 2 O atoms, and wherein each said ring is substituted by 0, 1, 2 or 3 groups selected from F, Cl, Br, $C_{1-6}$alk, $C_{1-4}$haloalk, —$OR^a$, —$OC_{1-4}$ haloalk, CN, —C(=O)$R^b$, —C(=O)$OR^a$, —$NR^aR^a$, —$NR^aR^c$, $R^7$, $R^8$ and oxo.

21. The compound of claim 1 wherein $R^1$ is selected from the group consisting of cyclohexyl, cyclopentyl, cyclopentenyl, cyclohexenyl, cycloheptyl, azetidinyl, phenyl, 2-pyridyl, 3-pyridyl, morpholinyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, and quinolinyl, all of which are substituted by 0, 1 or 2 groups selected from F, Cl, Br, $C_{1-6}$alk, $C_{1-4}$haloalk, —$OR^a$, CN, —C(=O)$R^b$, —C(=O)$OR^a$, —$SR^a$, $R^7$, and oxo.

22. The compound of claim 1 wherein $R^1$ is -L-$R^7$ wherein L is —$CH_2$—.

23. The compound of claim 1 wherein $R^1$ is $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^b$, —C(=O)$NR^aR^a$, —C(=$NR^a$)$NR^aR^a$, —$OC(=O)R^b$, —OC(=O)$NR^aR^a$, —$OC_{2-6}$alkNR$^aR^a$, —$OC_{2-6}$alkOR$^a$, —$SR^a$, —S(=O)$R^b$, —S(=O)$_2R^b$, —S(=O)$_2NR^aR^a$, —$NR^aR^a$, —N($R^a$)C(=O)$R^b$, N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alkNR$^aR^a$, —$NR^aC_{2-6}$alkOR$^a$, —$C_{1-6}$alkNR$^aR^a$, —$C_{1-6}$alkOR$^a$, $R^8$ and oxo.

24. The compound of claim 1 wherein $R^1$ is selected from the group consisting of:

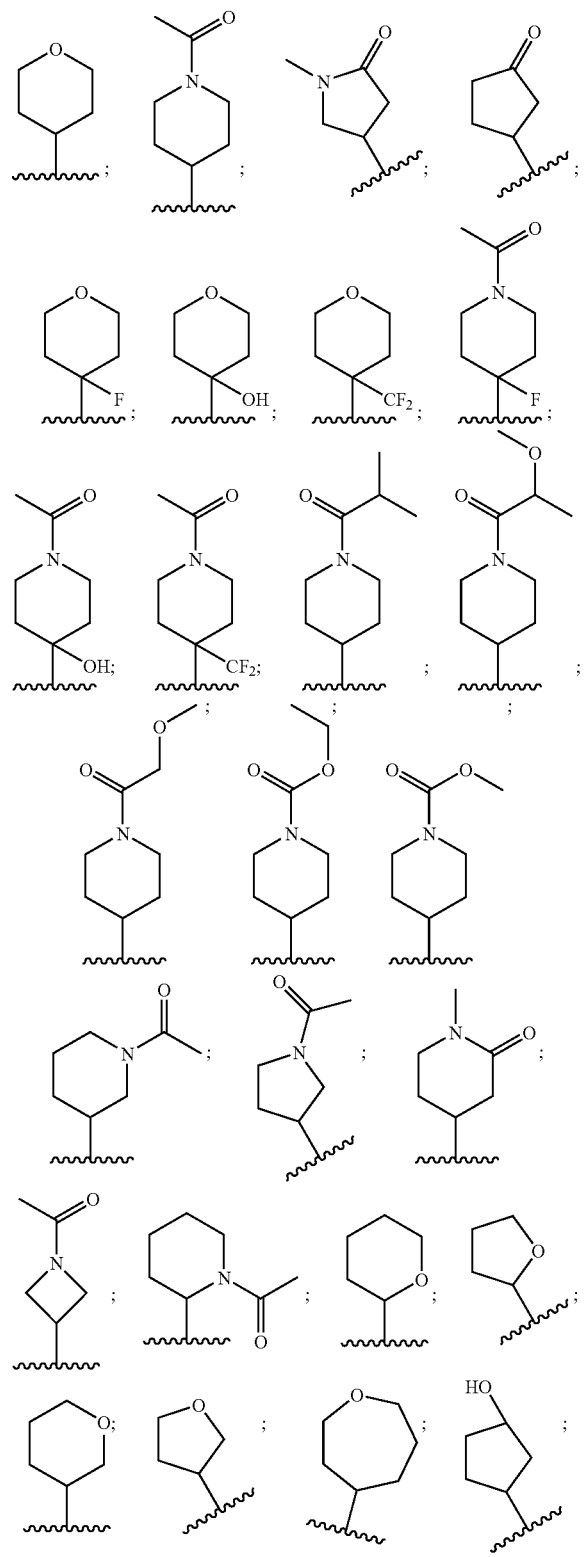

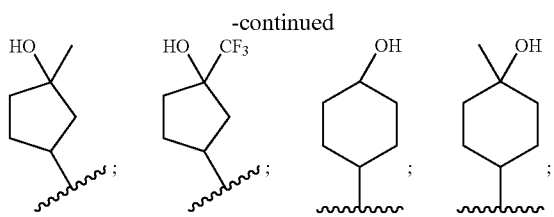

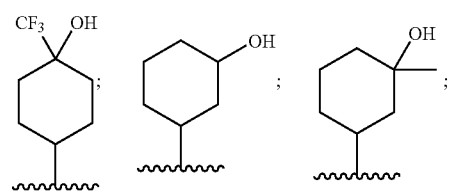

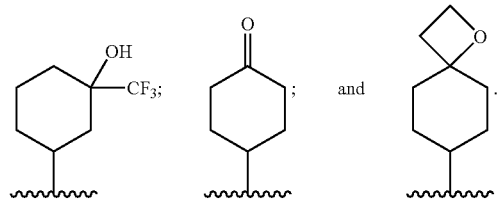

25. The compound of claim 1 wherein $R^2$ is, independently in each instance, F, Cl, Br, CN, OH, $OC_{1-4}alk$, $C_{1-4}alk$ or $C_{1-4}haloalk$.

26. The compound of claim 1 wherein $R^3$ is, independently in each instance, F, Cl, Br, CN, OH, $OC_{1-4}alk$, $C_{1-4}alk$ or $C_{1-4}haloalk$.

27. The compound of claim 1 wherein $R^4$ is F or CN.

28. The compound of claim 1 wherein $R^5$ is methyl or $-CH_2-C_6H_5-F$.

29. The compound of claim 1 wherein $R^6$ is methyl, $-CH_2-CH_2-F$ or $R^c$.

30. The compound of claim 1 wherein $R^7$ is a saturated 3-, 4-, 5-, or 6-membered monocyclic ring containing 0 or 1 N atom and 0 or 1 O atom, which is substituted by 0, 1, 2 or 3 $-OR^a$.

31. The compound of claim 1 wherein $R^8$ is $C_{1-6}alk$ substituted by 0 or 1 $-OR^a$.

32. The compound of claim 1 wherein $R^a$ is H or $C_{1-6}alk$ substituted by 0 or 1 $-OH$, $-OC_{1-4}alk$, $-OC(=O)C_{1-4}alk$, or $-N(C_{1-4}alk)C_{1-4}alk$.

33. The compound of claim 1 wherein $R^c$ is a $C_{0-4}alk$-linked saturated, partially-saturated or unsaturated 3-, 5-, or 6-membered monocyclic ring containing 0 or 1 N atom and 0 or 1 atom selected from O and S, which is substituted by 0, 1, or 2 groups selected from F, $C_{1-6}alk$, $C_{1-4}haloalk$, $-OR^a$, $R^7$, or $R^8$.

34. The compound of claim 1 wherein $R^c$ is a $C_{0-4}alk$-linked saturated, partially-saturated or unsaturated 9- or 10-membered monocyclic ring containing 0 or 1 N atom and 0 or 1 atom selected from O and S, which is substituted by 0, 1, or 2 groups selected from F, $C_{1-6}alk$, $C_{1-4}haloalk$, $-OR^a$, $R^7$, or $R^8$.

35. The compound of claim 1 wherein the group of formula:

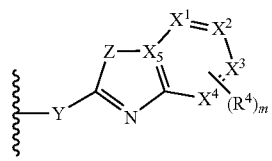

is selected from the group consisting of

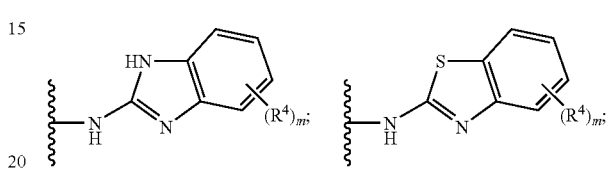

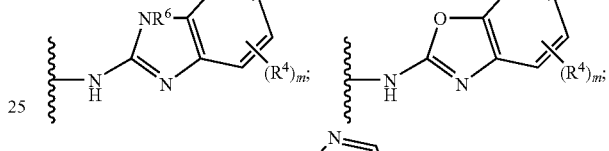

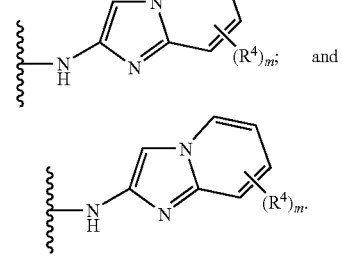

36. The compound of claim 1 wherein the group of formula:

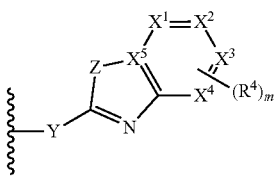

is selected from the group consisting of

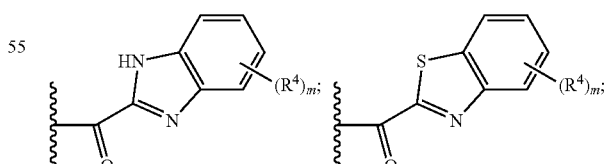

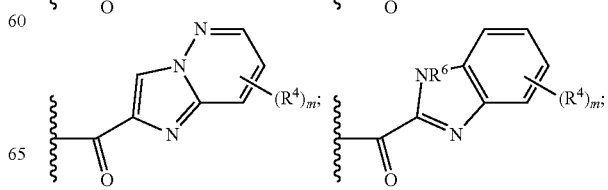

-continued

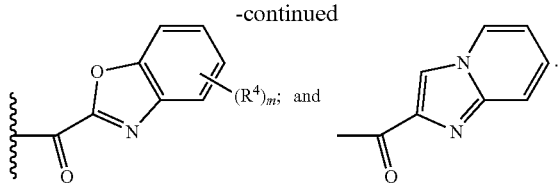

37. A pharmaceutical composition comprising a compound according to claim 1 and a pharmaceutically-acceptable diluent or carrier.

38. A compound having the structure of formula II:

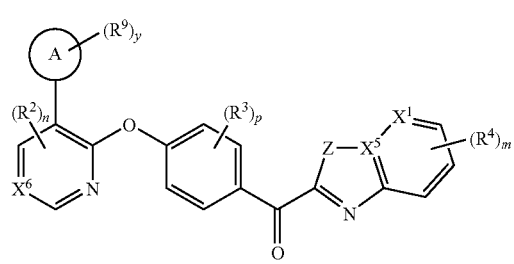

(II)

or any pharmaceutically-acceptable salt thereof, wherein:
Z is NH, NR$^6$, S or O;
m is 0, 1, 2, 3 or 4;
n is 0, 1 or 2;
p is 0, 1 or 2;
y is 0, 1, 2, 3 or 4;
X$^1$ is N or CH;
X$^5$ is C;
X$^6$ is CH;
Ring A is a carbon-linked-saturated or carbon-linked-partially-unsaturated 4-, 5-, 6-, 7-, 8-, 9-, 10-, 11-, or 12-membered carbocyclic ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;
R$^2$ is, independently in each instance, F, Cl, Br, CN, OH, OC$_{1-4}$alk, C$_{1-4}$alk or C$_{1-4}$haloalk;
R$^3$ is, independently in each instance, F, Cl, Br, CN, OH, OC$_{1-4}$alk, C$_{1-4}$alk, C$_{1-4}$haloalk, or —NR$^a$C$_{1-4}$alk;
R$^4$ is independently in each instance, F, Cl, CH$_3$, CN, CF$_3$, CHF$_2$, CH$_2$F, OR$^a$, or NR$^a$R$^a$;
R$^5$ is C$_{1-8}$alk, C$_{1-4}$haloalk, —C(=O)R$^b$, or R$^c$;
R$^6$ is C$_{1-8}$alk, C$_{1-4}$haloalk, —C(=O)R$^b$, or R$^c$;
R$^7$ is a saturated, partially-saturated or unsaturated 3-, 4-, 5-, 6-, or 7-membered monocyclic or 8-, 9-, 10-, 11-, or 12-membered bicyclic ring containing 0, 1, 2, 3, or 4 N atoms and 0 or 1 atoms selected from O and S, which is substituted by 0, 1 or 2 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^8$ and oxo;

R$^8$ is a C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O) OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo;

R$^9$ is independently selected from the group consisting of H, F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —NR$^a$R$^c$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^7$, R$^8$ and oxo;

R$^a$ is independently, at each instance, H or R$^b$;
R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk; and
R$^c$ is a C$_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, wherein said C$_{0-4}$alk and said ring moiety may be substituted by 0, 1, 2 or 3 groups selected from F, Cl, Br, C$_{1-6}$alk, C$_{1-4}$haloalk, R$^7$, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^7$, and oxo.

39. The compound of claim 38 wherein Z is NH, N—$C_{1-4}$alk, or S.

40. The compound of claim 38 wherein Z is S.

41. The compound of claim 38 wherein the group of formula:

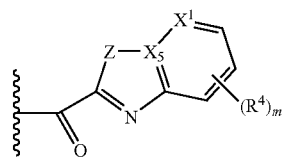

is selected from the group consisting of

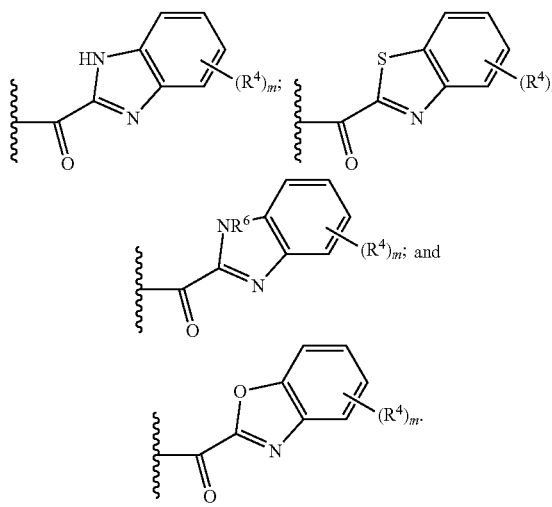

42. The compound of claim 38 wherein ring A is a carbon-linked-saturated or carbon-linked-partially-saturated 4-, 5-, 6-, 7-, 8-, 9-, 10-, 11-, or 12-membered carbocycle ring containing 0, 1 or 2 N atoms and containing 0 or 1 S or O atom.

43. The compound of claim 38 wherein ring A is a carbon-linked-saturated 4-, 5-, 6-, 7-membered carbocycle ring containing 0, 1 or 2 N atoms and containing 0 or 1 S or O atom.

44. The compound of claim 38 wherein ring A is a carbon-linked-partially-saturated 4-, 5-, 6-, 7-, 8-, 9-, 10-membered carbocycle ring containing 0, 1 or 2 N atoms and containing 0 or 1 S or O atom.

45. The compound of claim 38 wherein ring A is a nitrogen-linked-saturated 4-, 5-, 6-, 7-membered carbocycle ring containing 0, 1 or 2 N atoms and containing 0 or 1 S or O atom.

46. The compound of claim 38 wherein ring A is a nitrogen-linked-partially-saturated 4-, 5-, 6-, 7-, 8-, 9-, 10-membered carbocycle ring containing 0, 1 or 2 N atoms and containing 0 or 1 S or O atom.

47. The compound of claim 38 wherein ring A is a nitrogen-linked-unsaturated 4-, 5-, 6-, 8-, 10-, or 12-membered carbocycle ring containing 0, 1 or 2 N atoms and containing 0 or 1 S or O atom.

48. The compound of claim 38 wherein ring A is selected from the group consisting of cyclohexyl, cyclopentyl, cyclopentenyl, cyclohexenyl, cycloheptyl, azetidinyl, morpholinyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, all of which are substituted by 0, 1, 2 or 3 groups selected from all of which are substituted by 0, 1 or 2 groups selected from F, Cl, Br, $C_{1-6}$alk, $C_{1-4}$haloalk, —OR$^a$, CN, —C(=O)R$^b$, —C(=O)OR$^a$, —SR$^a$, R$^7$, and oxo.

49. The compound of claim 38 wherein ring A is selected from the group consisting of:

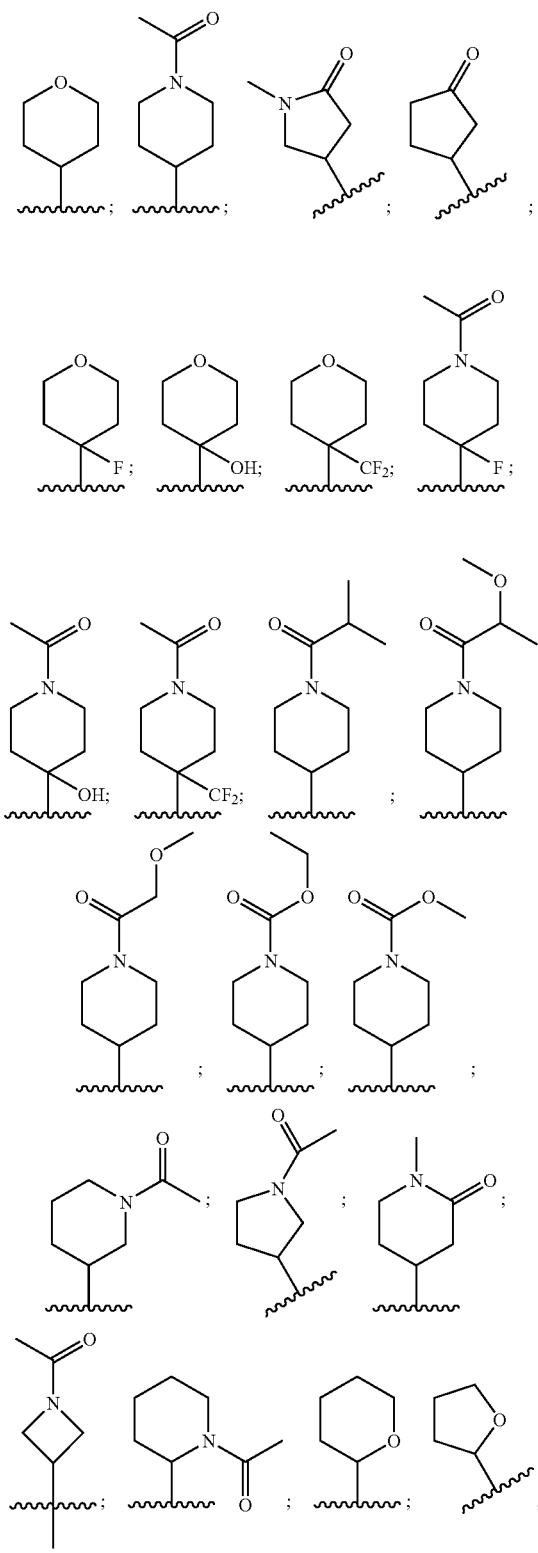

-continued

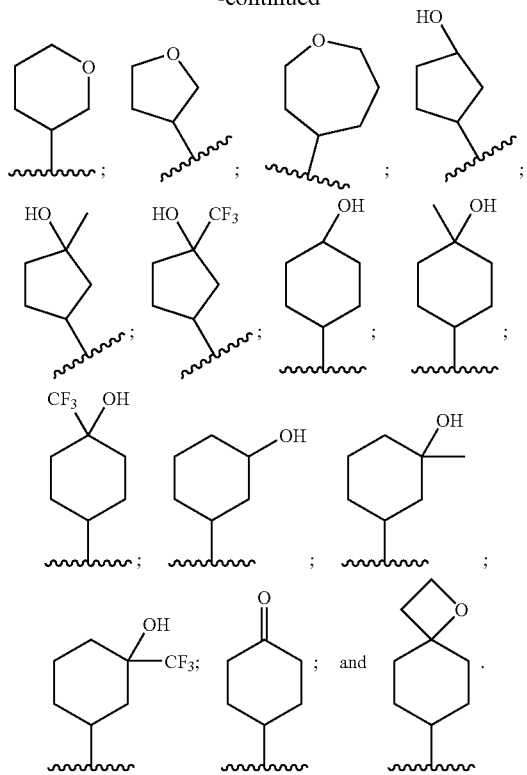

50. The compound of claim 38 wherein m is 0 or 1.
51. The compound of claim 38 wherein n is 0 or 1.
52. The compound of claim 38 wherein p is 0 or 1.
53. The compound of claim 38 wherein y is 0, 1, 2, or 3.
54. The compound of claim 38 wherein $R^9$ is selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, -$NsR^aR^c$, $R^7$, $R^8$ and oxo.
55. The compound of claim 38 wherein $R^2$ is, independently in each instance, F, Cl, Br, CN, OH, $OC_{1-4}$alk, $C_{1-4}$alk or $C_{1-4}$haloalk.
56. The compound of claim 38 wherein $R^3$ is, independently in each instance, F, Cl, Br, CN, OH, $OC_{1-4}$alk, $C_{1-4}$alk or $C_{1-4}$haloalk.
57. The compound of claim 38 wherein $R^4$ is F or CN.
58. The compound of claim 38 wherein $R^6$ is methyl, —$CH_2$—$CH_2$—F, or $R^c$.
59. The compound of claim 38 wherein $R^7$ is a saturated 3-, 4-, 5-, or 6-membered monocyclic ring containing 0 or 1 N atom and 0 or 10 atom, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alkN$R^aR^a$, —$OC_{2-6}$alkO$R^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alkN$R^aR^a$, —$NR^aC_{2-6}$alkO$R^a$, —$C_{1-6}$alkN$R^aR^a$, —$C_{1-6}$alkO$R^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo.
60. The compound of claim 38 wherein $R^8$ is $C_{1-6}$alk substituted by 0 or 1 —$OR^a$.
61. The compound of claim 38 wherein $R^a$ is H or $C_{1-6}$alk substituted by 0 or 1 —OH, —$OC_{1-4}$alk, —$OC(=O)C_{1-4}$alk, or —N($C_{1-4}$alk)$C_{1-4}$alk.

62. The compound of claim 38 wherein $R^c$ is a $C_{0-4}$alk-linked saturated, partially-saturated or unsaturated 3-, 4-, 5-, or 6-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.
63. The compound of claim 38 wherein $R^c$ is a $C_{0-4}$alk-linked saturated, partially-saturated or unsaturated 9- or 10-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.
64. A pharmaceutical composition comprising a compound according to claim 38 and a pharmaceutically-acceptable diluent or carrier.
65. A compound having the structure of formula III:

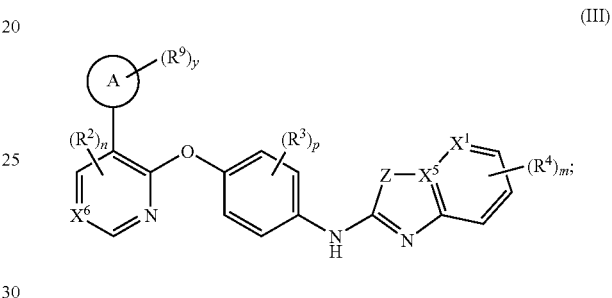

(III)

or any pharmaceutically-acceptable salt thereof, wherein:
Z is NH, $NR^6$, S, or O;
m is 0, 1, 2, 3 or 4;
n is 0, 1 or 2;
p is 0, 1 or 2;
y is 0, 1, 2, 3 or 4;
$X^1$ is CH;
$X^5$ is C;
$X^6$ is CH;
Ring A is a carbon-linked-saturated or carbon-linked-partially-unsaturated 4-, 5-, 6-, 7-, 8-, 9-, 10-, 11-, or 12-membered carbocyclic ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;
$R^2$ is, independently in each instance, F, Cl, Br, CN, OH, $OC_{1-4}$alk, $C_{1-4}$alk or $C_{1-4}$haloalk;
$R^3$ is, independently in each instance, F, Cl, Br, CN, OH, $OC_{1-4}$alk, $C_{1-4}$alk or $C_{1-4}$haloalk;
$R^4$ is independently in each instance, F, Cl, $CH_3$, CN, $CF_3$, $CHF_2$, $CH_2F$, $OR^a$, or $NR^aR^a$;
$R^5$ is $C_{1-8}$alk, $C_{1-4}$haloalk, —C(=O)$R^b$, or $R^c$;
$R^6$ is $C_{1-8}$alk, $C_{1-4}$haloalk, —C(=O)$R^b$, or $R^c$;
$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2, 3, or 4 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O) $NR^aR^a$, —$OC_{2-6}$alkN$R^aR^a$, —$OC_{2-6}$alkO$R^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$lkOC(=O)R$^b$, —C$_{1-6}$alkC(=O)NR$^a$R$^a$, —C$_{1-6}$alkC(=O)OR$^a$, R$^8$ and oxo;

R$^8$ is a C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo;

R$^9$ is independently selected from the group consisting of H, F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —NR$^a$R$^c$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^7$, R$^8$ and oxo;

R$^a$ is independently, at each instance, H or R$^b$;

is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk; and R$^c$ is a C$_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, wherein said C$_{0-4}$alk and said ring moiety may be substituted by 0, 1, 2 or 3 groups selected from F, Cl, Br, C$_{1-6}$alk, C$_{1-4}$haloalk, R$^7$, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R$^7$, R$^8$, and oxo.

66. The compound of claim 65 wherein Z is NH, N—C$_{1-4}$alk, or S.

67. The compound of claim 65 wherein Z is S.

68. The compound of claim 65 wherein the group of formula:

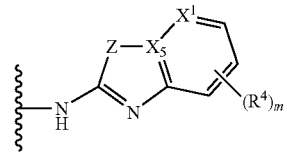

is selected from the group consisting of

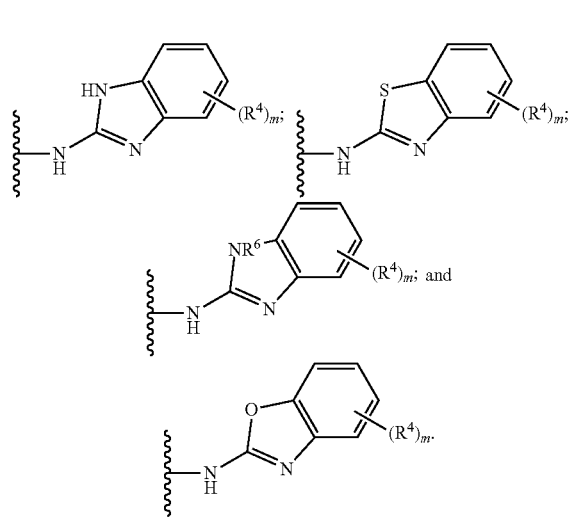

69. The compound of claim 65 wherein ring A is a carbon-linked-saturated or carbon-linked-partially-saturated 4-, 5-, 6-, 7-, 8-, 9-, 10-, 11-, or 12-membered carbocycle ring containing 0, 1 or 2 N atoms and containing 0 or 1 S or O atom.

70. The compound of claim 65 wherein ring A is a carbon-linked-saturated 4-, 5-, 6-, 7-membered carbocycle ring containing 0, 1 or 2 N atoms and containing 0 or 1 S or O atom.

71. The compound of claim 65 wherein ring A is a carbon-linked-partially-saturated 4-, 5-, 6-, 7-, 8-, 9-, 10-membered carbocycle ring containing 0, 1 or 2 N atoms and containing 0 or 1 S or O atom.

72. The compound of claim 65 wherein ring A is a nitrogen-linked-saturated 4-, 5-, 6-, 7-membered carbocycle ring containing 0, 1 or 2 N atoms and containing 0 or 1 S or O atom.

73. The compound of claim 65 wherein ring A is a nitrogen-linked-partially-saturated 4-, 5-, 6-, 7-, 8-, 9-, 10-membered carbocycle ring containing 0, 1 or 2 N atoms and containing 0 or 1 S or O atom.

74. The compound of claim 65 wherein ring A is a nitrogen-linked-unsaturated 4-, 5-, 6-, 8-, 10-, or 12-membered carbocycle ring containing 0, 1 or 2 N atoms and containing 0 or 1 S or O atom.

75. The compound of claim 65 wherein ring A is selected from the group consisting of cyclohexyl, cyclopentyl, cyclopentenyl, cyclohexenyl, cycloheptyl, azetidinyl, morpholinyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, all of which are substituted by 0, 1, 2 or 3 groups selected from all of which are substituted by 0, 1 or 2 groups selected from F, Cl, Br, C$_{1-6}$alk, C$_{1-4}$haloalk, —OR$^a$, CN, —C(=O)R$^b$, —C(=O)OR$^a$, —SR$^a$, R$^7$, and oxo.

76. The compound of claim 65 wherein ring A is selected from the group consisting of:

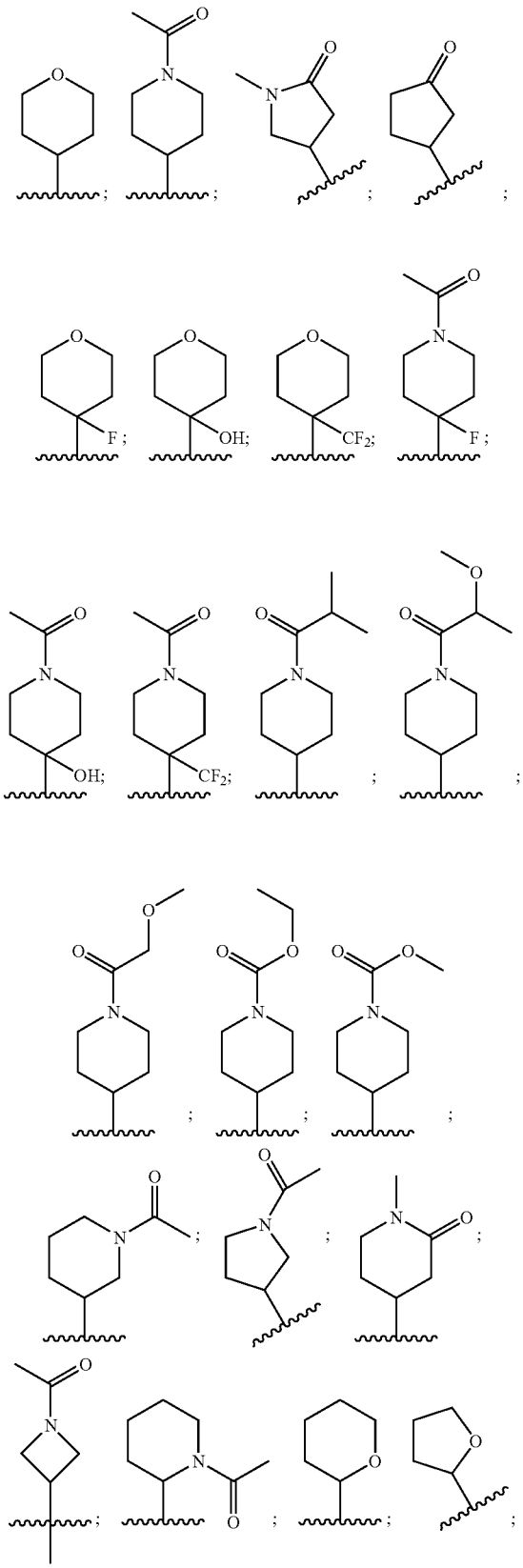

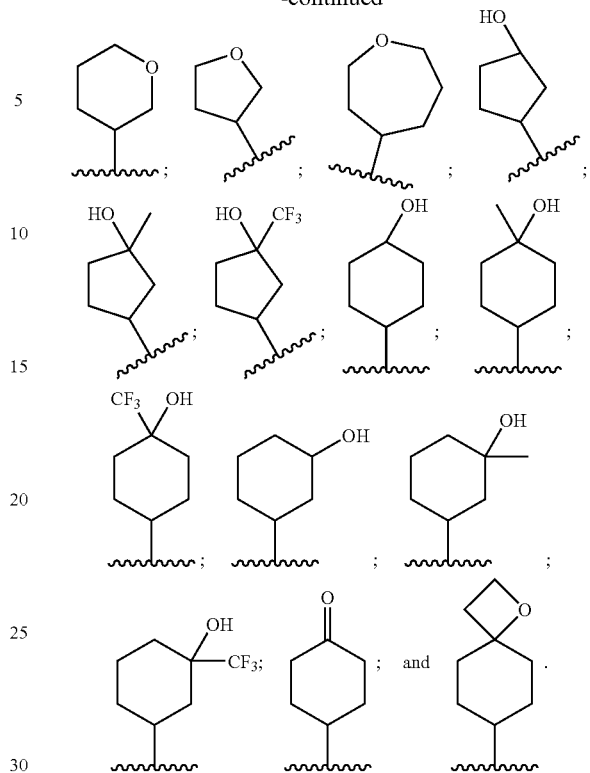

77. The compound of claim 65 wherein m is 0 or 1.
78. The compound of claim 65 wherein n is 0 or 1.
79. The compound of claim 65 wherein p is 0 or 1.
80. The compound of claim 65 wherein y is 0, 1, 2, or 3.
81. The compound of claim 65 wherein $R^9$ is selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, —$NR^aR^c$, $R^7$, $R^8$ and oxo.
82. The compound of claim 65 wherein $R^2$ is, independently in each instance, F, Cl, Br, CN, OH, $OC_{1-4}$alk, $C_{1-4}$alk or $C_{1-4}$haloalk.
83. The compound of claim 65 wherein $R^3$ is, independently in each instance, F, Cl, Br, CN, OH, $OC_{1-4}$alk, $C_{1-4}$alk or $C_{1-4}$haloalk.
84. The compound of claim 65 wherein $R^4$ is F or CN.
85. The compound of claim 65 wherein $R^6$ is methyl, —$CH_2$—$CH_2$—F, or $R^c$.
86. The compound of claim 65 wherein $R^7$ is a saturated 3-, 4-, 5-, or 6-membered monocyclic ring containing 0 or 1 N atom and 0 or 1 O atom, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$) $NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$) S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo.
87. The compound of claim 65 wherein $R^8$ is $C_{1-6}$alk substituted by 0 or 1 —$OR^a$.
88. The compound of claim 65 wherein $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

89. The compound of claim 65 wherein $R^c$ is a $C_{0-4}$alk-linked saturated, partially-saturated or unsaturated 3-, 4-, 5-, or 6-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

90. The compound of claim 65 wherein $R^c$ is a $C_{0-4}$alk-linked saturated, partially-saturated or unsaturated 9- or 10-membered monocyclic ring containing 0 or 1 N atom and 0 or 1 atom selected from O and S, which is substituted by 0, 1, or 2 groups selected from F, $C_{1-6}$alk, $C_{1-4}$haloalk, —$OR^a$, $R^7$, or $R^8$.

91. A pharmaceutical composition comprising a compound according to claim 65 and a pharmaceutically-acceptable diluent or carrier.

92. A compound of claim 1, or any pharmaceutically-acceptable salt thereof, selected from the group consisting of:
- (1H-Benzo[d]imidazol-2-yl)(4-(3-(trifluoromethyl)pyridin-2-yloxy)phenyl)methanone;
- (4-(3-Ethynylpyridin-2-yloxy)phenyl)(1-methyl-1H-benzo[d]imidazol-2-yl)-methanone;
- 4-(2-(4-(1H-benzo[d]imidazole-2-carbonyl)phenoxy)pyridin-3-yl)benzonitrile;
- (4-(3,3'-Bipyridin-2-yloxy)phenyl)(1H-imidazo[4,5-b]pyridin-2-yl)methanone;
- (4-(3-(9H-purin-6-yl)pyridin-2-yloxy)phenyl)(1H-benzo[d]imidazol-2-yl)methanone;
- 2-(4-(3-(2-methylpyridin-4-yl)pyridin-2-yloxy)benzyl)-1H-benzo[d]imidazole;
- (1H-benzo[d]imidazol-2-yl)(4-(3-(piperidin-1-yl)pyridin-2-yloxy)phenyl)methanone;
- (4-(3-chloropyridin-2-yloxy)phenyl)(6-fluoro-1H-benzo[d]imidazol-2-yl)methanone;
- (4-(3-bromopyridin-2-yloxy)phenyl)(1H-imidazo[4,5-b]pyridin-2-yl)methanone;
- (5-fluoro-1H-benzo[d]imidazol-2-yl)(4-(3-(trifluoromethyl)pyridin-2-yloxy)-phenyl)methanone;
- (1H-imidazo[4,5-b]pyridin-2-yl)(4-(3-(trifluoromethyl)pyridin-2-yloxy)phenyl)methanone;
- (5,6-difluoro-1H-benzo[d]imidazol-2-yl)(4-(3-(trifluoromethyl)pyridin-2-yloxy)phenyl)methanone;
- (1H-benzo[d]imidazol-2-yl)(4-(3-bromopyridin-2-yloxy)phenyl)methanone;
- (4-(3-bromopyridin-2-yloxy)phenyl)(1-methyl-1H-benzo[d]imidazol-2-yl)methanone;
- (1H-benzo[d]imidazol-2-yl)(4-(3-(3-hydroxy-3-methylbut-1-ynyl)pyridin-2-yloxy)phenyl)methanone;
- 4-(2-(4-(1H-benzo[d]imidazole-2-carbonyl)phenoxy)pyridin-3-yl)benzoic acid;
- 3-(2-(4-(1H-benzo[d]imidazole-2-carbonyl)phenoxy)pyridin-3-yl)benzonitrile;
- (1H-benzo[d]imidazol-2-yl)(4-(3-cyclopentenylpyridin-2-yloxy)phenyl)methanone;
- (1H-benzo[d]imidazol-2-yl)(4-(3-(2-methylpyridin-4-yl)pyridin-2-yloxy)phenyl)methanone;
- (1H-benzo[d]imidazol-2-yl)(4-(3-(2-(trifluoromethyl)pyridin-4-yl)pyridin-2-yloxy)phenyl)methanone;
- tert-butyl 4-(2-(4-(1H-benzo[d]imidazole-2-carbonyl)phenoxy)pyridin-3-yl)-5,6-dihydropyridine-1(2H)-carboxylate;
- 3-(2-(4-(1H-benzo[d]imidazole-2-carbonyl)phenoxy)pyridin-3-yl)benzoic acid;
- (1H-benzo[d]imidazol-2-yl)(4-(3-(4-(methylsulfonyl)phenyl)pyridin-2-yloxy)phenyl)methanone;
- (1H-benzo[d]imidazol-2-yl)(4-(3-(3-(methylsulfonyl)phenyl)pyridin-2-yloxy)phenyl)methanone;
- (1H-benzo[d]imidazol-2-yl)(4-(3-(4-methoxyphenyl)pyridin-2-yloxy)phenyl)methanone;
- (1H-benzo[d]imidazol-2-yl)(4-(3-(3-methoxyphenyl)pyridin-2-yloxy)phenyl)methanone;
- (4-(3-bromopyridin-2-yloxy)phenyl)(1-(tetrahydro-2H-pyran-2-yl)-1H-benzo[d]imidazol-2-yl)methanone;
- (1H-benzo[d]imidazol-2-yl)(4-(3-(pyrimidin-5-yl)pyridin-2-yloxy)phenyl)methanone;
- (4-(3,3'-bipyridin-2-yloxy)phenyl)(1H-benzo[d]imidazol-2-yl)methanone;
- (1H-benzo[d]imidazol-2-yl)(4-(6'-methyl-3,3'-bipyridin-2-yloxy)phenyl)methanone;
- (1H-benzo[d]imidazol-2-yl)(4-(3-(quinolin-5-yl)pyridin-2-yloxy)phenyl)methanone;
- -(1H-benzo[d]imidazol-2-yl)(4-(3-(quinolin-4-yl)pyridin-2-yloxy)phenyl)methanone;
- 2-(4-(1H-benzo[d]imidazole-2-carbonyl)phenoxy)-3,4'-bipyridine-2'-carbonitrile;
- (1H-benzo[d]imidazol-2-yl)(4-(2'-methoxy-3,3'-bipyridin-2-yloxy)phenyl)methanone;
- (1H-benzo[d]imidazol-2-yl)(4-(5'-methoxy-3,3'-bipyridin-2-yloxy)phenyl)methanone;
- (1H-benzo[d]imidazol-2-yl)(4-(6'-methoxy-3,3'-bipyridin-2-yloxy)phenyl)methanone;
- (1H-benzo[d]imidazol-2-yl)(4-(6-methoxy-2,3'-bipyridin-2'-yloxy)phenyl)methanone;
- (1H-benzo[d]imidazol-2-yl)(4-(3-methoxy-2,3'-bipyridin-2'-yloxy)phenyl)methanone;
- (1H-benzo[d]imidazol-2-yl)(4-(5-methoxy-2,3'-bipyridin-2'-yloxy)phenyl)methanone;
- (1H-benzo[d]imidazol-2-yl)(4-(3-(2-methoxyquinolin-3-yl)pyridin-2-yloxy)phenyl)methanone;
- (1H-benzo[d]imidazol-2-yl)(4-(3-(2-methoxyphenyl)pyridin-2-yloxy)phenyl)methanone;
- (4-(3'-methoxy-3,4'-bipyridin-2-yloxy)phenyl)(1-methyl-1H-benzo[d]imidazol-2-yl)methanone;
- (1H-benzo[d]imidazol-2-yl)(4-(3-(pyrrolidin-1-yl)pyridin-2-yloxy)phenyl)methanone;
- (1H-benzo[d]imidazol-2-yl)(4-(3-morpholinopyridin-2-yloxy)phenyl)methanone;
- (4-(2',6'-dimethoxy-3,3'-bipyridin-2-yloxy)phenyl)(1-methyl-1H-benzo[d]imidazol-2-yl)methanone;
- (1H-benzo[d]imidazol-2-yl)(4-(4'-methoxy-3,3'-bipyridin-2-yloxy)phenyl)methanone;
- (1H-benzo[d]imidazol-2-yl)(4-(5'-(methylthio)-3,3'-bipyridin-2-yloxy)phenyl)methanone;
- (1H-benzo[d]imidazol-2-yl)(4-(2'-chloro-3,4'-bipyridin-2-yloxy)phenyl)methanone;
- (1H-benzo[d]imidazol-2-yl)(4-(2'-fluoro-3,4'-bipyridin-2-yloxy)phenyl)methanone;
- (4-(2'-chloro-3,4'-bipyridin-2-yloxy)phenyl)(1-methyl-1H-benzo[d]imidazol-2-yl)methanone;
- (4-(2'-fluoro-3,4'-bipyridin-2-yloxy)phenyl)(1-methyl-1H-benzo[d]imidazol-2-yl)methanone;
- (1-methyl-1H-benzo[d]imidazol-2-yl)(4-(2'-methyl-3,4'-bipyridin-2-yloxy)phenyl)methanone;
- (1H-benzo[d]imidazol-2-yl)(4-(2'-fluoro-3,3'-bipyridin-2-yloxy)phenyl)methanone;
- (1H-benzo[d]imidazol-2-yl)(4-(2'-hydroxy-3,4'-bipyridin-2-yloxy)phenyl)methanone;
- 2-(4-(2'-(trifluoromethyl)-3,4'-bipyridin-2-yloxy)benzyl)-1H-benzo[d]imidazole;
- (1H-benzo[d]imidazol-2-yl)(4-(4-methoxy-2,3'-bipyridin-2'-yloxy)phenyl)methanone;
- (4-(4-methoxy-2,3'-bipyridin-2'-yloxy)phenyl)(1-methyl-1H-benzo[d]imidazol-2-yl)methanone;

4-(2-(4-(1-methyl-1H-benzo[d]imidazole-2-carbonyl)phenoxy)pyridin-3-yl)pyridin-2(1H)-one;

(6-fluoro-1-methyl-1H-benzo[d]imidazol-2-yl)(4-(3-(tetrahydro-2H-pyran-4-yl)pyridin-2-yloxy)phenyl)methanone and (5-fluoro-1-methyl-1H-benzo[d]imidazol-2-yl)(4-(3-(tetrahydro-2H-pyran-4-yl)pyridin-2-yloxy)phenyl)methanone;

(4-(5-chloro-2'-methyl-3,4'-bipyridin-2-yloxy)phenyl)(1-methyl-1H-benzo[d]imidazol-2-yl)methanone;

(1H-benzo[d]imidazol-2-yl)(4-(2',5-dimethyl-3,4'-bipyridin-2-yloxy)phenyl)methanone;

(4-(2',5-dimethyl-3,4'-bipyridin-2-yloxy)phenyl)(1-methyl-1H-benzo[d]imidazol-2-yl)methanone;

(1H-benzo[d]imidazol-2-yl)(4-(5-chloro-2'-methyl-3,4'-bipyridin-2-yloxy)phenyl)methanone;

N-(4-(3-Cyclopropylpyridin-2-yloxy)phenyl)benzo[d]thiazol-2-amine;

2-(4-(Benzo[d]thiazol-2-ylamino)phenoxy)nicotinic acid;

2-(4-(benzo[d]thiazol-2-ylamino)phenoxy)-N-(cyclopropylmethyl)nicotinamide;

N-(4-(3-Morpholinopyridin-2-yloxy)phenyl)benzo[d]thiazol-2-amine;

N-(4-(3-(4-methoxypiperidin-1-yl)pyridin-2-yloxy)phenyl)benzo[d]thiazol-2-amine;

N-(4-(3-methylpyridin-2-yloxy)phenyl)benzo[d]thiazol-2-amine;

N-(4-(3-methylpyridin-2-yloxy)phenyl)benzo[d]oxazol-2-amine;

N-(4-(3-(2-methylpyridin-4-yl)pyridin-2-yloxy)phenyl)-1H-benzo[d]imidazol-2-amine;

N-(4-(3-methylpyridin-2-yloxy)phenyl)-1H-benzo[d]imidazol-2-amine;

N-(4-(3-morpholinopyridin-2-yloxy)phenyl)-1H-imidazo[4,5-b]pyridin-2-amine;

2-(4-(1-methyl-1H-benzo[d]imidazol-2-ylamino)phenoxy)nicotinonitrile;

1-methyl-N-(4-(3-(morpholinomethyl)pyridin-2-yloxy)phenyl)-1H-benzo[d]imidazol-2-amine;

benzo[d]thiazol-2-yl(4-(3-bromopyridin-2-yloxy)phenyl)methanone;

Benzo[d]thiazol-2-yl(4-(3-(3,6-dihydro-2H-pyran-4-yl)pyridin-2-yloxy)phenyl)methanol;

N-(4-(3-(1,2,3,6-Tetrahydropyridin-4-yl)pyridin-2-yloxy)phenyl)benzo[d]thiazol-2-amine;

1-(4-(2-(4-(Benzo[d]thiazol-2-ylamino)phenoxy)pyridin-3-yl)piperazin-1-yl)ethanone;

N-(4-(3,3'-Bipyridin-2-yloxy)phenyl)-N-methylbenzo[d]thiazol-2-amine;

N-(4-(3,3'-Bipyridin-2-yloxy)phenyl)-1-methyl-1H-benzo[d]imidazol-2-amine;

N-(4-(3-(Tetrahydro-2H-pyran-4-yl)pyridin-2-yloxy)phenyl)-1H-benzo[d]imidazol-2-amine;

N-(4-(3-bromopyridin-2-yloxy)phenyl)-1H-benzo[d]imidazol-2-amine;

6,7-difluoro-N-(4-(3-methylpyridin-2-yloxy)phenyl)-1H-benzo[d]imidazol-2-amine;

N-(4-(3-(trifluoromethyl)pyridin-2-yloxy)phenyl)-1H-benzo[d]imidazol-2-amine;

6,7-difluoro-N-(4-(3-(trifluoromethyl)pyridin-2-yloxy)phenyl)-1H-benzo[d]imidazol-2-amine;

1-methyl-N-(4-(3-methylpyridin-2-yloxy)phenyl)-1H-benzo[d]imidazol-2-amine;

1-methyl-N-(4-(3-(trifluoromethyl)pyridin-2-yloxy)phenyl)-1H-benzo[d]imidazol-2-amine;

4-methyl-N-(4-(3-(trifluoromethyl)pyridin-2-yloxy)phenyl)-1H-benzo[d]imidazol-2-amine;

N-(4-(pyridin-2-yloxy)phenyl)-1H-benzo[d]imidazol-2-amine;

N-(4-(3-fluoropyridin-2-yloxy)phenyl)-1-methyl-1H-benzo[d]imidazol-2-amine;

5-fluoro-N-(4-(3-(trifluoromethyl)pyridin-2-yloxy)phenyl)-1H-benzo[d]imidazol-2-amine;

2-(4-(3-(trifluoromethyl)pyridin-2-yloxy)phenylamino)-1H-benzo[d]imidazole-5-carbonitrile;

6-chloro-5-fluoro-N-(4-(3-(trifluoromethyl)pyridin-2-yloxy)phenyl)-1H-benzo[d]imidazol-2-amine;

N-(4-(3-cyclopropylpyridin-2-yloxy)phenyl)-1-methyl-1H-benzo[d]imidazol-2-amine;

N-(4-(3-chloropyridin-2-yloxy)phenyl)-1-methyl-1H-benzo[d]imidazol-2-amine;

4-fluoro-N-(4-(3-(trifluoromethyl)pyridin-2-yloxy)phenyl)-1H-benzo[d]imidazol-2-amine;

5,7-difluoro-N-(4-(3-(trifluoromethyl)pyridin-2-yloxy)phenyl)-1H-benzo[d]imidazol-2-amine;

5,6-difluoro-N-(4-(3-(trifluoromethyl)pyridin-2-yloxy)phenyl)-1H-benzo[d]imidazol-2-amine;

N-(2-fluoro-4-(3-(trifluoromethyl)pyridin-2-yloxy)phenyl)-1H-benzo[d]imidazol-2-amine;

1-isopropyl-5-(trifluoromethyl)-N-(4-(3-(trifluoromethyl)pyridin-2-yloxy)phenyl)-1H-benzo[d]imidazol-2-amine;

N-(4-(3-(trifluoromethyl)pyridin-2-yloxy)phenyl)-1H-imidazo[4,5-b]pyridin-2-amine;

N-(4-(3-(trifluoromethyl)pyridin-2-yloxy)phenyl)-1H-imidazo[4,5-c]pyridin-2-amine;

N-(4-(3-(trifluoromethyl)pyridin-2-yloxy)phenyl)-7H-purin-8-amine;

1-methyl-5-(trifluoromethyl)-N-(4-(3-(trifluoromethyl)pyridin-2-yloxy)phenyl)-1H-benzo[d]imidazol-2-amine;

5-fluoro-1-methyl-N-(4-(3-(trifluoromethyl)pyridin-2-yloxy)phenyl)-1H-benzo[d]imidazol-2-amine;

5-chloro-1-ethyl-N-(4-(3-(trifluoromethyl)pyridin-2-yloxy)phenyl)-1H-benzo[d]imidazol-2-amine;

4-fluoro-N-(4-(3-(2-methylpyridin-4-yl)pyridin-2-yloxy)phenyl)-1H-benzo[d]imidazol-2-amine;

4,6-difluoro-N-(4-(3-(2-methylpyridin-4-yl)pyridin-2-yloxy)phenyl)-1H-benzo[d]imidazol-2-amine;

N-(4-(3-fluoropyridin-2-yloxy)phenyl)-1H-benzo[d]imidazol-2-amine;

N-(3-fluoro-4-(3-(trifluoromethyl)pyridin-2-yloxy)phenyl)-1H-benzo[d]imidazol-2-amine;

N-(6-(3-(trifluoromethyl)pyridin-2-yloxy)pyridin-3-yl)-1H-benzo[d]imidazol-2-amine;

N-(4-(3-cyclopropylpyridin-2-yloxy)phenyl)-1H-imidazo[4,5-b]pyridin-2-amine;

N-(4-(3-cyclopropylpyridin-2-yloxy)phenyl)-1H-imidazo[4,5-c]pyridin-2-amine;

N-(4-(3-morpholinopyridin-2-yloxy)phenyl)-1H-imidazo[4,5-c]pyridin-2-amine;

N-(4-(3-cyclopropylpyridin-2-yloxy)phenyl)benzo[d]oxazol-2-amine;

N-(2-fluoro-4-(3-(trifluoromethyl)pyridin-2-yloxy)phenyl)benzo[d]thiazol-2-amine;

N-(5-(3-(trifluoromethyl)pyridin-2-yloxy)pyridin-2-yl)-1H-benzo[d]imidazol-2-amine;

2-(4-(benzo[d]thiazol-2-ylamino)phenoxy)-N-(furan-2-ylmethyl)nicotinamide;

N-(4-(3-bromopyridin-2-yloxy)phenyl)benzo[d]thiazol-2-amine;

1-((2-(4-(benzo[d]thiazol-2-ylamino)phenoxy)pyridin-3-yl)methyl)pyrrolidin-3-ol;

4-(2-(4-(benzo[d]thiazole-2-carbonyl)phenoxy)pyridin-3-yl)benzonitrile;
(4-(3,3'-bipyridin-2-yloxy)phenyl)(benzo[d]thiazol-2-yl)methanone;
benzo[d]thiazol-2-yl(4-(3-morpholinopyridin-2-yloxy)phenyl)methanone;
4-(2-(4-(benzo[d]thiazol-2-ylamino)phenoxy)pyridin-3-yl)benzonitrile;
3-(2-(4-(benzo[d]thiazol-2-ylamino)phenoxy)pyridin-3-yl)benzonitrile;
N-(4-(3-cyclopentenylpyridin-2-yloxy)phenyl)benzo[d]thiazol-2-amine;
N-(4-(3,3'-bipyridin-2-yloxy)phenyl)benzo[d]thiazol-2-amine;
N-(4-(3-(2-methoxypyrimidin-5-yl)pyridin-2-yloxy)phenyl)benzo[d]thiazol-2-amine;
N-(4-(3-(pyrimidin-5-yl)pyridin-2-yloxy)phenyl)benzo[d]thiazol-2-amine;
methyl 4-(2-(4-(benzo[d]thiazol-2-ylamino)phenoxy)pyridin-3-yl)benzoate;
N-(4-(3-(3-methoxyphenyl)pyridin-2-yloxy)phenyl)benzo[d]thiazol-2-amine;
N-(4-(6'-methoxy-3,3'-bipyridin-2-yloxy)phenyl)benzo[d]thiazol-2-amine;
N-(4-(6'-chloro-3,3'-bipyridin-2-yloxy)phenyl)benzo[d]thiazol-2-amine;
N-(4-(2'-methyl-3,4'-bipyridin-2-yloxy)phenyl)benzo[d]thiazol-2-amine;
N-(4-(2'-fluoro-3,4'-bipyridin-2-yloxy)phenyl)benzo[d]thiazol-2-amine;
N-(4-(3-(quinolin-5-yl)pyridin-2-yloxy)phenyl)benzo[d]thiazol-2-amine;
N-(4-(3-(2,3-dihydrobenzo[b][1,4]dioxin-6-yl)pyridin-2-yloxy)phenyl)benzo[d]thiazol-2-amine;
N-(4-(3-(2,3-dihydrobenzofuran-5-yl)pyridin-2-yloxy)phenyl)benzo[d]thiazol-2-amine;
N-(4-(3-(benzo[d][1,3]dioxol-5-yl)pyridin-2-yloxy)phenyl)benzo[d]thiazol-2-amine;
N-(4-(3-cyclohexenylpyridin-2-yloxy)phenyl)benzo[d]thiazol-2-amine;
N-(4-(3-(quinolin-4-yl)pyridin-2-yloxy)phenyl)benzo[d]thiazol-2-amine;
N-(4-(3-(3,6-dihydro-2H-pyran-4-yl)pyridin-2-yloxy)phenyl)benzo[d]thiazol-2-amine;
N-(4-(6'-methyl-3,3'-bipyridin-2-yloxy)phenyl)benzo[d]thiazol-2-amine;
N-(4-(2'-methoxy-3,4'-bipyridin-2-yloxy)phenyl)benzo[d]thiazol-2-amine;
N-(4-(3,3'-bipyridin-2-yloxy)phenyl)-1H-benzo[d]imidazol-2-amine;
1-methyl-N-(4-(6'-methyl-3,3'-bipyridin-2-yloxy)phenyl)-1H-benzo[d]imidazol-2-amine;
N-(4-(6'-methyl-3,3'-bipyridin-2-yloxy)phenyl)-1H-benzo[d]imidazol-2-amine;
N-(4-(3-cyclopentenylpyridin-2-yloxy)phenyl)benzo[d]thiazol-2-amine;
N-(4-(5'-(methylthio)-3,3'-bipyridin-2-yloxy)phenyl)benzo[d]thiazol-2-amine;
N-(4-(4'-methoxy-3,3'-bipyridin-2-yloxy)phenyl)benzo[d]thiazol-2-amine;
(1H-benzo[d]imidazol-2-yl)(4-(3-(tetrahydro-2H-pyran-4-yl)pyridin-2-yloxy)phenyl)methanone;
(1H-Imidazo[4,5-b]pyridin-2-yl)(4-(3-(tetrahydro-2H-pyran-4-yl)pyridin-2-yloxy)phenyl)methanol;
2-(difluoro(4-(3-(tetrahydro-2H-pyran-4-yl)pyridin-2-yloxy)phenyl)methyl)-1H-benzo[d]imidazole;
(4-(3-(3,6-dihydro-2H-pyran-4-yl)pyridin-2-yloxy)phenyl)(1-methyl-1H-benzo[d]imidazol-2-yl)methanone;
(1-methyl-1H-benzo[d]imidazol-2-yl)(4-(3-(tetrahydro-2H-pyran-4-yl)pyridin-2-yloxy)phenyl)methanone;
1-(4-Methoxybenzyl)-N-(4-(3-(tetrahydro-2H-pyran-4-yl)pyridin-2-yloxy)phenyl)-1H-benzo[d]imidazol-2-amine;
7-Methoxy-N-(4-(3-(tetrahydro-2H-pyran-4-yl)pyridin-2-yloxy)phenyl)-1H-benzo[d]imidazol-2-amine;
N-(4-(3-(Tetrahydro-2H-pyran-4-yl)pyridin-2-yloxy)phenyl)benzo[d]thiazol-2-amine;
N-(4-(3-(tetrahydro-2H-pyran-4-yl)pyridin-2-yloxy)phenyl)benzo[d]oxazol-2-amine;
N-(4-(3-(4-fluorotetrahydro-2H-pyran-4-yl)pyridin-2-yloxy)phenyl)benzo[d]thiazo-2-amine;
4-(2-(4-(benzo[d]thiazol-2-ylamino)phenoxy)pyridin-3-yl)tetrahydro-2H-pyran-4-ol;
(1H-benzo[d]imidazol-2-yl)(4-(3-(4-(difluoromethyl)tetrahydro-2H-pyran-4-yl)pyridin-2-yloxy)phenyl)methanone;
(1H-benzo[d]imidazol-2-yl)(4-(3-(tetrahydro-2H-pyran-3-yl)pyridin-2-yloxy)phenyl)methanone;
N-(4-(3-(Tetrahydro-2H-pyran-3-yl)pyridin-2-yloxy)phenyl)benzo[d]thiazol-2-amine;
(±)-N-(4-(3-(tetrahydro-2H-pyran-2-yl)pyridin-2-yloxy)phenyl)benzo[d]thiazol-2-amine;
(1H-benzo[d]imidazol-2-yl)(4-(3-((1R,4R)-4-hydroxycyclohexyl)pyridin-2-yloxy)phenyl)methanone;
(1H-benzo[d]imidazol-2-yl)(4-(3-((1S,4S)-4-hydroxycyclohexyl)pyridin-2-yloxy)phenyl)methanone;
4-(2-(4-(benzo[d]thiazol-2-ylamino)phenoxy)pyridin-3-yl)cyclohex-3-enol;
4-(2-(4-(benzo[d]thiazol-2-ylamino)phenoxy)pyridin-3-yl)cyclohexanol;
(1H-benzo[d]imidazol-2-yl)(4-(3-((1R,4R)-4-hydroxy-4-methylcyclohexyl)pyridin-2-yloxy)phenyl)methanone;
(1R,4R)-4-(2-(4-(benzo[d]thiazol-2-ylamino)phenoxy)pyridin-3-yl)-1-methylcyclohexanol;
(1H-Benzo[d]imidazol-2-yl)(4-(3-((1S,4S)-4-hydroxy-4-(trifluoromethyl)cyclohexyl)pyridin-2-yloxy)phenyl)methanone;
(1H-Benzo[d]imidazol-2-yl)(4-(3-((1R,4R)-4-hydroxy-4-(trifluoromethyl)cyclohexyl)pyridin-2-yloxy)phenyl)methanone;
(1H-benzo[d]imidazol-2-yl)(4-(3-((1S,4S)-4-ethyl-4-hydroxycyclohexyl)pyridin-2-yloxy)phenyl)methanone;
(1H-benzo[d]imidazol-2-yl)(4-(3-((1R,4R)-4-ethyl-4-hydroxycyclohexyl)pyridin-2-yloxy)phenyl)methanone;
(4-(3-((4S,7S)-1-Oxaspiro[3.5]nonan-7-yl)pyridin-2-yloxy)phenyl)(1H-benzo[d]imidazol-2-yl)methanone;
4-(2-(4-(1H-Benzo[d]imidazole-2-carbonyl)phenoxy)pyridin-3-yl)cyclohexanone;
4-(2-(4-(Benzo[d]thiazol-2-ylamino)phenoxy)pyridin-3-yl)cyclohexanone;
4-(2-(4-(1H-benzo[d]imidazole-2-carbonyl)phenoxy)pyridin-3-yl)cycloheptanone;
(1H-Benzo[d]imidazol-2-yl)(4-(3-(oxepan-4-yl)pyridin-2-yloxy)phenyl)methanone;
N-(4-(3-(oxepan-4-yl)pyridin-2-yloxy)phenyl)benzo[d]thiazol-2-amine;
5-(2-(4-(1H-benzo[d]imidazole-2-carbonyl)phenoxy)pyridin-3-yl)azepan-2-one;
5-(2-(4-(1H-benzo[d]imidazole-2-carbonyl)phenoxy)pyridin-3-yl)-1-methylazepan-2-one;
(rac)-cis-3-(2-(4-(benzo[d]thiazol-2-ylamino)phenoxy)pyridin-3-yl)cyclohexanol;

(rac)-trans-3-(2-(4-(benzo[d]thiazol-2-ylamino)phenoxy)pyridin-3-yl)cyclohexanol;
(rac)-E-3-(2-(4-(benzo[d]thiazol-2-ylamino)phenoxy)pyridin-3-yl)-1-methylcyclohexanol;
4-(2-(4-(Benzo[d]thiazol-2-ylamino)phenoxy)pyridin-3-yl)-1-methylpiperidin-2-one;
4-(2-(4-(1H-Benzo[d]imidazole-2-carbonyl)phenoxy)pyridin-3-yl)-1-methylpiperidin-2-one;
(R)-4-(2-(4-(1H-benzo[d]imidazole-2-carbonyl)phenoxy)pyridin-3-yl)-1-methylpyrrolidin-2-one;
(S)-4-(2-(4-(1H-benzo[d]imidazole-2-carbonyl)phenoxy)pyridin-3-yl)-1-methylpyrrolidin-2-one;
4-(2-(4-(benzo[d]thiazol-2-ylamino)phenoxy)pyridin-3-yl)-1-methylpyrrolidin-2-one
1-(4-(2-(4-(1H-benzo[d]imidazole-2-carbonyl)phenoxy)pyridin-3-yl)piperidin-1-yl)ethanone;
1-(4-(2-(4-(benzo[d]thiazol-2-ylamino)phenoxy)pyridin-3-yl)-5,6-dihydropyridin-1(2H)-yl)ethanone;
1-(4-(2-(4-(benzo[d]thiazol-2-ylamino)phenoxy)pyridin-3-yl)piperidin-1-yl)ethanone;
tert-butyl 4-(2-(4-(1H-benzo[d]imidazole-2-carbonyl)phenoxy)pyridin-3-yl)piperidine-1-carboxylate;
(1H-benzo[d]imidazol-2-yl)(4-(3-(piperidin-4-yl)pyridin-2-yloxy)phenyl)methanone;
1-(5-(2-(4-(1H-benzo[d]imidazole-2-carbonyl)phenoxy)pyridin-3-yl)-3,4-dihydropyridin-1(2H)-yl)ethanone;
(S)-1-(3-(2-(4-(1H-benzo[d]imidazole-2-carbonyl)phenoxy)pyridin-3-yl)piperidin-1-yl)ethanone;
(R)-1-(3-(2-(4-(1H-benzo[d]imidazole-2-carbonyl)phenoxy)pyridin-3-yl)piperidin-1-yl)ethanone;
(S)-1-(3-(2-(4-(benzo[d]thiazol-2-ylamino)phenoxy)pyridin-3-yl)piperidin-1-yl)ethanone;
(R)-1-(3-(2-(4-(benzo[d]thiazol-2-ylamino)phenoxy)pyridin-3-yl)piperidin-1-yl)ethanone;
(R)-1-(2-(2-(4-(1H-benzo[d]imidazole-2-carbonyl)phenoxy)pyridin-3-yl)piperidin-1-yl)ethanone;
(S)-1-(2-(2-(4-(1H-benzo[d]imidazole-2-carbonyl)phenoxy)pyridin-3-yl)piperidin-1-yl)ethanone;
1-(3-(2-(4-(1H-benzo[d]imidazole-2-carbonyl)phenoxy)pyridin-3-yl)pyrrolidin-1-yl)ethanone;
N-(4-(3-(tetrahydrofuran-2-yl)pyridin-2-yloxy)phenyl)benzo[d]thiazol-2-amine;
(R)-(1H-benzo[d]imidazol-2-yl)(4-(3-(tetrahydrofuran-2-yl)pyridin-2-yloxy)phenyl)methanone (S)-(1H-benzo[d]imidazol-2-yl)(4-(3-(tetrahydrofuran-2-yl)pyridin-2-yloxy)phenyl)methanone;
N-(4-(3-(tetrahydrofuran-3-yl)pyridin-2-yloxy)phenyl)benzo[d]thiazol-2-amine;
(1-(2-fluoroethyl)-1H-benzo[d]imidazol-2-yl)(4-(3-(tetrahydrofuran-3-yl)pyridin-2-yloxy)phenyl)methanone;
3-(2-(4-(1H-benzo[d]imidazole-2-carbonyl)phenoxy)pyridin-3-yl)cyclopent-2-enone;
(1H-benzo[d]imidazol-2-yl)(4-(3-(3-hydroxycyclopentyl)pyridin-2-yloxy)phenyl)methanone;
3-(2-(4-(benzo[d]thiazol-2-ylamino)phenoxy)pyridin-3-yl)cyclopent-2-enone;
3-(2-(4-(benzo[d]thiazol-2-ylamino)phenoxy)pyridin-3-yl)cyclopentanol;
3-(2-(4-(1H-benzo[d]imidazole-2-carbonyl)phenoxy)pyridin-3-yl)cyclopentanone;
3-(2-(4-(benzo[d]thiazol-2-ylamino)phenoxy)pyridin-3-yl)cyclopentanone;
(1H-benzo[d]imidazol-2-yl)(4-(3-((1S,3S)-3-hydroxy-3-(trifluoromethyl)cyclopentyl)pyridin-2-yloxy)phenyl)methanone;
(1H-benzo[d]imidazol-2-yl)(4-(3-((1S,3R)-3-hydroxy-3-methylcyclopentyl)pyridin-2-yloxy)phenyl)methanone;
3-(2-(4-(benzo[d]thiazol-2-ylamino)phenoxy)pyridin-3-yl)-1-methylcyclopentanol;
1H-benzimidazol-2-yl(4-((3-(1,1-dioxidotetrahydro-2H-thiopyran-4-yl)-2-pyridinyl)oxy)phenyl)methanone;
(1H-Benzo[d]imidazol-2-yl)(4-(2'-fluoro-6-methoxy-3,4'-bipyridin-2-yloxy)phenyl)methanone;
(1H-benzo[d]imidazol-2-yl)(4-(3-(4-fluorotetrahydro-2H-pyran-4-yl)pyridin-2-yloxy)phenyl)methanone;
(4-(3-(4-fluorotetrahydro-2H-pyran-4-yl)pyridin-2-yloxy)phenyl)(1-methyl-1H-benzo[d]imidazol-2-yl)methanone;
1-(4-(2-(4-(1-methyl-1H-benzo[d]imidazole-2-carbonyl)phenoxy)pyridin-3-yl)piperidin-1-yl)ethanone;
(±)-(1H-benzo[d]imidazol-2-yl)(4-(3-(tetrahydro-2H-pyran-2-yl)pyridin-2-yloxy)phenyl)methanone;
(1H-benzo[d]imidazol-2-yl)(4-(3-((1S,4S)-4-hydroxy-4-methylcyclohexyl)pyridin-2-yloxy)phenyl)methanone;
(1S,4S)-4-(2-(4-(benzo[d]thiazol-2-ylamino)phenoxy)pyridin-3-yl)-1-methylcyclohexanol;
(rac)-cis-(1H-benzo[d]imidazol-2-yl)(4-(3-(3-hydroxycyclohexyl)pyridin-2-yloxy)phenyl)methanone;
(rac)-trans-(1H-benzo[d]imidazol-2-yl)(4-(3-(3-hydroxycyclohexyl)pyridin-2-yloxy)phenyl)methanone;
(rac)-E-(1H-benzo[d]imidazol-2-yl)(4-(3-(3-hydroxy-3-methylcyclohexyl)pyridin-2-yloxy)phenyl)methanone;
(1H-benzo[d]imidazol-2-yl)(4-(3-(tetrahydrofuran-3-yl)pyridin-2-yloxy)phenyl)methanone;
2-(4-(1H-benzo[d]imidazole-2-carbonyl)phenoxy)-N-(2-(pyridin-2-yl)ethyl)nicotinamide;
2-(4-(1H-benzo[d]imidazole-2-carbonyl)phenoxy)-N-phenethylnicotinamide;
(S)-2-(4-(1H-benzo[d]imidazole-2-carbonyl)phenoxy)-N-(2-phenylpropyl)nicotinamide;
(R)-2-(4-(1H-benzo[d]imidazole-2-carbonyl)phenoxy)-N-(1-hydroxy-3-phenylpropan-2-yl)nicotinamide;
(S)-2-(4-(1H-benzo[d]imidazole-2-carbonyl)phenoxy)-N-(1-hydroxy-3-phenylpropan-2-yl)nicotinamide;
(S)-2-(4-(1H-benzo[d]imidazole-2-carbonyl)phenoxy)-N-(1-methoxy-3-phenylpropan-2-yl)nicotinamide;
2-(4-(1H-benzo[d]imidazole-2-carbonyl)phenoxy)-N-(2-(thiophen-2-yl)ethyl)nicotinamide;
(S)-2-(4-(1H-benzo[d]imidazole-2-carbonyl)phenoxy)-N-(1-methoxypropan-2-yl)nicotinamide;
2-(4-(1H-benzo[d]imidazole-2-carbonyl)phenoxy)-N-(2-(pyridin-2-yl)ethyl)nicotinamide;
2-(4-(1H-benzo[d]imidazole-2-carbonyl)phenoxy)-N-(2-hydroxyethyl)nicotinamide;
(rac)-2-(4-(1H-benzo[d]imidazole-2-carbonyl)phenoxy)-N-(1-(pyridin-2-yl)propan-2-yl)nicotinamide;
2-(4-(1H-benzo[d]imidazole-2-carbonyl)phenoxy)-N-(2-methyl-2-(pyridin-2-yl)propyl)nicotinamide;
2-(4-(1H-benzo[d]imidazole-2-carbonyl)phenoxy)-N-(1-benzylcyclopropyl)nicotinamide;
(S)-2-(4-(1H-benzo[d]imidazole-2-carbonyl)phenoxy)-N-(1-hydroxy-3-(4-methoxyphenyl)propan-2-yl)nicotinamide;
(S)-2-(4-(1H-benzo[d]imidazole-2-carbonyl)phenoxy)-N-(1-hydroxy-3-(4-hydroxyphenyl)propan-2-yl)nicotinamide;
2-(4-(1H-benzo[d]imidazole-2-carbonyl)phenoxy)-N-(2,3-dihydro-1H-inden-2-yl)nicotinamide;
(R)-2-(4-(1H-benzo[d]imidazole-2-carbonyl)phenoxy)-N-(2-phenylpropyl)nicotinamide;

2-(4-(1H-benzo[d]imidazole-2-carbonyl)phenoxy)-N-(1-(4-fluorophenyl)-2-methylpropan-2-yl)nicotinamide;
(rac)-2-(4-(1H-benzo[d]imidazole-2-carbonyl)phenoxy)-N-(1-(4-fluorophenyl)propan-2-yl)nicotinamide;
(R)-(1H-benzo[d]imidazol-2-yl)(4-(3-(tetrahydrofuran-3-yl)pyridin-2-yloxy)phenyl)methanone;
(S)-(1H-benzo[d]imidazol-2-yl)(4-(3-(tetrahydrofuran-3-yl)pyridin-2-yloxy)phenyl)methanone;
(R)-N-(4-(3-(tetrahydrofuran-3-yl)pyridin-2-yloxy)phenyl)benzo[d]thiazol-2-amine;
(S)-N-(4-(3-(tetrahydrofuran-3-yl)pyridin-2-yloxy)phenyl)benzo[d]thiazol-2-amine;
(S)-(1H-benzo[d]imidazol-2-yl)(4-(3-(tetrahydrofuran-2-yl)pyridin-2-yloxy)phenyl)methanone;
(R)-(1H-benzo[d]imidazol-2-yl)(4-(3-(tetrahydrofuran-2-yl)pyridin-2-yloxy)phenyl)methanone;
(1H-benzo[d]imidazol-2-yl)(4-(3-((1R,3R)-3-(hydroxymethyl)cyclopentyl)pyridin-2-yloxy)phenyl)methanone;
(1H-benzo[d]imidazol-2-yl)(4-(3-((1R,3S)-3-(hydroxymethyl)cyclopentyl)pyridin-2-yloxy)phenyl)methanone;
(1H-benzo[d]imidazol-2-yl)(4-(3-((1S,3S)-3-(hydroxymethyl)cyclopentyl)pyridin-2-yloxy)phenyl)methanone;
(1H-benzo[d]imidazol-2-yl)(4-(3-((1S,3R)-3-(hydroxymethyl)cyclopentyl)pyridin-2-yloxy)phenyl)methanone;
(1H-benzo[d]imidazol-2-yl)(4-(3-((1S,3R)-3-hydroxycyclohexyl)pyridin-2-yloxy)phenyl)methanone;
(1H-benzo[d]imidazol-2-yl)(4-(3-((1R,3S)-3-hydroxycyclohexyl)pyridin-2-yloxy)phenyl)methanone;
(1H-benzo[d]imidazol-2-yl)(4-(3-((1S,3S)-3-hydroxycyclohexyl)pyridin-2-yloxy)phenyl)methanone;
(1H-benzo[d]imidazol-2-yl)(4-(3-((1R,3R)-3-hydroxycyclohexyl)pyridin-2-yloxy)phenyl)methanone;
(1R,4R)-4-(2-(4-(benzo[d]thiazol-2-ylamino)phenoxy)pyridin-3-yl)cyclohexanol;
(1R,4S)-4-(2-(4-(benzo[d]thiazol-2-ylamino)phenoxy)pyridin-3-yl)cyclohexanol;
(1R,3S)-3-(2-(4-(benzo[d]thiazol-2-ylamino)phenoxy)pyridin-3-yl)cyclohexanol;
(1S,3R)-3-(2-(4-(benzo[d]thiazol-2-ylamino)phenoxy)pyridin-3-yl)cyclohexanol;
(1S,3S)-3-(2-(4-(benzo[d]thiazol-2-ylamino)phenoxy)pyridin-3-yl)cyclohexanol;
(1R,3R)-3-(2-(4-(benzo[d]thiazol-2-ylamino)phenoxy)pyridin-3-yl)cyclohexanol;
(R)-1-(3-(2-(4-(1H-benzo[d]imidazole-2-carbonyl)phenoxy)pyridin-3-yl)piperidin-1-yl)ethanone;
(S)-1-(3-(2-(4-(1H-benzo[d]imidazole-2-carbonyl)phenoxy)pyridin-3-yl)piperidin-1-yl)ethanone;
((1H-benzo[d]imidazol-2-yl)(4-(3-((1S,3R)-3-hydroxycyclopentyl)pyridin-2-yloxy)phenyl)methanone;
((1H-benzo[d]imidazol-2-yl)(4-(3-((1R,3S)-3-hydroxycyclopentyl)pyridin-2-yloxy)phenyl)methanone;
((1H-benzo[d]imidazol-2-yl)(4-(3-((1S,3S)-3-hydroxycyclopentyl)pyridin-2-yloxy)phenyl)methanone;
((1H-benzo[d]imidazol-2-yl)(4-(3-((1R,3R)-3-hydroxycyclopentyl)pyridin-2-yloxy)phenyl)methanone;
(1R,3S)-3-(2-(4-(benzo[d]thiazol-2-ylamino)phenoxy)pyridin-3-yl)cyclopentanol;
(1R,3R)-3-(2-(4-(benzo[d]thiazol-2-ylamino)phenoxy)pyridin-3-yl)cyclopentanol;
(1S,3R)-3-(2-(4-(benzo[d]thiazol-2-ylamino)phenoxy)pyridin-3-yl)cyclopentanol;
(1S,3S)-3-(2-(4-(benzo[d]thiazol-2-ylamino)phenoxy)pyridin-3-yl)cyclopentanol;
(S)-3-(2-(4-(1H-benzo[d]imidazole-2-carbonyl)phenoxy)pyridin-3-yl)cyclopentanone;
(R)-3-(2-(4-(1H-benzo[d]imidazole-2-carbonyl)phenoxy)pyridin-3-yl)cyclopentanone;
(1H-benzo[d]imidazol-2-yl)(4-(3-((1R,3S)-3-hydroxy-3-methylcyclopentyl)pyridin-2-yloxy)phenyl)methanone;
(1H-benzo[d]imidazol-2-yl)(4-(3-((1S,3S)-3-hydroxy-3-methylcyclopentyl)pyridin-2-yloxy)phenyl)methanone;
(1H-benzo[d]imidazol-2-yl)(4-(3-((1R,3R)-3-hydroxy-3-methylcyclopentyl)pyridin-2-yloxy)phenyl)methanone;
(1H-benzo[d]imidazol-2-yl)(4-(3-((1S,3R)-3-hydroxy-3-methylcyclopentyl)pyridin-2-yloxy)phenyl)methanone;
(1S,3R)-3-(2-(4-(benzo[d]thiazol-2-ylamino)phenoxy)pyridin-3-yl)-1-methylcyclopentanol;
(1R,3R)-3-(2-(4-(benzo[d]thiazol-2-ylamino)phenoxy)pyridin-3-yl)-1-methylcyclopentanol;
(1R,3S)-3-(2-(4-(benzo[d]thiazol-2-ylamino)phenoxy)pyridin-3-yl)-1-methylcyclopentanol;
(1S,3S)-3-(2-(4-(benzo[d]thiazol-2-ylamino)phenoxy)pyridin-3-yl)-1-methylcyclopentanol;
(1H-benzo[d]imidazol-2-yl)(4-(3-((1R,3R)-3-hydroxy-3-(trifluoromethyl)cyclopentyl)pyridin-2-yloxy)phenyl)methanone;
(1H-benzo[d]imidazol-2-yl)(4-(3-((1S,3S)-3-hydroxy-3-(trifluoromethyl)cyclopentyl)pyridin-2-yloxy)phenyl)methanone;
(S)-2-(4-(1H-benzo[d]imidazole-2-carbonyl)phenoxy)-N-(1-(4-fluorophenyl)propan-2-yl)nicotinamide;
(R)-2-(4-(1H-benzo[d]imidazole-2-carbonyl)phenoxy)-N-(1-(4-fluorophenyl)propan-2-yl)nicotinamide;
(S)-2-(4-(1H-benzo[d]imidazole-2-carbonyl)phenoxy)-N-(1-(pyridin-2-yl)propan-2-yl)nicotinamide;
(R)-2-(4-(1H-benzo[d]imidazole-2-carbonyl)phenoxy)-N-(1-(pyridin-2-yl)propan-2-yl)nicotinamide;
(1S,3S)-3-(2-(4-(benzo[d]thiazol-2-ylamino)phenoxy)pyridin-3-yl)-1-methylcyclohexanol;
(1R,3R)-3-(2-(4-(benzo[d]thiazol-2-ylamino)phenoxy)pyridin-3-yl)-1-methylcyclohexanol;
(1H-benzo[d]imidazol-2-yl)(4-(3-((1S,3S)-3-hydroxy-3-methylcyclohexyl)pyridin-2-yloxy)phenyl)methanone;
(1H-benzo[d]imidazol-2-yl)(4-(3-((1R,3R)-3-hydroxy-3-methylcyclohexyl)pyridin-2-yloxy)phenyl)methanone; or any pharmaceutically-acceptable salt thereof.

93. A compound selected from the group consisting of:
(4-(3,4'-bipyridin-2-yloxy)phenyl)(1H-benzo[d]imidazol-2-yl)methanone;
(1H-benzo[d]imidazol-2-yl)(4-(3-(2-methoxypyridin-4-yl)pyridin-2-yloxy)phenyl)methanone;
(1H-benzo[d]imidazol-2-yl)(4-(3-(1-methyl-1H-pyrazol-4-yl)pyridin-2-yloxy)phenyl)methanone;
(1H-benzo[d]imidazol-2-yl)(4-(3-(1-cyclopropyl-1H-pyrazol-4-yl)pyridin-2-yloxy)phenyl)methanone;
(1H-benzo[d]imidazol-2-yl)(4-(3-(pyrimidin-4-yl)pyridin-2-yloxy)phenyl)methanone;
(1H-benzo[d]imidazol-2-yl)(4-(3'-methoxy-3,4'-bipyridin-2-yloxy)phenyl)methanone;
(5-fluoro-1H-benzo[d]imidazol-2-yl)(4-(2'-fluoro-3,4'-bipyridin-2-yloxy)phenyl)methanone;
(1H-benzo[d]imidazol-2-yl)(4-(3'-methoxy-3,4'-bipyridin-2-yloxy)phenyl)methanone;
N-(4-(3,4'-Bipyridin-2-yloxy)phenyl)benzo[d]thiazol-2-amine;
N-(4-(3-(pyridin-4-yl)pyridin-2-yloxy)phenyl)-1H-benzo[d]imidazol-2-amine;

N-(4-(3-(pyrimidin-4-yl)pyridin-2-yloxy)phenyl)-1H-benzo[d]imidazol-2-amine;
4,6-difluoro-N-(4-(3-(pyrimidin-4-yl)pyridin-2-yloxy)phenyl)-1H-benzo[d]imidazol-2-amine;
4-fluoro-N-(4-(3-(pyrimidin-4-yl)pyridin-2-yloxy)phenyl)-1H-benzo[d]imidazol-2-amine;
4-fluoro-N-(4-(3-(pyridin-4-yl)pyridin-2-yloxy)phenyl)-1H-benzo[d]imidazol-2-amine;
4,6-difluoro-N-(4-(3-(pyridin-4-yl)pyridin-2-yloxy)phenyl)-1H-benzo[d]imidazol-2-amine;
N-(4-(3-(pyridin-4-yl)pyridin-2-yloxy)phenyl)benzo[d]thiazol-2-amine;
N-(4-(3'-methoxy-3,4'-bipyridin-2-yloxy)phenyl)benzo[d]thiazol-2-amine;
N-(4-(3-(pyrimidin-4-yl)pyridin-2-yloxy)phenyl)benzo[d]thiazol-2-amine;
N-(4-(2'-(trifluoromethyl)-3,4'-bipyridin-2-yloxy)phenyl)benzo[d]thiazol-2-amine;
or any pharmaceutically acceptable salt thereof.

94. A pharmaceutical composition comprising a compound according to claim 93 and a pharmaceutically-acceptable diluent or carrier.

* * * * *